US010835596B2

(12) United States Patent
Jones et al.

(10) Patent No.: US 10,835,596 B2
(45) Date of Patent: Nov. 17, 2020

(54) COMPOSITIONS AND METHODS FOR FLAVIVIRUS VACCINATION

(71) Applicant: ETUBICS CORPORATION, Seattle, WA (US)

(72) Inventors: Frank R. Jones, Seattle, WA (US); Joseph Balint, Seattle, WA (US); Adrian Rice, Seattle, WA (US); Yvette Latchman, Seattle, WA (US); Elizabeth Gabitzsch, Seattle, WA (US)

(73) Assignee: Etubics Corporation, Seattle, WA (US)

( * ) Notice: Subject to any disclaimer, the term of this patent is extended or adjusted under 35 U.S.C. 154(b) by 11 days.

(21) Appl. No.: 16/317,739

(22) PCT Filed: Jul. 14, 2017

(86) PCT No.: PCT/US2017/042269
§ 371 (c)(1),
(2) Date: Jan. 14, 2019

(87) PCT Pub. No.: WO2018/014006
PCT Pub. Date: Jan. 18, 2018

(65) Prior Publication Data
US 2020/0171140 A1    Jun. 4, 2020

Related U.S. Application Data

(60) Provisional application No. 62/363,131, filed on Jul. 15, 2016.

(51) Int. Cl.
| | | |
|---|---|---|
| *C12Q 1/70* | (2006.01) | |
| *G01N 33/53* | (2006.01) | |
| *A61K 39/00* | (2006.01) | |
| *C12N 15/00* | (2006.01) | |
| *G01N 33/00* | (2006.01) | |
| *A61K 39/12* | (2006.01) | |
| *C12N 15/86* | (2006.01) | |

(52) U.S. Cl.
CPC .............. *A61K 39/12* (2013.01); *C12N 15/86* (2013.01); *A61K 2039/5258* (2013.01); *A61K 2039/572* (2013.01); *A61K 2039/70* (2013.01); *C12N 2710/10343* (2013.01); *C12N 2770/24122* (2013.01); *C12N 2770/24134* (2013.01); *C12N 2770/24234* (2013.01)

(58) Field of Classification Search
CPC ........ Y02A 50/51; Y02A 50/53; Y02A 50/60; Y02A 50/58; G01N 33/54306
See application file for complete search history.

(56) References Cited

U.S. PATENT DOCUMENTS

| 2013/0224144 A1* | 8/2013 | Balint .................. A61K 38/217 424/85.1 |
| 2013/0337008 A1* | 12/2013 | Bruder .................. A61K 39/12 424/204.1 |

FOREIGN PATENT DOCUMENTS

| WO | WO 2009/006479 | 1/2009 |
| WO | WO 2015/142963 | 9/2015 |
| WO | WO 2016/112188 | 7/2016 |
| WO | WO 2016/112195 | 7/2016 |

OTHER PUBLICATIONS

Larocca et al., "Vaccine protection against Zika virus from Brazil", 2016, 536:pp. 474-478 and Extended pp. 1-10.*
Bassi et al., "Vaccination with Replication Deficient Adenovectors Encoding YF-17D Antigens Induces Long-Lasting Protection from Severe Yellow Fever Virus Infection in Mice", PLoS Neglected Tropical Diseases 2016, vol. 10, Iss. 2, e 0004464, 17 pages.
Jacobs et al., "Protection elicited by a replication-defective adenovirus vector expressing the tick-borne encephalitis virus non-structural glycoprotein NS1", Journal of General Virology 1994, vol. 75, Iss. 9, pp. 2399-2402.
Khanam et al., "An adenovirus type 5 (AdV5) vector encoding an envelope domain III-based tetravalent antigen elicits immune responses against all four dengue viruses in the presence of prior AdV5 immunity", Vaccine, 2009, vol. 27, Iss. 43, pp. 6011-6021.
Korrapati et al., "Adenovirus Delivered Short Hairpin RNA Targeting a Conserved Site in the 5' Nontranslated Region Inhibits All Four Serotypes of Dengue Viruses", PLoS Neglected Tropical Diseases, 2012, vol. 6, Iss. 7, e1735, 12 pages.
Official Action for Australian Patent Application No. 2017297608 dated Aug. 28, 2019, 4 pages.
Larocca et al., "Vaccine protection against Zika virus from Brazil," Nature, 2016, vol. 536, pp. 474-478.
Wang et al., "2A self-cleaving peptide-based multi-gene expression system in the silkworm *Bombyx mori*," Scientific Reports, 2015, Iss. 5, Article 16273, 10 pages.
International Preliminary Report on Patentability dated Jan. 15, 2019 for International (PCT) Patent Application No. PCT/US2017/042269, 6 pages.
Official Action for Australian Patent Application No. 2017297608 dated Feb. 25, 2020, 2 pages.
Notice of Acceptance for Australian Patent Application No. 2017297608 dated Mar. 4, 2020, 3 pages.
Official Action (English translation) for Japanese Patent Application No. 2019-501629 dated Jan. 14, 2020, 3 pages.
Official Action for Canadian Patent Application No. 3,030,447 dated Nov. 25, 2019, 5 pages.
International Search Report and Written Opinion prepared by the U.S. Patent and Trademark Office dated Sep. 5, 2017, for International Application No. PCT/US2017/042269.

(Continued)

*Primary Examiner* — Barry A Chestnut
(74) *Attorney, Agent, or Firm* — Sheridan Ross P.C.

(57) ABSTRACT

Compositions of a recombinant adenovirus based vector vaccine containing one or more flavivirus antigen genes are disclosed herein. Methods for constructing and producing such vaccines and methods of using these vaccines to generate immune responses against flaviviruses are also described. Compositions described herein allow for vaccinations in subjects with preexisting immunity to adenovirus.

16 Claims, 13 Drawing Sheets
Specification includes a Sequence Listing.

(56) References Cited

OTHER PUBLICATIONS

Official Action (English translation) for Japanese Patent Application No. 2019-501629 dated May 12, 2020, 2 pages.
Amalfitano et al. "Production and Characterization of Improved Adenovirus Vectors with the E1, E2b, and E3 Genes Deleted", Journal of Virology, 1998, vol. 72, Iss. 2, pp. 926-933.
Gabitzsch, et al., "A preliminary and comparative evaluation of a novel Ad5 [E1-, E2b-] recombinant-based vaccine used to induce cell mediated immune responses", Immunology Letters, 2009, vol. 122, Iss. 1, pp. 44-51.
Lopez-Camacho et al., "Rational Zika vaccine design via the modulation of antigen membrane anchors in chimpanzee adenoviral vectors", Nature Communications, 2018, vol. 9, 11 pages.
Schmitz et al., "Next generation dengue vaccines: A review of candidates in preclinical development", Vaccine, 2011, vol. 29, Iss. 42, pp. 7276-7284.
Shan et al., "Zika Virus: Diagnosis, Therapeutics, and Vaccine", ACS Infectious Diseases, 2016, vol. 2, Iss. 3, pp. 170-172.
Extended European Search Report for European Patent Application No. 17828593.8 dated Feb. 26, 2020, 14 pages.
Official Action (with English translation) for South Korean Patent Application No. 10-2019-7004311 dated Jul. 29, 2020, 13 pages.

\* cited by examiner

Ad5 [E1-, E2b-]-ZIKAV-E

E.C7 Cells

Viral Particles

Immunization

Flavivirus Quad Gene Insert

| C Gene | T2A* | M Gene | P2A | E Gene | T2A* | NS Gene |

- C Gene — T2A* : 2A sequence with Gly-Ser-Gly Linker from *Thosea Asigna* Virus
- M Gene — P2A : 2A Sequence with Gly-Ser-Gly Linker from Porcine Teschovirus-1
- E Gene — T2A* : 2A Sequence with Gly-Ser-Gly Linker from *Thosea Asigna* Virus

* T2A Sequences Differ in Codon Usage to Prevent Homologous Recombination

FIG. 3B

4 Translation Products in Stoichiometric Abundance

- C Protein — T2A
- M protein — P2A
- E protein — T2A
- NS protein

Residual N-term Proline from 2A Sequences → P- (C Protein, M protein, E protein)

- Residual 20 aa C-term from T2A
- Residual 21 aa C-term from P2A
- Residual 20 aa C-term from T2A

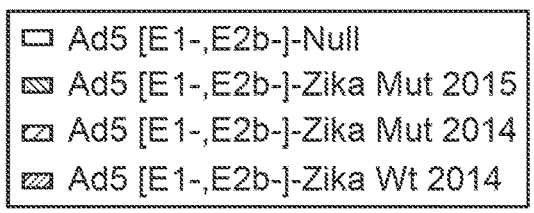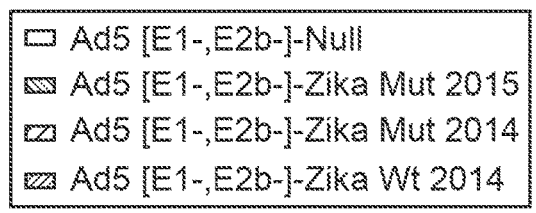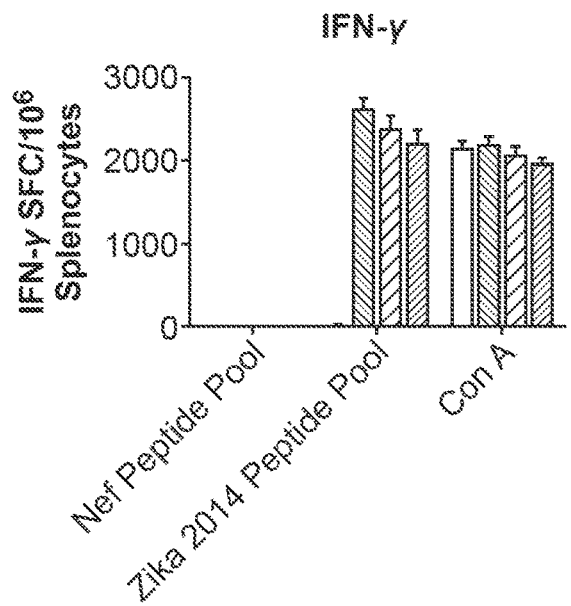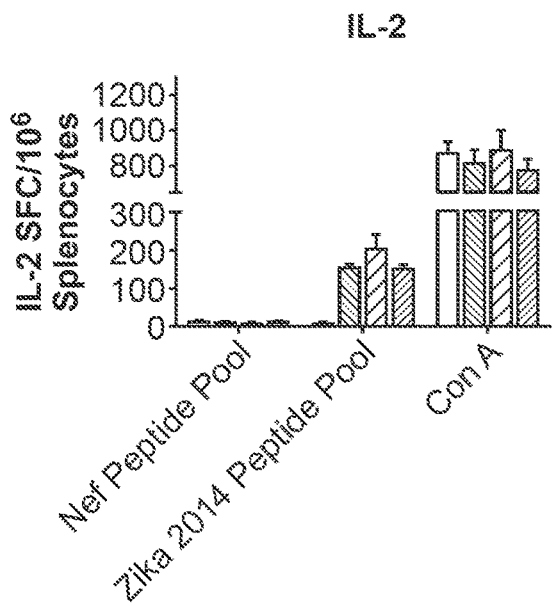
FIG. 6A    FIG. 6B
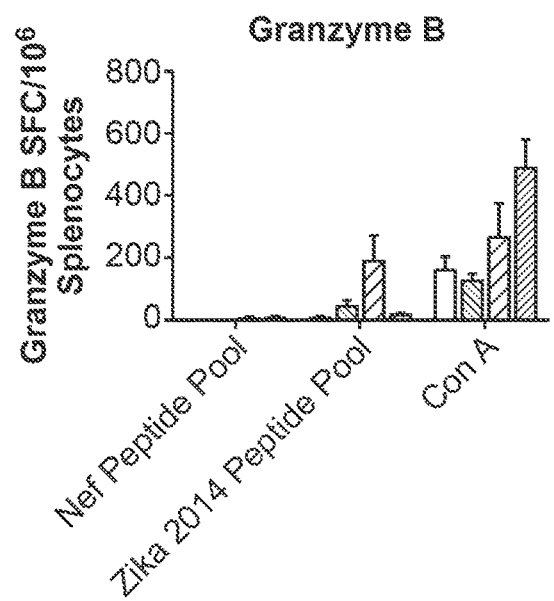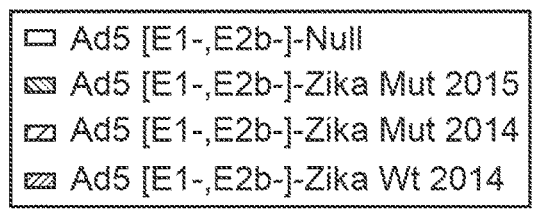
FIG. 6C

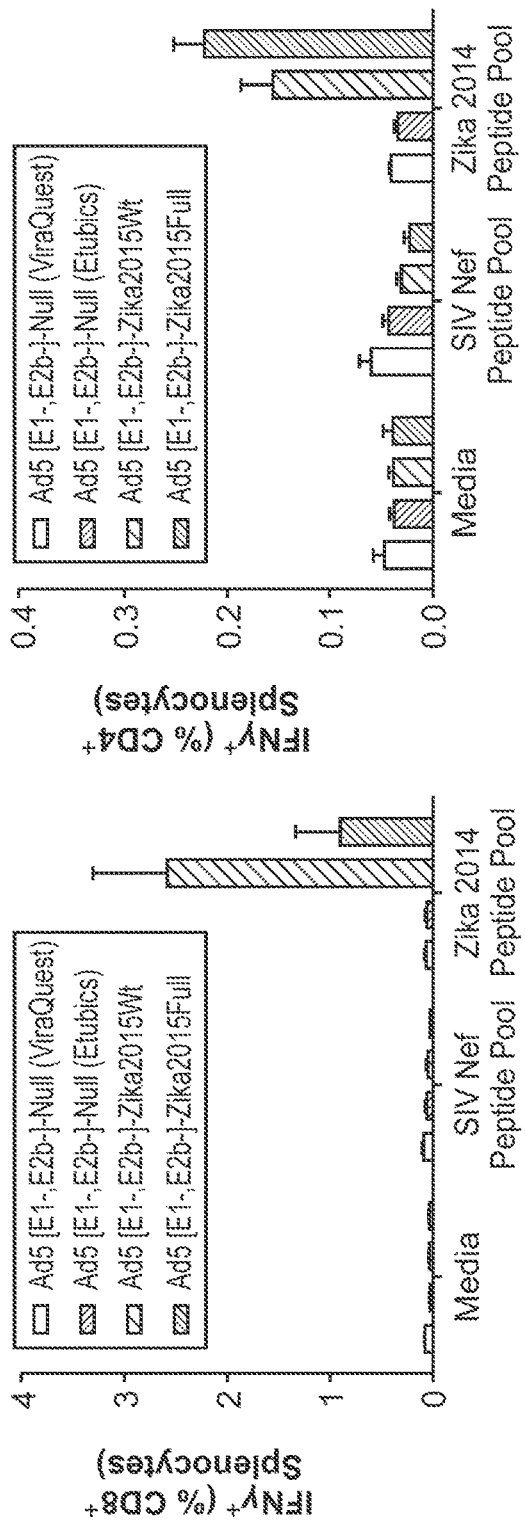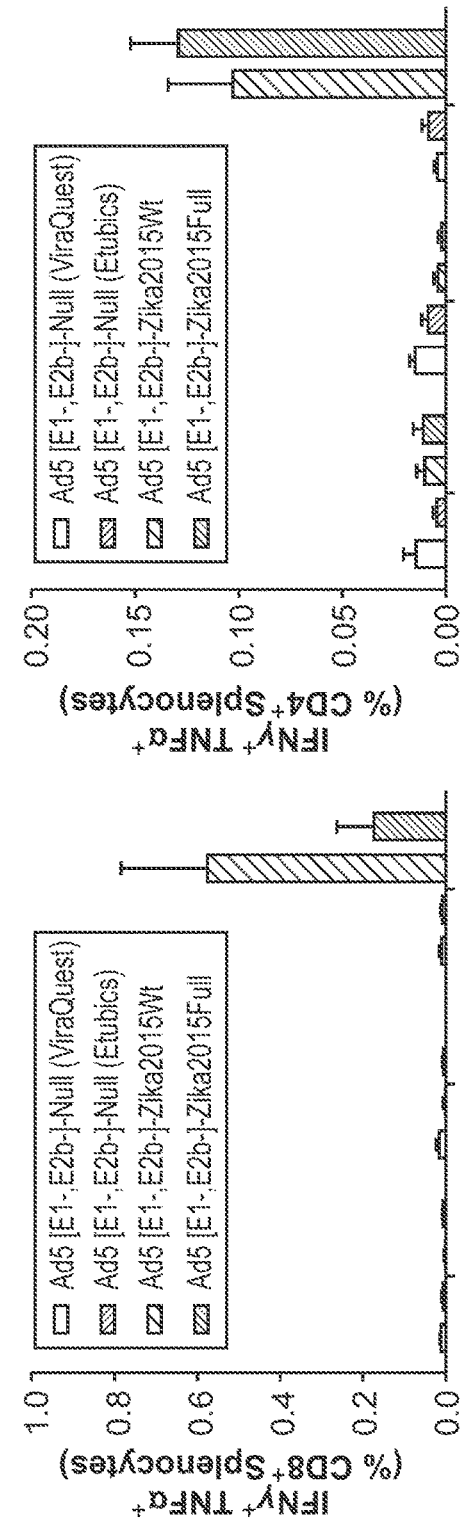

COMPOSITIONS AND METHODS FOR FLAVIVIRUS VACCINATION

CROSS REFERENCE TO RELATED APPLICATIONS

This application is a national stage application under 35 U.S.C. 371 and claims the benefit of PCT Application No. PCT/US2017/042269 having an international filing date of 14 Jul. 2017, which designated the United States, which PCT application claimed the benefit of U.S. Provisional Application No. 62/363,131, filed Jul. 15, 2016, the disclosures of each of which are herein incorporated by reference in their entireties.

SEQUENCE LISTING

The instant application contains a Sequence Listing which has been submitted electronically in ASCII format and is hereby incorporated by reference in its entirety. Said ASCII copy, created on Jul. 5, 2017, is named 39891-724_601_SL.txt and is 430,874 bytes in size.

BACKGROUND

Vaccines help the body fight disease by training the immune system to recognize and destroy harmful substances and diseased cells. Vaccines can be largely grouped into two types, preventive and treatment vaccines. Preventive vaccines are given to healthy people to prevent the development of specific diseases, while treatment vaccines, also referred to as immunotherapies, are given to a person who has been diagnosed with disease to help stop the disease from growing and spreading or as a preventive measure.

Viral vaccines are currently being developed to help fight infectious diseases and cancers. These viral vaccines work by inducing expression of a small fraction of genes associated with a disease within the host's cells, which in turn, enhance the ability of the host's immune system to identify and destroy diseased cells. As such, clinical response of a viral vaccine can depend on the ability of the vaccine to obtain a high-level of immunogenicity and have sustained long-term expression.

Therefore, there remains a need to discover novel compositions and methods for enhanced therapeutic response to complex diseases and especially to newly emerging disease threats.

SUMMARY

In various aspects, the present disclosure provides a composition comprising: a replication defective virus vector comprising a deletion in an E2b gene region; and a sequence encoding a flavivirus target antigen. In some aspects, the sequence encoding a flavivirus target antigen comprises a sequence encoding a plurality of flavivirus target antigens. In further aspects, the sequence encoding a plurality of flavivirus target antigens comprises a plurality of gene inserts each corresponding to a target antigen, wherein each gene insert is separated by a nucleic acid sequence encoding a self-cleaving 2A peptide. In some aspects, the self-cleaving 2A peptide is derived from Porcine teschovirus-1 virus or Thosea asigna virus. In some aspects, the plurality of flavivirus target antigens comprises three flavivirus target antigens or four flavivirus target antigens.

In some aspects, the replication defective virus vector is an adenovirus vector. In further aspects, the replication defective virus vector is an adenovirus 5 (Ad5) vector. In still further aspects, the replication defective virus vector comprises a deletion in an E1 gene region, an E3 gene region, an E4 gene region, or any combination thereof. In some aspects, the deletion in the E2b gene region comprises a plurality of deletions in the E2b gene region.

In some aspects, the deletion in the E2b gene region, the deletion in the E1 gene region, the deletion in the E3 gene region, the deletion in the E4 gene region, or any combination thereof, each comprises at least one base pair comprises.

In other aspects, the deletion in the E2b gene region, the deletion in the E1 gene region, the deletion in the E3 gene region, the deletion in the E4 gene region, or any combination thereof results from a translocation of two or more base pairs. In some aspects, the deletion in the E2b gene region, the deletion in the E1 gene region, the deletion in the E3 gene region, the deletion in the E4 gene region, or any combination thereof each comprises at least 20, at least 30, at least 40, at least 50, at least 60, at least 70, at least 80, at least 90, at least 100, at least 110, at least 120, at least 130, at least 140, or at least 150 base pairs. In other aspects, the deletion in the E2b gene region, the deletion in the E1 gene region, the deletion in the E3 gene region, the deletion in the E4 gene region, or any combination thereof each comprises more than 150, more than 160, more than 170, more than 180, more than 190, more than 200, more than 250, or more than 300 base pairs.

In some aspects, the flavivirus target antigen comprises an antigen of a virus selected from a group consisting of yellow fever virus (YFV), Japanese encephalitis virus (JEV), Tick-borne encephalitis virus (TBEV), Dengue virus (DENV), West Nile virus (WNV), zika virus (ZIKAV), or any combination thereof. In further aspects, the flavivirus target antigen comprises an antigen of a virus selected from the group consisting of YFV, ZIKAV, or both.

In still further aspects, the flavivirus target antigen comprises an antigen of ZIKAV. In some aspects, the flavivirus target antigen comprises an antigen selected from the group consisting of C (capsid protein), E (envelope protein), prM (pre-membrane protein), M (membrane protein), NS1, NS2A, NS2B, NS3, NS4A, NS4B, and NS5, or any combination thereof. In some aspects, the flavivirus target antigen comprises an antigen selected from the group consisting of E, prM, M, NS1, NS2A, NS2B, NS3, NS4A, NS4B, and NS5, or any combination thereof. In some aspects, the flavivirus target antigen comprises an antigen selected from the group consisting of and E, prM, M, and NS3, or any combination thereof.

In some aspects, the sequence encoding a flavivirus target antigen comprises an N-terminal GCCGCCACC sequence. In some aspects, the sequence encoding a flavivirus target antigen comprises a sequence encoding for a mutation, and wherein the mutation comprises isoleucine (I) to aspartic acid (D), leucine (L) to aspartic acid (D), aspartic acid (D) to isoleucine (I), aspartic acid (D) to leucine (L), or any combination thereof.

In further aspects, the mutation occurs at I21D, L175D, L240D, D37I, D43L, D266I, D129L, D218L, or any combination thereof. In some aspects, the sequence encoding a flavivirus target antigen comprises at least 70%, at least 75%, at least 80%, at least 85%, at least 90%, at least 92%, at least 95%, at least 97%, or at least 99% sequence identity to a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, and SEQ ID NO: 37, or any combination thereof.

In some aspects, the sequence encoding a flavivirus target antigen comprises at least 70%, at least 75%, at least 80%, at least 85%, at least 90%, at least 92%, at least 95%, at least 97%, or at least 99% sequence identity to a sequence selected from the group consisting of SEQ ID NO: 15-SEQ ID NO: 19. In some aspects, the sequence encoding a flavivirus target antigen is an amino acid sequence, and wherein the amino acid sequence comprises at least 70%, at least 75%, at least 80%, at least 85%, at least 90%, at least 92%, at least 95%, at least 97%, or at least 99% sequence identity to a sequence selected from the group consisting of SEQ ID NO: 26, SEQ ID NO: 28, SEQ ID NO: 30, SEQ ID NO: 32, SEQ ID NO: 34, and SEQ ID NO: 36, or any combination thereof.

In some aspects, the sequence encoding a flavivirus target antigen is a nucleotide sequence, and wherein the nucleotide sequence comprises at least 70%, at least 75%, at least 80%, at least 85%, at least 90%, at least 92%, at least 95%, at least 97%, or at least 99% sequence identity to a sequence selected from the group consisting of SEQ ID NO: 27, SEQ ID NO: 29, SEQ ID NO: 31, SEQ ID NO: 33, SEQ ID NO: 35, and SEQ ID NO: 37, or any combination thereof.

In some aspects, the replication defective virus vector further comprises an element to increase the expression of the flavivirus target antigen. In further aspects, the element comprises at least one element, at least 2 elements, at least 3 elements, at least 4 elements, or at least 5 elements. In some aspects, the element comprises an internal ribosome binding site.

In other aspects, the element comprises a constitutive promoter. In some aspects, the element comprises an inducible promoter. In some aspects, the element comprises a transcription enhancer. In some aspects, the transcription enhancer is a Rous sarcoma virus (RSV) enhancer. In some aspects, the element does not contain a palindromic sequence.

In some aspects, the replication defective virus vector further comprises a nucleic acid sequence encoding a protein that increases flavivirus target antigen immunogenicity. In some aspects, the replication defective virus vector is not a gutted vector. In some aspects, the composition or the replication defective virus vector further comprises a nucleic acid sequence encoding a costimulatory molecule or an immunological fusion partner.

In various aspects, the present disclosure provides a pharmaceutical composition comprising any one of the above compositions and a pharmaceutically acceptable carrier.

In various aspects, the present disclosure provides a cell comprising any one of the above compositions. In some aspects, the cell is a host cell. In further aspects, the cell is a dendritic cell (DC).

In various aspects, the present disclosure provides a method of preparing a vaccine, comprising preparing the above described pharmaceutical composition.

In various aspects, the present disclosure provides a method of generating an immune response against a flavivirus target antigen in a subject, comprising: administering to the subject any one of the above compositions or the above described pharmaceutical composition. In some aspects, the subject has not been infected with a flavivirus. In some aspects, the target flavirus antigen is from a flavivirus, wherein the flavivirus comprises yellow fever virus (YFV), Japanese encephalitis virus (JEV), Tick-borne encephalitis virus (TBEV), Dengue virus (DENV), West Nile virus (WNV), zika virus (ZIKAV), or any combination thereof.

In various aspects, the present disclosure provides a method of preventing Zika virus infection in a subject, the method comprising administering to the subject a composition comprising: a replication defective virus vector comprising a deletion in an E2b gene region; and a sequence encoding at least one Zika virus target antigen.

In some aspects, the subject has preexisting immunity to an adenovirus or an adenovirus vector. In some aspects, the subject is a human or a non-human animal. In some aspects, the administering is intravenously, subcutaneously, intralymphatically, intratumorally, intradermally, intramuscularly, intraperitoneally, intrarectally, intravaginally, intranasally, orally, via bladder instillation, or via scarification. In some aspects, the administering of the composition to the subject is at least one time, is repeated at least twice, or is repeated at least three times.

In some aspects, the administering of the composition to the subject comprises $1\times10^9$ to $5\times10^{12}$ virus particles per dose. In further aspects, the administering of the composition to the subject comprises at least $10^9$ virus particles, at least $10^{10}$ virus particles, or at least $10^{11}$ virus particles per dose. In some aspects, the replication defective virus vector is an adenovirus vector. In further aspects, the replication defective virus vector is an adenovirus 5 (Ad5) vector.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 1 exemplifies an Ad5 [E1-, E2b-]-ZIKAV-E vaccine derived from SEQ ID NO: 13 and SEQ ID NO: 14 that has been generated.

FIG. 2 illustrates a schematic of a multi-targeted triple gene insert for a flavivirus vaccine of the present disclosure.

FIG. 2A illustrates a schematic representations of a triple gene construct containing genes encoding capsid protein (C), membrane protein (M) and envelope protein (E) of flavivirus to be used for insertion into Ad5 [E1-, E2b-].

FIG. 2B illustrates the translation products in stoichiometric abundance of FIG. 2A.

FIG. 3 illustrates a schematic of a multi-targeted quad gene insert for a flavivirus vaccine of the present disclosure.

FIG. 3A illustrates a schematic representations of a quad gene construct containing genes encoding capsid protein (C), membrane protein (M), envelop protein (E), and NS protein of flavivirus to be used for insertion into Ad5 [E1-, E2b-].

FIG. 3B illustrates the translation products in stoichiometric abundance of FIG. 3A.

FIG. 4 illustrates cell-mediated immune (CMI) responses and antibody responses in splenocytes from immunized mice after exposure to Zika peptide pools. Immunogenicity studies of an Ad5 [E1-, E2b-]-ZIKAV-E vaccine were conducted in mice.

FIG. 4A illustrates CMI responses as determined by ELISpot spot forming cells (SFC) for IFN-γ secreting cells in mice injected with Ad5 [E1-, E2b-]-null (empty vector control) or Ad5 [E1-, E2b-]-ZIKA-E. Note the CMI responses induced in immunized mice (white bar) but not control mice (hatched black bar). Specificity was confirmed by lack of reactivity against an irrelevant antigen Nef peptide pool. Note that for the Nef peptide pool and the Zika peptide pool, the left bar represents SFC from mice injected with the empty vector control, and the right bar represents SFC from mice injected with Ad5 [E1-, E2b-]-ZIKA-E.

FIG. 4B illustrates CMI responses as determined by ELISpot spot forming cells (SFC) for IL-2 secreting cells in mice injected with Ad5 [E1-, E2b-]-null (empty vector control) or Ad5 [E1-, E2b-]-ZIKA-E. The CMI responses induced in immunized mice (white bar) but not control mice (black hatched bar). Specificity was confirmed by lack of reactivity against an irrelevant antigen Nef peptide pool. Note that for the Nef peptide pool and the Zika peptide pool, the left bar represents SFC from mice injected with the empty vector control, and the right bar represents SFC from mice injected with Ad5 [E1-, E2b-]-ZIKA-E.

FIG. 4C illustrates anti-ZIKA-E IgG antibody response as determined by a quantitative ELISA in mice injected with Ad5 [E1-, E2b-]-null (empty vector control) or Ad5 [E1-, E2b-]-ZIKA-E. Antibody responses were induced in immunized mice (white bar, G4M1-5) but not control mice (black bar, G1M1-5). Note that the left G1M1, G1M2, G1M3, G1M4, and G1M5 represent the antibody response from mice injected with the empty vector control, and the right G1M1, G1M2, G1M3, G1M4, and G1M5 represent the antibody response from mice injected with Ad5 [E1-, E2b-]-ZIKA-E.

FIG. 5 illustrates the informational spectrum method (ISM) based phylogenetic tree of nonredundant envelope proteins (E) from Zika viruses isolated in Brazil from 2014-2015.

FIG. 6 illustrates cell mediated immune (CMI) responses and cytolytic T lymphocyte (CTL) responses in splenocytes from mice immunized with Ad5 [E1-, E2b-]-Zika-E vaccines. Mice (C57BL/6 strain) were immunized two times at two-week intervals with $1\times10^{10}$ virus particles (VPs) of an Ad5 [E1-, E2b-]-Zika vaccine or with $1\times10^{10}$ VPs Ad5 [E1-, E2b-]-null (empty vector control). Three types of Zika vaccines were tested. The first Zika vaccine tested was the Ad5 [E1-, E2b-]-Zika mut 2015, which comprises a Zika antigen protein encoded by the nucleotide sequence of SEQ ID NO: 34 and by the amino acid sequence of SEQ ID NO: 35 (SEQ ID NO: 34 is the nucleotide sequence and SEQ ID NO: 35 is the amino acid sequence corresponding to SEQ ID NO: 34). The Zika mut 2015 antigen in SEQ ID NO: 35 corresponds to amino acids 409-690 of the 3423-aa Zika polyprotein (SEQ ID NO: 23), which is the truncated portion of the extracellular domain of the Zika envelope protein. The Zika mut 2015 antigen comprises point mutations as compared to the Zika wt 2015 antigen. These point mutations include D37I, D43L, D266I, D129L, D218L (position numbering does not count the N-terminal methionine) and these mutations can result in decreased anti-human C1q responses compared to wild type. The second Zika vaccine tested was the Ad5 [E1-, E2b-]-Zika wt 2014, which comprises a Zika antigen protein encoded by the nucleotide sequence of SEQ ID NO: 26 and by the amino acid sequence of SEQ ID NO: 27 (SEQ ID NO: 26 is the nucleotide sequence and SEQ ID NO: 27 is the amino acid sequence corresponding to SEQ ID NO: 26). The Zika wt 2014 antigen shown in SEQ ID NO: 27 corresponds to amino acids 409-690 of the 3423-aa Zika polyprotein (SEQ ID NO: 23), which is the truncated portion of the extracellular domain of the Zika envelope protein. The third Zika vaccine tested was the Ad5 [E1-, E2b-]-Zika mut 2014, which comprises the Zika antigen a protein encoded by the nucleotide sequence of SEQ ID NO: 28 and by the amino acid sequence of SEQ ID NO: 29 (SEQ ID NO: 28 is the nucleotide sequence and SEQ ID NO: 29 is the amino acid sequence corresponding to SEQ ID NO: 28). The Zika mut 2014 antigen of SEQ ID NO: 29 corresponds to amino acids 409-690 of the 3423-aa Zika polyprotein (SEQ ID NO: 23), which is the truncated portion of the extracellular domain of the Zika envelope protein. The Zika mut 2014 antigen comprises point mutations as compared to the Zika wt 2014 antigen. These point mutations include I21D, L175D, L240D (position numbering does not count the N-terminal methionine) and these mutations can result in decreased anti-human C1q responses compared to wild type. One week after the final immunization of each Ad5 [E1-, E2b-]-Zika-E vaccine, splenocytes isolated from the immunized mice were exposed to Zika wt virus peptide pools and then ELISPOT assays were used to measure CMI responses (IFN-γ and IL-2 secreting spot forming cells (SFC)) and CTL responses (Granzyme-B secreting SFCs). Specificity of responses is shown by the lack of reactivity of splenocytes to an SIV-nef peptide pool (negative control). Reactivity of splenocytes to Concanavalin A (Con A) was used as a positive control. Error bars show SEM and five mice were in each group.

FIG. 6A illustrates IFN-γ CMI responses after exposure of splenocytes from immunized mice and control mice to Zika 2014 peptide pools and controls.

FIG. 6B illustrates IL-2 CMI responses after exposure of splenocytes from immunized mice and control mice to Zika 2014 peptide pools or controls.

FIG. 6C illustrates Granzyme B CTL responses after exposure of splenocytes from immunized mice and control mice to Zika 2014 peptide pools or controls.

Figure 2A:
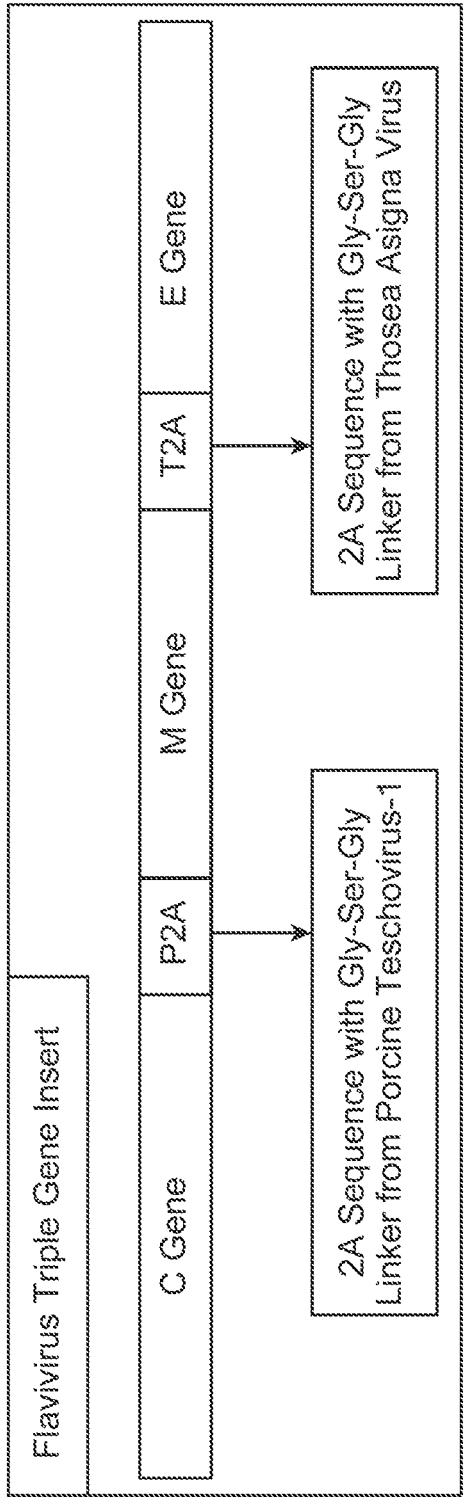

FIG. 7 illustrates lymphocyte activation as measured by intracellular expression of IFN-γ and IFN-γ/TNF-α in splenocytes from mice immunized with Ad5 [E1-, E2b-]-Zika-E vaccines using flow cytometry. Mice (C57B1/6 strain) were immunized two times at two-week intervals with $1\times10^{10}$ virus particles (VPs) of an Ad5 [E1-, E2b-]-Zika vaccine or with $1\times10^{10}$ VPs Ad5 [E1-, E2b-]-null (empty vector control). Three types of Zika vaccines were tested. The first Zika vaccine tested was the Ad5 [E1-, E2b-]-Zika mut 2015, which comprises a Zika antigen protein encoded by the nucleotide sequence of SEQ ID NO: 34 and by the amino acid sequence of SEQ ID NO: 35 (SEQ ID NO: 34 is the nucleotide sequence and SEQ ID NO: 35 is the amino acid sequence corresponding to SEQ ID NO: 34). The Zika mut 2015 antigen of SEQ ID NO: 35 corresponds to amino acids 409-690 of the 3423-aa Zika polyprotein (SEQ ID NO: 23), which is the truncated portion of the extracellular domain of the Zika envelope protein. The Zika mut 2015 antigen comprises point mutations as compared to the Zika wt 2015 antigen. These point mutations include D37I, D43L, D266I, D129L, D218L (position numbering does not count the N-terminal methionine) and these mutations can result in decreased anti-human C1q responses compared to wild type. The second Zika vaccine tested was the Ad5 [E1-, E2b-]-Zika wt 2014, which comprises a Zika antigen protein encoded by the nucleotide sequence of SEQ ID NO: 26 and by the amino acid sequence of SEQ ID NO: 27 (SEQ ID NO: 26 is the nucleotide sequence and SEQ ID NO: 27 is the amino acid sequence corresponding to SEQ ID NO: 26). The Zika wt 2014 antigen of SEQ ID NO: 27 corresponds to amino acids 409-690 of the 3423-aa Zika polyprotein (SEQ ID NO: 23), which is the truncated portion of the extracellular domain of the Zika envelope protein. The third Zika vaccine tested was the Ad5 [E1-, E2b-]-Zika mut 2014, which comprises a Zika antigen protein encoded by the nucleotide sequence of SEQ ID NO: 28 and by the amino acid sequence of SEQ ID NO: 29 (SEQ ID NO: 28 is the nucleotide sequence and SEQ ID NO: 29 is the amino acid sequence corresponding to SEQ ID NO: 28). The Zika mut 2014 antigen of SEQ ID NO: 29 corresponds to amino acids 409-690 of the 3423-aa Zika polyprotein (SEQ ID NO: 23), which is the truncated portion of the extracellular domain of the Zika envelope protein. The Zika mut 2014 antigen comprises point mutations as compared to the Zika wt 2014 antigen. These point mutations include I21D, L175D, L240D (position numbering does not count the N-terminal methionine) and these mutations can result in decreased anti-human C1q responses compared to wild type. One week after the final immunization, splenocytes isolated from the immunized mice were exposed to Zika wt virus peptide pools and flow cytometry was used to measure intracellular cytokine production of IFN-γ and IFN-γ/TNF-α in CD8+ cells and CD4+ cells. Specificity of responses is shown by the lack of reactivity of splenocytes to an SIV-nef peptide pool (negative control). Reactivity of splenocytes to PMA/ionomycin was used as a positive control. Data are reported as the percent of CD8+ or CD4+ splenocytes expressing IFN-γ or IFN-γ and TNF-α and error bars show SEM. Each group had five mice.

Figure 7A:
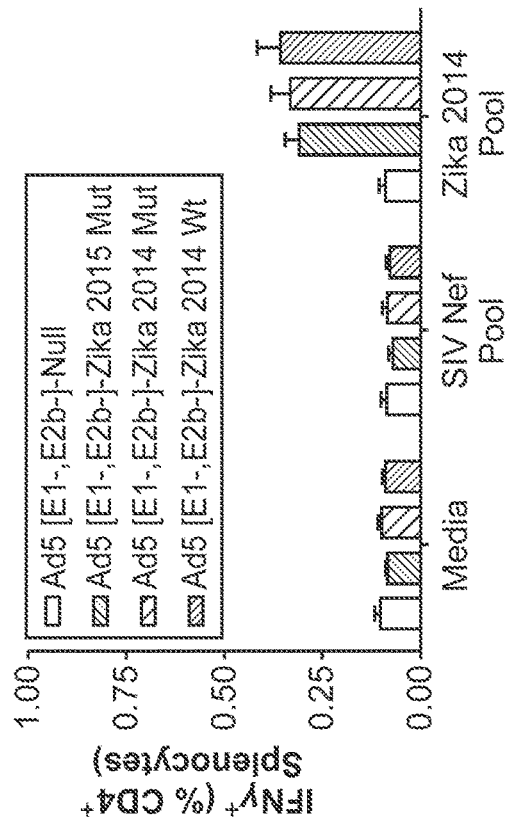

FIG. 7A illustrates lymphocyte activation as measured by intracellular expression of IFN-γ in CD8+ splenocytes after exposure of splenocytes from immunized mice and control mice to Zika 2014 peptide pools or controls using flow cytometry.

Figure 7C:
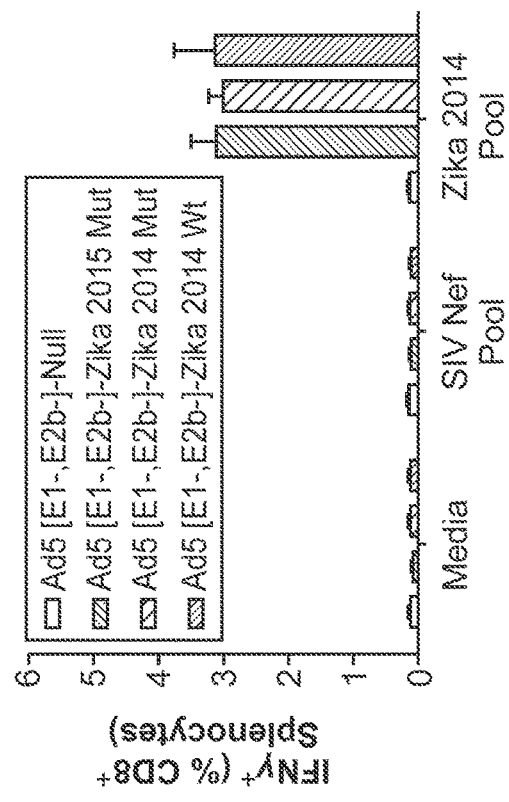
Figure 7B:
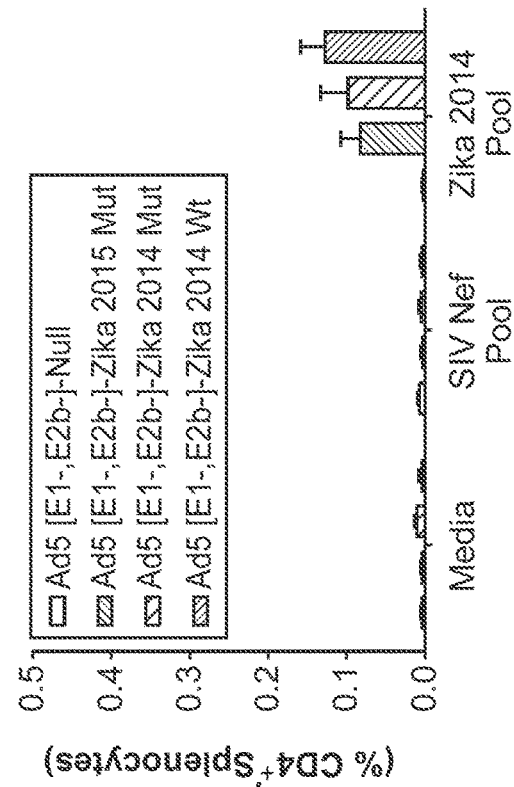

FIG. 7B illustrates lymphocyte activation as measured by intracellular expression of IFN-γ in CD4+ splenocytes after exposure of splenocytes from immunized mice and control mice to Zika 2014 peptide pools or controls using flow cytometry.

FIG. 7C illustrates lymphocyte activation as measured by intracellular expression of IFN-γ and TNF-α in CD8+ splenocytes after exposure of splenocytes from immunized mice and control mice to Zika 2014 peptide pools or controls using flow cytometry.

Figure 7D:
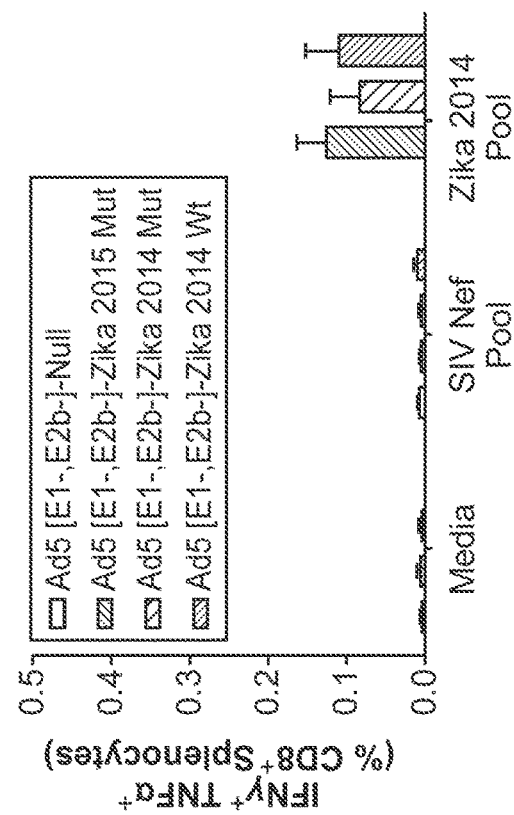

FIG. 7D illustrates lymphocyte activation as measured by intracellular expression of IFN-γ and TNF-α in CD4+ splenocytes after exposure of splenocytes from immunized mice and control mice to Zika 2014 peptide pools or controls using flow cytometry.

Figure 8:
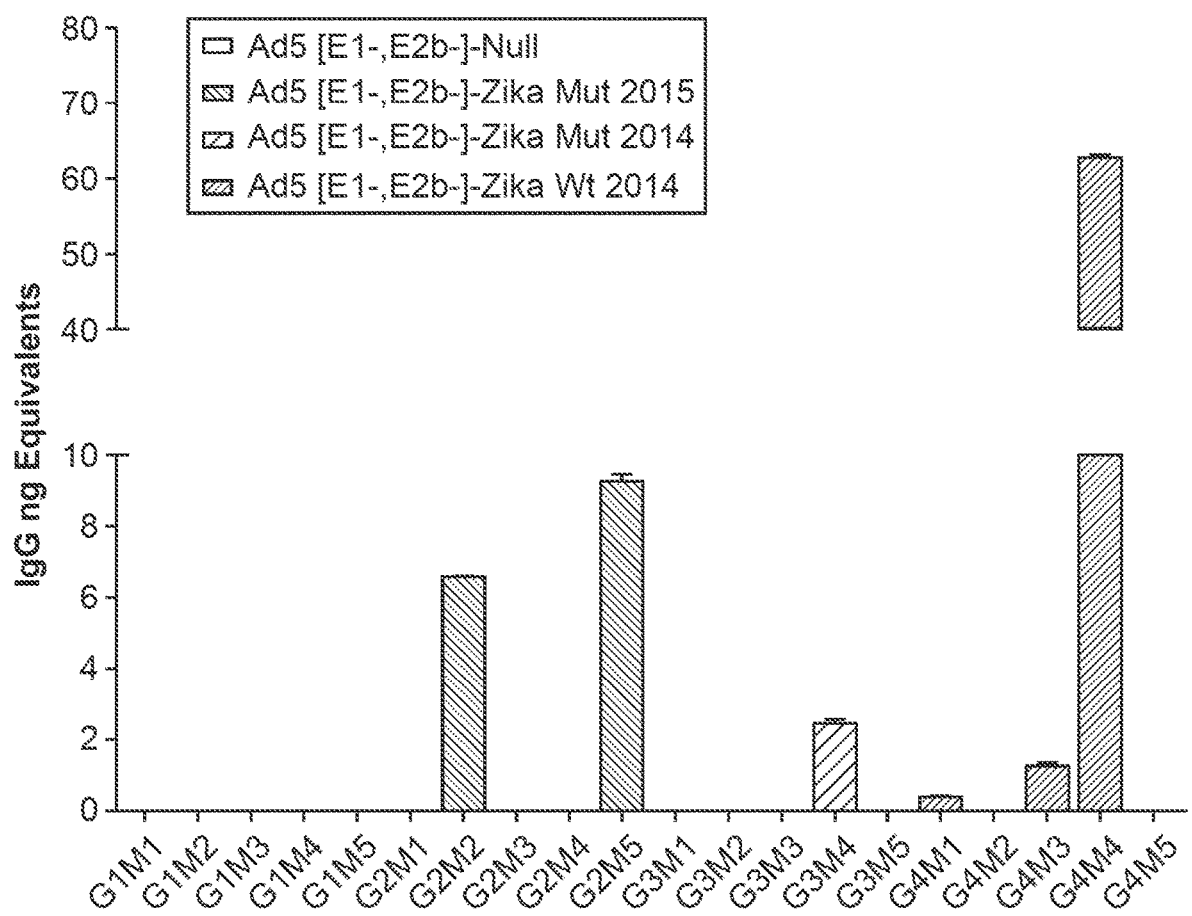

FIG. 8 illustrates anti-Zika IgG antibody response in the serum of mice immunized with Ad5 [E1-, E2b-]-Zika-E vaccines. Blood was drawn from the cheek pouch and analyzed using a quantitative ELISA or IgG antibody using methods set forth in Gabitzsch et al. (Cancer Gene Ther. 2011 May; 18(5): 326-335). Mice (C57B1/6 strain, 5 mice per group) were immunized two times at two-week intervals with $1\times10^{10}$ virus particles (VPs) of an Ad5 [E1-, E2b-]-Zika-E vaccine or with $1\times10^{10}$ VPs Ad5 [E1-, E2b-]-null (empty vector control). Three types of Zika vaccines were tested. The first Zika vaccine tested was the Ad5 [E1-, E2b-]-Zika mut 2015, which comprises a Zika antigen protein encoded by the nucleotide sequence of SEQ ID NO: 34 and by the amino acid sequence of SEQ ID NO: 35 (SEQ ID NO: 34 is the nucleotide sequence and SEQ ID NO: 35 is the amino acid sequence corresponding to SEQ ID NO: 34). The Zika mut 2015 antigen in SEQ ID NO: 35 corresponds to amino acids 409-690 of the 3423-aa Zika polyprotein (SEQ ID NO: 23), which is the truncated portion of the extracellular domain of the Zika envelope protein. The Zika mut 2015 antigen comprises point mutations as compared to the Zika wt 2015 antigen. These point mutations include D37I, D43L, D266I, D129L, D218L (position numbering does not count the N-terminal methionine) and these mutations can result in decreased anti-human C1q responses compared to wild type. The second Zika vaccine tested was the Ad5 [E1-, E2b-]-Zika wt 2014, which comprises a Zika antigen protein encoded by the nucleotide sequence of SEQ ID NO: 26 and by the amino acid sequence of SEQ ID NO: 27 (SEQ ID NO: 26 is the nucleotide sequence and SEQ ID NO: 27 is the amino acid sequence corresponding to SEQ ID NO: 26). The Zika wt 2014 antigen of SEQ ID NO: 27 corresponds to amino acids 409-690 of the 3423-aa Zika polyprotein (SEQ ID NO: 23), which is the truncated portion of the extracellular domain of the Zika envelope protein. The third Zika vaccine tested was the Ad5 [E1-, E2b-]-Zika mut 2014, which comprises a Zika antigen protein encoded by the nucleotide sequence of SEQ ID NO: 28 and by the amino acid sequence of SEQ ID NO: 29 (SEQ ID NO: 28 is the nucleotide sequence and SEQ ID NO: 29 is the amino acid sequence corresponding to SEQ ID NO: 28). The Zika mut 2014 antigen of SEQ ID NO: 29 corresponds to amino acids 409-690 of the 3423-aa Zika polyprotein (SEQ ID NO: 23), which is the truncated portion of the extracellular domain of the Zika envelope protein. The Zika mut 2014 antigen comprises point mutations as compared to the Zika wt 2014 antigen. These point mutations include I21D, L175D, L240D (position numbering does not count the N-terminal methionine) and these mutations can result in decreased anti-human C1q responses compared to wild type. One week after the final immunization, serum from mice was tested for induction of an antibody response by an enzyme linked immunosorbent assay (ELISA). The y-axis shows nanograms (ng) of anti-Zika IgG in serum. The x-axis shows each group and mouse tested (e.g., "G1M1" indicates Group 1 Mouse 1). Note that mice from Group 1 were immunized with Ad5 [E1-, E2b-]-Null, mice from Group 2 were immunized with Ad5 [E1-, E2b-]-Zika Mut 2015, mice from Group 3 were immunized with Ad5 [E1-, E2b-]-Zika Mut 2014, and mice from Group 4 were immunized with Ad5 [E1-, E2b-]-Zika Wt 2014. Error bars show SEM.

Figure 9:
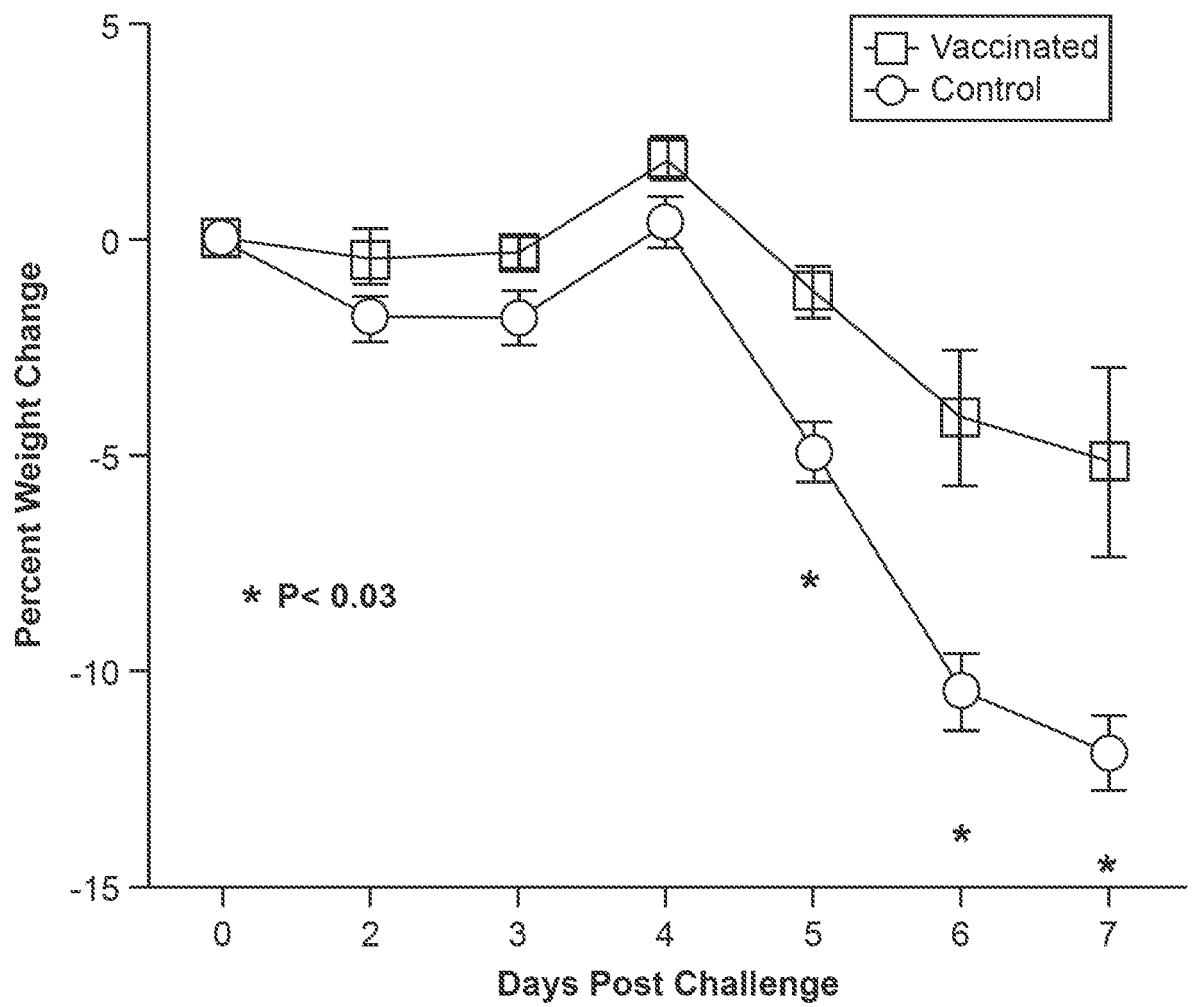

FIG. 9 illustrates weight loss in a mouse model of Zika virus infection (Rossi et al. Am J Trop Med Hyg. 2016 Jun. 1; 94(6):1362-9) after vaccination with Ad5 [E1-, E2b-]-Zika-E vaccine or injection with Ad5 [E1-, E2b-]-null empty vector as controls. Groups of A129 mice (n=10/group) were immunized once with $1\times10^{10}$ VPs of Ad5 [E1-, E2b-]-Zika-E 2015wt or with $1\times10^{10}$ VPs of Ad5 [E1-, E2b-]-null (controls). Thirty days post-immunization, mice were challenged with a pathogenic strain of Zika virus ($5\times10^5$ plaque forming units (PFU) of Zika virus strain FSS13025 injected intraperitoneally (IP)). Mice were monitored for weight change.

Figure 10:
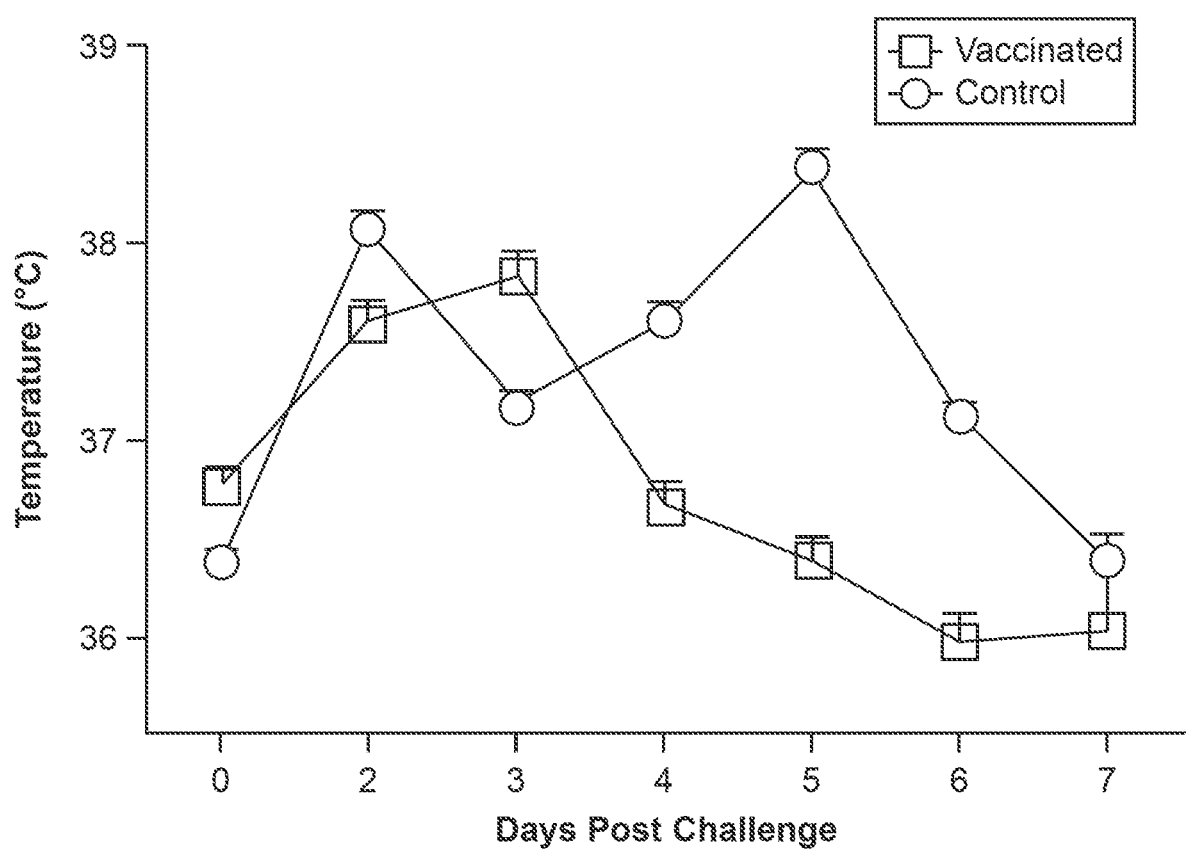

FIG. 10 illustrates temperature change in a mouse model of Zika virus infection (Rossi et al. Am J Trop Med Hyg. 2016 Jun. 1; 94(6):1362-9) after vaccination with Ad5 [E1-, E2b-]-Zika-E vaccine or with Ad5 [E1-, E2b-]-null empty vector as controls. Groups of A129 mice (n=10/group) were immunized once with $1\times10^{10}$ VPs of Ad5 [E1-, E2b-]-Zika-E 2015wt or with $1\times10^{10}$ VPs of Ad5 [E1-, E2b-]-null (controls). Thirty days post-immunization, mice were challenged with a pathogenic strain of Zika virus ($5\times10^5$ PFU of Zika virus strain FSS13025 injected intraperitoneally (IP)). Mice were monitored for temperature change.

FIG. 11 illustrates cell mediated immune (CMI) responses and cytolytic T lymphocyte (CTL) responses in splenocytes from mice immunized with Ad5 [E1-, E2b-]-Zika vaccines. C57BL/6 mice (n=5/group) were immunized two times at two-week intervals with $1 \times 10^{10}$ virus particles (VPs) of an Ad5 [E1-, E2b-]-Zika vaccine or with $1 \times 10^{10}$ VPs Ad5 [E1-, E2b-]-null (empty vector control). Two types of Zika vaccines were tested, including Ad5 [E1-, E2b-]-Zika wildtype (wt) 2015, which comprises a Zika antigen a protein encoded by the nucleotide sequence of SEQ ID NO: 32 and by the amino acid sequence of SEQ ID NO: 33 (SEQ ID NO: 32 is the nucleotide sequence and SEQ ID NO: 33 is the amino acid sequence corresponding to SEQ ID NO: 32). The Zika wt 2015 antigen of SEQ ID NO: 33 corresponds to amino acids 409-690 of the 3423-aa Zika polyprotein (SEQ ID NO: 23), which is the truncated portion of the extracellular domain of the Zika envelope protein. The second Zika vaccine tested was Ad5 [E1-, E2b-]-Zika wildtype (wt) 2015 full length (FL), which comprises a Zika antigen protein encoded by the nucleotide sequence of SEQ ID NO: 36 and by the amino acid sequence of SEQ ID NO: 37 (SEQ ID NO: 36 is the nucleotide sequence and SEQ ID NO: 37 is the amino acid sequence corresponding to SEQ ID NO: 36). The Zika antigen in Ad5 [E1-, E2b-]-Zika wildtype (wt) 2015 full length (FL) comprises the full envelope protein corresponds to amino acids 271-805 of the 3423-aa Zika polyprotein (SEQ ID NO: 23) including two C-terminal transmembrane anchor domains and the extracellular loop, two transmembrane domains immediately upstream of the envelope protein in the ZIKAV genome, which encodes a portion of the M protein to ensure targeting to the plasma membrane, and a KOZAK sequence at the N-terminus (GCCGCCACC) to ensure initiation of translation, two transmembrane domains just prior to the extracellular loop, and the extracellular loop. The inclusion of transmembrane domains can serve as a signal sequence to ensure migration of mRNA-loaded ribosomes to the endoplasmic reticulum, glycosylation, and eventual migration and tethering of the protein to the plasma membrane, which can all ultimately improve antigenicity and thereby generate immune responses. Two Ad5 [E1-, E2b-]-nulls were used as comparative control vectors including Ad5 [E1-, E2b-]-null (Viraquest) and Ad5 [E1-, E2b-]-null (E) (an internally manufactured null control vector). Splenocytes were isolated seven days after the final immunization and exposed to a Zika 2014 peptide pool, an SIV-Nef peptide pool (negative control), a SIV-Gag peptide pool (negative control), and Concanavalin A (positive control), and were assessed for CMI responses (IFN-γ and IL-2) and CTL responses (Granzyme B) by ELISPOT. Data are reported as the number of spot forming cells (SFCs) per $10^6$ splenocytes and error bars show SEM.

Figure 11A:
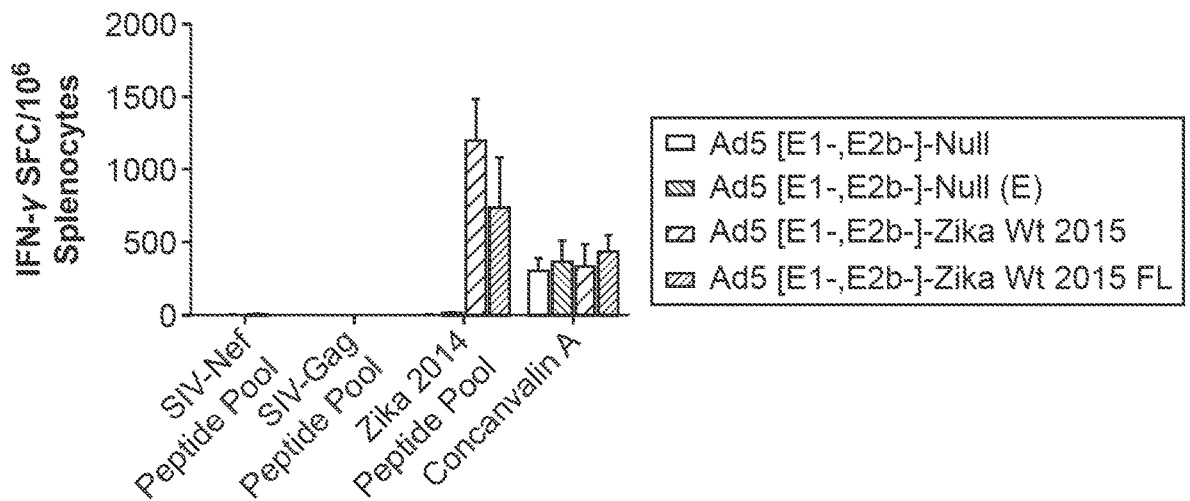

FIG. 11A illustrates IFN-γ CMI responses of splenocytes from immunized mice and control mice after exposure to Zika 2014 peptide pools or controls.

Figure 11B:
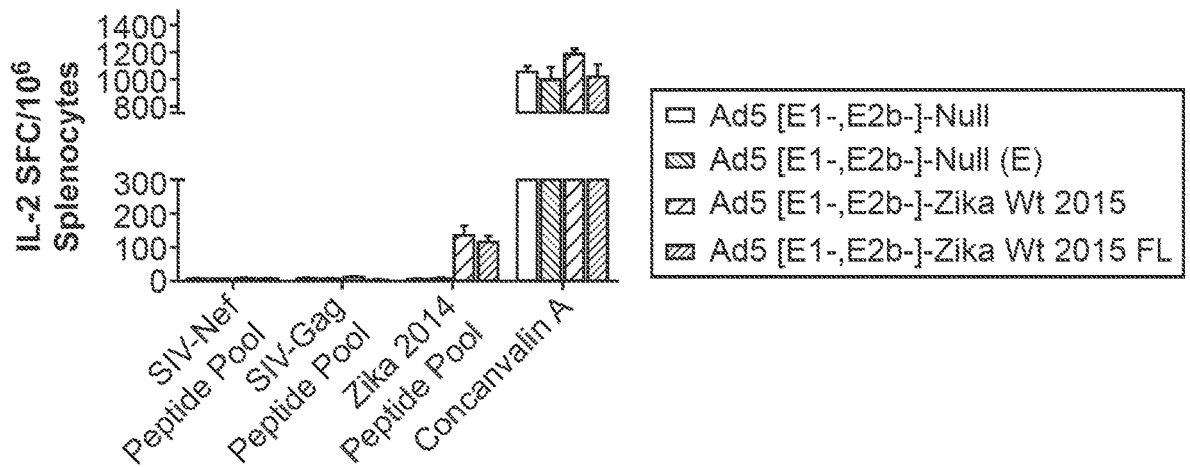

FIG. 11B illustrates IL-2 CMI responses of splenocytes from immunized mice and control mice after exposure to Zika 2014 peptide pools or controls.

Figure 11C:
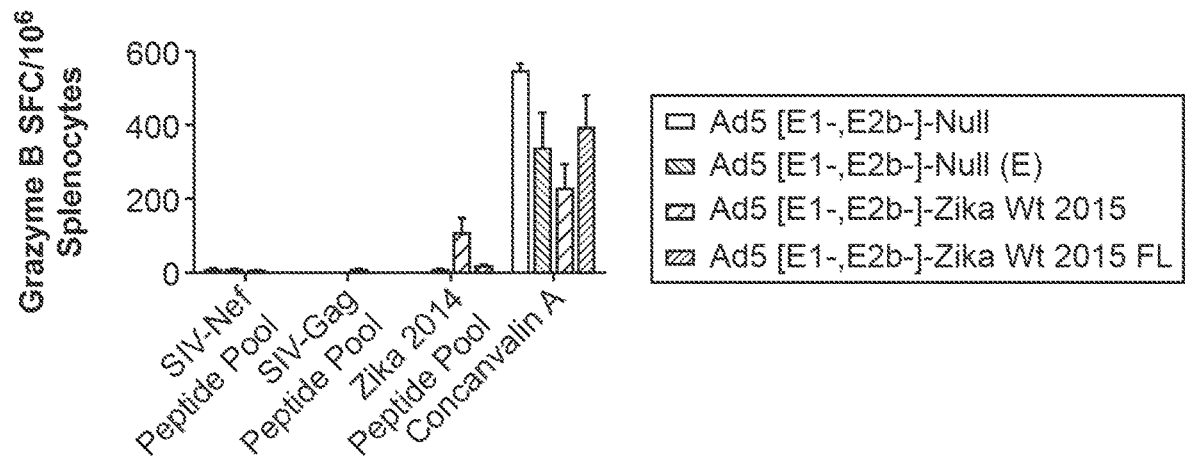

FIG. 11C illustrates Granzyme B CTL responses of splenocytes from immunized mice and control mice to Zika 2014 peptide pools or controls.

FIG. 12 illustrates lymphocyte activation as measured by intracellular expression of IFN-γ and IFN-γ/TNF-α in splenocytes from mice immunized with Ad5 [E1-, E2b-]-Zika vaccines using flow cytometry. C57BL/6 mice were immunized two times at two-week intervals with $1 \times 10^{10}$ virus particles (VPs) of an Ad5 [E1-, E2b-]-Zika vaccine or with $1 \times 10^{10}$ VPs Ad5 [E1-, E2b-]-null (empty vector control). Two types of Zika vaccines were tested, including Ad5 [E1-, E2b-]-Zika wildtype (wt) 2015, which comprises a Zika antigen protein encoded by the nucleotide sequence of SEQ ID NO: 32 and the amino acid sequence of SEQ ID NO: 33 (SEQ ID NO: 32 is the nucleotide sequence and SEQ ID NO: 33 is the amino acid sequence corresponding to SEQ ID NO: 32). The Zika wt 2015 antigen of SEQ ID NO: 33 corresponds to amino acids 409-690 of the 3423-aa Zika polyprotein (SEQ ID NO: 23), which is the truncated portion of the extracellular domain of the Zika envelope protein. The second Zika vaccine tested was a Ad5 [E1-, E2b-]-Zika wildtype (wt) 2015 full length (FL), which comprises a Zika antigen protein encoded by the nucleotide sequence of SEQ ID NO: 36 and by the amino acid sequence of SEQ ID NO: 37 (SEQ ID NO: 36 is the nucleotide sequence and SEQ ID NO: 37 is the amino acid sequence corresponding to SEQ ID NO: 36). The Zika antigen in Ad5 [E1-, E2b-]-Zika wildtype (wt) 2015 full length (FL) comprises the full envelope protein corresponds to amino acids 271-805 of the 3423-aa Zika polyprotein (SEQ ID NO: 23) including two C-terminal transmembrane anchor domains and the extracellular loop, two transmembrane domains immediately upstream of the envelope protein in the ZIKAV genome, which encodes a portion of the M protein to ensure targeting to the plasma membrane, and a KOZAK sequence at the N-terminus (GCCGCCACC) to ensure initiation of translation, two transmembrane domains just prior to the extracellular loop, and the extracellular loop. The inclusion of transmembrane domains can serve as a signal sequence to ensure migration of mRNA-loaded ribosomes to the endoplasmic reticulum, glycosylation, and eventual migration and tethering of the protein to the plasma membrane, which can ultimately improve antigenicity and thereby generate immune responses. Two Ad5 [E1-, E2b-]-nulls were used as comparative control vectors including Ad5 [E1-, E2b-]-null (Viraquest) and Ad5 [E1-, E2b-]-null (E) (an internally manufactured null control vector). Seven days after the final immunization, splenocytes isolated from immunized mice were exposed to Zika virus peptide pools and flow cytometry was used to measure intracellular cytokine production of IFN-γ and IFN-γ/TNF-α in CD8+ cells and CD4+ cells. Specificity of responses is shown by the lack of reactivity of splenocytes to an SIV-nef peptide pool (negative control) and media (negative control) and reactivity of splenocytes to PMA/ionomycin (data not shown) (positive control). Data are reported as the percent of CD8+ or CD4+ splenocytes expressing IFN-γ or IFN-γ and TNF-α and error bars show SEM.

FIG. 12A illustrates lymphocyte activation as measured by flow cytometry analysis of intracellular expression of IFN-γ in CD8+ splenocytes after exposure of splenocytes from immunized mice and control mice to Zika 2014 peptide pools and controls.

FIG. 12B illustrates lymphocyte activation as measured by flow cytometry analysis of intracellular expression of IFN-γ in CD4+ splenocytes after exposure of splenocytes from immunized mice and control mice to Zika 2014 peptide pools and controls.

FIG. 12C illustrates lymphocyte activation as measured by flow cytometry analysis of intracellular expression of IFN-γ and TNF-α in CD8+ splenocytes after exposure of splenocytes from immunized mice and control mice to Zika 2014 peptide pools and controls.

FIG. 12D illustrates lymphocyte activation as measured by flow cytometry analysis of intracellular expression of IFN-γ and TNF-α in CD4+ splenocytes after exposure of splenocytes from immunized mice and control mice to Zika 2014 peptide pools and controls.

Figure 13:
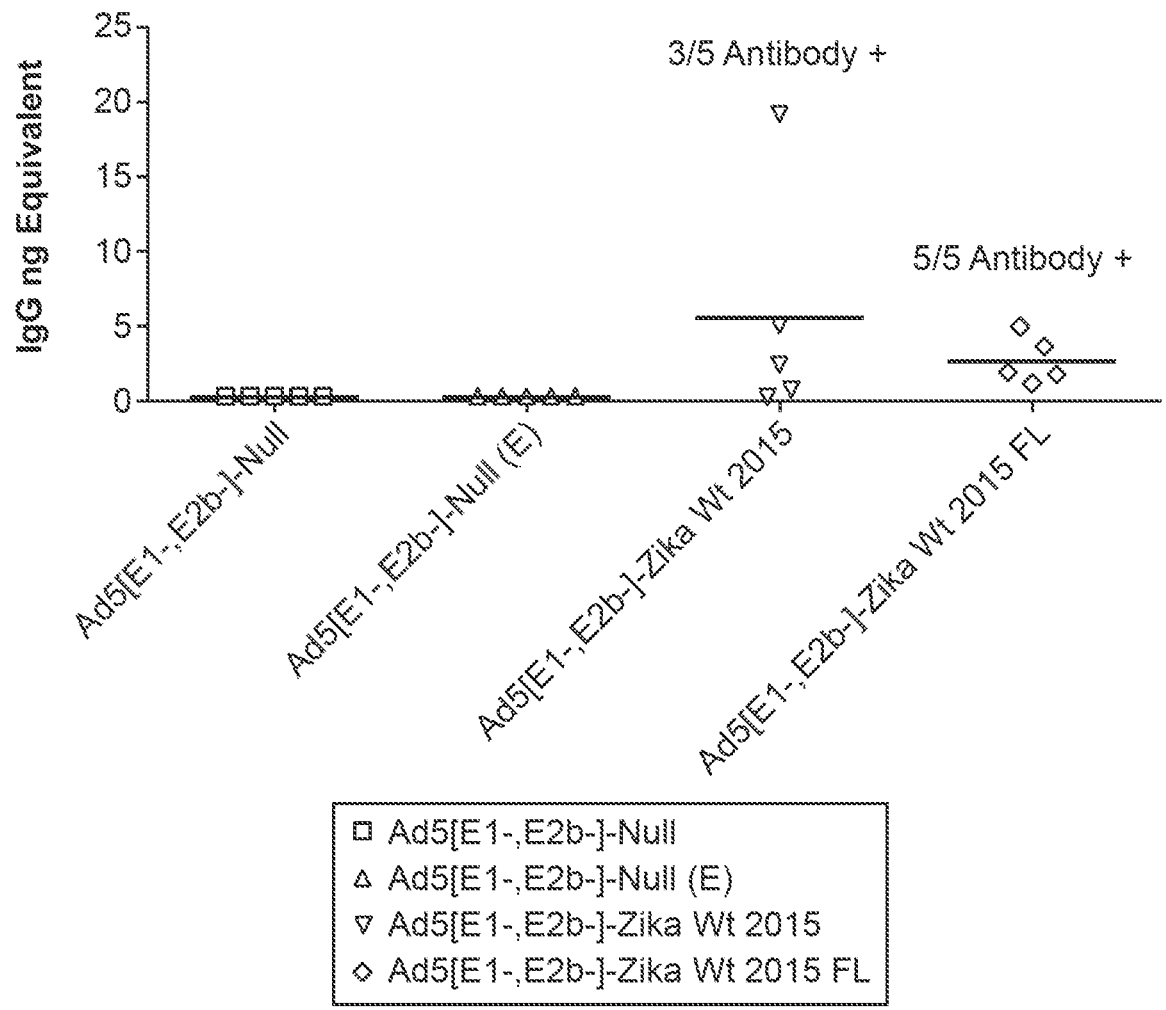

FIG. 13 illustrates anti-Zika IgG responses in the serum of mice immunized with Ad5 [E1-, E2b-]-Zika vaccines. C57BL/6 mice (n=5/group) were immunized two times at two-week intervals with $1\times10^{10}$ virus particles (VPs) of an Ad5 [E1-, E2b-]-Zika wildtype (wt) 2015 vaccine or an Ad5 [E1-, E2b-]-Zika wt 2015 full length (FL) vaccine. Two Ad5 [E1-, E2b-]-nulls were used as comparative control vectors including Ad5 [E1-, E2b-]-null (Viraquest) and Ad5 [E1-, E2b-]-null (E) (an internally manufactured null control vector). Sera were collected from mice seven days after the final immunization and assessed by an enzyme linked immunosorbent assay (ELISA) for antigen specific antibodies against Zika virus envelope protein-1. The y-axis shows nanograms (ng) of anti-Zika IgG in serum. In the Ad5 [E1-, E2b-]-Zika wt 2015 group, three out of five (3/5) were antibody positive. In the Ad5 [E1-, E2b-]-Zika wt 2015 FL group, five out of five (5/5) were antibody positive.

DETAILED DESCRIPTION

The following passages describe different aspects of the invention in greater detail. Each aspect can be combined with any other aspect or aspects unless clearly indicated to the contrary. In particular, any feature indicated as being preferred or advantageous can be combined with any other feature indicated as being preferred or advantageous.

As used herein, unless otherwise indicated, the article "a" means one or more unless explicitly otherwise provided for.

As used herein, unless otherwise indicated, terms such as "contain," "containing," "include," "including," and the like mean "comprising."

As used herein, unless otherwise indicated, the term "or" can be conjunctive or disjunctive.

As used herein, unless otherwise indicated, any embodiment can be combined with any other embodiment.

As used herein, unless otherwise indicated, some inventive embodiments herein contemplate numerical ranges. A variety of aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

The term "adenovirus" or "Ad" can refer to a group of non-enveloped DNA viruses from the family Adenoviridae. In addition to human hosts, these viruses can be found in, but are not limited to, avian, bovine, porcine and canine species. The use of any adenovirus from any of the four genera of the family Adenoviridae (e.g., Aviadenovirus, Mastadenovirus, Atadenovirus and Siadenovirus) can be contemplated as the basis of an E2b deleted virus vector, or vector containing other deletions as described herein. In addition, several serotypes can be found in each species. Ad also can pertain to genetic derivatives of any of these viral serotypes, including but not limited to, genetic mutation, deletion or transposition of homologous or heterologous DNA sequences.

A "helper adenovirus" or "helper virus" can refer to an Ad that can supply viral functions that a particular host cell cannot (the host can provide Ad gene products such as E1 proteins). This virus can be used to supply, in trans, functions (e.g., proteins) that are lacking in a second virus, or helper dependent virus (e.g., a gutted or gutless virus, or a virus deleted for a particular region such as E2b or other region as described herein); the first replication-incompetent virus can be said to "help" the second, helper dependent virus thereby permitting the production of the second viral genome in a cell.

The term "Adenovirus5 null (Ad5null)," as used herein, can refer to a non-replicating Ad that may not contain any heterologous nucleic acid sequences for expression.

The term "First Generation adenovirus," as used herein, can refer to an Ad that has the early region 1 (E1) deleted. In additional cases, the nonessential early region 3 (E3) can also be deleted.

The term "gutted" or "gutless," as used herein, can refer to an adenovirus vector that has been deleted of all viral coding regions.

The term "transfection" as used herein can refer to the introduction of foreign nucleic acid into eukaryotic cells. Transfection can be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" can refer to the introduction and integration of foreign nucleic acid, DNA or RNA, into the genome of the transfected cell. The term "stable transfectant" can refer to a cell which has stably integrated foreign DNA into the genomic DNA.

The term "reporter gene" can indicate a nucleotide sequence that encodes a reporter molecule (including an enzyme). A "reporter molecule" can be detectable in any of a variety of detection systems, including, but not limited to enzyme-based detection assays (e.g., ELISA, as well as enzyme-based histochemical assays), fluorescent, radioactive, and luminescent systems.

In one embodiment, the *E. coli* β-galactosidase gene (available from Pharmacia Biotech, Pistacataway, N.J.), green fluorescent protein (GFP) (commercially available from Clontech, Palo Alto, Calif.), the human placental alkaline phosphatase gene, the chloramphenicol acetyltransferase (CAT) gene or other reporter genes that are known to the art can be employed.

As used herein, the terms "nucleic acid molecule encoding," "DNA sequence encoding," and "DNA encoding" can refer to the order or sequence of deoxyribonucleotides along a strand of deoxyribonucleic acid. The order of these deoxyribonucleotides can determine the order of amino acids along the polypeptide (protein) chain. The nucleic acid sequence thus can code for the amino acid sequence.

The term "heterologous nucleic acid sequence," as used herein, can refer to a nucleotide sequence that is ligated to, or is manipulated to become ligated to, a nucleic acid sequence to which it is not ligated in nature, or to which it is ligated at a different location in nature. Heterologous nucleic acid can include a nucleotide sequence that is naturally found in the cell into which it is introduced or the heterologous nucleic acid can contain some modification relative to the naturally occurring sequence.

The term "transgene" can refer to any gene coding region, either natural or heterologous nucleic acid sequences or fused homologous or heterologous nucleic acid sequences, introduced into the cells or genome of a test subject. In the current invention, transgenes can be carried on any viral vector that is used to introduce the transgenes to the cells of the subject.

The term "Second Generation Adenovirus," as used herein, can refer to an Ad that has all or parts of the E1, E2, E3, and, in certain embodiments, E4 DNA gene sequences deleted (removed) from the virus.

The term "subject," as used herein, can refer to any animal, e.g., a mammal or marsupial. Subjects can include but are not limited to humans, non-human primates (e.g., rhesus or other types of macaques), mice, pigs, horses, donkeys, cows, sheep, rats and fowl of any kind.

In certain aspects, there can be provided methods for producing a vaccine that generates immune responses against various flaviviruses using an adenovirus vector that allows for multiple vaccinations to generate broadly reactive immune responses against flaviviruses.

One aspect provides a method of generating an immune response against several flavivirus target antigens in a subject comprising administering to the subject an adenovirus vector comprising: a) a replication defective adenovirus vector, wherein the adenovirus vector has a deletion in the E2b region, and b) nucleic acids encoding multiple flavivirus target antigens; and readministering the adenovirus vector at least once to the subject; thereby generating an immune response against the flavivirus target antigens.

Another aspect provides a method for generating an immune response against several flavivirus target antigens in a subject, wherein the subject has preexisting immunity to adenovirus, comprising: administering to the individual an adenovirus vector comprising: a) a replication defective adenovirus vector, wherein the adenovirus vector has a deletion in the E2b region, and b) nucleic acids encoding multiple flavivirus target antigens; and readministering the adenovirus vector at least once to the individual; thereby generating an immune response against the flavivirus target antigens.

I. Flavivirus Target Antigens

In certain embodiments, flavivirus antigens such as C, prM, E, M, and nonstructural proteins, such as NS1, NS2A, NS2B, NS3, NS4A, NS4B, and NS5, can be used, for example, in a vaccine composition or a composition comprising an adenovirus vector as described herein.

For example, E and M antigens can be used. The main correlate of protection against natural flavivirus infection can be the level of Abs that are specific for E in the serum and mucosa. Humoral responses to E protein can be measured as neutralization titer which has been used as a surrogate for protection. The M protein may not be a major target for the humoral response; however, expression of M can indicate proper folding of E and hence, proper antigen display.

NS3 can also be used in certain aspects. Studies have shown that NS3 contains conserved regions that can provide a wider range of flavivirus protection when used in experimental vaccines, including those employing Ad5 vectors (Papageorgiou, L et al. Molecular BioSystems. 2016 DOI: 10.1039/c5mb00706b; Duangchinda T et al. PNAS. 2010 107(39):16922-16927).

In a further aspect, the target antigens can be comprised of antigens derived from various flavivirus proteins. In certain aspects, the flavivirus proteins can be derived from any flavivirus, including but not limited to yellow fever virus (YFV), Japanese encephalitis virus (JEV), Tick-borne encephalitis viruses (TBEVs), Dengue virus (DENV), West Nile virus (WNV), zika virus (ZIKAV). In certain embodiments, the at least one flavivirus virus protein can be a flavivirus protein selected from the group consisting of C, prM, M, E, NS1, NS2A, NS2B, NS3, NS4A, NS4B, NS5. In certain embodiments, the at least one flavivirus virus protein can comprise proteins selected from the group consisting of M, E, and NS1. In certain embodiments, the at least one flavivirus virus protein can comprise proteins selected from the group consisting of M, E, and NS2A. In certain embodiments, the at least one flavivirus virus protein can comprise proteins selected from the group consisting of M, E, and NS2B. In certain embodiments, the at least one flavivirus virus protein can comprise proteins selected from the group consisting of M, E, and NS3. In certain embodiments, the at least one flavivirus virus protein can comprise proteins selected from the group consisting of M, E, and NS4A. In certain embodiments, the at least one flavivirus virus protein can comprise proteins selected from the group consisting of M, E, and NS4B. In certain embodiments, the at least one flavivirus virus protein can comprise proteins selected from the group consisting of M, E, and NS5. in some embodiments, the at least one target antigen has at least 50%, at least 60%, at least 70%, at least 75%, at least 80%, at least 85%, at least 90%, at least 92%, at least 95%, at least 97%, or at least 100% sequence identity to any one of the antigen sequence of C, prM, M, E, NS1, NS2A, NS2B, NS3, NS4A, NS4B, or NS5, or other antigen sequence described herein. In some embodiments the at least one target antigen is structural and/or non-structural antigen of a flavivirus. For example, in some embodiments, the at least one target antigen used herein is a yellow fever virus (YFV) antigen encoded by the sequence set forth in SEQ ID NO: 1 (YFV JN628281.1), or a fragment thereof. In other embodiments, the at least one target antigen used herein is a Japanese encephalitis virus (JEV) antigen encoded by the sequence set forth in SEQ ID NO: 2 (JEV AY508812.1) or a fragment thereof. In some embodiments, the at least one target antigen used herein is a Tick-borne encephalitis virus (TBEV)-fe antigen encoded by the sequence set forth in SEQ ID NO: 3 (TBEV-fe KJ755186) or a fragment thereof. In other embodiments, the at least one target antigen used herein is a Tick-borne encephalitis virus (TBEV)-si antigen encoded by the sequence set forth in SEQ ID NO: 4 (TBEV-si KP331441) or a fragment thereof. In some embodiments, the at least one target antigen used herein is a Tick-borne encephalitis virus (TBEV)-eu antigen encoded by the sequence set forth in SEQ ID NO: 5 (TBEV-eu TEU27495) or a fragment thereof. In other embodiments, the at least one target antigen used herein is a Dengue virus-1 (DENV-1) antigen encoded by the sequence set forth in SEQ ID NO: 6 (DENV-1 KF887994.1) or a fragment thereof. In some embodiments, the at least one target antigen used herein is a Dengue virus-2 (DENV-2) antigen encoded by the sequence set forth in SEQ ID NO: 7 (DENV-2 HQ026763) or a fragment thereof. In other embodiments, the at least one target antigen used herein is a Dengue virus-3 (DENV-3) antigen encoded by the sequence set forth in SEQ ID NO: 8 (DENV-3 KP406805) or a fragment thereof. In some embodiments, the at least one target antigen used herein is a DENV-4 antigen encoded by the sequence set forth in SEQ ID NO: 9 (DENV-4 KJ596658) or a fragment thereof. In other embodiments, the at least one target antigen used herein is a West Nile virus (WNV) antigen encoded by the sequence set forth in SEQ ID NO: 10 (WNV GQ903680) or a fragment thereof. In some embodiments, the at least one target antigen used herein is a Zika virus (ZIKAV) antigen encoded by the sequence set forth in SEQ ID NO: 11 (ZIKAV KF383118) or a fragment thereof. In other embodiments, the at least one target antigen used herein is a ZIKAV antigen encoded by the sequence set forth in SEQ ID NO: 12 (ZIKAV KF383121) or a fragment thereof. In some embodiments, the at least one target antigen used herein is a ZIKAV antigen encoded by the sequence set forth in SEQ ID NO: 13 (AMA12087-Modified: GP1 from Zika virus isolate AMA12087 (Brazil-2015) with mutations: D37I D43L D266I D129L D218L). In further embodiments, the at least one target antigen used herein is a ZIKAV antigen, which comprises mutations D37I, D43L, D266I, D129L, D218L, as in SEQ ID NO: 13. In other embodiments, the at least one target antigen used herein is a ZIKAV antigen encoded by the sequence set forth in SEQ ID NO: 14 (AHL43503-Modified: E from Zika virus isolate AHL43503 (Brazil-2014) with mutations I21D L175D L240D). In further embodiments, the at least one target antigen used herein is a ZIKAV antigen, which comprises mutations I21D, L175D, L240D, as in SEQ ID NO: 14. In some embodiments, the at least one target antigen used herein is a ZIKAV antigen encoded by the sequence set forth in SEQ ID NO: 15 (AHL43505 (Brazil-2014)). In further embodiments, the at least one target antigen used herein is a ZIKAV antigen, which is a partial zika virus, as in SEQ ID NO: 15. In some embodiments, the at least one target antigen used herein is a ZIKAV antigen encoded by the sequence set forth in any one of SEQ ID NO: 16-SEQ ID NO: 21 (SEQ ID NO: 16 is AHL43503 (Brazil-2014), SEQ ID NO: 17 is AHL43502 (Brazil-2014), SEQ ID NO: 18 is AHL43501 (Brazil-2014), SEQ ID NO: 19 is AMA12087 (Brazil-2015), SEQ ID NO: 20 is Zika virus isolate MEX/InDRE/14/2015 polyprotein gene, partial cds GenBank: KU686218.1, SEQ ID NO: 21 is Zika virus strain Haiti/1225/2014, complete genome; GenBank: KU509998.3). In other embodiments, the at least one target antigen used herein is a yellow fever virus (YFV) antigen encoded by the sequence set forth in SEQ ID NO: 22 (YFV 17D vaccine strain; GenBank ID: X03700.1). In some embodiments, the at least one target antigen used herein is the full ZIKAV polyprotein antigen encoded by the sequence set forth in SEQ ID NO: 23 (full zika polyprotein sequence—Acession AHL43505). In some embodiments, the at least one target antigen used herein is a ZIKAV antigen encoded by the sequence set forth in any one of SEQ ID NO: 24-SEQ ID NO: 25. In some embodiments, the at least one target antigen used herein is a ZIKAV antigen encoded by the sequence set forth in SEQ ID NO: 26, which is a Zika wt 2014 antigen (AHL43503) comprising a truncated portion of the extracellular domain of the Zika envelope protein corresponding to amino acids 409-690 of SEQ ID NO: 23 and also comprising a KOZAK sequence at the N-terminus (GCCGCCACC) to ensure initiation of translation. In some embodiments, the at least one target antigen used herein is a ZIKAV antigen encoded by the sequence set forth in SEQ ID NO: 27, which is the amino acid version of the Zika wt 2014 antigen (AHL43503) set forth in SEQ ID NO: 26. In some embodiments, the at least one target antigen used herein is a ZIKAV antigen encoded by the sequence set forth in SEQ ID NO: 28, which is a Zika mut 2014 antigen (AHL43503) comprising a truncated portion of the extracellular domain of the Zika envelope protein corresponding to amino acids 409-690 of SEQ ID NO: 23, a KOZAK sequence at the N-terminus (GCCGCCACC) to ensure initiation of translation, and point mutations that result in the following amino acid mutations in SEQ ID NO: 29 (not counting the N-terminal Methionine): I21D, L175D, L240D. In some embodiments, the at least one target antigen used herein is a ZIKAV antigen encoded by the sequence set forth in SEQ ID NO: 29, which is the amino acid version of the Zika mut 2014 antigen (AHL43503) set forth in SEQ ID NO: 28. In some embodiments, the at least one target antigen used herein is a ZIKAV antigen encoded by the sequence set forth in SEQ ID NO: 30, which is a Zika full 2014 antigen (AHL43503) comprising the full envelope protein corresponds to amino acids 271-805 of the 3423-aa Zika polyprotein (SEQ ID NO: 23) including two C-terminal transmembrane anchor domains and the extracellular loop, and two transmembrane domains immediately upstream of the envelope protein in the ZIKAV genome, which encodes a portion of the M protein to ensure targeting to the plasma membrane, and a KOZAK sequence at the N-terminus (GCCGCCACC) to ensure initiation of translation, two transmembrane domains just prior to the extracellular loop, and the extracellular loop. In some embodiments, the at least one target antigen used herein is a ZIKAV antigen encoded by the sequence set forth in SEQ ID NO: 31, which is the amino acid version of the Zika full 2014 antigen (AHL43503) set forth in SEQ ID NO: 30. In some embodiments, the at least one target antigen used herein is a ZIKAV antigen encoded by the sequence set forth in SEQ ID NO: 32, which is a Zika wt 2015 antigen (AHL12087) comprising a truncated portion of the extracellular domain of the Zika envelope protein corresponding to amino acids 409-690 of SEQ ID NO: 23 and also comprising a KOZAK sequence at the N-terminus (GCCGCCACC) to ensure initiation of translation. In some embodiments, the at least one target antigen used herein is a ZIKAV antigen encoded by the sequence set forth in SEQ ID NO: 33, which is amino acid version of the Zika wt 2015 antigen (AHL12087) set forth in SEQ ID NO: 32. In some embodiments, the at least one target antigen used herein is a ZIKAV antigen encoded by the sequence set forth in SEQ ID NO: 34, which is a Zika mut 2015 antigen (AHL12087) comprising a truncated portion of the extracellular domain of the Zika envelope protein corresponding to amino acids 409-690 of SEQ ID NO: 23, a KOZAK sequence at the N-terminus (GCCGCCACC) to ensure initiation of translation, and point mutations that result in the following amino acid mutations in SEQ ID NO: 35 (not counting the N-terminal Methionine): D37I, D43L, D266I, D129L, D218L. In some embodiments, the at least one target antigen used herein is a ZIKAV antigen encoded by the sequence set forth in SEQ ID NO: 35, which is the amino acid version of the Zika mut 2015 antigen (AHL12087) set forth in SEQ ID NO: 34. In some embodiments, the at least one target antigen used herein is a ZIKAV antigen encoded by the sequence set forth in SEQ ID NO: 36, which is a Zika full 2015 antigen (AHL12087) comprising the full envelope protein corresponds to amino acids 271-805 of the 3423-aa Zika polyprotein (SEQ ID NO: 23) including two C-terminal transmembrane anchor domains and the extracellular loop, and two transmembrane domains immediately upstream of the envelope protein in the ZIKAV genome, which encodes a portion of the M protein to ensure targeting to the plasma membrane, and a KOZAK sequence at the N-terminus (GCCGCCACC) to ensure initiation of translation, two transmembrane domains just prior to the extracellular loop, and the extracellular loop. In some embodiments, the at least one target antigen used herein is a ZIKAV antigen encoded by the sequence set forth in SEQ ID NO: 37, which is the amino acid version of the Zika full 2015 antigen (AHL12087) set forth in SEQ ID NO: 36.

In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 1 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 2 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 3 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 4 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 5 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 6 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 7 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 8 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 9 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 10 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 11 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 12 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 13 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 14 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 15 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 16 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 17 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 18 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 19 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 20 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 21 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 22 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 23 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 24 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 25 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 26 or a fragment thereof. In particular embodiments, the amino acid sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 27 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 28 or a fragment thereof. In particular embodiments, the amino acid sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 29 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 30 or a fragment thereof. In particular embodiments, the amino acid sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 31 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 32 or a fragment thereof. In particular embodiments, the amino acid sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 33 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 34 or a fragment thereof. In particular embodiments, the amino acid sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 35 or a fragment thereof. In particular embodiments, the nucleotide sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 36 or a fragment thereof. In particular embodiments, the amino acid sequence of the antigen has a region at least 50%, 60%, 65%, 70%, 75%, 80%, 85%, 90%, 95%, 98%, 99%, 99.5%, 99.9%, or 100% (or any range or value derived therefrom) identity to SEQ ID NO: 37 or a fragment thereof.

In certain embodiments, the target antigen is a Zika virus protein, such as an envelope glycoprotein (E) from Zika viruses. In particular embodiments, the target antigen has a region at least 50%, 60%, 65%, 70%, 75%, 80%, 85%, 90%, 95%, 98%, 99%, 99.5%, 99.9%, 100% (or any range or value derivable therefrom) identity to SEQ ID NO: 13 or a fragment thereof. In particular embodiments, the target antigen has a region at least 50%, 60%, 65%, 70%, 75%, 80%, 85%, 90%, 95%, 98%, 99%, 99.5%, 99.9%, 100% (or any range or value derivable therefrom) identity to SEQ ID NO: 14 or a fragment thereof. In particular embodiments, the target antigen has a region at least 50%, 60%, 65%, 70%, 75%, 80%, 85%, 90%, 95%, 98%, 99%, 99.5%, 99.9%, 100% (or any range or value derivable therefrom) identity to SEQ ID NO: 15 or a fragment thereof. In particular embodiments, the target antigen has a region at least 50%, 60%, 65%, 70%, 75%, 80%, 85%, 90%, 95%, 98%, 99%, 99.5%, 99.9%, 100% (or any range or value derivable therefrom) identity to SEQ ID NO: 16 or a fragment thereof. In particular embodiments, the target antigen has a region at least 50%, 60%, 65%, 70%, 75%, 80%, 85%, 90%, 95%, 98%, 99%, 99.5%, 99.9%, 100% (or any range or value derivable therefrom) identity to SEQ ID NO: 17 or a fragment thereof. In particular embodiments, the target antigen has a region at least 50%, 60%, 65%, 70%, 75%, 80%, 85%, 90%, 95%, 98%, 99%, 99.5%, 99.9%, 100% (or any range or value derivable therefrom) identity to SEQ ID NO: 18 or a fragment thereof. In particular embodiments, the target antigen has a region at least 50%, 60%, 65%, 70%, 75%, 80%, 85%, 90%, 95%, 98%, 99%, 99.5%, 99.9%, 100% (or any range or value derivable therefrom) identity to SEQ ID NO: 19 or a fragment thereof. In particular embodiments, the target antigen has a region at least 50%, 60%, 65%, 70%, 75%, 80%, 85%, 90%, 95%, 98%, 99%, 99.5%, 99.9%, 100% (or any range or value derivable therefrom) identity to SEQ ID NO: 11 or a fragment thereof. In particular embodiments, the target antigen has a region at least 50%, 60%, 65%, 70%, 75%, 80%, 85%, 90%, 95%, 98%, 99%, 99.5%, 99.9%, 100% (or any range or value derivable therefrom) identity to SEQ ID NO: 12 or a fragment thereof. In particular embodiments, the target antigen has a region at least 50%, 60%, 65%, 70%, 75%, 80%, 85%, 90%, 95%, 98%, 99%, 99.5%, 99.9%, 100% (or any range or value derivable therefrom) identity to SEQ ID NO: 20 or a fragment thereof. In particular embodiments, the target antigen has a region at least 50%, 60%, 65%, 70%, 75%, 80%, 85%, 90%, 95%, 98%, 99%, 99.5%, 99.9%, 100% (or any range or value derivable therefrom) identity to SEQ ID NO: 21 or a fragment thereof. In particular embodiments, the target antigen has a region at least 50%, 60%, 65%, 70%, 75%, 80%, 85%, 90%, 95%, 98%, 99%, 99.5%, 99.9%, 100% (or any range or value derivable therefrom) identity to SEQ ID NO: 23 or a fragment thereof. In particular embodiments, the target antigen has a region at least 50%, 60%, 65%, 70%, 75%, 80%, 85%, 90%, 95%, 98%, 99%, 99.5%, 99.9%, 100% (or any range or value derivable therefrom) identity to SEQ ID NO: 24 or a fragment thereof. In particular embodiments, the target antigen has a region at least 50%, 60%, 65%, 70%, 75%, 80%, 85%, 90%, 95%, 98%, 99%, 99.5%, 99.9%, 100% (or any range or value derivable therefrom) identity to SEQ ID NO: 25 or a fragment thereof.

In certain aspects, target antigens comprise any antigen from flavivirus family. Genus flavivirus of the family Flaviviridae contains many viruses of public health and/or veterinary concern. Flaviviruses are vector-borne viruses, with some groups transmitted by mosquitos and some by ticks. The flaviviruses that are of particular interest with respect to public health are: yellow fever virus (YFV), Japanese encephalitis virus (JEV), tick-borne encephalitis viruses (TBEVs), dengue virus (DENV), West Nile virus (WNV), and Zika virus (ZIKAV).

YFV is estimated to cause 200,000 cases and 30,000 deaths per year. YFV is endemic to sub-Saharan Africa and South America. YFV infections can be mostly asymptomatic. However, about 15% of cases can develop into more serious forms of disease, such as hemorrhagic fever. There are several effective live attenuated vaccines available. However, serious adverse events can be associated with these vaccines, such as meningoencephalitis, Guillain-Barré syndrome and acute disseminated encephalomyelitis.

JEV is endemic to East Southeast and South Asia and, more recently, has been found in Australia. Case fatality rates for JEV are between 5-40%, with children and elderly individuals more susceptible to severe disease. Psychoneurological sequelae can occur in 20-50% of survivors. JEV is estimated to case 70,000 cases and 20,000 deaths per year. Five distinct genotypes of JEV exist, however all vaccine strains belong to genotype III. The effectiveness of the vaccines against the other four genotypes is not well established.

There are three subtypes of TBEV that are known to cause human disease. The subtypes are Far Eastern (TBEV-fe), Siberian, (TBEV-si), and European (TBEV-eu). TBEVs are all transmitted by ticks. It is believed that 10-30% of cases can be asymptomatic, however TBEVs can cause myelitis, meningitis, and encephalitis. Fatality rates vary across the subtypes with TBEV-fe having the highest rate at greater than 20%.

DENV has four subtypes, DENV-1, DENV-2, DENV-3, and DENV-4. Taken together the subtypes cause an estimated 50-100 million infections every year and no licensed vaccine exists. One of the issues limiting production of DENV vaccines is the necessity of providing immunity to all four serotypes in one vaccine. Although an initial infection with DENV can be self-limiting, subsequent infections with a heterotypic virus can lead to dengue shock syndrome (DSS) and dengue hemorrhagic fever (DHF). Approximately 20,000 deaths occur each year from dengue, with most of the fatalities associated with DSS and DHF. Attempts at making a vaccine against all four serotypes using live-attenuated viruses have failed because of competition between the vaccine strains.

WNV is widely distributed throughout Africa, Europe, Asia, Australia and the Americas. Most infections can be asymptomatic, but WNV can also cause neurologic disease in humans, horses and companion animals.

ZIKAV has recently emerged in South America. ZIKAV was first isolated in Africa in 1947 and was subsequently found to be the causative agent of outbreaks of jaundice in Equatorial Africa. The most recent outbreak in South America has highlighted that ZIKAV, as with many flaviviruses, can cause neuronal disease. Although most ZIKAV infections can be mild or asymptomatic, infection can lead to serious neurological symptoms, such as fetal brain damage, microcephaly and Guillain-Barré syndrome. It is believed that infections that occur in the first trimester of pregnancy can lead to brain damage and microcephaly in the fetus. The severity of the current flavivirus outbreak in the Americas, especially Brazil, has highlighted the medical need for a long-lasting flavivirus vaccine that protects at-risk populations, particularly women of child-bearing age who do not have routine access to medical care.

Other examples of flaviviruses that can be targeted using the adenovirus vectors described herein include Absettarov virus, Apoi virus, Hansalova virus, Hypr virus, Iheus virus, Israel turkey meningoencephalits, Kokobera virus, Koutango virus, Kunjin virus, Kyasanur Forest virus, Langat virus, Louping ill virus, Modoc virus, Murray Valley encephalitis virus, Negishi virus, Omsk hemorrhagic fever, Powassan virus, Rio Bravo virus, Rocio virus, Spondweni virus, St. Louis encephalitis virus, and Wesselbron virus.

In some embodiments, antigens (e.g., any Zika antigen) in Ad5 [E1-, E2b-]-based vectors of this disclosure comprises mutations that can reduce the ability of the vaccine to generate anti-human C1q responses in a subject. For example, in some embodiments, point mutations can include D37I, D43L, D266I, D129L, D218L (position numbering does not count the N-terminal methionine) as in the Zika mut 2015 antigen (nucleotide sequence encoding the Zika mut 2015 antigen is SEQ ID NO: 34, amino acid sequence encoding the Zika mut 2015 antigen is SEQ ID NO: 35). In other embodiments, point mutations can include I21D, L175D, L240D (position numbering does not count the N-terminal methionine) as in the Zika mut 2014 antigen (nucleotide sequence encoding the Zika mut 2014 antigen is SEQ ID NO: 28, amino acid sequence encoding the Zika mut 2014 antigen is SEQ ID NO: 29).

In some embodiments, antigens (e.g., any Zika antigen) in Ad5 [E1-, E2b-]-based vectors of this disclosure comprise a sequence that corresponds to amino acids 409-690 of the 3423-aa Zika polyprotein (SEQ ID NO: 23), which is the truncated portion of the extracellular domain of the Zika envelope protein. For example, sequences of such antigens are set forth in SEQ ID NO: 26-SEQ ID NO: 29 or SEQ ID NO: 32-SEQ ID NO: 35.

In some embodiments, antigens (e.g., any Zika antigen) in Ad5 [E1-, E2b-]-based vectors of this disclosure comprise two transmembrane domains and the extracellular loop as well as the majority of the envelope protein and corresponds to amino acids 271-805 of the 3423-aa Zika polyprotein (SEQ ID NO: 23). For example, sequences of such antigens are set forth in SEQ ID NO: 30-SEQ ID NO: 31 or SEQ ID NO: 36-SEQ ID NO: 37. The inclusion of transmembrane domains can serve as a signal sequence to ensure migration of mRNA-loaded ribosomes to the endoplasmic reticulum, glycosylation, and eventual migration and tethering of the protein to the plasma membrane, which can all ultimately improve antigenicity and thereby generate immune responses.

II. Adenovirus Vectors

In certain aspects, adenovirus vectors can be used in compositions and methods for the delivery of flavivirus antigens, particularly Zika viral antigens.

The recombinant Ad5 [E1-, E2b-] vector vaccine platform is new, having additional deletions in the early gene 2b (E2b) region that can remove the viral DNA polymerase (pol) and/or the pre terminal protein (pTP) genes, and can be propagated in the E.C7 human cell line (Amalfitano A, Begy C R, Chamberlain J S Proc Natl Acad Sci USA. 1996 93:3352-6; Amalfitano A, Chamberlain J S Gene Ther. 1997 4:258-63; Amalfitano A et al. J Virol. 1998 72:926-33; Seregin S S and Amalfitano A Expert Opin Biol Ther. 2009 9:1521-31). The vector can have an expanded gene-carrying/cloning capacity of up to 12 kb, compared to the 7 kb capacity of current Ad5 [E1-] vectors, which is sufficient to allow inclusion of multiple genes (Amalfitano A et al. J Virol. 1998 72:926-33; Seregin S S and Amalfitano A Expert Opin Biol Ther. 2009 9:1521-31). Additional deletions of the E2b region can confer advantageous immune properties such as eliciting potent immune responses to specific antigens while minimizing immune responses to Ad5 viral proteins.

Importantly, pre-clinical and clinical studies in cancer and infectious disease demonstrate that Ad5 [E1-, E2b-]-based vectors can induce potent CMI and Ab responses against vectored antigens, even in the presence of Ad5 immunity (Osada T et al. Cancer Gene Ther. 2009 16:673-82; Gabitzsch E S et al. Vaccine. 2009 27:6394-8; Gabitzsch E S et al. Immunol Lett. 2009 122:44-51; Gabitzsch E S et al. Cancer Immunol Immunother. 2010 59:1131-5; Gabitzsch E S et al. Cancer Gene Ther. 2011 18:326-35; Gabitzsch E S et al. Vaccine 2011 29:8101-7; Jones F R et al. Vaccine 2011 29:7020-6; Gabitzsch E S, Jones F R J Clin Cell Immunol. 2011 S4:001. doi:10.4172/2155-9899. S4-001; Gabitzsch E S et al. Vaccine 2012 30:7265-70; Wieking B G et al. Cancer Gene Ther. 2012 19:667-74; Morse M A et al. Cancer Immunol Immunother. 2013 62:1293-1301; Balint et al. Cancer Immunol Immunother. 2015 64:977-87; Rice A E et al. Cancer Gene Ther. 2015 22:454-62; Gabitzsch E S et al. Oncotarget 2015 Sep. 7).

The advanced recombinant adenovirus serotype 5 (Ad5) vector platform can give the opportunity to develop a novel broadly cross-reactive vaccine for flavivirus. This vector can be delivered directly by subcutaneous injection for exposure of defined flavivirus antigens to antigen-presenting cells (APCs) that induce potent immune responses. Importantly, the Ad5 recombinant vector can replicate episomally and may not insert the genome into the host cell genome, thereby ensuring that there is no gene integration and disruption of vital cellular gene functions (Imler J L Vaccine. 1995 13:1143-51; Ertl H C, Xiang Z J Immunol. 1996 156:3579-82; Amalfitano, A Curr Opin Mol Ther. 2003 5:362-6).

Unfortunately, a major challenge facing current Ad5-based vectors is the presence of pre-existing immunity to Ad5. Most people exhibit neutralizing Abs against Ad5, the most widely used subtype for human vaccines, with two-thirds of people studied having lympho-proliferative responses against Ad5 (Chirmule N et al. Gene Ther. 1999 6:1574-83). This immunity can prevent the use of current early gene 1 (E1) region-deleted Ad5 vectors (Ad5 [E1-]) as a platform for a flavivirus vaccine. Ad5 immunity inhibits immunization, and especially re-immunization with recombinant Ad5 vectors, and can preclude immunization of a vaccinee against a second disease antigen as well. Overcoming the problem of pre-existing Ad5 vector immunity has been the subject of intense investigation. However, use of other Ad serotypes or even non-human forms of Ad can lead directly to altered production of important chemokines and cytokines, gene dysregulation, and have significantly different biodistribution and tissue toxicities (Appledorn D M et al. Gene Ther. 2008 15:885-901; Hartman Z C et al. Virus Res. 2008 132:1-14). Even if these approaches succeed in an initial immunization, subsequent vaccinations can be problematic due to induced immune responses to the Ad subtype. To help avoid the Ad immunization barrier and circumvent the adverse conditions for current Ad5 [E1-] vectors, an improved Ad5 vector platform was constructed, described above.

Further, the Ad5 [E1-, E2b-] vectors can display reduced inflammation during the first 24 to 72 hours after injection compared to current Ad5 [E1-] vectors (Nazir S A, Metcalf J P J Investig Med. 2005 53:292-304; Schaack J Proc Natl Acad Sci USA. 2004 101:3124-9; Schaack J Viral Immunol. 2005 18:79-88). The lack of Ad5 [E1-, E2b-] late gene expression renders infected cells less vulnerable to anti-Ad5 activity and permits them to produce and express the transgene for extended periods of time (Gabitzsch E S, Jones F R J Clin Cell Immunol. 2011 S4:001. doi:10.4172/2155-9899. S4-001; Hodges B L J Gene Med. 2000 2:250-9). Reduced inflammatory responses against Ad5 [E1-, E2b-] viral proteins and the resulting evasion of pre-existing Ad5 immunity can increase the ability of Ad5 [E1-, E2b-] to infect APC cells, resulting in greater immunization of the inoculee. In addition, increased infection of other cell types can provide the high levels of antigen presentation needed for potent CD4+ and CD8+ T cell responses, leading to memory T cell development. Thus it appears that deletion of the E2b region can confer advantageous immune properties, such as eliciting potent immune responses to specific antigens, while minimizing immune responses to Ad5 proteins even in the presence of pre-existing Ad5 immunity.

Results demonstrated the ability of recombinant Ad5 [E1-, E2b-] platform-based vaccines to overcome pre-existing and/or Ad5 vector-induced immunity and induce significant protective immune responses. These studies established that new Ad5 E2b-] vector-based vaccines 1) can induce significantly higher CMI responses compared to current Ad5 [E1-] vectors, 2) can be utilized for multiple immunization regimens designed to induce potent CMI responses, 3) can induce significant antigen-specific CMI responses in animals with pre-existing Ad5 immunity, and 4) can induce significant anti-tumor responses or protect against infectious disease in animals with high levels of pre-existing Ad5 immunity.

Certain aspects relate to methods and adenovirus vectors for generating immune responses against flavivirus target antigens. In particular, certain aspects can provide an improved Ad-based vaccine such that multiple vaccinations against more than one antigenic target entity can be achieved. Importantly, vaccination can be performed in the presence of preexisting immunity to the Ad and/or administered to subjects previously immunized multiple times with the adenovirus vector as described herein or other adenovirus vectors. The adenovirus vector can be administered to subjects multiple times to induce an immune response against a variety of flavivirus antigens, including but not limited to, the production of broad based antibody and cell-mediated immune responses against flaviviruses that cause polyarthralgias or encephalitis.

Certain aspects provide the use of E2b deleted adenovirus vectors, such as those described in U.S. Pat. Nos. 6,063,622; 6,451,596; 6,057,158; and 6,083,750 (all incorporated herein in their entirety by reference). As described in the '622 patent, in order to further cripple viral protein expression, and also to decrease the frequency of generating replication competent Ad (RCA), adenovirus vectors containing deletions in the E2b region can be provided in certain aspects. Propagation of these E2b deleted adenovirus vectors requires cell lines that express the deleted E2b gene products.

In further aspects, there can be provided packaging cell lines; for example E.C7 (formally called C-7), derived from the HEK-203 cell line (Amalfitano A et al. Proc Natl Acad Sci USA 1996 93:3352-56; Amalfitano A et al. Gene Ther 1997 4:258-63).

Further, the E2b gene products, DNA polymerase and preterminal protein, can be constitutively expressed in E.C7, or similar cells along with the E1 gene products. Transfer of gene segments from the Ad genome to the production cell line can have immediate benefits: (1) increased carrying capacity of the recombinant DNA polymerase and preterminal protein-deleted adenovirus vector, since the combined coding sequences of the DNA polymerase and preterminal proteins that can be theoretically deleted approaches 4.6 kb; and (2) a decreased potential of RCA generation, since two or more independent recombination events would be required to generate RCA.

Therefore, the E1, Ad DNA polymerase and preterminal protein expressing cell lines can enable the propagation of adenovirus vectors with a carrying capacity approaching 13 kb, without the need for a contaminating helper virus (Mitani et al. Proc. Natl. Acad. Sci. USA 1995 92:3854; Hodges et al. J Gene Med 2000 2:250-259; Amalfitano and Parks Curr Gene Ther 2002 2:111-133).

In addition, when genes critical to the viral life cycle are deleted (e.g., the E2b genes), a further crippling of Ad to replicate or express other viral gene proteins can occur. This can decrease immune recognition of virally infected cells, and can allow for extended durations of foreign transgene expression.

Important attributes of E1, DNA polymerase, and preterminal protein deleted vectors, however, can include their inability to express the respective proteins from the E1 and E2b regions, as well as a predicted lack of expression of most of the viral structural proteins. For example, the major late promoter (MLP) of Ad is responsible for transcription of the late structural proteins L1 through L5 (Doerfler, In Adenovirus DNA, The Viral Genome and Its Expression (Martinus Nijhoff Publishing Boston, 1986). Though the MLP can be minimally active prior to Ad genome replication, the highly toxic Ad late genes can be primarily transcribed and translated from the MLP only after viral genome replication has occurred (Thomas and Mathews Cell 1980 22:523). This cis-dependent activation of late gene transcription can be a feature of DNA viruses in general, such as in the growth of polyoma and SV-40. The DNA polymerase and preterminal proteins can be absolutely required for Ad replication (unlike the E4 or protein IX proteins) and thus their deletion can be extremely detrimental to adenovirus vector late gene expression, and the toxic effects of that expression in cells such as APCs.

In certain embodiments, the adenovirus vectors contemplated for use include E2b deleted adenovirus vectors that have a deletion in the E2b region of the Ad genome and the E1 region but do not have any other regions of the Ad genome deleted. In another embodiment, the adenovirus vectors contemplated for use can include E2b deleted adenovirus vectors that have a deletion in the E2b region of the Ad genome and deletions in the E1 and E3 regions, but no other regions deleted. In a further embodiment, the adenovirus vectors contemplated for use can include adenovirus vectors that have a deletion in the E2b region of the Ad genome and deletions in the E1, E3 and partial or complete removal of the E4 regions but no other deletions.

In another embodiment, the adenovirus vectors contemplated for use include adenovirus vectors that have a deletion in the E2b region of the Ad genome and deletions in the E1 and E4 regions but no other deletions. In an additional embodiment, the adenovirus vectors contemplated for use can include adenovirus vectors that have a deletion in the E2a, E2b and E4 regions of the Ad genome but no other deletions.

In one embodiment, the adenovirus vectors for use herein comprise vectors having the E1 and DNA polymerase functions of the E2b region deleted but no other deletions. In a further embodiment, the adenovirus vectors for use herein have the E1 and the preterminal protein functions of the E2b region deleted and no other deletions.

In another embodiment, the adenovirus vectors for use herein have the E1, DNA polymerase and the preterminal protein functions deleted, and no other deletions. In one particular embodiment, the adenovirus vectors contemplated for use herein are deleted for at least a portion of the E2b region and the E1 region, but are not "gutted" adenovirus vectors. In this regard, the vectors can be deleted for both the DNA polymerase and the preterminal protein functions of the E2b region.

The term "E2b deleted," as used herein, can refer to a specific DNA sequence that is mutated in such a way so as to prevent expression and/or function of at least one E2b gene product. Thus, in certain embodiments, "E2b deleted" can refer to a specific DNA sequence that is deleted (removed) from the Ad genome. E2b deleted or "containing a deletion within the E2b region" can refer to a deletion of at least one base pair within the E2b region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, the deletion is of more than 150, 160, 170, 180, 190, 200, 250, or 300 base pairs within the E2b region of the Ad genome. An E2b deletion can be a deletion that prevents expression and/or function of at least one E2b gene product and therefore, encompasses deletions within exons encoding portions of E2b-specific proteins as well as deletions within promoter and leader sequences. In certain embodiments, an E2b deletion is a deletion that prevents expression and/or function of one or both of the DNA polymerase and the preterminal protein of the E2b region. In a further embodiment, "E2b deleted" can refer to one or more point mutations in the DNA sequence of this region of an Ad genome such that one or more encoded proteins is non-functional. Such mutations can include residues that are replaced with a different residue leading to a change in the amino acid sequence that result in a nonfunctional protein.

As would be understood by the skilled artisan upon reading the present disclosure, other regions of the Ad genome can be deleted. Thus to be "deleted" in a particular region of the Ad genome, as used herein, can refer to a specific DNA sequence that is mutated in such a way so as to prevent expression and/or function of at least one gene product encoded by that region. In certain embodiments, to be "deleted" in a particular region can refer to a specific DNA sequence that is deleted (removed) from the Ad genome in such a way so as to prevent the expression and/or the function encoded by that region (e.g., E2b functions of DNA polymerase or preterminal protein function). "Deleted" or "containing a deletion" within a particular region can refer to a deletion of at least one base pair within that region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted from a particular region. In another embodiment, the deletion is more than 150, 160, 170, 180, 190, 200, 250, or 300 base pairs within a particular region of the Ad genome. In some embodiments, any one of the above described deletions can also be a result of translocation of two or more base pairs.

These deletions can be such that expression and/or function of the gene product encoded by the region can be prevented. Thus deletions can encompass deletions within exons encoding portions of proteins as well as deletions within promoter and leader sequences. In a further embodiment, "deleted" in a particular region of the Ad genome can refer to one or more point mutations in the DNA sequence of this region of an Ad genome such that one or more encoded proteins is non-functional. Such mutations can include residues that are replaced with a different residue leading to a change in the amino acid sequence that can result in a nonfunctional protein.

The adenovirus vectors comprising one or more deletions can be generated using recombinant techniques known in the art (see e.g., Amalfitano et al. J. Virol. 1998 72:926-33; Hodges, et al., J Gene Med 2000 2:250-59). As would be recognized by the skilled artisan, the adenovirus vectors for use can be successfully grown to high titers using an appropriate packaging cell line that constitutively expresses E2b gene products and products of any of the necessary genes that can have been deleted. In certain embodiments, HEK-293-derived cells that not only constitutively express the E1 and DNA polymerase proteins, but also the Ad-preterminal protein, can be used. In one embodiment, E.C7 cells are used to successfully grow high titer stocks of the adenovirus vectors (see e.g., Amalfitano et al. J. Virol. 1998 72:926-33; Hodges et al. J Gene Med 2000 2:250-59).

In order to delete critical genes from self-propagating adenovirus vectors, the proteins encoded by the targeted genes can be first coexpressed in HEK-293 cells, or similar, along with the E1 proteins. Therefore, only those proteins which are non-toxic when coexpressed constitutively (or toxic proteins inducibly expressed) can be utilized. Coexpression in HEK-293 cells of the E1 and E4 genes has been demonstrated (utilizing inducible, not constitutive, promoters) (Yeh et al. J. Virol. 1996 70:559; Wang et al. Gene Therapy 1995 2:775; and Gorziglia et al. J. Virol. 1996 70:4173). The E1 and protein IX genes (a virion structural protein) have been coexpressed (Caravokyri and Leppard J. Virol. 1995 69:6627), and coexpression of the E1, E4, and protein IX genes has also been described (Krougliak and Graham Hum. Gene Ther. 1995 6:1575). The E1 and 100 k genes have been successfully expressed in transcomplementing cell lines, as have E1 and protease genes (Oualikene et al. Hum Gene Ther 2000 11:1341-53; Hodges et al. J. Virol 2001 75:5913-20).

Cell lines coexpressing E1 and E2b gene products for use in growing high titers of E2b deleted Ad particles are described in U.S. Pat. No. 6,063,622. The E2b region encodes the viral replication proteins which can be absolutely required for Ad genome replication (Doerfler, supra and Pronk et al. Chromosoma 1992 102:S39-S45). Useful cell lines constitutively express the approximately 140 kDa Ad-DNA polymerase and/or the approximately 90 kDa preterminal protein. In particular, cell lines that have high-level, constitutive coexpression of the E1, DNA polymerase, and preterminal proteins, without toxicity (e.g., E.C7), can be desirable for use in propagating Ad for use in multiple vaccinations. These cell lines can permit the propagation of adenovirus vectors deleted for the E1, DNA polymerase, and preterminal proteins.

The recombinant Ad can be propagated using techniques known in the art. For example, in certain embodiments, tissue culture plates containing E.C7 cells are infected with the adenovirus vector virus stocks at an appropriate MOI (e.g., 5) and incubated at 37.0° C. for 40-96 h. The infected cells are harvested, resuspended in 10 mM Tris-CI (pH 8.0), and sonicated, and the virus is purified by two rounds of cesium chloride density centrifugation. In certain techniques, the virus containing band is desalted over a Sephadex CL-6B column (Pharmacia Biotech, Piscataway, N.J.), sucrose or glycerol is added, and aliquots are stored at −80° C. In some embodiments, the virus will be placed in a solution designed to enhance its stability, such as A195 (Evans et al. J Pharm Sci 2004 93:2458-75). The titer of the stock can be measured (e.g., by measurement of the optical density at 260 nm of an aliquot of the virus after SDS lysis). In another embodiment, plasmid DNA, either linear or circular, encompassing the entire recombinant E2b deleted adenovirus vector can be transfected into E.C7, or similar cells, and incubated at 37.0° C. until evidence of viral production is present (e.g., the cytopathic effect). The conditioned media from these cells can then be used to infect more E.C7, or similar cells, to expand the amount of virus produced, before purification.

Purification can be accomplished by two rounds of cesium chloride density centrifugation or selective filtration. In certain embodiments, the virus can be purified by column chromatography, using commercially available products (e.g., Adenopure from Puresyn, Inc., Malvem, Pa.) or custom made chromatographic columns.

In certain embodiments, the recombinant Ad can comprise enough of the virus to ensure that the cells to be infected are confronted with a certain number of viruses. Thus, there can be provided a stock of recombinant Ad, particularly, an RCA-free stock of recombinant Ad. The preparation and analysis of Ad stocks is well known in the art. Viral stocks can vary considerably in titer, depending largely on viral genotype and the protocol and cell lines used to prepare them. The viral stocks can have a titer of at least about $10^6$, $10^7$, or $10^8$ virus particles (VPs)/ml, and many such stocks can have higher titers, such as at least about $10^9$, $10^{10}$, $10^{11}$, or $10^{12}$ VPs/ml.

III. Heterologous Nucleic Acids

The adenovirus vectors also can comprise heterologous nucleic acid sequences that encode several target antigens of interest, fragments or fusions thereof, against which it is desired to generate an immune response. In some embodiments, the adenovirus vectors comprise heterologous nucleic acid sequences that encode several proteins, fusions thereof or fragments thereof, which can modulate the immune response. Thus, certain aspects provide the Second Generation E2b deleted adenovirus vectors that comprise a heterologous nucleic acid sequence.

As such, certain aspects provide nucleic acid sequences, which can also be referred to herein as polynucleotides that encode several flavivirus target antigens of interest. As such, certain aspects provide polynucleotides that encode target antigens from any source as described further herein, vectors comprising such polynucleotides and host cells transformed or transfected with such expression vectors. The terms "nucleic acid" and "polynucleotide" are used essentially interchangeably herein. As will be also recognized by the skilled artisan, polynucleotides can be single-stranded (coding or antisense) or double-stranded, and can be DNA (genomic, cDNA or synthetic) or RNA molecules. RNA molecules can include hnRNA molecules, which contain introns and correspond to a DNA molecule in a one-to-one manner, and mRNA molecules, which do not contain introns. Additional coding or non-coding sequences can, but need not, be present within a polynucleotide, and a polynucleotide can, but need not, be linked to other molecules and/or support materials. An isolated polynucleotide, as used herein, can mean that a polynucleotide is substantially away from other coding sequences. For example, an isolated DNA molecule as used herein does not contain large portions of unrelated coding DNA, such as large chromosomal fragments or other functional genes or polypeptide coding regions. Of course, this can refer to the DNA molecule as originally isolated, and does not exclude genes or coding regions later added to the segment recombinantly in the laboratory.

As will be understood by those skilled in the art, the polynucleotides can include genomic sequences, extra-genomic and plasmid-encoded sequences and smaller engineered gene segments that express, or can be adapted to express target antigens as described herein, fragments of antigens, peptides and the like. Such segments can be naturally isolated, or modified synthetically by the hand of man.

Polynucleotides can comprise a native sequence (i.e., an endogenous sequence that encodes a target antigen polypeptide/protein/epitope or a portion thereof) or can comprise a sequence that encodes a variant or derivative of such a sequence. In certain embodiments, the polynucleotide sequences set forth herein encode target antigen proteins as described herein. In some embodiments, polynucleotides represent a novel gene sequence that has been optimized for expression in specific cell types {i.e., human cell lines) that can substantially vary from the native nucleotide sequence or variant but encode a similar protein antigen.

In other related embodiments, there can be provided polynucleotide variants having substantial identity to native sequences encoding proteins (e.g., target antigens of interest) as described herein, for example those comprising at least 70% sequence identity, particularly at least 75% up to 99% or higher, sequence identity compared to a native polynucleotide sequence encoding the polypeptides using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

In certain aspects, polynucleotide variants will contain one or more substitutions, additions, deletions and/or insertions, particularly such that the immunogenicity of the epitope of the polypeptide encoded by the variant polynucleotide or such that the immunogenicity of the heterologous target protein is not substantially diminished relative to a polypeptide encoded by the native polynucleotide sequence. As described elsewhere herein, the polynucleotide variants can encode a variant of the target antigen, or a fragment (e.g., an epitope) thereof wherein the propensity of the variant polypeptide or fragment (e.g., epitope) thereof to react with antigen-specific antisera and/or T-cell lines or clones is not substantially diminished relative to the native polypeptide. The term "variants" can also encompass homologous genes of xenogeneic origin.

Certain aspects can provide polynucleotides that comprise or consist of at least about 5 up to a 1000 or more contiguous nucleotides encoding a polypeptide, including target protein antigens, as described herein, as well as all intermediate lengths there between. It will be readily understood that "intermediate lengths," in this context, can mean any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence as described herein can be extended at one or both ends by additional nucleotides not found in the native sequence encoding a polypeptide as described herein, such as an epitope or heterologous target protein. This additional sequence can consist of 1 up to 20 nucleotides or more, at either end of the disclosed sequence or at both ends of the disclosed sequence.

In certain embodiments, the polynucleotides, or fragments thereof, regardless of the length of the coding sequence itself, can be combined with other DNA sequences, such as promoters, expression control sequences, polyadenylation signals, additional restriction enzyme sites, multiple cloning sites, other coding segments, and the like, such that their overall length can vary considerably. It is therefore contemplated that a nucleic acid fragment of almost any length can be employed and the total length may be limited by the ease of preparation and use in the intended recombinant DNA protocol. For example, illustrative polynucleotide segments with total lengths of about 1000, 2000, 3000, 4000, 5000, 6000, 7000, 8000, 9000, 10,000, about 500, about 200, about 100, about 50 base pairs in length, and the like, (including all intermediate lengths) are contemplated to be useful in many implementations.

When comparing polynucleotide sequences, two sequences can be said to be "identical" if the sequence of nucleotides in the two sequences is the same when aligned for maximum correspondence, as described below. Comparisons between two sequences can be performed by comparing the sequences over a comparison window to identify and compare local regions of sequence similarity. A "comparison window" as used herein, can refer to a segment of at least about 20 contiguous positions, usually 30 to about 75, 40 to about 50, in which a sequence can be compared to a reference sequence of the same number of contiguous positions after the two sequences are optimally aligned.

Optimal alignment of sequences for comparison can be conducted using the Megalign program in the Lasergene suite of bioinformatics software (DNASTAR, Inc., Madison, Wis.), using default parameters. This program embodies several alignment schemes described in the following references: Dayhoff M O (1978) A model of evolutionary change in proteins—Matrices for detecting distant relationships. In Dayhoff M O (ed.) Atlas of Protein Sequence and Structure, National Biomedical Research Foundation, Washington D.C. Vol. 5, Suppl. 3, pp. 345-358; Hein J Unified Approach to Alignment and Phylogenes, pp. 626-645 (1990); Methods in Enzymology vol.183, Academic Press, Inc., San Diego, Calif.; Higgins D G and Sharp P M CABIOS 1989 5:151-53; Myers E W and Muller W CABIOS 1988 4:11-17; Robinson E D Comb. Theor 1971 11A 05; Saitou N, Nei M MoI. Biol. Evol. 1987 4:406-25; Sneath P H A and Sokal R R Numerical Taxonomy—the Principles and Practice of Numerical Taxonomy, Freeman Press, San Francisco, Calif. (1973); Wilbur W J and Lipman DJ Proc. Natl. Acad., Sci. USA 1983 80:726-30.

Alternatively, optimal alignment of sequences for comparison can be conducted by the local identity algorithm of Smith and Waterman, Add. APL. Math 1981 2:482, by the identity alignment algorithm of Needleman and Wunsch J. MoI. Biol. 1970 48:443, by the search for similarity methods of Pearson and Lipman, Proc. Natl. Acad. Sci. USA 1988 85:2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One example of algorithms that are suitable for determining percent sequence identity and sequence similarity are the BLAST and BLAST 2.0 algorithms, which are described in Altschul et al., Nucl. Acids Res. 1977 25:3389-3402, and Altschul et al. J. MoI. Biol. 1990 215:403-10, respectively. BLAST and BLAST 2.0 can be used, for example with the parameters described herein, to determine percent sequence identity for the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff and Henikoff, Proc. Natl. Acad. Sci. USA 1989 89:10915) alignments, (B) of 50, expectation (E) of 10, M=5, N=−4 and a comparison of both strands.

In certain aspects, the "percentage of sequence identity" is determined by comparing two optimally aligned sequences over a window of comparison of at least 20 positions, wherein the portion of the polynucleotide sequence in the comparison window can comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage can be calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there can be many nucleotide sequences that encode a particular antigen of interest, or fragment thereof, as described herein. Some of these polynucleotides can bear minimal homology to the nucleotide sequence of any native gene. Nonetheless, polynucleotides that vary due to differences in codon usage are specifically contemplated in certain aspects. Further, alleles of the genes comprising the polynucleotide sequences provided herein are also contemplated. Alleles are endogenous genes that can be altered as a result of one or more mutations, such as deletions, additions and/or substitutions of nucleotides. The resulting mRNA and protein can, but need not, have an altered structure or function. Alleles can be identified using standard techniques (such as hybridization, amplification and/or database sequence comparison).

Therefore, in another embodiment, a mutagenesis approach, such as site-specific mutagenesis, is employed for the preparation of variants and/or derivatives of the target antigen sequences, or fragments thereof, as described herein. By this approach, specific modifications in a polypeptide sequence can be made through mutagenesis of the underlying polynucleotides that encode them. These techniques can provide a straightforward approach to prepare and test sequence variants, for example, incorporating one or more of the foregoing considerations, by introducing one or more nucleotide sequence changes into the polynucleotide.

Site-specific mutagenesis can allow the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations can be employed in a selected polynucleotide sequence to improve, alter, decrease, modify, or otherwise change the properties of the polynucleotide itself, and/or alter the properties, activity, composition, stability, or primary sequence of the encoded polypeptide.

Polynucleotide segments or fragments encoding the polypeptides can be readily prepared by, for example, directly synthesizing the fragment by chemical means, as is commonly practiced using an automated oligonucleotide synthesizer. Also, fragments can be obtained by application of nucleic acid reproduction technology, such as the PCR™ technology of U.S. Pat. No. 4,683,202, by introducing selected sequences into recombinant vectors for recombinant production, and by other recombinant DNA techniques generally known to those of skill in the art of molecular biology (see for example, Current Protocols in Molecular Biology, John Wiley and Sons, NY, N.Y.).

In order to express a desired target antigen polypeptide or fragment thereof, or fusion protein comprising any of the above, as described herein, the nucleotide sequences encoding the polypeptide, or functional equivalents, can be inserted into an appropriate Ad as described elsewhere herein using recombinant techniques known in the art. The appropriate adenovirus vector can contain the necessary elements for the transcription and translation of the inserted coding sequence and any desired linkers. Methods that are well known to those skilled in the art can be used to construct these adenovirus vectors containing sequences encoding a polypeptide of interest and appropriate transcriptional and translational control elements. These methods can include in vitro recombinant DNA techniques, synthetic techniques, and in vivo genetic recombination. Such techniques are described, for example, in Amalfitano et al. J. Virol. 1998 72:926-33; Hodges et al. J Gene Med 2000 2:250-259; Sambrook J et al. (1989) Molecular Cloning, A Laboratory Manual, Cold Spring Harbor Press, Plainview, N.Y., and Ausubel F M et al. (1989) Current Protocols in Molecular Biology, John Wiley & Sons, New York. N.Y.

A variety of vector/host systems can be utilized to contain and produce polynucleotide sequences. These can include, but are not limited to, microorganisms such as bacteria transformed with recombinant bacteriophage, plasmid, or cosmid DNA vectors; yeast transformed with yeast vectors; insect cell systems infected with virus vectors (e.g., baculovirus); plant cell systems transformed with virus vectors (e.g., cauliflower mosaic virus, CaMV; tobacco mosaic virus, TMV) or with bacterial vectors (e.g., Ti or pBR322 plasmids); or animal cell systems.

The "control elements" or "regulatory sequences" present in an adenovirus vector can be those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, sequences encoding a polypeptide of interest can be ligated into an Ad transcription/translation complex consisting of the late promoter and tripartite leader sequence. Insertion in a non-essential E1 or E3 region of the viral genome can be used to obtain a viable virus that is capable of expressing the polypeptide in infected host cells (Logan J and Shenk T (1984) Proc. Natl. Acad. Sci 1984 87:3655-59). In addition, transcription enhancers, such as the Rous sarcoma virus (RSV) enhancer, can be used to increase expression in mammalian host cells. Transcriptional enhancers can comprise one element, at least two elements, at least three elements, at least four elements, at least five elements, or at least six elements.

Specific initiation signals can also be used to achieve more efficient translation of sequences encoding a polypeptide of interest. Such signals include the ATG initiation codon and adjacent sequences. In cases where sequences encoding the polypeptide, its initiation codon, and upstream sequences is inserted into the appropriate expression vector, no additional transcriptional or translational control signals may be needed. However, in cases where only coding sequence, or a portion thereof, is inserted, exogenous translational control signals including the ATG initiation codon can be provided. Furthermore, the initiation codon can be in the correct reading frame to ensure translation of the entire insert. Exogenous translational elements and initiation codons can be of various origins, both natural and synthetic. The efficiency of expression can be enhanced by the inclusion of enhancers that are appropriate for the particular cell system which is used, such as those described in the literature (Scharf D. et al. Results Probl. Cell Differ. 1994 20:125-62). Specific termination sequences, either for transcription or translation, can also be incorporated in order to achieve efficient translation of the sequence encoding the polypeptide of choice.

A variety of protocols for detecting and measuring the expression of polynucleotide-encoded products (e.g., target antigens of interest), using either polyclonal or monoclonal antibodies specific for the product are known in the art. Examples can include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide can be used for some applications, but a competitive binding assay can also be employed. These and other assays are described, among other places, in Hampton R et al. (1990; Serological Methods, a Laboratory Manual, APS Press, St Paul. Minn.) and Maddox D E et al. J. Exp. Med. 1983 758:1211-16). The adenovirus vectors can comprise nucleic acid sequences encoding several flavivirus antigens of interest.

In certain embodiments, elements that increase the expression of the desired target antigen are incorporated into the nucleic acid sequence of the adenovirus vectors described herein. Such elements include internal ribosome binding sites (IRES; Wang and Siddiqui Curr. Top. Microbiol. Immunol 1995 203:99; Ehrenfeld and Semler Curr. Top. Microbiol. Immunol. 1995 203:65; Rees et al., Biotechniques 1996 20:102; Sugimoto et al. Biotechnology 1994 2:694). IRES can increase translation efficiency. As well, other sequences can enhance expression. For some genes, sequences especially at the 5' end can inhibit transcription and/or translation. These sequences can be palindromes that can form hairpin structures. Any such sequences in the nucleic acid to be delivered can be deleted or not deleted.

Expression levels of the transcript or translated product can be assayed to confirm or ascertain which sequences affect expression. Transcript levels can be assayed by any known method, including Northern blot hybridization, RNase probe protection and the like. Protein levels can be assayed by any known method, including ELISA. As would be recognized by the skilled artisan, the adenovirus vectors comprising heterologous nucleic acid sequences can be generated using recombinant techniques known in the art, such as those described in Maione et al. Proc Natl Acad Sci USA 2001 98:5986-91; Maione et al. Hum Gene Ther 2000 1:859-68; Sandig et al. Proc Natl Acad Sci USA, 2000 97:1002-07; Harui et al. Gene Therapy 2004 11:1617-26; Parks et al. Proc Natl Acad Sci USA 1996 93:13565-570; Dello Russo et al. Proc Natl Acad Sci USA 2002 99:12979-984; Current Protocols in Molecular Biology, John Wiley and Sons, NY, N.Y.).

As noted above, the adenovirus vectors can comprise nucleic acid sequences that encode several flavivirus target proteins or antigens of interest. In this regard, the vectors can contain nucleic acid encoding 1 to 4 or more different target antigens of interest. The target antigens can be a full length protein or can be a fragment (e.g., an epitope) thereof. The adenovirus vectors can contain nucleic acid sequences encoding multiple fragments or epitopes from one target protein of interest or can contain one or more fragments or epitopes from numerous different target flavivirus antigen proteins of interest.

In some aspects, the nucleic acid sequences encode a plurality of flavivirus target antigens. The nucleic acid sequence encoding the plurality of flavivirus target antigens can comprise a plurality of gene inserts each corresponding to a target antigen and wherein each gene insert is separated by a nucleic acid sequence encoding a self-cleaving 2A peptide. In some aspects, the self-cleaving 2A peptide (i.e., the cleavable linker) is derived from Porcine teschovirus-1 or Thosea asigna virus or the like.

Examples of cleavable linkers can include 2A linkers (e.g., T2A), 2A-like linkers or functional equivalents thereof and combinations thereof. In some embodiments, the linkers include the picornaviral 2A-like linker, CHYSEL sequences of Porcine teschovirus (P2A), Thosea asigna virus (T2A) or combinations, variants and functional equivalents thereof.

In certain embodiments, immunogenic fragments bind to an MHC class I or class II molecule. As used herein, an immunogenic fragment can be said to "bind to" an MHC class I or class II molecule if such binding is detectable using any assay known in the art. For example, the ability of a polypeptide to bind to MHC class I can be evaluated indirectly by monitoring the ability to promote incorporation of 125I labeled β2-microglobulin (β2m) into MHC class 1/β2m/peptide heterotrimeric complexes (see Parker et al., J. Immunol. 752:163, 1994). Alternatively, functional peptide competition assays that are known in the art can be employed. Immunogenic fragments of polypeptides can generally be identified using well known techniques, such as those summarized in Paul, Fundamental Immunology, 3rd ed., 243-247 (Raven Press, 1993) and references cited therein. Representative techniques for identifying immunogenic fragments include screening polypeptides for the ability to react with antigen-specific antisera and/or T-cell lines or clones. An immunogenic fragment of a particular target polypeptide can be a fragment that reacts with such antisera and/or T-cells at a level that is not substantially less than the reactivity of the full length target polypeptide (e.g., in an ELISA and/or T-cell reactivity assay). In other words, an immunogenic fragment can react within such assays at a level that is similar to or greater than the reactivity of the full length polypeptide. Such screens can generally be performed using methods well known to those of ordinary skill in the art, such as those described in Harlow and Lane, Antibodies: A Laboratory Manual, Cold Spring Harbor Laboratory, 1988.

Target antigens can include but are not limited to antigens derived from any of the flaviviruses. Target antigens can include proteins produced by any of the infectious flaviviruses described herein, such as, C, E, prM, M, NS1, NS2A, NS2B, NS3, NS4A, NS4B, and NS5. As used herein, an "infectious agent" can be any species capable of infecting a host. Infectious agents can include, for example, any virus within the flavivirus genus.

The adenovirus vector can also include nucleic acid sequences that encode proteins that increase the immunogenicity of the target antigen. In this regard, the protein produced following immunization with the adenovirus vector containing such a protein can be a fusion protein comprising the target antigen of interest fused to a protein that increases the immunogenicity of the target antigen of interest.

IV. Combination Therapies

Certain embodiments provide a combination immunotherapy and vaccine compositions for the treatment and prevention of infectious diseases. Some embodiments provide combination multi-targeted vaccines, immunotherapies and methods for enhanced therapeutic response to complex diseases such as infectious diseases. Each component of the combination therapy can be independently included in a vaccine composition for prevention of Zika infection or infection by any flavivirus.

"Treatment" can refer to administration of a therapeutically effective dose of the vaccines of this disclosure to a subject. The treatment can be administered in a pharmaceutical composition to a subject. The subject can also be healthy and disease free at the time of treatment and, in this case, the treatment can be referred to as a preventative vaccination. The subject can be suffering from a disease condition at the time of treatment and, in this case, the treatment can be referred to as preventative vaccination.

A "subject" can refer to any animal, including, but not limited to, humans, non-human primates (e.g., rhesus or other types of macaques), mice, pigs, horses, donkeys, cows, sheep, rats and fowls. A "subject" can be used herein interchangeably with "individual" or "patient."

In some aspects, the vector comprises at least one antigen. In some aspects, the vector comprises at least two antigens. In some aspects, the vaccine formulation comprises 1:1 ratio of vector to antigen. In some aspects, the vaccine comprises 1:2 ratio of vector to antigen. In some aspects, the vaccine comprises 1:3 ratio of vector to antigen. In some aspects, the vaccine comprises 1:4 ratio of vector to antigen. In some aspects, the vaccine comprises 1:5 ratio of vector to antigen. In some aspects, the vaccine comprises 1:6 ratio of vector to antigen. In some aspects, the vaccine comprises 1:7 ratio of vector to antigen. In some aspects, the vaccine comprises 1:8 ratio of vector to antigen. In some aspects, the vaccine comprises 1:9 ratio of vector to antigen. In some aspects, the vaccine comprises 1:10 ratio of vector to antigen.

In some aspects, the vaccine is a combination vaccine, wherein the vaccine comprises at least two vectors each containing at least a single antigen.

When a mixture of different antigens are simultaneously administered or expressed from a same or different vector in a subject, they can compete with one another. As a result the formulations comprising different concentration and ratios of expressed antigens in a combination immunotherapy or vaccine can be evaluated and tailored to the subject or group of subjects to ensure that effective and sustained immune responses occur after administration.

Composition that comprises multiple antigens can be present at various ratios. For example, formulations with more than vector can have various ratios. For example, immunotherapies or vaccines can have two different vectors in a stoichiometry of 1:1, 1:2, 1:3, 1:4, 1:5, 1:6, 1:7, 1:8, 1:9, 1:10, 1:15, 1:20, 1:30, 2:1, 2:3, 2:4, 2:5, 2:6, 2:7, 2:8, 3:1, 3:3, 3:4, 3:5, 3:6, 3:7, 3:8, 3:1, 3:3, 3:4, 3:5, 3:6, 3:7, 3:8, 4:1, 4:3, 4:5, 4:6, 4:7, 4:8, 5:1, 5:3, 5:4, 5:6, 5:7, 5:8, 6:1, 6:3, 6:4, 6:5, 6:7, 6:8, 7:1, 7:3, 7:4, 7:5, 7:6, 7:8, 8: 1, 8:3, 8:4, 8:5, 8:6, or 8:7.

In some embodiments, at least one of the recombinant nucleic acid vectors is a replication defective adenovirus vector that comprises a replication defective adenovirus 5 vector comprising a first identity value. In some embodiments, the replication defective adenovirus vector comprises a deletion in the E2b region. In some embodiments, the replication defective adenovirus vector further comprises a deletion in the E1 region. In some embodiments, the replication defective adenovirus vector comprises a deletion in an E1 region, and E2b region, an E3 region, an E4 region, or any combination thereof.

Specific therapies that can be used in combination with any Ad5 [E1-, E2b-] vaccine of the present disclosure are described in further detail below.

A. Costimulatory Molecules

In addition to the use of a recombinant adenovirus-based vector vaccine containing Zika virus antigens, co-stimulatory molecules can be incorporated into said vaccine that will increase immunogenicity.

Initiation of an immune response requires at least two signals for the activation of naive T cells by APCs (Damle, et al. J Immunol 148:1985-92 (1992); Guinan, et al. Blood 84:3261-82 (1994); Hellstrom, et al. Cancer Chemother Pharmacol 38:S40-44 (1996); Hodge, et al. Cancer Res 39:5800-07 (1999)). An antigen specific first signal is delivered through the T cell receptor (TCR) via the peptide/major histocompatibility complex (MHC) and causes the T cell to enter the cell cycle. A second, or costimulatory, signal can be delivered for cytokine production and proliferation.

At least three distinct molecules normally found on the surface of professional antigen presenting cells (APCs) have been reported as capable of providing the second signal critical for T cell activation: B7-1 (CD80), ICAM-1 (CD54), and LFA-3 (human CD58) (Damle, et al. J Immunol 148: 1985-92 (1992); Guinan, et al. Blood 84: 3261-82 (1994); Wingren, et al. Crit Rev Immunol 15: 235-53 (1995); Parra, et al. Scand. J Immunol 38: 508-14 (1993); Hellstrom, et al. Ann NY Acad Sci 690: 225-30 (1993); Parra, et al. J Immunol 158: 637-42 (1997); Sperling, et al. J Immunol 157: 3909-17 (1996); Dubey, et al. J Immunol 155: 45-57 (1995); Cavallo, et al. Eur J Immunol 25: 1154-62 (1995)).

For example, these costimulatory molecules can be distinct T cell ligands. B7-1 interacts with the CD28 and CTLA-4 molecules, ICAM-1 interacts with the CD11a/CD18 (LFA-1/beta-2 integrin) complex, and LFA-3 interacts with the CD2 (LFA-2) molecules. Therefore, in a certain embodiment, it would be desirable to have a recombinant adenovirus vector that contains B7-1, ICAM-1, and LFA-3, respectively, that, when combined with a recombinant adenovirus-based vector vaccine comprising one or more nucleic acids encoding target antigens such as Zika virus antigens, will further increase/enhance anti-Zika immune responses directed to specific target antigens.

V. Immunological Fusion Partner

The viral vectors or composition described herein can further comprise nucleic acid sequences that encode proteins, or an "immunological fusion partner," that can increase the immunogenicity of the target antigen such as Zika virus antigens, or any target flavivirus antigen of the present disclosure. In this regard, the protein produced following immunization with the viral vector containing such a protein can be a fusion protein comprising the target antigen of interest fused to a protein that increases the immunogenicity of the target antigen of interest. Furthermore, combination therapy with Ad5 [E1-, E2b-] vectors encoding for a Zika virus antigen and an immunological fusion partner can result in boosting the immune response, such that the combination of both therapeutic moieties acts to synergistically boost the immune response more than either the Ad5 [E1-, E2b-] vectors encoding for the Zika virus antigen alone, or the immunological fusion partner alone. For example, combination therapy with Ad5 [E1-, E2b-] vectors encoding for Zika virus antigens and an immunological fusion partner can result in synergistic enhancement of stimulation of antigen-specific effector CD4+ and CD8+ T cells, stimulation of NK cell response directed towards killing infected cells, stimulation of neutrophils or monocyte cell responses directed towards killing infected cells via antibody dependent cell-mediated cytotoxicity (ADCC), antibody dependent cellular phagocytosis (ADCP) mechanisms, or any combination thereof. This synergistic boost can vastly improve survival outcomes after administration to a subject in need thereof. In certain embodiments, combination therapy with Ad5 [E1-, E2b-] vectors encoding for Zika virus antigens and an immunological fusion partner can result in generating an immune response comprises an increase in target antigen-specific CTL activity of about 1.5 to 20, or more fold in a subject administered the adenovirus vectors as compared to a control. In another embodiment, generating an immune response comprises an increase in target-specific CTL activity of about 1.5 to 20, or more fold in a subject administered the Ad5 [E1-, E2b-] vectors encoding for Zika virus antigens and an immunological fusion partner as compared to a control. In a further embodiment, generating an immune response that comprises an increase in target antigen-specific cell-mediated immunity activity as measured by ELISpot assays measuring cytokine secretion, such as interferon-gamma (IFN-γ), interleukin-2 (IL-2), tumor necrosis factor-alpha (TNF-α), or other cytokines, of about 1.5 to 20, or more fold as compared to a control. In a further embodiment, generating an immune response comprises an increase in target-specific antibody production of between 1.5 and 5 fold in a subject administered the Ad5 [E1-, E2b-] vectors encoding for Zika virus antigens and an immunological fusion partner as described herein as compared to an appropriate control. In another embodiment, generating an immune response comprises an increase in target-specific antibody production of about 1.5 to 20, or more fold in a subject administered the adenovirus vector as compared to a control.

As an additional example, combination therapy with Ad5 [E1-, E2b-] vectors encoding for target epitope antigens and an immunological fusion partner can result in synergistic enhancement of stimulation of antigen-specific effector CD4+ and CD8+ T cells, stimulation of NK cell response directed towards killing infected cells, stimulation of neutrophils or monocyte cell responses directed towards killing infected cells via antibody dependent cell-mediated cytotoxicity (ADCC), antibody dependent cellular phagocytosis (ADCP) mechanisms, or any combination thereof. This synergistic boost can vastly improve survival outcomes after administration to a subject in need thereof. In certain embodiments, combination therapy with Ad5 [E1-, E2b-] vectors encoding for target epitope antigens and an immunological fusion partner can result in generating an immune response comprises an increase in target antigen-specific CTL activity of about 1.5 to 20, or more fold in a subject administered the adenovirus vectors as compared to a control. In another embodiment, generating an immune response comprises an increase in target-specific CTL activity of about 1.5 to 20, or more fold in a subject administered the Ad5 [E1-, E2b-] vectors encoding for target epitope antigens and an immunological fusion partner as compared to a control. In a further embodiment, generating an immune response that comprises an increase in target antigen-specific cell-mediated immunity activity as measured by ELISpot assays measuring cytokine secretion, such as interferon-gamma (IFN-γ), interleukin-2 (IL-2), tumor necrosis factor-alpha (TNF-α), or other cytokines, of about 1.5 to 20, or more fold as compared to a control. In a further embodiment, generating an immune response comprises an increase in target-specific antibody production of between 1.5 and 5 fold in a subject administered the adenovirus vectors as described herein as compared to an appropriate control. In another embodiment, generating an immune response comprises an increase in target-specific antibody production of about 1.5 to 20, or more fold in a subject administered the adenovirus vector as compared to a control.

In one embodiment, such an immunological fusion partner is derived from a *Mycobacterium* sp., such as a *Mycobacterium tuberculosis*-derived Ra12 fragment. The immunological fusion partner derived from *Mycobacterium* sp. can be any one of the sequences set forth in SEQ ID NO: 38-SEQ ID NO: 46 and SEQ ID NO: 109-SEQ ID NO: 114. Oligonucleotides, Met-His tags, and enterokinase recognition sites, which can be used to construct these *Mycobacterium* sp.-derived Ra12 sequences are set forth in any one of SEQ ID NO: 115-SEQ ID NO: 122, also shown in TABLE 2. Ra12 compositions and methods for their use in enhancing the expression and/or immunogenicity of heterologous polynucleotide/polypeptide sequences are described in U.S. Pat. No. 7,009,042, which is herein incorporated by reference in its entirety. Briefly, Ra12 refers to a polynucleotide region that is a subsequence of a *Mycobacterium tuberculosis* MTB32A nucleic acid. MTB32A is a serine protease of 32 kDa encoded by a gene in virulent and avirulent strains of *M. tuberculosis*. The nucleotide sequence and amino acid sequence of MTB32A have been described (see, e.g., U.S. Pat. No. 7,009,042; Skeiky et al., Infection and Immun. 67:3998-4007 (1999), incorporated herein by reference in their entirety). C-terminal fragments of the MTB32A coding sequence can be expressed at high levels and remain as soluble polypeptides throughout the purification process. Moreover, Ra12 can enhance the immunogenicity of heterologous immunogenic polypeptides with which it is fused. A Ra12 fusion polypeptide can comprise a 14 kDa C-terminal fragment corresponding to amino acid residues 192 to 323 of MTB32A. Other Ra12 polynucleotides generally can comprise at least about 15, 30, 60, 100, 200, 300, or more nucleotides that encode a portion of a Ra12 polypeptide. Ra12 polynucleotides can comprise a native sequence (i.e., an endogenous sequence that encodes a Ra12 polypeptide or a portion thereof) or can comprise a variant of such a sequence. Ra12 polynucleotide variants can contain one or more substitutions, additions, deletions and/or insertions such that the biological activity of the encoded fusion polypeptide is not substantially diminished, relative to a fusion polypeptide comprising a native Ra12 polypeptide. Variants can have at least about 70%, 80%, or 90% identity, or more, to a polynucleotide sequence that encodes a native Ra12 polypeptide or a portion thereof.

In certain aspects, an immunological fusion partner can be derived from protein D, a surface protein of the gram-negative bacterium *Haemophilus influenzae* B. The immunological fusion partner derived from protein D can be the sequence set forth in SEQ ID NO: 47. In some cases, a protein D derivative comprises approximately the first third of the protein (e.g., the first N-terminal 100-110 amino acids). A protein D derivative can be lipidated. Within certain embodiments, the first 109 residues of a Lipoprotein D fusion partner is included on the N-terminus to provide the polypeptide with additional exogenous T-cell epitopes, which can increase the expression level in *E. coli* and can function as an expression enhancer. The lipid tail can ensure optimal presentation of the antigen to antigen presenting cells. Other fusion partners can include the non-structural protein from influenza virus, NS1 (hemagglutinin). Typically, the N-terminal 81 amino acids are used, although different fragments that include T-helper epitopes can be used.

In certain aspects, the immunological fusion partner can be the protein known as LYTA, or a portion thereof (particularly a C-terminal portion). The immunological fusion partner derived from LYTA can be the sequence set forth in SEQ ID NO: 48. LYTA is derived from *Streptococcus pneumoniae*, which synthesizes an N-acetyl-L-alanine amidase known as amidase LYTA (encoded by the LytA gene). LYTA is an autolysin that specifically degrades certain bonds in the peptidoglycan backbone. The C-terminal domain of the LYTA protein is responsible for the affinity to the choline or to some choline analogues such as DEAE. This property can be exploited for the development of *E. coli* C-LYTA expressing plasmids useful for expression of fusion proteins. Purification of hybrid proteins containing the C-LYTA fragment at the amino terminus can be employed. Within another embodiment, a repeat portion of LYTA can be incorporated into a fusion polypeptide. A repeat portion can, for example, be found in the C-terminal region starting at residue 178. One particular repeat portion incorporates residues 188-305.

In some embodiments, the target antigen is fused to an immunological fusion partner, which can also be referred to herein as an "immunogenic component," comprising a cytokine selected from the group of IFN-γ, TNFα, IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, CD27 ligand, CD30 ligand, 4-1BBL, Trail, OPG-L, APRIL, LIGHT, TWEAK, BAFF, TGF-β1, and MIF. The target antigen fusion can produce a protein with substantial identity to one or more of IFN-γ, TNFα IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. The target antigen fusion can encode a nucleic acid encoding a protein with substantial identity to one or more of IFN-γ, TNF=, IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. In some embodiments, the target antigen fusion further comprises one or more immunological fusion partner, which can also be referred to herein as an "immunogenic components," comprising a cytokine selected from the group of IFN-γ, TNFα, IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. The sequence of IFN-γ can be, but is not limited to, a sequence as set forth in SEQ ID NO: 49. The sequence of TNFα can be, but is not limited to, a sequence as set forth in SEQ ID NO: 50. The sequence of IL-2 can be, but is not limited to, a sequence as set forth in SEQ ID NO: 51. The sequence of IL-8 can be, but is not limited to, a sequence as set forth in SEQ ID NO: 52. The sequence of IL-12 can be, but is not limited to, a sequence as set forth in SEQ ID NO: 53. The sequence of IL-18 can be, but is not limited to, a sequence as set forth in SEQ ID NO: 54. The sequence of IL-7 can be, but is not limited to, a sequence as set forth in SEQ ID NO: 55. The sequence of IL-3 can be, but is not limited to, a sequence as set forth in SEQ ID NO: 56. The sequence of IL-4 can be, but is not limited to, a sequence as set forth in SEQ ID NO: 57. The sequence of IL-5 can be, but is not limited to, a sequence as set forth in SEQ ID NO: 58. The sequence of IL-6 can be, but is not limited to, a sequence as set forth in SEQ ID NO: 59. The sequence of IL-9 can be, but is not limited to, a sequence as set forth in SEQ ID NO: 60. The sequence of IL-10 can be, but is not limited to, a sequence as set forth in SEQ ID NO: 61. The sequence of IL-13 can be, but is not limited to, a sequence as set forth in SEQ ID NO: 62. The sequence of IL-15 can be, but is not limited to, a sequence as set forth in SEQ ID NO: 63. The sequence of IL-16 can be, but is not limited to, a sequence as set forth in SEQ ID NO: 90. The sequence of IL-17 can be, but is not limited to, a sequence as set forth in SEQ ID NO: 91. The sequence of IL-23 can be, but is not limited to, a sequence as set forth in SEQ ID NO: 92. The sequence of IL-32 can be, but is not limited to, a sequence as set forth in SEQ ID NO: 93.

In some embodiments, the target antigen is fused or linked to an immunological fusion partner, also referred to herein as an "immunogenic component," comprising a cytokine selected from the group of IFN-γ, TNFα IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. In some embodiments, the target antigen is co-expressed in a cell with an immunological fusion partner, also referred to herein as an "immunogenic component," comprising a cytokine selected from the group of IFN-γ, TNFα IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF.

In some embodiments, the target antigen is fused or linked to an immunological fusion partner, comprising CpG ODN (e.g., Class A, B, or C CpG ODNs; non-limiting examples sequences are shown in SEQ ID NO: 124-SEQ ID NO: 135 in which phosphodiester bases are in capital letters, phosphorothioate bases are in lower case letters, and palindromes are underlined and the colon denotes the reflection point), cholera toxin (a non-limiting example sequence is shown in SEQ ID NO: 65), a truncated A subunit coding region derived from a bacterial ADP-ribosylating exotoxin (a non-limiting example sequence is shown in (a non-limiting example sequence is shown in SEQ ID NO: 66), a truncated B subunit coding region derived from a bacterial ADP-ribosylating exotoxin (a non-limiting example sequence is shown in SEQ ID NO: 67), Hp91 (a non-limiting example sequence is shown in SEQ ID NO: 68), CCL20 (a non-limiting example sequence is shown in SEQ ID NO: 69 and SEQ ID NO: 123), CCL3 (a non-limiting example sequence is shown in SEQ ID NO: 70), GM-CSF (a non-limiting example sequence is shown in SEQ ID NO: 71), G-CSF (a non-limiting example sequence is shown in SEQ ID NO: 72), LPS peptide mimic (non-limiting example sequences are shown in SEQ ID NO: 73-SEQ ID NO: 84), shiga toxin (a non-limiting example sequence is shown in SEQ ID NO: 85), diphtheria toxin (a non-limiting example sequence is shown in SEQ ID NO: 86), or $CRM_{197}$ (a non-limiting example sequence is shown in SEQ ID NO: 89).

In some embodiments, the target antigen is fused or linked to an immunological fusion partner, comprising an IL-15 superagonist. Interleukin 15 (IL-15) is a naturally occurring inflammatory cytokine secreted after viral infections. Secreted IL-15 can carry out its function by signaling via its cognate receptor on effector immune cells, and thus, can lead to overall enhancement of effector immune cell activity.

Based on IL-15's broad ability to stimulate and maintain cellular immune responses, it is believed to be a promising immunotherapeutic drug. However, major limitations in clinical development of IL-15 can include low production yields in standard mammalian cell expression systems and short serum half-life. Moreover, the IL-15:IL-15Ra complex, comprising proteins co-expressed by the same cell, rather than the free IL-15 cytokine, can be responsible for stimulating immune effector cells bearing IL-15 βγc receptor.

To contend with these shortcomings, a novel IL-15 super-agonist mutant (IL-15N72D) was identified that has increased ability to bind IL-15Rβγc and enhanced biological activity. Addition of either mouse or human IL-15Rα and Fc fusion protein (the Fc region of immunoglobulin) to equal molar concentrations of IL-15N72D can provide a further increase in IL-15 biologic activity, such that IL-15N72D:IL-15Rα/Fc super-agonist complex exhibits a median effective concentration (EC50) for supporting IL-15-dependent cell growth that was greater than 10-fold lower than that of free IL-15 cytokine.

In some embodiments, the IL-15 superagonist can be a novel IL-15 superagonist mutant (IL-15N72D). In certain embodiments, addition of either mouse or human IL-15Rα and Fc fusion protein (the Fc region of immunoglobulin) to equal molar concentrations of IL-15N72D can provide a further increase in IL-15 biologic activity, such that IL-15N72D:IL-15Rα/Fc super-agonist complex exhibits a median effective concentration ($EC_{50}$) for supporting IL-15-dependent cell growth that can be greater than 10-fold lower than that of free IL-15 cytokine Thus, in some embodiments, the present disclosure provides a IL-15N72D:IL-15Rα/Fc super-agonist complex with an EC50 for supporting IL-15-dependent cell growth that is greater than 2-fold lower, greater than 3-fold lower, greater than 4-fold lower, greater than 5-fold lower, greater than 6-fold lower, greater than 7-fold lower, greater than 8-fold lower, greater than 9-fold lower, greater than 10-fold lower, greater than 15-fold lower, greater than 20-fold lower, greater than 25-fold lower, greater than 30-fold lower, greater than 35-fold lower, greater than 40-fold lower, greater than 45-fold lower, greater than 50-fold lower, greater than 55-fold lower, greater than 60-fold lower, greater than 65-fold lower, greater than 70-fold lower, greater than 75-fold lower, greater than 80-fold lower, greater than 85-fold lower, greater than 90-fold lower, greater than 95-fold lower, or greater than 100-fold lower than that of free IL-15 cytokine.

In some embodiments, the IL-15 super agonist is a biologically active protein complex of two IL-15N72D molecules and a dimer of soluble IL-15Rα/Fc fusion protein, also known as ALT-803. The composition of ALT-803 and methods of producing and using ALT-803 are described in U.S. Patent Application Publication 2015/0374790, which is herein incorporated by reference. It is known that a soluble IL-15Rα fragment, containing the so-called "sushi" domain at the N terminus (Su), can bear most of the structural elements responsible for high affinity cytokine binding. A soluble fusion protein can be generated by linking the human IL-15RαSu domain (amino acids 1-65 of the mature human IL-15Rα protein) with the human IgG1 CH2-CH3 region containing the Fc domain (232 amino acids). This IL-15RαSu/IgG1 Fc fusion protein can have the advantages of dimer formation through disulfide bonding via IgG1 domains and ease of purification using standard Protein A affinity chromatography methods.

In some embodiments, ALT-803 can have a soluble complex consisting of 2 protein subunits of a human IL-15 variant associated with high affinity to a dimeric IL-15Rα sushi domain/human IgG1 Fc fusion protein. The IL-15 variant is a 114 amino acid polypeptide comprising the mature human IL-15 cytokine sequence with an Asn to Asp substitution at position 72 of helix C N72D). The human IL-15R sushi domain/human IgG1 Fc fusion protein comprises the sushi domain of the IL-15R subunit (amino acids 1-65 of the mature human IL-15Rα protein) linked with the human IgG1 CH2-CH3 region containing the Fc domain (232 amino acids). Aside from the N72D substitution, all of the protein sequences are human. Based on the amino acid sequence of the subunits, the calculated molecular weight of the complex comprising two IL-15N72D polypeptides (an example IL-15N72D sequence is shown in SEQ ID NO: 87) and a disulfide linked homodimeric IL-15RαSu/IgG1 Fc protein (an example IL-15RαSu/Fc domain is shown in SEQ ID NO: 88) is 92.4 kDa. In some embodiments, a recombinant vector encoding for a target antigen and for ALT-803 can have any sequence described herein to encode for the target antigen and can have SEQ ID NO: 87, SEQ ID NO: 87, SEQ ID NO: 88, and SEQ ID NO: 88, in any order, to encode for ALT-803.

Each IL-15N720 polypeptide can have a calculated molecular weight of approximately 12.8 kDa and the IL-15RαSu/IgG 1 Fc fusion protein can have a calculated molecular weight of approximately 33.4 kDa. Both the IL-15N72D and IL-15RαSu/IgG 1 Fc proteins can be glycosylated resulting in an apparent molecular weight of ALT-803 of approximately 114 kDa by size exclusion chromatography. The isoelectric point (pI) determined for ALT-803 can range from approximately 5.6 to 6.5. Thus, the fusion protein can be negatively charged at pH 7.

Combination therapy with Ad5 [E1-, E2b-] vectors encoding for a Zika virus antigen and ALT-803 can result in boosting the immune response, such that the combination of both therapeutic moieties acts to synergistically boost the immune response more than either therapy alone. For example, combination therapy with Ad5 [E1-, E2b-] vectors encoding for Zika virus antigens and ALT-803 can result in synergistic enhancement of stimulation of antigen-specific effector CD4+ and CD8+ T cells, stimulation of NK cell response directed towards killing infected cells, stimulation of neutrophils or monocyte cell responses directed towards killing infected cells via antibody dependent cell-mediated cytotoxicity (ADCC), or antibody dependent cellular phagocytosis (ADCP) mechanisms. Combination therapy with Ad5 [E1-, E2b-] vectors encoding for Zika virus antigens and ALT-803 can synergistically boost any one of the above responses, or a combination of the above responses, to vastly improve survival outcomes after administration to a subject in need thereof.

Any of the immunogenicity enhancing agents described herein can be fused or linked to a target antigen by expressing the immunogenicity enhancing agents and the target antigen in the same recombinant vector, using any recombinant vector described herein.

Nucleic acid sequences that encode for such immunogenicity enhancing agents can comprise a nucleic acid sequence encoding for any one of SEQ ID NO: 38-SEQ ID NO: 63, SEQ ID NO: 65-SEQ ID NO: 93 and SEQ ID NO: 109-SEQ ID NO: 135 are summarized in TABLE 1.

TABLE 1

Sequences of Immunological Fusion Partners

| SEQ ID NO | Sequence |
|---|---|
| SEQ ID NO: 38 | TAASDNFQLSQGGQGFAIPIGQAMAIAGQIRSGGGSPTVHIGPTAFLGL<br>GVVDNNGNGARVQRVVGSAPAASLGISTGDVITAVDGAPINSATAM<br>ADALNGHHPGDVISVTWQTKSGGTRTGNVTLAEGPPA |
| SEQ ID NO: 39 | MHHHHHHTAASDNFQLSQGGQGFAIPIGQAMAIAGQIRSGGGSPTVHI<br>GPTAFLGLGVVDNNGNGARVQRVVGSAPAASLGISTGDVITAVDGAP<br>INSATAMADALNGHHPGDVISVTWQTKSGGTRTGNVTLAEGPPAEFD<br>DDDKDPPDPHQPDMTKGYCPGGRWGFGDLAVCDGEKYPDGSFWHQ<br>WMQTWFTGPQFYFDCVSGGEPLPGPPPPGGCGGAIPSEQPNAP |
| SEQ ID NO: 40 | MHHHHHHTAASDNFQLSQGGQGFAIPIGQAMAIAGQIRSGGGSPTVHI<br>GPTAFLGLGVVDNNGNGARVQRVVGSAPAASLGISTGDVITAVDGAP<br>INSATAMADALNGHHPGDVISVTWQTKSGGTRTGNVTLAEGPPAEFP<br>LVPRGSPMGSDVRDLNALLPAVPSLGGGGGCALPVSGAAQWAPVLD<br>FAPPGASAYGSLGGPAPPPAPPPPPPPPPHSFIKQEPSWGGAEPHEEQC<br>LSAFTVHFSGQFTGTAGACRYGPFGPPPPSQASSGQARMFPNAPYLPS<br>CLESQPAIRNQGYSTVTFDGTPSYGHTPSHHAAQFPNHSFKHEDPMG<br>QQGSLGEQQYSVPPPVYGCHTPTDSCTGSQALLLRTPYSSDNLYQMT<br>SQLECMTWNQMNLGATLKGHSTGYESDNHTTPILCGAQYRIHTHGV<br>FRGIQDVRRVPGVAPTLVRSASETSEKRPFMCAYSGCNKRYFKLSHL<br>QMHSRKHTGEKPYQCDFKDCERRFFRSDQLKRHQRRHTGVKPFQCK<br>TCQRKFSRSDHLKTHTRTHTGEKPFSCRWPSCQKKFARSDELVRHHN<br>MHQRNMTKLQLAL |
| SEQ ID NO: 41 | MHHHHHHTAASDNFQLSQGGQGFAIPIGQAMAIAGQIRSGGGSPTVHI<br>GPTAFLGLGVVDNNGNGARVQRVVGSAPAASLGISTGDVITAVDGAP<br>INSATAMADALNGHHPGDVISVTWQTKSGGTRTGNVTLAEGPPAEFI<br>EGRGSGCPLLENVISKTINPQVSKTEYKELLQEFIDDNATTNAIDELKE<br>CFLNQTDETLSNVEVFMQLIYDSSLCDLF |
| SEQ ID NO: 42 | MHHHHHHTAASDNFQLSQGGQGFAIPIGQAMAIAGQIRSGGGSPTVHI<br>GPTAFLGLGVVDNNGNGARVQRVVGSAPAASLGISTGDVITAVDGAP<br>INSATAMADALNGHHPGDVISVTWQTKSGGTRTGNVTLAEGPPAEF<br>MVDFGALPPEINSARMYAGPGSASLVAAAQMWDSVASDLFSAASAF<br>QSVVWGLTVGSWIGSSAGLMVAAASPYVAWMSVTAGQAELTAAQV<br>RVAAAAYETAYGLTVPPPVIAENRAELMILIATNLLGQNTPAIAVNEA<br>EYGEMWAQDAAAMFGYAAATATATATLLPFEEAPEMTSAGGLLEQ<br>AAAVEEASDTAAANQLMNNVPQALQQLAQPTQGTTPSSKLGGLWKT<br>VSPHRSPISNMVSMANNHMSMTNSGVSMTNTLSSMLKGFAPAAAAQ<br>AVQTAAQNGVRAMSSLGSSLGSSGLGGGVAANLGRAASVGSLSVPQ<br>AWAAANQAVTPAARALPLTSLTSAAERGPGQMLGGLPVGQMGARA<br>GGGLSGVLRVPPRPYVMPHSPAAGDIAPPALSQDRFADFPALPLDPSA<br>MVAQVGPQVVNINTKLGYNNAVGAGTGIVIDPNGVVLTNNHVIAGA<br>TDINAFSVGSGQTYGVDVVGYDRTQDVAVLQLRGAGGLPSAAIGGG<br>VAVGEPVVAMGNSGGQGGTPRAVPGRVVALGQTVQASDSLTGAEET<br>LNGLIQFDAAIQPGDSGGPVVNGLGQVVGMNTAAS |
| SEQ ID NO: 43 | TAASDNFQLSQGGQGFAIPIGQAMAIAGQI |
| SEQ ID NO: 44 | TAASDNFQLSQGGQGFAIPIGQAMAIAGQIKLPTVHIGPTAFLGLGVV<br>DNNGNGARVQRVVGSAPAASLGISTGDVITAVDGAPINSATAMADAL<br>NGHHPGDVISVTWQTKSGGTRTGNVTLAEGPPA |
| SEQ ID NO: 45 | TAASDNFQLSQGGQGFAIPIGQAMAIAGQIRSGGGSPTVHIGPTAFLGL<br>GVVDNNGNGARVQRVVGSAPAASLGISTGDVITAVDGAPINSATAM<br>ADALNGHHPGDVISVTWQTKSGGTRTGNVTLAE |
| SEQ ID NO: 46 | MSNSRRRSLRWSWLLSVLAAVGLGLATAPAQAAPPALSQDRFADFP<br>ALPLDPSAMVAQVGPQVVNINTKLGYNNAVGAGTGIVIDPNGVVLTN<br>NHVIAGATDINAFSVGSGQTYGVDVVGYDRTQDVAVLQLRGAGGLP<br>SAAIGGGVAVGEPVVAMGNSGGQGGTPRAVPGRVVALGQTVQASDS<br>LTGAEETLNGLIQFDAAIQPGDSGGPVVNGLGQVVGMNTAASDNFQL<br>SQGGQGFAIPIGQAMAIAGQIRSGGGSPTVHIGPTAFLGLGVVDNNGN<br>GARVQRVVGSAPAASLGISTGDVITAVDGAPINSATAMADALNGHHP<br>GDVISVTWQTKSGGTRTGNVTLAEGPPA |
| SEQ ID NO: 47 | MKLKTLALSLLAAGVLAGCSSHSSNMANTQMKSDKIIIAHRGASGYL<br>PEHTLESKALAFAQQADYLEQDLAMTKDGRLVVIHDHFLDGLTDVA<br>KKFPHRHRKDGRYYVIDFTLKEIQSLEMTENFETKDGKQAQVYPNRF<br>PLWKSHFRIHTFEDEIEFIQGLEKSTGKKVGIYPEIKAPWFHHQNGKDI<br>AAETLKVLKKYGYDKKTDMVYLQTFDFNELKRIKTELLPQMGMDLK<br>LVQLIAYTDWKETQEKDPKGYWVNYNYDWMFKPGAMAEVVKYAD<br>GVGPGWYMLVNKEESKPDNIVYTPLVKELAQYNVEVHPYTVRKDAL<br>PAFFTDVNQMYDVLLNKSGATGVFTDFPDTGVEFLKGIK |

TABLE 1-continued

Sequences of Immunological Fusion Partners

| SEQ ID NO | Sequence |
| --- | --- |
| SEQ ID NO: 48 | MEINVSKLRTDLPQVGVQPYRQVHAHSTGNPHSTVQNEADYHWRKD<br>PELGFFSHIVGNGCIMQVGPVDNGAWDVGGGWNAETYAAVELIESH<br>STKEEFMTDYRLYIELLRNLADEAGLPKTLDTGSLAGIKTHEYCTNNQ<br>PNNHSDHVDPYPYLAKWGISREQFKHDIENGLTIETGWQKNDTGYW<br>YVHSDGSYPKDKFEKINGTWYYFDSSGYMLADRWRKHTDGNWYWF<br>DNSGEMATGWKKIADKWYYFNEEGAMKTGWVKYKDTWYYLDAK<br>EGAMVSNAFIQSADGTGWYYLKPDGTLADRPEFRMSQMA |
| SEQ ID NO: 49 | MKYTSYILAFQLCIVLGSLGCYCQDPYVKEAENLKKYFNAGHSDVAD<br>NGTLFLGILKNWKEESDRKIMQSQIVSFYFKLFKNFKDDQSIQKSVETI<br>KEDMNVKFFNSNKKKRDDFEKLTNYSVTDLNVQRKAIHELIQVMAE<br>LSPAAKTGKRKRSQMLFRGRRASQ |
| SEQ ID NO: 50 | MSTESMIRDVELAEEEALPKKTGGPQGSRRCLFLSLFSFLIVAGATTLFC<br>LLHFGVIGPQREEFPRDLSLISPLAQAVRSSSRTPSDKPVAHVVANPQA<br>EGQLQWLNRRANALLANGVELRDNQLVVPSEGLYLIYSQVLFKGQG<br>CPSTHVLLTHTISRIAVSYQTKVNLLSAIKSPCQRETPEGAEAKPWYEP<br>IYLGGVFQLEKGDRLSAEINRPDYLDFAESGQVYFGIIAL |
| SEQ ID NO: 51 | MYRMQLLSCIALSLALVTNSAPTSSSTKKTQLQLEHLLLDLQMILNGI<br>NNYKNPKLTRMLTFKFYMPKKATELKHLQCLEEELKPLEEVLNLAQS<br>KNFHLRPRDLISNINVIVLELKGSETTFMCEYADETATIVEFLNRWITF<br>CQSIISTLT |
| SEQ ID NO: 52 | MTSKLAVALLAAFLISAALCEGAVLPRSAKELRCQCIKTYSKPFHPKFI<br>KELRVIESGPHCANTEIIVKLSDGRELCLDPKENWVQRVVEKFLKRAE<br>NS |
| SEQ ID NO: 53 | MEPLVTWVVPLLFLFLLSRQGAACRTSECCFQDPPYPDADSGSASGPR<br>DLRCYRISSDRYECSWQYEGPTAGVSHFLRCCLSSGRCCYFAAGSAT<br>RLQFSDQAGVSVLYTVTLWVESWARNQTEKSPEVTLQLYNSVKYEPP<br>LGDIKVSKLAGQLRMEWETPDNQVGAEVQFRHRTPSSPWKLGDCGP<br>QDDDTESCLCPLEMNVAQEFQLRRRQLGSQGSSWSKWSSPVCVPPEN<br>PPQPQVRFSVEQLGQDGRRRLTLKEQPTQLELPEGCQGLAPGTEVTYR<br>LQLHMLSCPCKAKATRTLHLGKMPYLSGAAYNVAVISSNQFGPGLN<br>QTWHIPADTHTEPVALNISVGTNGTTMYWPARAQSMTYCIEWQPVG<br>QDGGLATCSLTAPQDPDPAGMATYSWSRESGAMGQEKCYYITIFASA<br>HPEKLTLWSTVLSTYHFGGNASAAGTPHHVSVKNHSLDSVSVDWAP<br>SLLSTCPGVLKEYVVRCRDEDSKQVSEHPVQPTETQVTLSGLRAGVA<br>YTVQVRADTAWLRGVWSQPQRFSIEVQVSDWLIFFASLGSFLSILLVG<br>VLGYLGLNRAARHLCPPLPTPCASSAIEFPGGKETWQWINPVDFQEEA<br>SLQEALVVEMSWDKGERTEPLEKTELPEGAPELALDTELSLEDGDRC<br>KAKM |
| SEQ ID NO: 54 | MAAEPVEDNCINFVAMKFIDNTLYFIAEDDENLESDYFGKLESKLSVI<br>RNLNDQVLFIDQGNRPLFEDMTDSDCRDNAPRTIFIISMYKDSQPRGM<br>AVTISVKCEKISTLSCENKIISFKEMNPPDNIKDTKSDIIFFQRSVPGHDN<br>KMQFESSSYEGYFLACEKERDLFKLILKKEDELGDRSIMFTVQNED |
| SEQ ID NO: 55 | MFHVSFRYIFGLPPLILVLLPVASSDCDIEGKDGKQYESVLMVSIDQLL<br>DSMKEIGSNCLNNEFNFFKRHICDANKEGMFLFRAARKLRQFLKMNS<br>TGDFDLHLLKVSEGTTILLNCTGQVKGRKPAALGEAQPTKSLEENKSL<br>KEQKKLNDLCFLKRLLQEIKTCWNKILMGTKEH |
| SEQ ID NO: 56 | MSRLPVLLLLQLLVRPGLQAPMTQTTSLKTSWVNCSNMIDEIITHLKQ<br>PPLPLLDFNNLNGEDQDILMENNLRRPNLEAFNRAVKSLQNASAIESIL<br>KNLLPCLPLATAAPTRHPIHIKDGDWNEFRRKLTFYLKTLENAQAQQT<br>TLSLAIF |
| SEQ ID NO: 57 | MGLTSQLLPPLFFLLACAGNFVHGHKCDITLQEIIKTLNSLTEQKTLCT<br>ELTVTDIFAASKNTTEKETFCRAATVLRQFYSHHEKDTRCLGATAQQF<br>HRHKQLIRFLKRLDRNLWGLAGLNSCPVKEANQSTLENFLERLKTIM<br>REKYSKCSS |
| SEQ ID NO: 58 | MRMLLHLSLLALGAAYVYAIPTEIPTSALVKETLALLSTHRTLLIANET<br>LRIPVPVHKNHQLCTEEIFQGIGTLESQTVQGGTVERLFKNLSLIKKYI<br>DGQKKKCGEERRRVNQFLDYLQEFLGVMNTEWIIES |
| SEQ ID NO: 59 | MNSFSTSAFGPVAFSLGLLLVLPAAFPAPVPPGEDSKDVAAPHRQPLT<br>SSERIDKQIRYILDGISALRKETCNKSNMCESSKEALAENNLNLPKMA<br>EKDGCFQSGFNEETCLVKIITGLLEFEVYLEYLQNRFESSEEQARAVQ<br>MSTKVLIQFLQKKAKNLDAITTPDPTTNASLLTKLQAQNQWLQDMTT<br>HLILRSFKEFLQSSLRALRQM |

TABLE 1-continued

Sequences of Immunological Fusion Partners

| SEQ ID NO | Sequence |
|---|---|
| SEQ ID NO: 60 | MVLTSALLLCSVAGQGCPTLAGILDINFLINKMQEDPASKCHCSANVT<br>SCLCLGIPSDNCTRPCFSERLSQMTNTTMQTRYPLIFSRVKKSVEVLKN<br>NKCPYFSCEQPCNQTTAGNALTFLKSLLEIFQKEKMRGMRGKI |
| SEQ ID NO: 61 | MHSSALLCCLVLLTGVRASPGQGTQSENSCTHFPGNLPNMLRDLRDA<br>FSRVKTFFQMKDQLDNLLLKESLLEDFKGYLGCQALSEMIQFYLEEV<br>MPQAENQDPDIKAHVNSLGENLKTLRLRLRRCHRFLPCENKSKAVEQ<br>VKNAFNKLQEKGIYKAMSEFDIFINYIEAYMTMKIRN |
| SEQ ID NO: 62 | MALLLTTVIALTCLGGFASPGPVPPSTALRELIEELVNITQNQKAPLCN<br>GSMVWSINLTAGMYCAALESLINVSGCSAIEKTQRMLSGFCPHKVSA<br>GQFSSLHVRDTKIEVAQFVKDLLLHLKKLFREGQFNRNFESIIICRDRT |
| SEQ ID NO: 63 | MDFQVQIFSFLLISASVIMSRANWVNVISDLKKIEDLIQSMHIDATLYT<br>ESDVHPSCKVTAMKCFLLELQVISLESGDASIHDTVENLIILANNSLSS<br>NGNVTESGCKECEELEEKNIKEFLQSFVHIVQMFINTS |
| SEQ ID NO: 65 | MIKLKFGVFFTVLLSSAYAHGTPQNITDLCAEYHNTQIYTLNDKIFSYT<br>ESLAGKREMAIITFKNGAIFQVEVPGSQHIDSQKKAIERMKDTLRIAYL<br>TEAKVEKLCVWNNKTPHAIAAISMAN |
| SEQ ID NO: 66 | MVKIIFVFFIFLSSFSYANDDKLYRADSRPPDEIKQSGGLMPRGQNEYF<br>DRGTQMNINLYDHARGTQTGFVRHDDGYVSTSISLRSAHLVGQTILS<br>GHSTYYIYVIATAPNMFNVNDVLGAYSPHPDEQEVSALGGIPYSQIYG<br>WYRVHFGVLDEQLHRNRGYRDRYYSNLDIAPAADGYGLAGFPPEHR<br>AWREEPWIHHAPPGCGNAPRSSMSNTCDEKTQSLGVKFLDEYQSKV<br>KRQIFSGYQSDIDTHNRIKDEL |
| SEQ ID NO: 67 | MIKLKFGVFFTVLLSSAYAHGTPQNITDLCAEYHNTQIHTLNDKILSYT<br>ESLAGNREMAIITFKNGATFQVEVPGSQHIDSQKKAIERMKDTLRIAY<br>LTEAKVEKLCVWNNKTPHAIAAISMAN |
| SEQ ID NO: 68 | DPNAPKRPPSAFFLFCSE |
| SEQ ID NO: 69 | MCCTKSLLLAALMSVLLLHLCGESEAASNFDCCLGYTDRILHPKFIVG<br>FTRQLANEGCDINAIIFHTKKKLSVCANPKQTWVKYIVRLLSKKVKN<br>M |
| SEQ ID NO: 70 | MQVSTAALAVLLCTMALCNQFSASLAADTPTACCFSYTSRQIPQNFIA<br>DYFETSSQCSKPGVIFLTKRSRQVCADPSEEWVQKYVSDLELSA |
| SEQ ID NO: 71 | MWLQSLLLLGTVACSISAPARSPSPSTQPWEHVNAIQEARRLLNLSRD<br>TAAEMNETVEVISEMFDLQEPTCLQTRLELYKQGLRGSLTKLKGPLT<br>MMASHYKQHCPPTPETSCATQIITFESFKENLKDFLLVIPFDCWEPVQE |
| SEQ ID NO: 72 | MAGPATQSPMKLMALQLLLWHSALWTVQEATPLGPASSLPQSFLLK<br>CLEQVRKIQGDGAALQEKLCATYKLCHPEELVLLGHSLGIPWAPLSSC<br>PSQALQLAGCLSQLHSGLFLYQGLLQALEGISPELGPTLDTLQLDVAD<br>FATTIWQQMEELGMAPALQPTQGAMPAFASAFQRRAGGVLVASHLQ<br>SFLEVSYRVLRHLAQP |
| SEQ ID NO: 73 | QEINSSY |
| SEQ ID NO: 74 | SHPRLSA |
| SEQ ID NO: 75 | SMPNPMV |
| SEQ ID NO: 76 | GLQQVLL |
| SEQ ID NO: 77 | HELSVLL |
| SEQ ID NO: 78 | YAPQRLP |
| SEQ ID NO: 79 | TPRTLPT |
| SEQ ID NO: 80 | APVHSSI |
| SEQ ID NO: 81 | APPHALS |
| SEQ ID NO: 82 | TFSNRFI |
| SEQ ID NO: 83 | VVPTPPY |
| SEQ ID NO: 84 | ELAPDSP |

TABLE 1-continued

Sequences of Immunological Fusion Partners

| SEQ ID NO | Sequence |
|---|---|
| SEQ ID NO: 85 | TPDCVTGKVEYTKYNDDDTFTVKVGDKELFTNRWNLQSLLLSAQITG<br>MTVTIKQNACHNGGGFSEVIFR |
| SEQ ID NO: 86 | MSRKLFASILIGALLGIGAPPSAHAGADDVVDSSKSFVMENFSSYHGT<br>KPGYVDSIQKGIQICPKSGTQGNYDDDWKGFYSTDNKYDAAGYSVDN<br>ENPLSGKAGGVVKVTYPGLTKVLALKVDNAETIKKELGLSLTEPLME<br>QVGTEEFIKRFGDASRVVLSLPFAEGSSSVEYINNWEQAKALSVELEI<br>NFETRGKRGQDAMYEYMAQACAGNRVRRSVGSSLSCINLDWDVIRD<br>KTKTKIESLKEHGPIKNKMSESPNKTVSEEKAKQYLEEFHQTALEHPE<br>LSELKTVTGTNPVFAGANYAAWAVNVAQVIDSETADNLEKTTAALSI<br>LPGIGSVMGIADGAVHHNTEEIVAQSIALSSLMVAQAIPLVGELVDIGF<br>AAYNFVESIINLFQVVHNSYNRPAYSPGHKTQPFLHDGYAVSWNTVE<br>DSIIRTGFQGESGHDIKITAENTPLPIAGVLLPTIPGKLDVNKSKTHISVN<br>GRKIRMRCRAIDGDVTFCRPKSPVYVGNGVHANLHVAFHRSSSEKIH<br>SNEISSDSIGVLGYQKTVDHTKVNSKLSLFFEIKS |
| SEQ ID NO: 87 | NWVNVISDLKKIEDLIQSMHIDATLYTESDVHPSCKVTAMKCFLLELQ<br>VISLESGDASIHDTVENLIILANDSLSSNGNVTESGCKECEELEEKNIKE<br>FLQSFVHIVQMFINTS |
| SEQ ID NO: 88 | ITCPPPMSVEHADIWVKSYSLYSRERYICNSGFKRKAGTSSLTECVLN<br>KATNVAHWTTPSLKCIREPKSCDKTHTCPPCPAPELLGGPSVFLFPPKP<br>KDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHN<br>HYTQKSLSLSPGK |
| SEQ ID NO: 89 | GADDVVDSSKSFVMENFSSYHGTKPGYVDSIQKGIQKPKSGTQGNYD<br>DDWKEFYSTDNKYDAAGYSVDNENPLSGKAGGVVKVTYPGLTKVL<br>ALKVDNAETIKKELGLSLTEPLMEQVGTEEFIKRFGDASRVVLSLPF<br>AEGSSSVEYINNWEQAKALSVELEINFETRGKRGQDAMYEYMAQAC<br>AGNRVRRSVGSSLSCINLDWDVIRDKTKTKIESLKEHGPIKNKMSESP<br>NKTVSEEKAKQYLEEFHQTALEHPELSELKTVTGTNPVFAGANYAA<br>WAVNVAQVIDSETADNLEKTTAALSILPGIGSVMGIADGAVHHNTEEI<br>VAQSIALSSLMVAQAIPLVGELVDIGFAAYNFVESIINLFQVVHNSYNR<br>PAYSPGHKTQPFLHDGYAVSWNTVEDSIIRTGFQGESGHDIKITAENTP<br>LPIAGVLLPTIPGKLDVNKSKTHISVNGRKIRMRCRAIDGDVTFCRPKS<br>PVYVGNGVHANLHVAFHRSSSEKIHSNEISSDSIGVLGYQKTVDHTKV<br>NSKLSLFFEIKS |
| SEQ ID NO: 90 | MESHSRAGKSRKSAKFRSISRSLMLCNAKTSDDGSSPDEKYPDPFEISL<br>AQGKEGIFHSSVQLADTSEAGPSSVPDLALASEAAQLQAAGNDRGKT<br>CRRIFFMKESSTASSREKPGKLEAQSSNFLFPKACHQRARSNSTSVNPY<br>CTREIDFPMTKKSAAPTDRQPYSLCSNRKSLSQQLDCPAGKAAGTSRP<br>TRSLSTAQLVQPSGGLQASVISNIVLMKGQAKGLGFSIVGGKDSIYGPI<br>GIYVKTIFAGGAAAADGRLQEGDEILELNGESMAGLTHQDALQKFKQ<br>AKKGLLTLTVRTRLTAPPSLCSHLSPPLCRSLSSSTCITKDSSSFALESPS<br>APISTAKPNYRIMVEVSLQKEAGVGLGIGLCSVPYFQCISGIFVHTLSP<br>GSVAHLDGRLRCGDEIVEISDSPVHCLTLNEVYTILSRCDPGPVPIIVSR<br>HPDPQVSEQQLKEAVAQAVENTKFGKERHQWSLEGVKRLESSWHGR<br>PTLEKEREKNSAPPHRRAQKVMIRSSSDSSYMSGSPGGSPGSGSAEKP<br>SSDVDISTHSPSLPLAREPVVLSIASSRLPQESPPLPESRDSHPPLRLKKS<br>FEILVRKPMSSKPKPPPRKYFKSDSDPQKSLEERENSSCSSGHTPPTCG<br>QEARELLPLLLPQEDTAGRSPSASAGCPGPGIGPQTKSSTEGEPGWRR<br>ASPVTQTSPIKHPLLKRQARMDYSFDTTAEDPWVRISDCIKNLFSPIMS<br>ENHGHMPLQPNASLNEEEGTQGHPDGTPPKLDTANGTPKVYKSADSS<br>TVKKGPPVAPKPAWFRQSLKGLRNRASDPRGLPDPALSTQPAPASRE<br>HLGSHIRASSSSSSIRQRISSFETFGSSQLPDKGAQRLSLQPSSGEAAKP<br>LGKHEEGRFSGLLGRGAAPTLVPQQPEQVLSSGSPAASEARDPGVSES<br>PPPGRQPNQKTLPPGPDPLLRLLSTQAEESQGPVLKMPSQRARSFPLTR<br>SQSCETKLLDEKTSKLYSISSQVSSAVMKSLLCLPSSISCAQTPCIPKEG<br>ASPTSSSNEDSAANGSAETSALDTGFSLNLSELREYTEGLTEAKEDDD<br>GDHSSLQSGQSVISLLSSEELKKLIEEVKVLDEATLKQLDGIHVTILHK<br>EEGAGLGFSLAGGADLENKVITVHRVFPNGLASQEGTIQKGNEVLSIN<br>GKSLKGTTHHDALAILRQAREPRQAVIVTRKLTPEAMPDLNSSTDSAA<br>SASAASDVSVESTEATVCTVTLEKMSAGLGFSLEGGKGSLHGDKPLTI<br>NRIFKGAASEQSETVQPGDEILQLGGTAMQGLTRFEAWNIIKALPDGP<br>VTIVIRRKSLQSKETTAAGDS |
| SEQ ID NO: 91 | MTPGKTSLVSLLLLLSLEAIVKAGITIPRNPGCPNSEDKNFPRTVMVNL<br>NIHNRNTNTNPKRSSDYYNRSTSPWNLHRNEDPERYPSVIWEAKCRH<br>LGCINADGNVDYHMNSVPIQQEILVLRREPPHCPNSFRLEKILVSVGCT<br>CVTPIVHHVA |

TABLE 1-continued

Sequences of Immunological Fusion Partners

| SEQ ID NO | Sequence |
|---|---|
| SEQ ID NO: 92 | RAVPGGSSPAWTQCQQLSQKLCTLAWSAHPLVGHMDLREEGDEETT NDVPHIQCGDGCDPQGLRDNSQFCLQRIHQGLIFYEKLLGSDIFTGEPS LLPDSPVGQLHASLLGLSQLLQPEGHHWETQQIPSLSPSQPWQRLLLR FKILRSLQAFVAVAARVFAHGAATLSPIWELKKDVYVVELDWYPDAP GEMVVLTCDTPEEDGITWTLDQSSEVLGSGKTLTIQVKEFGDAGQYT CHKGGEVLSHSLLLLHKKEDGIWSTDILKDQKEPKNKTFLRCEAKNY SGRFTCWWLTTISTDLTFSVKSSRGSSDPQGVTCGAATLSAERVRGDN KEYEYSVECQEDSACPAAEESLPIEVMVDAVHKLKYENYTSSFFIRDII KPDPPKNLQLKPLKNSRQVEVSWEYPDTWSTPHSYFSLTFCVQVQGK SKREKKDRVFTDKTSATVICRKNASISVRAQDRYYSSSWSEWASVPC S |
| SEQ ID NO: 93 | MCFPKVLSDDMKKLKARMVMLLPTSAQGLGAWVSACDTEDTVGHL GPWRDKDPALWCQLCLSSQHQAIERFYDKMQNAESGRGQVMSSLAE LEDDFKEGYLETVAAYYEEQHPELTPLLEKERDGLRCRGNRSPVPDV EDPATEEPGESFCDKVMRWFQAMLQRLQTWWHGVLAWVKEKVVA LVHAVQALWKQFQSFCCSLSELFMSSFQSYGAPRGDKEELTPQKCSE PQSSK |
| SEQ ID NO: 109 | GACTACGTTGGTGTAGAAAAATCCTGCCGCCCGGACCCTTAAGGC TGGGACAATTTCTGATAGCTACCCCGACACAGGAGGTTACGGGAT GAGCAATTCGCGCCGCCGCTCACTCAGGTGGTCATGGTTGCTGAGC GTGCTGGCTGCCGTCGGGCTGGGCCTGGCCACGGCGCCGGCCCAG GCGGCCCCGCCGGCCTTGTCGCAGGACCGGTTCGCCGACTTCCCCG CGCTGCCCCTCGACCCGTCCGCGATGGTCGCCCAAGTGGGGCCAC AGGTGGTCAACATCAACACCAAACTGGGCTACAACAACGCCGTGG GCGCCGGGACCGGCATCGTCATCGATCCCAACGGTGTCGTGCTGA CCAACAACCACGTGATCGCGGGCGCCACCGACATCAATGCGTTCA GCGTCGGCTCCGGCCAAACCTACGGCGTCGATGTGGTCGGGTATG ACCGCACCCAGGATGTCGCGGTGCTGCAGCTGCGCGGTGCCGGTG GCCTGCCGTCGGCGGCGATCGGTGGCGGCGTCGCGGTTGGTGAGC CCGTCGTCGCGATGGGCAACAGCGGTGGGCAGGGCGGAACGCCCC GTGCGGTGCCTGGCAGGGTGGTCGCGCTCGGCCAAACCGTGCAGG CGTCGGATTCGCTGACCGGTGCCGAAGAGACATTGAACGGGTTGA TCCAGTTCGATGCCGCGATCCAGCCCGGTGATTCGGGCGGGCCCGT CGTCAACGGCCTAGGACAGGTGGTCGGTATGAACACGGCCGCGTC CGATAACTTCCAGCTGTCCCAGGGTGGGCAGGGATTCGCCATTCCG ATCGGGCAGGCGATGGCGATCGCGGGCCAGATCCGATCGGGTGGG GGGTCACCCACCGTTCATATCGGGCCTACCGCCTTCCTCGGCTTGG GTGTTGTCGACAACAACGGCAACGGCGCACGAGTCCAACGCGTGG TCGGGAGCGCTCCGGCGGCAAGTCTCGGCATCTCCACCGGCGACG TGATCACCGCGGTCGACGGCGCTCCGATCAACTCGGCCACCGCGA TGGCGGACGCGCTTAACGGGCATCATCCCGGTGACGTCATCTCGGT GACCTGGCAAACCAAGTCGGGCGGCACGCGTACAGGGAACGTGAC ATTGGCCGAGGGACCCCCGGCCTGATTTCGTCGCGGATACCACCC GCCGGCCGGCCAATTGGATTGGCGCCAGCCGTGATTGCCGCGTGA GCCCCCGAGTTCCGTCTCCCGTGCGCGTGGCATCGTGGAAGCAATG AACGAGGCAGAACACAGCGTCGAGCACCCTCCCGTGCAGGGCAGT CACGTCGAAGGCGGTGTGGTCGAGCATCCGGATGCCAAGGACTTC GGCAGCGCCGCCGCCCTGCCCGCCGATCCGACCTGGTTTAAGCAC GCCGTCTTCTACGAGGTGCTGGTCCGGGCGTTCTTCGACGCCAGCG CGGACGGTTCCGGCGATCTGCGTGGACTCATCGATCGCCTCGACTA CCTGCAGTGGCTTGGCATCGACTGCATCTGGTTGCCGCCGTTCTAC GACTCGCCGCTGCGCGACGGCGGTTACGACATTCGCGACTTCTACA AGGTGCTGCCCGAATTCGGCACCGTCGACGATTTCGTCGCCCTGGT CGACGCCGCTCACCGGCGAGGTATCCGCATCATCACCGACCTGGT GATGAATCACACCTCGGAGTCGCACCCCTGGTTTCAGGAGTCCCGC CGCGACCCAGACGGACCGTACGGTGACTATTACGTGTGGAGCGAC ACCAGCGAGCGCTACACCGACGCCCGGATCATCTTCGTCGACACC GAAGAGTCGAACTGGTCATTCGATCCTGTCCGCCGACAGTTCTACT GGCACCGATTCTT |
| SEQ ID NO: 110 | ACGGCCGCGTCCGATAACTTCCAGCTGTCCCAGGGTGGGCAGGGA TTCGCCATTCCGATCGGGCAGGCGATGGCGATCGCGGGCCAGATC CGATCGGGTGGGGGGTCACCCACCGTTCATATCGGGCCTACCGCCT TCCTCGGCTTGGGTGTTGTCGACAACAACGGCAACGGCGCACGAG TCCAACGCGTGGTCGGGAGCGCTCCGGCGGCAAGTCTCGGCATCT CCACCGGCGACGTGATCACCGCGGTCGACGGCGCTCCGATCAACT CGGCCACCGCGATGGCGGACGCGCTTAACGGGCATCATCCCGGTG ACGTCATCTCGGTGACCTGGCAAACCAAGTCGGGCGGCACGCGTA CAGGGAACGTGACATTGGCCGAGGGACCCCCGGCC |
| SEQ ID NO: 111 | CATATGCATCACCATCACCATCACACGGCCGCGTCCGATAACTTCC AGCTGTCCCAGGGTGGGCAGGGATTCGCCATTCCGATCGGGCAGG CGATGGCGATCGCGGGCCAGATCCGATCGGGTGGGGGGTCACCCA |

TABLE 1-continued

Sequences of Immunological Fusion Partners

| SEQ ID NO | Sequence |
|---|---|
| | CCGTTCATATCGGGCCTACCGCCTTCCTCGGCTTGGGTGTTGTCGA<br>CAACAACGGCAACGGCGCACGAGTCCAACGCGTGGTCGGGAGCGC<br>TCCGGCGGCAAGTCTCGGCATCTCCACCGGCGACGTGATCACCGC<br>GGTCGACGGCGCTCCGATCAACTCGGCCACCGCGATGGCGGACGC<br>GCTTAACGGGCATCATCCCGGTGACGTCATCTCGGTGACCTGGCAA<br>ACCAAGTCGGGCGGCACGCGTACAGGGAACGTGACATTGGCCGAG<br>GGACCCCCGGCCGAATTCGACGACGACGACAAGGATCCACCTGAC<br>CCGCATCAGCCGGACATGACGAAAGGCTATTGCCCGGGTGGCCGA<br>TGGGGTTTTGGCGACTTGGCCGTGTGCGACGGCGAGAAGTACCCC<br>GACGGCTCGTTTTGGCACCAGTGGATGCAAACGTGGTTTACCGGCC<br>CACAGTTTTACTTCGATTGTGTCAGCGGCGGTGAGCCCCTCCCCGG<br>CCCGCCGCCACCGGGTGGTTGCGGTGGGGCAATTCCGTCCGAGCA<br>GCCCAACGCTCCCTGAGAATTC |
| SEQ ID NO: 112 | CATATGCATCACCATCACCATCACACGGCCGCGTCCGATAACTTCC<br>AGCTGTCCCAGGGTGGGCAGGGATTCGCCATTCCGATCGGGCAGG<br>CGATGGCGATCGCGGGCCAGATCCGATCGGGTGGGGGGTCACCCA<br>CCGTTCATATCGGGCCTACCGCCTTCCTCGGCTTGGGTGTTGTCGA<br>CAACAACGGCAACGGCGCACGAGTCCAACGCGTGGTCGGGAGCGC<br>TCCGGCGGCAAGTCTCGGCATCTCCACCGGCGACGTGATCACCGC<br>GGTCGACGGCGCTCCGATCAACTCGGCCACCGCGATGGCGGACGC<br>GCTTAACGGGCATCATCCCGGTGACGTCATCTCGGTGACCTGGCAA<br>ACCAAGTCGGGCGGCACGCGTACAGGGAACGTGACATTGGCCGAG<br>GGACCCCCGGCCGAATTCCCGCTGGTGCCGCGCGGCAGCCCGATG<br>GGCTCCGACGTTCGGGACCTGAACGCACTGCTGCCGGCAGTTCCGT<br>CCCTGGGTGGTGGTGGTGGTTGCGCACTGCCGGTTAGCGGTGCAG<br>CACAGTGGGCTCCGGTTCTGGACTTCGCACCGCCGGGTGCATCCGC<br>ATACGGTTCCCTGGGTGGTCCGGCACCGCCGCCGGCACCGCCGCC<br>GCCGCCGCCGCCGCCGCCGCACTCCTTCATCAAACAGGAACCGAG<br>CTGGGGTGGTGCAGAACCGCACGAAGAACAGTGCCTGAGCGCATT<br>CACCGTTCACTTCTCCGGCCAGTTCACTGGCACAGCCGGAGCCTGT<br>CGCTACGGGCCCTTCGGTCCTCCTCCGCCCAGCCAGGCGTCATCCG<br>GCCAGGCCAGGATGTTTCCTAACGCGCCCTACCTGCCCAGCTGCCT<br>CGAGAGCCAGCCCGCTATTCGCAATCAGGGTTACAGCACGGTCAC<br>CTTCGACGGGACGCCCAGCTACGGTCACACGCCCTCGCACCATGC<br>GGCGCAGTTCCCCAACCACTCATTCAAGCATGAGGATCCCATGGG<br>CCAGCAGGGCTCGCTGGGTGAGCAGCAGTACTCGGTGCCGCCCCC<br>GGTCTATGGCTGCCACACCCCCACCGACAGCTGCACCGGCAGCCA<br>GGCTTTGCTGCTGAGGACGCCCTACAGCAGTGACAATTTATACCAA<br>ATGACATCCCAGCTTGAATGCATGACCTGGAATCAGATGAACTTA<br>GGAGCCACCTTAAAGGGCCACAGCACAGGGTACGAGAGCGATAA<br>CCACACAACGCCCATCCTCTGCGGAGCCCAATACAGAATACACAC<br>GCACGGTGTCTTCAGAGGCATTCAGGATGTGCGACGTGTGCCTGG<br>AGTAGCCCCGACTCTTGTACGGTCGGCATCTGAGACCAGTGAGAA<br>ACGCCCCTTCATGTGTGCTTACTCAGGCTGCAATAAGAGATATTTT<br>AAGCTGTCCCACTTACAGATGCACAGCAGGAAGCACACTGGTGAG<br>AAACCATACCAGTGTGACTTCAAGGACTGTGAACGAAGGTTTTTTC<br>GTTCAGACCAGCTCAAAAGACACCAAAGGAGACATACAGGTGTGA<br>AACCATTCCAGTGTAAAACTTGTCAGCGAAAGTTCTCCCGGTCCGA<br>CCACCTGAAGACCCACACCAGGACTCATACAGGTGAAAAGCCCTT<br>CAGCTGTCGGTGGCCAAGTTGTCAGAAAAAGTTTGCCCGGTCAGA<br>TGAATTAGTCCGCCATCACAACATGCATCAGAGAAACATGACCAA<br>ACTCCAGCTGGCGCTTTGAGAATTC |
| SEQ ID NO: 113 | CATATGCATCACCATCACCATCACACGGCCGCGTCCGATAACTTCC<br>AGCTGTCCCAGGGTGGGCAGGGATTCGCCATTCCGATCGGGCAGG<br>CGATGGCGATCGCGGGCCAGATCCGATCGGGTGGGGGGTCACCCA<br>CCGTTCATATCGGGCCTACCGCCTTCCTCGGCTTGGGTGTTGTCGA<br>CAACAACGGCAACGGCGCACGAGTCCAACGCGTGGTCGGGAGCGC<br>TCCGGCGGCAAGTCTCGGCATCTCCACCGGCGACGTGATCACCGC<br>GGTCGACGGCGCTCCGATCAACTCGGCCACCGCGATGGCGGACGC<br>GCTTAACGGGCATCATCCCGGTGACGTCATCTCGGTGACCTGGCAA<br>ACCAAGTCGGGCGGCACGCGTACAGGGAACGTGACATTGGCCGAG<br>GGACCCCCGGCCGAATTCATCGAGGGAAGGGGCTCTGGCTGCCCC<br>TTATTGGAGAATGTGATTTCCAAGACAATCAATCCACAAGTGTCTA<br>AGACTGAATACAAAGAACTTCTTCAAGAGTTCATAGACGACAATG<br>CCACTACAAATGCCATAGATGAATTGAAGGAATGTTTTCTTAACCA<br>AACGGATGAAACTCTGAGCAATGTTGAGGTGTTTATGCAATTAAT<br>ATATGACAGCAGTCTTTGTGATTTATTTTAAGAATTC |
| SEQ ID NO: 114 | ATGCATCACCATCACCATCACACGGCCGCGTCCGATAACTTCCAGC<br>TGTCCCAGGGTGGGCAGGGATTCGCCATTCCGATCGGGCAGGCGA<br>TGGCGATCGCGGGCCAGATCCGATCGGGTGGGGGGTCACCCACCG<br>TTCATATCGGGCCTACCGCCTTCCTCGGCTTGGGTGTTGTCGACAA<br>CAACGGCAACGGCGCACGAGTCCAACGCGTGGTCGGGAGCGCTCC<br>GGCGGCAAGTCTCGGCATCTCCACCGGCGACGTGATCACCGCGGT |

TABLE 1-continued

Sequences of Immunological Fusion Partners

| SEQ ID NO | Sequence |
|---|---|
| | CGACGGCGCTCCGATCAACTCGGCCACCGCGATGGCGGACGCGCT<br>TAACGGGCATCATCCCGGTGACGTCATCTCGGTGACCTGGCAAAC<br>CAAGTCGGGCGGCACGCGTACAGGGAACGTGACATTGGCCGAGGG<br>ACCCCCGGCCGAATTCATGGTGGATTTCGGGGCGTTACCACCGGA<br>GATCAACTCCGCGAGGATGTACGCCGGCCCGGGTTCGGCCTCGCT<br>GGTGGCCGCGGCTCAGATGTGGGACAGCGTGGCGAGTGACCTGTT<br>TTCGGCCGCGTCGGCGTTTCAGTCGGTGGTCTGGGGTCTGACGGTG<br>GGGTCGTGGATAGGTTCGTCGGCGGGTCTGATGGTGGCGGCGGCC<br>TCGCCGTATGTGGCGTGGATGAGCGTCACCGCGGGGCAGGCCGAG<br>CTGACCGCCGCCCAGGTCCGGGTTGCTGCGGCGGCCTACGAGACG<br>GCGTATGGGCTGACGGTGCCCCCGCCGGTGATCGCCGAGAACCGT<br>GCTGAACTGATGATTCTGATAGCGACCAACCTCTTGGGGCAAAAC<br>ACCCCGGCCGATCGCGGTCAACGAGGCCGAATACGGCGAGATGTGG<br>GCCCAAGACGCCGCCGCGATGTTTGGCTACGCCGCGGCGACGGCG<br>ACGGCGACGGCGACGTTGCTGCCGTTCGAGGAGGCGCCGGAGATG<br>ACCAGCGCGGGTGGGCTCCTCGAGCAGGCCGCCGCGGTCGAGGAG<br>GCCTCCGACACCGCCGCGGCGAACCAGTTGATGAACAATGTGCCC<br>CAGGCGCTGCAACAGCTGGCCCAGCCCACGCAGGGCACCACGCCT<br>TCTTCCAAGCTGGGTGGCCTGTGGAAGACGGTCTCGCCGCATCGGT<br>CGCCGATCAGCAACATGGTGTCGATGGCCAACAACCACATGTCGA<br>TGACCAACTCGGGTGTGTCGATGACCAACACCTTGAGCTCGATGTT<br>GAAGGGCTTTGCTCCGGCGGCGGCCGCCCAGGCCGTGCAAACCGC<br>GGCGCAAAACGGGGTCCGGGCGATGAGCTCGCTGGGCAGCTCGCT<br>GGGTTCTTCGGGTCTGGGCGGTGGGGTGGCCGCCAACTTGGGTCG<br>GGCGGCCTCGGTCGGTTCGTTGTCGGTGCCGCAGGCCTGGGCCGC<br>GGCCAACCAGGCAGTCACCCCGGCGGCGCGGGCGCTGCCGCTGAC<br>CAGCCTGACCAGCGCCGCGGAAAGAGGGCCCGGGCAGATGCTGG<br>GCGGGCTGCCGGTGGGGCAGATGGGCGCCAGGGCCGGTGGTGGGC<br>TCAGTGGTGTGCTGCGTGTTCCGCCGCGACCCTATGTGATGCCGCA<br>TTCTCCGGCAGCCGGCGATATCGCCCCGCCGGCCTTGTCGCAGGAC<br>CGGTTCGCCGACTTCCCCGCGCTGCCCCTCGACCCGTCCGCGATGG<br>TCGCCCAAGTGGGGCCACAGGTGGTCAACATCAACACCAAACTGG<br>GCTACAACAACGCCGTGGGCGCCGGGACCGGCATCGTCATCGATC<br>CCAACGGTGTCGTGCTGACCAACAACCACGTGATCGCGGGCGCCA<br>CCGACATCAATGCGTTCAGCGTCGGCTCCGGCCAAACCTACGGCG<br>TCGATGTGGTCGGGTATGACCGCACCCAGGATGTCGCGGTGCTGC<br>AGCTGCGCGGTGCCGGTGGCCTGCCGTCGGCGGCGATCGGTGGCG<br>GCGTCGCGGTTGGTGAGCCCGTCGTCGCGATGGGCAACAGCGGTG<br>GGCAGGGCGGAACGCCCCGTGCGGTGCCTGGCAGGGTGGTCGCGC<br>TCGGCCAAACCGTGCAGGCGTCGGATTCGCTGACCGGTGCCGAAG<br>AGACATTGAACGGGTTGATCCAGTTCGATGCCGCGATCCAGCCCG<br>GTGATTCGGGCGGGCCCGTCGTCAACGGCCTAGGACAGGTGGTCG<br>GTATGAACACGGCCGCGTCCTAGG |
| SEQ ID NO: 123 | mcctkslllaalmsvlllhlcgeseasnfdcclgytdrilhpkfivgftrqlanegcdinaiifhtkkklsvcan<br>pkqtwvkyivrllskkvknm |
| SEQ ID NO: 124 | ggGGTCAACGTTGAgggggg |
| SEQ ID NO: 125 | ggGGGACGA:TCGTCgggggg |
| SEQ ID NO: 126 | gggGACGAC:GTCGTGgggggg |
| SEQ ID NO: 127 | tccatgacgttcctgatgct |
| SEQ ID NO: 128 | tccatgacgttcctgacgtt |
| SEQ ID NO: 129 | tcgtcgttttgtcgttttgtcgtt |
| SEQ ID NO: 130 | tcg tcg ttg tcg ttt tgt cgt t |
| SEQ ID NO: 131 | tcg acg ttc gtc gtt cgt cgt tc |
| SEQ ID NO: 132 | tcg cga cgt tcg ccc gac gtt cgg ta |
| SEQ ID NO: 133 | tcgtcgttttcggcgc:gcgccg |
| SEQ ID NO: 134 | tcgtcgtcgttc:gaacgacgttgat |
| SEQ ID NO: 135 | tcg cga acg ttc gcc gcg ttc gaa cgc gg |

TABLE 2

Tools to construct *Mycobacterium* sp.-Derived Ra12 Sequences

| SEQ ID NO | Sequence |
|---|---|
| SEQ ID NO: 115 | CAATTACATATGCATCACCATCACCATCACACGGC CGCGTCCGATAACTTC |
| SEQ ID NO: 116 | CTAATCGAATTCGGCCGGGGGTCCCTCGGCCAA |
| SEQ ID NO: 117 | CAATTAGAATTCGACGACGACGACAAGGATCCACC TGACCCGCATCAG |
| SEQ ID NO: 118 | CAATTAGAATTCTCAGGGAGCGTTGGGCTGCTC |
| SEQ ID NO: 119 | GCGAAGCTTATGAAGTTGCTGATGGTCCTCATGC |
| SEQ ID NO: 120 | CGGCTCGAGTTAAAATAAATCACAAAGACTGCTGT C |
| SEQ ID NO: 121 | MHHHHHH |
| SEQ ID NO: 122 | DDDK |

In some embodiments, the nucleic acid sequences for the target antigen and the immunological fusion partner are not separated by any nucleic acids. In other embodiments, a nucleic acid sequence that encodes for a linker can be inserted between the nucleic acid sequence encoding for any target antigen described herein and the nucleic acid sequence encoding for any immunological fusion partner described herein. Thus, in certain embodiments, the protein produced following immunization with the viral vector containing a target antigen, a linker, and an immunological fusion partner can be a fusion protein comprising the target antigen of interest followed by the linker and ending with the immunological fusion partner, thus linking the target antigen to an immunological fusion partner that increases the immunogenicity of the target antigen of interest via a linker. In some embodiments, the sequence of linker nucleic acids can be from about 1 to about 150 nucleic acids long, from about 5 to about 100 nucleic acids along, or from about 10 to about 50 nucleic acids in length. In some embodiments, the nucleic acid sequences can encode one or more amino acid residues. In some embodiments, the amino acid sequence of the linker can be from about 1 to about 50, or about 5 to about 25 amino acid residues in length. In some embodiments, the sequence of the linker comprises less than 10 amino acids. In some embodiments, the linker can be a polyalanine linker, a polyglycine linker, or a linker with both alanines and glycines.

Nucleic acid sequences that encode for such linkers can be any one of SEQ ID NO: 94-SEQ ID NO: 108 and are summarized in TABLE 3.

TABLE 3

Sequences of Linkers

| SEQ ID NO | Sequence |
|---|---|
| SEQ ID NO: 94 | MAVPMQLSCSR |
| SEQ ID NO: 95 | RSTG |
| SEQ ID NO: 96 | TR |
| SEQ ID NO: 97 | RSQ |
| SEQ ID NO: 98 | RSAGE |
| SEQ ID NO: 99 | RS |
| SEQ ID NO: 100 | GG |
| SEQ ID NO: 101 | GSGGSGGSG |
| SEQ ID NO: 102 | GGSGGSGGSGG |
| SEQ ID NO: 103 | GGSGGSGGSGGSGG |
| SEQ ID NO: 104 | GGSGGSGGSGGSGGSGG |
| SEQ ID NO: 105 | GGSGGSGGSGGSGGSGGSGG |
| SEQ ID NO: 106 | GGSGGSGGSGGSGGSGGSGGSGG |
| SEQ ID NO: 107 | GGSGGSGGSGGSGGSG |
| SEQ ID NO: 108 | GSGGSGGSGGSGGSGG |

VI. Methods of Use

The adenovirus vectors can be used in a number of vaccine settings for generating an immune response against one or more target antigens as described herein. The adenovirus vectors are of particular importance because of the unexpected finding that they can be used to generate immune responses in subjects who have preexisting immunity to Ad and can be used in vaccination regimens that include multiple rounds of immunization using the adenovirus vectors, regimens not possible using previous generation adenovirus vectors.

Generally, generating an immune response can comprise an induction of a humoral response and/or a cell-mediated response. In certain embodiments, it is desirable to increase an immune response against a target antigen of interest. As such "generating an immune response" or "inducing an immune response" can comprise any statistically significant change, e.g., increase in the number of one or more immune cells (T cells, B cells, antigen-presenting cells, dendritic cells, neutrophils, and the like) or in the activity of one or more of these immune cells (CTL activity, HTL activity, cytokine secretion, change in profile of cytokine secretion, etc.).

The skilled artisan would readily appreciate that a number of methods for establishing whether an alteration in the immune response has taken place are available. A variety of methods for detecting alterations in an immune response (e.g., cell numbers, cytokine expression, cell activity) are known in the art and are useful in the context of the instant invention. Illustrative methods are described in Current Protocols in Immunology, Edited by: John E. Coligan, Ada M. Kruisbeek, David H. Margulies, Ethan M. Shevach, Warren Strober (2001 John Wiley & Sons, NY, N.Y.) Ausubel et al. (2001 Current Protocols in Molecular Biology, Greene Publ. Assoc. Inc. & John Wiley & Sons, Inc., NY, N.Y.); Sambrook et al. (1989 Molecular Cloning, Second Ed., Cold Spring Harbor Laboratory, Plainview, N.Y.); Maniatis et al. (1982 Molecular Cloning, Cold Spring Harbor Laboratory, Plainview, N.Y.) and elsewhere. Illustrative methods useful in this context include intracellular cytokine staining (ICS), ELISpot, proliferation assays, cytotoxic T cell assays including chromium release or equivalent assays, and gene expression analysis using any number of polymerase chain reaction (PCR) or RT-PCR based assays.

In certain embodiments, generating an immune response comprises an increase in target antigen-specific CTL activity of about 1.5 to 20 or more fold, at least, about, or at most 1.5, 2, 3, 4, 5, 6, 7, 8, 9, 10, 11, 12, 13, 14, 15, 16, 17, 18, 19, or any range or number derived therefrom in a subject administered the adenovirus vectors as compared to a control. In another embodiment, generating an immune response comprises an increase in target-specific CTL activity of about 1.5 to 20, or more fold in a subject administered the adenovirus vectors as compared to a control. In a further embodiment, generating an immune response that comprises an increase in target antigen-specific cell mediated immunity activity as measured by ELISpot assays measuring cytokine secretion, such as interferon-gamma (IFN-γ), interleukin-2 (IL-2), tumor necrosis factor-alpha (TNF-α), granzyme, or other cytokines, of about 1.5 to 20, or more fold as compared to a control.

In a further embodiment, generating an immune response comprises an increase in target-specific antibody production of between 1.5 and 5 fold in a subject administered the adenovirus vectors as compared to an appropriate control. In another embodiment, generating an immune response comprises an increase in target-specific antibody production of about 1.5 to 20, or more fold in a subject administered the adenovirus vector as compared to a control.

Thus, certain aspects can provide methods for generating an immune response against flavivirus target antigens of interest comprising administering to the individual an adenovirus vector comprising: a) a replication defective adenovirus vector, wherein the adenovirus vector has a deletion in the E2b region, and b) nucleic acids encoding the target antigens; and readministering the adenovirus vector at least once to the individual; thereby generating an immune response against the target antigens. In certain embodiments, there can be provided methods wherein the vector administered is not a gutted vector.

In a further embodiment, methods can be provided for generating an immune response against flavivirus virus target antigens in an individual, wherein the individual has pre-existing immunity to Ad, by administering to the individual an adenovirus vector comprising: a) a replication defective adenovirus vector, wherein the adenovirus vector has a deletion in the E2b region, and b) nucleic acids encoding the target antigens; and re-administering the adenovirus vector at least once to the individual; thereby generating an immune response against the flavivirus virus target antigens.

With regard to preexisting immunity to Ad, this can be determined using methods known in the art, such as antibody-based assays to test for the presence of Ad antibodies. Further, in certain embodiments, the methods can include first determining that an individual has preexisting immunity to Ad then administering the E2b deleted adenovirus vectors as described herein.

In certain aspects, there can be provided methods of generating an immune response against flavivirus target antigens, such as those described elsewhere or herein.

In particular aspects, there can be provided methods of generating an immune response against flaviviruses, such as those described elsewhere herein.

As noted elsewhere herein, the adenovirus vectors can comprise nucleic acid sequences that encode one or more target antigens of interest from any one or more of the infectious agents against which an immune response is to be generated. For example, target antigens can include, but are not limited to, viral antigen proteins, such as C, E, prM, M, NS1, NS2A, NS2B, NS3, NS4A, NS4B, and NS5.

For administration, the adenovirus vector stock can be combined with an appropriate buffer, physiologically acceptable carrier, excipient or the like. In certain embodiments, an appropriate number of adenovirus vector particles are administered in an appropriate buffer, such as, sterile PBS.

In certain circumstances it can be desirable to deliver the adenovirus vector compositions disclosed herein parenterally, intravenously, intramuscularly, or even intraperitoneally. In certain embodiments, solutions as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. In other embodiments, E2b deleted adenovirus vectors can be delivered in pill form, delivered by swallowing or by suppository.

Illustrative pharmaceutical forms suitable for injectable use can include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria, molds and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity can be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it can include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions can be especially suitable for intravenous, intramuscular, subcutaneous and intraperitoneal administration. In this connection, a sterile aqueous medium that can be employed will be known to those of skill in the art in light of the present disclosure. For example, one dosage can be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage can necessarily occur depending on the condition of the subject being treated. Moreover, for human administration, preparations can need to meet sterility, pyrogenicity, and the general safety and purity standards as required by FDA Office of Biology standards.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" can refer to molecular entities and compositions that may not produce an allergic or similar untoward reaction when administered to a human.

Routes and frequency of administration of the therapeutic compositions described herein, as well as dosage, can vary from individual to individual, and from disease to disease, and can be readily established using standard techniques. In general, the pharmaceutical compositions and vaccines can be administered by injection (e.g., intracutaneous, intramuscular, intravenous, intraperitoneal, or subcutaneous), intranasally (e.g., by aspiration), in pill form (e.g., swallowing, suppository for vaginal or rectal delivery). In certain embodiments, between 1 and 3 doses can be administered over a 6 week period and further booster vaccinations can be given periodically thereafter.

In various embodiments, the replication defective adenovirus is administered at a dose that suitable for effecting such immune response. In some embodiments, the replication defective adenovirus is administered at a dose from about $1\times10^8$ virus particles to about $5\times10^{13}$ virus particles per immunization. In some cases, the replication defective adenovirus is administered at a dose that is from about $1\times10^9$ to about $5\times10^{12}$ virus particles per immunization. In some embodiments, the replication defective adenovirus is administered at a dose from about $1\times10^8$ virus particles to about $5\times10^8$ virus particles per immunization. In some embodiments, the replication defective adenovirus is administered at a dose from about $5\times10^8$ virus particles to about $1\times10^9$ virus particles per immunization. In some embodiments, the replication defective adenovirus is administered at a dose from about $1\times10^9$ virus particles to about $5\times10^9$ virus particles per immunization. In some embodiments, the replication defective adenovirus is administered at a dose from about $5\times10^9$ virus particles to about $1\times10^{10}$ virus particles per immunization. In some embodiments, the replication defective adenovirus is administered at a dose from about $1\times10^{10}$ virus particles to about $5\times10^{10}$ virus particles per immunization. In some embodiments, the replication defective adenovirus is administered at a dose from about $5\times10^{10}$ virus particles to about $1\times10^{11}$ virus particles per immunization. In some embodiments, the replication defective adenovirus is administered at a dose from about $1\times10^{11}$ virus particles to about $5\times10^{11}$ virus particles per immunization. In some embodiments, the replication defective adenovirus is administered at a dose from about $5\times10^{11}$ virus particles to about $1\times10^{12}$ virus particles per immunization. In some embodiments, the replication defective adenovirus is administered at a dose from about $1\times10^{12}$ virus particles to about $5\times10^{12}$ virus particles per immunization. In some embodiments, the replication defective adenovirus is administered at a dose from about $5\times10^{12}$ virus particles to about $1\times10^{13}$ virus particles per immunization. In some embodiments, the replication defective adenovirus is administered at a dose from about $1\times10^{13}$ virus particles to about $5\times10^{13}$ virus particles per immunization. In some embodiments, the replication defective adenovirus is administered at a dose from about $1\times10^8$ virus particles to about $5\times10^{10}$ virus particles per immunization. In some embodiments, the replication defective adenovirus is administered at a dose from about $1\times10^{10}$ virus particles to about $5\times10^{12}$ virus particles per immunization. In some embodiments, the replication defective adenovirus is administered at a dose from about $1\times10^{11}$ virus particles to about $5\times10^{13}$ virus particles per immunization. In some embodiments, the replication defective adenovirus is administered at a dose from about $1\times10^8$ virus particles to about $1\times10^{10}$ virus particles per immunization. In some embodiments, the replication defective adenovirus is administered at a dose from about $1\times10^{10}$ virus particles to about $1\times10^{12}$ virus particles per immunization. In some embodiments, the replication defective adenovirus is administered at a dose from about $1\times10^{11}$ virus particles to about $5\times10^{13}$ virus particles per immunization. In some cases, the replication defective adenovirus is administered at a dose that is greater than or equal to $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $1.5\times10^{12}$, $2\times10^{12}$, $3\times10^{12}$, or more virus particles (VP) per immunization. In some cases, the replication defective adenovirus is administered at a dose that is less than or equal to $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $1.5\times10^{12}$, $2\times10^{12}$, $3\times10^{12}$, or more virus particles per immunization. In various embodiments, a desired dose described herein is administered in a suitable volume of formulation buffer, for example a volume of about 0.1-10 mL, 0.2-8 mL, 0.3-7 mL, 0.4-6 mL, 0.5-5 mL, 0.6-4 mL, 0.7-3 mL, 0.8-2 mL, 0.9-1.5 mL, 0.95-1.2 mL, or 1.0-1.1 mL. Those of skill in the art appreciate that the volume may fall within any range bounded by any of these values (e.g., about 0.5 mL to about 1.1 mL).

A suitable dose can be an amount of an adenovirus vector that, when administered as described above, is capable of promoting a target antigen immune response as described elsewhere herein. In certain embodiments, the immune response is at least 10-50% above the basal (i.e., untreated) level. Such response can be monitored by measuring the target antigen antibodies in a patient or by vaccine-dependent generation of cytolytic effector cells capable of killing flavivirus infected cells in vitro, or other methods known in the art for monitoring immune responses.

In general, an appropriate dosage and treatment regimen can provide the adenovirus vectors in an amount sufficient to provide prophylactic benefit. Protective immune responses can generally be evaluated using standard proliferation, cytotoxicity or cytokine assays, which can be performed using samples obtained from a patient before and after immunization (vaccination).

While one advantage can be the capability to administer multiple vaccinations with the same adenovirus vectors, particularly in individuals with preexisting immunity to Ad, the adenoviral vaccines can also be administered as part of a prime and boost regimen. A mixed modality priming and booster inoculation scheme can result in an enhanced immune response.

Thus, one aspect is a method of priming a subject with a plasmid vaccine, such as a plasmid vector comprising a target antigen of interest, by administering the plasmid vaccine at least one time, allowing a predetermined length of time to pass, and then boosting by administering the adenovirus vector. Multiple primings, e.g., 1-3, can be employed, although more can be used. The length of time between priming and boost can vary from about six months to a year, but other time frames can be used.

Kits

A composition, immunotherapy, or vaccine described herein can be supplied in the form of a kit. The kits of the present disclosure may further comprise instructions regarding the dosage and/or administration including treatment regimen information.

In some embodiments, kits comprise the compositions and methods for providing immunotherapy or vaccines described. In some embodiments, a kit can further comprise components useful in administering the kit components and instructions on how to prepare the components. In some embodiments, the kit can further comprise software for conducting monitoring patient before and after treatment with appropriate laboratory tests, or communicating results and patient data with medical staff.

The components of the kit can be in dry or liquid form. If they are in dry form, the kit can include a solution to solubilize the dried material. The kit can also include transfer factor in liquid or dry form. In some embodiments, if the transfer factor is in dry form, the kit includes a solution to solubilize the transfer factor. The kit can also include containers for mixing and preparing the components. The kit can also include instrument for assisting with the administration such as, for example, needles, tubing, applicator, inhalant, syringe, pipette, forceps, measured spoon, eye dropper, or any such medically approved delivery vehicle. The kits or drug delivery systems as described herein also can include a means for containing compositions of the present disclosure in close confinement for commercial sale and distribution.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety to the same extent as if each individual publication, patent, or patent application was specifically and individually indicated to be incorporated by reference.

Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLES

The following examples are included to further describe some aspects of the present disclosure, and should not be used to limit the scope of the present disclosure.

Example 1

Production of Single-Targeted Ad5 [E1-, E2b-]-ZIKAV-E Vaccine

This example illustrates construction of a single-targeted Ad5 [E1-, E2b-] vector containing a ZIKAV-E (also referred to as "Envelope" or "E") antigen.

The Ad5-ZIKAV-E vaccines, which are used according to this example, are adenovirus serotype 5 (Ad5) vectors that are modified by removal of the E1, E2b, E3 gene regions, or any combination thereof (e.g. Ad5 [E1-, E2b-]), and insertion of any ZIKAV-E antigen disclosed here (e.g., any one of SEQ ID NO: 11-SEQ ID NO: 21 or SEQ ID NO: 23-SEQ ID NO: 37).

Nucleotide sequences encoding the ZIKAV-E antigen with amino acid sequences set forth in SEQ ID NO: 15, SEQ ID NO: 16, SEQ ID NO: 17, SEQ ID NO: 18, and SEQ ID NO: 19 are cloned into multiple Ad5 [E1-, E2b-]-based platforms to produce separate single-targeted Ad5 [E1-, E2b-]-ZIKAV-E vaccines, each containing one of SEQ ID NO: 15, SEQ ID NO: 16, SEQ ID NO: 17, SEQ ID NO: 18, and SEQ ID NO: 19. A separate ZIKAV-E vaccine is made with a nucleotide sequence having nucleotides 969-1274 of SEQ ID NO: 20 (i.e., a nucleotide sequence encoding an envelope protein of a Zika virus isolate obtained from Mexico). A different ZIKAV-E vaccine is made with a nucleotide sequence having nucleotides 977-2491 of SEQ ID NO: 21 (i.e., a nucleotide sequence encoding an envelope protein of a Zika virus strain obtained from Haiti). Any one of SEQ ID NO: 11-SEQ ID NO: 21 or SEQ ID NO: 23-SEQ ID NO: 37 are cloned into multiple Ad5 [E1-, E2b-]-based platforms to produce separate single-targeted Ad5 [E1-, E2b-]-ZIKAV-E vaccines, each containing one of SEQ ID NO: 11-SEQ ID NO: 21 or SEQ ID NO: 23-SEQ ID NO: 37.

For pre-clinical immunogenicity studies in mice, an Ad5 [E1-, E2b-ZIKAV-E vaccine was constructed using a ZIKA virus wild type E gene insert as shown in SEQ ID NO: 26 (Zika2014wt E gene insert nucleic acid sequence (starting with the start codon and ending with the stop codon). Subsequently, Ad5 [E1-, E2b-]-ZIKAV-E vaccines are produced in E.C7 cells as depicted schematically in FIG. 1. The replication-deficient viruses are propagated in the E.C7 packaging cell line, CsCl2 or ion-exchange column purified, and titered. Viral infectious titer is determined as plaque-forming units (PFUs) on an E.C7 cell monolayer. The virus particle (VP) concentration is determined by sodium dodecyl sulfate (SDS) disruption and spectrophotometry at 260 nm and 280 nm.

Example 2

Preparation of Multi-Targeted Ad5 [E1-, E2b-] Constructs Containing Multiple Flavivirus Antigens This example illustrates preparation of a multi-targeted Ad5 [E1-, E2b-] vector containing multiple flavivirus antigens, for example, any combination of Zika virus antigen disclosed herein (e.g., any combination of SEQ ID NO: 11-SEQ ID NO: 21 or SEQ ID NO: 23-SEQ ID NO: 37).

The Ad5-ZIKAV-E vaccine, which is used according to this example, is an adenovirus serotype 5 (Ad5) vector that is modified by removal of the E1, E2b, E3 gene regions, or any combination thereof (e.g., an Ad5 [E1-, E2b-]), and insertion of nucleotide sequences encoding flavivirus antigens.

An Ad5 [E1-, E2b-] vector containing a nucleotide sequence is produced, which encodes multiple flavivirus antigens. The individual flavivirus antigen gene sequences (including a triple gene insert having flavivirus gene sequences encoding a capsid protein, a membrane protein, and an envelope protein (E), and a quad gene insert having flavivirus gene sequences encoding capsid protein, a membrane protein, and an envelope protein (E) and a nonstructural protein (NS) are separated by "self-cleaving" 2A peptide derived from Porcine teschovirus-1 and Thosea asigna virus respectively (FIG. 2A and FIG. 3A) (de Felipe P and Ryan M Traffic 2004 5(8), 616-26; Hoist J et al. Nature Immunol. 2008 9:658-66; Kim J H et al. PloS One, 2011

Figure 2B:
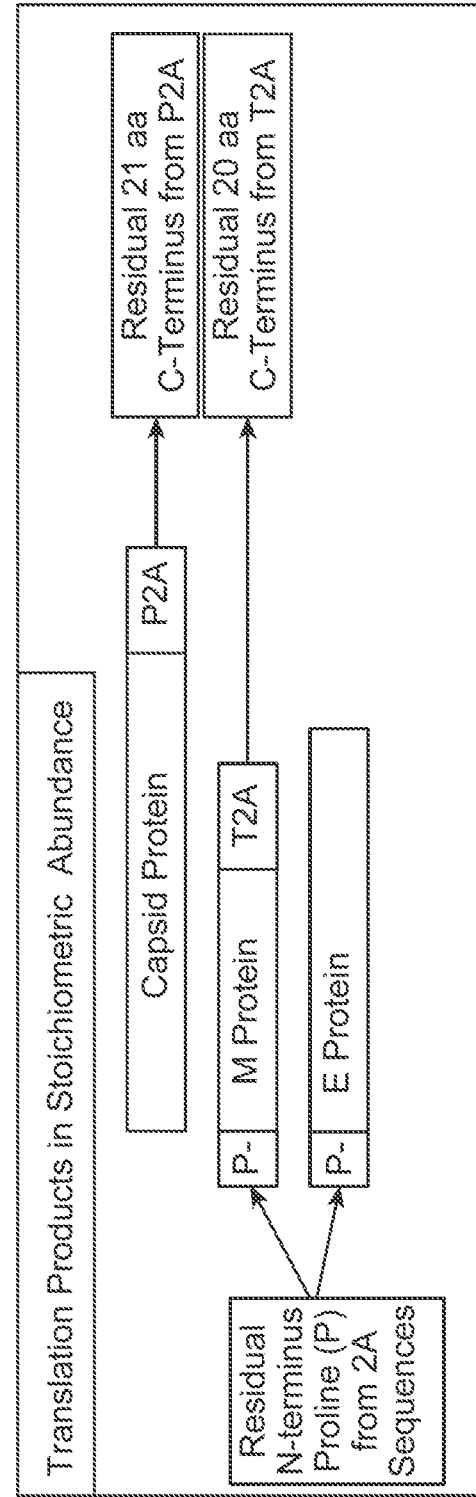
Figure 4A:
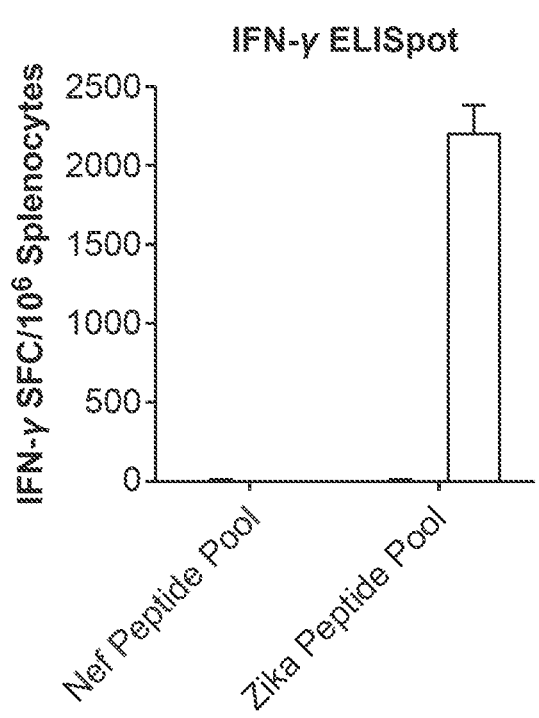
Figure 4B:
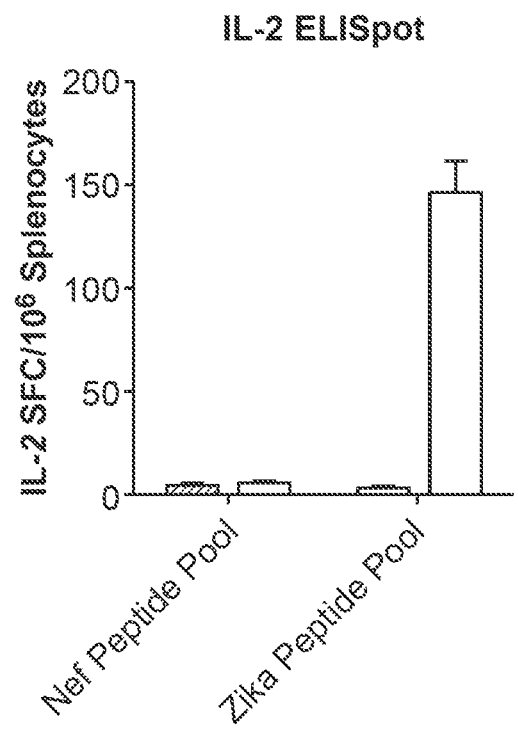
Figure 4C:
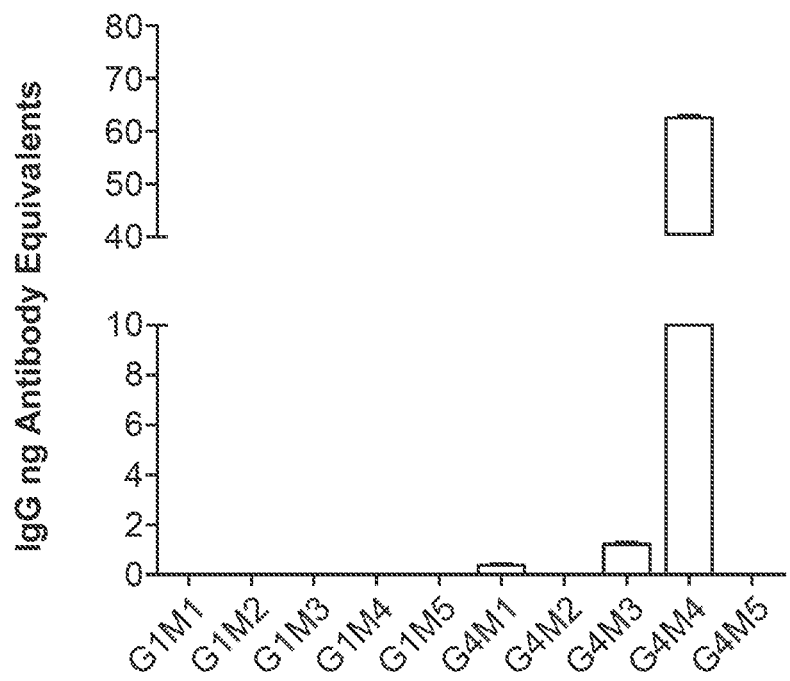
Figure 5:
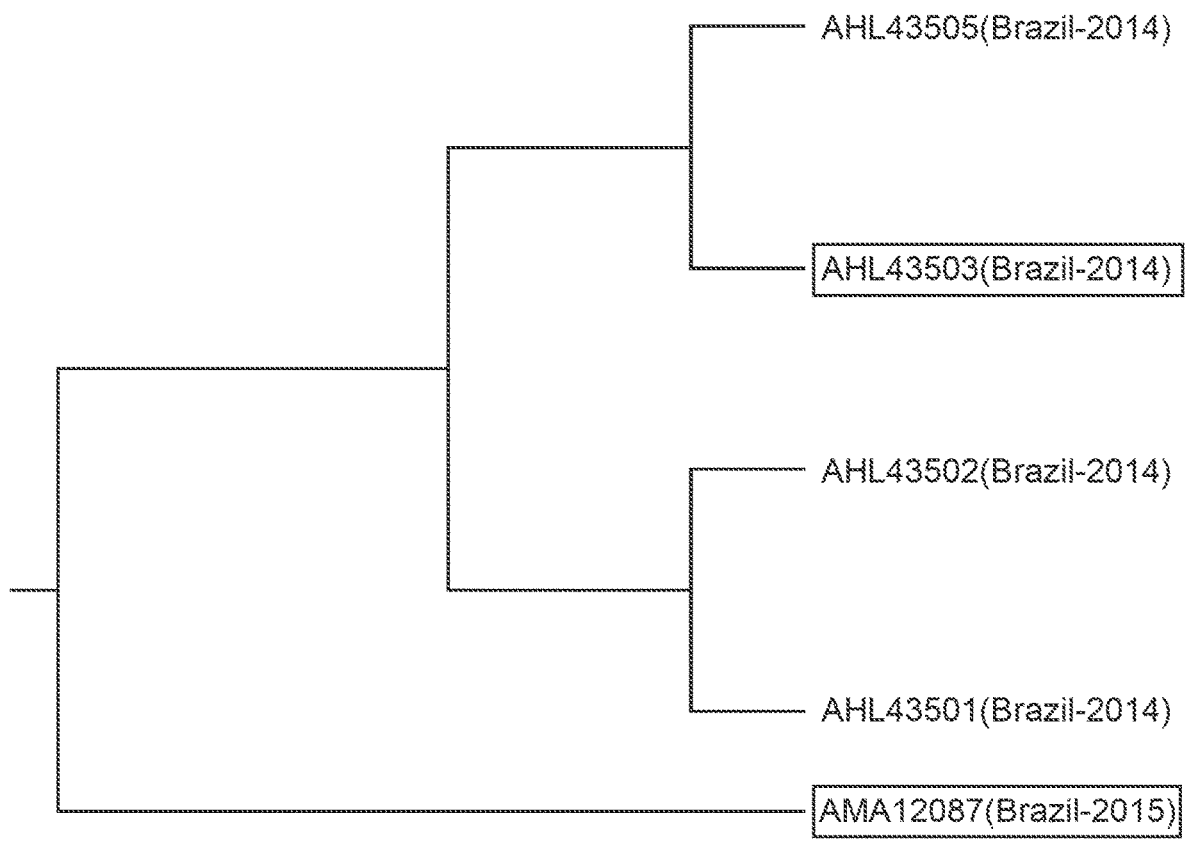

6(4), e18556. doi:10.1371/journal.pone.0018556). As the 2A peptides are translated on the ribosome, the peptide bond between the final two residues of the 2A peptide does not form, thereby resulting in distinctly expressed proteins in one ribosomal pass (FIG. 2B and FIG. 3B). The use of two 2A peptide sequences separating the three genes results in near stoichiometric expression of the three proteins (FIG. 2B and FIG. 3B).

Example 3

Multiple Injections of an Ad5 [E1-, E2b-]-ZIKAV-E Generates Immune Responses against the ZIKA E Antigen This example illustrates that injections of an Ad5 [E1-, E2b-]-ZIKAV-E vaccine induced immune responses against the ZIKA E antigen. Groups of five (5) mice each were immunized two (2) times subcutaneously at two (2) week intervals with a dose of $10^{10}$ VPs Ad5 [E1-, E2b-]-ZIKAV-E (test group mice G4M1-5, White bars). Control mice were injected with $10^{10}$ VP Ad5 [E1-, E2b-]-null (empty vector no sequence control) (control group mice G1M1-5, Black Hatched bars). One (1) week after the second immunization, mice were sacrificed and their spleens and sera harvested for determinations of induced immune responses against ZIKA-E antigen. As shown in FIGS. 4A-4C, cell-mediated immune (CMI) responses and antibody (Ab) responses were generated by immunizations (vaccinations) with Ad5 [E1-, E2b-]-ZIKAV-E.

Example 4

Pre-Clinical Studies of Ad5 [E1-, E2b-]-ZIKAV-E Vaccines in Mice

This example illustrates pre-clinical studies of Ad5 [E1-, E2b-]-Zika vaccines in mice including assessment of cell mediated immune (CMI) responses, cytolytic T lymphocyte (CTL) responses, intracellular cytokine expression, antibody secretion, and weight/temperature changes. Pre-clinical studies included administration of Ad5 [E1-, E2b-]-Zika vaccines comprising several different Zika antigen variants, a comparison to controls, and an assessment of the immune responses in mice.

Pre-Clinical Assessment of Ad5 [E1-, E2b-]-Zika Mutant (mut) 2015, Ad5 [E1-, E2b-]-Zika Wildtype (wt) 2014, Ad5 [E1-, E2b-]-Zika Mutant (mut) 2014 Vaccines All Ad5 [E1-, E2b-]-Zika vaccines included manufacture of vaccines with Zika inserts as described in EXAMPLE 1.

CMI and CTL Responses. CMI and CTL responses in mice were evaluated by an enzyme-linked immunospot (ELISPOT) assay. FIG. 6 illustrates cell mediated immune (CMI) responses and cytolytic T lymphocyte (CTL) responses in splenocytes from mice immunized with Ad5 [E1-, E2b-]-Zika-E vaccines. Mice (C57BL/6 strain) were immunized two times at two-week intervals with $1\times10^{10}$ virus particles (VPs) of an Ad5 [E1-, E2b-]-Zika vaccine or with $1\times10^{10}$ VPs Ad5 [E1-, E2b-]-null (empty vector control). Three types of Zika vaccines were tested. The first Zika vaccine tested was the Ad5 [E1-, E2b-]-Zika mut 2015, which comprises a Zika antigen protein encoded by the nucleotide sequence of SEQ ID NO: 34 and by the amino acid sequence of SEQ ID NO: 35 (SEQ ID NO: 34 is the nucleotide sequence and SEQ ID NO: 35 is the amino acid sequence corresponding to SEQ ID NO: 34). The Zika mut 2015 antigen of SEQ ID NO: 35 corresponds to amino acids 409-690 of the 3423-aa Zika polyprotein (SEQ ID NO: 23), which is the truncated portion of the extracellular domain of the Zika envelope protein. The Zika mut 2015 antigen comprises point mutations as compared to the Zika wt 2015 antigen. These point mutations include D37I, D43L, D266I, D129L, D218L (position numbering does not count the N-terminal methionine) and these mutations can result in decreased anti-human C1q responses compared to wild type. The second Zika vaccine tested was the Ad5 [E1-, E2b-]-Zika wt 2014, which comprises a Zika antigen protein encoded by the nucleotide sequence of SEQ ID NO: 26 and by the amino acid sequence of SEQ ID NO: 27 (SEQ ID NO: 26 is the nucleotide sequence and SEQ ID NO: 27 is the amino acid sequence corresponding to SEQ ID NO: 26). The Zika wt 2014 antigen of SEQ ID NO: 27 corresponds to amino acids 409-690 of the 3423-aa Zika polyprotein (SEQ ID NO: 23), which is the truncated portion of the extracellular domain of the Zika envelope protein. The third Zika vaccine tested was the Ad5 [E1-, E2b-]-Zika mut 2014, which comprises a Zika antigen protein encoded by the nucleotide sequence of SEQ ID NO: 28 and by the amino acid sequence of SEQ ID NO: 29 (SEQ ID NO: 28 is the nucleotide sequence and SEQ ID NO: 29 is the amino acid sequence corresponding to SEQ ID NO: 28). The Zika mut 2014 antigen of SEQ ID NO: 29 corresponds to amino acids 409-690 of the 3423-aa Zika polyprotein (SEQ ID NO: 23), which is the truncated portion of the extracellular domain of the Zika envelope protein. The Zika mut 2014 antigen comprises point mutations as compared to the Zika wt 2014 antigen. These point mutations include I21D, L175D, L240D (position numbering does not count the N-terminal methionine) and these mutations can result in decreased anti-human C1q responses compared to wild type. One week after the final immunization, splenocytes isolated from each mice were exposed to Zika wt virus peptide pools and ELISPOT assays were used to measure CMI responses (IFN-γ and IL-2 secreting spot forming cells (SFC)) and CTL responses (Granzyme-B secreting SFCs). Specificity of responses was shown by the lack of reactivity of splenocytes to an SIV-nef peptide pool (negative control) and by reactivity of splenocytes to Concanavalin A (Con A) (positive control). Error bars show SEM and five mice were in each group. FIG. 6A illustrates IFN-γ CMI responses after exposure of splenocytes from immunized mice and control mice to Zika 2014 peptide pools and controls. Higher numbers of SFCs were induced in immunized mice as compared to control mice. FIG. 6B illustrates IL-2 CMI responses after exposure of splenocytes from immunized mice and control mice to Zika 2014 peptide pools and controls. Higher numbers of SFCs were induced in immunized mice as compared to control mice. FIG. 6C illustrates Granzyme B CTL responses after exposure of splenocytes from immunized mice and control mice to Zika 2014 peptide pools and controls. Higher numbers of SFCs were induced in immunized mice as compared to control mice.

Intracellular Cytokine Expression. Flow cytometry analysis revealed the levels of lymphocyte activation as measured by evaluating intracellular cytokine expression. FIG. 7 illustrates lymphocyte activation as measured by flow cytometry analysis of intracellular expression of IFN-γ and IFN-γ/TNF-α in splenocytes from mice immunized with Ad5 [E1-, E2b-]-Zika-E vaccines. Mice (C57B1/6 strain) were immunized two times at two-week intervals with $1\times10^{10}$ virus particles (VPs) of an Ad5 [E1-, E2b-]-Zika vaccine or with $1\times10^{10}$ VPs Ad5 [E1-, E2b-]-null (empty vector control). Three types of Zika vaccines were tested. The first Zika vaccine tested was the Ad5 [E1-, E2b-]-Zika mut 2015, which comprises a Zika antigen protein encoded by the nucleotide sequence of SEQ ID NO: 34 and by the amino acid sequence of SEQ ID NO: 35 (SEQ ID NO: 34 is the nucleotide sequence and SEQ ID NO: 35 is the amino acid sequence corresponding to SEQ ID NO: 34). The Zika mut 2015 antigen of SEQ ID NO: 35 corresponds to amino acids 409-690 of the 3423-aa Zika polyprotein (SEQ ID NO: 23), which is the truncated portion of the extracellular domain of the Zika envelope protein. The Zika mut 2015 antigen comprises point mutations as compared to the Zika wt 2015 antigen. These point mutations include D37I, D43L, D266I, D129L, D218L (position numbering does not count the N-terminal methionine) and these mutations can result in decreased anti-human C1q responses compared to wild type. The second Zika vaccine tested was the Ad5 [E1-, E2b-]-Zika wt 2014, which comprises a Zika antigen protein encoded by the nucleotide sequence of SEQ ID NO: 26 and by the amino acid sequence of SEQ ID NO: 27 (SEQ ID NO: 26 is the nucleotide sequence and SEQ ID NO: 27 is the amino acid sequence corresponding to SEQ ID NO: 26). The Zika wt 2014 antigen of SEQ ID NO: 27 corresponds to amino acids 409-690 of the 3423-aa Zika polyprotein (SEQ ID NO: 23), which is the truncated portion of the extracellular domain of the Zika envelope protein. The third Zika vaccine tested and shown here is the Ad5 [E1-, E2b-]-Zika mut 2014, which comprises a Zika antigen protein encoded by the nucleotide sequence of SEQ ID NO: 28 and the amino acid sequence of SEQ ID NO: 29 (SEQ ID NO: 28 is the nucleotide sequence and SEQ ID NO: 29 is the amino acid sequence corresponding to SEQ ID NO: 28). The Zika mut 2014 antigen of SEQ ID NO: 29 corresponds to amino acids 409-690 of the 3423-aa Zika polyprotein (SEQ ID NO: 23), which is the truncated portion of the extracellular domain of the Zika envelope protein. The Zika mut 2014 antigen comprises point mutations as compared to the Zika wt 2014 antigen. These point mutations include I21D, L175D, L240D (position numbering does not count the N-terminal methionine) and these mutations can result in decreased anti-human C1q responses compared to wild type. One week after the final immunization, splenocytes isolated from immunized mice were exposed to Zika wt virus peptide pools and flow cytometry was used to measure intracellular cytokine production of IFN-γ and IFN-γ/TNF-α in CD8+ cells and CD4+ cells. Specificity of responses was shown by the lack of reactivity of splenocytes to an SIV-nef peptide pool (negative control) and by reactivity of splenocytes to PMA/ionomycin (positive control). Data are reported as the percent of CD8+ or CD4+ splenocytes expressing IFN-γ or IFN-γ and TNF-α and error bars show SEM. Each group had five mice. FIG. 7A illustrates lymphocyte activation as measured by flow cytometry analysis of intracellular expression of IFN-γ in CD8+ splenocytes after exposure of splenocytes from immunized mice and control mice to Zika 2014 peptide pools and controls. Higher percentages of cells from immunized mice responded to Zika virus peptides and secreted cytokines as compared to control mice. FIG. 7B illustrates lymphocyte activation as measured by flow cytometry analysis of intracellular expression of IFN-γ in CD4+ splenocytes after exposure of splenocytes from immunized mice and control mice to Zika 2014 peptide pools and controls. Higher percentages of cells from immunized mice responded to Zika virus peptides and secreted cytokines as compared to control mice. FIG. 7C illustrates lymphocyte activation as measured by flow cytometry analysis of intracellular expression of IFN-γ and TNF-α in CD8+ splenocytes after exposure of splenocytes from immunized mice and control mice to Zika 2014 peptide pools and controls. Higher percentages of cells from immunized mice responded to Zika virus peptides and secreted cytokines as compared to control mice. FIG. 7D illustrates lymphocyte activation as measured by flow cytometry analysis of intracellular expression of IFN-γ and TNF-α in CD4+ splenocytes after exposure of splenocytes from immunized mice and control mice to Zika 2014 peptide pools and controls. Higher percentages of cells from immunized mice responded to Zika virus peptides and secreted cytokines as compared to control mice.

Antigen-Specific Antibody Production. Zika-specific IgG antibodies were measured in the serum of immunized mice by an enzyme-linked immunosorbent assay (ELISA). FIG. 8 illustrates anti-Zika IgG responses in the serum of mice immunized with Ad5 [E1-, E2b-]-Zika-E vaccines. Blood was drawn from the cheek pouch and analyzed using a quantitative ELISA or IgG antibody using methods set forth in Gabitzsch et al. (Cancer Gene Ther. 2011 May; 18(5): 326-335). Mice (C57B1/6 strain, 5 mice per group) were immunized two times at two-week intervals with $1\times10^{10}$ virus particles (VPs) of an Ad5 [E1-, E2b-]-Zika-E vaccine or with $1\times10^{10}$ VPs Ad5 [E1-, E2b-]-null (empty vector control). Three types of Zika vaccines were tested. The first Zika vaccine tested was the Ad5 [E1-, E2b-]-Zika mut 2015, which comprises a Zika antigen protein encoded by the nucleotide sequence of SEQ ID NO: 34 and by the amino acid sequence of SEQ ID NO: 35 (SEQ ID NO: 34 is the nucleotide sequence and SEQ ID NO: 35 is the amino acid sequence corresponding to SEQ ID NO: 34). The Zika mut 2015 antigen of SEQ ID NO: 35 corresponds to amino acids 409-690 of the 3423-aa Zika polyprotein (SEQ ID NO: 23), which is the truncated portion of the extracellular domain of the Zika envelope protein. The Zika mut 2015 antigen comprises point mutations as compared to the Zika wt 2015 antigen. These point mutations include D37I, D43L, D266I, D129L, D218L (position numbering does not count the N-terminal methionine) and these mutations can result in decreased anti-human C1q responses compared to wild type. The second Zika vaccine tested was the Ad5 [E1-, E2b-]-Zika wt 2014, which comprises a Zika antigen protein encoded by the nucleotide sequence of SEQ ID NO: 26 and by the amino acid sequence of SEQ ID NO: 27 (SEQ ID NO: 26 is the nucleotide sequence and SEQ ID NO: 27 is the amino acid sequence corresponding to SEQ ID NO: 26). The Zika wt 2014 antigen of SEQ ID NO: 27 corresponds to amino acids 409-690 of the 3423-aa Zika polyprotein (SEQ ID NO: 23), which is the truncated portion of the extracellular domain of the Zika envelope protein. The third Zika vaccine tested was the Ad5 [E1-, E2b-]-Zika mut 2014, which comprises a Zika antigen protein encoded by the nucleotide sequence of SEQ ID NO: 28 and by the amino acid sequence of SEQ ID NO: 29 (SEQ ID NO: 28 is the nucleotide sequence and SEQ ID NO: 29 is the amino acid sequence corresponding to SEQ ID NO: 28). The Zika mut 2014 antigen shown in SEQ ID NO: 29 corresponds to amino acids 409-690 of the 3423-aa Zika polyprotein (SEQ ID NO: 23), which is the truncated portion of the extracellular domain of the Zika envelope protein. The Zika mut 2014 antigen comprises point mutations as compared to the Zika wt 2014 antigen. These point mutations include I21D, L175D, L240D (position numbering does not count the N-terminal methionine) and these mutations can result in decreased anti-human C1q responses compared to wild type. One week after the final immunization, serum from mice was tested for induction of antibody responses by an enzyme linked immunosorbent assay (ELISA). The y-axis shows nanograms (ng) of anti-Zika IgG in serum. The x-axis shows each group and mouse tested (e.g. "G1M1" indicates Group 1 Mouse 1). Antibody responses were induced in immunized mice, but not in control mice. Error bars show SEM.

Symptom Evaluation. Symptoms of Zika infection were evaluated in mice including changes in weight and temperature. FIG. 9 illustrates weight loss in a mouse model of Zika virus infection (Rossi et al. Am J Trop Med Hyg. 2016 Jun. 1; 94(6):1362-9) after vaccination with Ad5 [E1-, E2b-]-Zika-E vaccine or with Ad5 [E1-, E2b-]-null empty vector as controls. Groups of A129 mice (n=10/group) were immunized once with $1\times10^{10}$ VP of Ad5 [E1-, E2b-]-Zika-E or with $1\times10^{10}$ VP of Ad5 [E1-, E2b-]-null empty vector for controls. Thirty days post-immunization, mice were challenged with a pathogenic strain of Zika virus ($5\times10^5$ plaque forming units (PFU) of Zika virus strain FSS13025 injected intraperitoneally (IP)). Mice were monitored for weight change. FIG. 10 illustrates temperature change in a mouse model of Zika virus infection (Rossi et al. Am J Trop Med Hyg. 2016 Jun. 1; 94(6):1362-9) after vaccination with Ad5 [E1-, E2b-]-Zika-E vaccine or with Ad5 [E1-, E2b-]-null empty vector as controls. Groups of A129 mice (n=10/group) were immunized once with $1\times10^{10}$ VP of Ad5 [E1-, E2b-]-Zika-E 2015wt or with $1\times10^{10}$ VPs of Ad5 [E1-, E2b-]-null (controls). Thirty days post-immunization, mice were challenged with a pathogenic strain of Zika virus ($5\times10^5$ PFU of Zika virus strain FSS13025 injected intraperitoneally (IP)). Mice were monitored for temperature change.

Pre-Clinical Assessment of Ad5 [E1-, E2b-]-Zika Wildtype (wt) 2015 and Ad5 [E1-, E2b-]-Zika Wildtype (wt) 2015 Full Length (FL) Vaccines All Ad5 [E1-, E2b-]-Zika vaccines included manufacture of vaccines with Zika inserts as described in EXAMPLE 1.

CMI and CTL Responses. CMI and CTL responses in mice were evaluated by an enzyme-linked immunospot (ELISPOT) assay. FIG. 11 illustrates cell mediated immune (CMI) responses and cytolytic T lymphocyte (CTL) responses in splenocytes from mice immunized with Ad5 [E1-, E2b-]-Zika vaccines. C57BL/6 mice (n=5/group) were immunized two times at two-week intervals with $1\times10^{10}$ virus particles (VPs) of an Ad5 [E1-, E2b-]-Zika vaccine or with $1\times10^{10}$ VPs Ad5 [E1-, E2b-]-null (empty vector control). Two types of Zika vaccines were tested, including Ad5 [E1-, E2b-]-Zika wildtype (wt) 2015, which comprises a Zika antigen protein encoded by the nucleotide sequence of SEQ ID NO: 32 and by the amino acid sequence of SEQ ID NO: 33 (SEQ ID NO: 32 is the nucleotide sequence and SEQ ID NO: 33 is the amino acid sequence corresponding to SEQ ID NO: 32). The Zika wt 2015 antigen of SEQ ID NO: 33 corresponds to amino acids 409-690 of the 3423-aa Zika polyprotein (SEQ ID NO: 23), which is the truncated portion of the extracellular domain of the Zika envelope protein. The second Zika vaccine tested was the Ad5 [E1-, E2b-]-Zika wildtype (wt) 2015 full length (FL), which comprises a Zika antigen protein encoded by the nucleotide sequence of SEQ ID NO: 36 and by the amino acid sequence of SEQ ID NO: 37 (SEQ ID NO: 36 is the nucleotide sequence and SEQ ID NO: 37 is the amino acid sequence corresponding to SEQ ID NO: 36). The Zika antigen in Ad5 [E1-, E2b-]-Zika wildtype (wt) 2015 full length (FL) comprises the full envelope protein corresponds to amino acids 271-805 of the 3423-aa Zika polyprotein (SEQ ID NO: 23) including two C-terminal transmembrane anchor domains and the extracellular loop, two transmembrane domains immediately upstream of the envelope protein in the ZIKAV genome, which encodes a portion of the M protein to ensure targeting to the plasma membrane, and a KOZAK sequence at the N-terminus (GCCGCCACC) to ensure initiation of translation, two transmembrane domains just prior to the extracellular loop, and the extracellular loop. The inclusion of transmembrane domains can serve as a signal sequence to ensure migration of mRNA-loaded ribosomes to the endoplasmic reticulum, glycosylation, and eventual migration and tethering of the protein to the plasma membrane, which can all ultimately improve antigenicity and thereby generate immune responses. Two Ad5 [E1-, E2b-]-nulls were used as comparative control vectors including Ad5 [E1-, E2b-]-null (Viraquest) and Ad5 [E1-, E2b-]-null (E) (an internally manufactured null control vector). Splenocytes were isolated seven days after the final immunization and exposed to a Zika 2014 peptide pool, an SIV-Nef peptide pool (negative control), a SIV-Gag peptide pool (negative control), and Concanavalin A (positive control), and were assessed for CMI responses (IFN-γ and IL-2) and CTL responses (Granzyme B) by ELISPOT. Data are reported as the number of spot forming cells (SFCs) per $10^6$ splenocytes and error bars show SEM. FIG. 11A illustrates IFN-γ CMI responses after exposure of splenocytes from immunized mice and control mice to Zika 2014 peptide pools and controls. FIG. 11B illustrates IL-2 CMI responses after exposure of splenocytes from immunized mice and control mice to Zika 2014 peptide pools and controls. FIG. 11C illustrates Granzyme B CTL responses after exposure of splenocytes from immunized mice and control mice to Zika 2014 peptide pools and controls.

Intracellular Cytokine Expression. Flow cytometry analysis revealed the levels of lymphocyte activation as measured by evaluating intracellular cytokine expression. FIG. 12 illustrates lymphocyte activation as measured by flow cytometry analysis of intracellular expression of IFN-γ and IFN-γ/TNF-α in splenocytes from mice immunized with Ad5 [E1-, E2b-]-Zika vaccines. C57BL/6 mice were immunized two times at two-week intervals with $1\times10^{10}$ virus particles (VPs) of an Ad5 [E1-, E2b-]-Zika vaccine or with $1\times10^{10}$ VPs Ad5 [E1-, E2b-]-null (empty vector control). Two types of Zika vaccines were tested, including Ad5 [E1-, E2b-]-Zika wildtype (wt) 2015, which comprises a Zika antigen protein encoded by the nucleotide sequence of SEQ ID NO: 32 and by the amino acid sequence of SEQ ID NO: 33 (SEQ ID NO: 32 is the nucleotide sequence and SEQ ID NO: 33 is the amino acid sequence corresponding to SEQ ID NO: 32). The Zika wt 2015 antigen of SEQ ID NO: 33 corresponds to amino acids 409-690 of the 3423-aa Zika polyprotein (SEQ ID NO: 23), which is the truncated portion of the extracellular domain of the Zika envelope protein. The second Zika vaccine tested was the Ad5 [E1-, E2b-]-Zika wildtype (wt) 2015 full length (FL), which comprises a Zika antigen protein encoded by the nucleotide sequence of SEQ ID NO: 36 and by the amino acid sequence of SEQ ID NO: 37 (SEQ ID NO: 36 is the nucleotide sequence and SEQ ID NO: 37 is the amino acid sequence corresponding to SEQ ID NO: 36). The Zika antigen in Ad5 [E1-, E2b-]-Zika wildtype (wt) 2015 full length (FL) comprises the full envelope protein corresponds to amino acids 271-805 of the 3423-aa Zika polyprotein (SEQ ID NO: 23) including two C-terminal transmembrane anchor domains and the extracellular loop, two transmembrane domains immediately upstream of the envelope protein in the ZIKAV genome, which encodes a portion of the M protein to ensure targeting to the plasma membrane, and a KOZAK sequence at the N-terminus (GCCGCCACC) to ensure initiation of translation, two transmembrane domains just prior to the extracellular loop, and the extracellular loop. The inclusion of transmembrane domains can serve as a signal sequence to ensure migration of mRNA-loaded ribosomes to the endoplasmic reticulum, glycosylation, and eventual migration and tethering of the protein to the plasma membrane, which can all ultimately improve antigenicity and thereby generate immune responses. Two Ad5 [E1-, E2b-]-nulls were used as comparative control vectors including Ad5 [E1-, E2b-]-null (Viraquest) and Ad5 [E1-, E2b-]-null (E) (an internally manufactured null control vector). Seven days after the final immunization, splenocytes isolated from immunized mice were exposed to Zika virus peptide pools and flow cytometry was used to measure intracellular cytokine production of IFN-γ and IFN-γ/TNF-α in CD8+ cells and CD4+ cells. Specificity of responses was shown by the lack of reactivity of splenocytes to an SIV-nef peptide pool (negative control) and media (negative control) and reactivity of splenocytes to PMA/ionomycin (data not shown) (positive control). Data are reported as the percent of CD8+ or CD4+ splenocytes expressing IFN-γ or IFN-γ and TNF-α, and error bars show SEM. FIG. 12A illustrates lymphocyte activation as measured by flow cytometry analysis of intracellular expression of IFN-γ in CD8+ splenocytes after exposure of splenocytes from immunized mice and control mice to Zika 2014 peptide pools and controls. FIG. 12B illustrates lymphocyte activation as measured by flow cytometry analysis of intracellular expression of IFN-γ in CD4+ splenocytes after exposure of splenocytes from immunized mice and control mice to Zika 2014 peptide pools and controls. FIG. 12C illustrates lymphocyte activation as measured by flow cytometry analysis of intracellular expression of IFN-γ and TNF-α in CD8+ splenocytes after exposure of splenocytes from immunized mice and control mice to Zika 2014 peptide pools and controls. FIG. 12D illustrates lymphocyte activation as measured by flow cytometry analysis of intracellular expression of IFN-γ and TNF-α in CD4+ splenocytes after exposure of splenocytes from immunized mice and control mice to Zika 2014 peptide pools and controls.

Antigen-Specific Antibody Production. Zika-specific IgG antibodies were measured in the serum of immunized mice by an enzyme-linked immunosorbent assay (ELISA). FIG. 13 illustrates anti-Zika IgG responses in the serum of mice immunized with Ad5 [E1-, E2b-]-Zika vaccines. C57BL/6 mice (n=5/group) were immunized two times at two-week intervals with $1 \times 10^{10}$ virus particles (VPs) of an Ad5 [E1-, E2b-]-Zika wildtype (wt) 2015 vaccine or an Ad5 [E1-, E2b-]-Zika wt 2015 full length (FL) vaccine. Two Ad5 [E1-, E2b-]-nulls were used as comparative control vectors including Ad5 [E1-, E2b-]-null (Viraquest) and Ad5 [E1-, E2b-]-null (E) (an internally manufactured null control vector). Sera were collected from mice seven days after the final immunization and assessed by an enzyme linked immunosorbent assay (ELISA) for antigen specific antibodies against Zika virus envelope protein-1. The y-axis shows nanograms (ng) of anti-Zika IgG in serum. In the Ad5 [E1-, E2b-]-Zika wt 2015 group, three out of five (3/5) were antibody positive. In the Ad5 [E1-, E2b-]-Zika wt 2015 FL group, five out of five (5/5) were antibody positive.

Example 5

Prevention of Zika Infection with Ad5 [E1-, E2b-]-Zika Vaccines

This example illustrates prevention of Zika infection by prophylaxis with any Ad5 [E1-, E2b-]-Zika vaccine of this disclosure including an Ad5 [E1-, E2b-] with any one of, or any combination of, Zika antigens (e.g., SEQ ID NO: 11-SEQ ID NO: 21 or SEQ ID NO: 23-SEQ ID NO: 37) inserted into the adenovirus vector. An Ad5 [E1-, E2b-]-Zika vaccine is constructed as described in EXAMPLE 1 for single-targeted Zika vaccines or is constructed as described in EXAMPLE 2 for multi-targeted Zika vaccines. The Ad5 [E1-, E2b-]-Zika vaccine is administered to a subject, every two weeks for a total of two immunizations. Vaccines are administered subcutaneously. Cellular and humoral immune responses against Zika virus and protection against infection by Zika virus is induced after immunization of a subject with the Ad5 [E1-, E2b-]-Zika vaccine. In other words, prophylaxis immunity with the Ad5 [E1-, E2b-]-Zika vaccine is conferred to the subject. The subject is any animal including a human, a non-human primate, or any other non-human animal.

Example 6

Prevention of Zika Infection with Combination Prophylaxis with Ad5 [E1-, E2b-]-Zika Vaccines and Co-Stimulatory Molecules This example illustrates prevention of Zika infection by prophylaxis with any Ad5 [E1-, E2b-]-Zika vaccine of this disclosure including an Ad5 [E1-, E2b-] with any one of, or any combination of, Zika antigens (e.g., SEQ ID NO: 11-SEQ ID NO: 21 or SEQ ID NO: 23-SEQ ID NO: 37) inserted into the adenovirus vector in combination with any co-stimulatory molecule described herein. An Ad5 [E1-, E2b-]-Zika vaccine is constructed as described in EXAMPLE 1 for single-targeted Zika vaccines or is constructed as described in EXAMPLE 2 for multi-targeted Zika vaccines. The Ad5 [E1-, E2b-]-Zika vaccine is administered subcutaneously, intradermally, or intramuscularly to a subject once or every two weeks for a total of two immunizations. Ad vaccines are co-administered with a co-stimulatory molecule, such as a toll-like receptor (TLR) agonist mixed with the vaccine formulation. Cellular and humoral immune responses against Zika virus and protection against infection by Zika virus is induced after immunization of a subject with the Ad5 [E1-, E2b-]-Zika vaccine in combination with the co-stimulatory molecule. In other words, prophylaxis immunity with the Ad5 [E1-, E2b-]-Zika vaccine in combination with the co-stimulatory molecule is conferred to the subject. The subject is any animal including a human, a non-human primate, or any other non-human animal.

Example 7

Prevention of Zika Infection with Prophylaxis with Ad5 [E1-, E2b-]-Zika Vaccines and an Immunological Fusion Partner This example illustrates prevention of Zika infection by prophylaxis with any Ad5 [E1-, E2b-]-Zika vaccine of this disclosure including an Ad5 [E1-, E2b-] with any one of, or any combination of, Zika antigens (e.g., SEQ ID NO: 11-SEQ ID NO: 21 or SEQ ID NO: 23-SEQ ID NO: 37) inserted into the adenovirus vector as well as any immunological fusion partner described herein, also encoded by the adenovirus vector. An Ad5 [E1-, E2b-]-Zika vaccine is constructed as described in EXAMPLE 1 for single-targeted Zika vaccines or is constructed as described in EXAMPLE 2 for multi-targeted Zika vaccines and the Ad vector additionally encodes for any immunological fusion partner disclosed herein. The Ad5 [E1-, E2b-]-Zika vaccine is administered to a subject, every two weeks for a total of two immunizations. Vaccines with immunological fusion partners are administered subcutaneously. Enhanced cellular and humoral immune responses against Zika virus and protection against infection by Zika virus is induced after immunization of a subject with the Ad5 [E1-, E2b-]-Zika vaccine-immunological fusion partner. In other words, prophylaxis immunity with the Ad5 [E1-, E2b-]-Zika vaccine-immunological fusion partner is conferred to the subject. The subject is any animal including a human, a non-human primate, or any other non-human animal.

Example 8

Prevention of Yellow Fever Virus Infection with Ad5 [E1-, E2b-]-Yellow Fever Virus (YFV) Vaccines This example illustrates prevention of Yellow Fever Virus (YFV) infection by prophylaxis with any Ad5 [E1-, E2b-]-YFV vaccine of this disclosure including an Ad5 [E1-, E2b-] with any one of, or any combination of, YFV antigens (e.g., SEQ ID NO: 1 or SEQ ID NO: 22) inserted into the adenovirus vector. An Ad5 [E1-, E2b-]-YFV vaccine is constructed as adapted from EXAMPLE 1 for single-targeted YFV vaccines or is constructed as as adapted from EXAMPLE 2 for multi-targeted YFV vaccines. The Ad5 [E1-, E2b-]-YFV vaccine is administered to a subject, every two weeks for a total of two immunizations. Vaccines are administered subcutaneously. Cellular and humoral immune responses against yellow fever virus and protection against infection by yellow fever virus is induced after immunization of a subject with the Ad5 [E1-, E2b-]-YFV vaccine. In other words, prophylaxis immunity with the Ad5 [E1-, E2b-]-YFV vaccine is conferred to the subject. The subject is any animal including a human, a non-human primate, or any other non-human animal.

Example 9

Prevention of Japanese Encephalitis Virus Infection with Ad5 [E1-, E2b-]-Japanese Encephalitis Virus (JEV) Vaccines This example illustrates prevention of Japanese Encephalitis Virus (JEV) infection by prophylaxis with any Ad5 [E1-, E2b-]-JEV vaccine of this disclosure including an Ad5 [E1-, E2b-] with any one of, or any combination of, JEV antigens (e.g., SEQ ID NO: 2) inserted into the adenovirus vector. An Ad5 [E1-, E2b-]-JEV vaccine is constructed as as adapted from EXAMPLE 1 for single-targeted JEV vaccines or is constructed as adapted from EXAMPLE 2 for multi-targeted JEV vaccines. The Ad5 [E1-, E2b-]-JEV vaccine is administered to a subject, every two weeks for a total of two immunizations. Vaccines are administered subcutaneously. Cellular and humoral immune responses against Japanese Encephalitis virus and protection against infection by Japanese Encephalitis virus is induced after immunization of a subject with the Ad5 [E1-, E2b-]-JEV vaccine. In other words, prophylaxis immunity with the Ad5 [E1-, E2b-]-JEV vaccine is conferred to the subject. The subject is any animal including a human, a non-human primate, or any other non-human animal.

Example 10

Prevention of Tick-Borne Encephalitis Virus Infection with Ad5 [E1-, E2b-]-Tick-Borne Encephalitis Virus (TBEV) Vaccines This example illustrates prevention of Tick-borne encephalitis virus (TBEV) infection by prophylaxis with any Ad5 [E1-, E2b-]-TBEV vaccine of this disclosure including an Ad5 [E1-, E2b-] with any one of, or any combination of, TBEV antigens (e.g., SEQ ID NO: 3-SEQ ID NO: 5) inserted into the adenovirus vector. An Ad5 [E1-, E2b-]-TBEV vaccine is constructed as adapted from EXAMPLE 1 for single-targeted TBEV vaccines or is constructed as adapted from EXAMPLE 2 for multi-targeted TBEV vaccines. The Ad5 [E1-, E2b-]-TBEV vaccine is administered to a subject, every two weeks for a total of two immunizations. Vaccines are administered subcutaneously. Cellular and humoral immune responses against Tick-borne encephalitis virus and protection against infection by Tick-borne encephalitis virus is induced after immunization of a subject with the Ad5 [E1-, E2b-]-TBEV vaccine. In other words, prophylaxis immunity with the Ad5 [E1-, E2b-]-TBEV vaccine is conferred to the subject. The subject is any animal including a human, a non-human primate, or any other non-human animal.

Example 11

Prevention of Dengue Virus Infection with Ad5 [E1-, E2b-]-Dengue Virus (DENV) Vaccines This example illustrates prevention of Dengue virus (DENV) infection by prophylaxis with any Ad5 [E1-, E2b-]-DENV vaccine of this disclosure including an Ad5 [E1-, E2b-] with any one of, or any combination of, DENV antigens (e.g., SEQ ID NO: 6-SEQ ID NO: 9) inserted into the adenovirus vector. An Ad5 [E1-, E2b-]-DENV vaccine is constructed as adapted from EXAMPLE 1 for single-targeted DENV vaccines or is constructed as adapted from EXAMPLE 2 for multi-targeted DENV vaccines. The Ad5 [E1-, E2b-]-DENV vaccine is administered to a subject, every two weeks for a total of two immunizations. Vaccines are administered subcutaneously. Cellular and humoral immune responses against Dengue virus and protection against infection by Dengue virus is induced after immunization of a subject with the Ad5 [E1-, E2b-]-DENV vaccine. In other words, prophylaxis immunity with the Ad5 [E1-, E2b-]-DENV vaccine is conferred to the subject. The subject is any animal including a human, a non-human primate, or any other non-human animal.

Example 12

Prevention of West Nile Virus Infection with Ad5 [E1-, E2b-]-West Nile Virus (WNV) Vaccines This example illustrates prevention of West Nile Virus (WNV) infection by prophylaxis with any Ad5 [E1-, E2b-]-WNV vaccine of this disclosure including an Ad5 [E1-, E2b-] with any one of, or any combination of, WNV antigens (e.g., SEQ ID NO: 10) inserted into the adenovirus vector. An Ad5 [E1-, E2b-]-WNV vaccine is constructed as adapted from EXAMPLE 1 for single-targeted WNV vaccines or is constructed as adapted from EXAMPLE 2 for multi-targeted WNV vaccines. The Ad5 [E1-, E2b-]-WNV vaccine is administered to a subject, every two weeks for a total of two immunizations. Vaccines are administered subcutaneously. Cellular and humoral immune responses against West Nile virus and protection against infection by West Nile virus is induced after immunization of a subject with the Ad5 [E1-, E2b-]-WNV vaccine. In other words, prophylaxis immunity with the Ad5 [E1-, E2b-]-WNV vac-

Example 13

Prevention of Flavivirus Infections with Ad5 [E1-, E2b-]-Flavivirus Vaccines This example illustrates prevention of flavivirus infections by prophylaxis with any Ad5 [E1-, E2b-]-flavivirus vaccine of this disclosure. The Ad5 [E1-, E2b-]-flavivirus vaccine is comprised of any combination of: single-targeted or multi-targeted Ad5 [E1-, E2b-]-Zika vector as described in EXAMPLE 5, single-targeted or multi-targeted Ad5 [E1-, E2b-]-YFV vector as described in EXAMPLE 8, single-targeted or multi-targeted Ad5 [E1-, E2b-]-JEV vector as described in EXAMPLE 9, single-targeted or multi-targeted Ad5 [E1-, E2b-]-TBEV vector as described in EXAMPLE 10, single-targeted or multi-targeted Ad5 [E1-, E2b-]-DENV vector as described in EXAMPLE 11, single-targeted or multi-targeted Ad5 [E1-, E2b-]-WNV vector as described in EXAMPLE 12. Alternatively, the Ad5 [E1-, E2b-]-flavivirus vaccine is comprised of an Ad5 [E1-, E2b-] with any combination of at least two antigens from different flaviviruses inserted into the adenovirus vector. For example, the at least two antigens is comprised of any combination of a Zika antigen (e.g., any one of SEQ ID NO: 11-SEQ ID NO: 21 or SEQ ID NO: 23-SEQ ID NO: 37), a YFV antigen (e.g., SEQ ID NO: 1 or SEQ ID NO: 22), a JEV antigen (e.g., SEQ ID NO: 2), a TBEV antigen (e.g., SEQ ID NO: 3-SEQ ID NO: 5), a DENV antigen (e.g., SEQ ID NO: 6-SEQ ID NO: 9), and/or a WNV antigen (e.g., SEQ ID NO: 10).

The Ad5 [E1-, E2b-]-flavivirus vaccine is administered to a subject, every two weeks for a total of two immunizations. Vaccines are administered subcutaneously. Cellular and humoral immune responses against flavivirus and protection against infection by flavivirus is induced after immunization of a subject with the Ad5 [E1-, E2b-]-flavivirus vaccine. In other words, prophylaxis immunity with the Ad5 [E1-, E2b-]-flavivirus vaccine is conferred to the subject. The subject is any animal including a human, a non-human primate, or any other non-human animal.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

| SEQUENCES | |
|---|---|
| SEQ ID NO | Sequence |
| SEQ ID NO: 1 | AGTAAATCCTGTGTGCTAATTGAGGTGCATTGGTCTGCAAATCGAG<br>TTGCTAGGCAATAAACACATTTGGATTAATTTTAATCGTTCGTTGAG<br>CGATTAGCAGAGAACTGACCAGAACATGTCTGGTCGTAAAGCTCAG<br>GGAAAAACCCTGGGCGTCAATATGGTACGACGAGGAGTTCGCTCCT<br>TGTCAAACAAAATAAAACAAAAAACAAAACAAATTGGAAACAGAC<br>CTGGACCTTCAAGAGGTGTTCAAGGATTTATCTTTTTCTTTTTGTTC<br>AACATTTTGACTGGAAAAAAGATCACAGCCCACCTAAAGAGGTTGT<br>GGAAAATGCTGGACCCAAGACAAGGCTTGGCTGTTCTAAGGAAAG<br>TCAAGAGAGTGGTGGCCAGTTTGATGAGAGGATTGTCCTCAAGGAA<br>ACGCCGTTCCCATGATGTTCTGACTGTGCAATTCCTAATTTTGGGAA<br>TGCTGTTGATGACGGGTGGAGTGACCTTGGTGCGGAAAAACAGATG<br>GTTGCTCCTAAATGTGACATCTGAGGACCTCGGGAAAACATTCTCT<br>GTGGGCACAGGCAACTGCACAACAAACATTTTGGAAGCAAGTACT<br>GGTGCCCAGACTCAATGGAATACAACTGTCCCAATCTCAGTCCAAG<br>AGAGGAGCCAGATGACATTGATTGCTGGTGCTATGGGGTGGAAAA<br>CGTTAGAGTCGCATATGGTAAGTGTGACTCAGCAGGCAGGTCTAGG<br>AGGTCAAGAAGGGCCATTGACTTGCCTACGCATGAAAACCATGGTT<br>TGAAGACCCGGCAAGAAAAATGGATGACTGGAAGAATGGGTGAAA<br>GGCAACTCCAAAAGATTGAGAGATGGTTCGTGAGGAACCCCTTTTT<br>TGCAGTGACGGCTCTGACCATTGCCTACCTTGTGGGAAGCAACATG<br>ACGCAACGAGTCGTGATTGCCCTACTGGTCTTGGCTGTTGGTCCGG<br>CCTACTCAGCTCACTGCATTGGAATTACTGACAGGGATTTCATTGA<br>GGGGGTGCATGGAGGAACTTGGGTTTCAGCTACCCTGGAGCAAGAC<br>AAGTGTGTCACTGTTATGGCCCCTGACAAGCCTTCATTGGACATCTC<br>ACTAGAGACAGTAGCCATTGATAGACCTGCTGAGGTGAGGAAAGT<br>GTGTTACAATGCAGTTCTCACTCATGTGAAGATTAATGACAAGTGC<br>CCCAGCACTGGAGAGGCCCACCTAGCTGAAGAGAACGAAGGGGAC<br>AATGCGTGCAAGCGCACTTATTCTGATAGAGGCTGGGGCAATGGCT<br>GTGGCCTATTTGGGAAAGGGAGCATTGTGGCATGCGCCAAATTCAC<br>TTGTGCCAAATCCATGAGTTTGTTTGAGGTTGATCAGACCAAAATTC<br>AGTATGTCATCAGAGCACAATTGCATGTAGGGGCCAAGCAGGAAA<br>ATTGGACTACCGACATTAAGACTCTCAAGTTTGATGCCCTGTCAGG<br>CTCCCAGGAAGTCGAGTTCATTGGGTATGGAAAAGCTACACTGGAA<br>TGCCAGGTGCAAACTGCGGTGGACTTTGGTAACAGTTACATCGCTG<br>AGATGGAAACAGAGAGCTGGATAGTGGACAGACAGTGGGCCCAGG<br>ACTTGACCCTGCCATGGCAGAGTGGAAGTGGCGGGTGTGGAGAG<br>AGATGCATCATCTTGTCGAATTTGAACCTCCGCATGCCGCCACTATC<br>AGAGTACTGGCCCTGGGAAACCAGGAAGGCTCCTTGAAAACAGCT<br>CTTACTGGCGCAATGAGGGTTACAAAGGACACAAATGACAACAAC<br>CTTTACAAACTACATGGTGGACATGTTTCTTGCAGAGTGAAATTGTC<br>AGCTTTGACACTCAAGGGGACATCCTACAAAATATGCACTGACAAA |

| SEQ ID NO | Sequence |
|---|---|
| | ATGTTTTTGTCAAGAACCCAACTGACACTGGCCATGGCACTGTTGT
GATGCAGGTGAAAGTGTCAAAAGGAGCCCCCTGCAGGATTCCAGT
GATAGTAGCTGATGATCTTACAGCGGCAATCAATAAAGGCATTTTG
GTTACAGTTAACCCCATCGCCTCAACCAATGATGATGAAGTGCTGA
TTGAGGTGAACCCACCTTTTGGAGACAGCTACATTATCGTTGGGAG
AGGAGATTCACGTCTCACTTACCAGTGGCACAAAGAGGGAAGCTCA
ATAGGAAAGTTGTTCACTCAGACCATGAAAGGCGTGGAACGCCTGG
CCGTCATGGGAGACACCGCCTGGGATTTCAGCTCCGCTGGAGGGTT
CTTCACTTCGGTTGGGAAAGGAATTCATACGGTGTTTGGCTCTGCCT
TTCAGGGGCTATTTGGCGGCTTGAACTGGATAACAAAGGTCATCAT
GGGGGCGGTACTTATATGGGTTGGCATCAACACAAGAAACATGAC
AATGTCCATGAGCATGATCTTGGTAGGAGTGATCATGATGTTTTTGT
CTCTAGGAGTTGGGGCGGATCAAGGATGCGCCATCAACTTTGGCAA
GAGAGAGCTCAAGTGCGGAGATGGTATCTTCATATTTAGAGACTCT
GATGACTGGCTGAACAAGTACTCATACTATCCAGAAGATCCTGTGA
AGCTTGCATCAATAGTGAAAGCCTCTTTTGAAGAAGGGAAGTGTGG
CCTAAATTCAGTTGACTCCCTTGAGCATGAGATGTGGAGAAGCAGG
GCAGATGAGATCAATGCCATTTTTGAGGAAAACGAGGTGGACATTT
CTGTTGTCGTGCAGGATCCAAAGAATGTTTACCAGAGAGGAACTCA
TCCATTTTCCAGAATTCGGGATGGTCTGCAGTATGGTTGGAAGACTT
GGGGTAAGAACCTTGTGTTCTCCCCAGGGAGGAAGAATGGAAGCTT
CATCATAGATGGAAAGTCCAGGAAAGAATGCCCGTTTTCAAACCGG
GTCTGGAATTCTTTCCAGATAGAGGAGTTTGGGACGGGAGTGTTCA
CCACACGCGTGTACATGGACGCAGTCTTTGAATACACCATAGACTG
CGATGGATCTATCTTGGGTGCAGCGGTGAACGGAAAAAAGAGTGC
CCATGGCTCTCCAACATTTTGGATGGGAAGTCATGAAGTAAATGGG
ACATGGATGATCCACACCTTGGAGGCATTAGATTACAAGGAGTGTG
AGTGGCCACTGACACATACGATTGGAACATCAGTTGAAGAGAGTG
AAATGTTCATGCCGAGATCAATCGGAGGCCCAGTTAGCTCTCACAA
TCATATCCCTGGATACAAGGTTCAGACGAACGGACCTTGGATGCAG
GTACCACTAGAAGTGAAGAGAGAAGCTTGCCCAGGGACTAGCGTG
ATCATTGATGGCAACTGTGATGGACGGGGAAAATCAACCAGATCCA
CCACGGATAGCGGGAAAGTTATTCCTGAATGGTGTTGCCGCTCCTG
CACAATGCCGCCTGTGAGCTTCCATGGTAGTGATGGGTGTTGGTAT
CCCATGGAAATTAGGCCAAGGAAAACGCATGAAAGCCATCTGGTG
CGCTCCTGGGTTACAGCTGGAGAAATACATGCTGTCCCTTTTGGTTT
GGTGAGCATGATGATAGCAATGGAAGTGGTCCTAAGGAAAAGACA
GGGACCAAAGCAAATGTTGGTTGGAGGAGTAGTGCTCTTGGGAGC
AATGCTGGTCGGGCAAGTAACTCTCCTTGATTTGCTGAAACTCACA
GTGGCTGTGGGATTGCATTTCCATGAGATGAACAATGGAGGAGACG
CCATGTATATGGCGTTGATTGCTGCCTTTTCAATCAGACCAGGGCTG
CTCATCGGCTTTGGGCTCAGGACCCTATGGAGCCCTCGGGAACGCC
TTGTGCTGACCCTAGGAGCAGCCATGGTGGAGATTGCCTTGGGTGG
CGTGATGGGCGGCCTGTGGAAGTATCTAAATGCAGTTTCTCTCTGC
ATCCTGACAATAAATGCTGTTGCTTCTAGGAAAGCATCAAATACCA
TCTTGCCCCTCATGGCTCTGTTGACACCTGTCACTATGGCTGAGGTG
AGACTTGCCGCAATGTTCTTTTGTGCCGTGGTTATCATAGGGGTCCT
TCACCAGAATTTCAAGGACACCTCCATGCAGAAGACTATACCTCTG
GTGGCCCTCACACTCACATCTTACCTGGGCTTGACACAACCTTTTTT
GGGCCTGTGTGCATTTCTGGCAACCCGCATATTTGGGCGAAGGAGT
ATCCCAGTGAATGAGGCACTCGCAGCAGCTGGTCTAGTGGGAGTGC
TGGCAGGACTGGCTTTTCAGGAGATGGAGAACTTCCTTGGTCCGAT
TGCAGTTGGAGGACTCCTGATGATGCTGGTTAGCGTGGCTGGGAGG
GTGGATGGGCTAGAGCTCAAGAAGCTTGGTGAAGTTTCATGGGAAG
AGGAGGCGGAGATCAGCGGGAGTTCCGCCCGCTATGATGTGGCACT
CAGTGAACAAGGGGAGTTCAAGCTGCTTTCTGAAGAGAAAGTGCC
ATGGGACCAGGTTGTGATGACCTCGCTGGCCTTGGTTGGGGCTGCC
CTCCATCCATTTGCTCTTCTGCTGGTCCTTGCTGGGTGGCTGTTTCAT
GTCAGGGGAGCTAGGAGAAGTGGGGATGTCTTGTGGGATATTCCCA
CTCCTAAGATCATCGAGGAATGTGAACATCTGGAGGATGGGATTTA
TGGCATATTCCAGTCAACCTTCTTGGGGGCCTCCCAGCGAGGAGTG
GGAGTGGCACAGGGAGGGGTGTTCCACACAATGTGGCATGTCACA
AGAGGAGCTTTCCTTGTCAGGAATGGCAAGAAGTTGATTCCATCTT
GGGCTTCAGTAAAGGAAGACCTTGTCGCCTATGGTGGCTCATGGAA
GTTGGAAGGCAGATGGGATGGAGAGGAAGAGGTCCAGTTGATCGC
GGCTGTTCCAGGAAAGAACGTGGTCAACGTCCAGACAAAACCGAG
CTTGTTCAAAGTGAGGAATGGGGAGAAATCGGGGCTGTCGCTCTT
GACTATCCGAGTGGCACTTCAGGATCTCCTATTGTTAACAGGAACG
GAGAGGTGATTGGGCTGTACGGCAATGGCATCCTTGTCGGTGACAA
CTCCTTCGTGTCCGCCATATCCCAGACTGAGGTGAAGGAAGAAGGA
AAGGAGGAGCTCCAAGAGATCCCGACAATGCTAAAGAAAGGAATG
ACAACTGTCCTTGATTTTCATCCTGGAGCTGGGAAGACAAGACGTT
TCCTCCCACAGATCTTGGCCGAGTGCGCACGGAGACGCTTGCGCAC
TCTTGTGTTGGCCCCCACCAGGGTTGTTCTTTCTGAAATGAAGGAGG
CTTTTCACGGCCTGGACGTGAAATTCCACACACAGGCTTTTTCCGCT |

| SEQUENCES | |
|---|---|
| SEQ ID NO | Sequence |
| | CACGGCAGCGGGAGAGAAGTCATTGATGCTATGTGCCATGCCACCC |
| | TAACTTACAGGATGTTGGAACCAACTAGGGTTGTTAACTGGGAAGT |
| | GATCATTATGGATGAAGCCCATTTTTTGGATCCAGCTAGCATAGCC |
| | GCTAGAGGTTGGGCAGCGCACAGAGCTAGGGCAAATGAAAGTGCA |
| | ACAATCTTGATGACAGCCACACCGCCTGGGACTAGTGATGAATTTC |
| | CACATTCAAATGGTGAAATAGAAGATGTTCAAACGGACATACCCAG |
| | TGAGCCCTGGAACACAGGGCATGACTGGATCCTGGCTGACAAAAG |
| | GCCCACGGCATGGTTCCTTCCATCCATCAGAGCTGCAAATGTCATG |
| | GCTGCCTCTTTGCGTAAGGCTGGAAAGAGTGTGGTGGTCCTGAACA |
| | GGAAAACCTTTGAGAGAGAATACCCCACGATAAAGCAGAAGAAAC |
| | CTGACTTTATATTGGCCACTGACATAGCTGAAATGGGAGCCAACCT |
| | TTGCGTGGAGCGAGTGCTGGATTGCAGGACGGCTTTTAAGCCTGTG |
| | CTTGTGGATGAAGGGAGGAAGGTGGCAATAAAAGGGCCACTTCGT |
| | ATCTCCGCATCCTCTGCTGCTCAAAGGAGGGGGCGCATTGGGAGAA |
| | ATCCCAACAGAGATGGAGACTCATACTACTATTCTGAGCCTACAAG |
| | TGAAAATAATGCCCACCACGTCTGCTGGTTGGAGGCCTCAATGCTC |
| | TTGGACAACATGGAGGTGAGGGGTGGAATGGTCGCCCCACTCTATG |
| | GCGTTGAAGGAACTAAAACACCAGTTTCCCCTGGTGAAATGAGACT |
| | GAGGGATGACCAGAGGAAAGTCTTCAGAGAACTAGTGAGGAATTG |
| | TGACCTGCCCGTTTGGCTTTCGTGGCAAGTGGCCAAGGCTGGTTTG |
| | AAGACGAATGATCGTAAGTGGTGTTTTGAAGGCCCTGAGGAACATG |
| | AGATCTTGAATGACAGCGGTGAAACAGTGAAGTGCAGGGCTCCTG |
| | GAGGAGCAAAGAAGCCTCTGCGCCCAAGGTGGTGTGATGAAAGGG |
| | TGTCATCTGACCAGAGTGCGCTGTCTGAATTTATTAAGTTTGCTGAA |
| | GGTAGGAGGGGAGCTGCTGAAGTGCTAGTTGTGCTGAGTGAACTCC |
| | CTGATTTCCTGGCTAAAAAGGTGGAGAGGCAATGGATACCATCAG |
| | TGTGTTTCTCCACTCTGAGGAAGGCTCTAGGGCTTACCGCAATGCA |
| | CTATCAATGATGCCTGAGGCAATGACAATAGTCATGCTGTTTATAC |
| | TGGCTGGACTACTGACATCGGGAATGGTCATCTTTTTCATGTCTCCC |
| | AAAGGCATCAGTAGAATGTCTATGGCGATGGGCACAATGGCCGGCT |
| | GTGGATATCTCATGTTCCTTGGAGGCGTCAAACCCACTCACATCTCC |
| | TATATCATGCTCATATTCTTTGTCCTGATGGTGGTTGTGATCCCCGA |
| | GCCAGGGCAACAAAGGTCCATCCAAGACAACCAAGTGGCATACCT |
| | CATTATTGGCATCCTGACGCTGGTTTCAGCGGTGGCAGCCAACGAG |
| | CTAGGCATGCTGGAGAAAACCAAAGAGGACCTCTTTGGGAAGAAG |
| | AACTTAATTCCATCTAGTGCTTCACCCTGGAGTTGGCCGGATCTTGA |
| | CCTGAAGCCAGGAGCTGCCTGGACAGTGTACGTTGGCATTGTTACA |
| | ATGCTCTCTCCAATGTTGCACCACTGGATCAAAGTCGAATATGGCA |
| | ACCTGTCTCTGTCTGGAATAGCCCAGTCAGCCTCAGTCCTTTCTTTC |
| | ATGGACAAGGGGATACCATTCATGAAGATGAATATCTCGGTCATAA |
| | TGCTGCTGGTCAGTGGCTGGAATTCAATAACAGTGATGCCTCTGCT |
| | CTGTGGCATAGGGTGCGCCATGCTCCACTGGTCTCTCATTTTACCTG |
| | GAATCAAAGCGCAGCAGTCAAAGCTTGCACAGAGAAGGGTGTTCC |
| | ATGGCGTTGCCAAGAACCCTGTGGTTGATGGGAATCCAACAGTTGA |
| | CATTGAGGAAGCTCCTGAAATGCCTGCCCTTTATGAGAAGAAACTG |
| | GCTCTATATCTCCTTCTTGCTCTCAGCCTAGCTTCTGTTGCCATGTGC |
| | AGAACGCCCTTTTCATTGGCTGAAGGCATTGTCCTAGCATCAGCTG |
| | CCCTAGGGCCGCTCATAGAGGGAAACACCAGCCTTCTTTGGAATGG |
| | ACCCATGGCTGTCTCCATGACAGGAGTCATGAGGGGGAATCACTAT |
| | GCTTTTGTGGGAGTCATGTACAATCTATGGAAGATGAAAACTGGAC |
| | GCCGGGGGAGCGCGAATGGAAAAACTTTGGGTGAAGTCTGGAAGA |
| | GGGAACTGAATCTGTTGGACAAGCGACAGTTTGAGTTGTATAAAAG |
| | GACCGACATTGTGGAGGTGGATCGTGATACGGCACGCAGGCATTTG |
| | GCCGAAGGGAAGGTGGACACCGGGGTGGCGGTCTCCAGGGGGACC |
| | GCAAAGTTAAGGTGGTTCCATGAGCGTGGCTATGTCAAGCTGGAAG |
| | GTAGGGTGATTGACCTGGGGTGTGGCCGCGGAGGCTGGTGTTACTA |
| | CGCTGCTGCGCAAAAGGAAGTGAGTGGGGTCAAAGGATTTACTCTT |
| | GGAAGAGACGGCCATGAGAAACCCATGAATGTGCAAAGTCTGGGA |
| | TGGAACATCATCACCTTCAAGGACAAAACTGATATCCACCGCCTAG |
| | AACCAGTGAAATGTGACACCCTTTTGTGTGACATTGGAGAGTCATC |
| | ATCGTCATCGGTCACAGAGGGGGAAAGGACCGTGAGAGTTCTTGAT |
| | ACTGTAGAAAAATGGCTGGCTTGTGGGGTTGACAACTTCTGTGTGA |
| | AGGTGTTAGCTCCATACATGCCAGATGTTCTCGAGAAACTGGAATT |
| | GCTCCAAAGGAGGTTTGGCGGAACAGTGATCAGGAACCCTCTCTCC |
| | AGGAATTCCACTCATGAAATGTACTACGTGTCTGGAGCCCGCAGCA |
| | ATGTCACATTTACTGTGAACCAAACATCCCGCCTCCTGATGAGGAG |
| | AATGAGGCGTCCAACTGGAAAAGTGACCCTGGAGGCTGACGTCATC |
| | CTCCCAATTGGGACACGCAGTGTTGAGACAGACAAGGGACCCCTGG |
| | ACAAAGAGGCCATAGAAGAAAGGGTTGAGAGGATAAAATCTGAGT |
| | ACATGACCTCTTGGTTTTATGACAATGACAACCCCTACAGGACCTG |
| | GCACTACTGTGGCTCCTATGTCACAAAAACCTCAGGAAGTGCGGCG |
| | AGCATGGTAAATGGTGTTATTAAAATTCTGACATATCCATGGGACA |
| | GGATAGAGGAGGTCACAAGAATGGCAATGACTGACACAACCCCTT |
| | TTGGACAGCAAAGAGTGTTTAAAGAAAAAGTTGACACCAGAGCAA |
| | AGGATCCACCAGCGGGAACTAGGAAGATCATGAAAGTTGTCAACA |

| SEQ ID NO | Sequence |
|---|---|
| | GGTGGCTGTTCCGCCACCTGGCCAGAGAAAAGAACCCCAGACTGTG |
| | CACAAAGGAAGAATTTATTGCAAAAGTCCGAAGTCATGCAGCCATT |
| | GGAGCTTACCTGGAAGAACAAGAACAGTGGAAGACTGCCAATGAG |
| | GCTGTCCAAGACCCAAAGTTCTGGGAACTGGTGGATGAAGAAAGG |
| | AAGCTGCACCAACAAGGCAGGTGTCGGACTTGTGTGTACAACATGA |
| | TGGGGAAAAGAGAGAAGAAGCTGTCAGAGTTTGGGAAAGCAAAGG |
| | GAAGCCGTGCCATATGGTATATGTGGCTGGGAGCGCGGTATCTTGA |
| | GTTTGAGGCCCTGGGATTCCTGAATGAGGACCATTGGGCTTCCAGG |
| | GAAAACTCAGGAGGAGGAGTGGAAGGCATTGGCTTACAATACCTA |
| | GGATATGTGATCAGAGACCTGGCTGCAATGGATGGTGGTGGATTCT |
| | ACGCGGATGACACCGCTGGATGGGACACGCGCATCACAGAGGCAG |
| | ACCTTGATGATGAACAGGAGATCTTGAACTACATGAGCCCACATCA |
| | CAAAAAACTGGCACAAGCAGTGATGGAAATGACATACAAGAACAA |
| | AGTGGTGAAAGTGTTGAGACCAGCCCCAGGAGGGAAAGCCTACAT |
| | GGATGTCATAAGTCGACGAGACCAGAGAGGATCCGGGCAGGTAGT |
| | GACTTATGCTCTGAACACCATCACCAACTTGAAAGTCCAATTGATC |
| | AGAATGGCAGAAGCAGAGATGGTGATACATCACCAACATGTTCAA |
| | GATTGTGATGAATCAGTTCTGACCAGGCTGGAGGCATGGCTCACTG |
| | AGCACGGATGTAACAGACTGAAGAGGATGGCGGTGAGTGGAGACG |
| | ACTGTGTGGTCCGGCCCATCGATGACAGGTTCGGCCTGGCCCTGTC |
| | CCATCTCAACGCCATGTCCAAGGTTAGAAAGGACATATCTGAATGG |
| | CAGCCATCAAAAGGGTGGAATGATTGGGAGAATGTGCCCTTCTGTT |
| | CCCACCACTTCCATGAACTACAGCTGAAGGATGGCAGGAGGATTGT |
| | GGTGCCTTGCCGAGAACAGGACGAGCTCATTGGGAGAGGAAGGGT |
| | GTCTCCAGGAAACGGCTGGATGATCAAGGAAACAGCTTGCCTCAGC |
| | AAAGCCTATGCCAACATGTGGTCACTGATGTATTTTCACAAAAGGG |
| | ACATGAGGCTACTGTCATTGGCTGTTTCCTCAGCTGTTCCCACCTCA |
| | TGGGTTCCACAAGGACGCACAACATGGTCGATTCATGGGAAAGGG |
| | GAGTGGATGACCACGGAAGACATGCTTGAGGTGTGGAACAGAGTA |
| | TGGATAACCAACAACCCACACATGCAGGACAAGCAATGGTGAAA |
| | AAATGGAGAGATGTCCCTTATCTAACCAAGAGACAAGACAAGCTGT |
| | GCGGATCACTGATTGGAATGACCAATAGGGCCACCTGGGCCTCCCA |
| | CATCCATTTGGTCATCCATCGTATCCGAACGCTGATTGGACAGGAG |
| | AAATACACTGACTACCTAACAGTCATGGACAGGTATTCTGTGGATG |
| | CTGACCTGCAACTGGGTGAGCTTATCTGAAACACCATCTAACAGGA |
| | ATAACCGGGATACAAACCACGGTGGAGAACCGGACTCCCCACAA |
| | CCTGAAACCGGGATATAAACCACGGCTGGAGAACCGGACTCCGCA |
| | CTTAAAATGAAACAGAAACCGGGATAAAAACTACGGATGGAGAAC |
| | CGGACTCCACACATTGAGACAGAAGAAGTTGTCAGCCCAGAACCCC |
| | ACACGAGTTTTGCCACTGCTAAGCTGTGAGGCAGTGCAGGCTGGGA |
| | CAGCCGACCTCCAGGTTGCGAAAAACCTGGTTTCTGGGACCTCCCA |
| | CCCCAGAGTAAAAAGAACGGAGCCTCCGCTACCACCCTCCCACGTG |
| | GTGGTAGAAAGACGGGGTCTAGAGGTTAGAGGAGACCCTCCAGGG |
| | AACAAATAGTGGGACCATATTGACGCCAGGGAAAGACCGGAGTGG |
| | TTCTCTGCTTTTCCTCCAGAGGTCTGTGAGCACAGTTTGCTCAAGAA |
| | TAAGCAGACCTTTGGATGACAAACACAAAACCACT |
| SEQ ID NO: 2 | AGAAGTTTATCTGTGTGAACTTCTTGGCTTAGTATCGTTGAGAAGA |
| | ATCGAGAGATTAGTGCAGTTTAAACAGTTTTTTAGAACGGAAGATA |
| | ACCATGACTAAAAAACCAGGAGGGCCCGGTAAAAACCGGGCTATC |
| | AATATGCTGAAACGCGGCCTACCCCGCGTATTCCCACTAGTGGGAG |
| | TGAAGAGGGTAGTAATGAGCTTGTTGGACGGCAGAGGGCCAGTAC |
| | GTTTCGTGCTGGCTCTTATCACGTTCTTCAAGTTTACAGCATTAGCC |
| | CCGACCAAGGCGCTTTTAGGCCGATGGAAAGCAGTGGAAAAGAGT |
| | GTAGCAATGAAACATCTCACTAGTTTCAAACGAGAACTTGGAACAC |
| | TCATTGACGCCGTGAACAAGCGGGGCAGAAAGCAAAACAAAAGAG |
| | GAGGAAATGAAGGCTCAATCATGTGGCTTGCGAGCTTGGCAGTTGT |
| | CATAGCTTGTGCAGGAGCCATAAAGTTGTCAAATTTCCAGGGGAAG |
| | CTTTTGATGACCATTAACAACACGGACATTGCAGACGTTATCGTAA |
| | TTCCCACCTCAAAAGGAGAGAACAGATGCTGGGTCCGGGCAATCG |
| | ACGTCGGCTACATGTGTGAGGACACTATCACGTACGAATGTCCTAA |
| | GCTTGCCATGGGCAATGATCCAGAGGATGTGGACTGCTGGTGTGAC |
| | AACCAAGAAGTCTACGTCCAATATGGACGGTGCACGCGGACCAGG |
| | CATTCCAAGCGAAGCAGGAGATCCGTGTCGGTCCAAACACATGGG |
| | GAGAGTTCACTAGTGAATAAAAAAGAGGCTTGGCTGGATTCAACG |
| | AAAGCCACACGATATCTCATGAAAACTGAGAACTGGATCATAAGG |
| | AATCCTGGCTATGCTTTCCTGGCGGCGGTACTCGGCTGGATGCTTGG |
| | CAGTACCAACGGTCAACGCGTGGTATTCACCATCCTCCTGCTGCTG |
| | GTCGCTCCGGCTTACAGTTTTAATTGTCTGGGAATGGGCAATCGTG |
| | ACTTCATAGAAGGAGCCAGTGGAGCCACTTGGGTGGACTTGGTGCT |
| | AGAAGGAGATAGCTGCTTGACAATTATGGCAAACGACAAACCAAC |
| | ATTGGACGTCCGCATGATCAACATCGAAGCTAGCCAACTTGCCGAG |
| | GTTAGAAGTTACTGTTATCATGCTTCAGTCACTGACATCTCGACGGT |
| | GGCTCGGTGCCCCACGACTGGAGAAGCCCACAACGAGAAGCGAGC |
| | TGATAGTAGCTATGTGTGCAAACAAGGCTTCACTGATCGTGGGTGG |

| SEQ ID NO | Sequence |
|---|---|
| | GGCAACGGATGTGGACTTTTCGGGAAGGGAAGCATTGACACATGTG |
| | CAAAATTCTCCTGCACCAGCAAAGCGATTGGGAGAACAATCCAGCC |
| | AGAAAACATCAAATACAAAGTTGGCATTTTTGTGCATGGAGCCACT |
| | ACTTCGGAAAACCATGGGAATTATTCAGCGCAAGTTGGGGCGTCCC |
| | AGGCGGCAAAGTTCACAGTAACACCCAATGCTCCTTCGATAACCCT |
| | CAAACTTGGTGACTACGGAGAAGTCACACTGGACTGTGAGCCAAG |
| | GAGTGGACTGAACACTGAAGCGTTTTACGTCATGACCGTGGGGTCA |
| | AAGTCATTTCTGGTCCATAGGGAATGGTTTCATGACCTCGCTCTCCC |
| | CTGGACGTCCCCTTCGAGCACAGCGTGGAGAAACAGAGAACTCCTC |
| | ATGGAGTTTGAAGAGGCGCACGCCACAAAACAGTCCGTTGTTGCTC |
| | TTGGGTCACAGGAAGGAGGCCTCCATCAGGCGTTGGCAGGAGCCAT |
| | CGTGGTGGAGTACTCAAGTTCAGTGAAGTTAACATCAGGCCACCTG |
| | AAATGTAGGCTGAAAATGGACAAACTGGCTCTGAAAGGCACAACC |
| | TATGGCATGTGCACAGAAAAATTCTCCTTCGCGAAAAATCCGGCGG |
| | ACACTGGTCACGGGACAGTTGTCATTGAACTCTCCTACTCTGGGAG |
| | TGATGGCCCCTGCAAAATTCCGATTGTCTCCGTTGCGAGCCTCAATG |
| | ACATGACCCCCGTCGGGCGGCTGGTGACAGTGAACCCCTTCGTCGC |
| | GACTTCCAGTGCCAATTCAAAGGTGCTGGTCGAGATGGAACCCCCC |
| | TTCGGAGACTCCTACATCGTAGTTGGACGGGGAGACAAGCAGATCA |
| | ACCACCATTGGCATAAAGCTGGAAGCACGCTGGGCAAAGCCTTTTC |
| | AACAACTTTGAAGGGAGCTCAGAGACTGGCAGCGCTGGGTGACAC |
| | AGCCTGGGACTTTGGCTCCATTGGAGGGGTCTTCAACTCCATAGGA |
| | AAAGCCGTTCACCAAGTGTTTGGTGGTGCCTTCAGAACACTCTTCG |
| | GGGGAATGTCTTGGATCACACAAGGGCTAATGGGTGCCCTACTACT |
| | CTGGATGGGCGTCAACGCACGAGACCGATCAATTGCTTTGGCCTTC |
| | TTAGCCACAGGAGGTGTGCTCGTGTTTTTAGCGACCAATGTGCATG |
| | CTGACACTGGATGTGCCATTGACATCACAAGAAAAGAGATGAGGT |
| | GTGGAAGTGGCATCTTCGTGCACAACGACGTGGAAGCCTGGGTGGA |
| | TAGGTATAAATATTTGCCAGAAACGCCCAGATCCCTAGCAAAGATC |
| | GTCCACAAAGCGCACAAGGAAGGCGTGTGCGGAGTCAGATCTGTC |
| | ACTAGACTGGAGCATCAAATGTGGGAAGCCGTACGGGATGAATTG |
| | AACGTCCTGCTCAAAGAGAATGCAGTGGACCTCAGTGTGGTTGTGA |
| | ACAAGCCCGTGGGGAGATATCGCTCAGCCCCTAAACGCCTGTCCAT |
| | GACGCAAGAGAAGTTTGAAATGGGCTGGAAAGCATGGGGAAAAAG |
| | CATTCTCTTTGCCCCGGAATTGGCCAACTCCACATTTGTCGTAGATG |
| | GACCTGAGACAAAGGAATGCCCTGATGAGCACAGAGCTTGGAACA |
| | GCATGCAAATCGAAGACTTCGGCTTTGGCATCACATCAACCCGTGT |
| | GTGGCTGAAGATTAGAGAGGAGAGCACTGACGAGTGTGATGGAGC |
| | GATCATAGGTACGGCTGTCAAAGGACATGTGGCAGTCCATAGTGAC |
| | TTGTCGTACTGGATTGAGAGTCGCTACAACGACACATGGAAACTTG |
| | AGAGGGCAGTCTTTGGAGAAGTTAAATCCTGCACTTGGCCAGAGAC |
| | ACACACCCTATGGGGAGATGGTGTTGAGGAAAGTGAACTCATCATC |
| | CCGCACACCATAGCCGGACCAAAAAGCAAGCATAATCGGAGGGAA |
| | GGATATAAGACACAAAACCAGGGACCTTGGGACGAGAATGGCATA |
| | GTCTTGGACTTTGACTATTGCCCAGGGACAAAAGTCACCATTACAG |
| | AGGATTGTGGCAAGAGAGGCCCTTCGGTCAGAACCACTACTGACAG |
| | TGGAAAGTTGATCACTGACTGGTGCTGTCGCAGTTGCTCCCTTCCGC |
| | CCCTACGATTCCGGACAGAAAATGGCTGCTGGTACGGAATGGAAAT |
| | CAGACCTGTCAGGCATGATGAAACAACACTCGTCAGATCGCAGGTT |
| | GATGCTTTTAATGGTGAAATGGTTGACCCTTTTCAGCTGGGCCTTCT |
| | GGTGATGTTTCTGGCCACCCAGGAGGTCCTTCGCAAGAGGTGGACG |
| | GCCAGATTGACCATTCCTGCGGTTTTGGGGGCCCTACTTGTGCTGAT |
| | GCTTGGGGGCATCACTTACACTGATTTGGCGAGGTATGTGGTGCTA |
| | GTCGCTGCCTCTTTCGCAGAGGCCAACAGTGGAGGAGATGTCCTGC |
| | ACCTTGCTTTGATTGCCGTTTTCAAGATCCAACCAGCATTTTTAGTG |
| | ATGAACATGCTTAGCACGAGATGGACGAACCAAGAAAACGTGGTT |
| | CTGGTCCTAGGGGCTGCCTTTTTCCAATTGGCCTCAGTAGATCTGCA |
| | AATAGGAGTTCACGGAATCCTGAATGCCGCCGCTATAGCATGGATG |
| | ATTGTCCGGGCGATCACCTTCCCCACAACCTCCTCCGTCACCATGCC |
| | AGTCTTAGCGCTTCTAACTCCGGGAATGAGGGCTCTATACCTAGAT |
| | ACTTACAGAATCATCCTCCTCGTCATAGGGATTTGCTCTCTGCTGCA |
| | AGAGAGGAAAAGACCATGGCAAAAAAGAAAGGAGCTGTACTCTT |
| | GGGCTTAGCGCTCACATCCACTGGATGGTTTTCGCCCACCACTATA |
| | GCTGCCGGACTAATGGTCTGCAACCCAAACAAGAAGAGAGGGTGG |
| | CCAGCTACTGAGTTTTTGTCGGCAGTTGGATTGATGTTTGCCATCGT |
| | AGGTGGTTTGGCGGAGTTGGATATTGAATCCATGTCAATACCCTTC |
| | ATGCTGGCAGGTCTCATGGCAGTGTCCTACGTGGTGTCAGGAAAAG |
| | CAACAGATATGTGGCTTGAACGGGCTGCCGACATCAGCTGGGAGAT |
| | GGATGCTGCAATCACAGGAAGCAGTCGGAGGCTGGATGTGAAGCT |
| | AGATGATGACGGAGATTTTCACTTGATTGACGATCCCGGTGTTCCA |
| | TGGAAGGTCTGGGTCCTGCGCATGTCTTGCATTGGGTTAGCCGCCCT |
| | CACGCCTTGGGCCATTGTTCCCGCCGCTTTTGGTTATTGGCTCACTT |
| | TAAAAACAACAAAAAGAGGGGGCGTGTTTTGGGACACGCCATCCC |
| | CAAAACCTTGCTCAAAAGGAGACACCACTACAGGAGTTTACCGCAT |
| | TATGGCTAGAGGGATTCTTGGCACTTACCAGGCCGGCGTCGGAGTC |

-continued

| SEQUENCES | |
|---|---|
| SEQ ID NO | Sequence |
| | ATGTACGAGAATGTTTTCCACACACTATGGCACACAACTAGAGGAG |
| | CAGCTATTATGAGTGGAGAAGGAAAATTGACGCCATACTGGGGTA |
| | GTGTGAAAGAAGACCGCATAGCTTACGGAGGCCCATGGAGGTTTG |
| | ATCGAAAATGGAATGGAACTGATGACGTGCAAGTGATCGTGGTAG |
| | AACCGGGGAAGGCTGCAGTAAACATCCAGACAAAACCAGGAGTGT |
| | TTCGGACTCCCTTCGGGGAGGTTGGGGCTGTTAGTCTGGATTATCCG |
| | CGAGGAACATCCGGCTCACCCATTCTGGATTCCAATGGAGACATCA |
| | TAGGCCTGTACGGCAATGGAGTTGAGCTTGGCGATGGCTCATACGT |
| | CAGCGCCATCGTGCAGGGTGACCGTCAGGAGGAACCAGTCCCAGA |
| | AGCTTACACCCCAAACATGTTGAGAAAGAGACAGATGACCGTACTA |
| | GATTTGCACCCTGGTTCAGGGAAAACCAAGAAAATTCTGCCACAAA |
| | TAATTAAGGACGCTATTCAGCAGCGCCTAAGAACAGCTGTGTTGGC |
| | ACCGACGCGGGTGGTAGCAGCAGAAATGGCAGAAGCTTTGAGAGG |
| | GCTCCCAGTACGATATCAAACTTCAGCAGTGCAGAGAGAGCACCAA |
| | GGGAATGAAATAGTGGATGTGATGTGCCACGCCACTCTGACCCATA |
| | GACTGATGTCACCGAACAGAGTGCCCAACTACAACCTATTTGTCAT |
| | GGATGAAGCTCATTTCACCGACCCAGCCAGTATAGCCGCACGAGGA |
| | TACATTGCTACCAAGGTGGAATTAGGGGAGGCAGCAGCCATCTTTA |
| | TGACAGCGACCCCGCCTGGAACCACGGATCCTTTTCCTGACTCAAA |
| | TGCCCCAATCCATGATTTGCAAGATGAGATACCAGACAGGGCGTGG |
| | AGCAGTGGATACGAATGGATCACAGAATATGCGGGAAAAACCGTG |
| | TGGTTTGTGGCAAGCGTGAAAATGGGGAACGAGATTGCAATGTGCC |
| | TCCAAAGAGCGGGGAAAAAGGTCATCCAACTCAACCGCAAGTCCT |
| | ATGACACAGAATACCCAAAATGTAAGAATGGAGACTGGGATTTTGT |
| | CATCACCACTGACATTTCTGAAATGGGGGCCAACTTCGGTGCGAGC |
| | AGGGTCATCGACTGTAGAAAGAGCGTGAAGCCCACCATCTTAGAA |
| | GAGGGAGAAGGCAGAGTCATCCTCGGAAACCCATCGCCCATAACC |
| | AGTGCAAGCGCAGCTCAACGGAGGGGCAGAGTAGGCAGAAACCCT |
| | AACCAGGTTGGAGATGAATACCACTATGGGGGGGCCACCAGTGAA |
| | GATGACAGTAACCTAGCCCATTGGACAGAGGCAAAGATCATGTTAG |
| | ATAACATACACATGCCCAATGGACTGGTGGCCCAGCTCTATGGACC |
| | AGAGAGGGAAAAGGCCTTCACAATGGATGGCGAATACCGTCTCAG |
| | AGGTGAAGAAAAGAAAAACTTCTTAGAGCTGCTTAGGACGGCTGA |
| | CCTCCCGGTGTGGCTGGCCTACAAGGTGGCGTCCAATGGCATCCAG |
| | TACACCGATAGAAAGTGGTGTTTTGATGGGCCGCGTACGAATGCCA |
| | TACTGGAGGACAACACCGAGGTAGAGATAGTCACCCGGATGGGTG |
| | AGAGGAAAATCCTCAAGCCGAGATGGCTTGATGCAAGAGTTTATGC |
| | AGATCACCAAGCTCTCAAGTGGTTCAAAGACTTCGCAGCAGGAAAG |
| | AGATCAGCCGTTAGCTTCATAGAGGTGCTCGGTCGTATGCCTGAGC |
| | ATTTCATGGGAAAGACGCGGGAAGCTTTAGACACCATGTACTTGGT |
| | TGCAACGGCTGAGAAAGGTGGGAAAGCACACCGAATGGCTCTCGA |
| | AGAGCTGCCAGATGCACTGGAAACCATTACACTTATTGTTGCTATC |
| | ACTGTGATGACAGGAGGATTCTTTCTACTCATGATGCAGCGAAAGG |
| | GTATAGGGAAGATGGGTCTTGGAGCTCTAGTGCTCACGCTAGCTAC |
| | CTTCTTCCTGTGGGCGGCAGAGGTTCCCGGAACAAAAATAGCAGGG |
| | ACCCTGCTGATCGCCCTGCTGCTTATGGTGGTTCTCATCCCAGAACC |
| | GGAAAAGCAGAGGTCACAAACAGATAATCAACTGGCGGTGTTTCTC |
| | ATCTGTGTCTTGACCGTGGTTGGAGTGGTGGCAGCAAACGAGTACG |
| | GGATGCTAGAAAAACCAAAGCAGACCTCAAGAGCATGTTTGGCG |
| | GAAAGACGCAGGCATCAGGACTGACTGGATTACCAAGCATGGCAC |
| | TGGACCTGCGTCCAGCCACAGCTTGGGCACTGTATGGGGGAGCAC |
| | AGTCGTGCTAACCCCTCTTCTGAAGCACCTGATCACGTCGGAATAC |
| | GTCACCACATCGCTAGCCTCAATTAACTCACAAGCTGGCTCATTATT |
| | TGTCTTGCCACGAGGCGTGCCTTTTACCGACCTAGACTTGACCGTTG |
| | GCCTCGTCTTCCTTGGCTGTTGGGGTCAAATCACCCTCACAACGTTT |
| | TTGACAGCCATGGTTCTGGCGACACTTCACTATGGGTACATGCTCCC |
| | TGGATGGCAAGCAGAAGCACTCAGGGCTGCCCAGAGAAGGACAGC |
| | GGCTGGAATAATGAAGAATGCCGTTGTTGACGGAATGGTCGCCACT |
| | GATGTGCCTGAACTGGAAAGGACCACTCCTCTGATGCAAAAGAAA |
| | GTCGGACAGGTGCTCCTCATAGGGGTAAGCGTGGCAGCGTTCCTCG |
| | TCAACCCCAAAATCACCACTGTGAGAGAAGCAGGGGTGTTGGTGAC |
| | AGCGGCTACGCTCTCTTTGTGGGACAACGGAGCCAGTGCCGTTTGG |
| | AATTCCACCACTGCCACGGGACTCTGCCATGTAATGCGAGGTAGCT |
| | ACCTGGCTGGAGGCTCCATTGCTTGGACTCTCATCAAGAACGCTGA |
| | CAAGCCCTCCTTAAAAAGGGGAAGGCCTGGGGGCAGGACGCTAGG |
| | GGAGCAGTGGAAGGAAAAACTAAATGCCATGAGCAGAGAAGAGTT |
| | TTTTAAATACCGGAGAGAGGCCATAATCGAGGTGGACCGCACTGAA |
| | GCACGCAGGGCTAGACGTGAAAATAACATAGTGGGAGGACATCCG |
| | GTTTCGCGAGGCTCAGCAAAACTCCGTTGGCTCGTAGAGAAAGGAT |
| | TTGTCTCGCCAATAGGAAAAGTCATTGATCTAGGGTGTGGGCGTGG |
| | AGGATGGAGCTACTACGCAGCAACCCTGAAGAAGGTCCAGGAAGT |
| | CAGAGGATACACGAAAGGTGGGCGGACATGAAGAACCGATGCT |
| | CATGCAGAGCTACGGCTGGAACCTGGTCTCCATGAAGAGTGGAGTG |
| | GACGTGTTTTACAAACCTTCAGAGCCCAGTGACACTCTGTTCTGCG |
| | ACATAGGGGAATCCTCCCCGAGTCCAGAAGTAGAAGAACAACGCA |

-continued

| SEQ ID NO | Sequence |
|---|---|
|  | CACTACGCGTCCTAGAGATGACATCTGACTGGTTGCACCGAGGACC<br>TAGAGAGTTCTGTATAAAAGTTCTTTGCCCCTACATGCCCAAGGTTA<br>TAGAAAAAATGGAAGTCCTGCAACGCCGCTTCGGAGGTGGGCTAGT<br>GCGTCTTCCCCTGTCCCGCAACTCCAATCACGAGATGTACTGGGTTA<br>GTGGAGCCGCTGGCAATGTGGTGCACGCTGTGAACATGACCAGCCA<br>GGTACTACTGGGGCGAATGGATCGCACAGTGTGGAGAGGGCCAAA<br>GTATGAGGAAGATGTCAACTTAGGGAGCGGAACAAGAGCCGTGGG<br>AAAGGGAGAAGTCCATAGCAATCAGGAGAAAATCAAGAAGAGAAT<br>CCAGAAGCTTAAAGAAGAATTCGCCACAACGTGGCACAAAGACCC<br>TGAGCATCCATACCGCACTTGGACATACCACGGAAGCTATGAAGTG<br>AAGGCTACTGGCTCAGCTAGTTCTCTCGTCAACGGAGTGGTGAAGC<br>TCATGAGCAAACCTTGGGACGCCATTGCCAACGTCACCACCATGGC<br>CATGACTGACACCACCCCTTTTGGACAGCAAAGAGTTTTCAAGGAG<br>AAAGTTGACACGAAGGCTCCTGAGCCACCAGCTGGAGCTAAGGAA<br>GTGCTCAACGAGACCACCAACTGGCTGTGGGCCTACTTGTCACGGG<br>AAAAAAGACCCCGCTTGTGCACCAAGGAAGAATTCATAAAGAAAG<br>TCAATAGCAACGCGGCTCTTGGAGCAGTGTTCGCTGAACAGAATCA<br>ATGGAGCACGGCGCGTGAGGCTGTGGATGACCCGCGGTTTTGGGAG<br>ATGGTTGATGAAGAGAGGGAAAACCATCTGCGAGGAGAGTGTCAC<br>ACATGTATCTATAACATGATGGGAAAAAGAGAGAAGAAGCCTGGA<br>GAGTTTGGAAAAGCTAAAGGAAGCAGGGCCATTTGGTTCATGTGGC<br>TTGGAGCACGGTATCTAGAGTTTGAAGCTTTGGGGTTCCTGAATGA<br>AGATCATTGGCTGAGCCGAGAGAATTCAGGAGGTGGAGTGGAAGG<br>CTCAGGCGTCCAAAAGCTGGGATACATCCTCCGTGATATAGCAGGA<br>AAGCAAGGAGGAAAAATGTACGCTGATGATACCGCCGGGTGGGAC<br>ACTAGAATTACCAGAACTGATTTAGAAAATGAAGCCAAGGTGCTGG<br>AGCTTCTAGACGGTGAACACCGCATGCTCGCCCGAGCCATAATTGA<br>ATTGACTTACAGGCACAAAGTGGTCAAGGTCATGAGACCTGCAGCA<br>GAAGGAAAGACCGTGATGGACGTGATATCAAGGGAGGATCAAAGG<br>GGGAGTGGACAGGTGGTCACTTATGCTCTTAACACTTTCACGAACA<br>TCGCTGTCCAGCTCGTCAGGCTGATGGAGGCTGAGGGGTCATTGG<br>ACCACAACACTTGGAACAGCTACCTAGAAAAAACAAGATAGCTGT<br>CAGGACCTGGCTCTTTGAGAATGGAGAGGAGAGAGTGTCCAGGAT<br>GGCTATCAGCGGAGACGACTGTGTCGTCAAGCCGCTGGACGACAG<br>ATTCGCCACGCGCCCTCCACTTCCTCAACGCAATGTCAAAGGTCAGA<br>AAAGACATCCAGGAATGGAAGCCTTCACATGGCTGGCACGATTGGC<br>AGCAAGTTCCCTTCTGCTCTAACCATTTTCAGGAGATTGTGATGAAA<br>GATGGAAGGAGTATAGTTGTCCCGTGCAGAGGACAGGATGAGCTG<br>ATAGGCAGGGCTCGCATCTCCCCAGGAGCTGGATGGAATGTGAAG<br>GACACAGCTTGTCTGGCCAAAGCATATGCACAGATGTGGCTACTCC<br>TATACTTCCATCGTAGGGACTTGCGTCTCATGGCAAATGCGATTTGC<br>TCAGCAGTGCCAGTGGATTGGGTGCCCACGGGCAGGACATCCTGGT<br>CGATACACTCGAAAGGAGAGTGGATGACCACAGAAGACATGCTGC<br>AGGTCTGGAACAGAGTCTGGATTGAAGAAAATGAATGGATGGTGG<br>ACAAGACTCCAATAACAAGCTGGACAGACGTTCCGTATGTGGGAA<br>AGCGGGAGGACATCTGGTGTGGCAACCTCATCGGAACGCGATCCA<br>GAGCAACCTGGGCTGAGAACATCTACGCGGCGATAAACCAGGTTA<br>GAGCTGTCATTGGGAAAGAAAATTATGTTGACTACATGACCTCACT<br>CAGGAGATACGAAGATGTCTTGATCCAGGAAGACAGGGTCATCTA<br>GTGTGATTTAAGGTGGAAAAGCAGATTATGTAAATAATGTAAATGA<br>GAAAATGCATGCATATGGAGTCAGGCCAGCAAAAGCTGCCACCGG<br>ATACTGGGTAGACGGTGCTGTCTGCGTCCCAGTCCCAGGAGGACTG<br>GGTTAACAAATCTGACAACAGAAAGTGAGAAAACCCTCAGAACCG<br>TCTCGGAAGCAGGTCCCTGCTCACTGGAAGTTGAAGGACCAACGTC<br>AGGCCACAAATTTGTGCCACTCCGCTGAGGAGTGCGGCCTGCGCAG<br>CCCCAGGAGGACTGGGTTACCAAAGCCGTTGAGCCCCCACGGCCCA<br>AGCCTCGTCTAGGATGCAATAGACGAGGTGTAAGGACTAGAGGTTA<br>GAGGAGACCCCGTGGAAACAACAACATGCGGCCCAAGCCCCCTCC<br>AAGCTGTAGAGGAGGTGGAAGGACTAGAGGTTAGAGGAGACCCCG<br>CATTTGCATCAAACAGCATATTGACACCTGGGAATAGACTGGGAGA<br>TCTTCTGCTCTATCTCAACATCAGCTACTAGGCACAGAGCGCCGAA<br>GTATGTAGCTGGTGGTGAGGAAGAACACAGGATCT |
| SEQ ID NO: 3 | AGATTTTCTTGCACGTGTGTGCGTTTGCTCCGGATAGCAACAGCAG<br>CGAGGTTTGAGAGAGATAATTTCTCGTTTGACCAGTCGTGAACGTG<br>TTGAGAAAAAGACAGCTTAGGAGAACAAGAGCTGGGGATGGCCGG<br>GAAGGCCATTCTGAAAGGAAAGGGGGGCGGTCCCCCTCGACGAGT<br>GTCGAAAGAGACCGCGAGGAAGACGCGTCAATCTAGGGTCCAAAT<br>GCCAAATGGACTCGTGTTGATGCGCATGTTGGGGATTTTATGCAT<br>GCCGTGGCCGGCACCGCTAGGAGTCCCGTGTTGAAGTCTTTCTGGA<br>ATTCAGTCCCACTGAAACAGGCCATGGCAGCACTCCGGAAAATTAA<br>AAAGGCAGTGAGCACCCTGATGGTAGGTCTGCAAAGACGTGGCAA<br>AAGAAGGTCAGCAGCAGACTGGACAAGTTGGTTGCTGGTTCTGGTT<br>TTGGTGGGGGTGACACTTGCAGCCACAGTGCGGAAAGAAAGGGAT<br>GGCACTACCGTGATCAGAGCTGAAGGAAAAGATGCGGCAACCCAG |

| SEQ ID NO | Sequence |
|---|---|
| | GTGCGTGTGGAAAATGGCACCTGTGTGATCCTGGCCACGGACATGG |
| | GATCATGGTGTGATGACTCACTAACCTATGAGTGTGTGACCATAGA |
| | CCAGGGGGAGGAACCAGTTGACGTGGATTGCTTCTGCAGGAATGTT |
| | GATGGAGTTTACCTGGAGTATGGACGGTGTGGAAAACAAGAAGGA |
| | TCAAGAACAAGGCGCTCAGTGCTGATCCCGTCCCATGCCCAGGGAG |
| | ACCTCACAGGAAGGGGACACAAATGGTTAGAAGGGGATTCACTGC |
| | GGACGCATCTCACTAGGGTTGAAGGATGGGTCTGGAAGAACAAAG |
| | TGCTCACCCTGGCGGTGATCGCCATTGTGTGGCTGACCGTGGAAAG |
| | CGTGGTGACCAGGGTCGCCGTAGTGGTGGTGCTCTTGTGCCTGGCT |
| | CCGGTTTATGCCTCACGATGCACACATTTGGAAAACAGAGATTTTG |
| | TTACTGGCACTCAGGGAACCACTCGTGTGACTCTGGTGCTGGAACT |
| | GGGAGGATGCGTCACCATAACAGCCGAGGGGAAGCCCTCGATGGA |
| | CGTGTGGCTTGACTCCATTTATCAGGAGAATCCTGCCAAAACACGT |
| | GAGTACTGCCTGCACGCAAAGCTGTCGGACACCAAGGTCGCGGCCA |
| | GATGCCCCACAATGGGACCTGCCACTTTGGCTGAAGAGCACCAGAG |
| | TGGCACAGTGTGCAAGAGAGACCAGAGTGATCGAGGCTGGGGTAA |
| | TCATTGTGGATTATTTGGAAAAGGCAGCATTGTGACCTGCGTCAAG |
| | GCGTCCTGTGGGGCAAAAAAGAAGGCCACAGGACACGTGTATGAT |
| | GCCAACAAAATTGTGTACACGGTTAAAGTAGAGCCGCATACGGGG |
| | GATTACGTCGCCGCTAATGAGACCCATAGTGGAAGAAAAACAGCA |
| | TCCTTCACGGTTTCCTCGGAAAAAACCATCTTGACCATGGGAGACT |
| | ACGGAGATGTGTCCTTGTTGTGTCGAGTAGCTAGCGGTGTTGACCTT |
| | GCTCAGACTGTCATTCTGGAACTTGACAAGACTTCAGAACACCTAC |
| | CGACGGCCTGGCAGGTTCACCGGGACTGGTTCAATGATCTGGCCCT |
| | GCCGTGGAAACATGAAGGGGCACAGAACTGGAACAATGCTGAACG |
| | GCTAGTTGAGTTTGGAGCCCCACATGCTGTGAAAATGGATGTGTAT |
| | AACCTTGGAGACCAGACTGGAGTGTTGCTTAAGTCACTTGCTGGTG |
| | TTCCAGTGGCGCACATTGATGGAACCAAGTACCACCTGAAAAGTGG |
| | CCACGTGACATGCGAGGTAGGACTAGAAAAACTCAAGATGAAAGG |
| | TCTCACATACACAATGTGCGACAAGACGAAATTCACGTGGAAGAG |
| | AATCCCAACTGACAGTGGACATGATACAGTGGTCATGGAAGTTGCA |
| | TTCTCTGGAACCAAACCCTGTAGGATCCCGGTGAGGGCCGTGGCAC |
| | ACGGCTCTCCAGATGTGAATGTGGCTATGTTGATAACACCCAACCC |
| | CACAATCGAAACCAATGGTGGTGGTTTCATAGAAATGCAGTTACCG |
| | CCAGGAGACAACATCATCTATGTCGGGGAACTGAGTCACCAATGGT |
| | TCCAAAAAGGGAGTAGCATTGGAAGGGTCTTTCAAAAAACCAGGA |
| | AAGGTATAGAACGACTGACAGTGATCGGAGAACACGCCTGGGATT |
| | TTGGCTCAACTGGTGGATTCCTGACCTCGGTTGGCAAGGCGCTACA |
| | CACAGTTCTTGGTGGTGCCTTCAACAGCCTGTTTGGAGGAGTAGGG |
| | TTCTTGCCTAAGATCCTAGTGGGAGTGGTCCTGGCCTGGTTGGGCCT |
| | GAACATGAGGAATCCGACCATGTCCATGAGCTTCCTCCTGGCCGGA |
| | GGACTGGTTCTGGCCATGACACTCGGAGTCGGAGCTGATGTTGGCT |
| | GTGCTGTGGACACCGAACGGATGGAGCTCCGTTGTGGTGAGGGTCT |
| | GGTTGTATGGAGGGAGGTTTCCGAGTGGTATGACAATTATGCATAC |
| | TACCCTGAGACACCAGGAGCTCTTGCTTCGGCCATAAAAGAGACCT |
| | TCGAGGAGGGAACTTGTGGTATAGTGCCCCAAAACAGACTTGAAAT |
| | GGCCATGTGGAGAAGCTCGGCGACAGAACTGAATCTGGCCTTGGCG |
| | GAGGGAGACGCAAATCTCACAGTGGTGGTGGACAAACTTGATCCC |
| | ACAGACTATCGAGGTGGCATTCCTGGGCTGCTAAAGAAGGGGAAA |
| | GACATAAAGGTTTCTTGGAAGAGCTGGGGCCACTCAATGATCTGGA |
| | GTGTCCCCGAGGCCCCCGTCGGTTTATGGTGGGAACAGAGGGAAG |
| | CAGTGAGTGTCCACTAGAGAGAAGGAAAACAGGTGTCTTCACGGT |
| | GGCAGAGTTTGGGGTTGGCCTGAGAACAAAAGTATTCTTGGACTTC |
| | AGACAGGAATCAACACATGAGTGTGACACAGGAGTGATGGGAGCC |
| | GCTGTCAAGAATGGCATGGCAGTCCACACAGACCAGAGCCTCTGGA |
| | TGAAATCCGTGAGAAATGACACAGGGACCTACATAGTGGAACTTCT |
| | GGTTACTGACCTGAGAAATTGCTCATGGCCGGCTAGCCACACCATT |
| | GACAATGCTGAGGTGGTGGACTCAGAACTCTTCCTTCCAGCCAGTC |
| | TGGCAGGGCCTAGATCCTGGTATAACAGGATACCCGGGTACTCAGA |
| | ACAAGTGAAAGGACCATGGAAGTACTCGCCCATCCGAGTGACAAG |
| | AGAAGAGTGCCCTGGCACGAGGGTCACCATAAATGCCGACTGTGA |
| | CAAAAGGGGGCTTCTGTGAGGAGTACCACAGAGAGTGGCAAGGT |
| | GATTCCAGAGTGGTGCTGCCGAACGTGCACATTACCTCCAGTGACG |
| | TTCCGTACGGGGACAGACTGTTGGTATGCCATGGAAATACGACCAG |
| | TTCATGACCAGGGAGGGCTTGTTTCCTCAATGGTGGTGGCAGACAA |
| | TGGAGAGCTGCTTAGTGAGGGGGCATTCCCGGGATAGTGGCTTTG |
| | TTTGTGGTCCTTGAGTACGTCATCCGAGGGGGCCAGCCACTGGAA |
| | CAACGGCCATGTGGGAGGCATTGTTGTCCTTGCATTGCTCGTCACT |
| | GGTCTGGTGAGAATCGAAAGCCTGGTGCGTTATGTCGTGGCAGTTG |
| | GGATCACATTTCATCTTGAGCTAGGGCCAGAGATTGTGGCTCTGAC |
| | ACTGTTACAGGCTGTGTTTGAGTTGAGGGTTGGCCTGCTCAGCGCTT |
| | TTGCACTACGCAGCAACCTCACTGTCAGAGAGATGGTAACCATCTA |
| | CTTCCTTCTGCTGGTTTTGAGTTGGGATTGCCAGGTGAGGGTCTTG |
| | GGGCCCTATGGAAATGGGGAGATGCATTGGCCATGGGGCATTGAT |
| | TTTCAGAGCCTGCACGGCAGAGGAAAAGACTGGTGTTGGACTCCTG |

SEQUENCES

| SEQ ID NO | Sequence |
|---|---|
| | CTCATGGCTCTCATGACACAGCAAGACCTGGCGATTGCACACTATG<br>GACTCATGCTCTTCCTGGGCACGGCCTCATGTTGTTCAATCTGGAAA<br>CTGATTCGAGGACACAGAGAACAGAAGGGATTGACCTGGGTTGTCC<br>CCCTGGCCGGGCTACTCGGAGGAGAGGGCTCTGGAGTCAGACTGCT<br>GGCTTTTTGGGAACTGGCCATCCATGGAAGGAGACGGTCATTCAGT<br>GAACCACTGACTGTTGTGGGAGTCATGCTAACCCTGGCCAGCGGCA<br>TGATGCGGCACACCTCTCAGGAGGCCCTTTGCGCGCTCGCCGTGGC<br>CTCGTTCCTTCTGCTCATGCTGGTGCTAGGGACAAGGAAGATGCAG<br>CTAGTGGCTGAATGGAGTGGCTGTGTGGAGTGGCACCCAGAACTGA<br>TGAATGAAGGTGGAGAGGTGAGCCTGCGGGTCCGGCAGGACTCAA<br>TGGGAAACTTCCACCTGACAGAGCTTGAGAAAGAGGAGAGAGTGA<br>TGGCTTTCTGGCTGCTGGCAGGACTGGCGGCTTCGGCCTTCCACTGG<br>TCTGGCATTCTTGGTGTGATGGGATTGTGGACGCTGTCGGAAATGC<br>TGAGGACGGCTCGAAGATCAGATTTGGTCTTCTCTGGACAGGGGGG<br>ACGTGAGCGTGGTGACAGGCCCTTTGAGGTCAAGGATGGCGTCTAT<br>AGAATCTTCAGCCCAGGACTGCTCTGGGGGCAGCGCCAGGTGGGA<br>GTTGGCTATGGCTCCAAAGGTGTCCTACACACGATGTGGCATGTGA<br>CGAGAGGGGCGGCGCTGTCCATTGATGACGCCGTCGCAGGGCCCTA<br>TTGGGCTGACGTCAAAGAGGACGTTGTATGCTATGGTGGAGCCTGG<br>AGTCTTGAGGAGAAGTGGAAAGGTGAGACAGTGCAGGTTCATGCC<br>TTCCCACCGGGGAGAGCCCATGAGGTGCATCAATGTCAGCCCGGGG<br>AACTGCTCCTGGACACAGGTAGGAGGATAGGGGCAGTGCCAATTG<br>ATCTGGCAAAAGGGACATCTGGCAGCCCCATCCTCAACTCCCAAGG<br>AGTGGTTGTGGGACTGTATGGGAATGGACTGAAGACCAATGAAAC<br>CTACGTCAGCAGCATTGCTCAAGGTGAGGCTGAAAAAAGTCGACCC<br>AATCTCCTGCCGGCCGTCATTGGCACAGGCTGGACAGCAAAAGGGC<br>AGATCACAGTGCTGGACATGCACCCAGGCTCTGGGAAGACCCACA<br>GAGTCCTCCCGGAGCTCATTCGCCAATGCATTGACAGACGCCTAAG<br>GACATTGGTGTTGGCCCCAACCCGTGTGGTGCTCAAGGAAATGGAG<br>CGTGCCTTGAATGGGAAGAGAGTCATGTTCCATTCTCCGGCAGTTG<br>GAGATCAGCAGGTGGGAGGGGCCATCGTCGACGTGATGTGCCATG<br>CAACCTATGTCAATAGACGCCTGCTCCCGCAGGGGAGACAGAATTG<br>GGAAGTGGCAATCATGGATGAAGCCCATTGGACGGATCCACACAG<br>CATAGCCGCTCGGGGTCACCTGTACACCTTGGCTAAGGAAAACAAA<br>TGTGCCCTGGTTCTTATGACAGCAACGCCACCCGGGAAGAGCGAAC<br>CCTTCCCAGAGTCCAACGGGGCAATCACCAGTGAAGAGAAGCAGA<br>TCCCTGATGGGGAGTGGCGTGATGGGTTCGACTGGATCACCGAGTA<br>TGAGGGGCGTACCGCATGGTTCGTTCCCTCGATTGCAAAAGGTGGT<br>ACCATAGCCCGCACCCTGAGACAAAAAAGGAAAAAGCGTGATCTGT<br>CTGAACAGCAAGACATTTGAAAAGGACTACTCCAGAGTGAGAAAT<br>GAGAAACCCGACTTCGTGGTCACAACCGACATATCTGAAATGGGGG<br>CCAACCTCGATGTGAGCCGTGTCATAGACGGGCGAACAAACATCAA<br>ACCGGAAGAGGTTGATGGGAGAGTTGAGCTCACAGGGACCAGACG<br>TGTGACCACGGCCTCTGCGGCCCAACGCCGTGGGAGAGTCGGAAG<br>ACAGGAGGAAAGAACAGATGAATACATATACTCTGGACAGTGTGA<br>TGATGATGATAGTGGACTTGTGCAGTGGAAGGAAGCGCAGATACTT<br>CTTGACAACATAACAACACTGCGGGGGCCTGTGGCCACCTTTTATC<br>GACCAGAGCAGGACAAGATGCCAGAGGTGGCAGGTCATTTCCGCC<br>TCACAGAAGAGAAAGAAAGCACTTTCGACATCTTCTCACCCATTG<br>TGACTTCACGCCATGGTTGGCATGGCACGTCGCAGCAAACGTGTCT<br>AGTGTGACAAGTCGGAACTGGACTTGGGAAGGCCCTGAGGAGAAC<br>ACCGTGGATGAGGCCAATGAGATCTGGTCACCTTCAGGAGCCCGA<br>ATGGGGCTGAAAGAACACTGAGGCCAGTATGGAGGGATGCGCGTA<br>TGTTCAGAGAAGGACGTGACATCAGAGAGTTCATCGCGTATGCCTC<br>AGGGAGACGCAGCTTTGGAGATGTGTTGAGCGGAATGTCCGGTGTT<br>CCTGAGCTTCTGCGCCATAGATGTGTTAGCGCCATGGATGTCTTCTA<br>CACACTGATGCATGAGGAGCCTGGCAGCAGGGCAATGAAGATGGC<br>CGAGAGAGATGCTCCAGAGGCTTTTTGACGGTGGTAGAGATGATG<br>GTGCTCGGCCTGGCCACTCTTGGGGTCGTCTGGTGCTTTGTTGTTCG<br>CACCTCAATCAGTCGCATGATGCTTGGCACGCTGGTACTGCTGGCC<br>TCACTGGCGCTCCTGTGGGCCGGTGGTGTAAGCTACGGGATTATGG<br>CAGGAGTGGCCCTCATTTTCTACACGTTGTTGACGGTGCTGCAGCCT<br>GAAGCGGGGAAACAGAGGAGCAGTGATGACAACAAGTTGGCCTAC<br>TTCCTGTTGACGCTCTGCAGTCTAGCTGGACTGGTAGCCGCCAATG<br>AAATGGGATTTCTGGAGAAGACTAAGGCGGACCTGTCCACGGTGTT<br>GTGGAGTGAACATGAAGAGTTGCGGTCGTGGGAAGAGTGGACCAA<br>CATCGACATCCAGCCTGCACGTTCCTGGGGAACTTACGTGCTGGTG<br>GTCTCTTTGTTCACACCATACATAATTCACCAACTTCAGACCAAGAT<br>CCAACAACTCGTCAACAGCGCTGTTGCAACTGGGGCTCAGGCCATG<br>CGAGACCTCGGAGGAGGGGCTCCATTCTTTGGGGTAGCAGGGCATG<br>TAATGGCTTTGGGAGTGGCATCGCTAGTTGGTGCAACGCCAACATC<br>CTTGGTGGTTGGTGTTGGTCTGCGGCGTTCCACCTGGCCATTGTGG<br>TGTCCGGACTAGAGGCTGAGTTGACACAAAGAGCCCACAAAGTCTT<br>CTTCTCGGCAATGGTGCGCAATCCCATGGTGGATGGGAGACGTCATC<br>AATCCATTTGGAGAGGGAGAGGCAAAACCTGCTCCGTATGAGAGG |

| SEQ ID NO | Sequence |
|---|---|
| | AAAATGAGCCTGGTCTTGGCGATAGTGCTTTGCTTGATGTCGGTGG |
| | TCATGAACAGAACGGTGCCTTCTATCACTGAGGCTTCTGCTGTGGG |
| | ACTGGCGGCAGCGGGACAACTGCTCAGACCAGAGGCGGATACCCT |
| | GTGGACGATGCCAGTGGCCTGTGGCCTGAGCGGCGTGGTCAGGGGT |
| | AGCCTCTGGGGATTCTTGCCCCTCGGGCATAGACTCTGGCTAAGGG |
| | CCTCTGGGAGTAGGCGTGGTGGTTCTGAGGGGGACACTCTCGGTGA |
| | CTTGTGGAAACGGAAACTCAATGGCTGTACCAAAGAAGAGTTCTTC |
| | GCCTATAGACGCACTGGCATCCTGGAGACGGAAAGGGACAAGGCA |
| | CGGGAACTCCTCAGGAGAGGGGAGACCAACATGGGGCTGGCTGTG |
| | TCACGGGGCACGGCTAAACTTGCCTGGCTTGAGGAACGAGGTTACG |
| | CAACTCTCAAGGGTGAGGTCGTGGACCTTGGATGTGGAAGAGGCG |
| | GCTGGTCCTACTATGCGGCCTCTAGACCGGCTGTCATGAGTGTCAA |
| | AGCCTACACAATTGGTGGAAAGGGACACGAGACCCCAAAGATGGT |
| | GACAAGCTTGGGTTGGAACCTGATCAAGTTCAGAGCGGGAATGGAT |
| | GTGTTCAGCATGCAGCCACACCGAGCTGATACCATTATGTGTGACA |
| | TCGGAGAAAGCAACCCAGATGCCGTGGTGGAGGGTGAGAGGACAC |
| | GGAAAGTGATACTACTCATGGAACAGTGGAAAAACCGCAATCCCA |
| | CGGCTACCTGTGTGTTCAAGGTGTTGGCCCCATACCGCCCAGAGGT |
| | CATAGAAGCACTACACAGATTCCAACTGCAGTGGGGCGGAGGACT |
| | GGTGAGGACCCCTTTCTCGAGGAATTCAACCCATGAAATGTATTAC |
| | TCGACTGCTGTCACTGGAAACATTGTGAATTCAGTTAACATCCAAT |
| | CAAGAAAACTCTTGGCCCGGTTCGGGGACCAGAGGGGACCCACCA |
| | GGGTGCCTGAGCTGGACCTCGGAGTTGGGACTCGATGCGTTGTCTT |
| | GGCTGAGGACAAGGTGAAGGAAAAAGATGTGCAGGAGAGGATCAG |
| | TGCGCTGCGAGAGCAGTATGGTGAGACCTGGCATATGGACAGAGA |
| | GCACCCGTACAGGACCTGGCAGTACTGGGGCAGCTACCGCACCGC |
| | GCCAACCGGGTCAGCGGCGTCACTGATCAATGGAGTCGTGAAGCTT |
| | CTCAGCTGGCCATGGAACGCGCGGGAGGATGTCGTGCGAATGGCC |
| | ATGACTGACACCACAGCCTTTGGACAGCAGCGAGTGTTCAAAGAGA |
| | AGGTTGACACCAAGGCTCAGGAACCTCAGCCTGGCACAAAGGTCAT |
| | CATGAGAGCAGTGAATGACTGGATTCTGGAACGATTGGCACGGAA |
| | AAGCAAACCACGAATGTGCAGCAGAGAGGAGTTCATAGCGAAAGT |
| | GAAATCCAATGCGGCTCTGGGGGCTTGGTCTGATGAGCAGAACAGG |
| | TGGTCAAGTGCAAAAGAGGCTGTAGAGGATCCCGCATTCTGGCAGC |
| | TCGTGGATGAAGAGAGAGAGAGACACCTTGCTGGGAGATGCGCCC |
| | ACTGTGTGTACAACATGATGGGCAAAAGAGAAAAGAAGCTTGGAG |
| | AGTTTGGAGTGGCCAAAGGAAGCCGGGCCATATGGTACATGTGGCT |
| | GGGGAGCCGCTTTCTGGAGTTCGAAGCTCTTGGCTTTTTGAATGAG |
| | GACCACTGGGCCTCTAGGGGGTCCAGTGGATCTGGAGTGGAGGGA |
| | ATAAGCTTGAATTACCTGGGCTGGTACCTCAAAGGGTTGTCAACAC |
| | TGGAAGGAGGCCTTTTCTACGCGGATGACACAGCCGGCTGGGACAC |
| | CAAGGTCACCAACGCAGACCTAGAGGATGAAGAACAGCTCCTACG |
| | CTACATGGAGGGTGAACACAAGCAACTGGCGGCTACAATAATGCA |
| | GAAGGCATACCACGCCAAGGTGGTAAAAGTAGCCCGGCCCTCCCG |
| | AGATGGGGGCTGTGTCATGGATGTCATCACAAGAAGAGACCAAAG |
| | ACGCACAGAGCAGGTTGTGACTTATGCCCTCAACACCCTTACCAAC |
| | ATAAAGGTTCAGCTGATCCGTATGATGGAGGGGGAGGGAGTCATTG |
| | AGGCCTCGGACGCACATAATCCAAGATTACTCCGAGTGGAACGATG |
| | GCTGAGGAACCATGGAGAAGAACGTCTCGGAAGAATGCTCGTGAG |
| | CGGTGATGATTGTGTGGTGAGACCGGTGGATGACAGGTTCAGTAGG |
| | GCACTCTATTTTCTGAATGACATGGCCAAAACCAGGAAAGACATTG |
| | GGGAGTGGGAGCATTCGGTTGGCTTCTCGAACTGGGAGGAGGTTCC |
| | CTTCTGTTCACACCACTTCCACGAGTTGGTGATGAAAGATGGGCGT |
| | GCCCTCATAGTGCCATGCCGAGACCAAGATGAACTGGTTGGAAGAG |
| | CCCGCGTCTCACCAGGGTGCGGCTGGAGTGTCCGCGAAACTGCCTG |
| | CCTTTCAAAAGCTTATGGGCAGATGTGGCTGCTGAGTTACTTTCACC |
| | GGCGCGACTTGCGGACGCTTGGACTTGCCATCTGTTCGGCGGTGCC |
| | CATTGACTGGGTCCCCACTGGCCGCACGACCTGGAGCATCCATGCT |
| | AGCGGAGCCTGGATGACCACAGAGGACATGTTGGATGTCTGGAAC |
| | AGGGTGTGGATTCTGGACAACCCCTTCATGCACAGCAAAGAAAAG |
| | ATTGTGAATGGAGGGATGTCCCGTATCTCCCCAAATCCCATGACA |
| | TGCTGTGTTCCTCTCTTGTTGGGAGGAAAGAGAGGGCAGAGTGGGC |
| | TAAGAACATCTGGGGAGCAGTAGAGAAAGTCAGGAAGATGATCGG |
| | ACAAGAGAAGTTCAAGGACTACCTTTCCTGCATGGACCGGCATGAC |
| | TTGCACTGGGAGCTCAAACTGGAGAGCTCAATAATCTAAAACTAGA |
| | TTGTGACTGAGCACAACCTGGAGTGCTCGTTAAACATTGTCCAGAA |
| | CCAAAAACCACAGCAAACAATTCACAGAACACCCCCAGAGTGCCC |
| | CACGGCAACACGTCAGTGAGAGTGGCGACGGGAAAATGGTCGATC |
| | CCGACGTAGGGCACTCTGTAAAACTTTGTGAGACCCCCGGCACCAT |
| | GATAAGGCCGAACATGGTGCAAGAACGGGAGGCCCCCGGAAGCAT |
| | GCTTCCGGGAGGAGGGAAGAGAGAAATTGGCAACTCTCTTCAGGA |
| | TTCTTCCTCCTCCTATACCAAATTCCCCCTCAACAGAGGGGGGCG |
| | GTTCTTGTTCTCCCTGAGCCACCATCACCCAGACACAGATAGTCTGA |
| | CAAGGAGGTGACGTGTGACTCGGAAAAA |

| SEQ ID NO | Sequence |
|---|---|
| SEQ ID NO: 4 | AGATTCTGTGGCACGTGCGTGCGTTTGCTTCGGACAGCATTAGCAG<br>CGGTTGGTTTGAAAGAGATATTCTTTTGTTTCTACCAGTCGTGAACG<br>TGTTGAGGAAAAGACAGCTTAGGAGAACAAGAGCTGGGGATGGTC<br>AAGAAGGCCATCCTGAAAGGTAAGGGGGGCGGTCCCCCTCGACGA<br>GTGTCGAAAGAGACCGCAACGAAGACGCGTCAACCCAGAGTCCAA<br>ATGCCAAATGGGCTTGTGTTGATGCGCATGATGGGGATCTTGTGGC<br>ATGCCGTAGCTGGCACCGCGAGAAACCCCGTATTGAAGGCGTTCTG<br>GAACTCAGTCCCTCTGAAACAGGCCACAGCAGCACTGCGGAGGATC<br>AAAAGGACAGTGAGTGCCCTAATGGTTGGCTTGCAAAAACGTGGG<br>AAAAGGAGGTCAGCGACGACTGGATGAGCTGGTTGCTGGTCATTA<br>CTCTGTTGGGGATGACGCTTGCTGCAACGGTGAGGAAAGAAAGGG<br>ACGGCTCAACTGTGATCAGAGCTGAAGGGAAGGATGCAGCAACTC<br>AGGTGCGTGTGGAAAATGGCACCTGTGTGATCCTGGCTACTGACAT<br>GGGGTCATGGTGTGATGATTCACTGTCCTATGAGTGTGTGACCATA<br>GATCAAGGAGAAGAGCCTGTTGACGTGGATTGTTTTTGCCGGAACG<br>TTGATGGAGTCTATCTGGAGTATGGACGCTGCGGGAAACAGGAAG<br>GCTCACGGACAAGGCGCTCAGTGCTGATCCCGTCCCATGCTCAGGG<br>AGAGCTGACGGGGAGGGGACACAAATGGCTAGAAGGAGACTCGCT<br>GCGAACACACCTCACTAGAGTTGAGGGATGGGTCTGGAAGAACAA<br>GCTACTTGCCTTGGCGATGGTCACCGTTGTGTGGTTGACCATGGAG<br>AGTGTGGTGACCAGGGTCGCCGTTCTGGTTGTGCTCCTGTGTTTAGC<br>ACCGGTCTACGCTTCGCGTTGCACACACTTGGAAAACAGGGACTTT<br>GTGACTGGTACTCAGGGGACTACGAGGATCACTTTGGTGCTGGAGC<br>TGGGTGGATGTGTTACCATAACAGCTGAGGGGAAGCCTTCAATGGA<br>TGTGTGGCTTGACGCCATTTACCAGGAGAACCCTGCTAAGACACGT<br>GAGTACTGTCTACACGCCAAGTTGTCGGACACTAAGGTTGCAGCCA<br>GATGCCCAACGATGGGACCAGCCACTTTGGCTGAAGAACACCAGG<br>GTGGCACAGTGTGTAAGAGAGATCAGAGTGACCGAGGCTGGGGCA<br>ACCACTGTGGACTGTTTGGAAAGGGTAGCATTGTGGCCTGTGTCAA<br>GGCGGCTTGTGAGGCAAAAAAGAAAGCCACAGGACATGTGTACGA<br>CGCCAACAAAATAGTGTACACGGTCAAAGTCGAACCACACACGGG<br>AGACTATGTTGCCGCAAACGAGACACATAGTGGGAGGAAGACGGC<br>GTCCTTCACAGTTTCTTCAGAGAAAACCATTCTGACCATGGGTGAG<br>TATGGAGATGTGTCTTTGTTGTGCAGGGTCGCTAGTGGCGTTGACTT<br>GGCCCAGACCGTCATCCTTGAGCTTGACAAAACAGTGGAACACCTT<br>CCAACGGCTTGGCAGGTCCACAGGGATTGGTTCAATGATCTGGCTC<br>TGCCATGGAAACATGAGGGAGCGCAAAACTGGAATAACGCAGAAC<br>GACTGGTTGAATTTGGAGCTCCTCACGCTGTCAAGATGGACGTGTA<br>CAACCTCGGAGACCAGACTGGAGTGTTACTGAAGGCTCTCGCTGGG<br>GTTCCTGTGGCACACATTGAGGGAACCAAGTACCACCTGAAGAGTG<br>GCCATGTGACCTGCGAAGTCGGACTGGAAAAACTGAAGATGAAAG<br>GGCTTACGTACACAATGTGTGACAAGACAAAGTTCACATGGAAGA<br>GAGCTCCAACAGATAGTGGGCATGACACAGTGGTCATGGAAGTCA<br>CATTCTCTGGAATAAAGCCCTGTAGGATCCCAGTCAGGGCAGTGGC<br>ACATGGATCTCCAGATGTGAACGTGGCCATGCTGATAACGCCAAAC<br>CCAACAATTGAAAACAATGGAGGTGGTTTCATAGAGATGCAGCTGC<br>CCCCAGGGGATAACATCATCTATGTTGGGGAACTGAGTCATCAATG<br>GTTCCAAAAAGGGAGCAGCATCGGAAGGGTTTTTCAAAAGACCAA<br>GAAAGGCATAGAAAGACTGACAGTGATAGGAGAGCACGCCTGGGA<br>CTTCGGTTCTGCTGGAGGCTTTCTAAGTTCAATTGGGAAGGCGGTG<br>CATACGGTCCTTGGTGGTGCATTCAACAGCATCTTCGGGGGAGTAG<br>GGTTTCTACCAAAGCTTTTATTAGGAGTGGCATTGGCTTGGTTGGGC<br>CTGAACATGAGAAATCCTACAATGTCCATGAGCTTTCTCTTGGCTG<br>GAGGTCTGGTCTTGGCCATGACCCTTGGAGTGGGGGCGGATGTTGG<br>CTGCGCTGTGGACACGGAACGAATGGAGCTCCGCTGTGGCGAGGG<br>CCTGGTCGTGTGGAGAGAGGTCTCAGAATGGTATGACAACTATGCC<br>TACTACCCGGAGACACCGGGGGCCCTTGCATCAGCCATAAAGGAG<br>ACATTTGAGGAGGGAAGCTGTGGCGTAGTCCCCCAGAACAGGCTCG<br>AGATGGCCATGTGGAGAAGCTCGGTCACAGAGCTGAATCTGGCTCT<br>GGCGGAAGGGGAGGCAAATCTCACAGTGGTGGTGGACAAGTTTGA<br>CCCCACTGACTACCGAGGTGGTGTCCCTGGTTTACTGAAAAAAGGA<br>AAGGACATAAAAGTCTCCTGGAAAAGCTGGGGCCATTCAATGATCT<br>GGAGCATCCCCGAGGCCCCCCGTCGTTTCATGGTGGGCACGGAAGG<br>ACAAAGTGAGTGTCCCCTAGAGAGACGGAAGACAGGTGTTTTCACG<br>GTGGCAGAATTCGGGGTTGGCCTGAGAACAAAGGTCTTCTTGGATT<br>TCAGACAGAAACCAACACATGAGTGTGACACAGGAGTGATGGGAG<br>CTGCCGTCAAGAACGGCATGGCAATCCACACAGATCAAAGTCTCTG<br>GATGAGATCAATGAAAATGACACAGGCACCTACATAGTTGAACTT<br>CTGGTTACTGACCTGAGGAACTGCTCATGGCCTGCTAGCCACACTA<br>TCGACAATGCTGACATGGTGGACTCGGAGCTATTCCTTCCGGCGAG<br>CCTGGCAGGACCCAGATCCTGGTACAACAGGATACCCGGTTATTCA<br>GAACAGGTGAAAGGGCATGGAAGCACACGCCTATCCGAGTCATC<br>AGAGAGGAGTGTCCCGGCACGACCGTTACCATCAACGCCAAGTGTG<br>ACAAAAGAGGAGCATCTGTGAGGAGTACCACAGAGAGTGGCAAGG<br>TTATCCCAGAATGGTGCTGCCGAGCGTGCACAATGCCACCAGTGAC |

SEQUENCES

| SEQ ID NO | Sequence |
|---|---|
| | GTTCCGGACTGGAACTGATTGCTGGTATGCCATGGAAATACGGCCA |
| | GTCCATGACCAGGGGGGCTTGTTCGCTCAATGGTGGTTGCGGACA |
| | ACGGTGAATTACTTAGTGAGGGAGGGGTCCCCGGAATAGTGGCATT |
| | GTTTGTGGTCCTTGAATACATCATCCGTAGGAGACCCTCCACGGGA |
| | ACAACGGTTGTGTGGGGGGCATCGTCGTACTCGCTCTGCTTGTCA |
| | CCGGGATGGTCAGGATGGAGAGCCTGGTGCGCTATGTGGTGGCAGT |
| | GGGGATCACATTCCACCTTGAGCTAGGACCAGAGATCGTGGCCTTG |
| | ATGCTACTCCAGGCTGTGTTTGAGTTGAGGGTGGGTTTGCTCAGCG |
| | CATTTGCACTGCGCAGAAGCCTCACCGTCCGAGAGATGGTGACCAC |
| | CTACTTTCTTTTGTTGGTCCTGGAATTGGGGCTGCCGGGTGCGGGAC |
| | TTGAGGATCTCTGGAAATGGGGTGATGCACTGGCCATGGGGCGCT |
| | AATGTTCAGGGCTTGCACGGCAGAAGGAAAGACTGGAGCGGGGCT |
| | CTTGCTCATGGCTCTCATGACACAGCAGGATGTGGTGACTGTGCAT |
| | CATGGACTGGTGTGCTTTCTGAGTGTAGCTTCGGCTTGCTCGGTCTG |
| | GAGGCTGCTCAAGGGACACAGAGAGCAGAAGGGATTGACCTGGAT |
| | TGTCCCCCTGGCTAGATTGCTTGGGGGAGAGGGCTCTGGAATCAGG |
| | CTGCTGGCGTTTTGGGAGCTGGCAGCTCACAGAGGAAGACGATCTT |
| | TCAGTGAACCACTAACTGTGGTAGGAGTCATGCTAACACTGGCCAG |
| | CGGCATGATGCGACACACCTCCCAGGAGGCTCTCTGTGCACTCGCA |
| | GTGGCCTCGTTTCTCTTGTTGATGCTGGTGCTGGGGACAAGAAAGA |
| | TGCAGCTGGTTGCCGAATGGAGTGGCTGCGTGGAATGGCATCCGGA |
| | ACTAGTGAATGAGGGTGGAGAGGTTAGCCTGCGGGTCCGTCAGGA |
| | CGCAATGGGAAACTTTCACTTGACTGAGCTCGAGAAAGAGGAGAG |
| | AATGATGGCTTTTTGGCTGCTGGCCGGCTTGGCAGCTTCAGCCATTC |
| | ATTGGTCAGGCATTCTTGGTGTGATGGGACTGTGGACGCTCACGGA |
| | AATGCTGAGGTCATCCCGAAGGTCCGACCTGGTTTTCTCTGGACAG |
| | GGGGGCCGAGAGCGTGGTGACAGACCTTTCGAGGTTAAGGACGGT |
| | GTCTACAGGATTTTCAGCCCCGGCTTGTTCTGGGGTCAGAACCAAG |
| | TGGGAGTTGGCTACGGTTCCAAGGGTGTTTTGCACACGATGTGGCA |
| | CGTGACAAGAGGAGCGGCGCTGTCTATTGATGATGCTGTGGCCGGT |
| | CCCTACTGGGCTGATGTGAGGGAAGATGTCGTGTGCTACGGAGGAG |
| | CCTGGAGCCTGGAGGAAAAATGGAAAGGTGAAACAGTACAGGTCC |
| | ATGCCTTCCCACCGGGAAGGCCCATGAGGTGCATCAGTGCCAGCC |
| | TGGGGAGTTGATTCTTGACACCGGAAGGAAGCTTGGGGCAATACCA |
| | ATTGATTTGGTAAAAGGAACATCAGGCAGCCCCATTCTTAACGCCC |
| | AGGGAGTGGTTGTGGGGCTATACGGAAATGGCCTAAAAACTAATG |
| | AGACCTACGTCAGCAGCATTGCTCAGGGGGAAGCGGAGAAGAGTC |
| | GACCCAACCTCCCACAGGCTGTTGTGGGCACGGGCTGGACATCAAA |
| | GGGTCAGATCACAGTGCTGGACATGCACCCAGGCTCAGGGAAGAC |
| | CCACAGAGTCCTCCCGGAGCTCATTCGCCAATGCATTGACAGGCGC |
| | CTGAGAACGTTGGTGTTGGCTCCAACTCGTGTGGTGCTCAAAGAAA |
| | TGGAGCGCGCCTTGAATGGGAAACGGGTCAGGTTCCACTCACCAGC |
| | AGTCAGTGACCAACAGGCTGGAGGGGCAATTGTCGACGTGATGTGT |
| | CACGCAACCTACGTCAACAGACGGCTACTCCCACAGGGGAGACAA |
| | AATTGGGAGGTGGCAATCATGGACGAGGCCCACTGGACGGACCCC |
| | CACAGCATAGCTGCCAGAGGTCATTTGTACACTCTGGCAAAAGAAA |
| | ACAAGTGTGCATTGGTCTTGATGACAGCGACACCTCCTGGTAAGAG |
| | TGAACCCTTTCCGGAGTCTAACGGAGCCATTACTAGTGAGGAAAGA |
| | CAGATTCCTGATGGAGAGTGGCGTGACGGGTTTGACTGGATCACTG |
| | AGTATGAAGGGCGCACCGCCTGGTTTGTCCCTTCGATTGCAAAAGG |
| | TGGTGCCATAGCTCGCACCCTGAGACAGAAGGGGAAAAGTGTGAT |
| | CTGTTTGAACAGCAAAACCTTTGAAAAGGACTACTCCAGAGTGAGG |
| | GATGAGAAGCCTGACTTTGTGGTGACGACTGATATCTCGGAGATGG |
| | GAGCCAACCTTGACGTGAGCCGCGTCATAGATGGGAGGACAAACA |
| | TCAAGCCTGAGGAGGTTGATGGGAAGGTCGAGCTCATCGGGACCA |
| | GGCGCGTGACCACGGCTTCCGCTGCCCAACGGCGCGGAAGAGTTGG |
| | TCGGCAGGACGGACGAACAGACGAATACATATACTCTGGACAGTG |
| | TGATGATGATGACAGTGGATTAGTGCAATGGAAAGAGGCGCAAAT |
| | ACTTCTTGACAATATAACAACCTTGCGGGGGCCCGTGGCCACCTTC |
| | TATGGACCAGAACAGGACAAGATGCCGGAGGTGGCCGGTCACTTTC |
| | GACTCACTGAAGAGAAAAGAAAGCACTTCCGACATCTTCTCACCCA |
| | TTGTGACTTCACACCGTGGCTGGCATGGCACGTCGCAGCGAATGTG |
| | TCCAGCGTCACGGATCGAAGCTGGACATGGGAAGGGCCGGAGGCA |
| | AATGCCGTGGATGAGGCCAGTGGTGATTTGGTCACCTTTAGGAGCC |
| | CGAATGGGGCGGAGAGAACTCTGAGGCCGGTGTGGAAGGACGCAC |
| | GCATGTTCAAAGAGGGACGTGACATCAAAGAGTTCGTGGCGTACGC |
| | GTCTGGGCGTCGCAGCTTCGGAGATGTCCTGACAGGAATGTCGGGA |
| | GTTCCGGAGCTTTTGCGGCACAGATGCGTCAGTGCCCTGGATGTCTT |
| | CTACACACTCATGCATGAGGAACCTGGCAGCAGGGCAATGAGAAT |
| | GGCGGAGAGAGATGCCCCAGAGGCCTTTCTGACTATGGCTGAGATG |
| | ATGGTGCTGGGTTTGGCAACCCTGGGTGTCATCTGGTGCTTCGTCGT |
| | CCGGACTTCAATCAGCCGCATGATGCTGGGCACGCTGGTCCTGCTG |
| | GCCTCGTTGCTGCTCTTGTGGGCAGGTGGTGTCGGCTATGGGAACA |
| | TGGCCGGAGTGGCTCTCATCTTCTACGTTGCTGACGGTGCTGCA |
| | GCCCGACGCGGGAAAACAGACAAGCAGTGACGACAACAAACTGGC |

| SEQUENCES | |
|---|---|
| SEQ ID NO | Sequence |
| | ATATTTCTTGCTGACGCTCTGCAGCCTTGCTGGACTGGTTGCAGCCA<br>ATGAGATGGGTTTTCTGGAGAAGACCAAGGCAGACTTGTCCACGGT<br>GTTGTGGAGTGAACGGGAGGAACCCCGGCCATGGAGTGAATGGAC<br>GAATGTGGACATTCAGCCAGCGAGGTCCTGGGGGACCTATGTGCTG<br>GTGGTGTCTCTGTTTACACCTTACATCGTCCATCAACTGCAGACCAA<br>AATCCAACAACTTGTCAACAGTGCCGTGGCATCTGGAGCACAGGCC<br>ATGAGAGACCTTGGAGGAGGTGCCCCCTTCTTTGGTGTGGCGGGAC<br>ATGTCATGACCCTTGGGGTGGTGTCACTGATTGGGGCCACTCCCAC<br>CTCACTGATGGTGGGCGTTGGCTTAGCGGCATTCCATCTGGCCATTG<br>TTGTGTCTGGTCTGGAGGCTGAATTAACACAGAGAGCTCACAAGGT<br>CTTTTTCTCTGCAATGGTGCGCAACCCCATGGTGGATGGGGATGTC<br>ATCAACCCATTCGGGGAGGGGGAGGCAAAACCTGCTCTATATGAA<br>AGGAAAATGAGTCTGGTGTTGGCCATAGTGTTGTGCCTCATGTCGG<br>TGGTCATGAACCGAACGGTGGCCTCCATAACAGAAGCTTCAGCTGT<br>GGGACTGGCAGCAGCGGGACAGCTGCTTAGGCCGGAGGCTGACAC<br>ACTGTGGACGATGCCGGTTGCTTGTGGCATGAGTGGTGTGGTCAGG<br>GGTAGCCTGTGGGGGTTTCTGCCTCTTGGGCATAGACTCTGGCTTCG<br>AGCTTCTGGGGGCAGGCGTGGTGGTTCTGAGGGAGACACGCTTGGA<br>GATCTCTGGAAACGGAGGCTGAACAACTGCACCAGGGAGGAATTC<br>TTCGTGTACAGGCGCACTGGCATCTTGGAGACGGAGCGTGACAAGG<br>CTAGAGAGTTGCTCAGAAGAGGAGAGACCAATATGGGATTGGCTG<br>TCTCTCGGGCACGGCAAAGCTTGCCTGGCTTGAGGAACGCGGATA<br>TGCCACCCTCAAGGGAGAGGTGGTAGATCTTGGATGTGGAAGGGG<br>CGGCTGGTCCTATTATGCGGCATCCCGACCGGCGGTCATGAGTGTC<br>AGGGCATACACCATTGGTGGAAGAGGACACGAGGCTCCAAAGATG<br>GTAACAAGCCTGGGTTGGAACTTGATTAAATTCAGATCAGGAATGG<br>ACGTGTTCAGCATGCAGCCACACCGGGCTGACACTGTCATGTGTGA<br>CATCGGAGAGAGCAGCCCAGATGCCGCTGTGGAGGGTGAGAGGAC<br>AAGGAAAGTGATATTGCTCATGGAGCAATGGAAAAATAGGAACCC<br>CACGGCTGCCTGTGTGTTCAAGGTGCTGGCCCCATATCGCCCAGAA<br>GTGATAGAAGCACTGCACAGATTCCAACTGCAATGGGGGGGGGGT<br>CTGGTGAGGACCCCCTTTTCAAGGAACTCCACCCATGAGATGTATT<br>ACTCAACAGCTGTCACTGGGAACATAGTGAACTCCGTCAACGTACA<br>GTCGAGGAAACTTTTGGCTCGGTTTGGAGACCAGAGAGGGCCAACC<br>AGGGTGCCTGAACTTGACCTGGGAGTTGGAACTCGGTGTGTGGTCT<br>TGGCTGAGGACAAGGTAAAAGAACAAGACGTACAAGAGAGGATCA<br>GAGCGTTGCGGGAGCAGTACAGCGAAACCTGGCACATGGACGAGG<br>AACACCCGTACCGGACATGGCAGTACTGGGGTAGTTACCGCACGGC<br>ACCAACCGGCTCGGCGGCGTCACTGATTAATGGGGTTGTGAAACTT<br>CTCAGCTGGCCATGGAACGCACGGGAAGATGTGGTGCGCATGGCC<br>ATGACTGACACAACGGCTTTCGGACAGCAGAGAGTGTTCAAGGATA<br>AAGTTGACACAAAGGCACAAGAGCCTCAGCCCGGTACAAGAGTCA<br>TCATGAGAGCAGTAAATGATTGGATTTTGGAACGACTGGCGCAGAA<br>AAGCAAACCGCGCATGTGCAGCAAAGAGGAATTCATAGCAAAAGT<br>GAAATCAAATGCAGCCTTGGGAGCTTGGTCAGATGAGCAAAACAG<br>ATGGGCAAGTGCAAGGGAGGCTGTAGAGGATCCTGCATTCTGGCAC<br>CTCGTGGATGAAGAGAGAGAAAGGCACCTCATGGGGAGATGCGCG<br>CACTGCGTGTACAACATGATGGGCAAGAGAGAGAAGAAACTGGGA<br>GAGTTTGGAGTGGCGAAAGGAAGTCGGGCCATCTGGTACATGTGGC<br>TGGGGAGTCGCTTCCTGGAGTTCGAGGCTCTTGGATTCTTGAATGA<br>AGACCATTGGGCCTCTAGAGAGTCCAGTGGAGCTGGAGTTGAGGG<br>AATAAGCTTGAACTACCTGGGCTGGCACCTCCAGAAGTTGTCAACC<br>CTGAATGGAGGACTCTTCTATGCAGATGACACAGCTGGCTGGGACA<br>CGAAAGTCACCAATGCAGACCTAGAGGATGAAGAACAGATCCTAC<br>GGTACATGGAGGGTGAGCACAAACAATTGGCAACCACAATAATGC<br>AAAAAGCATACCATGCCAAAGTCGTGAAGGTCGCGAGGCCCTCCC<br>GTGATGGAGGCTGCATCATGGATGTCATCACAAGAAGAGATCAAA<br>GAGGCTCGGGCCAGGTTGTGACCTATGCCCTCAACACCCTCACCAA<br>CATAAAGGTGCAACTAATCCGAATGATGGAGGGGGAGGGGGTCAT<br>AGAGGCAGCGGATGCACACAACCCGAGACTGCTTCGAGTGGAGCG<br>CTGGCTGAAAGAACATGGAGAAGAGCGTCTTGGAAGAATGCTCGT<br>CAGTGGTGACGATTGTGTGGTGAGGCCCTTGGATGACAGATTTGGC<br>AAAGCACTTTACTTTTTGAATGACATGGCCAAGACCAGGAAAGACA<br>TTGGGGAATGGGAGCACTCGCCCGGCTTTTCAAGCTGGGAGGAGGT<br>CCCCTTTTGTTCACACCATTTCCACGAGCTAGTGATGAAGGACGGA<br>CGCGCCCTGGTGGTGCCGTGCCGAGACCAAGATGAACTCGTTGGGA<br>GGGCGCGCATCTCACCAGGGTGCGGCTGGAGTGTCCGCGAGACGG<br>CCTGCCTTTCAAAAGCCTACGGGCAGATGTGGCTGCTGAGCTACTT<br>CCATCGGCGAGACCTGAGGACGCTCGGGCTTGCCATCAACTCAGCA<br>GTGCCTGTCGATTGGGTTCCTACCGGCCGCACGACATGGAGCATCC<br>ATGCCAGTGGGCCTGGATGACCACAGAAGACATGCTGGATGTCTG<br>GAACCGGGTGTGGATTTTGGACAACCCTTTCATGCAGAACAAGGAA<br>AAGGTCATGGAGTGGAGGGATGTTCCGTACCTCCCTAAAGCTCAGG<br>ACATGTTATGTTCCTCCCTTGTCGGGAGGAAAGAAAGAGCAGAATG<br>GGCCAAGAACATCTGGGGAGCGGTGGAAAAGGTTAGGAAGATGAT |

| SEQ ID NO | Sequence |
|---|---|
| | AGGTCCTGAAAAGTTCAAGGACTATCTCTCCTGTATGGACCGCCAT
GACCTGCACTGGGAGCTCAGACTGGAGAGCTCAATAATCTAAACCC
AGACTGTGACAGAGCAAAACCCGGAGGGCTCGTAAAAGATTGTCC
GGAACCAAAAGGAAAGCAAGCAACTTATGGAATGCTGCGGCAGCG |
| SEQ ID NO: 5 | AGATTTTCTTGCACGTGCATGCGTTTGCTTCGGACAGCATTAGCAGC
GGTTGGTTTGAAAGAGATATTCTTTTGTTTCTACCAGTCGTGAACGT
GTTGAGAAAAAGACAGCTTAGGAGAACAAGAGCTGGGGATGGTCA
AGAAGGCCATCCTGAAAGGTAAGGGGGGCGGTCCCCCTCGACGAG
TGTCGAAAGAGACCGCAACGAAGACGCGTCAACCCAGAGTCCAAA
TGCCAAATGGGCTTGTGTTGATGCGCATGATGGGGATCTTGTGGCA
TGCCGTAGCCGGCACCGCGAGAAACCCCGTATTGAAGGCGTTCTGG
AACTCAGTCCCTCTGAAACAGGCAACAGCAGCACTGCGGAAGATC
AAAAGGACGGTGAGTGCCCTAATGGTTGGCTTGCAAAAACGTGGG
AAAAGGAGGTCAGCGACGGACTGGATGAGCTGGTTGCTGGTCATC
ACTCTGTTGGGGATGACGCTTGCTGCAACGGTGAGGAAAGAAAGG
GATGGCTCAACTGTGATCAGAGCTGAAGGAAAGGATGCAGCAACT
CAGGTGCGTGTGGAGAATGGCACCTGTGTGATCCTGGCTACTGACA
TGGGGTCATGGTGTGATGATTCACTGTCCTATGAGTGTGTGACCAT
AGATCAAGGAGAAGAGCCTGTTGACGTGGATTGTTTTTGCCGGAAC
GTTGATGGAGTCTATCTGGAGTACGGACGCTGTGGGAAACAGGAA
GGCTCACGGACAAGGCGCTCAGTGCTGATCCCATCCCATGCTCAGG
GAGAGCTGACGGGAAGGGGACACAAATGGCTAGAAGGAGACTCGC
TGCGAACACACCTTACTAGAGTTGAGGGATGGGTCTGGAAGAACA
AGCTACTTGCCTTGGCAATGGTTACCGTTGTGTGGTTGACCCTGGAG
AGTGTGGTGACCAGGGTTGCCGTTCTTGTTGTGCTCCTGTGTTTGGC
ACCGGTTTACGCTTCGCGTTGCACACACTTGGAAAACAGGGACTTT
GTGACTGGTACTCAGGGGACTACGAGGGTCACCTTGGTGCTGGAAC
TGGGTGGATGTGTTACTATAACAGCTGAGGGGAAGCCTTCAATGGA
TGTGTGGCTTGACGCCATTTACCAGGAGAACCCTGCTAAGACACGT
GAGTACTGTTTACACGCCAAGTTGTCGGACACTAAGGTTGCAGCCA
GATGCCCAACAATGGGACCAGCCACTTTGGCTGAAGAACACCAGG
GTGGCACAGTGTGTAAGAGAGATCAGAGTGATCGAGGCTGGGGCA
ACCACTGTGGACTGTTTGGAAAGGGTAGCATTGTGGCCTGTGTCAA
GGCGGCTTGTGAGGCAAAAAAGAAAGCCACAGGACATGTGTACGA
CGCCAACAAAATAGTGTACACGGTCAAAGTCGAACCACACACGGG
AGACTATGTTGCCGCAAACGAGACACATAGTGGGAGGAAGACGGC
ATCCTTCACAATTTCTTCAGAGAAAACCATTTTGACTATGGGTGAGT
ATGGAGATGTGTCTTTGTTGTGCAGGGTCGCTAGTGGCGTTGACTTG
GCCCAGACCGTCATCCTTGAGCTTGACAAGACAGTGGAACACCTTC
CAACGGCTTGGCAGGTCCATAGGGACTGGTTCAATGATCTGGCTCT
GCCATGGAAACATGAGGGAGCGCAAAACTGGAACAACGCAGAAAG
ACTGGTTGAATTTGGGGCTCCTCACGCTGTCAAGATGGACGTGTAC
AACCTCGGAGACCAGACTGGAGTGTTACTGAAGGCTCTCGCTGGGG
TTCCTGTGGCACACATTGAGGGAACCAAGTACCACCTGAAGAGTGG
CCACGTGACCTGCGAAGTGGGACTGGAAAAACTGAAGATGAAAGG
TCTTACGTACACAATGTGTGACAAAACAAAGTTCACATGGAAGAGA
GCTCCAACAGACAGTGGGCATGATACAGTGGTCATGGAAGTCACAT
TCTCTGGAACAAAGCCCTGTAGGATCCCAGTCAGGGCAGTGGCACA
TGGATCTCCAGATGTGAACGTGGCCATGCTGATAACGCCAAACCCA
ACAATTGAAAACAATGGAGGTGGCTTCATAGAGATGCAGCTGCCCC
CAGGGGATAACATCATCTATGTTGGGGAACTGAGTCATCAATGGTT
CCAAAAAGGGAGCAGCATCGGAAGGGTTTTCCAAAAGACCAAGAA
AGGCATAGAAAGACTGACAGTGATAGGAGAGCACGCCTGGGACTT
CGGTTCTGCTGGAGGCTTTCTGAGTTCAATTGGGAAGGCGGTACAT
ACGGTCCTTGGTGGCGCTTTCAACAGCATCTTCGGGGGAGTGGGGT
TTCTACCAAAACTTTTATTAGGAGTGGCATTGCTTGGTTGGGCCTG
AACATGAGAAACCCTACAATGTCCATGAGCTTTCTCTTGGCTGGAG
GTCTGGTCTTGGCCATGACCCTTGGAGTGGGGGCGGATGTTGGTTG
CGCTGTGGACACGGAACGAATGGAGCTCCGCTGTGGCGAGGGCCT
GGTCGTGTGGAGAGAGGTCTCAGAATGGTATGACAATTATGCCTAC
TACCCGGAGACACCGGGGGCCCTTGCATCAGCCATAAAGGAGACA
TTTGAGGAGGGAAGCTGTGGTGTAGTCCCCCAGAACAGGCTCGAGA
TGGCCATGTGGGAGAAGCTCGGTCACAGAGCTGAATTTGGCTCTGC
GGAAGGGGAGGCAAATCTCACAGTGGTGGTGGACAAGTTTGACCC
CACTGACTACCGAGGTGGTGTCCCTGGTTTACTGAAAAAAGGAAAG
GACATAAAAGTCTCCTGGAAAAGCTGGGGCCATTCAATGATCTGGA
GCATTCCTGAGGCCCCCGTCGCTTCATGGTGGGCACGGAAGGACA
AAGTGAGTGTCCCCTAGAGAGACGGAAGACAGGTGTTTTCACGGTG
GCAGAATTCGGGGTTGGCCTGAGAACAAAGGTCTTCTTGGATTTCA
GACAGGAACCAACACATGAGTGTGACACAGGAGTGATGGGAGCTG
CAGTCAAGAACGGCATGGCAATCCACACAGATCAAAGTCTCTGGAT
GAGATCAATGAAAAATGACACAGGCACTTACATAGTTGAACTTTTG
GTCACTGACCTGAGGAACTGCTCATGCCTGCTAGCCACACTATCG
ATAATGCTGACGTGGTGGACTCAGAGTTATTCCTTCCGGCGAGCCT |

| SEQ ID NO | Sequence |
|---|---|
| | GGCAGGACCCAGATCCTGGTACAACAGGATACCTGGCTATTCAGAA |
| | CAGGTGAAAGGGCCATGGAAGTACACGCCTATCCGAGTTATCAGA |
| | GAGGAGTGTCCCGGCACGACCGTTACCATCAACGCCAAGTGTGACA |
| | AAAGAGGAGCATCTGTGAGGAGTACCACAGAGAGTGGCAAGGTTA |
| | TCCCAGAATGGTGCTGCCGAGCGTGCACAATGCCACCAGTGACGTT |
| | CCGGACTGGAACTGATTGCTGGTATGCCATGGAAATACGGCCAGTC |
| | CATGACCAGGGGGGGCTTGTTCGCTCAATGGTGGTTGCGGACAACG |
| | GTGAATTACTTAGTGAGGGAGGAGTCCCCGGAATAGTGGCATTGTT |
| | TGTGGTCCTTGAATACATCATCCGTAGGAGGCCCTCCACGGGAACG |
| | ACGGTTGTGTGGGGGGGTATCGTCGTTCTCGCTCTGCTTGTCACCGG |
| | GATGGTCAGGATAGAGAGCCTGGTGCGCTATGTGGTGGCAGTGGG |
| | GATCACATTCCACCTTGAGCTGGGGCCAGAGATCGTGGCCTTGATG |
| | CTACTCCAGGCTGTGTTTGAGCTGAGGGTGGGTTTGCTCAGCGCATT |
| | TGCATTGCGCAGAAGCCTCACCGTCCGAGAGATGGTGACCACCTAC |
| | TTTCTTTTGCTGGTCCTGGAATTGGGGCTGCCGGGTGCGAGCCTTGA |
| | GGAGTTCTGGAAATGGGTGATGCACTGGCCATGGGGCGCTGATA |
| | TTCAGGGCTTGCACGGCAGAAGGAAAGACTGGAGCGGGGCTTTTGC |
| | TCATGGCTCTCATGACACAGCAGGATGTGGTGACTGTGCACCATGG |
| | ACTGGTGTGCTTCCTAAGTGTAGCTTCGGCATGCTCGGTCTGGAGG |
| | CTGCTCAAGGGACACAGAGAGCAGAAGGGATTGACCTGGGTTGTC |
| | CCCCTGGCTGGGTTGCTTGGGGGAGAGGGCTCTGGAATCAGACTGC |
| | TGGCGTTTTGGGAGTTGTCAGCGCACAGAGGAAGACGATCTTTCAG |
| | TGAACCACTAACTGTGGTAGGAGTCATGCTAACACTGGCCAGCGGC |
| | ATGATGCGACACACTTCCCAGGAGGCTCTCTGTGCACTCGCAGTGG |
| | CCTCGTTTCTCTTGCTGATGCTGGTGCTGGGGACAAGAAAGATGCA |
| | GCTGGTTGCCGAATGGAGTGGCTGCGTTGAATGGTATCCGGAACTA |
| | GTGAATGAGGGTGGAGAGGTTAGCCTGCGGGTCCGGCAGGACGCG |
| | ATGGGTAACTTTCACTTGACTGAGCTCGAGAAAGAAGAGAGAATG |
| | ATGGCTTTTTGGCTGATTGCCGGCTTGGCAGCTTCGGCCATTCACTG |
| | GTCAGGCATTCTTGGTGTGATGGGACTGTGGACGCTCACGGAAATG |
| | CTGAGGTCATCCCGAAGGTCTGACCTGGTTTTCTCTGGACAGGGGG |
| | GTCGAGAGCGTGGTGACAGACCTTTCGAGGTTAAGGACGGTGTCTA |
| | CAGGATTTTTAGCCCCGGCTTGTTCTGGGGTCAGAACCAGGTGGGA |
| | GTTGGCTACGGTTCCAAGGGTGTCTTGCACACGATGTGGCACGTGA |
| | CGAGAGGAGCGGCGCTGTCTATTGATGACGCTGTGGCCGGTCCCTA |
| | CTGGGCTGATGTGAGGGAAGATGTCGTGTGTTACGGAGGAGCCTGG |
| | AGCCTGGAGGAAAAATGGAAAGGTGAAACAGTACAGGTCCATGCC |
| | TTCCCACCGGGGAGGGCGCATGAGGTGCATCAGTGCCAGCCTGGGG |
| | AGTTGATCCTTGACACCGGAAGAAAGCTTGGGGCAATACCAATTGA |
| | TTTGGTGAAAGGAACATCAGGCAGCCCCATTCTCAACGCCCAGGGA |
| | GTGGTTGTGGGGCTATACGGAAATGGCCTAAAAACTAATGAGACCT |
| | ACGTCAGCAGCATTGCTCAAGGGGAAGCGGAGAAGAGTCGCCCCA |
| | ACCTCCCACAGGCTGTTGTGGGTACGGGCTGGACATCAAAGGGTCA |
| | GATCACAGTGCTGGACATGCACCCAGGCTCGGGGAAGACCCACAG |
| | AGTCCTCCCGGAGCTCATTCGCCAATGCATTGACAGGCGCCTGAGA |
| | ACGTTGGTGTTGGCTCCAACTCGTGTGGTACTCAAAGAAATGGAGC |
| | GTGCTTTGAATGGGAAACGGGTCAGGTTCCACTCACCAGCAGTCAG |
| | TGACCAACAGGCTGGAGGGGCAATTGTCGATGTGATGTGTCACGCA |
| | ACCTATGTCAACAGAAGGCTACTCCCACAGGGAAGACAAAATTGG |
| | GAGGTGGCAATCATGGATGAGGCCCACTGGACGGACCCCCACAGC |
| | ATAGCTGCCAGAGGTCATTTGTATACTCTGGCAAAAGAAAACAAGT |
| | GTGCACTGGTCTTGATGACAGCGACACCTCCTGGTAAGAGTGAACC |
| | CTTTCCGGAGTCCAATGGAGCCATTACTAGTGAGGAAAGACAGATT |
| | CCTGATGGGGAGTGGCGTGACGGGTTTGACTGGATCACTGAGTATG |
| | AAGGGCGCACCGCCTGGTTTGTCCCTTCGATTGCAAAAGGTGGTGC |
| | TATAGCTCGCACCTTGAGACAGAAGGGGAAAAGTGTGATTTGTTTG |
| | AACAGCAAAACCTTTGAAAAGGACTACTCCAGAGTGAGGGATGAG |
| | AAGCCTGACTTTGTGGTGACGACTGATATCTCGGAGATGGGAGCTA |
| | ACCTTGACGTGAGCCGCGTCATAGATGGGAGGACAAACATCAAGC |
| | CCGAGGAGGTTGATGGGAAAGTCGAGCTCACCGGGACCAGGCGAG |
| | TGACCACGGCTTCCGCTGCCCAACGGCGCGGAAGAGTTGGTCGGCA |
| | AGACGGACGAACAGATGAATACATATACTCTGGACAGTGTGATGAT |
| | GATGACAGTGGATTAGTGCAATGGAAAGAGGCGCAAATACTTCTTG |
| | ACAACATAACAACCTTGCGGGGGCCCGTGGCCACCTTCTATGGACC |
| | AGAACAGGACAAGATGCCGGAGGTGGCCGGTCACTTTCGACTCACT |
| | GAAGAGAAAGAAAGCACTTCCGACATCTTCTCACCCATTGTGACT |
| | TCACACCGTGGCTGGCATGGCACGTCGCAGCGAATGTATCCAGCGT |
| | CACGGATCGAAGCTGGACATGGGAAGGGCCGGAGGCAAATGCCGT |
| | GGATGAGGCCAGTGGTGACTTGGTCACCTTTAGGAGCCCGAATGGG |
| | GCGGAGAGAACTCTCAGGCCGGTGTGGAAGGACGCACGTATGTTC |
| | AAAGAGGGACGTGACATCAAAGAGTTCGTGGCGTACGCGTCTGGG |
| | CGTCGCAGCTTCGGAGATGTTCTGACAGGAATGTCGGGAGTTCCTG |
| | AGCTCCTGCGGCACAGATGCGTCAGTGCCCTGGATGTCTTCTACAC |
| | GCTTATGCATGAGGAACCTGGCAGCAGGGCAATGAGAATGGCGGA |
| | GAGAGATGCCCCAGAGGCCTTTCTGACTATGGTTGAGATGATGGTG |

| SEQ ID NO | Sequence |
|---|---|
| | CTGGGTTTGGCAACCCTGGGTGTCATCTGGTGCTTCGTCGTCCGGAC
TTCAATCAGCCGCATGATGCTGGGCACGCTGGTCCTGCTGGCCTCCT
TGCTACTCTTGTGGGCAGGTGGCGTCGGCTATGGGAACATGGCTGG
AGTGGCTCTCATCTTTTACACGTTGCTGACGGTGCTGCAGCCTGAGG
CGGGAAAACAGAGAAGCAGTGACGACAACAAACTGGCATATTTCT
TGCTGACGCTCTGCAGCCTTGCTGGACTGGTTGCAGCCAATGAGAT
GGGCTTTCTGGAGAAGACCAAGGCAGACTTGTCCACGGCGCTGTGG
AGTGAACGGGAGGAACCCCGGCCATGGAGTGAATGGACGAATGTG
GACATCCAGCCAGCGAGGTCCTGGGGGACCTATGTGCTGGTGGTGT
CTCTGTTCACACCTTACATCATCCACCAACTGCAGACCAAAATCCA
ACAACTTGTCAACAGTGCCGTGGCATCTGGTGCACAGGCCATGAGA
GACCTTGGGGGAGGTGCCCCCTTCTTTGGTGTGGCGGGACATGTCA
TGACCCTCGGGGTGGTGTCACTGATTGGGGCTACTCCCACCTCACT
GATGGTGGGCGTTGGCTTGGCTGGCCACTCCATCTGGCCATTGTGGTG
TCTGGTCTGGAGGCTGAATTAACACAGAGAGCTCATAAGGTCTTTT
TCTCTGCAATGGTGCGCAACCCCATGGTGGATGGGGATGTCATCAA
CCCATTCGGGGAGGGGGAGGCAAAACCTGCTCTATATGAAAGGAA
AATGAGTCTGGTGTTGGCCACAGTGTTGTGCCTCATGTCGGTGGTC
ATGAACCGAACGGTGGCCTCCATAACAGAGGCTTCAGCAGTGGGA
CTGGCAGCAGCGGGACAGCTGCTTAGACCGGAGGCTGACACGTTGT
GGACGATGCCGGTTGCTTGTGGCATGAGTGGTGTGGTCAGGGGTAG
CCTGTGGGGTTTTTGCCTCTTGGGCATAGACTCTGGCTTCGAGCCT
CTGGGGGTAGGCGTGGTGGTTCTGAGGGAGACACGCTTGGAGATCT
CTGGAAGCGGAGGCTGAACAACTGCACGAGGGAGGAATTCTTTGT
GTACAGGCGCACCGGCATCCTGGAGACGGAACGTGACAAGGCTAG
AGAGTTGCTCAGAAGAGGAGAGACCAATGTGGGATTGGCTGTCTCT
CGGGGCACGGCAAAGCTTGCCTGGCTTGAGGAACGCGGATATGCC
ACCCTCAAGGGAGAGGTGGTAGATCTTGGATGTGGAAGGGGCGGC
TGGTCCTATTATGCGGCATCCCGACCGGCAGTCATGAGTGTCAGGG
CATATACCATTGGTGGAAAAGGGCACGAGGCTCCAAAGATGGTAA
CAAGCCTGGGTTGGAACTTGATTAAATTCAGATCAGGAATGGACGT
GTTCAGCATGCAGCCACACCGGGCTGACACTGTCATGTGTGACATC
GGAGAGAGCAGCCCAGATGCCGCTGTGGAGGGTGAGAGGACAAGG
AAAGTGATACTGCTCATGGAGCAATGGAAAAACAGGAACCCCACG
GCTGCCTGTGTGTTCAAGGTGCTGGCCCCATATCGCCCAGAAGTGA
TAGAGGCACTGCACAGATTCCAACTGCAATGGGGGGGGGGTCTGGT
GAGGACCCCTTTTTCAAGGAACTCCACCCATGAGATGTATTACTCA
ACAGCCGTCACTGGGAACATAGTGAACTCCGTCAATGTACAGTCGA
GGAAACTTTTGGCTCGGTTTGGAGACCAGAGAGGGCCAACCAAGGT
GCCTGAACTCGACCTGGGAGTTGGAACGAGGTGTGTGGTCTTAGCT
GAGGACAAGGTGAAAGAACAAGACGTACAAGAGAGGATCAGAGC
GTTGCGGGAGCAATACAGCGAAACCTGGCATATGGACGAGGAACA
CCCCGTACCGGACATGGCAGTACTGGGGCAGCTACCGCACGGCACC
AACCGGCTCGGCGGCGTCACTGATCAATGGGGTTGTGAAACTTCTC
AGCTGGCCATGGAACGCACGGGAAGATGTGGTGCGCATGGCTATG
ACTGACACAACGGCTTTCGGACAGCAGAGAGTGTTCAAAGATAAA
GTTGACACAAAGGCACAGGAGCCTCAGCCCGGTACAAGAGTCATC
ATGAGAGCTGTAAATGATTGGATTTTGGAACGACTGGCGCAGAAAA
GCAAACCGCGCATGTGCAGCAGGGAAGAATTCATAGCAAAAGTGA
AATCAAATGCAGCCTTGGGAGCTTGGTCAGATGAGCAAAACAGAT
GGGCAAGTGCAAGAGAGGCTGTAGAGGATCCTGCATTCTGGCGCCT
CGTGGATGAAGAGAGAGAAAGGCACCTCATGGGGAGATGTGCGCA
CTGCGTGTACAACATGATGGGCAAGAGAGAAAAGAAACTGGGAGA
GTTCGGAGTGGCGAAAGGAAGTCGGGCCATTTGGTACATGTGGCTG
GGGAGTCGCTTTTTGGAGTTCGAGGCTCTTGGATTCTTGAATGAAG
ACCATTGGGCCTCTAGAGAGTCCAGTGGAGCTGGAGTTGAGGGAAT
AAGCTTGAACTACCTGGGCTGGCACCTCAAGAAGTTGTCAACCCTG
AATGGAGGACTCTTCTATGCAGATGACACAGCTGGCTGGGACACGA
AAGTTACCAATGCAGACTTAGAGGATGAAGAACAGATCCTACGGT
ACATGGAGGGTGAGCACAAACAATTGGCAACCACAATAATGCAAA
AAGCATACCATGCCAAAGTCGTGAAGGTCGCGAGGCCTTCCCGTGA
TGGAGGCTGCATCATGGATGTCATCACAAGAAGAGACCAAAGAGG
TTCGGGTCAGGTTGTGACCTATGCCCTTAACACCCTCACCAACATA
AAGGTGCAATTAATCCGAATGATGGAAGGGGAAGGGGTCATAGAG
GCAGCGGATGCACACAACCCGAGACTGCTTCGAGTGGAGCGCTGG
CTGAAAGAACACGGAGAAGAGCGTCTTGGAAGAATGCTCGTCAGT
GGTGACGATTGTGTGGTGAGGCCCTTGGATGACAGATTTGGCAAAG
CACTTTACTTTCTGAATGACATGGCCAAGACCAGGAAGGACATTGG
GGAATGGGAGCACTCAGCCGGCTTTTCAAGCTGGGAGGAGGTACCC
TTTTGTTCACACCATTTCCACGAGCTAGTGATGAAGGATGGACGAC
CCCTGGTGGTGCCGTGCCGAGACCAAGATGAACTCGTTGGGAGGGC
GCGCATCTCACCGGGGTGCGGCTGGAGTGTCCGCGAGACGGCCTGC
CTTTCAAAAGCCTACGGGCAGATGTGGCTGCTGAGCTACTTCCACC
GACGAGACCTGAGGACGCTCGGCTTGCCATTAACTCAGCAGTGCC
TGCCGATTGGGTTCCTACCGGCCGCACGACGTGGAGCATTCATGCC |

-continued

| SEQ ID NO | Sequence |
|---|---|
| | AGTGGGGCCTGGATGACCACAGAAGACATGCTGGACGTTTGGAAC<br>CGGGTGTGGATTCTGGACAACCCTTTCATGCAGAACAAGGAAAGGG<br>TCATGGAGTGGAGGGATGTTCCGTACCTCCCTAAAGCTCAGGACAT<br>GTTATGTTCCTCCCTTGTTGGGAGGAGAGAAAGAGCAGAATGGGCC<br>AAGAACATCTGGGGAGCGGTGGAAAAGGTGAGGAAGATGATAGGT<br>CCTGAAAAGTTCAAGGACTATCTCTCCTGTATGGACCGCCATGACC<br>TGCACTGGGAGCTCAGACTGGAGCTCAATAATCTAAACCCAGAC<br>TGTGACAGAGCAAAACCCGGAAGGCTCGTAAAAGATTGTCCGGAA<br>CCAAAAGAAAAGCAAGCAACTCACAGAGATAGAGCTCGGACTGGA<br>GAGCTCTTTAAACAAAAAAAAAAAAAAAAAAAAAAAAAAAAAA<br>AAAAAAAAAAAAAAAAAAAGCCAGAATTGAGCTGAACCTGGAGAGC<br>TCATTAAATACAGTCCAGACGAAACAAAACATGACAAAGCAAAGA<br>GGCTGAGCTAAAAGTTCCCACTACGGGACTGCTTCATAGCGGTTTG<br>TGGGGGGAGGCTAGGAGGCGAAGCCACAGATCATGGAATGATGCG<br>GCAGCGCGCGAGAGCGACGGGGAAGTGGTCGCACCCGACGCACCA<br>TCCATGAAGCAATACTTCGTGAGACCCCCCCTGACCAGCAAAGGGG<br>GCAGACCGGTCAGGGGTGAGGAATGCCCCCAGAGTGCATTACGGC<br>AGCACGCCAGTGAGAGTGGCGACGGGAAAATGGTCGATCCCGACG<br>TAGGGCACTCTGAAAAATTTTGTGAGACCCCCTGCATCATGATAAG<br>GCCGAACATGGTGCATGAAGGGGAGGCCCCCGGAAGCACGCTTC<br>CGGGAGGAGGGAAGAGAGAAATTGGCAGCTCTCTTCAGGATTTTTC<br>CTCCTCCTATACAAAATTCCCCCTCGGTAGAGGGGGGCGGTTCTT<br>GTTCTCCCTGAGCCACCATCACCCAGACACAGGTAGTCTGACAAGG<br>AGGTGATGTGTGACTCGGAAAAACACCCGCT |
| SEQ ID NO: 6 | AGTTGTTAGTCTGTCTGGACCGACAAGAACAGTTTCGAATCGGAAG<br>CTTGCTTAACGTAGTTCTAACAGTTTTTTATTAGAGAGCAGATCTCT<br>GATGAACAACCAACGAAAAAAGACGGCTCGACCGTCTTTCAATATG<br>CTGAAACGCGCGAGAAACCGCGTGTCAACTGTTTCACAGTTGGCGA<br>AGAGATTCTCAAAAGGATTGCTCTCAGGCCAAGGACCCATGAAATT<br>GGTGATGGCTTTCATAGCATTCCTAAGATTTCTAGCCATACCCCCAA<br>CAGCAGGAATTTTGGCTAGATGGGGTTCATTCAAGAAGAGTGGAGC<br>GATCAAAGTGCTACGGGGTTTCAAGAAAGAAATCTCAAACATGTTG<br>AATATAATGAATAGAAGGAAAAGATCTGTGACCATGCTCCTTATGC<br>TGATGCCTACAGCCTTGGCGTTCCATTTGACTACACGAGGGGGAGA<br>GCCGCACATGATAGTCAGCAAGCAGGAAAGAGGAAAATCACTCTT<br>GTTTAAGACCTCAGCAGGTGTCAACATGTGCACCCTTATAGCGATG<br>GATTTGGGAGAGTTATGTGAGGACACAATGACTTACAAATGCCCTC<br>GAATCACTGAAGCTGAACCAGATGACGTTGATTGTTGGTGTAATGC<br>CACAGACACATGGGTGACCTATGGAACATGTTCCCAAACTGGCGAG<br>CACCGACGAGACAAACGTTCCGTCGCACTGGCCCCACACGTGGGAC<br>TTGGTTTGGAAACAAGAACCGAAACGTGGATGTCCTCTGAAGGCGC<br>TTGGAAACAGATACAAAGAGTGGGACTTGGGCCCTGAGCACACCC<br>AGGATTCACGGTGATAGCCCTTTTTCTAGCACATGCCATAGGAACA<br>TCCATCACTCAGAAAGGGATTATTTTCATTTTGTTAATGCTGGTAAC<br>ACCATCCATGGCCATGCGATGCGTGGGAATAGGCAGCAGGGACTTC<br>GTGGAAGGACTGTCAGGAGCAACCTGGGTAGATGTGGTACTGGAA<br>CATGGAAGTTGCGTCACCACCATGGCAAAAGACAAACCAACATTG<br>GACATTGAACTTTTGAAGACGGAAGTCACAAACCCTGCCATCCTGC<br>GCAAACTGTGCATTGAAGCTAAAATATCAAACACCACCACCGACTC<br>AAGATGCCCAACACAAGGAGAAGCCACACTGGTGGAAGAACAAGA<br>CGCGAACTTTGTGTGTCGACGAACGTTTGTGGACAGAGGCTGGGGC<br>AATGGCTGTGGGCTCTTCGGAAAAGGAAGCCTAATAACGTGTGCTA<br>AGTTCAAGTGTGTGACAAAACTGGAAGGAAAGATAGTTCAATATG<br>AAAACTTGAAATATTCAGTAATAGTCACCGTTCACACCGGAGACCA<br>GCACCAGGTGGGAAATGAAAGCACAGAACATGGGACAACTGCAAC<br>TATAACACCTCAAGCTCCTACGACGGAAATACAGCTGACTGACTAC<br>GGAGCTCTTACATTGGATTGTTCACCTAGAACAGGACTAGACTTTA<br>ATGAAATGGTGTTGTTGACAATGAAAGAAAAATCATGGCTAGTCCA<br>CAAACAATGGTTTCTAGACCTACCACTGCCTTGGACCTCGGGAGCT<br>TCAACATCACAAGAGACTTGGAACAGACAAGATTTGCTGGTGACAT<br>TTAAGACAGCCCATGCAAAGAAGCAGGAAGTAGTCGTACTAGGAT<br>CACAAGAAGGAGCAATGCACACTGCGTTGACCGGAGCAACAGAAA<br>TCCAAACGTCTGGAACGACAACAATTTTTGCAGGACACTTGAAATG<br>CAGACTAAAGATGGACAAACTGACTCTAAAAGGGATGTCATATGTG<br>ATGTGCACAGGCTCATTCAAGCTAGAGAAAGAAGTGGCTGAGACC<br>CAGCATGGAACCGTTCTAGTGCAGATTAAATATGAAGGAACAGATG<br>CACCATGCAAGATCCCTTTTTCGACCCAAGATGAAAAAGGAGTAAC<br>CCAGAATGGGAGATTGATAACAGCTAACCCTATAGTTACTGACAAA<br>GAAAAACCAGTCAACATTGAGGCAGAACCGCCTTTTGGTGAGAGTT<br>ACATCGTAATAGGAGCAGGTGAAAAAGCTTTGAAACTAAGCTGGTT<br>TAAGAAAGGAAGCAGCATAGGGAAATGCTTGAGGCAACTGCCAG<br>AGGAGCTCGAAGGATGCCATACTGGGAGACACCGCATGGGACTT<br>TGGTTCTATAGGAGGAGTGTTCACGTCTGTTGGAAAATTAGTACAC<br>CAGATTTTTGGAACTGCATATGGAGTTTTGTTCAGCGGTGTTTCCTG |

-continued

| SEQUENCES | |
|---|---|
| SEQ ID NO | Sequence |
| | GACCATGAAAATAGGAATAGGGGTTCTGCTGACATGGCTAGGATTA |
| | AACTCAAGGAGCACGTCCCTTTCGATGACGTGCATTGCAGTTGGCC |
| | TAGTAACACTATACCTAGGAGTCATGGTTCAGGCGGATTCAGGATG |
| | TGTAATTAATTGGAAAGGTAGAGAACTCAAATGTGGAAGTGGCATT |
| | TTTGTCACCAATGAAGTTCACACTTGGACAGAGCAATACAAATTTC |
| | AAGCTGACTCCCCAAAGAGACTATCAGCAGCCATCGGGAAGGCAT |
| | GGGAGGAGGGTGTGTGGAATTCGATCAGCAACTCGTCTCGAGAA |
| | CATCATGTGGAAGCAAATATCAAATGAACTGAATCACATCTTACTT |
| | GAAAATGACATGAAATTCACAGTGGTTGTAGGAGATGTTGCTGGGA |
| | TCTTGGCTCAAGGAAAGAAAATGATTAGGCCACAACCCATGGAATA |
| | CAAATACTCGTGGAAAAGCTGGGGAAAGGCTAAAATCATAGGGGC |
| | AGATGTACAGAACACCACCTTTATCATCGACGGCCCAAACACCCCA |
| | GAATGCCCTGATGACCAAAGAGCATGGAACATTTGGGAAGTTGAG |
| | GACTATGGATTTGGAATTTTCACGACAAACATATGGCTGAAACTGC |
| | GTGATTCCTATACCCAAGTGTGTGACCACCGGCTAATGTCAGCTGC |
| | CATCAAGGACAGCAAGGCAGTTCACGCTGACATGGGGTACTGGAT |
| | AGAAAGTGAAAAGAACGAGACCTGGAAGCTGGCAAGAGCTTCTTT |
| | CATAGAAGTTAAAACATGTATCTGGCCAAAATCCCACACTCTATGG |
| | AGTAATGGAGTTCTGGAAAGTGAAATGATAATTCCAAAGATCTATG |
| | GAGGACCAATATCTCAGCACAACTACAGACCAGGATATTTCACACA |
| | AACAGCAGGGCCGTGGCACCTGGGCAAGTTGGAACTGGATTTTGAT |
| | TTGTGTGAGGGCACCACAGTTGTTGTGGATGAACATTGTGGAAATC |
| | GAGGACCATCTCTTAGGACCACAACAGTCACAGGAAAGATAATTCA |
| | TGAATGGTGTTGCAGATCTTGCACGCTACCACCCTTACGTTTCAGAG |
| | GAGAAGATGGGTGCTGGTACGGTATGGAAATCAGACCAGTCAAGG |
| | AAAAGGAAGAAAATCTAGTCAAATCAATGGTCTCTGCAGGGTCAG |
| | GGGAAGTGGACAGCTTTTCACTAGGACTGCTATGCATATCAATAAT |
| | GATCGAAGAGGTGATGAGATCCAGATGGAGTAGAAAAATGCTGAT |
| | GACTGGAACACTGGCTGTGTTCCTCCTTCTCATAATAGGACAATTG |
| | ACATGGAATGATCTGATCAGATTATGCATCATGGTTGGAGCCAACG |
| | CTTCCGACAGGATGGGATGGGAACGACGTACCTAGCTCTGATGGC |
| | CACTTTTAAAATGAGACCGATGTTTGCTGTAGGGCTATTATTTCGCA |
| | GACTAACATCCAGAGAAGTTCTTCTTCTAACAATTGGATTGAGTCT |
| | AATGGCATCTGTGGAGTTACCAAATTCCTTGGAGGAGCTGGGGGAT |
| | GGACTTGCAATGGGCATTATGATTTTAAAATTACTGACTGACTTTCA |
| | ATCACATCAGCTGTGGGCTACCTTGCTGTCCTTGACATTTATCAAAA |
| | CAACGTTTTCCTTGCACTATGCATGGAAGACAATGGCTATGGTACT |
| | GTCAATTGTATCTCTCTTCCCCTTATGCCTGTCCACGACCTCCCAAA |
| | AAACAACATGGCTTCCGGTGCTATTGGGATCCCTTGGATGCAAACC |
| | ACTAACCATGTTTCTTATAGCAGAAAACAAAATCTGGGGAAGGAGA |
| | AGTTGGCCCCTCAATGAAGGAATCATGGCTGTTGGAATAGTCAGCA |
| | TCCTACTAAGTTCACTTCTCAAGAATGATGTGCCGCTAGCTGGGCC |
| | ACTAATAGCTGGAGGCATGCTAATAGCATGTTATGTTATATCTGGA |
| | AGCTCAGCCGACCTATCACTAGAGAAAGCAGCTGAGGTCTCCTGGG |
| | AAGAAGAAGCAGAACACTCTGGTGCCTCACACAACATATTAGTGG |
| | AGGTCCAAGATGATGGAACCATGAAGATAAAGGATGAAGAGAGAG |
| | ATGACACGCTAACCATTCTCCTTAAAGCAACTCTGCTAGCAGTTTCA |
| | GGGGTGTATCCATTATCAATACCAGCGACCCTTTTCGTGTGGTACTT |
| | TTGGCAGAAAAGAAACAGAGATCTGGAGTGTTATGGGACACACC |
| | CAGCCCTCCAGAAGTGGAAAGAGCAGTTCTTGATGATGGTATCTAT |
| | AGAATTATGCAGAGAGGACTGTTGGGCAGGTCCCAAGTAGGGGTA |
| | GGAGTTTTCCAAGAAAACGTGTTCCACACAATGTGGCATGTCACCA |
| | GGGGAGCTGTACTCATGTATCAAGGGAAGAGACTGGAACCGAGCT |
| | GGGCTAGTGTCAAAAAAGACCTGATCTCATATGGAGGAGGTTGGA |
| | GGCTTCAAGGATCCTGGAACACAGGAGGAAGAAGTGCAGGTAATTG |
| | CTGTTGAACCAGGGAAAAACCCCAAAAATGTACAAACAGCGCCGG |
| | GCACCTTTAAGACCCCTGAAGGTGAAGTTGGAGCCATTGCCCTAGA |
| | TTTTAAACCCGGCACATCTGGATCTCCCATCGTGAACAGAGAAGGA |
| | AAAATAGTAGGTCTTTATGGAAATGGAGTAGTGACAACAAGTGGA |
| | ACCTACGTCAGTGCCATAGCTCAAGCTCAAAGCATCACAAGAAGGG |
| | CCCCTACCAGAGATTGAAGACGAGGTGTTTAGGAAAAGAAACTTA |
| | ACAATAATGGACCTACATCCAGGATCGGGGAAAACAAGAAGATAC |
| | CTTCCAGCCATAGTCCGTGAGGCCATAAAAAGGAAGCTGCGCACAC |
| | TAATTTTGGCTCCCACAAGGGTTGTCGCTTCCGAAATGGCAGAGGC |
| | GCTCAAGGGAATGCCAATAAGGTACCAAACAACAGCAGTAAAGAG |
| | TGAACACACAGGAAAGAGATAGTTGATCTCATGTGTCACGCCACT |
| | TTCACCATGCGCCTCCTGTCTCCCGTGAGAGTTCCCAATTACAACAT |
| | GATTATCATGGATGAAGCACATTTCACCGATCCATCCAGTATAGCG |
| | GCCAGAGGGTACATCTCAACCCGAGTGGGCATGGGTGAAGCAGCT |
| | GCAATCTTCATGACAGCCACTCCCCCAGGATCAGTGGAGGCCTTTC |
| | CACAGAGCAACGCAGTAATCCAAGATGAGGAAAGAGACATTCCTG |
| | AGAGATCATGGAACTCAGGCTATGAGTGGATCACTGACTTCCCAGG |
| | TAAAACAGTTTGGTTTGTTCCAAGCATTAAATCAGGAAATGACATA |
| | GCCAACTGCTTAAGAAAGAATGGGAAACGGGTGATTCAATTGAGC |
| | AGGAAAACCTTTGATACAGAGTACCAAAAAACAAAAAACAACGAC |

| SEQUENCES | |
|---|---|
| SEQ ID NO | Sequence |
| | TGGGACTACGTCGTCACAACAGACATCTCCGAAATGGGAGCAAATT |
| | TCCGAGCAGACAGGGTGATAGACCCAAGACGGTGTCTGAAACCGG |
| | TAATACTAAAAGATGGTCCAGAGCGTGTCATTTTAGCAGGACCAAT |
| | GCCAGTGACTGTGGCCAGTGCCGCCCAGAGGAGAGGAAGAATTGG |
| | AAGGAACCACAATAAGGAAGGTGATCAGTACATCTACATGGGACA |
| | GCCTTTAAACAACGATGAAGATCACGCTCACTGGACAGAAGCAAA |
| | AATGCTCCTTGACAATATAAACACACCAGAAGGGATTATCCCAGCC |
| | CTCTTCGAGCCGGAGAGAGAAAAGAGTGCAGCAATAGACGGGGAA |
| | TACAGACTGCGGGGTGAGGCAAGGAAAACGTTTGTGGAGCTCATG |
| | AGAAGAGGAGATCTACCTGTCTGGCTATCTTACAAAGTTGCCTCAG |
| | AAGGCTTCCAGTACTCTGACAGAAGATGGTGCTTTGACGGGGAAAG |
| | GAACAACCAGGTGTTGGAGGAGAACATGGACGTGGAGATCTGGAC |
| | AAAAGAGGGAGAAAGAAAGAAACTACGACCCCGCTGGCTGGATGC |
| | CAGAACATACTCAGACCCACTAGCCCTGCGCGAGTTTAAAGAGTTT |
| | GCAGCAGGGAGAAGAAGCGTCTCAGGTGATCTAATATTGGAAATA |
| | GGGAAACTTCCACAACACTTGACGCAAAGGGCCCAGAATGCCTTGG |
| | ACAACCTGGTTATGTTGCACAACTCCGAACAAGGAGGAAGAGCCTA |
| | CAGACATGCAATGGAAGAACTGCCAGACACCATAGAAACGTTGAT |
| | GCTCCTAGCTTTGATAGCTGTGTTAACTGGTGGAGTGACACTGTTCT |
| | TCCTATCAGGAAGGGGCTTAGGGAAAACATCTATTGGCCTACTCTG |
| | CGTAATGGCTTCAAGCGTACTGCTATGGATGGCCAGTGTAGAGCCC |
| | CATTGGATAGCGGCCTCCATCATACTGGAGTTCTTCCTGATGGTGCT |
| | GCTTATTCCAGAGCCAGACAGACAACGCACTCCGCAGGACAATCAG |
| | CTGGCATATGTGGTGATAGGTTTGTTATTCATGATACTGACAGTAGC |
| | AGCCAATGAGATGGGACTGCTGGAAACCACAAAGAAAGACTTAGG |
| | GATTGGCCATGTGGCTGTTGGAAATCACCACCATGCCGCAATGCTG |
| | GACGTAGACTTACATCCAGCTTCAGCCTGGACCCTCTATGCAGTGG |
| | CCACAACAATTATCACTCCCATGATGAGGCACACAATCGAAAACAC |
| | AACGGCAAACATTTCCCTGACAGCCATTGCAAACCAGGCAGCTATA |
| | TTGATGGGACTTGACAAAGGATGGCCAATATCGAAGATGGACATA |
| | GGAGTTCCACTTCTCGCCTTGGGGTGCTATTCCCAAGTGAATCCACT |
| | GACGCTGACAGCGGCGGTATTGATGCTAGTGGCTCATTACGCCATA |
| | ATTGGACCTGGACTGCAAGCAAAAGCTACTAGAGAAGCTCAAAAA |
| | AGGACAGCGGCCGGGATAATGAAAAATCCAACCGTTGATGGGATT |
| | GTTGCAATAGATTTGGACCCTGTGGTTTATGATGCAAAATTTGAGA |
| | AACAACTAGGCCAAATAATGTTGTTGATACTATGCACATCACAGAT |
| | CCTCTTGATGCGGACTACATGGGCCTTGTGCGAATCCATCACACTG |
| | GCCACTGGACCTCTGACCACGCTTTGGGAGGGATCTCCAGGAAAAT |
| | TTTGGAACACCACGATAGCGGTTTCCATGGCAAACATTTTCAGAGG |
| | AAGTTATCTAGCAGGAGCAGGTCTGGCCTTCTCATTAATGAAATCT |
| | CTAGGAGGAGGTAGGAGAGGCACGGGAGCCCAAGGGGAAACACTG |
| | GGAGAGAAATGGAAAAGACAGCTGAACCAACTGAGCAAGTCAGAA |
| | TTTAACACCTATAAAAGGAGTGGGATTATGGAAGTGGACATCCG |
| | AAGCAAAAGAGGGATTGAAAAGAGGAGAAACAACCAAACATGCA |
| | GTGTCGAGAGGAACCGCTAAACTGAGATGGTTTGTGGAGAGGAAC |
| | CTTGTCAAACCAGAAGGGAAAGTCATAGACCTCGGCTGTGGAAGA |
| | GGTGGCTGGTCATACTATTGCGCTGGGCTGAAGAAAGTCACGAAG |
| | TGAAGGGATATACAAAAGGGGGACCTGGACATGAGGAACCAATCC |
| | CAATGGCGACCTATGGATGGAACCTAGTAAAGCTGCACTCTGGGAA |
| | AGACGTATTCTTTATACCACCTGAGAAATGTGACACCCTTTTGTGTG |
| | ATATTGGTGAGTCCTCCCCAAACCCAACTATAGAGGAAGGAAGAAC |
| | GCTACGCGTCCTAAAGATGGTGGAACCATGGCTCAGAGGAAACCA |
| | ATTTTGCATAAAGATTCTGAATCCCTACATGCCAAGTGTGGTGGAA |
| | ACTCTGGAGCAAATGCAAAGAAAACATGGAGGAATGCTAGTGCGA |
| | AATCCACTTTCAAGAAATTCTACTCATGAAATGTACTGGGTTTCATG |
| | TGGAACAGGAAACATTGTGTCAGCAGTAAACATGACATCTAGAATG |
| | TTGCTAAATCGATTCACAATGGCTCACAGGAAACCAACATATGAAA |
| | GAGATGTGGACCTAGGCGCCGGAACAAGACATGTGGCAGTGGAAC |
| | CAGAGGTAGCTAACCTAGATATCATTGGCCAGAGGATAGAGAACA |
| | TAAAACATGAACATAAGTCAACATGGTATTATGATGAGGACAATCC |
| | ATATAAAACATGGGCCTATCATGGATCATATGAGGTCAAGCCATCA |
| | GGATCAGCCTCATCCATGGTCAATGGCGTGGTGAAACTGCTCACCA |
| | AGCCATGGGATGTCATCCCCATGGTTACACAAATAGCCATGACTGA |
| | CACTACACCCTTTGGACAACAGAGGGTGTTTAAAGAGAAAGTTGAC |
| | ACACGCACACCAAAAGCAAACGAGGCACAGCACAAATCATGGAG |
| | GTGACAGCCAAGTGGTTATGGGGTTTTCTTTCTAGAAACAAGAAAC |
| | CAAGAATTTGCACAAGAGAGGAGTTCACAAGAAAGTTAGGTCAA |
| | ACGCAGCCATTGGAGCAGTGTTCGTTGATGAAAATCAATGGAACTC |
| | AGCAAAAGAAGCAGTGGAAGATGAGCGGTTCTGGGACTTGTGCA |
| | TAAAGAGGGGAGCTTCACAAACAGGGAAATGTGCCACGTGTGT |
| | TTACAACATGATGGGAAGAGAGAGAAAAAGCTAGGAGAGTTCGG |
| | AAAGGCAAAGGAAGTCGTGCAATATGGTACATGTGGTTGGGAGC |
| | ACGCTTTCTAGAGTTCGAAGCTCTTGGTTTCATGAACGAAGATCACT |
| | GGTTCAGCAGAGAGAATTCATTCAGCGGAGTGGAAGGAGAAGGAC |
| | TCCACAAACTTGGATATATACTCAGAGACATATCAAAGATTCCAGG |

| SEQ ID NO | Sequence |
|---|---|
| | GGGAAACATGTATGCAGATGACACAGCCGGATGGGATACAAGGAT
AACTGAGGATGACCTTCAGAATGAGGCCAGAATTACTGACATCATG
GAACCCGAACATGCCCTACTGGCTAAGTCAATCTTCAAGCTGACCT
ACCAAAATAAGGTGGTAAGGGTACAGAGACCAGCAAAAAATGGAA
CCGTGATGGATGTCGTATCCAGACGTGACCAGAGAGGAAGTGGCC
AGGTCGGAACTTATGGCTTAAACACTTTCACCAACATGGAAGCCCA
GCTGATAAGACAAATGGAGTCTGAGGGAATCTTTTCACCCAGCGAA
TTAGAGACCCCAAATTTAGCCGAGAGAGTTCTCGCCTGGCTGGAAA
AATATGGCGTCGAAAGGCTGAAAAGAATGGCAATCAGCGGAGATG
ATTGCGTGGTGAAACCAATTGATGATAGGTTTGCAACAGCCTTAAC
AGCTCTGAATGATATGGGAAAAGTAAGAAAAGATATACCACAATG
GGAACCTTCAAAAGGATGGAATGATTGGCAACAAGTGCCTTTTTGT
TCACACCACTTCCACCAGCTGATTATGAAGGATGGGAGGGAAATAG
TGGTGCCATGCCGCAACCAAGATGAACTTGTGGGTAGGGCTAGAGT
ATCACAAGGTGCTGGATGGAGCCTGAGAGAAACTGCATGCCTAGG
CAAGTCATATGCACAGATGTGGCAGCTGATGTACTTCCACAGGAGA
GACCTGAGACTAGCCGCTAATGCTATCTGTTCAGCCGTTCCAGTTA
ATTGGATCCCAACCAGCCGCACCACCTGGTCGATCCATGCCCATCA
CCAATGGATGACAACAGAAGACATGCTGTCAGTGTGGAATAGGGTT
TGGATAGAGGAAAACCCATGGATGGAGGACAAAACCCATATATCC
AGTTGGGGAGATGTTCCATATTTAGGGAAAAGGGAAGATCAATGGT
GTGGATCCCTGATAGGCTTAACAGCAAGGGCCACCTGGGCCACCAA
CATACAAGTGGCCATAAACCAAGTGAGAAAACTAATTGGGAATGA
GAATTACCTAGATTACATGACATCAATGAAGAGATTCAAGAACGAG
AGTGATCCCGAAGGGGCACTCTGGTGAGTCAACACATTTACAAAAT
AAAGGAAAATAAGAAATCAAACAAGGCAAGAAGTCAGGCCGGATT
AAGCCATAGTACGGTAAGAGCTATGCTGCCTGTGAGCCCCGTCTAA
GGACGTAAAATGAAGTCAGGCCGAAAGCCACGGCTTGAGCAAACC
GTGCTGCCTGTAGCTCCATCGTGGGGATGTAAAAACCTGGGAGGCT
GCAACCCATGGAAGCTGTACGCATGGGGTAGCAGACTAGTGGTTAG
AGGAGACCCCTCCCGAAACATAACGCAGCAGCGGGGCCCAACACC
AGGGGAAGCTGTACCCTGGTGGTAAGGACTAGAGGTTAGAGGAGA
CCCCCCGCACAACAATAAACAGCATATTGACGCTGGGAGAGACCA
GAGATCCTGCTGTCTCTACAGCATCATTCCAGGCACAGAACGCCAG
AAAATGGAATGGTGCTGTTGAATCAACAGGTT |
| SEQ ID NO: 7 | ATGAATAACCAACGAAAAAGGCGAGAAGTACGCCTTTCAATATG
CTGAAACGCGAGAGAAACCGCGTGTCAACTGTGCAACAGCTGACA
AAGAGATTCTCACTTGGAATGCTGCAAGGACGCGGACCATTAAAC
TGTTCATGGCCCTTGTGGCGTTCCTTCGTTTCCTAACAATCCCACCA
ACAGCAGGGATACTAAAAGATGGGGAACGATCAAGAAATCAAA
GCTATCAATGTTTTGAGAGGGTTCAGGAAAGAGATTGGAAGGATGC
TGAACATCTTGAACAGGAGACGTAGGACAGCAGGCGTAATTGTTAT
GTTGATTCCAACAGCGATGGCGTTCCATTTAACCACACGCAATGGA
GAACCACACATGATCGTTGGTAGGCAGGAGAAAGGGAAAAGTCTT
CTGTTCAAAACAGAGGATGGTGTTAACATGTGTACCCTCATGGCCA
TGGACCTTGGTGAGTTGTGTGAAGATACAATCACGTACAAGTGTCC
CCTCCTCAGACAAAATGAACCAGAAGACATAGATTGTTGGTGCAAC
TCTACGTCCACATGGGTAACTTATGGGACATGTACCACCACAGGAG
AACACAGAAGAGAAAAAGATCAGTGGCGCTCGTTCCACATGTGG
GTATGGGACTGGAGACACGAACTGAAACATGGATGTCATCGGAAG
GGGCCTGGAAGCATGTTCAGAGAATTGAAACCTGGATCTTGAGACA
TCCAGGTTTTACCATAATGGCAGCGATCCTGGCATACACCATAGGA
ACGACACACTTCCAAAGGGCCTTGATTTTCATCTTACTGACAGCTGT
CGCTCCTTCAATGACAATGCGCTGCATAGGAATATCAAATAGAGAC
TTCGTAGAAGGGGTTTCAGGAGGAAGCTGGGTTGACATCGTTTTAG
AACATGGAAGTTGTGTGACGACGATGGCAAAAAACAAACCAACAT
TGGATTTTGAACTGATAAAAACAGAAGCCAAACAACCTGCCACTCT
AAGGAAGTACTGTATAGAAGCAAAGCTGACCAACACAACAACAGA
ATCGCGTTGCCCAACACAAGGGGAACCCAGTCTAAATGAAGAGCA
GGACAAAAGGTTCATCTGCAAACACTCCATGGTAGACAGAGGATG
GGGAAATGGATGTGGATTATTTGGAAAGGGAGGCATTGTGACCTGT
GCTATGTTTACATGCAAAAAGAACATGGAAGGAAAAATCGTACAG
CCAGAAAATTTGGAATACACCATCGTGATAACACCTCACTCAGGAG
AAGAGCACGCTGTAGGTAATGACACAGGAAAGCATGGCAAGGAAA
TCAAAATAACACCACAGAGTTCCACCACAGAAGCAGAACTGACAG
GCTATGGCACTGTCACGATGGAGTGCTCTCCGAGAACGGGCCTCGA
CTTCAATGAGATGGTGCTGCTGCAGATGGAAGACAAAGCTTGGCTG
GTGCACAGGCAATGGTTCCTAGACCTGCCGTTGCCATGGCTACCCG
GAGCGGATACAAGGATCAAATTGGATACAGAAAGAGACATTGG
TCACTTTCAAAAATCCCCACGCCAAGAAACAGGATGTCGTTGTCTT
AGGGTCTCAAGAAGGGGCCATGCACACGGCACTCACAGGGGCTAC
AGAAATCCAGATGTCATCAGGAAACTTACTGTTCACGGGACATCTC
AAGTGCAGGCTGAGAATGGACAAACTACAGCTCAAAGGAATGTCA
TACTCTATGTGTACAGGAAAGTTTAAAATCGTGAAGGAAATAGCAG |

| SEQ ID NO | Sequence |
|---|---|
| | AAACACAACATGGAACAATAGTTATCAGAGTACAATATGAAGGGG |
| | ACGGTTCTCCATGTAAGATCCCTTTTGAGATAACAGATTTGGAAAA |
| | AAGACACGTCTTAGGACGCCTGATTACAGTTAACCCAATCGTAACA |
| | GAAAAAGATAGCCCAGTCAACATAGAAGCAGAACCCCCATTCGGA |
| | GACAGCTACATCATCGTAGGAGTAGAGCCGGGACAACTGAAACTC |
| | AATTGGTTTAAGAAGGGAAGCTCCATCGGCCAAATGTTTGAGACAA |
| | CAATGAGAGGAGCAAAGAGAATGGCCATTTTAGGTGACACAGCCT |
| | GGGATTTTGGATCCCTGGGAGGAGTGTTTACATCTATAGGAAAGGC |
| | TCTCCATCAAGTTTTCGGAGCAATCTATGGGCTGCTTTTAGTGGGG |
| | TCTCATGGACTATGAAAATCCTCATAGGAGTCATCATCACATGGAT |
| | AGGAATGAATTCACGTAGCACCTCACTGTCTGTGTCGCTAGTATTG |
| | GTGGGAGTCGTGACACTGTACCTGGGAGCTATGGTGCAGGCTGATA |
| | GTGGTTGCATTGTGAGCTGGAAAAATAAAGAACTGAAATGTGGCA |
| | GCGGGATCTTCATTACAGATAACGTACACACATGGACAGAGCAATA |
| | TAAGTTCCAACCAGAATCCCCTTCAAAATTAGCTTCAGCTATCCAA |
| | AAAGCTCATGAAGAAGGCATTTGTGGAATCCGCTCAGTAACAAGAT |
| | TGGAGAATCTGATGTGAAACAAATAACACCAGAATTGAATCATAT |
| | TCTATCAGAAAATGAGGTAAAGTTGACCATTATGACAGGAGACATT |
| | AAAGGAATCATGCAGGCAGGAAAACGATCCTTGCGGCCTCAGCCC |
| | ACTGAGCTGAAGTACTCATGGAAAACATGGGGAAAGGCGAAAATG |
| | CTCTCTACAGAGTCTCACAATCAGACCTTTCTTATTGATGGCCCTGA |
| | AACAGCAGAATGCCCCAACACAAACAGAGCTTGGAACTCACTGGA |
| | AGTTGAAGACTATGGTTTTGGAGTTTTTACCACCAATATATGGCTAA |
| | AATTGAGAGAAAAACAGGATGTATTTTGTGACTCAAAACTCATGTC |
| | AGCGGCCATTAAAGACAACAGAGCCGTCCATGCCGATATGGGTTAT |
| | TGGATAGAAAGTGCACTCAATGACACATGGAAGATGGAGAAAGCC |
| | TCCTTCATTGAAGTTAAAAGCTGCCACTGGCCAAAGTCACACACCC |
| | TCTGGAGCAATGGAGTATTAGAAAGTGAGATGATAATTCCAAAAA |
| | ATTTTGCCGGGCCAGTGTCACAACACAACTACAGACCAGGCTACCA |
| | TACACAAACAGCAGGACCTTGGCATCTAGGTAAGCTTGAGATGGAC |
| | TTTGATTTCTGCGAAGGAACTACAGTGGTGGTGACTGAGGACTGTG |
| | GAAATAGGGGACCCTCTTTAAGAACGACCACTGCCTCTGGAAAGCT |
| | CATAACAGAATGGTGCTGCCGATCCTGCACACTACCACCTCTAAGA |
| | TACAGAGGTGAGGATGGATGCTGGTACGGGATGGAAATCAGACCT |
| | TTGAAAGAGAAAGAAGAGAACTTGGTCAACTCCTTGGTCACAGCCG |
| | GACATGGGCAGATTGACAACTTTTCACTAGGAGTCTTGGGAATGGC |
| | ACTGTTCCTGGAAGAAATGCTTAGGACCCGAGTAGGAACGAAACAT |
| | GCAATACTGCTAGTTGCACTATCTTTCGTGACATTGATTACTGGGAA |
| | CATGTCTTTTAGAGACCTGGGAAGAGTGATGGTCATGGTGGGCGCT |
| | ACCATGACGGATGACATAGGTATGGGAGTGACTTATCTTGCCCTAC |
| | TAGCAGCTTTCAAAGTTAGACCAACTTTTGCAGCTGGACTACTCTTG |
| | AGAAAACTGACCTCCAAGGAATTGATGATGGCCACCATAGGAATC |
| | GCACTCCTTTCCCAAAGCACCTTGCCAGAGACCATTCTAGAACTGA |
| | CTGATGCGTTAGCCTTGGGCATGATGGCCCTCAAAATAGTGAGAAA |
| | TATGGAAAAATACCAATTGGCAGTGACTATCATGGCTATTTCGTGT |
| | GTCCCAAATGCAGTGATATTGCAAACGCATGGAAGGTGAGTTGCA |
| | CAATATTGGCAGCGGTGTCCGTTTCTCCACTGCTCCTAACATCCTCA |
| | CAGCAGAAAGCGGATTGGATACCACTGGCATTGACGATAAAAGGT |
| | CTCAACCCAACAGCCATTTTTCTAACAACTCTTTCGAGAACCAGCA |
| | AGAAAAGGAGCTGGCCGCTAAATGAAGCTATCATGGCAGTCGGGA |
| | TGGTGAGCATTTTAGCCAGTTCTCTCCTAAAGAATGATATTCCTATG |
| | ACAGGTCCATTAGTGGCTGGAGGGCTCCTCACCGTATGTTACGTGC |
| | TCACTGGACGAGCGGCCGATTTGGAACTGGAGAGAGCTGCCGATGT |
| | AAAATGGGAAGATCAGGCAGAAATATCAGGAAGCAGCCCAATCCT |
| | GTCAATAACAATATCAGAAGATGGCAGCATGTCGATAAAAAATGA |
| | AGAGGAAGAACAAACACTGACCATACTCATTAGAACGGGATTGTT |
| | GGTGATCTCAGGAGTCTTTCCAGTATCGATACCAATTACGGCAGCA |
| | GCATGGTACCTGTGGGAAGTGAAGAAACAACGGGCTGGAGTATTG |
| | TGGGACGTCCCTTCACCCCCACCAGTGGGAAAAGCCGAACTGGAAG |
| | ATGGAGCCTATAGAATCAAGCAAAGAGGGATTCTTGGATATTCTCA |
| | GATTGGAGCCGGAGTTTACAAAGAAGGAACATTCCATACAATGTGG |
| | CACGTCACACGTGGTGCTGTTCTGATGCATAGAGGGAAGAGGATTG |
| | AACCATCATGGGCAGATGTCAAGAAAGATCTAATATCATATGGGGG |
| | AGGCTGGAAGCTAGAAGGAGAATGGAAGGAAGGAGAGGAAGTCC |
| | AAGTCCTGGCATTGGAACCTGGAAAAAATCCCAGAGCTGTCCAAAC |
| | GAAACCTGGAATTTTCAAAACCAACACCGGAACCATAGGCGCTGTA |
| | TCTCTGGACTTTTCCCCTGGAACGTCAGGATCTCCAATTGTCGACAG |
| | AAAAGGAAAAGTTGTGGGTCTTTACGGTAATGGTGTTGTCACAAGG |
| | AGTGGAGCATACGTAAGTGCCATAGCCCAGACCGAAAAAAGCATT |
| | GAAGACAATCCAGAGATCGAAGATGACATTTTCCGAAAGAAAAGA |
| | TTGACCATCATGGACCTCCATCCAGGGGCAGGAAAGACAAAAAGA |
| | TACCTTCCAGCCATAGTTAGAGAAGCCATAAAACGTGGCTTGAGAA |
| | CATTAATCCTGGCTCCCACTAGAGTCGTGGCAGCTGAAATGGAGGA |
| | AGCTCTTAGAGGACTTCCAATAAGATACCAAACCCCAGCCATCAGA |
| | GCCGAGCACACCGGGCGAGAGATCGTGGACCTAATGTGTCATGCCA |

SEQUENCES

| SEQ ID NO | Sequence |
|---|---|
| | CATTTACTATGAGGCTGCTATCACCAGTCAGAGTGCCAAATTACAA |
| | CCTGATTATCATGGACGAAGCCCACTTCACAGACCCAGCAAGCATA |
| | GCAGCTAGAGGATACATTTCAACTCGAGTAGAGATGGGTGAAGCA |
| | GCCGGGATTTTTATGACAGCCACTCCTCCGGGAAGCAGAGACCCAT |
| | TTCCTCAGAGCAATGCACCAATCATGGATGAGGAAAGAGAAATCCC |
| | TGAGCGTTCATGGAATTCAGGACATGAATGGGTCACGGATTTTAAA |
| | GGGAAGACTGTTTGGTTTGTTCCAAGTATAAAAGCAGGAAATGACA |
| | TAGCAGCTTGTCTTAGGAAAAATGGAAAGAAAGTGATACAACTCA |
| | GTAGGAAGACTTTTGACTCTGAGTATGCTAAGACTAGAGCCAATGA |
| | TTGGGACTTTGTGGTCACAACTGACATTTCAGAAATGGGTGCCAAC |
| | TTCAAGGCTGAGAGGGTTATAGACCCTAGACGCTGCATGAAACCAG |
| | TTATACTAACAGATGGCGAAGAGCGGGTGATCTTGGCAGGACCTAT |
| | GCCAGTGACCCACTCTAGTGCAGCGCAAAGAAGAGGGAGAATAGG |
| | AAGAAATCCAAAAAATGAAAATGACCAGTACATATACATGGGGGA |
| | ACCTCTCGAAAATGATGAAGACTGTGCACACTGGAAAGAAGCTAA |
| | AATGCTCCTAGATAACATCAACACACCCGAAGGAATCATTCCTAGT |
| | ATGTTCGAACCAGAGCGTGAAAAGTGGATGCCATTGATGGTGAAT |
| | ACCGTTTGAGAGGAGAAGCAAGGAAAACCTTTGTGGACCTAATGA |
| | GAAGAGGGGACTTACCAGTCTGGTTGGCCTACAAAGTGGCAGCTGA |
| | AGGCATCAACTACGCTGACAGAAAGTGGTGTTTTGATGGAATTAAG |
| | AACAACCAAATACTGGAAGAAAATGTGGAAGTGGAAATCTGGACA |
| | AAAGAAGGGGAAAGGAAAAAATTAAAACCCAGATGGTTGGATGCT |
| | AGGATCTATTCTGACCCACTGGCACTAAAAGAATTCAAGGAATTTG |
| | CAGCTGGAAGAAAATCTTTGACCCTGAACCTAATCACAGAAATGGG |
| | TAGGCTTCCAACTTTCATGACTCAGAAGGCAAGAAACGCACTGGAC |
| | AACTTGGCTGTGCTGCATACGGCTGAGGTAGGTGGAAAGGCGTACA |
| | CTCATGCTCTCAGTGAACTGCCGGAGACTCTGGAGACACTGCTTCT |
| | ACTGACACTCCTGGCAGCAGTCACAGGAGGAATCTTCTTATTCTTA |
| | ATGAGCGGAAAAGGTATAGGGAAGATGACTCTGGGAATGTGTTGC |
| | ATAATCACAGCTAGCATTCTCCTATGGTATGCACAGATACAACCAC |
| | ACTGGATAGCAGCTTCAATAATACTGGAGTTTTTTCTCATAGTTTTG |
| | CTCATTCCAGAACCAGAAAAACAGAGAACACCCCAAGACAACCAA |
| | TTGACCTACGTTGTCATAGCCATCCTCACAGTGGTGGCTGCAACCAT |
| | GGCAAACGAGATGGGTTTCCTGGAAAAAACCAAGAAAGACCTCGG |
| | ATTTGGAAGCATTACAACCCAGGAATCTGAGAGCAACATCCTGGAC |
| | ATAGATCTACGTCCTGCATCAGCATGGACGCTGTATGCCGTGGCTA |
| | CAACATTTGTCACACCAATGTTGCGACATAGCATTGAAAATTCCTC |
| | AGTAAATGTCTCCCTAACAGCCATTGCTAACCAAGCTACAGTGCTA |
| | ATGGGTCTTGGGAAAGGATGGCCATTGTCAAAGATGGACATCGGA |
| | GTTCCCCTCCTTGCCATTGGATGCTACTCACAAGTCAACCCTATAAC |
| | CCTCACAGCAGCTCTTCTTTTATTGGTAGCACATTATGCCATTATAG |
| | GGCCAGGACTTCAAGCAAAAGCAACCAGAGAAGCTCAGAAAAGAG |
| | CAGCAGCAGGCATCATGAAAAACCCAACAGTCGATGGAATAACAG |
| | TGATTGACCTAGAACCAATACCCTATGATCCAAAATTTGAAAAGCA |
| | GTTAGGACAAGTAATGCTCCTAATCCTCTGCGTGACTCAAGTATTA |
| | ATGATGAGGACTACATGGGCTTTGTGTGAGGCTCTAACCCTAGCGA |
| | CCGGGCCCATCTCCACACTGTGGGAAGGAAATCCAGGGAGGTTTTG |
| | GAACACCACCATTGCAGTGTCAATGGCTAACATCTTTAGGGGGAGC |
| | TACTTGGCCGGAGCTGGACTTCTCTTTTCCATCATGAAGAACACAA |
| | CAAACACAAGAAGAGGAACTGGCAACGTAGGAGAGACACTTGGAG |
| | AAAAATGGAAAAGCCGATTAAATGCACTGGGAAAAAGTGAATTTC |
| | AGATCTACAAGAAAAGTGGAATCCAGGAAGTGGATAGAACCCTAG |
| | CAAAAGAAGGCATCAAAGAGGAGAAACGGACCACCATGCTGTGT |
| | CACGAGGATCAGCAAAACTGAGATGGTTCGTCGAGAGAAACATGG |
| | TCACACCGGAAGGGAAGGTGGTGGATCTTGGTTGCGGCAGAGGGG |
| | GCTGGTCATACTATTGTGGGGGACTAAAGAATGTAAGAGAAGTCAA |
| | AGGCCTAACAAAAGGAGGACCAGGACACGAAGAACCCATCCCCAT |
| | GTCAACATATGGGTGGAATCTAGTGCGTCTGCAAAGTGGGGTCGAC |
| | GTTTTCTTCACCCCGCCAGAAAAGTGTGATACATTGTTGTGTGACAT |
| | AGGGGAGTCGTCACCAAATCCCACGATAGAAGCAGGACGAACACT |
| | CAGAGTCCTCAACTTAGTGGAAAATTGGCTGAACAATAACACCCAA |
| | TTTTGCATAAAGGTCCTCAATCCATATATGCCCTCAGTCATAGAAA |
| | AAATGGAAACACTACAAAGGAAATATGGAGGAGCCTTAGTGAGGA |
| | ATCCACTCTCACGAAACTCCACGCATGAAATGTACTGGGTATCTAA |
| | TGCTACCGGGAACATAGTGTCATCAGTGAACATGATTTCAAGGATG |
| | TTGATTAACAGATTCACAATGAAACATAAGAAAGCCACCTACGAGC |
| | CAGATGTTGACCTAGGAAGTGGAACCCGCAACATTGGAATTGAAA |
| | GTGAGATACCAAATCTAGACATAATAGGAAGAGAATAGAGAAAA |
| | TAAAACAAGAGCATGAAACATCATGGCATTATGACCAAGACCACC |
| | CATACAAAACGTGGGCTTACCATGGCAGCTATGAAACAAACAAA |
| | CTGGATCAGCATCATCTATGGTGAACGGAGTGGTCAGACTGCTGAC |
| | AAAACCTTGGGACGTCGTCCCTATGGTGACACAGATGGCAATGACA |
| | GACACGACTCCATTTGGACAACAGCGCGTTTTCAAAGAGAAAGTGG |
| | ACACGAGAACTCAAGAACCGAAGGAAGGCACAAAGAAACTGATGA |
| | AAATTACGGCAGAGTGGCTTTGGAAAGAACTAGGAAAGGAAAGA |

| SEQ ID NO | Sequence |
|---|---|
|  | CACCTAGAATGTGTACCAGAGAAGAATTCACAAGAAAAGTGAGAA<br>GCAATGCAGCCTTGGGGGCCGTATTCACTGATGAGAACAAATGGAA<br>ATCGGCACGTGAGGCTGTTGAAGATGGTAGGTTTTGGGAGCTGGTT<br>GACAGGGAAAGAAATCTCCATCTTGAAGGAAAGTGTGAAACATGT<br>GTGTACAACATGATGGGAAAAAGAGAAGAAACTAGGGGAGTTC<br>GGCAAGGCAAAAGGTAGCAGAGCCATATGGTACATGTGGCTTGGA<br>GCACGCTTCTTAGAGTTTGAAGCCCTAGGATTTCTGAATGAAGATC<br>ACTGGTTCTCCAGAGGGAACTCCCTGAGTGGAGTGGAAGGAGAAG<br>GGCTGCACAGGCTAGGCTACATTTTAAGAGAGGTGGGCAAGAAGG<br>AAGGAGGAGCAATGTACGCCGATGATACAGCAGGATGGGACACAA<br>GAATCACACTAGAAGACTTAAAAAATGAAGAAATGGTAACAAACC<br>ACATGAAAGGAGAACACAAGAAACTAGCCGAGGCCATATTCAAAT<br>TAACGTACCAAAATAAGGTGGTGCGTGTGCAAAGACCAACACCAA<br>GAGGCACAGTAATGGATATCATATCGAGAAAAGACCAAAGAGGCA<br>GTGGGCAAGTCGGTACCTATGGCCTTAATACTTTCACCAATATGGA<br>AGCCCAATTAATTAGACAGATGGAAGGAGAAGGAATCTTCAAAAG<br>CATCCAGCACCTGACCGCCACAGAAGAAATCGCTGTACAGAACTGG<br>TTAGCAAGAGTGGGGCGTGAAAGGCTATCAAGAATGGCCATCAGT<br>GGAGATGACTGTGTTGTAAAACCTATAGATGACAGATTTGCAAGTG<br>CTTTAACAGCTCTAAATGACATGGGAAAAGTTAGGAAAGATATACA<br>ACAATGGGAACCTTCAAGAGGATGGAACGATTGGACACAGGTGCC<br>TTTCTGTTCACACCATTTTCATGAGTTAGTCATGAAAGATGGTCGCG<br>TGCTCGTAGTCCCATGCAGAAACCAAGATGAACTGATTGGCAGAGC<br>CCGAATTTCCCAGGGAGCCGGGTGGTCTTTGAAGGAGACGGCTTGT<br>TTGGGGAAGTCTTACGCCCAAATGTGGACCCTGATGTACTTCCACA<br>GACGTGACCTCAGATTGGCGGCAAATGCCATTTGCTCGGCAGTCCC<br>GTCACATTGGGTTCCAACAAGTCGAACAACCTGGTCCATACACGCC<br>AAGCATGAATGGATGACGACGAAGACATGCTGGCAGTCTGGAAC<br>AGGGTGTGGATCCAAGAAACCCATGGATGGAAGACAAAACTCCA<br>GTGGAATCATGGGAAGAAGTCCCATACCTGGGGAAAAGGGAAGAC<br>CAATGGTGCGGCTCATTGATTGGGCTAACAAGCAGGGCTACCTGGG<br>CAAAGAATATCCAGACAGCAATAAATCAAGTCAGATCCCTTATAGG<br>CAATGAGGGATACACAGACTACATGCCATCCATGAAGAGATTCAG<br>AAGGGAAGAGGAAGAGGCAGGTGTCCTATGGTAG |
| SEQ ID NO: 8 | AGTTGTTAGTCTACGTGGACCGACAAGAACAGTTTCGACTCGGAAG<br>CTTGCTTAACGTAGTGCTGACAGTTTTTTATTAGAGAGCAGATCTCT<br>GATGAACAACCAACGGAAAAAGACGGGAAAACCGTCTATCAATAT<br>GCTGAAACGCGTGAGAAACCGTGTGTCAACTGGATCACAGTTGGCG<br>AAGAGATTCTCAAGAGGATTGCTGAACGGCCAAGGACCAATGAAA<br>TTGGTTATGGCGTTTATAGCTTTCCTCAGATTTCTAGCCATTCCACC<br>GACAGCAGGAGTCTTGGCTAGATGGGGTACCTTTAAGAAGTCGGGG<br>GCTATTAAGGTCTTAAAAGGCTTCAAGAAGGAGATCTCAAACATGC<br>TGAGCATTATCAACAAACGGAAAAAGACATCGCTCTGTCTCATGAT<br>GATGTTACCAGCAACACTTGCTTTCCACTTAACTTCACGAGATGGA<br>GAGCCGCGCATGATTGTGGGGAAGAATGAAAGAGGAAAATCCCTA<br>CTTTTTAAGACAGCCTCTGGAATCAACATGTGCACACTCATAGCCA<br>TGGATTTGGGAGAGATGTGTGATGACACGGTCACTTACAAATGCCC<br>CCACATTACCGAAGTGGAGCCTGAAGACATTGACTGCTGGTGCAAC<br>CTTACATCGACATGGGTGACTTATGGAACATGCAATCAAGCTGGAG<br>AGCATAGACGCGATAAGAGATCAGTGGCGTTAGCTCCCCATGTCGG<br>CATGGGACTGGACTCACGCACTCAAACCTGGATGTCGGCTGAAGGA<br>GCTTGGAGACAAGTCGAGAAGGTAGAGACATGGGCCCTTAGGCAC<br>CCAGGGTTTACCATACTAGCCCTATTTCTTGCCCATTACATAGGCAC<br>TTCCTTGACCCAGAAAGTGGTTATTTTTATACTATTAATGCTGGTCA<br>CCCCATCCATGACAATGAGATGTGTGGGAGTAGGAAACAGAGATTT<br>TGTGGAAGGCCTATCGGGAGCTACGTGGGTTGACGTGGTGCTCGAG<br>CACGGTGGGTGTGTGACTACCATGGCTAAGAACAAGCCCACGCTGG<br>ACATAGAGCTTCAGAAGACCGAGGCCACCCAACTGGCGACCCTAA<br>GGAAGCTATGCATTGAGGGAAAAATTACCAACATAACAACCGACT<br>CAAGATGTCCCACCCAAGGGGAAGCGATTTTACCTGAGGAGCAGG<br>ACCAGAACTACGTGTGTAAGCATACATACGTGGACAGAGGCTGGG<br>GAAACGGTTGTGGTTTGTTTGGCAAGGGAAGCTTGGTGACATGCGC<br>GAAATTTCAATGTTTAGAATCAATAGAGGGAAAAGTGGTGCACAT<br>GAGAACCTCAAATACACCGTCATCATCACAGTGCACACAGGAGACC<br>AACACCAGGTGGGAAATGAAACGCAGGGAGTTACGGCTGAGATAA<br>CACCCCAGGCATCAACCGCTGAAGCCATTTTACCTGAATATGGAAC<br>CCTCGGGCTAGAATGCTCACCACGGACAGGTTTGGATTTCAATGAA<br>ATGATTTTATTGACAATGAAGAACAAAGCATGGATGGTACATAGAC<br>AATGGTTCTTTGACTTACCCCTACCATGGACATCAGGAGCTACAAC<br>AGAAACACCAACTTGGAACAGGAAAGAGCTTCTTGTGACATTTAAA<br>AATGCACATGCAAAAAAGCAAGAAGTAGTTGTCCTTGGATCACAA<br>GAGGGAGCAATGCATACAGCACTGACAGGAGCTACAGAGATCCAA<br>ACCTTAGGAGGCACAAGTATTTTTGCGGGGCACTTAAAATGTAGAC<br>TCAAGATGGACAAATTGGAACTCAAGGGGATGAGCTATGCAATGT |

SEQUENCES

| SEQ ID NO | Sequence |
|---|---|
| | GCTTGAATACCTTTGTGTTGAAGAAAGAAGTCTCCGAAACGCAGCA<br>TGGGACAATACTCATTAAGGTTGAGTACAAAGGGAAAGATGCACC<br>CTGCAAGATTCCTTTCTCCACGGAGGATGGACAAGGGAAAGCTCAC<br>AATGGCAGACTGATCACAGCCAATCCAGTGGTGACCAAGGAGGAG<br>GAGCCTGTCAACATTGAGGCTGAACCTCCTTTTGGGGAAAGTAATA<br>TAGTAATTGGAATTGGAGACAAAGCCCTGAAAATCAACTGGTACAG<br>GAAGGGAAGCTCGATTGGGAAGATGTTCGAGGCCACTGCCAGAGG<br>TGCAAGGCGCATGGCCATCTTGGGAGACACAGCCTGGGACTTTGGA<br>TCAGTGGGTGGTGTTTTGAATTCATTAGGGAAAATGGTCCACCAAA<br>TATTTGGGAGTGCTTACACAGCCCTATTTGGTGGAGTCTCCTGGATA<br>ATGAAAATTGGAATAGGTGTCCTCTTAACCTGGATAGGGTTGAATT<br>CAAAAAACACTTCTATGTCATTTTCATGCATTGCGATAGGAATCATT<br>ACACTCTATCTGGGAGTCGTGGTGCAAGCTGACATGGGGTGTGTCA<br>TAAACTGGAAAGGCAAAGAACTCAAATGTGGAAGTGGAATTTTCGT<br>CACTAATGAGGTCCACACCTGGACAGAGCAATACAAATTTCAAGCA<br>GACTCCCCCAAAAGACTGGCAACAGCCATTGCAGGCGCTTGGGAG<br>AATGGAGTGTGCGGAATTAGGTCAACAACCAGAATGGAGAACCTC<br>TTGTGGAAGCAAATAGCCAATGAACTGAACTACATATTATGGGAAC<br>ACAACATTAAATTAACGGTAGTTGTAGGCGACATAACTGGGGTCTT<br>AGAGCAAGGGAAAAGAACACTAACACCACAACCCATGGAGCTAAA<br>ATATTCTTGGAAAACATGGGGAAAGGCAAAAATAGTGACAGCTGA<br>AACACAAAATTCCTCTTTCATAATAGATGGGCCAAGCACACCGGAG<br>TGTCCAAGTGCCTCAAGAGCATGGAATGTGTGGGAGGTGGAAGATT<br>ACGGGTTCGGAGTTTTCACAACCAACATATGGCTGAAACTCCGAGA<br>GGTGTACACCCAACTATGTGACCATAGGCTAATGTCGGCAGCCGTC<br>AAGGATGAGAGGGCCGTACACGCCGACATGGGCTATTGGATAGAA<br>AGCCAAAAGAATGGAAGTTGGAAGCTAGAAAAAGCATCCCTCATA<br>GAGGTGAAAACCTGCACATGGCCAAAATCACACACTCTTTGGAGCA<br>ATGGTGTGCTAGAGAGTGACATGATTATCCCAAAGAGTCTAGCTGG<br>TCCCATTTCGCAACACAACCACAGGCCCGGGTACCACACCCAAACG<br>GCAGGACCCTGGCACTTAGGAAAATTGGAGCTGGACTTCAACTATT<br>GTGAAGGAACAACAGTTGTCATCTCAGAAAACTGTGGGACAAGAG<br>GCCCATCATTGAGAACAACAACAGTGTCAGGGAAGTTGATACACG<br>AATGGTGTTGCCGCTCGTGCACACTTCCTCCCCTGCGATACATGGG<br>AGAAGACGGCTGCTGGTATGGCATGGAAATCAGACCCATTAATGA<br>GAAAGAAGAGAACATGGTAAAGTCTCTAGCCTCAGCAGGGAGTGG<br>AAAGGTGGACAACTTCACAATGGGTGTCTTGTGTTTGGCAATCCTC<br>TTTGAAGAGGTGATGAGAGGAAAATTTGGGAAAAAACACATGATT<br>GCAGGGGTTCTCTTCACGTTTGTGCTCCTCCTCTCAGGGCAAATAAC<br>ATGGAGAGACATGGCGCACACACTCATAATGATTGGGTCCAACGCC<br>TCTGACAGAATGGGGATGGGCGTCACTTACCTAGCTCTAATTGCAA<br>CATTTAAAATTCAGCCATTCTTGGCTTTGGGATTCTTCCTGAGGAAA<br>CTGACATCTAGAGAAAATTTATTGCTGGGAGTTGGGTTGGCCATGG<br>CAGCAACGTTACGACTGCCAGAGGACATTGAACAAATGGCGAATG<br>GAATTGCTTTGGGGCTCATGGCTCTTAAACTGATAACACAATTTGA<br>AACATACCAACTATGGACGGCATTAGTTTCCCTAACGTGTTCAAAT<br>ACAATTTTCACGTTGACTGTTGCCTGGAGAACAGCCACTCTGATTTT<br>AGCCGGAATTTCGCTTTTGCCAGTGTGCCAGTCTTCGAGCATGAGG<br>AAAACAGATTGGCTCCCAATGACTGTGGCAGCTATGGGAGTTCCAC<br>CCCTACCACTTTTTATTTTCAGTCTGAAAGATACACTCAAAAGGAG<br>AAGCTGGCCACTGAATGAGGGGGTGATGGCAGTTGGACTTGTGAGC<br>ATTCTAGCTAGTTCTCTCCTTAGGAATGATGTGCCCATGGCTGGACC<br>ATTAGTGGCTGGGGGCTTGCTGATAGCGTGCTACGTCATAACTGGC<br>ACGTCAGCAGACCTCACTGTAGAAAAGCAGCAGATGTAACATGG<br>GAGGAAGAGGCCGAGCAAACAGGAGTGTCCCACAATTTAATGATC<br>ACAGTTGATGATGATGGAACAATGAGAATAAAAGATGACGAGACT<br>GAGAACATCTTAACAGTGCTTTTAAAAACAGCACTACTAATAGTAT<br>CAGGCATCTTTCCATACTCCATACCCGCAACACTGTTGGTCTGGCAT<br>ACTTGGCAAAAGCAAACCCAAAGATCCGGCGTCCTATGGGACGTAC<br>CCAGCCCCCAGAGACACAGAAAGCGGAACTGGAAGAAGGGGTCT<br>ATAGGATCAAACAGCAAGGAATTTTTGGGAAAACCCAAGTGGGGG<br>TTGGAGTACAGAAAGAAGGAGTTTTCCACACCATGTGGCACGTCAC<br>AAGAGGGGCAGTGTTGACACACAATGGGAAAAGACTGGAACCAAA<br>CTGGGCTAGCGTGAAAAAAGATCTGATTTCATACGGAGGAGGATG<br>GAGATTGAGTGCACAATGGCAAAAGGGGGAGGAGGTGCAGGTTAT<br>TGCCGTAGAGCCTGGGAAGAACCCAAAGAACTTTCAAACCATGCCA<br>GGCATTTTTCAGACAACAACAGGGGAATAGGAGCAATTGCACTG<br>GATTTCAAGCCTGGAACTTCAGGATCTCCCATCATAAACAGAGAGG<br>GAAAGGTAGTGGGACTGTATGGCAATGGAGTGGTTACAAAGAATG<br>GAGGCTATGTCAGTGGAATAGCGCAAACAAATGCAGAACCAGATG<br>GACCGACACCAGAGTTGGAAGAAGAGATGTTCAAAAAGCGAAATC<br>TAACCATAATGGATCTTCATCCTGGGTCAGGAAAGACGCGGAAATA<br>TCTTCCAGCTATTGTTAGAGAGGCAATCAAGAGACGCTTAAGGACT<br>CTAATTTTGGCACCAACAAGGGTAGTTGCAGCTGAGATGAAGAAG<br>CATTGAAAGGGCTCCCAATAAGGTATCAAACAACTGCAACAAAATC |

| SEQ ID NO | Sequence |
|---|---|
| | TGAACACACAGGAAGAGAGATTGTTGATCTAATGTGTCACGCAACG |
| | TTCACAATGCGCTTGCTGTCACCAGTCAGGGTTCCAAACTACAACTT |
| | GATAATAATGGATGAGGCTCATTTCACAGACCCAGCCAGTATAGCG |
| | GCTAGAGGGTACATATCAACTCGTGTAGGAATGGGAGAGGCAGCC |
| | GCAATTTTCATGACAGCAACACCCCCTGGAACAGCTGATGCCTTTC |
| | CTCAGAGCAACGCTCCAATTCAAGATGAAGAGAGAGACATACCGG |
| | AACGCTCATGGAATTCAGGCAATGAATGGATTACTGACTTTGTTGG |
| | GAAGACAGTGTGGTTTGTCCCTAGCATCAAAGCCGGAAATGACATA |
| | GCAAACTGCTTGCGGAAAAATGGAAAAAAGGTCATTCAACTCAGC |
| | AGGAAGACCTTTGACACAGAATATCAAAAGACCAAACTGAATGAT |
| | TGGGACTTTGTGGTGACAACAGACATTTCAGAAATGGGAGCCAATT |
| | TCAAAGCAGATAGAGTGATCGACCCAAGAAGATGTCTCAAGCCGG |
| | TGATTTTGACAAATGGACCCGAGCGGGTGATCCTGGCTGGACCAAT |
| | GCCAGTCACCGTAGCGAGCGCTGCGCAAAGGAGAGGGAGAGTTGG |
| | CAGGAACCCACAAAAGAAAATGACCAGTACATATTCATGGGCCA |
| | GCCTCTCAACAATGATGAAGACCATGCTCACTGGACAGAAGCAAA |
| | AATGCTGCTGGACAACATCAACACACCAGAAGGGATTATACCAGCT |
| | CTCTTTGAACCAGAAAGGGAGAAGTCAGCCGCCATAGACGGCGAA |
| | TACCGCCTGAAGGGTGAGTCCAGGAAGACTTTCGTGGAACTCATGA |
| | GGAGGGGTGACCTCCCAGTTTGGCTAGCCCATAAAGTAGCATCAGA |
| | AGGGATCAAATATACAGATAGAAAATGGTGCTTTGATGGAGAACG |
| | TAATAATCAAATTTTAGAGGAGAATATGGATGTGGAAATCTGGACA |
| | AAGGAAGGAGAAAAGAAAAAACTGAGACCTAGGTGGCTTGATGCC |
| | CGCACTTATTCAGATCCTTTAGCACTCAAGGAATTCAAGGATTTTGC |
| | AGCTGGCAGAAAGTCAATCGCCCTTGATCTTGTGACAGAAATAGGA |
| | AGAGTGCCTTCACACTTAGCCCACAGAACGAGAAACGCCCTGGACA |
| | ATTTGGTGATGCTGCACACGTCAGAACATGGCGGTAGGGCCTACAG |
| | GCATGCAGTGGAGGAACTACCAGAAACGATGGAAACACTCTTACTC |
| | CTGGGACTGATGATCTTGTTAACAGGTGGAGCAATGCTCTTCTTGAT |
| | ATCAGGTAAAGGGATTGGAAAGACTTCAATAGGACTCATTTGTGTA |
| | ATTGCTTCCAGCGGCATGTTATGGATGGCTGATGTCCCACTCCAATG |
| | GATCGCGTCGGCTATAGTCCTGGAGTTTTTTATGATGGTGTTGCTCA |
| | TACCAGAACCAGAAAAGCAGAGAACTCCCCAAGCAACCAACTCG |
| | CATATATGTCGTGATAGGCATACTTACATTGGCTGCAATAGTAGCGGC |
| | CAATGAAATGGGACTGTTGGAAACTACAAAGAGAGATTTAGGAAT |
| | GTCTAAAGAACCAGGTGTTGTTTCTCCAACCAGCTATTTGGACGTG |
| | GACTTGCACCCAGCATCAGCCTGGACATTGTACGCCGTGGCCACAA |
| | CAGTAATAACACCAATGTTGAGACACACCATAGAGAATTCCACAGC |
| | AAATGTGTCCCTGGCAGCCATAGCTAACCAGGCAGTGGTCCTGATG |
| | GGTTTAGACAAAGGATGGCCGATATCGAAAATGGACTTGGGCGTAC |
| | CACTATTGGCACTGGGTTGCTATTCACAAGTGAACCCACTAACTCTT |
| | GCAGCGGCAGTACTTTTGCTAGTCACACATTATGCAATTATAGGTC |
| | CAGGATTGCAGGCAAAAGCCACTCGTGAAGCTCAGAAAAGGACAG |
| | CTGCTGGAATAATGAAGAATCCAACGGTGGATGGAATAATGACAA |
| | TAGACCTAGATCCTGTAATATATGATTCAAAATTTGAAAAGCAACT |
| | AGGACAGGTTATGCTCCTGGTTCTGTGTGCAGTTCAACTTTTGTTAA |
| | TGAGAACATCATGGGCCTTGTGTGAAGCTCTAGCCCTAGCCACAGG |
| | ACCAATAACAACACTCTGGGAAGGATCACCTGGGAAGTTCTGGAAC |
| | ACCACGATAGCTGTTTCCATGGCGAACATCTTTAGAGGGAGCTATT |
| | TAGCAGGAGCTGGGCTTGCTTTTTCTATCATGAAATCAGTTGGAAC |
| | AGGAAAGAGAGGAACAGGGTCACAAGGTGAAACCTTAGGAGAAA |
| | AGTGGAAAAGAAATTAAATCAGTTATCCCGGAAAGAGTTTGACCT |
| | TTACAAGAAATCCGGAATCACCGAAGTGGATAGAACAGAAGCCAA |
| | AGAAGGGTTAAAAAGAGGAGAAATAACACACCATGCCGTGTCCAG |
| | AGGCAGCGCAAAACTTCAATGGTTCGTGGAGAGAAACATGGTCATT |
| | CCCGAAGGAAGAGTCATAGACTTAGGTTGTGGAAGAGGAGGCTGG |
| | TCATATTACTGTGCAGGACTGAAAAAAGTTACAGAAGTGCGAGGAT |
| | ACACAAAAGGCGGCCCAGGACACGAAGAACCAGTACCTATGTCTA |
| | CATACGGATGGAACATAGTCAAGTTAATGAGTGGAAAGGATGTTTT |
| | TTATCTGCCACCTGAAAAGTGTGATACCCTATTGTGTGACATTGGA |
| | GAATCTTCACCAAGCCCAACAGTGGAAGAAACAGAACCATAAGA |
| | GTCTTGAAGATGGTTGAACCATGGCTAAAAAACAACCAGTTTTGCA |
| | TTAAAGTATTGAACCCATACATGCCAACTGTGATTGAGCACTTAGA |
| | AAGACTACAAAGGAAACATGGAGGAATGCTTGTGAGAAATCCACT |
| | CTCACGAAACTCCACGCACGAAATGTATTGGATATCCAATGGTACA |
| | GGCAACATCGTCTCTTCAGTCAACATGGTATCCAGATTGCTACTGA |
| | ACAGATTCACAATGACACACAGGAGACCCACCATAGAGAAAGATG |
| | TGGATTTAGGAGCAGGAACCCGACATGTCAATGCGGAACCAGAAA |
| | CACCCAACATGGATGTCATTGGGGAAAGAATAAAAAGGATCAAAG |
| | AGGAGCATAGTTCAACATGGCACTATGATGATGAAAATCCTTACAA |
| | AACGTGGGCTTACCATGGATCCTATGAAGTAAAAGCCACAGGCTCA |
| | GCCTCCTCCATGATAAATGGAGTCGTGAAACTCCTCACAAAACCAT |
| | GGGATGTGGTGCCCATGGTGACACAGATGGCAATGACAGATACAA |
| | CTCCATTTGGCCAGCAAAGAGTTTTTAAAGAGAAAGTGGACACCAG |
| | GACACCTAGGCCCATGCCAGGAACAAGAAAGGTTATGGAGATCAC |

| SEQ ID NO | Sequence |
|---|---|
| | AGCGGAGTGGCTTTGGAGGACCCTGGGAAGGAACAAAAGACCCAG<br>ATTATGCACAAGGGAGGAGTTCACAAAGAAGGTCAGAACCAACGC<br>AGCTATGGGCGCTGTCTTCACAGAAGAGAACCAATGGGACAGTGC<br>GAGAGCTGCTGTTGAGGACGAAGAATTTTGGAAACTTGTGGACAGA<br>GAACGTGAACTCCACAAACTGGGCAAGTGTGGAAGCTGCGTTTACA<br>ACATGATGGGCAAGAGAGAGAAAAACTTGGAGAGTTTGGTAAAG<br>CAAAAGGCAGTAGGGCTATATGGTACATGTGGTTGGGAGCCAGGT<br>ACCTTGAGTTCGAGGCGCTCGGATTCCTCAATGAAGACCACTGGTT<br>CTCGCGTGAAAACTCTTACAGTGGAGTAGAAGGAGAAGGACTGCA<br>CAAGCTGGGATACATCTTGAGAGATATTTCCAAGATACCCGGAGGA<br>GCCATGTATGCTGATGACACAGCCGGTTGGGACACAAGAATAACA<br>GAAGATGACCTGCACAATGAGGAAAAAATCACACAGCAGATGGAC<br>CCTGAACACAGGCAGCTAGCGAACGCTATATTCAAGCTCACATACC<br>AAAACAAAGTGGTCAAAGTCCAACGACCAACTCCAAAGGGCACGG<br>TAATGGACATCATATCTAGGAAAGACCAAAGAGGCAGTGGACAGG<br>TGGGAACTTATGGTCTGAACACATTCACCAACATGGAAGCCCAGCT<br>AATCAGACAAATGGAAGGAGAAGGCGTGTTGTCAAAGGCAGACCT<br>CGAGAACCCCCATCCGCTAGAGAAGAAAATTACACAATGGTTGGA<br>AACTAAAGGAGTGGAGAGGTTAAAAAGAATGGCCATCAGCGGGGA<br>TGATTGCGTAGTGAAACCAATCGACGACAGATTCGCCAATGCCCTG<br>CTTGCCCTGAACGATATGGGAAAGGTTAGGAAGGACATACCTCAAT<br>GGCAGCCATCAAAGGGATGGCATGATTGGCAACAGGTCCCTTTCTG<br>CTCCCACCACTTTCATGAATTGATCATGAAAGATGGAAGAAAGTTG<br>GTAGTTCCCTGCAGACCCCAGGACGAACTAATAGGAAGAGCGAGA<br>ATCTCTCAAGGAGCAGGATGGAGCCTTAGAGAAACTGCATGTCTAG<br>GGAAAGCCTACGCTCAAATGTGGACTCTCATGTATTTTCACAGAAG<br>AGATCTTAGACTAGCATCCAACGCCATATGTTCAGCAGTACCAGTC<br>CATTGGGTCCCCACGAGCAGAACGACATGGTCTATTCATGCTCACC<br>ATCAGTGGATGACTACAGAAGACATGCTTACTGTCTGGAACAGGGT<br>GTGGATAGAGGACAATCCATGGATGGAAGACAAAACTCCAGTCAC<br>AACGTGGGAAGATGTTCCATATCTAGGGAAGAGAGAAGACCAATG<br>GTGCGGATCACTCATAGGTCTCACTTCCAGAGCAACCTGGGCCCAG<br>AACATACTCACAGCAATCCAACAGGTGAGAAGCCTCATAGGCAAT<br>GAAGAGTTTCTGGACTACATGCCTTCGATGAAGAGATTCAGGAAGG<br>AGGAGGAGTCAGAGGGAGCCATTTGGTAAAAGCAGGAGGCAAACT<br>GTCAGGCCACCTTAAGCCACAGTACGGAAGAAGCTGTGCAGCCTGT<br>GAGCCCCGTCCAAGGACGTTAAAAGAAGAAGTCAGGCCCAAAAGC<br>CACGGTTTGAGCAAACCGTGCTGCCTGTAGCTCCGTCGTGGGGACG<br>TAAAGCCTGGGAGGCTGCAAACCGTGGAAGCTGTACGCACGGTGT<br>AGCAGACTAGTGGTTAGAGGAGACCCCTCCCATGACACAACGCAG<br>CAGCGGGGCCCGAGCACTGAGGGAAGCTGTACCTCCTTGCAAAGG<br>ACTAGAGGTTATAGGAGACCCCCCGCAAACAAAAACAGCATATTG<br>ACGCTGGGAGAGACCAGAGATCCTGCTGTCTCCTCAGCATCATTCC<br>AGGCACAGAACGCCAGAAAATGGAATGGTGCTGTTGAATCAACAG<br>GTTCT |
| SEQ ID NO: 9 | AGTTGTTAGTCTGTGTGGACCGACAAGGACAGTTCCAAATCGGAAG<br>CTTGCTTAACACAGTTCTAACAGTTTATTTGAATAGAGAGCAGATCT<br>CTGGAAAAATGAACCAACGAAAAAGGTGGTTAGACCACCTTTCA<br>ATATGCTGAAACGCGAGAGAAACCGCGTATCAACCCCTCAAGGGTT<br>GGTGAAGAGATTCTCAACCGGACTTTTTTCTGGGAAAGGACCCTTA<br>CGGATGGTGCTAGCACTCATCACGTTTTTGCGAGTCCTTTCCATCCC<br>ACCAACAGCAGGGATTCTGAAGAGATGGGGACAGTTGAAGAAAAA<br>TAAGGCCATTAAGATACTGATTGGATTCAGGAAGGAGATAGGCCGC<br>ATGCTGAACATCTTGAACGGGAGAAAAAGGTCAACGATAACATTGT<br>TGTGCTTGATTCCCACCGTAATGGCGTTTCACTTGTCAACAAGAGAT<br>GGCGAACCCCTCATGATAGTGGCAAAACATGAAAGGGGAGACCT<br>CTCTTGTTTAAGACAACAGAGGGGATCAACAAATGCACTCTCATTG<br>CCATGGACTTGGGTGAAATGTGTGAGGACACTGTCACGTACAAATG<br>CCCCCTACTGGTCAATACCGAACCTGAAGACATTGATTGCTGGTGC<br>AACCTCACGTCTACCTGGGTCATGTATGGGACATGCACCCAGAGCG<br>GAGAACGGAGCGAGAGAAGCGCTCAGTAGCTTTAACACCACATT<br>CAGGAATGGGATTGGAAACAAGAGCTGAGACATGGATGTCATCGG<br>AAGGAGCTTGGAAGCATGCTCAGAGAGTAGAGAGCTGGATACTCA<br>GAAACCCAGGATTTGCACTCTTGGCAGGATTATGGCTTATATGATT<br>GGGCAAACAGGGATCCAGCGAACTGTCTTCTTTGTCCTAATGATGC<br>TGGTCGCCCCATCCTACGGAATGCGATGCGTAGGAGTAGGAAACAG<br>AGACTTTGTGGAAGGAGTCTCAGGTGGAGCATGGGTCGACCTGGTG<br>CTAGAACATGGAGGATGCGTCACAACCATGGCCCAGGGAAAACCA<br>ACCTTGGATTTTGAACTGACCAAGACAACAGCCAAGGAAGTGGCTC<br>TGTTAAGAACCTATTGCATTGAAGCCTTAATATCAAACATAACTAC<br>GGCAACAAGATGTCCAACGCAAGGAGAGCCTTATCTGAAAGAGGA<br>ACAGGACCAACAGTACATTTGCCGTAGAGATGTGGTAGATAGAGG<br>ATGGGGCAATGGCTGTGGCTTGTTTGGAAAAGGAGGAGTTGTGACA<br>TGTGCGAAGTTCTCATGTTCGGGGAAGATAACAGGCAATCTGGTCC |

| SEQ ID NO | Sequence |
|---|---|
| | AAATTGAGAACCTTGAATACACAGTGGTTGTGACAGTCCACAATGG |
| | AGACACCCATGCAGTAGGAAATGACACATCCAACCATGGGGTTAC |
| | AGCCACGATAACTCCCAGGTCACCATCGGTTGAAGTCAAACTGCCG |
| | GACTATGGAGAACTAACACTTGATTGTGAACCCAGGTCTGGAATTG |
| | ACTTCAATGAGATGATCCTAATGAAAATGAAAAAGAAAACATGGC |
| | TCGTGCATAAGCAATGGTTTTTGGATCTGCCTCTTCCATGGACGACA |
| | GGAGCAGATACATCAGAGGTTCACTGGAATTACAAAGAGAGAATG |
| | GTGACATTTAAGGTTCCTCATGCCAAGAGACAGGATGTGACAGTGC |
| | TGGGATCTCAGGAAGGAGCCATGCATTCTGCCCTCGCTGGAGCCAC |
| | AGAAGTGGACTCCGGTGATGGAAATCACATGTTTGCAGGACATCTC |
| | AAGTGCAAAGTCCGCATGGAGAAATTGAGAATCAAGGGAATGTCA |
| | TACACGATGTGTTCAGGAAAGTTTTCAATTGACAAAGAGATGGCAG |
| | AAACACAGCATGGGACAACAGTGGTGAAAGTCAAGTATGAAGGTG |
| | CTGGAGCTCCGTGTAAAGTCCCCATAGAGATAAGAGATGTAAACAA |
| | GGAGAAAGTGGTTGGGCGCGTTATCTCAGCCACCCCTTTGGCTGAG |
| | AACACCAATAGTGTAACCAACATAGAATTAGAACCCCCCTTTGGGG |
| | ACAGCTACATAGTGATAGGTGTTGGAAACAGCGCACTAACACTCCA |
| | TTGGTTCAGGAAAGGGAGTTCCATTGGCAAGATGTTTGAGTCCACA |
| | TACAGAGGTGCAAAACGCATGGCCATCCTAGGTGAAACAGCTTGG |
| | GATTTTGGTTCCGTTGGTGGACTGTTCACATCATTGGGAAAGGCTGT |
| | GCACCAGGTTTTTGGAAGTGTGTATACAACCATGTTTGGAGGAGTC |
| | TCATGGATGATTAGAATCCTAATTGGGTTCTTAGTGTTGTGGATTGG |
| | CACGAACTCAAGGAACACTTCAATGGCCATGACGTGCATAGCTGTT |
| | GGGGGAATCACTCTGTTTTTGGGCTTCACGGTTCAAGCGGACATGG |
| | GTTGTGTGGTGTCATGGAGTGGGAGAGAATTGAAGTGTGGAAGCG |
| | GAATTTTTGTGGTTGACAACGTGCACACTTGGACAGAACAGTACAA |
| | ATTCCAACCAGAGTCCCCAGCGAGACTAGCGTCTGCAATATTAAAT |
| | GCCCACAAAGATGGGGTCTGTGGAATTAGATCAACCACGAGGCTG |
| | GAAAATGTTATGTGGAAGCAAATAACCAATGAGCTAAACTATGTTC |
| | TCTGGGAAGGAGGACATGATCTCACTGTAGTGGCTGGGGACGTGAA |
| | AGGGGTGTTGACCAAGGGCAAGAGAGCACTCACACCCCCAGCGAG |
| | CGATCTGAAATATTCATGGAAGACATGGGGGAAAGCAAAATCTTC |
| | ACCCCTGAAGCAAGAAACAGCACATTTTTAATAGACGGACCAGATA |
| | CCTCTGAATGCCCCAATGAACGAAGAGCATGGAATTCTTTTGAGGT |
| | GGAAGACTATGGATTTGGCATGTTCACGACCAACATATGGATGAAA |
| | TTCCGAGAAGGAAGTTCAGAAGTGTGTGACCACAGGCTGATGTCAG |
| | CTGCAATTAAAGACCAGAAAGCTGTGCATGCTGACATGGGTTATTG |
| | GATAGAGAGCTCAAAAAACCAGACCTGGCAGATAGAAAGAGCATC |
| | TCTCATTGAAGTGAAAACATGTCTGTGGCCCAAGACCCATACACTG |
| | TGGAGCAATGGAGTGCTGGAGAGCCAGATGCTTATTCCAAAATCAT |
| | ATGCAGGCCCTTTTTCACAGCACAATTACCGCCAGGGCTATGCTAC |
| | GCAAACCGTGGGTCCATGGCACTTGGGCAAACTAGAGATAGACTTT |
| | GGAGAATGCCCCGGAACAACAGTTACAATTCAGGAGAATTGTGAC |
| | CATAGAGGCCCATCTTTGAGGACCACCACTGCATCTGGAAAACTAG |
| | TCACGCAATGGTGTTGCCGCTCCTGCACAATGCCCCCCTTAAGGTTC |
| | TTAGGAGAAGATGGGTGCTGGTATGGGATGGAGATTAGGCCCTTGA |
| | GTGAAAAGAAGAGAACATGGTTAAATCACAGGTGACGGCCGGAC |
| | AGGGCACATCGGAAACTTTTTCTATGGGTCTGTTGTGCCTGACCTTG |
| | TTTGTGGAAGAATGCTTGAGAAGAAGAGTCACCAGAAAACACATG |
| | ATATTAGCTGTGGTAATCACTCTTTGTGCTATCATCCTGGGGGGCCT |
| | CACACATGGATGGACTTGCTACGAGCCCTCATCATATTGGGGGACACT |
| | ATGTCTGGCAGAATAGGAGGACAGACCCACCTAGCCATCATGGCA |
| | GTGTTCAAGATGTCACCAGGATACGTGCTGGGTGTGTTTTTAAGGA |
| | AACTCACTTCAAGAGAGACAGCACTAATGGTAATAGGAATGGCCAT |
| | GACAACAACACTTTCAATTCCACATGACCTCATGGAACTCATTGAT |
| | GGAATATCACTAGGACTAATTTTGCTAAAAATAGTAACACAGTTTG |
| | ACAACACCCAAGTGGGAACCTTAGCTCTTTCCTTGACTTTCATAAG |
| | ATCAACAATGTCATTGGTCATGGCCTGGAGGACCATTATGGCTGTG |
| | CTGTTTGTGGTCACACTCATTCCTTTGTGTAGGACAAGCTGTCTTCA |
| | AAAACAGTCTCATTGGGTAGAAATAACAGCACTCATCTTAGGAGCC |
| | CAAGCTCTGCCAGTGTACCTAATGACTCTTATGAAAGGAGCCTCAA |
| | GAAGATCTTGGCCTCTTAACGAAGGCATAATGGCTGTGGGGTTGGT |
| | TAGTCTCTTAGGAAGCGCTCTTTTAAAGAATGATGTCCCTTTAGCTG |
| | GCCCAATGGTGGCAGGAGGCTTACTTCTGGCGGCTTACGTAATGAG |
| | TGGCAGCTCAGCAGATCTGTCACTAGAGAAGGCCGCTAATGTGCAG |
| | TGGGATGAAATGGCAGACATAACAGGCTCAAGTCCAATCATAGAA |
| | GTGAAGCAAGATGAGGATGGCTCTTTCTCCATACGGGACGTCGAGG |
| | AAACCAATATGATAACCCTTTTGGTGAAACTGGCACTGATAACGGT |
| | GTCAGGTCTCTACCCCTTGGCAATTCCAATCACAATGACCTTATGGT |
| | ACATGTGGCAAGTGAAAACACAAAGATCAGGAGCCCTGTGGGACG |
| | TTCCTTCACCCGCTGCCACTCAAAAAGCCGCACTGTCCGAAGGAGT |
| | GTACAGGATCATGCAAAGAGGGTTATTCGGGAAACCCAGGTTGG |
| | AGTAGGGATACACATGGAAGGTGTATTTCACACAATGTGGCATGTC |
| | ACAAGAGGATCGGTGATCTGCCACGAGACTGGGAGATTGGAGCCA |
| | TCTTGGGCTGACGTCAGGAATGACATGATATCATACGGTGGGGGAT |

| SEQ ID NO | Sequence |
|---|---|
| | GGAGGCTTGGAGATAAATGGGACAAAGAAGAAGACGTTCAGGTCC |
| | TCGCTATAGAACCAGGGAAAAATCCCAAACATGTCCAAACGAAAC |
| | CTGGCCTTTTCAAGACCCTAACTGGAGAAATTGGAGCAGTAACATT |
| | AGATTTCAAACCCGGAACGTCTGGTTCTCCCATTATCAACAGGAAA |
| | GGAAAAGTCATCGGACTCTATGGAAATGGAGTGGTTACCAAATCAG |
| | GTGATTACGTCAGTGCCATAACGCAAGCCGAAAGAATTGGAGAGC |
| | CAGATTATGAAGTGGATGAGGACATTTTTCGGAAGAAAAGACTAAC |
| | TATAATGGACTTACACCCCGGAGCTGGAAAGACAAAAAGAATTCTT |
| | CCATCAATAGTGAGAGAAGCCTTAAAAAGGAGGCTGCGAACTTTG |
| | ATTCTGGCTCCCACGAGAGTAGTGGCGGCCGAGATGGAAGAGGCC |
| | CTACGTGGACTGCCAATCCGTTACCAAACCCCAGCTGTGAAATCAG |
| | AACACACAGGAAGAGAGATTGTAGACCTCATGTGCCATGCAACCTT |
| | CACAACAAGACTTTTGTCATCAACCAGAGTTCCAAACTATAACCTT |
| | ATAGTAATGGATGAAGCACATTTCACCGATCCTTCCAGTGTCGCGG |
| | CTAGAGGATACATCTCGACCAGGGTGGAAATGGGAGAGGCAGCAG |
| | CCATCTTCATGACCGCAACCCCTCCCGGAGCGACGGATCCATTTCC |
| | CCAGAGCAACAGCCCAATAGAAGACATCGAGAGAGAGATTCCGGA |
| | AAGGTCATGGAACACAGGGTTCGACTGGATAACAGACTACCAAGG |
| | GAAAACTGTGTGGTTTGTTCCTAGCATAAAAGCTGGAAATGACATT |
| | GCAAATTGTTTGAGGAAGTCGGGAAAGAAAGTTATCCAGTTGAGTA |
| | GGAAAACCTTTGATACAGAATATCCAAAAACGAAGCTCACGGACT |
| | GGGACTTTGTGGTCACTACAGACATATCTGAAATGGGGCTAACTT |
| | TAGAGCTGGGAGAGTGATAGACCCTAGAAGATGCCTCAAGCCAGTT |
| | ATCCTAACAGATGGGCCAGAGAGAGTCATCTTAGCAGGTCCCATTC |
| | CAGTGACTCCAGCAAGCGCTGCCCAAAGAAGAGGGCGAATAGGAA |
| | GGAACCCAGCACAAGAAGACGACCAATACGTTTTCTCCGGAGACCC |
| | ACTAAAAAATGATGAAGATCATGCCCACTGGACAGAAGCAAAGAT |
| | GCTGCTTGACAATATCTACACCCCAGAAGGGATCATTCCAACATTG |
| | TTTGGTCCGGAAAGGGAAAAAACCCAAGCTATTGATGGAGAGTTTC |
| | GCCTCAGAGGGGAACAAAGGAAGACTTTTGTGGAATTAATGAGGA |
| | GAGGAGACCTTCCGGTGTGGCTGAGTTATAAGGTAGCTTCTGCTGG |
| | CATTTCTTACAAAGATCGGGAATGGTGCTTCACTGGGGAAAGAAAT |
| | AACCAAATTTTAGAAGAAAACATGGAGGTTGAAATTTGGACTAGA |
| | GAGGGAGAAAAGAAAAAACTGAGGCCAAAATGGTTAGATGCACGT |
| | GTATACGCTGACCCCATGGCTTTGAAGGATTTCAAGGAGTTTGCCA |
| | GTGGAAGGAAGAGTATAACTCTCGACATCCTGACAGAGATCGCCA |
| | GTTTGCCAACCTACCTTTCCTCTAGGGCCAAGCTCGCCCTTGACAAC |
| | ATAGTTATGCTCCACACAACAGAAAGAGGAGGGAGGGCCTATCAA |
| | CACGCCCTGAACGAACTTCCGGAGTCACTGGAAACACTCATGCTTG |
| | TAGCCTTACTGGGTGCTATGACAGCAGGTATCTTCCTGTTTTTCATG |
| | CAAGGTAAAGGAATAGGGAAATTGTCAATGGGTTTGATAACCATTG |
| | CGGTGGCTAGTGGCTTGCTCTGGGTAGCAGAAATTCAACCCCAGTG |
| | GATAGCGGCCTCAATCATACTGGAGTTTTTCCTCATGGTACTGTTGA |
| | TACCAGAACCAGAAAAACAAAGGACCCCACAAGACAATCAATTGA |
| | TCTACGTCATATTGACCATTCTCACCATTATTGGTCTAATAGCAGCC |
| | AACGAGATGGGGCTGATAGAAAAAACAAAAACGGATTTTGGGTTT |
| | TACCAGGTAAAAACAGAAACCACCATCCTCGATGTGGACCTGAGAC |
| | CAGCTTCAGCATGGACGCTCTATGCGGTAGCCACCACAATTCTGAC |
| | TCCCATGCTGAGACACACCATAGAAAATACGTCGGCCAACCTATCT |
| | TTAGCAGCCATTGCCAACCAGGCAGCCGTCCTAATGGGGCTTGGAA |
| | AAGGATGGCCACTCCACAGAATGGACCTCGGTGTGCCGCTGTTAGC |
| | AATGGGATGCTATTCTCAAGTGAACCCAACAACCTTGACAGCATCC |
| | TTAGTCATGCTTCTAGTCCATTATGCAATAATAGGCCCAGGATTGCA |
| | GGCAAAAGCCACAAGAGAGGCCCAGAAAAGGACAGCTGCTGGAAT |
| | CATGAAAAATCCCACAGTGGACGGGATAACAGTGATAGATCTAGA |
| | ACCAATATCCTATGACCCAAAATTTGAAAAGCAATTAGGGCAGGTC |
| | ATGCTACTCGTCTTGTGTGCTGGACAACTACTCTTGATGAGAACAA |
| | CATGGGCTTTCTGTGAAGTCTTGACTTTGGCTACAGGACCAATCTTG |
| | ACCTTGTGGGAGGGCAACCCGGGAAGGTTTTGGAACACGACCATA |
| | GCCGTATCTACCGCCAACATTTTCAGGGGAAGTTACTTGGCAGGAG |
| | CTGGACTGGCTTTTTCACTCATAAAGAATGCACAAACCCCCAGGAG |
| | GGGAACTGGGACCGCAGGAGAGACACTGGGAGAGAAGTGGAAGA |
| | GACAGCTAAACTCATTAGACAGAAAAGAGTTTGAAGAGTATAAAA |
| | GAAGTGGAATACTAGAAGTGGACAGGACTGAAGCCAAGTCCGCCC |
| | TGAAAGATGGGTCCAAAATCAAGCATGCAGTATCTAGAGGGTCCA |
| | GTAAGATTAGATGGATCGTAGAGAGGGATGGTAAAGCCAAAAG |
| | GGAAAGTTGTAGATCTTGGCTGTGGGAGAGGAGGATGGTCTTATTA |
| | CATGGCAACACTCAAGAACGTGACTGAAGTGAAAGGGTATACAAA |
| | AGGAGGTCCAGGACATGAAGAACCGATTCCTATGGCTACTTATGGC |
| | TGGAATTTGGTCAAACTCCATTCAGGGGTTGACGTGTTCTACAAAC |
| | CCACAGAGCAAGTGGACACCCTGCTCTGTGATATTGGGGAGTCATC |
| | TTCTAATCCAACAATAGAGGAAGGAAGAACATTGAGAGTTTTGAAG |
| | ATGGTGGAGCCATGGCTCTCTTCAAAACCTGAATTCTGCATCAAGG |
| | TCCTTAACCCCTACATGCCAACAGTCATAGAAGAGCTGGAGAAACT |
| | GCAGAGAAAACATGGTGGGAACCTTGTCAGATGCCCGCTGTCCAGG |

| SEQ ID NO | Sequence |
|---|---|
| | AACTCCACCCATGAGATGTATTGGGTGTCAGGAGCGTCGGGAAACA |
| | TCGTGAGCTCTGTGAACACAACATCAAAGATGTTGTTGAACAGGTT |
| | CACAACAAGGCATAGGAAACCCACTTATGAGAAGGACGTAGATCT |
| | TGGGGCAGGAACGAGAAGTGTCTCCACTGAAACAGAAAAACCAGA |
| | CATGACAATCATTGGGAGAAGGCTTCAGCGATTGCAAGAAGAGCA |
| | CAAAGAAACATGGCATTATGATCAAGAAAACCCATACAGAACCTG |
| | GGCGTATCATGGAAGCTATGAAGCTCCTTCGACAGGCTCTGCGTCC |
| | TCCATGGTGAACGGGGTGGTGAAACTGCTAACAAAACCCTGGGATG |
| | TAATTCCGATGGTGACTCAGTTAGCCATGACAGACACAACCCCTTT |
| | TGGGCAACAAAGAGTGTTCAAAGAAAAGGTGGATACCAGAACACC |
| | GCAACCAAAACCAGGCACACGAATGGTTATGACCACGACAGCCAA |
| | TTGGCTATGGGCCCTCCTTGGAAAGAAGAAAAATCCCAGACTGTGC |
| | ACAAGGGAAGAGTTCATCTCAAAAGTTAGATCAAACGCAGCCATA |
| | GGCGCAGTCTTCCAAGAGGAACAGGGATGGACATCAGCCAGTGAA |
| | GCTGTGAATGACAGCCGGTTTTGGGAACTGGTTGACAAAGAAAGG |
| | GCCCTTCACCAAGAAGGGAAATGTGAATCGTGTGTCTACAACATGA |
| | TGGGAAAACGTGAGAAAAAGTTAGGGGAGTTTGGCAGAGCCAAGG |
| | GAAGCCGAGCAATCTGGTATATGTGGCTAGGAGCGCGGTTTCTGGA |
| | ATTTGAAGCCCTGGGTTTTTTGAATGAAGATCATTGGTTTGGCAGA |
| | GAAAACTCATGGAGTGGAGTGGAAGGGGAAGGTCTGCACAGATTG |
| | GGATACATCCTGGAGGAGATAGACAAGAAGGATGGAGACCTAATG |
| | TATGCTGATGACACAGCAGGCTGGGACACAAGAATCACTGAGGAT |
| | GACCTCCAAAATGAGGAACTGATCACGGAACAGATGGCTCCCCACC |
| | ACAAGATCCTAGCCAAAGCCATTTTCAAACTAACCTACCAAAACAA |
| | AGTGGTGAAAGTCCTCAGACCCACACCGAGAGGAGCGGTGATGGA |
| | TATCATATCCAGGAAAGACCAGAGAGGTAGTGGACAAGTTGGAAC |
| | ATATGGTTTGAACACATTCACCAACATGGAAGTTCAACTCATCCGC |
| | CAAATGGAAGCAGAAGGAGTCATCACACAAGATGACATGCAGAAC |
| | CCTAAAGGGTTGAAAGAAAGAGTTGAGAAATGGCTGAGAGAGTGT |
| | GGTGTCGACAGGTTAAAGAGGATGGCAATTAGTGGAGACGATTGC |
| | GTGGTGAAACCCCTAGATGAGAGGTTTGGCACCTCCCTCCTCTTCTT |
| | GAACGACATGGGAAAGGTGAGGAAAGACATTCCGCAGTGGGAACC |
| | ATCTAAGGGATGGAAAAACTGGCAAGAGGTTCCTTTTTGCTCCCAC |
| | CACTTTCACAAGATCTTTATGAAGGATGGCCGCTCACTAGTTGTTCC |
| | ATGTAGAAACCAGGATGAACTGATAGGGAGAGCCAGAATCTCGCA |
| | GGGGGCTGGATGGAGCTTAAGGGAAACAGCTTGCCTAGGCAAAGC |
| | TTACGCCCAGATGTGGTCGCTTATGTACTTCCACAGAAGGGATCTG |
| | CGTTTAGCCTCCATGGCCATATGCTCAGCAGTTCCAACGGAATGGT |
| | TTCCAACAAGCAGAACAACATGGTCAATCCATGCTCATCACCAATG |
| | GATGACCACTGAAGACATGCTCAAGGTGTGGAACAGAGTGTGGAT |
| | AGAAGACAACCCCAATATGATTGACAAGACTCCAGTCCATTCGTGG |
| | GAAGATATACCTTACCTAGGGAAAAGAGAGGATTTGTGGTGTGGAT |
| | CCCTGATTGGACTTTCTTCTAGAGCCACCTGGGCGAAGAACATTCA |
| | CACGGCCATAACTCAGGTCAGGAATCTGATCGGAAAAGAGGAATA |
| | CGTGGATTATATGCCAGTAATGAAAAGATACAGTGCTCCTTCAGAG |
| | AGTGAAGGAGTTCTGTAATCACCAACAACAAACACCAAAGGCTATT |
| | GAAGTCAGGCCACTTGTGCCACGGCTTGAGCAAACCGTGCTGCCTG |
| | TAGCTCCGCCAATAATGGGAGGCGTAATAATCCCTAGGGAGGCCAT |
| | GCGCCACGGAAGCTGTACGCGTGGCATATTGGACTAGCGGTTAGAG |
| | GAGACCCCTCCCATCACTGACAAAACGCAGCAAAGGGGGCCCGA |
| | AGCCAGGAGGAAGCTGTACTCCTGGTGGAAGGACTAGAGGTTAGA |
| | GGAGACCCCCCCAACATAAAAACAGCATATTGACGCTGGGAAAGA |
| | CCAGAGATCCTGCTGTCTCTACAACATCAATCCAGGCACAGAGCGC |
| | CACAAGATGGATTGGTGTTGTTGATCCAACAGGTTCT |
| SEQ ID NO: 10 | AGTAGTTCGCCCGTGTGAGCTGACAAACTTAGTAGTGTTTGTGAGG |
| | ATTAATAACGATTAACACAGTGTGAGCTGTTTCTTAGCACGAAGAT |
| | CTCGATGTCTAAGAAACCAGGAGGGCCCGGCAAAAGCCGGGCTGT |
| | CAATATGCTAAAACGCGGTATGCCCCGCGGATTGTCCTTGATAGGA |
| | CTGAAGAGGGCTATGTTGAGTCTGATCGACGGGAAGGGCCCTATAC |
| | GCTTTGTGTTGGCTCTTTTGGCGTTCTTCAGATTCACTGCAATTGCTC |
| | CGACTCGTGCGGTGCTGGAAAGGTGGAGAGGCGTCAACAAACAAA |
| | CAGCAATGAAGCATCTCTTGAGTTTTAAGAAAGAACTAGGAACTTT |
| | GACCAGTGCCATTAACCGCCGGAGCACAAAACAAAAGAAAAGAGG |
| | AGGTCCAGCAGGCTTGACCATCCTGTTTGGGCTGATGTCTTGCGCTG |
| | GAGCCGTGATCCTATCCAACTTCCAGGGCAAAGTGATGATGACCGT |
| | CAATGCAACCGATGTCACCGACGTGATCACCATTCCAACAGCCGCC |
| | GGGAAAAACCTGTGCATCGTTAGAGCGATGGATGTGGATACCTCT |
| | GTGATGATACCATCACGTATGAATGTCCGGTTCTAGCTGCTGGAAA |
| | CGACCCTGAGGACATTGACTGCTGGTGCACGAAATCATCCGTCTAT |
| | GTGCGATATGGAAGATGTACGAAGACCCGGCATTCCCGCCGCAGCA |
| | GAAGGTCTTTGACAGTCCAGACACATGGAGAAGCACATTGGTTAA |
| | TAAGAAGGGAGCTTGGCTGGACAGCACAAAAGCCACGAGATATCT |
| | GGTAAAGACAGAATCATGGATACTGAGAAACCCTGGCTACGCCCTC |
| | GTCGCAGCTGTTATTGGATGGATGCTAGGGAGCAACACAATGCAGC |

| SEQ ID NO | Sequence |
|---|---|
| | GCGTCGTGTTTGCCATCCTATTGCTTTTGGTAGCACCAGCATACAGT
TTCAACTGCCTGGGAATGAGCAGCAGGGACTTCCTGGAGGGAGTGT
CTGGAGCCACATGGGTTGACCTGATACTAGAGGGCGACAGTTGTGT
GACCATAATGTCAAAAGACAAACCAACAATTGATGTCAAGATGAT
GAAAATGGAAGCGGCCAATCTTGCGGATGTGCGTCATTACTGCTAT
CTAGCTTCGGTCAGTGAACTGTCAACAAGAGCCGCATGCCCAACCA
TGGGTGAAGCCCACAACGAGAAAGAGCTGATCCCGCCTTTGTTTG
CAAGCAAGGAGTTGTGGACAGAGGATGGGGAAATGGATGTGGATT
GTTTGGAAAGGGTAGCATTGACACATGCGCAAAGTTTGCTTGCACA
ACCAAGGCGACTGGCTGGATCATTCAGAAGGAAAACATCAAGTAC
GAGGTCGCCATCTTTGTGCATGGCCCCACGACTGTCGAATCTCATG
GCAATTATTCAACACAAGTGGGAGCCACTCAGGCTGGAAGATTCAG
TATAACCCCGTCGGCACCATCTTACACGCTGAAGTTGGGTGAGTAT
GGTGAAGTCACGGTTGACTGTGAGCCACGGTCAGGGATAGACATCA
GCCTACATGTCATGTCAGTTGGTGCTAAGTCTTTTCTGGTTCATCGA
GAATGGTTCATGGACCTGAACCTGCCATGGAGTAGCGCTGGAGGCA
CTACGTGGAGAAACCGGGAAGCTCTGATGAATTTGAAGAACCTCA
TGCCACTAAACAGTCTGTTGTAGCCTTGGGATCGCAAGAAGGTGCT
CTGCACCAAGCCCTGGCTGGAGCGATTCCCGTTGAGTTCTCAAGTA
ACACTGTGAAGTTGACATCAGGGCATTTGAAGTGCAGGGTGAAGAT
GGAGAAGCTGCAACTGAAGGGAACGACATATGGAGTGTGTTCAAA
AGCATTCAAATTTGTTGGGACTCCCGCTGACACTGGACATGGGACG
GTGGTGCTGGAACTGCAGTACACTGGGACAGATGGGCCCTGCAAA
GTGCCCATCTCTTCCGTGGCTTCTCTAAATGACCTCACGCCCGTGGG
AAGATTGGTGACTGTGAATCCTTTTGTGTCTGTGGCCACGGCCAACT
CAAAGATCTTGATTGAAATTGAACCCCCATTTGGTGACTCTTATATT
GTGGTAGGGAGAGGGGAGCAGCAAATAAACCACCATTGGCACAAA
TCTGGAAGCAGCATTGGAAAAGCCTTCACGACTACTCTGAGAGGAG
CGCAACGACTTGCAGCGCTTGGAGACACAGCTTGGGACTTCGGATC
GGTTGGAGGGGTTTTCACCTCGGTTGGGAAAGCCATACACCAAGTC
TTTTGGAGGAGCTTTTAGATCACTTTTTGGAGGGATGTCCTGGATTAC
ACAGGGACTTCTAGGGGCTCTTCTACTGTGGATGGGGATCAATGCT
CGTGATAGGTCAATTGCTATGACGTTCCTTGCGGTTGGAGGAGTTTT
GCTCTTCCTCTCGGTTAACGTCCACGCTGACACGGGCTGTGCCATCG
ATCTTGGTAGGCAAGAGCTTCGGTGCGGGAGCGGAGTGTTTGTTCA
CAATGATGTGGAAGCTTGGATGGATCGCTACAAATTCTACCCGGAG
ACGCCACAAGGCTTAGCAAAAATTATCCAGAAAGCACGTGCAGAA
GGAGTTTGTGGTCTGCGCTCTGTCTCCAGACTCGAACACCAGATGT
GGGAGGCCATCAAGGATGAGTTGAACACCCTGCTGAAAGAGAACG
GAGTTGACTTAAGTGTCGTGGTTGAAAAACAGAATGGGATGTACAA
AGCAGCGCCAAAACGCCTGGCCGCCACCACCGAGAAACTGGAGAT
GGGCTGGAAAGCTTGGGGCAAGAGCATCATCTTCGCTCCAGAACTA
GCTAACAACACCTTTGTCATTGATGGTCCTGAGACCGAAGAATGCC
CAACAGCTAGCCGAGCATGGAACAGCATGGAGGTGGAGGATTTTG
GGTTTGGACTGACGAGCACCCGGATGTTCCTGAAGATCCGGGAGAC
GAACACGACGGAGTGCGACTCGAAGATCATTGGAACCGCCATTAA
GAACAACATGGCTGTGCACAGTGACCTGTCATACTGGATAGAAAGT
GGACTCAATGACACCTGGAAGCTTGAGAGAGCGGTTCTAGGAGAG
GTCAAATCATGCACCTGGCCTGAGACCCACACCCTATGGGGCGATG
GAGTTCTAGAAAGTGATCTCATCATACCCATTACCTTAGCAGGGCC
CAGGAGCAACCACAACAGAAGACCAGGGTACAAAACTCAGAATCA
AGGCCCATGGGATGAGGGACGTGTTGAGATTGACTTTGACTATTGC
CCAGGAACAACAGTAACCTTAAGTGACAGTTGTGGACACCGTGGAC
CCGCGGCACGCACGACCACCGAGAGTGGGAAGCTCATTACCGATTG
GTGCTGTAGGAGTTGCACCCTTCCTCCATTACGGTTCAGAACCGAA
AATGGGTGTTGGTATGGAATGGAAATTCGCCCTCTGCGACACGATG
AAAAGACCCTCGTGCAGTCGAAAGTAAACGCGTACAACGCCGACA
TGATTGATCCTTTTCAGCTGGGCCTTCTGGTCGTATTCTTGGCCACC
CAGGAGGTCCTTCGCAAGAGGTGGACGGCCAAGATCAGCATTCCG
GCTATTCTGCTTGCGCTCGTGGTCCTCGTGCTTGGGGGTATCACGTA
CACTGATGTTTTGAGGTATGTCATTCTTGTTGGAGCCGCGTTTGCTG
AAGCAAACTCAGGCGGAGATGTTGTGCATTTGGCGCTTATGGCCAC
ATTCAAAATTCAGCCAGTTTTCTTGGTGGCCTCTTTCTTAAAAGCAA
GGTGGACCAACCAAGAGAGCATTTTGCTTATGCTTGCGGCTGCCTT
TTTCCAAATGGCTTATTATGATGCCAGGAACGTCTTGGCATGGGAT
ATGCCTGATGTTTTGAATTCCCTTTCCGTCGCCTGGATGATTCTCAG
GGCCATAAGCTTTACCAACACCTCAAATGTGGTGGTGCCGCTACTG
GCCCTTTTGACACCTGGGTTAAAATGCTTGAATCTGGATGTGTACCG
GATTTTGCTGCTTATGGTTGGAGTTGGAAGCCTCATAAAAGAAAG
AGGAGCTCTGCAGCAAAAAAGAAAGGAGCCTGCCTCATCTGCCTA
GCACTGGCGTCCACAGAGGTGTTCAATCCAATGATACTAGCAGCTG
GGCTGATGGCTTGCGATCCCAATCGCAAGCGAGGCTGGCCTGCCAC
AGAAGTGATGACCGCGGTTGGACTTATGTTTGCCATTGTTGGGGGT
CTAGCAGAACTTGACATAGATTCTATGGCTATCCCCATGACCATCG
CCGGACTTATGTTTGTGGCATTTGTCATCTCTGGGAAATCGACGGAC |

| SEQ ID NO | Sequence |
|---|---|
| | ATGTGGATCGTGAGGGCGGCCGACATCACTTGGGAGAGCGACGCT |
| | GAAATCACAGGTTCTAGCGAGAGAGTGGATGTTAGGTTGGATGATG |
| | ATGGGAACTTCCAGTTGATGAACGATCCTGGGGCACCATGGAAAAT |
| | CTGGATGCTCAGAATGGCCTGCTTGGCAATAAGTGCCTACACACCC |
| | TGGGCCATACTCCCCTCAGTCATTGGATTTTGGATAACCCTTCAATA |
| | CACAAAGCGGGGAGGTGTTCTTTGGGACACACCATCGCCCAAAGA |
| | GTACAAGAAGGGTGACACCACTACCGGCGTCTACAGGATCATGACC |
| | CGAGGTCTGCTCGGAAGTTACCAGGCTGGAGCCGGTGTGATGGTAG |
| | AAGGAGTGTTCCACACACTGTGGCACACCACCAAAGGAGCAGCTCT |
| | CATGAGCGGCGAAGGGAGTCTAGATCCCTATTGGGGAGCGTGAA |
| | AGAAGACCGACTGTGCTATGGAGGGCCTTGGAAACTCCAACACAA |
| | GTGGAATGGACATGATGAGGTTCAAATGATTGTCGTGAAACCAGGA |
| | GAAAACGTGAGGAACGTTCAAACAAAACCCGGAGTGTTTAAGACA |
| | CCAGAAGGAGAGATCGGGGCAGTCACGCTAGACTACCCCACCGGA |
| | ACGTCAGGCTCTCCCATTGTGGACAAAAATGGGGACGTGATTGGGC |
| | TGTATGGGAACGGCGTCATCATGCCGAATGGCGCGTACATGAGCGC |
| | CATTGTGCAAGGAGAGAGAATGGAAGAACCGGCGCCAGCTGGTTT |
| | TGAGCCTGAAATGCTGAGGAAGAAACAAATTTCTGTCCTTGACCTG |
| | CACCCCGGATCAGGAAAGACACGCAAAATACTTCCCCAGATCATTA |
| | AGGAGGCTATCAACAAGAGACTGAGGACGGCCGTGCTCGCACCAA |
| | CCAGGGTCGTTGCCGCTGAGATGGCTGAGGCCTTGAGAGGACTCCC |
| | CATTCGATACCAAACCTCAGCGGTGCACAGAGAGCACAGTGGAAA |
| | TGAAATCGTTGATGTGATGTGCCGCCCCCTCACGCACAGGTTGATG |
| | TCTCCACACAGAGTTCCCAATTACAATCTGTTTGTAATGGATGAGG |
| | CCCATTTCACGGACCCAGCTAGTATTGCAGCTAGAGGATACATAGC |
| | AACCAAGGTTGAACTGGGCGAAGCCGCCGCGATCTTCATGACGGCG |
| | ACGCCGCCCGGGACCTCAGACCCCTTCCCAGAGTCCAATGCCCCTA |
| | TTTCAGATATGCAAACAGAGATCCCAGATAGAGCTTGGAACACCGG |
| | ATATGAATGGATAACCGAATACATCGGAAAGACCGTCTGGTTCGTT |
| | CCAAGTGTTAAGATGGGAAATGAAATTGCTCTCTGTCTGCAACGGG |
| | CGGGGAAGAAAGTGATCCAGCTGAACAGAAAGTCCTATGAGACAG |
| | AGTATCCCAAGTGTAAAAACGATGATTGGGACTTTGTTGTCACCAC |
| | GGATATATCAGAAATGGGAGCTAACTTCAAGGCCAATAGAGTGATT |
| | GATAGTCGCAAGAGCGTGAAACCCACTATCATTGAGGAAGGCGAT |
| | GGGAGAGTCATTCTGGGAGAACCCTCAGCTATTACAGCTGCTAGTG |
| | CAGCCCAGAGGAGAGGACGCATAGGAAGAAATCCATCACAAGTTG |
| | GCGATGAGTATTGCTATGGAGGGCACACAAATGAAGATGACTCCA |
| | ACTTTGCTCATTGGACAGAGGCCCGCATCATGCTAGACAATATCAA |
| | CATGCCAAATGGTTTAGTGGCCCAGCTATACCAGCCTGAGCGAGAG |
| | AAAGTGTACACCATGGACGGGGAGTACAGGCTAAGAGGGGAAGAA |
| | CGGAAGAACTTCCTTGAGTTCCTAAGAACAGCTGATTTGCCGGTCT |
| | GGCTCGCCTACAAAGTGGCGGCGGCAGGAATATCATATCACGATCG |
| | AAAGTGGTGCTTTGATGGACCCCGAACCAACACGATTCTGGAAGAT |
| | AACACCGAAGTGGAAGTTATCACAAAGCTAGGTGAGAGGAAGATC |
| | TTAAGACCCAGGTGGGCAGATGCCAGAGTGTACTCGGACCACCAA |
| | GCCCTAAAGTCTTTTAAGGATTTTGCATCAGGGAAACGATCGCAGA |
| | TCGGGCTTATTGAGGTGCTTGGGAGGATGCCCGAACACTTTATGGG |
| | GAAAACTTGGGAGGCCCTGGACACTATGTATGTGGTGGCAACCGCT |
| | GAAAAAGGAGGCCGAGCTCACAGGATGGCTCTTGAGGAGCTTCCG |
| | GACGCCCTTCAGACAATAGCTTTGATCACGCTCTTGAGTGTGATGTC |
| | CCTGGGCGTGTTTTTTCTTCTTATGCAAAGGAAAGGCATAGGCAAG |
| | ATTGGCTTGGGAGGAGTGATCCTAGGAGCGGCCACATTCTTTTGCT |
| | GGATGGCTGACGTCCCGGGAACGAAAATAGCGGGCATGCTCTTGCT |
| | CTCCCTGCTGCTCATGATTGTTTTGATTCCAGAGCCAGAAAAGCAG |
| | CGCTCACAGACTGACAATCAGCTTGCTGTGTTTTTGATCTGTGTGCT |
| | CACACTGGTCAGCGCCGTGGCCGCCAATGAAATGGGTTGGCTGGAC |
| | AAAACAAAGAATGACATTAGCAGCCTGTTGGGGTACAAGTCAGAA |
| | GCCAGAGAAACAACTCTGGGAGTTGAAAGCTTCTTGCTTGATCTGC |
| | GGCCAGCCACGGCATGGTCACTTTACGCCGTGACAACAGCCGTTCT |
| | CACCCCTCTGCTGAAGCATCTAATCACGTCAGACTACATTAACACTT |
| | CGTTGACTTCAATAAACGTCCAAGCCAGCGCGTTGTTCACTCTGGCT |
| | AGAGGCTTCCCTTTTGTGGATGTTGGTGTCTCAGCTCTCTTGTTGGC |
| | GGCTGGGTGTTGGGGTCAGGTAACACTGACAGTGACAGTGACCGCA |
| | GCTTCTCTGCTTTTTTGCCACTATGCTTACATGGTGCCAGGCTGGCA |
| | AGCAGAAGCTATGCGATCCGCTCAGCGGCGTACTGCTGCCGGTATC |
| | ATGAAGAATGCAGTGGTGGATGGGATCGTGGCCACTGATGTGCCTG |
| | AACTTGAGCGAACGACCCCAGTCATGCAGAAGAAAGTTGGACAGA |
| | TCATGCTGATCTTGGTGTCAGTGGCCGCAGTGGTCGTCAATCCATCA |
| | GTGAGGACCGTTAGAGAGGCTGGAATCTTGACCACAGCAGCAGTG |
| | GTCACACTATGGGAAAATGGTGCCAGTTCAGTGTGGAATGCAACAA |
| | CAGCCATTGGCCTTTGCCATATTATGCGAGGGGAATACTATCGTG |
| | TCTTTCCATCACGTGGACTCTCATCAAAAACATGGAGAAGCCCGGC |
| | CTCAAGAGGGGAGGAGCCAAGGGGCGCACACTAGGAGAAGTTTGG |
| | AAGGAGAGGCTCAACCACATGACAAAGGAAGAGTTCACCAGATAC |
| | AGGAAAGAAGCCATCACTGAGGTTGACCGCTCCGCCGCAAAACAT |

SEQUENCES

| SEQ ID NO | Sequence |
|---|---|
| | GCTAGAAAAGAAGGAAACATTACTGGAGGCCACCCGGTTTCGCGG |
| | GGAACCGCGAAGTTACGGTGGCTAGTGGAAAGGAGATTCCTCGAG |
| | CCAGTGGGGAAGGTTGTGGACCTTGGGTGTGGCAGAGGCGGTTGGT |
| | GCTATTACATGGCCACCCAGAAGAGGGTGCAGGAAGTAAAAGGGT |
| | ACACGAAAGGGGGGCCTGGCCATGAAGAGCCACAACTGGTGCAAA |
| | GCTATGGTTGGAATATTGTCACCATGAAAAGTGGAGTTGATGTGTT |
| | TTACAGACCATCAGAAGTGAGTGACACACTGCTCTGTGACATTGGA |
| | GAGTCATCATCAAGTGCCGAGGTGGAAGAACATCGAACCGTCCGG |
| | GTTTTGGAGATGGTGGAAGATTGGTTGCACAGAGGACCGAAGGAG |
| | TTTTGCATCAAGGTGCTCTGTCCTTACATGCCTAAAGTGATTGAGAA |
| | GATGGAAACACTTCAAAGGCGATATGGAGGTGGTCTCGTGAGGAA |
| | CCCTCTCTCACGTAACTCCACCCATGAGATGTACTGGGTGAGCCGT |
| | GCGTCAGGCAACATCGTCCACTCCGTCAACATGACGAGTCAGGTGC |
| | TCTTAGGGAGGATGGAAAAGAAAACATGGAAAGGGCCCCAGTATG |
| | AGGAAGATGTTAATCTGGGAAGTGGAACGCGAGCCGTAGGGAAGC |
| | CTCTCCTTAATTCTGATACCAGCAAAATCAAGAATCGAATCGAGAG |
| | GTTGAAAAAGAATACAGTTCCACGTGGCACCAAGACGTGAACCA |
| | TCCTTACAGGACCTGGAACTACCATGGAAGTTACGAAGTGAAACCA |
| | ACCGGCTCAGCTAGCTCCCTTGTGAATGGGGTAGTCAGACTGCTAT |
| | CAAAACCGTGGGACACCATTACCAACGTGACCACGATGGCTATGAC |
| | TGATACCACCCCTTTTGGTCAGCAACGAGTGTTCAAGGAGAAGGTG |
| | GACACGAAAGCTCCAGAGCCTCCGGAAGGAGTCAAACATGTCCTC |
| | AATGAGACCACAAATTGGCTGTGGGCCTTTTTGGCTCGTGAGAAGA |
| | AGCCCAGGATGTGTTCGCGAGAGGAATTCATTGCCAAAGTCAACAG |
| | CAACGCCGCTCTTGGAGCAATGTTTGAAGAACAGAACCAATGGAA |
| | GAACGCCAGAGAAGCCGTAAATGACCCAAAGTTCTGGGAAATGGT |
| | TGATGAGGAACGTGAGGCGCACCTTCGCGGGGAATGCAATACCTGC |
| | ATATACAACATGATGGGCAAGAGAGAGAAGAAACCTGGAGAGTTT |
| | GGTAAAGCCAAAGGCAGCAGAGCCATTTGGTTCATGTGGCTAGGG |
| | GCTCGCTTTTTAGAGTTTGAAGCTCTTGGGTTTCTCAACGAGGATCA |
| | CTGGCTAGGCAGAAAGAACTCAGGAGGCGGAGTTGAAGGCCTGGG |
| | GCTCCAGAAGCTTGGTTACATCTTGAAAGCGGTCGGGACAAAACCT |
| | GGAGGAAAGATCTACGCTGATGACACGGCCGGCTGGGACACACGC |
| | ATCACCAAAGCTGACCTCGAAAATGAAGCGAAGGTCCTTGAATTGC |
| | TGGATGGGGAACATCGGCGCTTAGCACGGTCCATCATTGAGCTAAC |
| | TTATCGACACAAAGTCGTGAAGGTGATGAGACCAGCGGCCGACGG |
| | AAAGACTGTGATGGACGTTATCTCTAGAGAGGACCAGAGAGGAAG |
| | CGGCCAAGTGGTTACCTACGCTCTGAACACCTTCACCAATTTAGCA |
| | GTCCAACTGGTGAGGATGATGGAAGGGGAAGGAGTCATAGGACCT |
| | GATGACGTTGAAAAACTGGGAAAGGGAAAAGGGCCCAAGGTCAGA |
| | ACCTGGCTGTTTGAGAATGGCGAGGAGCGCCTCAGCCGCATGGCCG |
| | TCAGTGGTGATGATTGCGTGGTGAAGCCTTTGGACGACCGGTTTGC |
| | CACGTCACTGCACTTCCTTAACGCTATGTCAAAGGTCCGGAAAGAT |
| | ATCCAGGAATGGAAACCCTCGACAGGATGGTATGACTGGCAGCAG |
| | GTTCCATTTTGCTCGAACCATTTCACGGAACTGATCATGAAGGACG |
| | GCAGGACGCTGATCGTCCCATGTCGTGGACAGGACGAGCTGATTGG |
| | ACGTGCCAGGATCTCTCCAGGAGCTGGATGGAACGTGCGCGACACT |
| | GCCTGCTTGGCGAAATCATACGCTCAGATGTGGCTGCTGCTCTACTT |
| | CCACCGCCGTGACTTGAGACTGATGGCCAATGCTATTTGTTCCGCA |
| | GTGCCCGTTAACTGGGTTCCCACAGGGCGCACCACCTGGTCGATCC |
| | ATGCAAAAGGGGAATGGATGACAACAGAGGACATGCTTGCAGTCT |
| | GGAATAGGGTGTGGATTGAGGAGAATGAATGGATGGAAGATAAAA |
| | CGCCAGTTGAGAAGTGGAGTGATGTTCCATACTCTGGGAAGAGAGA |
| | AGACATCTGGTGTGGCAGCCTGATTGGCACGCGAATCCGTGCCACT |
| | TGGGCTGAAAAACATCCATGTGGCAATCAATCAGGTCCGCGCGGTGA |
| | TTGGGGAAGAGAAATATGTGGACTACATGAGCTCTTTGAGGAGATA |
| | TGAAGACACCATTATAGTGGAAGATACTGTTTTGTAGATAATGAAG |
| | TTGAGATGAATAGTTTGTGATTGTAGTTTAGTTAATTTTATAATAAT |
| | AGTCATTTGGATTATGATTAGACATGTAGGTGTAGGATAGTGTTAT |
| | AGTTAGTGTAGTGTATATAAAATTAATTAAGAATGGAAGTCAGGCC |
| | AGATTAATGCTGCCACCGGAAGTTGAGTAGACGGTGCTGCCTGCGA |
| | CTCAACCCCAGGAGGACTGGGTGACCAAAGCTGCGAGGTGATCCA |
| | CGTAAGCCCTCAGAACCGTTTCGGAAGGAGGACCCCACGTGCTTTA |
| | GCCCCAAAGCCCAATGTCAGACCACACTTTGGTGTGCCACTCTGCG |
| | GAGAGTGCAGTCTGCGATAGTGCCCCAGGTGGACTGGGTCAACAA |
| | AGGCAAAACATCGCCCCACGCGGCCATAACCCTGGCTATGGTGTTA |
| | ACCAGGGAGAAGGGACTAGTGGTTAGAGGAGATCCCCGCGTTAAA |
| | AAGTGCACGGCCCAATCTTGGCTGAAGCTGTAAGCCAAGGGAAGG |
| | ATCTAGAGGTTAGAGGGAGAACCCCGTGCCAAAAACACCAAAAGA |
| | AACAGCATATTGACACCTGGGATAGACTAGGGGATCTTCTGCTCTG |
| | CACAACCAGCCACACGGCACAGTGCGCCGATATAGGTGGCTGGTG |
| | GTGCGAGAACACAGGATCT |
| SEQ ID NO: 11 | ATGAAAAACCCAAAGAAGAAATCCGGAAGATTCCGGATTGTCAAT |
| | ATGCTAAAACGCGGAGTAGCCCGTGTAAACCCCTTGGGAGGTTTGA |

| SEQ ID NO | Sequence |
|---|---|
| | AGAGGTTGCCAGCCGGACTTCTGCTGGGTCATGGACCCATCAGAAT |
| | GGTTTTGGCGATACTAGCCTTTTTGAGATTTACAGCAATCAAGCCAT |
| | CACTGGGCCTTATCAACAGATGGGGTTCCGTGGGGAAAAAAGAGG |
| | CTATGGAAATAATAAAGAAGTTCAAGAAAGATCTTGCTGCCATGTT |
| | GAGAATAATCAATGCTAGGAAAGAGAGGAAGAGACGTGGCGCAGA |
| | CACCAGCATCGGAATCATTGGCCTCCTGCTGACTACAGCCATGGCA |
| | GCAGAGATCACTAGACGCGGGAGTGCATACTACATGTACTTGGATA |
| | GGAGCGATGCCGGGAAGGCCATTTCGTTTGCTACCACATTGGGAGT |
| | GAACAAGTGCCACGTACAGATCATGGACCTCGGGCACATGTGTGAC |
| | GCCACCATGAGTTATGAGTGCCCTATGCTGGATGAGGGAGTGGAAC |
| | CAGATGATGTCGATTGCTGGTGCAACACGACATCAACTTGGGTTGT |
| | GTACGGAACCTGTCATCACAAAAAAGGTGAGACACGGCGATCTAG |
| | AAGATCTGTGTCGCTCCGTTATCACTATACAAGGAAGTTGCAAACG |
| | CGGTCGCAGACATGGTTAGAATCAAGAGAATACAAGAAGCACTTG |
| | ATCATGGTCGAAAACTGGATATTCAGGAACCCCGGGTTTGCCATAG |
| | TGTCCGTTGCCATTACCTGGCTGATGGGAAGCTTGACGAGCCAAAA |
| | AGTCATATACTTGGTCATGATAGTGTTGATTGTCCCGGCATACAGTA |
| | TCAGCTGCATTGGAGTCAGCAATAGAGACTTAGTGGAGGGCATGTC |
| | AGGTGGGACCTGGGTTGATGTTGTCTTGGAACATGGAGGGTGCGTT |
| | ACCGAGATGGCACAGGACAAGCCAACAGTTGACATAGAGTTGGTC |
| | ACGATGACGGTTAGTAACATGGCCGAGGTAAGATCCTATTGCTACG |
| | AGGCATCGTTATCCGACATGGCTTCGGCCAGTCGTTGCCCAACACA |
| | AGGCGAACCCTCCCTCGACAAGCAATCAGACACTCAATCTGTATGC |
| | AAAAGAACATTAGGAGACAGAGGTTGGGGAAATGGTTGTGGGATT |
| | TTTGGCAAAGGGAGCTTGGTGACATGTTCCAAGTTCACGTGTTGTA |
| | AGAAGATGCCCGGGAAGAGCATTCAACCGGAAAATCTGGAGTATC |
| | GGATAATGCTCCCAGTGCATGGCTCCCAGCATAGCGGGATGATTGT |
| | GAATGACATAGGACATGAAACTGACGAAAACAGAGCGAAAGTCGA |
| | GGTCACACCCAATTCACCAAGAGCAGAAGCAACCTTGGGAGGTTTT |
| | GGAAGCTTGGGACTTGACTGTGAACCAAGGACAGGCCTTGACTTCT |
| | CAGATCTGTATTATCTGACCATGAACAACAAGCATTGGTTGGTGCA |
| | CAAGGAGTGGTTTCATGACATCCCATTACCTTGGCATGCTGGTGCA |
| | GACACTGGAACTCCACACTGGAACAACAAAGAGGCATTGGTGGAG |
| | TTCAAGGACGCCCACGCCAAGAGGCAAACTGTTGTGGTTCTGGGGA |
| | GCCAAGAGGGAGCTGTTCACACGGCCCTCGCTGGAGCTCTGGAGGC |
| | TGAGATGGATGGTGCAAAGGGAAGGCTATTCTCTGGCCATTTGAAA |
| | TGCCGCCTAAAAATGGACAAGCTTAGGTTGAAGGGTGTGTCATATT |
| | CCCTGTGTACTGCAGCGTTCACATTTACCAAGGTCCCAGCTGAAAC |
| | ATTGCATGGAACAGTTACAGTGGAGGTGCAGTCTGCAGGGACAGAT |
| | GGACCCTGCAAGGTCCCAGCCCAGATGGCGGTGGACATGCAGACC |
| | CTGACCCCAGTTGGAAGGCTGATAACCGCCAACCCCGTGATTACTG |
| | AAAGCACTGAGAACTCAAAGATGATGTTGGAGCTTGACCCACCATT |
| | TGGGGATTCTTACATTGTCATAGGAGTTGGGGACAAGAAAATCACC |
| | CACCACTGGCATAGGAGTGGTAGCACCATCGGAAAGGCATTTGAA |
| | GCCACTGTGAGAGGCGCCAAGAGAATGGCAGTCCTGGGGGATACA |
| | GCCTGGGACTTCGGATCAGTCGGGGGTGTGTTCAACTCACTGGGTA |
| | AGGGCATTCACCAGATTTTTGGAGCAGCCTTCAAATCACTGTTTGG |
| | AGGAATGTCCTGGTTCTCACAGATCCTCATAGGCACGCTGCTAGTG |
| | TGGTTAGGTTTGAACACAAAGAATGGATCTATCTCCCTCACATGCTT |
| | GGCCCTGGGGGGAGTGATGATCTTCCTCTCCACGGCTGTTTCTGCTG |
| | ACGTGGGTGCTCAGTGGACTTCTCAAAAAAGGAAACGAGATGTG |
| | GCACGGGGGTATTCATCTATAATGATGTTGAAGCCTGGAGGGACCG |
| | GTACAAGTACCATCCTGACTCCCCCCGCAGATTGGCAGCAGCAGTC |
| | AAGCAGGCCTGGGAAGAGGGGATCTGTGGGATCTCATCCGTTTCAA |
| | GAATGGAAAACATCATGTGGAAATCAGTAGAAGGGGAGCTCAATG |
| | CTATCCTAGAGGAGAATGGAGTTCAACTGACAGTTGTTGTGGGATC |
| | TGTAAAAAACCCCATGTGGAGAGGTCCACAAAGATTGCCAGTGCCT |
| | GTGAATGNGCTGCCCCATGGCTGGAAAGCCTGGGGGAAATCGTATT |
| | TTGTTAGGGCGGCAAAGACCAACAACAGTTTTGTTGTCGACGGTGA |
| | CACACTGAAGGAATGTCCGCTTAAGCACAGAGCATGGAATAGTTTT |
| | CTTGTGGAGGATCACGGGTTTGGAGTCTTCCACACCAGTGTTTGGCT |
| | TAAGGTCAGAGAAGATTACTCATTAGAATGTGACCCAGCCGTCATA |
| | GGAACAGCTGTTAAGGGAAGGGAGGCCGCGCACAGTGATCTGGGC |
| | TATTGGATTGAAAGTGAAAAGAATGACACATGGAGGCTGAAGAGG |
| | GCCCACCTGATTGAGATGAAAACATGTGAATGGCCAAAGTCTCACA |
| | CATTGTGGACAGATGGAGTAGAAGAAAGTGATCTTATCATACCCAA |
| | GTCTTTAGCTGGTCCACTCAGCCACCACAACACCAGAGAGGGTTAC |
| | AGAACCCAAGTGAAAGGCCATGGCACAGTGAAGAGCTTGAAATC |
| | CGGTTTGAGGAATGTCCAGGCACCAAGGTTCACGTGGAGGAGACAT |
| | GCGGAACTAGAGGACCATCTCTGAGATCAACTACTGCAAGTGGAA |
| | GGGTCATTGAGGAATGGTGCTGTAGGGAATGCACAATGCCCCCACT |
| | ATCGTTTCGAGCAAAAGACGGCTGCTGGTATGGAATGGAGATAAG |
| | GCCCAGGAAAGAACCAGAGAGCAACTTAGTGAGGTCAATGGTGAC |
| | AGCGGGGTCAACCGATCATATGGACCACTTCTCTCTTGGAGTGCTT |
| | GTGATTCTACTCATGGTGCAGGAGGGGTTGAAGAAGAGAATGACC |

| SEQ ID NO | Sequence |
|---|---|
| | ACAAAGATCATCATGAGCACATCAATGGCAGTGCTGGTAGTCATGA |
| | TCTTGGGAGGATTTTCAATGAGTGACCTGGCCAAGCTTGTGATCCT |
| | GATGGGTGCTACTTTCGCAGAAATGAACACTGGAGGAGATGTAGCT |
| | CACTTGGCATTGGTAGCGGCATTTAAAGTCAGACCAGCCTTGCTGG |
| | TCTCCTTCATTCTCAGAGCCAATTGGACACCCCGTGAGAGCATGCT |
| | GCTAGCCCTGGCTTCGTGTCTTCTGCAAACTGCGATCTCTGCTCTTG |
| | AAGGTGACTTGATGGTCCTCGTTAATGGATTTGCTTTGGCCTGGTTG |
| | GCAATTCGAGCAATGGCCGTGCCACGCACTGACAACATCGCTCTAG |
| | CAATCTTGGCTGCTCTAACACCACTAGCTCGAGGCACACTGCTCGT |
| | GGCATGGAGAGCGGGCCTGGCTACTTGTGGAGGGTTCATGCTCCTC |
| | TCCCTGAAAGGGAAAGGTAGTGTGAAGAAGAACCTGCCATTTGTCA |
| | TGGCCCTGGGATTGACAGCTGTGAGGGTAGTAGACCCTATTAATGT |
| | GGTAGGACTACTGTTACTCACAAGGAGTGGGAAGCGGAGCTGGCC |
| | CCCTAGTGAAGTTCTCACAGCCGTTGGCCTGATATGTGCACTGGCC |
| | GGAGGGTTTGCCAAGGCAGACATTGAGATGGCTGGACCCATGGCTG |
| | CAGTAGGCTTGCTAATTGTCAGCTATGTGGTCTCGGGAAGAGTGT |
| | GGACATGTACATTGAAAGAGCAGGTGACATCACATGGGAAAAGGA |
| | CGCGGAAGTCACTGGAAACAGTCCTCGGCTTGACGTGGCACTGGAT |
| | GAGAGTGGTGATTTCTCCTTGGTAGAGGAAGATGGTCCACCCATGA |
| | GAGAGATCATACTCAAGGTGGTCCTGATGGCCATCTGTGGCATGAA |
| | CCCAATAGCTATACCTTTTGCTGCAGGAGCGTGGTATGTGTATGTG |
| | AAGACTGGGAAAAGGAGTGGCGCCCTCTGGGACGTGCCTGCTCCCA |
| | AAGAAGTGAAGAAAGGAGAGACCACAGATGGAGTGTACAGAGTGA |
| | TGACTCGCAGACTGCTAGGTTCAACACAGGTTGGAGTGGGAGTCAT |
| | GCAAGAGGGAGTCTTCCACACCATGTGGCACGTTACAAAAGGAGC |
| | CGCACTGAGGAGCGGTGAGGGAAGACTTGATCCATACTGGGGGGA |
| | TGTCAAGCAGGACTTGGTGTCATACTGTGGGCCTTGGAAGTTGGAT |
| | GCAGCTTGGGATGGACTTAGCGAGGTACAGCTTTTGGCCGTACCTC |
| | CCGGAGAGAGGGCCAGAAACATTCAGACCCTGCCTGGAATATTCA |
| | AGACAAAGGACGGGGACATCGGAGCAGTTGCTCTGGACTACCCTG |
| | CAGGGACCTCAGGATCTCCGATCCTAGACAAATGTGGAAGAGTGAT |
| | AGGACTCTATGGCAATGGGGTTGTGATCAAGAATGGAAGCTATGTT |
| | AGTGCTATAACCCAGGGAAAGAGGGAGGAGGAGACTCCGGTTGAA |
| | TGTTTCGAACCCTCGATGCTGAAGAAGAAGCAGCTAACTGTCCTGG |
| | ATCTGCATCCAGGAGCCGGAAAAACCAGGAGAGTTCTTCCTGAAAT |
| | AGTCCGTGAAGCCATAAAAAAGAGACTCCGGACAGTGATCTTGGC |
| | ACCAACTCCAGTTGAGAGATCATACTCAAGGTGGTCCTTGTGGCCA |
| | TCTGTGGCACGTACCCAGACAACAGCAGTCAACGTCACCCATTCTG |
| | GGACAGAAATCGTTGATTTGATGTGCCATGCCACTTTCACTTCACGC |
| | TTACTACAACCCATCAGAGTCCCTAATTACAATCTCAACATCATGG |
| | ATGAAGCCCACTTCACAGACCCCTCAAGTATAGCTGCAAGAGGATA |
| | CATATCAACAAGGGTTGAAATGGGCGAGGCGGCTGCCATTTTTATG |
| | ACTGCCACACCACCAGGAACCCGTGATGCGTTTCCTGACTCTAACT |
| | CACCAATCATGGACACAGAAGTGGAAGTCCCAGAGAGAGCCTGGA |
| | GCTCAGGCTTTGATTGGGTGACAGACCATTCTGGGAAAACAGTTTG |
| | GTTCGTTCCAAGCGTGAGATCTGGAGAAGAAAGCGCAGCCTGTCTG |
| | ACAAAGGCTGGAAAGCGGGTCATACAGCTCAGCAGGAAGACTTTT |
| | GAGACAGAATTTCAGAAAACAAAAAATCAAGAGTGGGACTTTGTC |
| | ATAACAACTGACATCTCAGAGATGGGCGCCAACTTCAAGGCTGACC |
| | GGGTCATAGACTCTAGGAGATGCCTAAAGCCAGTCATACTTGATGG |
| | TGAGAGAGTCATCTTGGCTGGGCCCATGCCTGTCACGCATGCTAGT |
| | GCTGCTCAGAGGAGAGGACGTATAGGCAGGAACCCTAACAAACCT |
| | GGAGATGAGTACATGTATGGAGGTGGGTGTGCAGAGACTGATGAA |
| | GACCATGCACACTGGCTTGAAGCAAGAATGCTTCTTGACAACATCT |
| | ACCTCCAGGATGGCCTCATAGCCTCGCTCTATCGGCCTGAGGCCGA |
| | TAAGGTAGCCGCCATTGAGGGAGAGTTTAAGCTGAGGACAGAGCA |
| | AAGGAAGACCTTCGTGGAACTCATGAAGAGGGAGACCTTCCCGTC |
| | TGGCTAGCCTATCAGGTTGCATCTGCCGGAATAACTTACACAGACA |
| | GAAGATGGTGCTTTGATGGCACAACCAACAACACCATAATGGAAG |
| | ACAGCGTACCAGCAGAGGTGTGGACAAAGTATGGAGAGAAGAGAG |
| | TGCTCAAACCGAGATGATGGATGCTAGGGTCTGTTCAGACCATGC |
| | GGCCCTGAAGTCGTTCAAAGAATTCGCCGCTGGAAAAAGAGGAGC |
| | GGCTTTGGGAGTAATGGAGGCCCTGGGAACACTGCCAGGACACAT |
| | GACAGAGAGGTTTCAGGAAGCCATTGACAACCTCGCCGTGCTCATG |
| | CGAGCAGAGACTGGAAGCAGGCCTTATAAGGCAGCGGCAGCCCAA |
| | CTGCCGGAGACCCTAGAGACCATTATGCTCTTAGGTTTGCTGGGAA |
| | CAGTTTCACTGGGGATCTTCTTCGTCTTGATGCGAATAAGGGCATC |
| | GGGAAGATGGGCTTTGGAATGGTAACCCTTGGGGCCAGTGCATGGC |
| | TCATGTGGCTTTCGGAAATTGAACCAGCCAGAATTGCATGTGTCCT |
| | CATTGTTGTGTTTTTATTACTGGTGGTGCTCATACCCGAGCCAGAGA |
| | AGCAAAGATCTCCCCAAGATAACCAGATGGCAATTATCATCATGGT |
| | GGCAGTGGGCCTTCTAGGTTTGATAACTGCAAACGAACTTGGATGG |
| | CTGGAAAGAACAAAAAATGACATAGCTCATCTAATGGGAAGGAGA |
| | GAAGAAGGAGCAACCATGGGATTCTCAATGGACATTGATCTGCGGC |
| | CAGCCTCCGCCTGGGCTATCTATGCCGCATTGACAACTCTCATCACC |

| SEQ ID NO | Sequence |
|---|---|
| | CCAGCTGTCCAACATGCGGTAACCACTTCATACAACAACTACTCCT<br>TAATGGCGATGGCCACACAAGCTGGAGTGCTGTTTGGCATGGGCAA<br>AGGGATGCCATTTATGCATGGGGACCTTGGAGTCCCGCTGCTAATG<br>ATGGGTTGCTATTCACAATTAACACCCCTGACTCTGATAGTAGCTAT<br>CATTCTGCTTGTGGCGCACTACATGTACTTGATCCCAGGCCTACAAG<br>CGGCAGCAGCGCGTGCTGCCCAGAAAAGGACAGCAGCTGGCATCA<br>TGAAGAATCCCGTTGTGGATGGAATAGTGGTAACTGACATTGACAC<br>AATGACAATAGACCCCCAGGTGGAGAAGAAGATGGGACAAGTGTT<br>ACTCATAGCAGTAGCCATCTCCAGTGCTGTGCTGCTGCGGACCGCC<br>TGGGGATGGGGGGAGGCTGGAGCTCTGATCACAGCAGCGACCTCC<br>ACCTTGTGGGAAGGCTCTCCAAACAAATACTGGAACTCCTCTACAG<br>CCACCTCACTGTGCAACATCTTCAGAGGAAGCTATCTGGCAGGAGC<br>TTCCCTTATCTATACAGTGACGAGAAACGCTGGCCTGGTTAAGAGA<br>CGTGGAGGTGGGACGGGAGAGACTCTGGGAGAGAAGTGGAAAGCT<br>CGTCTGAATCAGATGTCGGCCCTGGAGTTCTACTCTTATAAAAAGT<br>CAGGTATCACTGAAGTGTGTAGAGAGGAGGCTCGCCGTGCCCTCAA<br>GGATGGAGTGGCCACAGGAGGACATGCCGTATCCCGGGGAAGTGC<br>AAAGCTCAGATGGTTGGTGGAGAGAGGATATCTGCAGCCCCATGG<br>GAAGGTTGTTGACCTCGGATGTGGCAGAGGGGCTGGAGCTATTAT<br>GCCGCCACCATCCGCAAAGTGCAGGAGGTGAGAGGATACACAAAG<br>GGAGGTCCCGGTCATGAAGAACCCATGCTGGTGCAAAGCTATGGGT<br>GGAACATAGTTCGTCTCAAGAGTGGAGTGGACGTCTTCCACATGGC<br>GGCTGAGCCGTGTGACACTCTGCTGTGTGACATAGGTGAGTCATCA<br>TCTAGTCCTGAAGTGGAAGAGACACGAACACTCAGAGTGCTCTCTA<br>TGGTGGGGACTGGCTTGAAAAAAGACCAGGGGCCTTCTGTATAAA<br>GGTGCTGTGCCCATACACCAGCACTATGATGAAACCATGGAGCGA<br>CTGCAACGTAGGCATGGGGGAGGATTAGTCAGAGTGCCATTGTCTC<br>GCAACTCCACACATGAGATGTACTGGGTCTCTGGGGCAAAAAGCAA<br>CATCATAAAAAGTGTGTCCACCACAAGTCAGCTCCTCCTGGGACGC<br>ATGGATGGCCCCAGGAGGCCAGTGAAATATGAGGAGGATGTGAAC<br>CTCGGCTCGGGTACACGAGCTGTGGCAAGCTGTGCTGAGGCTCCTA<br>ACATGAAAATCATCGGCAGGCGCATTGAGAGAATCCGCAATGAAC<br>ATGCAGAAACATGGTTTCTTGATGAAAACCACCCATACAGGACATG<br>GGCCTACCATGGGAGNTACGAAGCCCCCACGCAAGGATCAGCGTCT<br>TCCCTCGTGAACGGGGTTGTTAGACTCCTGTCAAAGCCTTGGGACG<br>TGGTGACTGGAGTTACAGGAATAGCCATGACTGACACCACACCATA<br>CGGCCAACAAAGAGTCTTCAAAGAAAAAGTGGACACCAGGGTGCC<br>AGATCCCCAAGAAGGCACTCGCCAGGTAATGAACATGGTCTCTTCC<br>TGGCTGTGGAAGGAGCTGGGGAAACGCAAGCGGCCACGCGTCTGC<br>ACCAAAGAAGAGTTTATCAACAAGGTGCGCAGCAATGCAGCACTG<br>GGAGCAATATTTGAAGAGGAAAAAGAATGGAAGACGGCTGTGGAA<br>GCTGTGAATGATCCAAGGTTTTGGGCCCTAGTGGATAGGGAGAGAG<br>AACACCACCTGAGAGGAGAGTGTCACAGCTGTGTGTACAACATGAT<br>GGGAAAAAGAGAAAAGAAGCAAGGAGAGTTCGGGAAAGCAAAAG<br>GTAGCCGCGCCATCTGGTACATGTGGTTGGGAGCCAGGTTTCTGGA<br>GTTTGAATCACTGGGGTTTCTGAATGAAGATCACTGGATGGGAAGA<br>GAGAACTCTGGAGGCGGAGTTGAAGGACTGGGACTGCAGAGACTG<br>GGCTATGTCCTTGAGGAGATGAGCCAGGCACCAGGAGGGAAGATG<br>TACGCAGATGACACTGCTGGCTGGGACACCCGCATTAGTAAGTTTG<br>ATCTGGAGAATGAAGCTTTGATTACCAACCAAATGGAGGAAGGGC<br>ACAGAACTCTGGCGTTGGCCGTGATTAAATACACATACCAAAACAA<br>AGTGGTGAAGGTCCTCAGACCAGCTGAAGGAGGAAAAACAGTTAT<br>GGACATCATTTCAAGACAAGACCAGAGAGGGAGTGGACAAGTTGT<br>CACTTATGCTCTCAACACATTCACCAACTTGGTGGTGCAGCTTATCC<br>GGAACATGGAAGCTGAGGAAGTGTTAGAGATGCAAGACTTATGGC<br>TGTTGAGGAAGCCAGAGAAAGTGACCAGATGGTTGCAGAGCAATG<br>GATGGGATAGACTCAAACGAATGGCGGTCAGTGGAGATGACTGCG<br>TTGTGAAGCCAATCGATGATAGGTTTGCACATGCCCTCAGGTTCTTG<br>AATGACATGGGAAAAGTTAGGAAAGACACACAGGAGTGGAAACCC<br>TCGACTGGATGGAGCAATTGGGAAGAAGTCCCGTTCTGCTCCCACC<br>ACTTCAACAAGCTGTACCTCAAGGATGGGAGATCCATTGTGGTCCC<br>TTGCCGCCACCAAGATGAACTGATTGGCCGAGCTCGCGTTTCACCA<br>GGGGCAGGATGGAGCATCCGGGAGACTGCCTGTCTTGCAAAATCAT<br>ATGCGCAGATGTGGCAGCTCCTTTATTTCCACAGAAGAGACCTTCG<br>ACTGATGGCTAATGCCATTTGCTCGGCTGTACCAGTTGACTGGGTA<br>CCAACTGGGAGAACCACCTGGTCAATCCATGGAAAGGGAGAATGG<br>ATGACCACTGAGGACATGCTCATGGTGTGGAATAGAGTGTGGATTG<br>AGGAGAACGACCATATGGAGGACAAGACTCCTGTAACAAAATGGA<br>CAGACATTCCCTATCTAGGAAAAAGGGAGGACTTATGGTGTGGATC<br>CCTTATAGGGCACAGACCCCGCACCACTTGGGCTGAAAACATCAAA<br>GACACAGTCAACATGGTGCGCAGGATCATAGGTGATGAAGAAAAG<br>TACATGGACTATCTATCCACCCAAGTCCGCTACTTGGGTGAGGAAG<br>GGTCCACACCCGGAGTGTTGTAA |

SEQUENCES

| SEQ ID NO | Sequence |
|---|---|
| SEQ ID NO: 12 | ATGAAAAACCCAAAGAAGAAATCCGGAGGATTCCGGATTGTCAAT<br>ATGCTAAAACGCGGAGTAGCCCGTGTAAACCCCTTGGGAGGTTTGA<br>AGAGGTTGCCAGCCGGACTTCTGCTGGGTCATGGACCCATCAGAAT<br>GGTTTTGGCGATACTAGCCTTTTTGAGATTTACAGCAATCAAGCCAT<br>CACTGGGCCTTATCAACAGATGGGGTTCCGTGGGAAAAAAGAGG<br>CTATGGAATAATAAAGAAGTTCAAGAAAGATCTTGCTGCCATGTT<br>GAGAATAATCAATGCTAGGAAAGAGAGGAAGAGACGTGGCGCAGA<br>CACCAGCATCGGAATCATTGGCCTCCTGCTGACTACAGCCATGGCA<br>GCAGAGATCACTAGACGCGGGAGTGCATACTACATGTACTTGGATA<br>GGAGCGATGCCGGGAAGGCCATTTCGTTTGCTACCACATTGGGAGT<br>GAACAAGTGCCACGTACAGATCATGGACCTCGGGCACATGTGTGAC<br>GCCACCATGAGTTATGAGTGCCCTATGCTGGATGAGGGAGTGGAAC<br>CAGATGATGTCGATTGCTGGTGCAACACGACATCAACTTGGGTTGT<br>GTACGGAACCTGTCATCACAAAAAGGTGAGGCACGGCGATCTAG<br>AAGAGCCGTGACGCTCCCTTCTCACTCTACAAGGAAGTTGCAAACG<br>CGGTCGCAGACCTGGTTAGAATCAAGAGAATACACGAAGCACTTG<br>ATCAAGGTTGAAAACTGGATATTCAGGAACCCCGGGTTTGCGCTAG<br>TGGCCGTTGCCATTGCCTGGCTTTTGGGAAGCTCGACGAGCCAAAA<br>AGTCATATACTTGGTCATGATACTGCTGATTGCCCCGGCATACAGT<br>ATCAGGTGCATTGGAGTCAGCAATAGAGACTTCGTGGAGGGCATGT<br>CAGGTGGGACCTGGGTTGATGTTGTCTTGGAACATGGAGGCTGCGT<br>TACCGTGATGGCACAGGACAAGCCAACAGTTGACATAGAGTTGGTC<br>ACGACGACGGTTAGTAACATGGCCGAGGTAAGATCCTATTGCTACG<br>AGGCATCGATATCGGACATGGCTTCGGACAGTCGTTGCCCAACACA<br>AGGTGAAGCCTACCTTGACAAGCAATCAGACACTCAATATGTCTGC<br>AAAAGAACATTAGTGGACAGAGGTTGGGGAAATGGTTGTGGACTTT<br>TTGGCAAAGGGAGCTTGGTGACATGTGCCAAGTTCACGTGTTCTAA<br>GAAGATGACCGGGAAGAGCATTCAACCGGAAAATCTGGAGTATCG<br>GATAATGCTATCAGTGCATGGCTCCCAGCATAGCGGGATGATTGTC<br>AATGATATAGGACATGAAACTGACGAAAACAGAGCGAAAGTCGAG<br>GTTACGCCTAATTCACCAAGAGCGGAAGCAACCTTGGGAGGCTTTG<br>GAAGCTTAGGACTTGACTGTGAACCAAGGACAGGCCTTGACTTTTC<br>AGATCTGTATTACCTGACCATGAACAATAAGCATTGGTTGGTGCAC<br>AAAGAGTGGTTTCATGACATCCCATTGCCTTGGCATGCTGGGGCAG<br>ACACCGGAACTCCACACTGGAACAACAAAGAGGCATTGGTAGAAT<br>TCAAGGATGCCCACGCCAAGAGGCAAACCGTCGTCGTTCTGGGGAG<br>CCAGGAAGGAGCCGTTCACACGGCTCTCGCTGGAGCTCTAGAGGCT<br>GAGATGGATGGTGCAAAGGGAAGGCTGTTCTCTGGCCATTTGAAAT<br>GCCGCCTAAAAATGGACAAGCTTAGATTGAAGGGCGTGTCATATTC<br>CTTGTGCACTGCGGCATTCACATTCACCAAGGTCCCAGCTGAAACA<br>CTGCATGGAACAGTCACAGTGGAGGTGCAGTATGCAGGGACAGAT<br>GGACCCTGCAAGGTCCCAGCCCAGATGGCGGTGGACATGCAGACC<br>CTGACCCCAGTTGGAAGGCTGATAACCGCCAACCCCGTGATTACTG<br>AAAGCACTGAGAACTCAAAGATGATGTTGGAGCTTGACCCACCATT<br>TGGGGATTCTTACATTGTCATAGGAGTTGGGGACAAGAAAATCACC<br>CACCACTGGCATAGGAGTGGTAGCACCATCGGAAAGGCATTTGAA<br>GCCACTGTGAGAGGCGCCAAGAGAATGGCAGTCCTGGGGGATACA<br>GCCTGGGACTTCGGATCAGTCGGGGGTGTGTTCAACTCACTGGGTA<br>AGGGCATTCACCAGATTTTTGGAGCAGCCTTCAAATCACTGTTTGG<br>AGGAATGTCCTGGTTCTCACAGATCCTCATAGGCACGCTGCTAGTG<br>TGGTTAGGTTTGAACACAAAGAATGGATCTATCTCCCTCACATGCTT<br>GGCCCTGGGGGGAGTGATGATCTTCCTCTCCACGGCTGTTTCTGCTG<br>ACGTGGGGTGCTCAGTGGACTTCTCAAAAAGAGAAACGAGATGTG<br>GCACGGGGGTATTCATCTATAATGATGTTGAAGCCTGGAGGGACCG<br>GTACAAGTACCATCCTGACTCCCCCCGCAGATTGGCAGCAGCAGTC<br>AAGCAGGCCTGGGAAGAGGGGATCTGTGGGATCTCATCCGTTTCAA<br>GAATGGAAAACATCATGTGGAAATCAGTAGAAGGGGAGCTCAATG<br>CTATCCTAGAGGAGAATGGAGTTCAACTGACAGTTGTTGTGGGATC<br>TGTAAAAAACCCCATGTGGAGAGGTCCACAAAGATTGCCAGTGCCT<br>GTGAATGGGCTGCCCCATGGCTGGAAAGCCTGGGGGAAATCGTATT<br>TTGTTAGGGCGGCAAAGACCAACAACAGTTTTGTTGTCGACGGTGA<br>CACACTGAAGGAATGTCCGCTTAAGCACAGAGCATGGAATAGTTTT<br>CTTGTGGAGGATCACGGGTTTGGAGTCTTCCACACCAGTGTTTGGCT<br>TAAGGTCAGAGAAGATTACTCATTAGAATGTGACCCAGCCGTCATA<br>GGAACAGCTGTTAAGGGAAGGGAGGCCGCGCACAGTGATCTGGGC<br>TATTGGATTGAAAGTGAAAAGAATGACACATGGAGGCTGAAGAGG<br>GCCCACCTGATTGAGATGAAAACATGTGAATGGCCAAAGTCTCACA<br>CATTGTGGACAGATGGAGTAGAAGAAAGTGATCTTATCATACCCAA<br>GTCTTTAGCTGGTCCACTCAGCCACCACAACACCAGAGAGGGTTAC<br>AGAACCCAAGTGAAAGGGCCATGCACAGTGAAGAGCTTGAAATC<br>CGGTTTGAGGAATGTCCAGGCACCAAGGTTCACGTGGAGGAGACAT<br>GCGGAACTAGAGGACCATCTCTGAGATCAACTACTGCAAGTGGAA<br>GGGTCATTGAGGAATGGTGCTGTAGGGAATGCACAATGCCCCCACT<br>ATCGTTTCGAGCAAAAGACGGCTGCTGGTATGGAATGGAGATAAG |

| SEQ ID NO | Sequence |
|---|---|
| | GCCCAGGAAAGAACCAGAGAGCAACTTAGTGAGGTCAATGGTGAC |
| | AGCGGGGTCAACCGATCATATGGACCACTTCTCTCTTGGAGTGCTT |
| | GTGATTCTACTCATGGTGCAGGAGGGGTTGAAGAAGAGAATGACC |
| | ACAAAGATCATCATGAGCACATCAATGGCAGTGCTGGTAGTCATGA |
| | TCTTGGGAGGATTTTCAATGAGTGACCTGGCCAAGCTTGTGATCCT |
| | GATGGGTGCTACTTTCGCAGAAATGAACACTGGAGGAGATGTAGCT |
| | CACTTGGCATTGGTAGCGGCATTTAAAGTCAGACCAGCCTTGCTGG |
| | TCTCCTTCATTCTCAGAGCCAATTGGACACCCCGTGAGAGCATGCT |
| | GCTAGCCCTGGCTTCGTGTCTTCTGCAAACTGCGATCTCTGCTCTTG |
| | AAGGTGACTTGATGGTCCTCGTTAATGGATTTGCTTTGGCCTGGTTG |
| | GCAATTCGAGCAATGGCCGTGCCACGCACTGACAACATCGCTCTAG |
| | CAATCTTGGCTGCTCTAACACCACTAGCTCGAGGCACACTGCTCGT |
| | GGCATGGAGAGCGGGCCTGGCTACTTGTGGAGGGTTCATGCTCCTC |
| | TCCCTGAAAGGGAAAGGTAGTGTGAAGAAGAACCTGCCATTTGTCA |
| | TGGCCCTGGGATTGACAGCTGTGAGGGTAGTAGACCCTATTAATGT |
| | GGTAGGACTACTGTTACTCACAAGGAGTGGGAAGCGGAGCTGGCC |
| | CCCTAGTGAAGTTCTCACAGCCGTTGGCCTGATATGTGCACTGGCC |
| | GGAGGGTTTGCCAAGGCAGACATTGAGATGGCTGGACCCATGGCTG |
| | CAGTAGGCTTGCTAATTGTCAGCTATGTGGTCTCGGGAAAGAGTGT |
| | GGACATGTACATTGAAAGAGCAGGTGACATCACATGGGAAAAGGA |
| | CGCGGAAGTCACTGGAAACAGTCCTCGGCTTGACGTGGCACTGGAT |
| | GAGAGTGGTGATTTCTCCTTGGTAGAGGAAGATGGTCCACCCATGA |
| | GAGAGATCATACTCAAGGTGGTCCTGATGGCCATCTGTGGCATGAA |
| | CCCAATAGCTATACCTTTTGCTGCAGGAGCGTGGTATGTGTATGTG |
| | AAGACTGGGAAAAGGAGTGGCGCCCTCTGGGACGTGCCTGCTCCCA |
| | AAGAAGTGAAGAAAGGAGAGACCACAGATGGAGTGTACAGAGTGA |
| | TGACTCGCAGACTGCTAGGTTCAACACAGGTTGGAGTGGGAGTCAT |
| | GCAAGAGGGAGTCTTCCACACCATGTGGCACGTTACAAAAGGAGC |
| | CGCACTGAGGAGCGGTGAGGGAAGACTTGATCCATACTGGGGGGA |
| | TGTCAAGCAGGACTTGGTGTCATACTGTGGGCCTTGGAAGTTGGAT |
| | GCAGCTTGGGATGGACTTAGCGAGGTACAGCTTTTGGCCGTACCTC |
| | CCGGAGAGAGGGCCAGAAACATTCAGACCCTGCCTGGAATATTCA |
| | AGACAAAGGACGGGACATCGGAGCAGTTGCTCTGGACTACCCTG |
| | CAGGGACCTCAGGATCTCCGATCCTAGACAAATGTGGAAGAGTGAT |
| | AGGACTCTATGGCAATGGGGTTGTGATCAAGAATGGAAGCTATGTT |
| | AGTGCTATAACCCAGGGAAAGAGGGAGGAGGAGACTCCGGTTGAA |
| | TGTTTCGAACCCTCGATGCTGAAGAAGAAGCAGCTAACTGTCCTGG |
| | ATCTGCATCCAGGAGCCGGAAAAACCAGGAGAGTTCTTCCTGAAAT |
| | AGTCCGTGAAGCCATAAAAAAGAGACTCCGGACAGTGATCTTGGC |
| | ACCAACTAGGGTTGTCGCTGCTGAGATGGAGGAAGCCTTGAGAGG |
| | ACTTCCGGTGCGTTACATGACAACAGCAGTCAACGTCACCCATTCT |
| | GGGACAGAAATCGTTGATTTGATGTGCCATGCCACTTTCACTTCAC |
| | GCTTACTACAACCCATCAGAGTCCCTAATTACAATCTCAACATCAT |
| | GGATGAAGCCCACTTCACAGACCCCTCAAGTATAGCTGCAAGAGGA |
| | TACATATCAACAAGGGTTGAAATGGGCGAGGCGGCTGCCATTTTTA |
| | TGACTGCCACACCACCAGGAACCCGTGATGCGTTTCCTGACTCTAA |
| | CTCACCAATCATGGACACAGAAGTGGAAGTCCCAGAGAGAGCCTG |
| | GAGCTCAGGCTTTGATTGGGTGACAGACCATTCTGGGAAAACAGTT |
| | TGGTTCGTTCCAAGCGTGAGAAACGGAAATGAAATCGCAGCCTGTC |
| | TGACAAAGGCTGGAAAGCGGGTCATACAGCTCAGCAGGAAGACTT |
| | TTGAGACAGAATTTCAGAAAACAAAAAATCAAGAGTGGGACTTTGT |
| | CATAACAACTGACATCTCAGAGATGGGCGCCAACTTCAAGGCTGAC |
| | CGGGTCATAGACTCTAGGAGATGCCTAAAACCAGTCATACTTGATG |
| | GTGAGAGAGTCATCTTGGCTGGGCCCATGCCTGTCACGCATGCTAG |
| | TGCTGCTCAGAGGAGAGGACGTATAGGCAGGAACCCTAACAAACC |
| | TGGAGATGAGTACATGTATGGAGGTGGGTGTGCAGAGACTGATGA |
| | AGGCCATGCACACTGGCTTGAAGCAAGAATGCTTCTTGACAACATC |
| | TACCTCCAGGATGGCCTCATAGCCTCGCTCTATCGGCCTGAGGCCG |
| | ATAAGGTAGCCGCCATTGAGGGAGAGTTTAAGCTGAGGACAGAGC |
| | AAAGGAAGACCTTCGTGGAACTCATGAAGAGAGGGAGACCTTCCCG |
| | TCTGGCTAGCCTATCAGGTTGCATCTGCCGGAATAACTTACACAGA |
| | CAGAAGATGGTGCTTTGATGGCACAACCAACAACACCATAATGGA |
| | AGACAGTGTACCAGCAGAGGTTTGGACAAAGTATGGAGAGAAGAG |
| | AGTGCTCAAACCGAGATGGATGGATGCTAGGGTCTGTTCAGACCAT |
| | GCGGCCCTGAAGTCGTTCAAAGAATTCGCCGCTGGAAAAAGAGGA |
| | GCGGCTTTGGGAGTAATGGAGGCCCTGGGAACACTGCCAGGACAC |
| | ATGACAGAGAGGTTTCAGGAAGCCATTGACAACCTCGCCGTGCTCA |
| | TGCGAGCAGAGACTGGAAGCAGGCCTTATAAGGCAGCGGCAGCCC |
| | AACTGCCGGAGACCCTAGAGACCATTATGCTCTTAGGTTTGCTGGG |
| | AACAGTTTCACTGGGGATCTTCTTTGTCTTGATGCGGAATAAGGGC |
| | ATCGGGAAGATGGGCTTTGGAATGGTAACCCTTGGGGCCAGTGCAT |
| | GGCTCATGTGGCTTTCGGAAATTGAACCAGCCAGAATTGCATGTGT |
| | CCTCATTGTTGTGTTTTTATTACTGGTGGTGCTCATACCCGAGCCAG |
| | AGAAGCAAAGATCTCCCCAAGATAACCAGATGGCAATTATCATCAT |
| | GGTGGCAGTGGGCCTTCTAGGTTTGATAACTGCAAACGAACTTGGA |

| SEQ ID NO | Sequence |
|---|---|
| | TGGCTGGAAAGAACAAAAAATGACATAGCTCATCTAATGGGAAGG<br>AGAGAAGAAGGAGCAACCATGGGATTCTCAATGGACATTGATCTG<br>CGGCCAGCCTCCGCCTGGGCTATCTATGCCGCATTGACAACTCTCAT<br>CACCCCAGCTGTCCAACATGCGGTAACCACTTCATACAACAACTAC<br>TCCTTAATGGCGATGGCCACACAAGCTGGAGTGCTGTTTGGCATGG<br>GCAAAGGGATGCCATTTTATGCATGGGACTTTGGAGTCCCGCTGCT<br>AATGATGGGTTGCTATTCACAATTAACACCCCTGACTCTGATAGTA<br>GCTATCATTCTGCTTGTGGCGCACTACATGTACTTGATCCCAGGCCT<br>ACAAGCGGCAGCAGCGCGTGCTGCCCAGAAAAGGACAGCAGCTGG<br>CATCATGAAGAATCCCGTTGTGGATGGAATAGTGGTAACTGACATT<br>GACACAATGACAATAGACCCCCAGGTGGAGAAGAAGATGGGACAA<br>GTGTTACTCATAGCAGTAGCCATCTCCAGTGCTGTGCTGCTGCGGA<br>CCGCCTGGGGATGGGGGGAGGCTGGAGCTCTGATCACAGCAGCGA<br>CCTCCACCTTGTGGGAAGGCTCTCCAAACAAATACTGGAACTCCTC<br>TACAGCCACCTCACTGTGCAACATCTTCAGAGGAAGCTATCTGGCA<br>GGAGCTTCCCTTATCTATACAGTGACGAGAAACGCTGGCCTGGTTA<br>AGAGACGTGGAGGTGGGACGGGAGAGACTCTGGGAGAGAAGTGGA<br>AAGCTCGTCTGAATCAGATGTCGGCCCTGGAGTTCTACTCTTATAA<br>AAAGTCAGGTATCACTGAAGTGTGTAGAGAGGAGGCTCGCCGTGCC<br>CTCAAGGATGGAGTGGCCACAGGAGGACATGCCGTATCCCGGGGA<br>AGTGCAAAGCTCAGATGGTTGGTGGAGAGAGGATATCTGCAGCCCC<br>ATGGGAAGGTTGTTGACCTCGGATGTGGCAGAGGGGGCTGGAGCT<br>ATTATGCCGCCACCATCCGCAAAGTGCAGGAGGTGAGAGGATACA<br>CAAAGGGAGGTCCCGGTCATGAAGAACCCATGCTGGTGCAAAGCT<br>ATGGGTGGAACATAGTTCGTCTCAAGAGTGGAGTGGACGTCTTCCA<br>CATGGCGGCTGAGCCGTGTGACACTCTGCTGTGTGACATAGGTGAG<br>TCATCATCTAGTCCTGAAGTGGAAGAGACACGAACACTCAGAGTGC<br>TCTCTATGGTGGGGGACTGGCTTGAAAAAAGACCAGGGGCCTTCTG<br>TATAAAGGTGCTGTGCCATACACCAGCACTATGATGGAAACCATG<br>GAGCGACTGCAACGTAGGCATGGGGGAGGATTAGTCAGAGTGCCA<br>TTGTCTCGCAACTCCACACATGAGATGTACTGGGTCTCTGGGGCAA<br>AAAGCAACATCATAAAAAGTGTGTCCACCACAAGTCAGCTCCTCCT<br>GGGACGCATGGATGGCCCCAGGAGGCCAGTGAAATATGAGGAGGA<br>TGTGAACCTCGGCTCGGGTACACGAGCTGTGGCAAGCTGTGCTGAG<br>GCTCCTAACATGAAAATCATCGGCAGGCGCATTGAGAGAATCCGCA<br>ATGAACATGCAGAAACATGGTTTCTTGATGAAAACCACCCATACAG<br>GACATGGGCCTACCATGGGAGCTACGAAGCCCCCACGCAAGGATC<br>AGCGTCTTCCCTCGTGAACGGGGTTGTTAGACTCCTGTCAAAGCCTT<br>GGGACGTGGTGACTGGAGTTACAGGAATAGCCATGACTGACACCA<br>CACCATACGGCCAACAAAGAGTCTTCAAAGAAAAAGTGGACACCA<br>GGGTGCCAGATCCCCAAGAAGGCACTCGCCAGGTAATGAACATGG<br>TCTCTTCCTGGCTGTGGAAGGAGCTGGGGAAACGCAAGCGGCCACG<br>CGTCTGCACCAAAGAAGAGTTTATCAACAAGGTGCGCAGCAATGCA<br>GCACTGGGAGCAATATTTGAAGAGGAAAAAGAATGGAAGACGGCT<br>GTGGAAGCTGTGAATGATCCAAGGTTTTGGGCCCTAGTGGATAGGG<br>AGAGAGAACACCACCTGAGAGGAGAGTGTCACAGCTGTGTGTACA<br>ACATGATGGGAAAAAGAGAAAAGAAGCAAGGAGAGTTCGGGAAA<br>GCAAAAGGTAGCCGCGCCATCTGGTACATGTGGTTGGGAGCCAGAT<br>TCTTGGAGTTTGAAGCCCTTGGATTCTTGAACGAGGACCATTGGAT<br>GGGAAGAGAGAACTCTGGAGGCGGAGTTGAAGGACTGGGACTGCA<br>GAGACTGGGCTATGTCCTTGAGGAGATGAGCCAGGCACCAGGAGG<br>GAAGATGTACGCAGATGACACTGCTGGCTGGGACACCCGCATTAGT<br>AAGTTTGATCTGGAGAATGAAGCTTTGATTACCAACCAAATGGAGG<br>AAGGGCACAGAACTCTGGCGTTGGCCGTGATTAAATACACATACCA<br>AAACAAAGTGGTGAAGGTCCTCAGACCAGCTGAAGGAGGAAAAAC<br>AGTTATGGACATCATTTCAAGACAAGACCAGAGAGGGAGTGGACA<br>AGTTGTCACTTATGCTCTCAACACATTCACCAACTTGGTGGTGCAGC<br>TTATCCGGAACATGGAAGCTGAGGAAGTGTTAGAGATGCAAGACTT<br>ATGGCTGTTGAGGAAGCCAGAGAAAGTGACCAGATGGTTGCAGAG<br>CAATGGATGGGATGGACTCAAACGAATGGCGGTCAGTGGAGATGA<br>CTGCGTTGTGAAGCCAATCGATGATAGGTTTGCACATGCCCTCAGG<br>TTCTTGAATGACATGGGAAAAGTTAGGAAAGACACACAGGAGTGG<br>AAACCCTCGACTGGATGGAGCAATTGGGAAGAAGTCCCGTTCTGCT<br>CCCACCACTTCAACAAGCTGTACCTCAAGGATGGGAGATCCATTGT<br>GGTCCCTTGCCGCCACCAAGATGAACTGATTGGCCGAGCTCGCGTT<br>TCACCAGGGGCAGGATGGAGCATCCGGGAGACTGCCTGTCTTGCAA<br>AATCATATGCGCAGATGTGGCAGCTCCTTTATTTCCACAGAAGAGA<br>CCTTCGACTGATGGCTAATGCCATTTGCTCGGCTGTACCAGTTGACT<br>GGGTACCAACTGGGAGAACCACCTGGTCAATCCATGGAAAGGGAG<br>AATGGATGACC |
| SEQ ID NO: 13 | FACSKKMTGKSIQPENLEYRIMLSVHGSQHSGMIVNITGHETLENRAK<br>VEITPNSPRAEATLGGFGSLGLDCEPRTGLDFSDLYYLTMNNKHWLVH<br>KEWFHDIPLPWHAGADTGTPHWNNKEALVEFKLAHAKRQTVVVLGS<br>QEGAVHTALAGALEAEMDGAKGRLSSGHLKCRLKMDKLRLKGVSYS |

SEQUENCES

| SEQ ID NO | Sequence |
|---|---|
| | LCTAAFTFTKIPAETLHGTVTVEVQYAGTLGPCKVPAQMAVDMQTLT<br>PVGRLITANPVITESTENSKMMLELDPPFGISYIVIGVGEKKITHHW |
| SEQ ID NO: 14 | FTCCKKMPGKSIQPENLEYRDMLPVHGSQHSGMIVNDIGHETDENRAK<br>VEVTPNSPRAEATLGGFGSLGLDCEPRTGLDFSDLYYLTMNNKHWLV<br>HKEWFHDIPLPWHAGADTGTPHWNNKEALVEFKDAHAKRQTVVVLG<br>SQEGAVHTALAGALEAEMDGAKGRLFSGHLKCRDKMDKLRLKGVSY<br>SLCTAAFTFTKVPAETLHGTVTVEVQSAGTDGPCKVPAQMAVDMQTL<br>TPVGRDITANPVITESTENSKMMLELDPPFGDSYIVIGVGDKKITHHW |
| SEQ ID NO: 15 | FTCSKKMTGKSIQPENLEYRIMLSVHGSQHSGMIVNDIGHETDENRAK<br>VEVTPNSPRAEATLGGFGSLGLDCEPRTGLDFSDLYYLTMNNKHWLV<br>HKEWFHDIPLPWHAGADTGTPHWNNKEALVEFKDAHAKRQTVVVLG<br>SQEGAVHTALAGALEAEMDGAKGRLFSGHLKCRLKMDKLRLKGVSY<br>SLCTAAFTFTKVPAETLHGTVTVEVQYAGTDGPCKVPAQMAVDMQTL<br>TPVGRLITANPVITESTENSKMMLELDPPFGDSYIVIGVGDKKITHHW |
| SEQ ID NO: 16 | FTCCKKMPGKSIQPENLEYRIMLPVHGSQHSGMIVNDIGHETDENRAK<br>VEVTPNSPRAEATLGGFGSLGLDCEPRTGLDFSDLYYLTMNNKHWLV<br>HKEWFHDIPLPWHAGADTGTPHWNNKEALVEFKDAHAKRQTVVVLG<br>SQEGAVHTALAGALEAEMDGAKGRLFSGHLKCRLKMDKLRLKGVSY<br>SLCTAAFTFTKVPAETLHGTVTVEVQSAGTDGPCKVPAQMAVDMQTL<br>TPVGRLITANPVITESTENSKMMLELDPPFGDSYIVIGVGDKKITHHW |
| SEQ ID NO: 17 | FTCSKKMTGKSIQPENLEYRIMLSVHGSQHSGMIVNDIGHETDENRAK<br>VEVTPNSPRAEATLGGFGSLGLDCEPRTGLDFSDLYYLTMNNKHRLVR<br>KEWFHDIPLPWHAGADTGTPHWNNKEALVEFKDAHAKRQTVVVLGS<br>QEGAVHTALAGALEAEMDGAKGRLFSGHLKCRLKMDKLRLKGVSYS<br>LCTAAFTFTKVPAETLHGTVTVEVQYAGTDGPCKVPAQMAVDMQTL<br>TPVGRLITANPVITESTENSKMMLELDPPFGDSYIVIGVGDKKITHHW |
| SEQ ID NO: 18 | FTCSKKMTGKSIQPENLEYRIMLSVHGSQHSGMIVNDIGHETDENRAK<br>VEVTPNSPRAEATLGGFGSLGLDCEPRTGLDFSDLYYLTMNNKHWLV<br>HKEWFHDIPLPWHAGADTGTPHWNNKEALVEFKDAHAKRQTVVVLG<br>SQEGAVHTALAGALEAEMDGAKGRLFSGHLKCRLKMDKLRLKGVSY<br>SLCTAVCTAAKVPAETLHGTVTVEVQYAGTDGPCKVPAQMAVDMQT<br>LTPVGRLITANPVITESTENSKMMLELDPPFGDSYIVIGVGDKKITHHW |
| SEQ ID NO: 19 | FACSKKMTGKSIQPENLEYRIMLSVHGSQHSGMIVNDTGHETDENRAK<br>VEITPNSPRAEATLGGFGSLGLDCEPRTGLDFSDLYYLTMNNKHWLVH<br>KEWFHDIPLPWHAGADTGTPHWNNKEALVEFKDAHAKRQTVVVLGS<br>QEGAVHTALAGALEAEMDGAKGRLSSGHLKCRLKMDKLRLKGVSYS<br>LCTAAFTFTKIPAETLHGTVTVEVQYAGTDGPCKVPAQMAVDMQTLT<br>PVGRLITANPVITESTENSKMMLELDPPFGDSYIVIGVGEKKITHHW |
| SEQ ID NO: 20 | CTGTTGCTGCTTCAGACTGCGACAGTTCGAGTTTGAAGCGAAAGCT<br>AGCAACAGTATCAACAGGTTTTATTTGGATTTGGAAACGAGAGTTT<br>CTGGTCATGAAAAACCCAAAAAGAAATCCGGAGGATTCCGGATT<br>GTCAATATGCTAAAACGCGGAGTAGCCCGTGTGAGCCCCTTTGGGG<br>GCTTGAAGAGGCTGCCAGCCGGACTTCTGCTGGGTCATGGGCCCAT<br>CAGGATGGTCTTGGCGATTCTAGCCTTTTTGAGATTCACGGCAATCA<br>AGCCATCACTGGGTCTCATCAATAGATGGGGTTCAGTGGGGAAAAA<br>AGAGGCTATGGAAATAATAAAGAAGTTCAAGAAAGATCTGGCTGC<br>CATGCTGAGAATAATCAATGCTAGGAAGGAGAAGAAGAGACGAGG<br>CGCAGAAACTAGTGTCGGAATTGTTGGCCTCCTGCTGACCACAGCT<br>ATGGCAGCGGAGGTCACTAGACGTGGGAGTGCATACTATATGTACT<br>TGGACAGAAACGATGCTGGGGAGGCCATATCTTTTCCAACCACATT<br>GGGGATGAATAAGTGTTATATACAGATCATGGATCTTGGACACATG<br>TGTGATGCCACCATGAGCTATGAATGCCCTATGCTGGATGAGGGGG<br>TGGAACCAGATGACGTCGATTGTTGGTGCAACACGACGTCAACTTG<br>GGTTGTGTACGGAACCTGCCATCACAAAAAAGGTGAAGCACGGAG<br>ATCTAGAAGAGCCGTGACGCTCCCCTCCCATTCCACTAGGAAGCTG<br>CAAACGCGGTCGCAAACCTGGTTGGAATCAAGAGAATACACAAAG<br>CACTTGATTAGAGTCGAAAATTGGATATTCAGGAACCCTGGTTTCG<br>CTTTAGCAGCAGCTGCCATCGCGTGGCTTTTGGGAAGCTCAACGAG<br>CCAAAAAGTCATATACTTGGTCATGATACTGCTGATTGCCCCGGCA<br>TACAGCATCAGGTGCATAGGAGTCAGCAATAGGGACTTTGTGAAG<br>GTATGTCAGGTGGGACTTGGGTTGATGTTGTCTTGGAACATGGAGG<br>TTGTGTCACCGTAATGGCACAGGACAAACCGACTGTCGACATAGAG<br>CTGGTTACAACAACAGTCAGCAACATGGCGGAGGTAAGATCCTACT<br>GCTATGAGGCATCAATATCAGACATGGCTTCGCCCAGCCGCTGCCC<br>AACACAAGCCGCTGCCTACCTTGACAAGCAATCAGACACTCAATAT<br>GTCTGCAAAAGAACGTTAGTGGACAGCGACTGGGTT |

| SEQ ID NO | Sequence |
|---|---|
| SEQ ID NO: 21 | AGTTGTTACTGTTGCTGACTCAGACTGCGACAGTTCGAGTTTGAAG<br>CGAAAGCTAGCAACAGTATCAACAGGTTTTATTTGGATTTGGAAAC<br>GAGAGTTTCTGGTCATGAAAAACCCAAAAAAGAAATCCGGAGGAT<br>TCCGGATTGTCAATATGCTAAAACGCGGAGTAGCCCGTGTGAGCCC<br>CTTTGGGGGCTTGAAGAGGCTGCCAGCCGGACTTCTGCTGGGTCAT<br>GGGCCCATCAGGATGGTCTTGGCAATTCTAGCCTTTTTGAGATTCAC<br>GGCAATCAAGCCATCACTGGGTCTCATCAATAGATGGGGTTCAGTG<br>GGGAAAAAAGAGGCTATGGAAATAATAAAGAAGTTCAAGAAAGAT<br>CTGGCTGCCATGCTGAGAATAATCAATGCTAGGAAGGAGAAGAAG<br>AGACGAGGCGCAGATACTAGTGTCGGAATTGTTGGCCTCCTGCTGA<br>CCACAGCTATGGCAGCGGAGGTCACTAGACGTGGGAGTGCATACTA<br>TATGTACTTGGACAGAAACGATGCTGGGGAGGCCATATCTTTTCCA<br>ACCACATTGGGGATGAATAAGTGTTATATACAGATCATGGATCTTG<br>GACACATGTGTGATGCCACCATGAGCTATGAATGCCCTATGCTGGA<br>TGAGGGGGTGGAACCAGATGACGTCGATTGTTGGTGCAACACGAC<br>GTCAACTTGGGTTGTGTACGGAACCTGCCATCACAAAAAAGGTGAA<br>GCACGGAGATCTAGAAGAGCTGTGACGCTCCCCTCCCATTCCACTA<br>GGAAGCTGCAAACGCGGTCGCAAACCTGGTTGGAATCAAGAGAAT<br>ACACAAAGCACTTGATTAGAGTCGAAAATTGGATATTCAGGAACCC<br>TGGCTTCGCGTTAGCAGCAGCTGCCATCGCTTGGCTTTTGGGAAGCT<br>CAACGAGCCAAAAAGTCATATACTTGGTCATGATACTGCTGATTGC<br>CCCGGCATACAGCATCAGGTGCATAGGAGTCAGCAATAGGGACTTT<br>GTGGAAGGTATGTCAGGTGGGACTTGGGTTGATGTTGTCTTGGAAC<br>ATGGAGGTTGTGTCACCGTAATGGCACAGGACAAACCGACTGTCGA<br>CATAGAGCTGGTTACAACAACAGTCAGCAACATGGCGGAGGTAAG<br>ATCCTACTGCTATGAGGCATCAATATCAGACATGGCTTCGGACAGC<br>CGCTGCCCAACACAAGGTGAAGCCTACCTTGACAAGCAATCAGACA<br>CTCAATATGTCTGCAAAAGAACGTTAGTGGACAGAGGCTGGGGAA<br>ATGGATGTGGACTTTTTGGCAAAGGGAGTCTGGTGACATGCGCTAA<br>GTTTGCATGCTCCAAGAAAATGACCGGGAAGAGCATCCAGCCAGA<br>GAATCTGGAGTACCGGATAATGCTGTCAGTTCATGGCTCCCAGCAC<br>AGTGGGATGATCGTTAATGACACAGGACATGAAACTGATGAGAAT<br>AGAGCGAAGGTTGAGATAACGCCCAATTCACCAAGAGCCGAAGCC<br>ACCCTGGGGGGTTTTGGAAGCCTAGGACTTGATTGTGAACCGAGGA<br>CAGGCCTTGACTTTTCAGATTTGTATTACTTGACTATGAATAACAAG<br>CACTGGTTGGTTCACAAGGAGTGGTTCCACGACATTCCATTACCTTG<br>GCACGCTGGGGCAGACACCGGAACTCCACACTGGAACAACAAAGA<br>AGCACTGGTAGAGTTCAAGGACGCACATGCCAAAAGGCAAACTGT<br>CGTGGTTCTAGGGAGTCAAGAAGGAGCAGTTCACACGGCCCTTGCT<br>GGAGCTCTGGAGGCTGAGATGGATGGTGCAAAGGGAAGGCTGTCC<br>TCTGGCCACTTGAAATGTCGCCTGAAAATGGATAAACTTAGATTGA<br>AGGGCGTGTCATACTCCTTGTGTACCGCAGCGTTCACATTCCACCAA<br>GATCCCGGCTGAAACACTGCACGGGACAGTCACAGTGGAGGTACA<br>GTACGCAGGGACAGATGGACCTTGCAAGGTTCCAGCTCAGATGGCG<br>GTGGACATGCAAACTCTGACCCCAGTTGGGAGGTTGATAACCGCTA<br>ACCCCGTAATCACTGAAAGCACTGAGAACTCTAAGATGATGCTGAA<br>ACTTGATCCACCATTTGGGGACTCTTACATTGTCATAGGAGTCGGG<br>GAGAAGAAGATCACCCACCACTGGCACAGGAGTGGCAGCACCATT<br>GGAAAAGCATTTGAAGCCACTGTGAGAGGTGCCAAGAGAATGGCA<br>GTCTTGGGAGACACAGCCTGGGACTTTGGATCAGTTGGAGGCGCTC<br>TCAACTCATTGGGCAAGGGCATCCATCAAATTTTTGGAGCAGCTTT<br>CAAATCATTGTTTGGAGGAATGTCCTGGTTCTCACAAATTCTCATTG<br>GAACGTTGCTGATGTGGTTGGGTCTGAACACAAAGAATGGATCTAT<br>TTCCCTTATGTGCTTGGCCTTAGGGGAGTGTTGATCTTCTTATCCA<br>CAGCCGTCTCTGCTGATGTGGGGTGCTCGGTGGACTTCTCAAAGAA<br>GGGAGACGAGATGCGGTACAGGGGTGTTCGTCTATAACGACGTTGAA<br>GCCTGGAGGGACAGGTACAAGTACCATCCTGACTCCCCCCGTAGAT<br>TGGCAGCAGCAGTCAAGCAAGCCTGGGAAGATGGTATCTGCGGGA<br>TCTCCTCTGTTTCAAGAATGGAAAACATCATGTGGAGATCAGTAGA<br>AGGGGAGCTCAACGCAATCCTGGAAGAGAATGGAGTTCAACTGAC<br>GGTCGTTGTGGGATCTGTAAAAAACCCCATGTGGAGAGGTCCACAG<br>AGATTGCCCGTGCCTGTGAACGAGCTGCCCCACGGCTGGAAGGCTT<br>GGGGGAAATCGCACTTCGTCAGAGCAGCAAAGACAAATAACAGCT<br>TTGTCGTGGATGGTGACACACTGAAGGAATGCCCACTCAAACATAG<br>AGCATGGAACAGCTTTCTTGTGGAGGATCATGGGTTCGGGGTATTT<br>CACACTAGTGTCTGGCTCAAGGTTAGAGAAGATTATTCATTAGAGT<br>GTGATCCAGCCGTTATTGGAACAGCTGTTAAGGGAAAGGAGGCTGT<br>ACACAGTGATCTAGGCTACTGGATTGAGAGTGAGAAGAATGCAC<br>ATGGAGGCTGAAGAGGGCCCATCTGATCGAGATGAAAACATGTGA<br>ATGGCCAAAGTCCCACACATTGTGGACAGATGGAATAGAAGAGAG<br>TGATCTGATCATACCCAAGTCTTTAGCTGGGCCACTCAGCCATCAC<br>AATACCAGAGAGGGCTACAGGACCCAAATGAAAGGGCCATGGCAC<br>AGTGAAGAGCTTGAAATTCGGTTTGAGGAATGCCCAGGCACTAAGG<br>TCCACGTGGAGGAAACATGTGGAACAAGAGGACCATCTCTGAGAT |

| SEQ ID NO | Sequence |
|---|---|
| | CAACCACTGCAAGCGGAAGGGTGATCGAGGAATGGTGCTGCAGGG |
| | AGTGCACAATGCCCCCACTGTCGTTCCGGGCTAAAGATGGCTGTTG |
| | GTATGGAATGGAGATAAGGCCCAGGAAAGAACCAGAAAGCAACTT |
| | AGTAAGGTCAATGGTGACTGCAGGATCAACTGATCACATGGATCAC |
| | TTCTCCCTTGGAGTGCTTGTGATTCTGCTCATGGTGCAGGAAGGGCT |
| | GAAGAAGAGAATGACCACAAAGATCATCATAAGCACATCAATGGC |
| | AGTGCTGGTAGCTATGATCCTGGGAGGATTTTCAATGAGTGACCTG |
| | GCTAAGCTTGCAATTTTGATGGGTGCCACCTTCGCGGAAATGAACA |
| | CTGGAGGAGATGTAGCTCATCTGGCGCTGATAGCGGCATTCAAAGT |
| | CAGACCAGCGTTGCTGGTATCTTTCATCTTCAGAGCTAATTGGACAC |
| | CCCGTGAAAGCATGCTGCTGGCCTTGGCCTCGTGTCTTTTGCAAACT |
| | GCGATCTCCGCCTTGGAAGGCGACCTGATGGTTCTCATCAATGGTTT |
| | TGCTTTGGCCTGGTTGGCAATACGAGCGATGGTTGTTCCACGCACT |
| | GATAACATCACCTTGGCAATCCTGGCTGCTCTGACACCACTGGCCC |
| | GGGGCACACTGCTTGTGGCGTGGAGAGCAGGCCTTGCTACTTGCGG |
| | GGGGTTTATGCTCCTCTCTCTGAAGGGAAAAGGCAGTGTGAAGAAG |
| | AACTTACCATTTGTCATGGCCCTGGGACTAACCGCTGTGAGGCTGG |
| | TCGACCCCATCAACGTGGTGGGGCTGCTGTTGCTCACAAGGAGTGG |
| | GAAGCGGAGCTGGCCCCCTAGCGAAGTACTCACAGCTGTTGGCCTG |
| | ATATGCGCATTGGCTGGAGGGTTCGCCAAGGCAGATATAGAGATGG |
| | CTGGGCCCATGGCCGCGGTCGGTCTGCTAATTGTCAGTTACGTGGT |
| | CTCAGGAAAGAGTGTGGACATGTACATTGAAAGAGCAGGTGACAT |
| | CACATGGGAAAAAGATGCGGAAGTCACTGGAAACAGTCCCCGGCT |
| | CGATGTGGCGCTAGATGAGAGTGGTGATTTCTCCCTGGTGGAGGAT |
| | GACGGTCCCCCCATGAGAGAGATCATACTCAAGGTGGTCCTGATGA |
| | CCATCTGTGGCATGAACCCAATAGCCATACCCTTTGCAGCTGGAGC |
| | GTGGTACGTATACGTGAAGACTGGAAAAAGGAGTGGTGCTCTATGG |
| | GATGTGCCTGCTCCCAAGGAAGTAAAAAAGGGGGAGACCACAGAT |
| | GGAGTGTACAGAGTAATGACTCGTAGACTGCTAGGTTCAACACAAG |
| | TTGGAGTGGGAGTTATGCAAGAGGGGGTCTTTCACACTATGTGGCA |
| | CGTCACAAAAGGATCCGCGCTGAGAAGCGGTGAAGGGAGACTTGA |
| | TCCATACTGGGGAGATGTCAAGCAGGATCTGGTGTCATACTGTGGT |
| | CCATGGAAGCTAGATGCCGCCTGGGACGGGCACAGCGAGGTGCAG |
| | CTCTTGGCCGTGCCCCCCGGAGAGAGAGCGAGGAACATCCAGACTC |
| | TGCCCGGAATATTTAAGACAAAGGATGGGGACATTGGAGCGGTTGC |
| | GCTGGATTACCCAGCAGGAACTTCAGGATCTCCAATCCTAGACAAG |
| | TGTGGGAGAGTGATAGGACTTTATGGCAATGGGGTCGTGATCAAAA |
| | ATGGGAGTTATGTTAGTGCCATCACCCAAGGGAGGAGGGAGGAAG |
| | AGACTCCTGTTGAGTGCTTCGAGCCTTCGATGCTGAAGAAGAAGCA |
| | GCTAACTGTCTTAGACTTGCATCCTGGAGCTGGGAAAACCAGGAGA |
| | GTTCTTCCTGAAATAGTCCGTGAAGCCATAAAAACAAGACTCCGTA |
| | CTGTGATCTTAGCTCCAACCAGGGTTGTCGCTGCTGAAATGGAGGA |
| | AGCCCTTAGAGGGCTTCCAGTGCGTTATATGACAACAGCAGTCAAT |
| | GTCACCCACTCTGGAACAGAAATCGTCGACTTAATGTGCCATGCCA |
| | CCTTCACTTCACGTCTACTACAGCCAATCAGAGTCCCCAACTATAAT |
| | CTGTATATTATGGATGAGGCCCACTTCACAGATCCCTCAAGTATAG |
| | CAGCAAGAGGATACATTTCAACAAGGGTTGAGATGGGCGAGGCGG |
| | CTGCCATCTTCATGACCGCCACGCCACCAGGAACCCGTGACGCATT |
| | TCCGGACTCCAACTCACCAATTATGGACACCGAAGTGGAAGTCCCA |
| | GAGAGAGCCTGGAGCTCAGGCTTTGATTGGGTGACGGATTATTCTG |
| | GAAAAACAGTTTGGTTTGTTCCAAGCGTGAGGAACGGCAATGAGAT |
| | CGCAGCTTGTCTGACAAAGGCTGGAAAACGGGTCATACAGCTCAGC |
| | AGAAAGACTTTTGAGACAGAGTTCCAGAAAACAAAACATCAAGAG |
| | TGGGACTTTGTCGTGACAACTGACATTTCAGAGATGGGCGCCAACT |
| | TTAAAGCTGACCGTGTCATAGATTCCAGGAGATGCCTAAAGCCGGT |
| | CATACTTGATGGCGAGAGAGTCATTCTGGCTGGACCCATGCCTGTC |
| | ACACATGCCAGCGCTGCCCAGAGGAGGGGCGCATAGGCAGGAAT |
| | CCCAACAAACCTGGAGATGAGTATCTGTATGGAGGTGGGTGCGCAG |
| | AGACTGACGAAGACCATGCACACTGGCTTGAAGCAAGAATGCTCCT |
| | TGACAATATTTACCTCCAAGATGGCCTCATAGCCTCGCTCTATCGAC |
| | CTGAGGCCGACAAAGTAGCAGCCATTGAGGGAGAGTTCAAGCTTA |
| | GGACGGAGCAAAGGAAGACCTTTGTGGAACTCATGAAAAGAGGAG |
| | ATCTTCCTGTTTGGCTGGCCTATCAGGTTGCATCTGCCGGAATAACC |
| | TACACAGATAGAAGATGGTGCTTTGATGGCACGACCAACAACACCA |
| | TAATGGAAGACAGTGTGCCGGCAGAGGTGTGGACCAGACACGGAG |
| | AGAAAAGAGTGCTCAAACCGAGGTGGATGGACGCCAGAGTTTGTT |
| | CAGATCATGCGGCCCTGAAGTCATTCAAGGAGTTTGCCGCTGGGAA |
| | AAGAGGAGCGGCTTTTGGAGTGATGGAAGCCCTGGGAACACTGCC |
| | AGGACACATGACAGAGAGATTCCAGGAAGCCATTGACAACCTCGC |
| | TGTGCTCATGCGGGCAGAGACTGGAAGCAGGCCTTACAAAGCCGC |
| | GGCGGCCCAATTGCCGGAGACCCTAGAGACCATTATGCTTTTGGGG |
| | TTGCTGGGAACAGTCTCGCTGGGAATCTTTTTCGTCTTGATGAGGAA |
| | CAAGGGCATAGGGAAGATGGGCTTTGGAATGGTGACTCTTGGGGCC |
| | AGCGCATGGCTCATGTGGCTCTCGGAAATTGAGCCAGCCAGAATTG |
| | CATGTGTCCTCATTGTTGTGTTCCTATTGCTGGTGGTGCTCATACCT |

| SEQ ID NO | Sequence |
|---|---|
| | GAGCCAGAAAAGCAAAGATCTCCCCAGGACAACCAAATGGCAATC |
| | ATCATCATGGTAGCAGTAGGTCTTCTGGGCTTGATTACCGCCAATG |
| | AACTCGGATGGTTGGAGAGAACAAAGAGTGACCTAAGCCATCTAA |
| | TGGGAAGGAGAGAGGAGGGGGCAACCATGGGATTCTCAATGGACA |
| | TTGACCTGCGGCCAGCCTCAGCTTGGGCCATCTATGCTGCCTTGACA |
| | ACTTTCATTACCCCAGCCGTCCAACATGCAGTGACCACTTCATACA |
| | ACAACTACTCCTTAATGGCGATGGCCACGCAAGCTGGAGTGTTGTT |
| | TGGTATGGGCAAAGGGATGCCATTCTACGCATGGGACTTTGGAGTC |
| | CCGCTGCTAATGATAGGTTGCTACTCACAATTAACGCCCCTGACCCT |
| | AATAGTGGCCATCATTTTGCTCGTGGCGCACTACATGTACTTGATCC |
| | CAGGGCTGCAGGCAGCAGCTGCGCGTGCTGCCCAGAAGAGAACGG |
| | CAGCTGGCATCATGAAGAACCCTGTTGTGGATGGAATAGTGGTGAC |
| | TGACATTGACACAATGACAATTGACCCCCAAGTGGAGAAAAAGAT |
| | GGGACAGGTGCTACTCATGGCAGTAGCCGTCTCCAGCGCCATACTG |
| | TCGCGGACCGCCTGGGGGTGGGGGGAGGCTGGGGCCCTGATCACA |
| | GCCGCAACTTCCACTTTGTGGGAAGGCTCTCCGAACAAGTACTGGA |
| | ACTCCTCTACAGCCACTTCACTGTGTAACATTTTTAGGGGAAGTTAC |
| | TTGGCTGGAGCTTCTCTAATCTACACAGTAACAAGAAACGCTGGCT |
| | TGGTCAAGAGACGTGGGGGTGGAACAGGAGAGACCCTGGGAGAGA |
| | AATGGAAGGCCCGCTTGAACCAGATGTCGGCCCTGGAGTTCTACTC |
| | CTACAAAAAGTCAGGCATCACCGAGGTGTGCAGAGAAGAGGCCCG |
| | CCGCGCCCTCAAGGACGGTGTGGCAACGGGAGGCCATGCTGTGTCC |
| | CGAGGAAGTGCAAAGCTGAGATGGTTGGTGGAGCGGGGATACCTG |
| | CAGCCCTATGGAAAGGTCATTGATCTTGGATGTGGCAGAGGGGGCT |
| | GGAGTTACTACGCCGCCACCATCCGCAAAGTTCAAGAAGTGAAAG |
| | GATACACAAAAGGAGGCCCTGGTCATGAAGAACCCGTGTTGGTGC |
| | AAAGCTATGGGTGGAACATAGTCCGTCTTAAGAGTGGGGTGGACGT |
| | CTTTCATATGGCGGCTGAGCCGTGTGACACGTTGCTGTGTGACATA |
| | GGTGAGTCATCATCTAGTCCTGAAGTGGAAGAAGCACGGACGCTCA |
| | GAGTCCTCTCCATGGTGGGGGATTGGCTTGAAAAAAGACCAGGAGC |
| | CTTTTGTATAAAAGTGTTGTGCCCATACACCAGCACTATGATGGAA |
| | ACCCTGGAGCGACTGCAGCGTAGGTATGGGGAGGACTGGTCAGA |
| | GTGCCACTCTCCCGCAACTCTACACATGAGATGTACTGGGTCTCTG |
| | GAGCGAAAAGCAACACCATAAAAAGTGTGTCCACCACGAGCCAGC |
| | TCCTCTTGGGGCGCATGGACGGGCCTAGGAGGCCAGTGAAATATGA |
| | GGAGGATGTGAATCTCGGCTCTGGCACGCGGGCTGTGGTAAGCTGC |
| | GCTGAAGCTCCCAACATGAAGATCATTGGTAACCGCATTGAAAGGA |
| | TCCGCAGTGAGCACGCGGAAACGTGGTTCTTTGACGAGAACCACCC |
| | ATATAGGACATGGGCTTACCATGGAAGCTATGAGGCCCCCACACAA |
| | GGGTCAGCGTCCTCTCTAATAAACGGGGTTGTCAGGCTCCTGTCAA |
| | AACCCTGGGATGTGGTGACTGGAGTCACAGGAATAGCCATGACCG |
| | ACACCACACCGTATGGTCAGCAAAGAGTTTTCAAGGAAAAAGTGG |
| | ACACTAGGGTGCCAGACCCCCAAGAAGGCACTCGTCAGGTTATGAG |
| | CATGGTCTCTTCCTGGTTGTGGAAAGAGCTAGGCAAACACAAACGG |
| | CCACGAGTCTGTACCAAAGAAGAGTTCATCAACAAGGTTCGTAGCA |
| | ATGCAGCATTAGGGGCAATATTTGAAGAGGAAAAAGAGTGGAAGA |
| | CTGCAGTGGAAGCTGTGAACGATCCAAGGTTCTGGGCTCTAGTGGA |
| | CAAGGAAAGAGAGCACCACCTGAGAGGAGAGTGCCAGAGTTGTGT |
| | GTACAACATGATGGGAAAAAGAGAAAAGAAACAAGGGGAATTTGG |
| | AAAGGCCAAGGGCAGCCGCGCCATCTGGTATATGTGGCTAGGGGCT |
| | AGATTTCTAGAGTTCGAAGCCCTTGGATTCTTGAACGAGGATCACT |
| | GGATGGGGAGAGAGAACTCAGGAGGTGGTGTTGAAGGGCTGGGAT |
| | TACAAAGACTCGGATATGTCCTAGAAGAGATGAGTCGCATACCAGG |
| | AGGAAGGATGTATGCAGATGACACTGCTGGCTGGGACACCCGCATC |
| | AGCAGGTTTGATCTGGAGAATGAAGCTCTAATCACCAACCAAATGG |
| | AGAAAGGGCACAGGGCCTTGGCATTGGCCATAATCAAGTACACAT |
| | ACCAAAACAAAGTGGTAAAGGTCCTTAGACCAGCTGAAAAAGGGA |
| | AGACAGTTATGGACATTATTCGAGACAAGACCAAAGGGGAGCG |
| | GACAAGTTGTCACTTACGCTCTTAACACATTTACCAACCTAGTGGTG |
| | CAACTCATTCGGAATATGGAGGCTGAGGAAGTTCTAGAGATGCAAG |
| | ACTTGTGGCTGCTGCGGAGGTCAGAGAAAGTGACCAACTGGTTGCA |
| | GAGCAACGGATGGGATAGGCTCAAACGAATGGCAGTCAGTGGAGA |
| | TGATTGCGTTGTGAAGCCAATTGATGATAGGTTTGCACATGCCCTC |
| | AGGTTCTTGAATGATATGGGAAAAGTTAGGAAGGACACACAAGAG |
| | TGGAAACCCTCAACTGGATGGGACAACTGGGAAGAAGTTCCGTTTT |
| | GCTCCCACCACTTCAACAAGCTCCATCTCAAGGACGGGAGGTCCAT |
| | TGTGGTTCCCTGCCGCACCAAGATGAACTGATTGGCCGGGCCCGC |
| | GTCTCTCCAGGGCGGGATGGAGCATCCGGGAGACTGCTTGCCTAG |
| | CAAAATCATATGCGCAAATGTGGCAGCTCCTTTATTTCCACAGAAG |
| | GGACCTCCGACTGATGGCCAATGCCATTTGTTCATCTGTGCCAGTTG |
| | ACTGGGTTCCAACTGGGAGAACTACCTGGTCAATCCATGGAAAGGG |
| | AGAATGGATGACCACTGAAGACATGCTTGTGGTGTGAACAGAGT |
| | GTGGATTGAGGAGAACGACCACATGGAAGACAAGACCCCAGTTAC |
| | GAAATGGACAGACATTCCCTATTTGGGAAAAGGGAAGACTTGTG |
| | GTGTGGATCTCTCATAGGGCACAGACCGCGCACCACCTGGGCTGAG |

| SEQ ID NO | Sequence |
|---|---|
| | AACATTAAAAACACAGTCAACATGGTGCGCAGGATCATAGGTGAT
GAAGAAAAGTACATGGACTACCTATCCACCCAAGTTCGCTACTTGG
GTGAAGAAGGGTCTACACCTGGAGTGCTGTAAGCACCAATCTTAAT
GTTGTCAGGCCTGCTAGTCAGCCACAGCTTGGGGAAAGCTGTGCAG
CCTGTGACCCCCCCAGGAGAAGCTGGGAAACCAAGCCTATAGTCAG
GCCGAGAACGCCATGGCACGGAAGAAGCCATGCTGCCTGTGAGCC
CCTCAGAGGACACTGAGTCAAAAAACCCCACGCGCTTGGAGGCGC
AGGATGGGAAAAGAAGGTGGCGACCTTCCCCACCCTTCAATCTGGG
GCCTGAACTGGAGATCAGCTGTGGATCTCCAGAAGAGGGACTAGTG
GTTAGAGGAGACCCCCCGGAAAACGCAAAACAGCATATTGACGCT
GGGAAAGACCAGAGACTCCATGAGTTTCCACCACGCTGGCCGCCAG
GCACAGATCGCCGAATAGCGGCGGCCGGTGTGGGAAATCCATGG
GTCTT |
| SEQ ID NO: 22 | AGTAAATCCTGTGTGCTAATTGAGGTGCATTGGTCTGCAAATCGAG
TTGCTAGGCAATAAACACATTTGGATTAATTTTAATCGTTCGTTGAG
CGATTAGCAGAGAACTGACCAGAACATGTCTGGTCGTAAAGCTCAG
GGAAAAACCCTGGGCGTCAATATGGTACGACGAGGAGTTCGCTCCT
TGTCAAACAAAATAAAACAAAAAACAAAACAAATTGGAAACAGAC
CTGGACCTTCAAGAGGTGTTCAAGGATTTATCTTTTTCTTTTTGTTC
AACATTTTGACTGGAAAAAAGATCACAGCCCACCTAAAGAGGTTGT
GGAAAATGCTGGACCCAAGACAAGGCTTGGCTGTTCTAAGGAAAG
TCAAGAGAGTGGTGGCCAGTTTGATGAGAGGATTGTCCTCAAGGAA
ACGCCGTTCCCATGATGTTCTGACTGTGCAATTCCTAATTTTGGGAA
TGCTGTTGATGACGGGTGGAGTGACCTTGGTGCGAAAAACAGATG
GTTGCTCCTAAATGTGACATCTGAGGACCTCGGGAAAACATTCTCT
GTGGGCACAGGCAACTGCACAACAAACATTTTGGAAGCCAAGTACT
GGTGCCCAGACTCAATGGAATACAACTGTCCCAATCTCAGTCCAAG
AGAGGAGCCAGATGACATTGATTGCTGGTGCTATGGGTGGAAAA
CGTTAGAGTCGCATATGGTAAGTGTGACTCAGCAGGCAGGTCTAGG
AGGTCAAGAAGGGCCATTGACTTGCCTACGCATGAAAACCATGGTT
TGAAGACCCGGCAAGAAAAATGGATGACTGGAAGAATGGGTGAAA
GGCAACTCCAAAAGATTGAGAGATGGTTCGTGAGGAACCCCTTTTT
TGCCAGTGACGGCTCTGACCATTGCCTACCTTGTGGGAAGCAACATG
ACGCAACGAGTCGTGATTGCCCTACTGGTCTTGGCTGTTGGTCCGG
CCTACTCAGCTCACTGCATTGGAATTACTGACAGGGATTCATTGA
GGGGGTGCATGGAGGAACTTGGGTTTCAGCTACCCTGGAGCAAGAC
AAGTGTGTCACTGTTATGGCCCCTGACAAGCCTTCATTGGACATCTC
ACTAGAGACAGTAGCCATTGATAGACCTGCTGAGGTGAGGAAAGT
GTGTTACAATGCAGTTCTCACTCATGTGAAGATTAATGACAAGTGC
CCCAGCACTGGAGAGGCCCACCTAGCTGAAGAGAACGAAGGGGAC
AATGCGTGCAAGCGCACTTATTCTGATAGAGGCTGGGGCAATGGCT
GTGGGCCTATTTGGGAAAGGGAGCATTGTGGCATGCGCCAAATTCAC
TTGTGCCAAATCCATGAGTTTGTTTGAGGTTGATCAGACCAAAATTC
AGTATGTCATCAGAGCACAATTGCATGTAGGGGCCAAGCAGGAAA
ATTGGAATACCGACATTAAGACTCTCAAGTTTGATGCCCTGTCAGG
CTCCCAGGAAGTCGAGTTCATTGGGTATGGAAAAGCTACACTGGAA
TGCCAGGTGCAAACTGCGGTGGACTTTGGTAACAGTTACATCGCTG
AGATGGAAACAGAGAGCTGGATAGTGGACAGACAGTGGGCCAGG
ACTTGACCCTGCCATGGCAGAGTGGAAGTGGCGGGTGTGGAGAG
AGATGCATCATCTTGTCGAATTTGAACCTCCGCATGCCGCCACTATC
AGAGTACTGGCCCTGGGAAACCAGGAAGGCTCCTTGAAAACAGCT
CTTACTGGCGCAATGAGGGTTACAAAGGACACAAATGACAACAAC
CTTTACAAACTACATGGTGGACATGTTTCTTGCAGAGTGAAATTGTC
AGCTTTGACACTCAAGGGGACATCCTACAAAATATGCACTGACAAA
ATGTTTTTTGTCAAGAACCCAACTGACACTGGCCATGGCACTGTTGT
GATGCAGGTGAAGTGTCAAAAGGAGCCCCCTGCAGGATTCCAGT
GATAGTAGCTGATGATCTTACAGCGGCAATCAATAAAGGCATTTTG
GTTACAGTTAACCCCATCGCCTCAACCAATGATGATGAAGTGCTGA
TTGAGGTGAACCCACCTTTTGGAGACAGCTACATTATCGTTGGGAG
AGGAGATTCACGTCTCACTTACCAGTGGCACAAAGAGGGAAGCTCA
ATAGGAAAGTTGTTCACTCAGACCATGAAAGGCGTGGAACGCCTGG
CCGTCATGGGAGACACCGCCTGGGATTTCAGCTCCGCTGGAGGGTT
CTTCACTTCGGTTGGGAAAGGAATTCATACGGTGTTTGGCTCTGCCT
TTCAGGGGCTATTTGGCGGCTTGAACTGGATAACAAAGGTCATCAT
GGGGGCGGTACTTATATGGGTTGGCATCAACACAAGAAACATGAC
AATGTCCATGAGCATGATCTTGGTAGGAGTGATCATGATGTTTTGT
CTCTAGGAGTTGGGGCGGATCAAGGATGCGCCATCAACTTTGGCAA
GAGAGAGCTCAAGTGCGGAGATGGTATCTTCATATTTAGAGACTCT
GATGACTGGCTGAACAAGTACTCATACTATCCAGAAGATCCTGTGA
AGCTTGCATCAATAGTGAAAGCCTCTTTTGAAGAAGGGAAGTGTGG
CCTAAATTCAGTTGACTCCCTTGAGCATGAGATGTGGAGAAGCAGG
GCAGATGAGATCAATGCCATTTTTGAGGAAAACGAGGTGGACATTT
CTGTTGTCGTGCAGGATCCAAAGAATGTTTACCAGAGAGGAACTCA
TCCATTTTCCAGAATTCGGGATGGTCTGCAGTATGGTTGGAAGACTT |

-continued

| SEQ ID NO | Sequence |
|---|---|
| | GGGGTAAGAACCTTGTGTTCTCCCCAGGGAGGAAGAATGGAAGCTT |
| | CATCATAGATGGAAAGTCCAGGAAAGAATGCCCGTTTTCAAACCGG |
| | GTCTGGAATTCTTTCCAGATAGAGGAGTTTGGGACGGGAGTGTTCA |
| | CCACACGCGTGTACATGGACGCAGTCTTTGAATACACCATAGACTG |
| | CGATGGATCTATCTTGGGTGCAGCGGTGAACGGAAAAAAGAGTGC |
| | CCATGGCTCTCCAACATTTTGGATGGGAAGTCATGAAGTAAATGGG |
| | ACATGGATGATCCACACCTTGGAGGCATTAGATTACAAGGAGTGTG |
| | AGTGGCCACTGACACATACGATTGGAACATCAGTTGAAGAGAGTG |
| | AAATGTTCATGCCGAGATCAATCGGAGGCCCAGTTAGCTCTCACAA |
| | TCATATCCCTGGATACAAGGTTCAGACGAACGGACCTTGGATGCAG |
| | GTACCACTAGAAGTGAAGAGAGAAGCTTGCCCAGGGACTAGCGTG |
| | ATCATTGATGGCAACTGTGATGGACGGGGAAAATCAACCAGATCCA |
| | CCACGGATAGCGGGAAAGTTATTCCTGAATGGTGTTGCCGCTCCTG |
| | CACAATGCCGCCTGTGAGCTTCCATGGTAGTGATGGGTGTTGGTAT |
| | CCCATGGAAATTAGGCCAAGGAAAACGCATGAAAGCCATCTGGTG |
| | CGCTCCTGGGTTACAGCTGGAGAAATACATGCTGTCCCTTTTGGTTT |
| | GGTGAGCATGATGATAGCAATGGAAGTGGTCCTAAGGAAAAGACA |
| | GGGACCAAAGCAAATGTTGGTTGGAGGAGTAGTGCTCTTGGGAGC |
| | AATGCTGGTCGGGCAAGTAACTCTCCTTGATTTGCTGAAACTCACA |
| | GTGGCTGTGGGATTGCATTTCCATGAGATGAACAATGGAGGAGACG |
| | CCATGTATATGGCGTTGATTGCTGCCTTTTCAATCAGACCAGGGCTG |
| | CTCATCGGCTTTGGGCTCAGGACCCTATGGAGCCCTCGGGAACGCC |
| | TTGTGCTGACCCTAGGAGCAGCCATGGTGGAGATTGCCTTGGGTGG |
| | CGTGATGGGCGGCCTGTGGAAGTATCTAAATGCAGTTTCTCTCTGC |
| | ATCCTGACAATAAATGCTGTTGCTTCTAGGAAAGCATCAAATACCA |
| | TCTTGCCCCTCATGGCTCTGTTGACACCTGTCACTATGGCTGAGGTG |
| | AGACTTGCCGCAATGTTCTTTTGTGCCGTGGTTATCATAGGGGTCCT |
| | TCACCAGAATTTCAAGGACACCTCCATGCAGAAGACTATACCTCTG |
| | GTGGCCCTCACACTCACATCTTACCTGGGCTTGACACAACCTTTTTT |
| | GGGCCTGTGTGCATTTCTGGCAACCCGCATATTTGGGCGAAGGAGT |
| | ATCCCAGTGAATGAGGCACTCGCAGCAGCTGGTCTAGTGGGAGTGC |
| | TGGCAGGACTGGCTTTTCAGGAGATGGAGAACTTCCTTGGTCCGAT |
| | TGCAGTTGGAGGACTCCTGATGATGCTGGTTAGCGTGGCTGGGAGG |
| | GTGGATGGGCTAGAGCTCAAGAAGCTTGGTGAAGTTTCATGGGAAG |
| | AGGAGGCGGAGATCAGCGGGAGTTCCGCCCGCTATGATGTGGCACT |
| | CAGTGAACAAGGGGAGTTCAAGCTGCTTTCTGAAGAGAAAGTGCC |
| | ATGGGACCAGGTTGTGATGACCTCGCTGGCCTTGGTTGGGGCTGCC |
| | CTCCATCCATTTGCTCTTCTGCTGGTCCTTGCTGGGTGGCTGTTTTCAT |
| | GTCAGGGGAGCTAGGAGAAGTGGGGATGTCTTGTGGGATATTCCA |
| | CTCCTAAGATCATCGAGGAATGTGAACATCTGGAGGATGGGATTTA |
| | TGGCATATTCCAGTCAACCTTCTTGGGGGCCTCCCAGCGAGGAGTG |
| | GGAGTGGCACAGGGAGGGGTGTTCCACACAATGTGGCATGTCACA |
| | AGAGGAGCTTTCCTTGTCAGGAATGGCAAGAAGTTGATTCCATCTT |
| | GGGCTTCAGTAAAGGAAGACCTTGTCGCCTATGGTGGCTCATGGAA |
| | GTTGGAAGGCAGATGGGATGGAGAGGAAGAGGTCCAGTTGATCGC |
| | GGCTGTTCCAGGAAAGAACGTGGTCAACGTCCAGACAAAACCGAG |
| | CTTGTTCAAAGTGAGGAATGGGGGAGAAATCGGGGCTGTCGCTCTT |
| | GACTATCCGAGTGGCACTTCAGGATCTCCTATTGTTAACAGGAACG |
| | GAGAGGTGATTGGGCTGTACGGCAATGGCATCCTTGTCGGTGACAA |
| | CTCCTTCGTGTCCGCCATATCCCAGACTGAGGTGAAGGAAGAAGGA |
| | AAGGAGGAGCTCCAAGAGATCCCGACAATGCTAAAGAAAGGAATG |
| | ACAACTGTCCTTGATTTTCATCCTGGAGCTGGGAAGACAAGACGTT |
| | TCCTCCCACAGATCTTGGCCGAGTGCGCACGGAGACGCTTGCGCAC |
| | TCTTGTGTTGGCCCCCACCAGGGTTGTTCTTTCTGAAATGAAGGAGG |
| | CTTTTCACGGCCTGGACGTGAAATTCCACACACAGGCTTTTTCCGCT |
| | CACGGCAGCGGGAGAGAAGTCATTGATGCCATGTGCCATGCCACCC |
| | TAACTTACAGGATGTTGGAACCAACTAGGGTTGTTAACTGGGAAGT |
| | GATCATTATGGATGAAGCCCATTTTTTGGATCCAGCTAGCATAGCC |
| | GCTAGAGGTTGGGCAGCGCACAGAGCTAGGGCAAATGAAAGTGCA |
| | ACAATCTTGATGACAGCCACACCGCCTGGGACTAGTGATGAATTTC |
| | CACATTCAAATGGTGAAATAGAAGATGTTCAAACGGACATACCCAG |
| | TGAGCCCTGGAACACAGGGCATGACTGGATCCTAGCTGACAAAAG |
| | GCCCACGGCATGGTTCCTTCCATCCATCAGAGCTGCAAATGTCATG |
| | GCTGCCTCTTTGCGTAAGGCTGGAAAGAGTGTGGTGGTCCTGAACA |
| | GGAAAACCTTTGAGAGAGAATACCCCACGATAAAGCAGAAGAAAC |
| | CTGACTTTATATTGGCCACTGACATAGCTGAAATGGGAGCCAACCT |
| | TTGCGTGGAGCGAGTGCTGGATTGCAGGACGGCTTTTAAGCCTGTG |
| | CTTGTGGATGAAGGGAGGAAGGTGGCAATAAAAGGGCCACTTCGT |
| | ATCTCCGCATCCTCTGCTGCTCAAAGGAGGGGGCGCATTGGGAGAA |
| | ATCCCAACAGAGATGGAGACTCATACTACTATTCTGAGCCTACAAG |
| | TGAAAATAATGCCCACCACGTCTGCTGGTTGGAGGCCCTCAATGCTC |
| | TTGGACAACATGGAGGTGAGGGTGGAATGGTCGCCCCACTCTATG |
| | GCGTTGAAGGAACTAAAACACCAGTTTCCCCTGGTGAAATGAGACT |
| | GAGGGATGACCAGAGGAAAGTCTTCAGAGAACTAGTGAGGAATTG |
| | TGACCTGCCCGTTTGGCTTTCGTGGCAAGTGGCCAAGGCTGGTTTG |

| SEQ ID NO | Sequence |
|---|---|
| | AAGACGAATGATCGTAAGTGGTGTTTTGAAGGCCCTGAGGAACATG<br>AGATCTTGAATGACAGCGGTGAAACAGTGAAGTGCAGGGCTCCTG<br>GAGGAGCAAAGAAGCCTCTGCGCCCAAGGTGGTGTGATGAAAGGG<br>TGTCATCTGACCAGAGTGCGCTGTCTGAATTTATTAAGTTTGCTGAA<br>GGTAGGAGGGGAGCTGCTGAAGTGCTAGTTGTGCTGAGTGAACTCC<br>CTGATTTCCTGGCTAAAAAAGGTGGAGAGGCAATGGATACCATCAG<br>TGTGTTCCTCCACTCTGAGGAAGGCTCTAGGGCTTACCGCAATGCA<br>CTATCAATGATGCCTGAGGCAATGACAATAGTCATGCTGTTTATAC<br>TGGCTGGACTACTGACATCGGGAATGGTCATCTTTTTCATGTCTCCC<br>AAAGGCATCAGTAGAATGTCTATGGCGATGGGCACAATGGCCGGCT<br>GTGGATATCTCATGTTCCTTGGAGGCGTCAAACCCACTCACATCTCC<br>TATGTCATGCTCATATTCTTTGTCCTGATGGTGGTTGTGATCCCCGA<br>GCCAGGGCAACAAAGGTCCATCCAAGACAACCAAGTGGCATACCT<br>CATTATTGGCATCCTGACGCTGGTTTCAGCGGTGGCAGCCAACGAG<br>CTAGGCATGCTGGAGAAAACCAAAGAGGACCTCTTTGGGAAGAAG<br>AACTTAATTCCATCTAGTGCTTCACCCTGGAGTTGGCCGGATCTTGA<br>CCTGAAGCCAGGAGCTGCCTGGACAGTGTACGTTGGCATTGTTACA<br>ATGCTCTCTCCAATGTTGCACCACTGGATCAAAGTCGAATATGGCA<br>ACCTGTCTCTGTCTGGAATAGCCCAGTCAGCCTCAGTCCTTTCTTTC<br>ATGGACAAGGGGATACCATTCATGAAGATGAATATCTCGGTCATAA<br>TGCTGCTGGTCAGTGGCTGGAATTCAATAACAGTGATGCCTCTGCT<br>CTGTGGCATAGGGTGCGCCATGCTCCACTGGTCTCTCATTTTACCTG<br>GAATCAAAGCGCAGCAGTCAAAGCTTGCACAGAGAAGGGTGTTCC<br>ATGGCGTTGCCGAGAACCCTGTGGTTGATGGGAATCCAACAGTTGA<br>CATTGAGGAAGCTCCTGAAATGCCTGCCCTTTATGAGAAGAAACTG<br>GCTCTATATCTCCTTCTTGCTCTCAGCCTAGCTTCTGTTGCCATGTGC<br>AGAACGCCCTTTTCATTGGCTGAAGGCATTGTCCTAGCATCAGCTG<br>CCTTAGGGCCGCTCATAGAGGGAAACACCAGCCTTCTTTGGAATGG<br>ACCCATGGCTGTCTCCATGACAGGAGTCATGAGGGGGAATCACTAT<br>GCTTTTGTGGGAGTCATGTACAATCTATGGAAGATGAAAACTGGAC<br>GCCGGGGAGCGCGAATGGAAAAACTTTGGGTGAAGTCTGGAAGA<br>GGGAACTGAATCTGTTGGACAAGCGACAGTTTGAGTTGTATAAAAG<br>GACCGACATTGTGGAGGTGGATCGTGATACGGCACGCAGGCATTTG<br>GCCGAAGGGAAGGTGGACACCGGGGTGGCGGTCTCCAGGGGGACC<br>GCAAAGTTAAGGTGGTTCCATGAGCGTGGCTATGTCAAGCTGGAAG<br>GTAGGGTGATTGACCTGGGGTGTGGCCGCGGAGGCTGGTGTTACTA<br>CGCTGCTGCGCAAAAGGAAGTGAGTGGGGTCAAAGGATTTACTCTT<br>GGAAGAGACGGCCATGAGAAACCCATGAATGTGCAAAGTCTGGGA<br>TGGAACATCATCACCTTCAAGGACAAAACTGATATCCACCGCCTAG<br>AACCAGTGAAATGTGACACCCTTTTGTGTGACATTGGAGAGTCATC<br>ATCGTCATCGGTCACAGAGGGGGAAAGGACCGTGAGAGTTCTTGAT<br>ACTGTAGAAAAATGGCTGGCTTGTGGGGTTGACAACTTCTGTGTGA<br>AGGTGTTAGCTCCATACATGCCAGATGTTCTCGAGAAACTGGAATT<br>GCTCCAAAGGAGGTTTGGCGGAACAGTGATCAGGAACCCTCTCTCC<br>AGGAATTCCACTCATGAAATGTACTACGTGTCTGGAGCCCGCAGCA<br>ATGTCACATTTACTGTGAACCAAACATCCCGCCTCCTGATGAGGAG<br>AATGAGGCGTCCAACTGGAAAAGTGACCCTGGAGGCTGACGTCATC<br>CTCCCAATTGGGACACGCAGTGTTGAGACAGACAAGGGACCCCTGG<br>ACAAAGAGGCCATAGAAGAAAGGGTTGAGAGGATAAAATCTGAGT<br>ACATGACCTCTTGGTTTTATGACAATGACAACCCCTACAGGACCTG<br>GCACTACTGTGGCTCCTATGTCACAAAAACCTCAGGAAGTGCGGCG<br>AGCATGGTAAATGGTGTTATTAAAATTCTGACATATCCATGGGACA<br>GGATAGAGGAGGTCACAAGAATGGCAATGACTGACACAACCCCTT<br>TTGGACAGCAAAGAGTGTTTAAAGAAAAAGTTGACACCAGAGCAA<br>AGGATCCACCAGCGGGAACTAGGAAGATCATGAAAGTTGTCAACA<br>GGTGGCTGTTCCGCCACCTGGCCAGAGAAAAGAACCCCAGACTGTG<br>CACAAAGGAAGAATTTATTGCAAAAGTCCGAAGTCATGCAGCCATT<br>GGAGCTTACCTGGAAGAACAAGAACAGTGGAAGACTGCCAATGAG<br>GCTGTCCAAGACCCAAAGTTCTGGGAACTGGTGGATGAAGAAAGG<br>AAGCTGCACCAACAAGGCAGGTGTCGGACTTGTGTGTACAACATGA<br>TGGGGAAAAGAGAGAAGAAGCTGTCAGAGTTTGGGAAAGCAAAGG<br>GAAGCCGTGCCATATGGTATATGTGGCTGGGAGCGCGGTATCTTGA<br>GTTTGAGGCCCTGGGATTCCTGAATGAGGACCATTGGGCTTCCAGG<br>GAAAACTCAGGAGGAGGAGTGGAAGGCATTGGCTTACAATACCTA<br>GGATATGTGATCAGAGACCTGGCTGCAATGGATGGTGGTGGATTCT<br>ACGCGGATGACACCGCTGGATGGGACACGCGCATCACAGAGGCAG<br>ACCTTGATGATGAACAGGAGATCTTGAACTACATGAGCCCACATCA<br>CAAAAAACTGGCACAAGCAGTGATGGAAATGACATACAAGAACAA<br>AGTGGTGAAAGTGTTGAGACCAGCCCCAGGAGGGAAAGCCTACAT<br>GGATGTCATAAGTCGACGAGACCAGAGAGGATCCGGGCAGGTAGT<br>GACTTATGCTCTGAACACCATCACCAACTTGAAAGTCCAATTGATC<br>AGAATGGCAGAAGCAGAGATGGTGATACATCACCAACATGTTCAA<br>GATTGTGATGAATCAGTTCTGACCAGGCTGGAGGCATGGCTCACTG<br>AGCACGGATGTGACAGACTGAAGAGGATGGCGGTGAGTGGAGACG<br>ACTGTGTGGTCCGGCCCATCGATGACAGGTTCGGCCTGGCCCTGTC |

| SEQ ID NO | Sequence |
|---|---|
| | CCATCTCAACGCCATGTCCAAGGTTAGAAAGGACATATCTGAATGG
CAGCCATCAAAAGGGTGGAATGATTGGGAGAATGTGCCCTTCTGTT
CCCACCACTTCCATGAACTACAGCTGAAGGATGGCAGGAGGATTGT
GGTGCCTTGCCGAGAACAGGACGAGCTCATTGGGAGAGGAAGGGT
GTCTCCAGGAAACGGCTGGATGATCAAGGAAACAGCTTGCCTCAGC
AAAGCCTATGCCAACATGTGGTCACTGATGTATTTTCACAAAAGGG
ACATGAGGCTACTGTCATTGGCTGTTTCCTCAGCTGTTCCCACCTCA
TGGGTTCCACAAGGACGCACAACATGGTCGATTCATGGGAAAGGG
GAGTGGATGACCACGGAAGACATGCTTGAGGTGTGGAACAGAGTA
TGGATAACCAACAACCCACACATGCAGGACAAGACAATGGTGAAA
AAATGGAGAGATGTCCCTTATCTAACCAAGAGACAAGACAAGCTGT
GCGGATCACTGATTGGAATGACCAATAGGGCCACCTGGGCCTCCCA
CATCCATTTAGTCATCCATCGTATCCGAACGCTGATTGGACAGGAG
AAATACACTGACTACCTAACAGTCATGGACAGGTATTCTGTGGATG
CTGACCTGCAACTGGGTGAGCTTATCTGAAACACCATCTAACAGGA
ATAACCGGGATACAAACCACGGGTGGAGAACCGGACTCCCCACAA
CCTGAAACCGGGATATAAACCACGGCTGGAGAACCGGGCTCCGCA
CTTAAAATGAAACAGAAACCGGGATAAAAACTACGGATGGAGAAC
CGGACTCCACACATTGAGACAGAAGAAGTTGTCAGCCCAGAACCCC
ACACGAGTTTTGCCACTGCTAAGCTGTGAGGCAGTGCAGGCTGGGA
CAGCCGACCTCCAGGTTGCGAAAAACCTGGTTTCTGGGACCTCCCA
CCCCAGAGTAAAAAGAACGGAGCCTCCGCTACCACCCTCCCACGTG
GTGGTAGAAAGACGGGGTCTAGAGGTTAGAGGAGACCCTCCAGGG
AACAAATAGTGGGACCATATTGACGCCAGGGAAAGACCGGAGTGG
TTCTCTGCTTTTCCTCCAGAGGTCTGTGAGCACAGTTTGCTCAAGAA
TAAGCAGACCTTTGGATGACAAACACAAAACCACT |
| SEQ ID NO: 23 | MKNPKKKSGGFRIVNMLKRGVARVNPLGGLKRLPAGLLLGHGPIRMV
LAILAFLRFTAIKPSLGLINRWGSVGKKEAMEIIKKFKKDLAAMLRIINA
RKERKRRGADTSIGIIGLLLTTAMAAEITRRGSAYYMYLDRSDAGKAIS
FATTLGVNKCHVQIMDLGHTMCDATMSYECPMLDEGVEPDDVDCWC
NTTSTWVVYGTCHHKKGEARRSRRAVTLPSHSTRKLQTRSQTWLESR
EYTKHLIKVENWIFRNPGFALVAVAIAWLLGSSTSQKVIYLVMILLIAP
AYSIRCIGVSNRDFVEGMSGGTWVDVVLEHGGCVTVMAQDKPTVDIE
LVTTTVSNMAEVRSYCYEASISDMASDSRCPTQGEAYLDKQSDTQYV
CKRTLVDRGWGNGCGLFGKGSLVTCAKFTCSKKMTGKSIQPENLEYR
IMLSVHGSQHSGMIVNDIGHETDENRAKVEVTPNSPRAEATLGGFGSL
GLDCEPRTGLDFSDLYYLTMNNKEWLVHKEWFHDIPLPWHAGADTG
TPHWNNKEALVEFKDAHAKRQTVVVLGSQEGAVHTALAGALEAEMD
GAKGRLFSGHLKCRLKMDKLRLKGVSYSLCTAAFTFTKVPAETLHGT
VTVEVQYAGTDGPCKVPAQMAVDMQTLTPVGRLITANPVITESTENS
KMMLELDPPFGDSYIVIGVGDKKITHHWHRSGSTIGKAFEATVRGAKR
MAVLGDTAWDFGSVGGVFNSLGKGIHQIFGAAFKSLFGGMSWFSQILI
GTLLVWLGLNTKNGSISLTCLALGGVMIFLSTAVSADVGCSVDFSKRE
TRCGTGVFIYNDVEAWRDRYKYHPDSPRRLAAAVKQAWEEGICGISS
VSRMENIMWKSVEGELNAILEENGVQLTVVVGSVKNPMWRGPQRLP
VPVNGLPHGWKAWGKSYFVRAAKTNNSFVVDGDTLKECPLKHRAW
NSFLVEDHGFGVFHTSVWLKVREDYSLECDPAVIGTAVKGREAAHSD
LGYWIESEKNDTWRLKRAHLIEMKTCEWPKSHTLWTDGVEESDLIIPK
SLAGPLSHHNTREGYRTQVKGPWHSEELEIRFEECPGTKVHVEETCGT
RGPSLRSTTASGRVIEEWCCRECTMPPLSFRAKDGCWYGMEIRPRKEP
ESNLVRSMVTAGSTDHMDHFSLGVLVILLMVQEGLKKRMTTKIIMSTS
MAVLVVMILGGFSMSDLAKLVILMGATFAEMNTGGDVAHLALVAAF
KVRPALLVSFILRANWTPRESMLLALASCLLQTAISALEGDLMVLVNG
FALAWLAIRAMAVPRTDNIALAILAALTPLARGTLLVAWRAGLATCG
GFMLLSLKGKGSVKKNLPFVMALGLTAVRVVDPINVVGLLLLTRSGK
RSWPPSEVLTAVGLICALAGGFAKADIEMAGPMAAVGLLIVSYVVSGK
SVDMYIERAGDITWEKDAEVTGNSPRLDVALDESGDFSLVEEDGPPMR
EIILKVVLMAICGMNPIAIPFAAGAWYVYVKTGKRSGALWDVPAPKEV
KKGETTDGVYRVMTRRLLGSTQVGVGVMQEGVFHTMWHVTKGAAL
RSGEGRLDPYWGDVKQDLVSYCGPWKLDAAWDGLSEVQLLAVPPGE
RARNIQTLPGIFKTKDGDIGAVALDYPAGTSGSPILDKCGRVIGLYGNG
VVIKNGSYVSAITQGKREEETPVECFEPSMLKKKQLTVLDLHPGAGKT
RRVLPEIVREAIKKRLRTVILAPTRVVAAEMEEALRGLPVRYMTTAVN
VTHSGTEIVDLMCHATFTSRLLQPIRVPNYNLNIMDEAHFTDPSSIAAR
GYISTRVEMGEAAAIFMTATPPGTRDAFPDSNSPIMDTEVEVPERAWSS
GFDWVTDHSGKTVWFVPSVRNGNEIAACLTKAGKRVIQLSRKTFETEF
QKTKNQEWDFVITTDISEMGANFKADRVIDSRRCLKPVILDGERVILAG
PMPVTHASAAQRRGRIGRNPNKPGDEYMYGGGCAETDEGHAHWLEA
RMLLDNIYLQDGLIASLYRPEADKVAAIEGEFKLRTEQRKTFVELMKR
GDLPVWLAYQVASAGITYTDRRWCFDGTTNNTIMEDSVPAEVWTKY
GEKRVLKPRWMDARVCSDHAALKSFKEFAAGKRGAALGVMEALGTL
PGHMTERFQEAIDNLAVLMRAETGSRPYKAAAAQLPETLETIMLLGLL
GTVSLGIFFVLMRNKGIGKMGFGMVTLGASAWLMWLSEIEPARIACV
LIVVFLLLVVLIPEPEKQRSPQDNQMAIIIMVAVGLLGLITANELGWLER |

| SEQ ID NO | Sequence |
|---|---|
| | TKNDIAHLMGRREEGATMGFSMDIDLRPASAWAIYAALTTLITPAVQH
AVTTSYNNYSLMAMATQAGVLFGMGKGMPFYAWDFGVPLLMMGCY
SQLTPLTLIVAIILLVAHYMYLIPGLQAAAARAAQKRTAAGIMKNPVV
DGIVVTDIDTMTIDPQVEKKMGQVLLIAVAISSAVLLRTAWGWEAG
ALITAATSTLWEGSPNKYWNSSTATSLCNIFRGSYLAGASLIYTVTRNA
GLVKRRGGGTGETLGEKWKARLNQMSALEFYSYKKSGITEVCREEAR
RALKDGVATGGHAVSRGSAKLRWLVERGYLQPHGKVVDLGCRGG
WSYYAATIRKVQEVRGYTKGGPGHEEPMLVQSYGWNIVRLKSGVDV
FHMAAEPCDTLLCDIGESSSSPEVEETRTLRVLSMVGDWLEKRPGAFCI
KVLCPYTSTMMETMERLQRRHGGGLVRVPLSRNSTHEMYWVSGAKS
NIIKSVSTTSQLLLGRMDGPRRPVKYEEDVNLGSGTRAVASCAEAPNM
KIIGRRIERIRNEHAETWFLDENHPYRTWAYHGSYEAPTQGSASSLVNG
VVRLLSKPWDVVTGVTGIAMTDTTPYGQQRVFKEKVDTRVPDPQEGT
RQVMNMVSSWLWKELGKRKRPRVCTKEEFINKVRSNAALGAIFEEEK
EWKTAVEAVNDPRFWALVDREREHHLRGECHSCVYNMMGKREKKQ
GEFGKAKGSRAIWYMWLGARFLEFEALGFLNEDHWMGRENSGGGVE
GLGLQRLGYVLEEMSQAPGGKMYADDTAGWDTRISKFDLENEALITN
QMEEGHRTLALAVIKYTYQNKVVKVLRPAEGGKTVMDIISRQDQRGS
GQVVTYALNTFTNLVVQLIRNMEAEEVLEMQDLWLLRKPEKVTRWL
QSNGWDGLKRMAVSGDDCVVKPIDDRFAHALRFLNDMGKVRKDTQE
WKPSTGWSNWEEVPFCSHHFNKLYLKDGRSIVVPCRHQDELIGRARV
SPGAGWSIRETACLAKSYAQMWQLLYFHRRDLRLMANAICSAVPVD
WVPTGRTTWSIHGKGEWMT |
| SEQ ID NO: 24 | ATGTTCACCTGTTGCAAGAAGATGCCCGGCAAGAGCATCCAGCCCG
AGAACCTGGAATACCGGATCATGCTGCCTGTGCACGGCTCCCAGCA
CAGCGGCATGATCGTGAACGACATCGGCCACGAGACAGACGAGAA
CCGGGCCAAGGTGGAAGTGACCCCCAACAGCCCTAGAGCCGAGGC
CACACTGGGCGGCTTTGGATCTCTGGGCCTGGACTGCGAGCCTAGA
ACCGGCCTGGATTTCAGCGACCTGTACTACCTGACCATGAACAACA
AGCACTGGCTGGTGCACAAAGAGTGGTTCCACGACATCCCCCTGCC
CTGGCATGCCGGCGCTGATACAGGCACACCCCACTGGAACAACAA
AGAGGCCCTGGTGGAGTTCAAGGACGCCCACGCCAAGAGGCAGAC
CGTGGTGGTGCTGGGATCTCAGGAAGGCGCCGTGCATACAGCTCTG
GCTGGCGCCCTGGAAGCCGAAATGGATGGCGCTAAGGGCCGGCTG
TTTAGCGGCCACCTGAAGTGCCGGCTGAAGATGGACAAGCTGCGGC
TGAAGGGCGTGTCCTACAGCCTGTGTACCGCCGCCTTCACCTTCACC
AAGGTGCCCGCCGAAACCCTGCACGGCACCGTGACAGTGGAAGTG
CAGTCTGCCGGCACCGACGGCCCTTGTAAAGTGCCTGCTCAGATGG
CCGTGGACATGCAGACCCTGACCCCTGTGGGCAGACTGATCACCGC
CAACCCCGTGATCACCGAGAGCACCGAGAACAGCAAGATGATGCT
GGAACTGGACCCCCCCTTCGGCGACTCCTACATCGTGATCGGCGTG
GGAGAGAAGAAGATCACCCACCACTGGTGA |
| SEQ ID NO: 25 | MKNPKKKSGGFRIVNMLKRGVARVSPFGGLKRLPAGLLLGHGPIRMV
LAILAFLRFTAIKPSLGLINRWGSVGKKEAMEIIKKFKKDLAAMLRIINA
RKEKKRRGADTSVGIVGLLLTTAMAAEVTRRGSAYYMYLDRNDAGE
AISFPTTLGMNKCYIQIMDLGHMCDATMSYECPMLDEGVEPDDVDCW
CNTTSTWVVYGTCHHKKGEARRSRRAVTLPSHSTRKLQTRSQTWLES
REYTKHLIRVENWIFRNPGFALAAAAIAWLLGSSTSQKVIYLVMILLIA
PAYSIRCIGVSNRDFVEGMSGGTWVDVVLEHGGCVTVMAQDKPTVDI
ELVTTTVSNMAEVRSYCYEASISDMASDSRCPTQGEAYLDKQSDTQY
VCKRTLVDRGWGNGCGLFGKGSLVTCAKFACSKKMTGKSIQPENLEY
RIMLSVHGSQHSGMIVNDTGHETDENRAKVEITPNSPRAEATLGGFGS
LGLDCEPRTGLDFSDLYYLTMNNKHWLVHKEWFHDIPLPWHAGADT
GTPHWNNKEALVEFKDAHAKRQTVVVLGSQEGAVHTALAGALEAEM
DGAKGRLSSGHLKCRLKMDKLRLKGVSYSLCTAAFTFTKIPAETLHGT
VTVEVQYAGTDGPCKVPAQMAVDMQTLTPVGRLITANPVITESTENS
KMMLELDPPFGDSYIVIGVGEKKITHHWHRSGSTIGKAFEATVRGAKR
MAVLGDTAWDFGSVGGALNSLGKGIHQIFGAAFKSLFGGMSWFSQILI
GTLLMWLGLNTKNGSISLMCLALGGVLIFLSTAVSADVGCSVDFSKKE
TRCGTGVFVYNDVEAWRDRYKYHPDSPRRLAAAVKQAWEDGICGISS
VSRMENIMWRSVEGELNAILEENGVQLTVVVGSVKNPMWRGPQRLP
VPVNELPHGWKAWGKSYFVRAAKTNNSFVVDGDTLKECPLKHRAW
NSFLVEDHGFGVFHTSVWLKVREDYSLECDPAVIGTAVKGKEAVHSD
LGYWIESEKNDTWRLKRAHLIEMKTCEWPKSHTLWTDGIEESDLIIPKS
LAGPLSHHNTREGYRTQMKGPWHSEELEIRFEECPGTKVHVEETCGTR
GPSLRSTTASGRVIEEWCCRECTMPPLSFRAKDGCWYGMEIRPRKEPE
SNLVRSMVTAGSTDHMDHFSLGVLVILLMVQEGLKKRMTTKIIISTSM
AVLVAMILGGFSMSDLAKLAILMGATFAEMNTGGDVAHLALIAAFKV
RPALLVSFIFRANWTPRESMLLALASCLLQTAISALEGDLMVLINGFAL
AWLAIRAMVVPRTDNITLAILAALTPLARGTLLVAWRAGLATCGGFM
LLSLKGKGSVKKNLPFVMALGLTAVRLVDPINVVGLLLLTRSGKRSWP
PSEVLTAVGLICALAGGFAKADIEMAGPMAAVGLLIVSYVVSGKSVD
MYIERAGDITWEKDAEVTGNSPRLDVALDESGDFSLVEDDGPPMREIIL |

| SEQ ID NO | Sequence |
|---|---|
| | KVVLMTICGMNPIAIPFAAGAWYVYVKTGKRSGALWDVPAPKEVKK<br>GETTDGVYRVMTRRLLGSTQVGVGVMQEGVFHTMWHVTKGSALRS<br>GEGRLDPYWGDVKQDLVSYCGPWKLDAAWDGHSEVQLLAVPPGER<br>ARNIQTLPGIFKTKDGDIGAVALDYPAGTSGSPILDKCGRVIGLYGNGV<br>VIKNGSYVSAITQGRREEETPVECFEPSMLKKKQLTVLDLHPGAGKTR<br>RVLPEIVREAIKTRLRTVILAPTRVVAAEMEEALRGLPVRYMTTAVNV<br>THSGTEIVDLMCHATFTSRLLQPIRVPNYNLYIMDEAHFTDPSSIAARG<br>YISTRVEMGEAAAIFMTATPPGTRDAFPDSNSPIMDTEVEVPERAWSSG<br>FDWVTDHSGKTVWFVPSVRNGNEIAACLTKAGKRVIQLSRKTFETEFQ<br>KTKHQEWDFVVTTDISEMGANFKADRVIDSRRCLKPVILDGERVILAG<br>PMPVTHASAAQRRGRIGRNPNKPGDEYLYGGGCAETDEDHAHWLEA<br>RMLLDNIYLQDGLIASLYRPEADKVAAIEGEFKLRTEQRKTFVELMKR<br>GDLPVWLAYQVASAGITYTDRRWCFDGTTNNTIMEDSVPAEVWTRH<br>GEKRVLKPRWMDARVCSDHAALKSFKEFAAGKRGAAFGVMEALGTL<br>PGHMTERFQEAIDNLAVLMRAETGSRPYKAAAAQLPETLETIMLLGLL<br>GTVSLGIFFVLMRNKGIGKMGFGMVTLGASAWLMWLSEIEPARIACV<br>LIVVFLLLVVLIPEPEKQRSPQDNQMAIIIMVAVGLLGLITANELGWLER<br>TKSDLSHLMGRREEGATIGFSMDIDLRPASAWAIYAALTTFITPAVQHA<br>VTTSYNNYSLMAMATQAGVLFGMGKGMPFYAWDFGVPLLMIGCYSQ<br>LTPLTLIVAIILLVAHYMYLIPGLQAAAARAAQKRTAAGIMKNPVVDGI<br>VVTDIDTMTIDPQVEKKMGQVLLIAVAVSSAILSRTAWGWGEAGALIT<br>AATSTLWEGSPNKYWNSSTATSLCNIFRGSYLAGASLIYTVTRNAGLV<br>KRRGGGTETLGEKWKARLNQMSALEFYSYKKSGITEVCREEARRAL<br>KDGVATGGHAVSRGSAKLRWLVERGYLQPYGKVIDLGCGRGGWSYY<br>AATIRKVQEVKGYTKGGPGHEEPVLVQSYGWNIVRLKSGVDVFHMA<br>AEPCDTLLCDIGESSSSPEVEEARTLRVLSMVGDWLEKRPGAFCIKVLC<br>PYTSTMMETLERLQRRYGGGLVRVPLSRNSTHEMYWVSGAKSNTIKS<br>VSTTSQLLLGRMDGPRRPVKYEEDVDLGSGTRAVVSCAEAPNMKIIGN<br>RIERIRSEHAETWFFDENHPYRTWAYHGSYEAPTQGSASSLINGVVRLL<br>SKPWDVVTGVTGIAMTDTTPYGQQRVFKEKVDTRVPDPQEGTRQVM<br>SMVSSWLWKELGKHKRPRVCTKEEFINKVRSNAALGAIFEEEKEWKT<br>AVEEAVNDPRFWALVDKEREHHLRGECQSCVYNMMGKREKKQGEFG<br>KAKGSRAIWYMWLGARFLEFEALGFLNEDHWMGRENSGGGVEGLGL<br>QRLGYVLEEMSRIPGGRMYADDTAGWDTRISRFDLENEALITNQMEK<br>GHRALALAIIKYTYQNKVVKVLRPAEKGKTVMDIISRQDQRGSGQVV<br>TYALNTFTNLVVQLIRNMEAEEVLEMQDLWLLRRSEKVTNWLQSNG<br>WDRLKRMAVSGDDCVVKPIDDRFAHALRFLNDMGKVRKDTQEWKPS<br>TGWDNWEEVPFCSHHFNKLHLKDGRSIVVPCRHQDELIGRARVSPGA<br>GWSIRETACLAKSYAQMWQLLYFHRRDLRLMANAICSSVPVDWVPT<br>GRTTWSIHGKGEWMTTEDMLVVWNRVWIEENDHMEDKTPVTKWTD<br>IPYLGKREDLWCGSLIGHRPRTTWAENIKNTVNMVRRIIGDEEKYMDY<br>LSTQVRYLGEEGSTPGVL |
| SEQ ID NO: 26 | GCCGCCACCATGTTCACCTGTTGCAAGAAGATGCCCGGCAAGAGCA<br>TCCAGCCCGAGAACCTGGAATACCGGATCATGCTGCCTGTGCACGG<br>CTCCCAGCACAGCGGCATGATCGTGAACGACATCGGCCACGAGAC<br>AGACGAGAACCGGGCCAAGGTGGAAGTGACCCCCAACAGCCCTAG<br>AGCCGAGGCCACACTGGGCGGCTTTGGATCTCTGGGCCTGGACTGC<br>GAGCCTAGAACCGGCCTGGATTTCAGCGACCTGTACTACCTGACCA<br>TGAACAACAAGCACTGGCTGGTGCACAAAGAGTGGTTCCACGACAT<br>CCCCCTGCCCTGGCATGCCGGCGCTGATACAGGCACACCCCACTGG<br>AACAACAAAGAGGCCCTGGTGGAGTTCAAGGACGCCCACGCCAAG<br>AGGCAGACCGTGGTGGTGCTGGGATCTCAGGAAGGCGCCGTGCAT<br>ACAGCTCTGGCTGGCGCCCTGGAAGCCGAAATGGATGGCGCTAAG<br>GGCCGGCTGTTTAGCGGCCACCTGAAGTGCCGGCTGAAGATGGACA<br>AGCTGCGGCTGAAGGGCGTGTCCTACAGCCTGTGTACCGCCGCCTT<br>CACCTTCACCAAGGTGCCCGCCGAAACCCTGCACGGCACCGTGACA<br>GTGGAAGTGCAGTCTGCCGGCACCGACGGCCCTTGTAAAGTGCCTG<br>CTCAGATGGCCGTGGACATGCAGACCCTGACCCCTGTGGGCAGACT<br>GATCACCGCCAACCCCGTGATCACCGAGAGCACCGAGAACAGCAA<br>GATGATGCTGGAACTGGACCCCCCCTTCGGCGACTCCTACATCGTG<br>ATCGGCGTGGGAGACAAGAAGATCACCCACCACTGGTGA |
| SEQ ID NO: 27 | MFTCCKKMPGKSIQPENLEYRIMLPVHGSQHSGMIVNDIGHETDENRA<br>KVEVTPNSPRAEATLGGFGSLGLDCEPRTGLDFSDLYYLTMNNKHWL<br>VHKEWFHDIPLPWHAGADTGTPHWNNKEALVEFKDAHAKRQTVVVL<br>GSQEGAVHTALAGALEAEMDGAKGRLFSGHLKCRLKMDKLRLKGVS<br>YSLCTAAFTFTKVPAETLHGTVTVEVQSAGTDGPCKVPAQMAVDMQT<br>LTPVGRLITANPVITESTENSKMMLELDPPFGDSYIVIGVGDKKITHHW |
| SEQ ID NO: 28 | GCCGCCACCATGTTCACCTGTTGCAAGAAGATGCCCGGCAAGAGCA<br>TCCAGCCCGAGAACCTGGAATACCGGGACATGCTGCCTGTGCACGG<br>CTCTCAGCACAGCGGCATGATCGTGAACGACATCGGCCACGAGACA<br>GACGAGAACCGGGCCAAGGTGGAAGTGACCCCCAACAGCCCTAGA<br>GCCGAGGCCACACTGGGCGGCTTTGGATCTCTGGGCCTGGACTGCG |

-continued

| SEQ ID NO | Sequence |
|---|---|
| | AGCCTAGAACCGGCCTGGATTTCAGCGACCTGTACTACCTGACCAT<br>GAACAACAAGCACTGGCTGGTGCACAAAGAGTGGTTCCACGACAT<br>CCCCCTGCCCTGGCATGCCGGCGCTGATACAGGCACACCCCACTGG<br>AACAACAAAGAGGCCCTGGTGGAGTTCAAGGACGCCCACGCCAAG<br>AGGCAGACCGTGGTGGTGCTGGGATCTCAGGAAGGCGCCGTGCAT<br>ACAGCTCTGGCTGGCGCCCTGGAAGCCGAAATGGATGGCGCTAAG<br>GGCCGGCTGTTTAGCGGCCACCTGAAGTGCCGGGACAAGATGGAC<br>AAGCTGCGGCTGAAGGGCGTGTCCTACAGCCTGTGTACCGCCGCCT<br>TCACCTTCACCAAGGTGCCCGCCGAAACCCTGCACGGCACCGTGAC<br>AGTGGAAGTGCAGTCTGCCGGCACCGACGGCCCTTGTAAAGTGCCT<br>GCTCAGATGGCCGTGGACATGCAGACCCTGACCCCTGTGGGCAGAG<br>ACATCACCGCCAACCCCGTGATCACCGAGAGCACCGAGAACAGCA<br>AGATGATGCTGGAACTGGACCCCCCCTTCGGCGACTCCTACATCGT<br>GATCGGCGTGGGAGACAAGAAGATCACCCACCACTGGTGA |
| SEQ ID NO: 29 | MFTCCKKMPGKSIQPENLEYRDMLPVHGSQHSGMIVNDIGHETDENR<br>AKVEVTPNSPRAEATLGGFGSLGLDCEPRTGLDFSDLYYLTMNNKHW<br>LVHKEWFHDIPLPWHAGADTGTPHWNNKEALVEFKDAHAKRQTVVV<br>LGSQEGAVHTALAGALEAEMDGAKGRLFSGHLKCRDKMDKLRLKGV<br>SYSLCTAAFTFTKVPAETLHGTVTVEVQSAGTDGPCKVPAQMAVDMQ<br>TLTPVGRDITANPVITESTENSKMMLELDPPFGDSYIVIGVGDKKITHH<br>W |
| SEQ ID NO: 30 | GCCGCCACCATGCTGACCAGCCAGAAAGTGATCTACCTCGTGATGA<br>TCGTGCTGATTGTGCCCGCCTACAGCATCAGCTGCATCGGCGTGTCC<br>AACCGGGACCTGGTGGAAGGCATGTCTGGCGGCACATGGGTGGAC<br>GTGGTGCTGGAACATGGCGGCTGCGTGACAGAGATGGCCCAGGAC<br>AAGCCCACCGTGGACATCGAGCTCGTGACCATGACCGTGTCCAATA<br>TGGCCGAAGTGCGGAGCTACTGCTACGAGGCCAGCCTGAGCGATAT<br>GGCCAGCGCCAGCAGATGTCCTACCCAGGGCGAGCCCAGCCTGGA<br>CAAGCAGAGCGATACAGAGCGTGTGCAAGCGGACCCTGGGCGA<br>TAGAGGCTGGGGCAATGGCTGCGGCATCTTCGGCAAGGGCAGCCTC<br>GTGACCTGCAGCAAGTTCACCTGTTGCAAGAAGATGCCCGGCAAGA<br>GCATCCAGCCCGAGAACCTGGAATACCGGATCATGCTGCCTGTGCA<br>CGGCTCCCAGCACAGCGGCATGATCGTGAACGACATCGGCCACGA<br>GACAGACGAGAACCGGGCCAAGGTGGAAGTGACCCCCAACAGCCC<br>TAGAGCCGAGGCCACACTGGGCGGCTTTGGATCTCTGGGCCTGGAC<br>TGCGAGCCTAGAACCGGCCTGGATTTCAGCGACCTGTACTACCTGA<br>CCATGAACAACAAGCACTGGCTGGTGCACAAAGAGTGGTTCCACG<br>ACATCCCCCTGCCCTGGCATGCCGGCGCTGATACAGGCACACCCCA<br>CTGGAACAACAAAGAGGCTCTGGTGGAATTCAAGGACGCCCACGC<br>CAAGCGGCAGACCGTGGTGGTGCTGGGATCTCAGGAAGGCGCCGT<br>GCATACAGCTCTGGCTGGCGCCCTGGAAGCCGAAATGGATGGCGCC<br>AAGGGCAGGCTGTTTAGCGGCCACCTGAAGTGCCGGCTGAAGATG<br>GACAAGCTGCGGCTGAAGGGCGTGTCCTACAGCCTGTGTACCGCCG<br>CCTTCACCTTCACCAAGGTGCCCGCCGAAACCCTGCACGGCACCGT<br>GACAGTGGAAGTGCAGAGCGCCGGAACCGACGGCCCTTGTAAAGT<br>GCCTGCCCAGATGGCCGTGGATATGCAGACCCTGACCCCCGTGGGC<br>AGACTGATCACCGCCAACCCTGTGATCACCGAGAGCACCGAGAAC<br>AGCAAGATGATGCTGGAACTGGACCCCCCCTTCGGCGACTCCTACA<br>TCGTGATCGGCGTGGGAGACAAGAAGATCACCCACCACTGGCACA<br>GAAGCGGCAGCACCATCGGCAAGGCCTTTGAGGCTACAGTGCGGG<br>GAGCCAAGAGAATGGCCGTGCTGGGGGATACCGCCTGGGATTTTGG<br>CTCTGTGGGCGGCGTGTTCAACTCCCTGGGCAAGGGAATCCACCAG<br>ATCTTCGGCGCTGCCTTCAAGAGCCTGTTCGGCGGCATGAGCTGGT<br>TCAGCCAGATCCTGATCGGCACCCTGCTCGTGTGGCTGGGCCTGAA<br>CACCAAGAACGGCAGCATCTCCCTGACCTGCCTGGCTCTGGGCGGA<br>GTGATGATCTTCCTGAGCACCGCCGTGTCCGCCGATGTGGGCTGTA<br>GCGTGGACTTCAGCAAGAAGTGA |
| SEQ ID NO: 31 | MLTSQKVIYLVMIVLIVPAYSISCIGVSNRDLVEGMSGGTWVDVVLEH<br>GGCVTEMAQDKPTVDIELVTMTVSNMAEVRSYCYEASLSDMASASRC<br>PTQGEPSLDKQSDTQSVCKRTLGDRGWGNGCGIFGKGSLVTCSKFTCC<br>KKMPGKSIQPENLEYRIMLPVHGSQHSGMIVNDIGHETDENRAKVEVT<br>PNSPRAEATLGGFGSLGLDCEPRTGLDFSDLYYLTMNNKHWLVHKEW<br>FHDIPLPWHAGADTGTPHWNNKEALVEFKDAHAKRQTVVVLGSQEG<br>AVHTALAGALEAEMDGAKGRLFSGHLKCRLKMDKLRLKGVSYSLCT<br>AAFTFTKVPAETLHGTVTVEVQSAGTDGPCKVPAQMAVDMQTLTPVG<br>RLITANPVITESTENSKMMLELDPPFGDSYIVIGVGDKKITHHWHRSGS<br>TIGKAFEATVRGAKRMAVLGDTAWDFGSVGGVFNSLGKGIHQIFGAA<br>FKSLFGGMSWFSQILIGTLLVWLGLNTKNGSISLTCLALGGVMIFLSTA<br>VSADVGCSVDFSKK |
| SEQ ID NO: 32 | GCCGCCACCATGTTCGCCTGCAGCAAGAAGATGACCGGCAAGAGC<br>ATCCAGCCCGAGAACCTGGAATACCGGATCATGCTGAGCGTGCACG |

| SEQ ID NO | Sequence |
|---|---|
| | GCAGCCAGCACAGCGGCATGATCGTGAACGACACCGGCCACGAGA<br>CAGACGAGAACCGGGCCAAGGTGGAAATCACCCCCAACAGCCCTA<br>GAGCCGAGGCCACACTGGGCGGCTTTGGATCTCTGGGCCTGGACTG<br>CGAGCCTAGAACCGGCCTGGATTTCAGCGACCTGTACTACCTGACC<br>ATGAACAACAAGCACTGGCTGGTGCACAAAGAGTGGTTCCACGAC<br>ATCCCCCTGCCCTGGCATGCCGGCGCTGATACAGGCACACCCCACT<br>GGAACAACAAAGAGGCCCTGGTGGAGTTCAAGGACGCCCACGCCA<br>AGAGGCAGACCGTGGTGGTGCTGGGATCTCAGGAAGGCGCCGTGC<br>ATACAGCTCTGGCTGGCGCCCTGGAAGCCGAAATGGATGGCGCTAA<br>GGGCAGACTGAGCAGCGGCCACCTGAAGTGCCGGCTGAAGATGGA<br>CAAGCTGCGGCTGAAGGGCGTGTCCTACAGCCTGTGTACCGCCGCC<br>TTCACCTTCACCAAGATCCCCGCCGAGACACTGCACGGCACCGTGA<br>CAGTGGAAGTGCAGTACGCCGGCACCGACGGCCCTTGTAAAGTGCC<br>TGCTCAGATGGCCGTGGACATGCAGACCCTGACCCCTGTGGGCAGG<br>CTGATCACCGCCAACCCTGTGATCACCGAGAGCACCGAGAACAGC<br>AAGATGATGCTGGAACTGGACCCCCCCTTCGGCGACTCCTACATCG<br>TGATCGGCGTGGGAGAGAAGAAGATCACCCACCACTGGTGA |
| SEQ ID NO: 33 | MFACSKKMTGKSIQPENLEYRIMLSVHGSQHSGMIVNDTGHETDENR<br>AKVEITPNSPRAEATLGGFGSLGLDCEPRTGLDFSDLYYLTMNNKHWL<br>VHKEWFHDIPLPWHAGADTGTPHWNNKEALVEFKDAHAKRQTVVVL<br>GSQEGAVHTALAGALEAEMDGAKGRLSSGHLKCRLKMDKLRLKGVS<br>YSLCTAAFTFTKIPAETLHGTVTVEVQYAGTDGPCKVPAQMAVDMQT<br>LTPVGRLITANPVITESTENSKMMLELDPPFGDSYIVIGVGEKKITHHW |
| SEQ ID NO: 34 | GCCGCCACCATGTTCGCCTGCAGCAAGAAGATGACCGGCAAGAGC<br>ATCCAGCCCGAGAACCTGGAATACCGGATCATGCTGAGCGTGCACG<br>GCAGCCAGCACAGCGGCATGATCGTGAACATCACCGGCCACGAGA<br>CACTGGAAAACCGGGCCAAGGTGGAAATCACCCCCAACAGCCCTA<br>GAGCCGAGGCCACACTGGGCGGCTTTGGATCTCTGGGCCTGGACTG<br>CGAGCCTAGAACCGGCCTGGATTTCAGCGACCTGTACTACCTGACC<br>ATGAACAACAAGCACTGGCTGGTGCACAAAGAGTGGTTCCACGAC<br>ATCCCCCTGCCCTGGCATGCCGGCGCTGATACAGGCACACCCCACT<br>GGAACAACAAAGAGGCCCTGGTGGAGTTCAAGCTGGCCCACGCCA<br>AGAGACAGACCGTGGTGGTGCTGGGCTCTCAGGAAGGCGCCGTGC<br>ATACAGCTCTGGCTGGCGCCCTGGAAGCCGAAATGGATGGCGCCAA<br>GGGCAGACTGTCTAGCGGCCACCTGAAGTGCCGGCTGAAGATGGA<br>CAAGCTGCGGCTGAAGGGCGTGTCCTACAGCCTGTGTACCGCCGCC<br>TTCACCTTCACCAAGATCCCCGCCGAAACCCTGCACGGCACCGTGA<br>CAGTGGAAGTGCAGTACGCCGGCACCCTGGGCCCTTGTAAAGTGCC<br>TGCTCAGATGGCCGTGGACATGCAGACCCTGACCCCTGTGGGCAGG<br>CTGATCACCGCCAACCCTGTGATCACCGAGAGCACCGAGAACAGC<br>AAGATGATGCTGGAACTGGACCCCCCCTTCGGCATCTCCTACATCG<br>TGATCGGCGTGGGCGAGAAGAAGATCACCCACCACTGGTGA |
| SEQ ID NO: 35 | MFACSKKMTGKSIQPENLEYRIMLSVHGSQHSGMIVNITGHETLENRA<br>KVEITPNSPRAEATLGGFGSLGLDCEPRTGLDFSDLYYLTMNNKHWL<br>HKEWFHDIPLPWHAGADTGTPHWNNKEALVEFKLAHAKRQTVVVLG<br>SQEGAVHTALAGALEAEMDGAKGRLSSGHLKCRLKMDKLRLKGVSY<br>SLCTAAFTFTKIPAETLHGTVTVEVQYAGTLGPCKVPAQMAVDMQTL<br>TPVGRLITANPVITESTENSKMMLELDPPFGISYIVIGVGEKKITHHW |
| SEQ ID NO: 36 | GCCGCCACCATGAGCACCAGCCAGAAAGTGATCTACCTCGTGATGA<br>TCCTGCTGATCGCCCCTGCCTACAGCATCCGGTGTATCGGCGTGTCC<br>AACCGGGACTTCGTGGAAGGCATGAGCGGCGGCACATGGGTGGAC<br>GTGGTGCTGGAACATGGCGGCTGCGTGACAGTGATGGCCCAGGAC<br>AAGCCCACCGTGGACATCGAGCTCGTGACCACCACCGTGTCCAATA<br>TGGCCGAAGTGCGGAGCTACTGCTACGAGGCCAGCATCAGCGACAT<br>GGCCAGCGACAGCAGATGCCCTACACAGGGCGAGGCCTACCTGGA<br>CAAGCAGAGCGACACCCAGTACGTGTGCAAGCGGACCCTGGTGGA<br>TAGAGGCTGGGGCAATGGCTGCGGCCTGTTTGGCAAGGGCAGCCTC<br>GTGACCTGCGCCAAGTTCGCCTGCAGCAAGAAGATGACCGGCAAG<br>AGCATCCAGCCCGAGAACCTGGAATACCGGATCATGCTGAGCGTGC<br>ACGGCAGCCAGCACTCCGGCATGATCGTGAACGACACCGGCCACG<br>AGACAGACGAGAACCGGGCCAAGGTGGAAATCACCCCCAACAGCC<br>CTAGAGCCGAGGCCACACTGGGCGGCTTTGGATCTCTGGGCCTGGA<br>CTGCGAGCCTAGAACCGGCCTGGATTTCAGCGACCTGTACTACCTG<br>ACCATGAACAACAAACACTGGCTGGTGCACAAAGAGTGGTTCCAC<br>GACATCCCCCTGCCCTGGCATGCCGGCGCTGATACAGGCACACCCC<br>ACTGGAACAACAAAGAGGCCCTGGTGGAATTCAAGGACGCCCACG<br>CCAAGCGGCAGACCGTGGTGGTGCTGGGATCTCAGGAAGGCGCCG<br>TGCATACAGCTCTGGCTGGCGCCCTGGAAGCCGAAATGGATGGCGC<br>CAAAGGCAGACTGAGCAGCGGCCACCTGAAGTGCCGGCTGAAGAT<br>GGACAAGCTGCGGCTGAAGGGCGTGTCCTACAGCCTGTGTACCGCC<br>GCCTTCACCTTCACCAAGATCCCCGCCGAGACACTGCACGGCACCG |

| SEQ ID NO | Sequence |
|---|---|
| | TGACTGTGGAAGTGCAGTACGCCGGCACCGACGGCCCTTGTAAAGT<br>GCCTGCTCAGATGGCCGTGGATATGCAGACCCTGACCCCCGTGGGC<br>AGGCTGATCACAGCCAACCCTGTGATCACCGAGAGCACCGAGAAC<br>AGCAAGATGATGCTGGAACTGGACCCCCCCTTCGGCGACTCCTACA<br>TCGTGATCGGCGTGGGAGAGAAGAAGATCACCCACCACTGGCACA<br>GAAGCGGCAGCACCATCGGCAAGGCCTTTGAGGCTACAGTGCGGG<br>GAGCCAAGAGAATGGCCGTGCTGGGAGATACCGCCTGGGACTTTG<br>GCTCTGTGGGCGGAGCCCTGAACTCTCTGGGCAAGGGAATCCACCA<br>GATCTTCGGCGCTGCCTTCAAGAGCCTGTTCGGCGGCATGAGCTGG<br>TTCAGCCAGATCCTGATCGGCACCCTGCTGATGTGGCTGGGCCTGA<br>ACACCAAGAACGGCAGCATCTCCCTGATGTGCCTGGCTCTGGGAGG<br>CGTGCTGATCTTCCTGAGCACAGCCGTGTCTGCCGACGTGGGCTGC<br>AGCGTGGACTTCTCCAAGAAGTGA |
| SEQ ID NO: 37 | MSTSQKVIYLVMILLIAPAYSIRCIGVSNRDFVEGMSGGTWVDVVLEH<br>GGCVTVMAQDKPTVDIELVTTTVSNMAEVRSYCYEASISDMASDSRC<br>PTQGEAYLDKQSDTQYVCKRTLVDRGWGNGCGLFGKGSLVTCAKFA<br>CSKKMTGKSIQPENLEYRIMLSVHGSQHSGMIVNDTGHETDENRAKVE<br>ITPNSPRAEATLGGFGSLGLDCEPRTGLDFSDLYYLTMNNKHWLVHKE<br>WFHDIPLPWHAGADTGTPHWNNKEALVEFKDAHAKRQTVVVLGSQE<br>GAVHTALAGALEAEMDGAKGRLSSGHLKCRLKMDKLRLKGVSYSLC<br>TAAFTFTKIPAETLHGTVTVEVQYAGTDGPCKVPAQMAVDMQTLTPV<br>GRLITANPVITESTENSKMMLELDPPFGDSYIVIGVGEKKITHHWHRSG<br>STIGKAFEATVRGAKRMAVLGDTAWDFGSVGGALNSLGKGIHQIFGA<br>APKSLFGGMSWFSQILIGTLLMWLGLNTKNGSISLMCLALGGVLIFLST<br>AVSADVGCSVDFSKK |
| SEQ ID NO: 64 | MEGDGSDPEPPDAGEDSKSENGENAPIYCKRKPDINCFMIGCDNCNE<br>WFHGDCIRITEKMAKAIREWYCRECREKDPKLEIRYRHKKSRERDGNE<br>RDSSEPRDEGGGRKRPVPDPNLQRRAGSGTGVGAMLARGSASPHKSS<br>PQPLVATPSQHHQQQQQQIKRSARMCGECEACRRTEDCGHCDFCRDM<br>KKFGGPNKIRQKCRLRQCQLRARESYKYFPSSLPVTPSESLPRPRRPLP<br>TQQQPQPSQKLGRIREDEGAVASSTVKEPPEATATPEPLSDEDLPLDPD<br>LYQDFCAGAFDDNGLPWMSDTEESPFLDPALRKRAVKVKHVKRREK<br>KSEKKKEERYKRHRQKQHKDKWKHPERADAKDPASLPQCLGPGCV<br>RPAQPSSKYCSDDCGMKLAANRIYEILPQRIQQWQQSPCIAEEHGKKL<br>LERIRREQQSARTRLQEMERRFHELEAIILRAKQQAVREDEESNEGDSD<br>DTDLQIFCVSCGHPINPRVALRHMERCYAKYESQTSFGSMYPTRIEGAT<br>RLFCDVYNPQSKTYCKRLQVLCPEHSRDPKVPADEVCGCPLVRDVFEL<br>TGDFCRLPKRQCNRHYCWEKLRRAEVDLERVRVWYKLDELFEQERN<br>VRTAMTNRAGLLALMLHQTIQHDPLTTDLRSSADR |

What is claimed is:

1. A cell comprising a composition, wherein the composition comprises:
    a replication defective adenovirus vector comprising a deletion in an E1 gene region and a deletion in an E2b gene region; and
    a sequence encoding a Zika virus target antigen.

2. The cell of claim 1, wherein the sequence encoding a Zika virus target antigen comprises a sequence encoding a plurality of Zika virus target antigens.

3. The cell of claim 2, wherein the sequence encoding a plurality of Zika virus target antigens comprises a plurality of gene inserts each corresponding to a target antigen, wherein each gene insert is separated by a nucleic acid sequence encoding a self-cleaving 2A peptide.

4. The cell of claim 3, wherein the self-cleaving 2A peptide is derived from Porcine teschovirus-1 virus or Thosea asigna virus.

5. The cell of claim 1, wherein the replication defective virus vector further comprises a deletion in an E3 gene region, an E4 gene region, or any combination thereof.

6. The cell of claim 1, wherein the Zika virus target antigen comprises an antigen selected from the group consisting of C (capsid protein), E (envelope protein), prM (pre-membrane protein), M (membrane protein), NS1, NS2A, NS2B, NS3, NS4A, NS4B, and NS5, or any combination thereof.

7. The cell of claim 1, wherein the sequence encoding a Zika virus target antigen comprises an N-terminal GCCGC-CACC sequence.

8. The cell of claim 1, wherein the replication defective adenovirus vector further comprises a nucleic acid sequence encoding a protein that increases Zika virus target antigen immunogenicity.

9. The cell of claim 1, wherein the composition or the replication defective adenovirus vector further comprises a nucleic acid sequence encoding a costimulatory molecule or an immunological fusion partner.

10. A pharmaceutical composition comprising the cell according to claim 1 and a pharmaceutically acceptable carrier.

11. The cell of claim 1, wherein the cell is a dendritic cell (DC).

12. A method of preparing a vaccine, comprising preparing a pharmaceutical composition according to claim 10.

13. A method of generating an immune response against a Zika virus target antigen in a subject, comprising: administering to the subject a composition comprising the Zika virus target antigen of claim 6.

14. A method of preventing Zika virus infection in a subject, the method comprising administering to the subject a composition comprising:
    a replication defective adenovirus vector comprising a deletion in an E2b gene region; and
    a sequence encoding at least one Zika virus target antigen.

15. The method of claim 14, wherein the subject has preexisting immunity to an adenovirus or adenovirus vector.

16. The method of claim 14, wherein the administering of the composition to the subject comprises administering $1\times10^9$ to $5\times10^{12}$ virus particles per dose.

* * * * *

SEQUENCE LISTING

<160> NUMBER OF SEQ ID NOS: 135

<210> SEQ ID NO 1
<211> LENGTH: 10862
<212> TYPE: DNA
<213> ORGANISM: Yellow fever virus

<400> SEQUENCE: 1

```
agtaaatcct gtgtgctaat tgaggtgcat tggtctgcaa atcgagttgc taggcaataa      60
acacatttgg attaatttta atcgttcgtt gagcgattag cagagaactg accagaaacat     120 gtctggtcgt aaagctcagg gaaaaccct gggcgtcaat atggtacgac gaggagttcg      180
ctccttgtca aacaaaataa aacaaaaaac aaaacaaatt ggaaacagac ctggaccttc     240
aagaggtgtt caaggattta tcttttttctt tttgttcaac attttgactg gaaaaaagat     300
cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aattttggga atgctgttga tgacgggtgg     480
agtgaccttg gtgcggaaaa acagatggtt gctcctaaat gtgacatctg aggacctcgg     540
```

```
gaaaacattc tctgtgggca caggcaactg cacaacaaac attttggaag ccaagtactg    600
gtgcccagac tcaatggaat acaactgtcc caatctcagt ccaagagagg agccagatga    660
cattgattgc tggtgctatg ggtggaaaa cgttagagtc gcatatggta agtgtgactc    720
agcaggcagg tctaggaggt caagaagggc cattgacttg cctacgcatg aaaaccatgg    780
tttgaagacc cggcaagaaa aatggatgac tggaagaatg ggtgaaaggc aactccaaaa    840
gattgagaga tggttcgtga ggaaccccct ttttgcagtg acggctctga ccattgccta    900
ccttgtggga agcaacatga cgcaacgagt cgtgattgcc ctactggtct ggctgttgg    960
tccggcctac tcagctcact gcattggaat tactgacagg gatttcattg agggggtgca   1020
tggaggaact tgggtttcag ctaccctgga gcaagacaag tgtgtcactg ttatggcccc   1080
tgacaagcct tcattggaca tctcactaga gacagtagcc attgatagac ctgctgaggt   1140
gaggaaagtg tgttacaatg cagttctcac tcatgtgaag attaatgaca agtgccccag   1200
cactggagag gcccacctag ctgaagagaa cgaaggggac aatgcgtgca agcgcactta   1260
ttctgataga ggctggggca atggctgtgg cctatttggg aaagggagca ttgtggcatg   1320
cgccaaattc acttgtgcca aatccatgag tttgtttgag gttgatcaga ccaaaattca   1380
gtatgtcatc agagcacaat tgcatgtagg ggccaagcag gaaaattgga ctaccgacat   1440
taagactctc aagtttgatg ccctgtcagg ctcccaggaa gtcgagttca ttgggtatgg   1500
aaaagctaca ctggaatgcc aggtgcaaac tgcggtggac tttggtaaca gttacatcgc   1560
tgagatggaa acagagagct ggatagtgga cagacagtgg gcccaggact tgaccctgcc   1620
atggcagagt ggaagtggcg gggtgtggag agagatgcat catcttgtcg aatttgaacc   1680
tccgcatgcc gccactatca gagtactggc cctgggaaac caggaaggct ccttgaaaac   1740
agctcttact ggcgcaatga gggttacaaa ggacacaaat gacaacaacc tttacaaact   1800
acatggtgga catgtttctt gcagagtgaa attgtcagct ttgacactca aggggacatc   1860
ctacaaaata tgcactgaca aaatgttttt tgtcaagaac ccaactgaca ctggccatgg   1920
cactgttgtg atgcaggtga aagtgtcaaa aggagcccccc tgcaggattc cagtgatagt   1980
agctgatgat cttacagcgg caatcaataa aggcattttg gttacagtta acccccatcgc   2040
ctcaaccaat gatgatgaag tgctgattga ggtgaaccca cctttttggag acagctacat   2100
tatcgttggg agaggagatt cacgtctcac ttaccagtgg cacaaagagg gaagctcaat   2160
aggaaagttg ttcactcaga ccatgaaagg cgtggaacgc ctggccgtca tgggagacac   2220
cgcctgggat ttcagctccg ctggagggtt cttcacttcg gttgggaaag gaattcatac   2280
ggtgtttggc tctgcctttc aggggctatt tggcggcttg aactggataa caaaggtcat   2340
catgggggcg gtacttatat gggttggcat caacacaaga aacatgacaa tgtccatgag   2400
catgatcttg gtaggagtga tcatgatgtt tttgtctcta ggagttgggg cggatcaagg   2460
atgcgccatc aactttggca agagagagct caagtgcgga gatggtatct tcatatttag   2520
agactctgat gactggctga acaagtactc atactatcca aagatcctg tgaagcttgc   2580
atcaatagtg aaagcctctt ttgaagaagg gaagtgtggc ctaaattcag ttgactccct   2640
tgagcatgag atgtggagaa gcagggcaga tgagatcaat gccattttg aggaaaacga   2700
ggtggacatt tctgttgtcg tgcaggatcc aaagaatgtt taccagagag gaactcatcc   2760
atttttccaga attcgggatg gtctgcagta tggttggaag acttggggta agaaccttgt   2820
gttctccccca gggaggaaga atggaagctt catcatagat ggaaagtcca ggaaagaatg   2880
cccgtttttca aaccgggtct ggaattcttt ccagatagag gagtttggga cgggagtgtt   2940
```

```
caccacacgc gtgtacatgg acgcagtctt tgaatacacc atagactgcg atggatctat    3000
cttgggtgca gcggtgaacg gaaaaaagag tgcccatggc tctccaacat tttggatggg    3060
aagtcatgaa gtaaatggga catggatgat ccacaccttg gaggcattag attacaagga    3120
gtgtgagtgg ccactgacac atacgattgg aacatcagtt gaagagagtg aaatgttcat    3180
gccgagatca atcggaggcc cagttagctc tcacaatcat atccctggat acaaggttca    3240
gacgaacgga ccttggatgc aggtaccact agaagtgaag agagaagctt gcccagggac    3300
tagcgtgatc attgatggca actgtgatgg acggggaaaa tcaaccagat ccaccacgga    3360
tagcgggaaa gttattcctg aatggtgttg ccgctcctgc acaatgccgc ctgtgagctt    3420
ccatggtagt gatgggtgtt ggtatcccat ggaaattagg ccaaggaaaa cgcatgaaag    3480
ccatctggtg cgctcctggg ttacagctgg agaaatacat gctgtccctt ttggtttggt    3540
gagcatgatg atagcaatgg aagtggtcct aaggaaaaga cagggaccaa agcaaatgtt    3600
ggttggagga gtagtgctct gggagcaat gctggtcggg caagtaactc tccttgattt    3660
gctgaaactc acagtggctg tgggattgca tttccatgag atgaacaatg gaggagacgc    3720
catgtatatg gcgttgattg ctgccttttc aatcagacca gggctgctca tcggcttttgg    3780
gctcaggacc ctatggagcc ctcgggaacg ccttgtgctg accctaggag cagccatggt    3840
ggagattgcc ttgggtggcg tgatgggcgg cctgtggaag tatctaaatg cagtttctct    3900
ctgcatcctg acaataaatg ctgttgcttc taggaaagca tcaaatacca tcttgccect    3960
catggctctg ttgacacctg tcactatggc tgaggtgaga cttgccgcaa tgttcttttg    4020
tgccgtggtt atcataggg tccttcacca gaatttcaag gacacctcca tgcagaagac    4080
tatacctctg gtggccctca cactcacatc ttacctgggc ttgacacaac ctttttggg    4140
cctgtgtgca tttctggcaa cccgcatatt tgggcgaagg agtatcccag tgaatgaggc    4200
actcgcagca gctggtctag tgggagtgct ggcaggactg gcttttcagg agatggagaa    4260
cttccttggt ccgattgcag ttggaggact cctgatgatg ctggttagcg tggctgggag    4320
ggtggatggg ctagagctca gaagcttgg tgaagtttca tgggaagagg aggcggagat    4380
cagcgggagt tccgcccgct atgatgtggc actcagtgaa caaggggagt tcaagctgct    4440
ttctgaagag aaagtgccat gggaccaggt tgtgatgacc tcgctggcct tgbttggggc    4500
tgccctccat ccatttgctc ttctgctggt ccttgctggg tggctgtttc atgtcagggg    4560
agctaggaga agtggggatg tcttgtggga tattcccact cctaagatca tcgaggaatg    4620
tgaacatctg gaggatggga tttatggcat attccagtca accttcttgg gggcctccca    4680
gcgaggagtg ggagtggcac agggagggt gttccacaca atgtggcatg tcacaagagg    4740
agctttcctt gtcaggaatg gcaagaagtt gattccatct tgggcttcag taaaggaaga    4800
ccttgtcgcc tatggtggct catggaagtt ggaaggcaga tgggatggag aggaagaggt    4860
ccagttgatc gcggctgttc caggaaagaa cgtggtcaac gtccagacaa accgagctt    4920
gttcaaagtg aggaatgggg gagaaatcgg ggctgtcgct cttgactatc cgagtggcac    4980
ttcaggatct cctattgtta acaggaacgg agaggtgatt gggctgtacg gcaatggcat    5040
ccttgtcggt gacaactcct tcgtgtccgc catatcccag actgaggtga aggaagaagg    5100
aaaggaggag ctccaagaga tcccgacaat gctaaagaaa ggaatgacaa ctgtccttga    5160
ttttcatcct ggagctggga agacaagacg tttcctccca cagatcttgg ccgagtgcgc    5220
acggagacgc ttgcgcactc ttgtgttggc ccccaccagg gttgttcttt ctgaaatgaa    5280
```

```
ggaggctttt cacggcctgg acgtgaaatt ccacacacag gcttttccg ctcacggcag    5340 cgggagagaa gtcattgatg ctatgtgcca tgccacccta acttacagga tgttggaacc    5400
aactagggtt gttaactggg aagtgatcat tatggatgaa gcccatttt tggatccagc    5460 tagcatagcc gctagaggtt gggcagcgca cagagctagg gcaaatgaaa gtgcaacaat    5520
cttgatgaca gccacaccgc ctgggactag tgatgaattt ccacattcaa atggtgaaat    5580
agaagatgtt caaacggaca tacccagtga gccctggaac acagggcatg actggatcct    5640
ggctgacaaa aggcccacgg catggttcct tccatccatc agagctgcaa atgtcatggc    5700
tgcctctttg cgtaaggctg gaaagagtgt ggtggtcctg aacaggaaaa cctttgagag    5760
agaatacccc acgataaagc agaagaaacc tgactttata ttggccactg acatagctga    5820
aatgggagcc aacctttgcg tggagcgagt gctggattgc aggacggctt ttaagcctgt    5880
gcttgtggat gaagggagga aggtggcaat aaaagggcca cttcgtatct ccgcatcctc    5940
tgctgctcaa aggagggggc gcattgggag aaatcccaac agagatggag actcatacta    6000
ctattctgag cctacaagtg aaaataatgc ccaccacgtc tgctggttgg aggcctcaat    6060
gctcttggac aacatggagg tgaggggtgg aatggtcgcc ccactctatg cgttgaagg    6120 aactaaaaca ccagtttccc ctggtgaaat gagactgagg gatgaccaga ggaaagtctt    6180
cagagaacta gtgaggaatt gtgacctgcc cgtttggctt tcgtggcaag tggccaaggc    6240
tggtttgaag acgaatgatc gtaagtggtg ttttgaaggc cctgaggaac atgagatctt    6300
gaatgacagc ggtgaaacag tgaagtgcag ggctcctgga ggagcaaaga gcctctgcg    6360 cccaaggtgg tgtgatgaaa gggtgtcatc tgaccagagt gcgctgtctg aatttattaa    6420
gtttgctgaa ggtaggaggg gagctgctga agtgctagtt gtgctgagtg aactccctga    6480
tttcctggct aaaaaaggtg gagaggcaat ggataccatc agtgtgtttc tccactctga    6540
ggaaggctct agggcttacc gcaatgcact atcaatgatg cctgaggcaa tgacaatagt    6600
catgctgttt atactggctg gactactgac atcgggaatg gtcatctttt tcatgtctcc    6660
caaaggcatc agtagaatgt ctatggcgat gggcacaatg gccggctgtg gatatctcat    6720
gttccttgga ggcgtcaaac ccactcacat ctcctatatc atgctcatat tctttgtcct    6780
gatggtggtt gtgatccccg agccagggca acaaaggtcc atccaagaca accaagtggc    6840
atacctcatt attggcatcc tgacgctggt ttcagcggtg gcagccaacg agctaggcat    6900
gctggagaaa accaaagagg acctctttgg gaagaagaac ttaattccat ctagtgcttc    6960 accctgagt tggccggatc ttgacctgaa gccaggagct gcctggacag tgtacgttgg    7020
cattgttaca atgctctctc caatgttgca ccactggatc aaagtcgaat atggcaacct    7080
gtctctgtct ggaatagccc agtcagcctc agtcctttct ttcatggaca ggggatacc    7140 attcatgaag atgaatatct cggtcataat gctgctggtc agtggctgga attcaataac    7200
agtgatgcct ctgctctgtg gcataggtg cgccatgctc cactggtctc tcatttacc    7260 tggaatcaaa gcgcagcagt caaagcttgc acagagaagg gtgttccatg cgttgccaa    7320 gaaccctgtg gttgatggga tccaacagt tgacattgag gaagctcctg aaatgcctgc    7380
cctttatgag aagaaactgg ctctatatct ccttcttgct ctcagcctag cttctgttgc    7440
catgtgcaga acgcccttt cattggctga aggcattgtc ctagcatcag ctgccctagg    7500
gccgctcata gagggaaaca ccagccttct ttgaatgga cccatggctg tctccatgac    7560
aggagtcatg agggggaatc actatgcttt tgtgggagtc atgtacaaatc tatgaagat    7620 gaaaactgga cgccggggga gcgcgaatgg aaaaactttg ggtgaagtct ggaagaggga    7680
```

```
actgaatctg ttggacaagc gacagtttga gttgtataaa aggaccgaca ttgtggaggt    7740
ggatcgtgat acggcacgca ggcatttggc cgaagggaag gtggacaccg gggtggcggt    7800
ctccaggggg accgcaaagt taaggtggtt ccatgagcgt ggctatgtca agctggaagg    7860
tagggtgatt gacctggggt gtggccgcgg aggctggtgt tactacgctg ctgcgcaaaa    7920
ggaagtgagt ggggtcaaag gatttactct tggaagagac ggccatgaga aacccatgaa    7980
tgtgcaaagt ctgggatgga acatcatcac cttcaaggac aaaactgata tccaccgcct    8040
agaaccagtg aaatgtgaca ccctttttgtg tgacattgga gagtcatcat cgtcatcggt    8100
cacagagggg gaaaggaccg tgagagttct tgatactgta gaaaaatggc tggcttgtgg    8160
ggttgacaac ttctgtgtga aggtgttagc tccatacatg ccagatgttc tcgagaaact    8220
ggaattgctc caaaggaggt ttggcggaac agtgatcagg aaccctctct ccaggaattc    8280
cactcatgaa atgtactacg tgtctggagc ccgcagcaat gtcacattta ctgtgaacca    8340
aacatcccgc ctcctgatga ggagaatgag gcgtccaact ggaaaagtga ccctggaggc    8400
tgacgtcatc ctcccaattg gacacgcag tgttgagaca gacaagggac ccctggacaa    8460
agaggccata aagaaaggg ttgagaggat aaaatctgag tacatgacct cttggtttta    8520
tgacaatgac aaccctaca ggacctggca ctactgtggc tcctatgtca caaaaacctc    8580
aggaagtgcg gcgagcatgg taaatggtgt tattaaaatt ctgacatatc catgggacag    8640
gatagaggag gtcacaagaa tggcaatgac tgacacaacc ccttttggac agcaaagagt    8700
gtttaaagaa aaagttgaca ccagagcaaa ggatccacca gcgggaacta ggaagatcat    8760
gaaagttgtc aacaggtggc tgttccgcca cctggccaga gaaaagaacc ccagactgtg    8820
cacaaaggaa gaatttattg caaaagtccg aagtcatgca gccattggag cttacctgga    8880
agaacaagaa cagtggaaga ctgccaatga ggctgtccaa gacccaaagt ctgggaact    8940 ggtggatgaa gaaaggaagc tgcaccaaca aggcaggtgt cggacttgtg tgtacaacat    9000
gatgggaaaa agagagaaga agctgtcaga gtttgggaaa gcaaagggaa gccgtgccat    9060
atggtatatg tggctgggag cgcggtatct tgagtttgag gccctgggat tcctgaatga    9120
ggaccattgg gcttccaggg aaaactcagg aggaggagtg gaaggcattg gcttacaata    9180
cctaggatat gtgatcagag acctggctgc aatggatggt ggtggattct acgcggatga    9240
caccgctgga tgggacacgc gcatcacaga ggcagacctt gatgatgaac aggagatctt    9300
gaactacatg agcccacatc acaaaaaact ggcacaagca gtgatggaaa tgacatacaa    9360
gaacaaagtg gtgaaagtgt tgagaccagc cccaggaggg aaagcctaca tggatgtcat    9420
aagtcgacga gaccagagag gatccgggca ggtagtgact tatgctctga acaccatcac    9480
caacttgaaa gtccaattga tcagaatggc agaagcagag atggtgatac atcaccaaca    9540
tgttcaagat tgtgatgaat cagttctgac caggctggag gcatggctca ctgagcacgg    9600
atgtaacaga ctgaagagga tggcggtgag tggagacgac tgtgtggtcc ggcccatcga    9660
tgacaggttc ggcctggccc tgtcccatct caacgccatg tccaaggtta gaaaggacat    9720
atctgaatgg cagccatcaa aagggtggaa tgattgggag aatgtgccct tctgttccca    9780
ccacttccat gaactacagc tgaaggatgg caggaggatt gtggtgcctt gccgagaaca    9840
ggacgagctc attgggagag aagggtgtc tccaggaaac ggctggatga tcaaggaaac    9900
agcttgcctc agcaaagcct atgccaacat gtggtcactg atgtattttc acaaaaggga    9960
catgaggcta ctgtcattgg ctgtttcctc agctgttccc acctcatggg ttccacaagg   10020
```

| | | | | | |
|---|---|---|---|---|---|
| acgcacaaca | tggtcgattc | atgggaaagg | ggagtggatg | accacggaag | acatgcttga | 10080 |
| ggtgtggaac | agagtatgga | taaccaacaa | cccacacatg | caggacaaga | caatggtgaa | 10140 |
| aaaatggaga | gatgtccctt | atctaaccaa | gagacaagac | aagctgtgcg | gatcactgat | 10200 |
| tggaatgacc | aatagggcca | cctgggcctc | ccacatccat | ttggtcatcc | atcgtatccg | 10260 |
| aacgctgatt | ggacaggaga | aatacactga | ctacctaaca | gtcatggaca | ggtattctgt | 10320 |
| ggatgctgac | ctgcaactgg | gtgagcttat | ctgaaacacc | atctaacagg | aataaccggg | 10380 |
| atacaaacca | cgggtggaga | accggactcc | ccacaacctg | aaaccgggat | ataaaccacg | 10440 |
| gctggagaac | cggactccgc | acttaaaatg | aaacagaaac | cgggataaaa | actacgatg | 10500 |
| gagaaccgga | ctccacacat | tgagacagaa | gaagttgtca | gcccagaacc | ccacacgagt | 10560 |
| tttgccactg | ctaagctgtg | aggcagtgca | ggctgggaca | gccgacctcc | aggttgcgaa | 10620 |
| aaacctggtt | tctgggacct | cccacccag | agtaaaaaga | acggagcctc | cgctaccacc | 10680 |
| ctcccacgtg | gtggtagaaa | gacggggtct | agaggttaga | ggagaccctc | cagggaacaa | 10740 |
| atagtgggac | catattgacg | ccagggaaag | accggagtgg | ttctctgctt | ttcctccaga | 10800 |
| ggtctgtgag | cacagtttgc | tcaagaataa | gcagaccttt | ggatgacaaa | cacaaaacca | 10860 |
| ct | | | | | | 10862 |

<210> SEQ ID NO 2
<211> LENGTH: 10976
<212> TYPE: DNA
<213> ORGANISM: Japanese encephalitis virus

<400> SEQUENCE: 2

| | | | | | |
|---|---|---|---|---|---|
| agaagtttat | ctgtgtgaac | ttcttggctt | agtatcgttg | agaagaatcg | agagattagt | 60 |
| gcagtttaaa | cagtttttta | gaacggaaga | taaccatgac | taaaaaacca | ggagggcccg | 120 |
| gtaaaaaccg | ggctatcaat | atgctgaaac | gcggcctacc | ccgcgtattc | ccactagtgg | 180 |
| gagtgaagag | ggtagtaatg | agcttgttgg | acggcagagg | gccagtacgt | tcgtgctgg | 240 |
| ctcttatcac | gttcttcaag | tttacagcat | tagccccgac | caaggcgctt | ttaggccgat | 300 |
| ggaaagcagt | ggaaaagagt | gtagcaatga | acatctcac | tagtttcaaa | cgagaacttg | 360 |
| gaacactcat | tgacgccgtg | aacaagcggg | gcagaaagca | aaacaaaaga | ggaggaaatg | 420 |
| aaggctcaat | catgtggctt | gcgagcttgg | cagttgtcat | agcttgtgca | ggagccataa | 480 |
| agttgtcaaa | tttccagggg | aagcttttga | tgaccattaa | caacacggac | attgcagacg | 540 |
| ttatcgtaat | tcccacctca | aaaggagaga | acagatgctg | ggtccgggca | atcgacgtcg | 600 |
| gctacatgtg | tgaggacact | atcacgtacg | aatgtcctaa | gcttgccatg | ggcaatgatc | 660 |
| cagaggatgt | ggactgctgg | tgtgacaacc | aagaagtcta | cgtccaatat | ggacggtgca | 720 |
| cgcggaccag | gcattccaag | cgaagcagga | gatccgtgtc | ggtccaaaca | catggggaga | 780 |
| gttcactagt | gaataaaaaa | gaggcttggc | tggattcaac | gaaagccaca | cgatatctca | 840 |
| tgaaaactga | gaactggatc | ataaggaatc | ctggctatgc | tttcctggcg | gcggtactcg | 900 |
| gctggatgct | tggcagtacc | aacggtcaac | gcgtggtatt | caccatcctc | ctgctgctgg | 960 |
| tcgctccggc | ttacagtttt | aattgtctgg | gaatgggcaa | tcgtgacttc | atagaaggag | 1020 |
| ccagtggagc | cacttgggtg | gacttggtgc | tagaaggaga | tagctgcttg | acaattatgg | 1080 |
| caaacgacaa | accaacattg | gacgtccgca | tgatcaacat | cgaagctagc | caacttgccg | 1140 |
| aggttagaag | ttactgttat | catgcttcag | tcactgacat | ctcgacggtg | gctcggtgcc | 1200 |
| ccacgactgg | agaagcccac | aacgagaagc | gagctgatag | tagctatgtg | tgcaaacaag | 1260 |

```
gcttcactga tcgtgggtgg ggcaacggat gtggactttt cgggaaggga agcattgaca    1320
catgtgcaaa attctcctgc accagcaaag cgattgggag aacaatccag ccagaaaaca    1380
tcaaatacaa agttggcatt tttgtgcatg gagccactac ttcggaaaac catgggaatt    1440
attcagcgca agttggggcg tcccaggcgg caaagttcac agtaacaccc aatgctcctt    1500
cgataacccct caaacttggt gactacggag aagtcacact ggactgtgag ccaaggagtg    1560
gactgaacac tgaagcgttt tacgtcatga ccgtggggtc aaagtcattt ctggtccata    1620
gggaatggtt tcatgacctc gctctcccct ggacgtcccc ttcgagcaca gcgtggagaa    1680
acagagaact cctcatggag tttgaagagg cgcacgccac aaaacagtcc gttgttgctc    1740
ttgggtcaca ggaaggaggc ctccatcagg cgttggcagg agccatcgtg gtggagtact    1800
caagttcagt gaagttaaca tcaggccacc tgaaatgtag gctgaaaatg acaaactgg    1860
ctctgaaagg cacaacctat ggcatgtgca cagaaaaatt ctccttcgcg aaaaatccgg    1920
cggacactgg tcacgggaca gttgtcattg aactctccta ctctgggagt gatggcccct    1980
gcaaaattcc gattgtctcc gttgcgagcc tcaatgacat gaccccgtc gggcggctgg    2040
tgacagtgaa ccccttcgtc gcgacttcca gtgccaattc aaaggtgctg gtcgagatgg    2100
aaccccccctt cggagactcc tacatcgtag ttggacgggg agacaagcag atcaaccacc    2160
attggcataa agctggaagc acgctgggca aagccttttc aacaactttg aagggagctc    2220
agagactggc agcgctgggt gacacagcct gggactttgg ctccattgga ggggtcttca    2280
actccatagg aaaagccgtt caccaagtgt ttggtggtgc cttcagaaca ctcttcgggg    2340
gaatgtcttg gatcacacaa gggctaatgg gtgccctact actctggatg ggcgtcaacg    2400
cacgagaccg atcaattgct ttggccttct tagccacagg aggtgtgctc gtgttttttag    2460
cgaccaatgt gcatgctgac actggatgtg ccattgacat cacaagaaaa gagatgaggt    2520
gtggaagtgg catcttcgtg cacaacgacg tggaagcctg ggtggatagg tataaatatt    2580
tgccagaaac gcccagatcc ctagcaaaga tcgtccacaa agcgcacaag aaggcgtgt    2640
gcggagtcag atctgtcact agactggagc atcaaatgtg ggaagccgta cgggatgaat    2700
tgaacgtcct gctcaaagag aatgcagtgg acctcagtgt ggttgtgaac aagcccgtgg    2760
ggagatatcg ctcagcccct aaacgcctgt ccatgacgca agagaagttt gaaatgggct    2820
ggaaagcatg gggaaaaagc attctctttg ccccggaatt ggccaactcc acatttgtcg    2880
tagatggacc tgagacaaag gaatgccctg atgagcacag agcttggaac agcatgcaaa    2940
tcgaagactt cggctttggc atcacatcaa cccgtgtgtg gctgaagatt agagaggaga    3000
gcactgacga gtgtgatgga gcgatcatag gtacggctgt caaaggacat gtggcagtcc    3060
atagtgactt gtcgtactgg attgagagtc gctacaacga cacatggaaa cttgagaggg    3120
cagtctttgg agaagttaaa tcctgcactt ggccagagac acacaccctat ggggagatg    3180
gtgttgagga aagtgaactc atcatcccgc acaccatagc cggaccaaaa agcaagcata    3240
atcggaggga aggatataag acacaaaacc agggaccttg gacgagaat ggcatagtct    3300
tggactttga ctattgccca gggacaaaag tcaccattac agaggattgt ggcaagagag    3360
gccccttcggt cagaaccact actgacagtg aaagttgat cactgactgg tgctgtcgca    3420
gttgctccct tccgcccta cgattccgga cagaaaatgg ctgctggtac ggaatggaaa    3480
tcagacctgt caggcatgat gaaacaacac tcgtcagatc gcaggttgat gcttttaatg    3540
gtgaaatggt tgacccttttt cagctgggcc ttctggtgat gtttctggcc acccaggagg    3600
```

```
tccttcgcaa gaggtggacg gccagattga ccattcctgc ggttttgggg gccctacttg    3660
tgctgatgct tgggggcatc acttacactg atttggcgag gtatgtgtg ctagtcgctg     3720 cctctttcgc agaggccaac agtggaggag atgtcctgca ccttgctttg attgccgttt    3780
tcaagatcca accagcattt ttagtgatga acatgcttag cacgagatgg acgaaccaag    3840
aaaacgtggt tctggtccta ggggctgcct ttttccaatt ggcctcagta gatctgcaaa    3900
taggagttca cggaatcctg aatgccgccg ctatagcatg gatgattgtc cgggcgatca    3960
ccttccccac aacctcctcc gtcaccatgc cagtcttagc gcttctaact ccgggaatga    4020
gggctctata cctagatact tacagaatca tcctcctcgt catagggatt tgctctctgc    4080
tgcaagagag gaaaaagacc atggcaaaaa agaaggagc tgtactcttg ggcttagcgc     4140
tcacatccac tggatggttt tcgcccacca ctatagctgc cggactaatg gtctgcaacc    4200
caaacaagaa gagagggtgg ccagctactg agttttttgtc ggcagttgga ttgatgtttg    4260
ccatcgtagg tggtttggcg gagttggata ttgaatccat gtcaataccc ttcatgctgg    4320
caggtctcat ggcagtgtcc tacgtggtgt caggaaaagc aacagatatg tggcttgaac    4380
gggctgccga catcagctgg gagatggatg ctgcaatcac aggaagcagt cggaggctgg    4440
atgtgaagct agatgatgac ggagattttc acttgattga cgatcccggt gttccatgga    4500
aggtctgggt cctgcgcatg tcttgcattg ggttagccgc cctcacgcct gggccattg     4560 ttcccgccgc ttttggttat tggctcactt taaaaacaac aaaaagaggg ggcgtgtttt    4620
gggacacgcc atccccaaaa ccttgctcaa aggagacac cactacagga gtttaccgca     4680
ttatggctag agggattctt ggcacttacc aggccggcgt cggagtcatg tacgagaatg    4740
ttttccacac actatggcac acaactagag gagcagctat tatgagtgga gaaggaaat     4800 tgacgccata ctggggtagt gtgaaagaag accgcatagc ttacggaggc ccatggaggt    4860
ttgatcgaaa atggaatgga actgatgacg tgcaagtgat cgtggtagaa ccggggaagg    4920
ctgcagtaaa catccagaca aaaccaggag tgtttcggac tcccttcggg gaggttgggg    4980
ctgttagtct ggattatccg cgaggaacat ccggctcacc cattctggat tccaatggag    5040
acatcatagg cctgtacggc aatggagttg agcttggcga tggctcatac gtcagcgcca    5100
tcgtgcaggg tgaccgtcag gaggaaccag tcccagaagc ttacacccca aacatgttga    5160
gaaagagaca gatgaccgta ctagatttgc accctggttc agggaaaacc aagaaaattc    5220
tgccacaaat aattaaggac gctattcagc agcgcctaag aacagctgtg ttggcaccga    5280
cgcgggtggt agcagcagaa atggcagaag ctttgagagg gctcccagta cgatatcaaa    5340
cttcagcagt gcagagagag caccaaggga atgaaatagt ggatgtgatg tgccacgcca    5400
ctctgaccca tagactgatg tcaccgaaca gagtgcccaa ctacaaccta tttgtcatgg    5460
atgaagctca tttcaccgac ccagccagta tagccgcacg aggatacatt gctaccaagg    5520
tggaattagg ggaggcagca gccatctta tgacagcgac cccgcctgga accacgatc     5580 cttttcctga ctcaaatgcc ccaatccatg atttgcaaga tgagatacca gacagggcgt    5640
ggagcagtgg atacgaatgg atcacagaat atgcgggaaa aaccgtgtgg tttgtggcaa    5700
gcgtgaaaat ggggaacgag attgcaatgt gcctccaaag agcggggaaa aaggtcatcc    5760
aactcaaccg caagtcctat gacacagaat acccaaaatg taagaatgga gactgggatt    5820
ttgtcatcac cactgacatt tctgaaatgg gggccaactt cggtgcgagc agggtcatcg    5880
actgtagaaa gagcgtgaag cccaccatct tagaagaggg agaaggcaga gtcatcctcg    5940
gaaacccatc gcccataacc agtgcaagcg cagctcaacg gaggggcaga gtaggcagaa    6000
```

```
accctaaccca ggttggagat gaataccact atgggggggc caccagtgaa gatgacagta   6060
acctagccca ttggacagag gcaaagatca tgttagataa catacacatg cccaatggac   6120
tggtggccca gctctatgga ccagagaggg aaaaggcctt cacaatggat ggcgaatacc   6180
gtctcagagg tgaagaaaag aaaaacttct tagagctgct taggacggct gacctcccgg   6240
tgtggctggc ctacaaggtg gcgtccaatg gcatccagta caccgataga aagtggtgtt   6300
ttgatgggcc gcgtacgaat gccatactgg aggacaacac cgaggtagag atagtcaccc   6360
ggatgggtga gaggaaaatc ctcaagccga gatggcttga tgcaagagtt tatgcagatc   6420
accaagctct caagtggttc aaagacttcg cagcaggaaa gagatcagcc gttagcttca   6480
tagaggtgct cggtcgtatg cctgagcatt tcatgggaaa gacgcgggaa gctttagaca   6540
ccatgtactt ggttgcaacg gctgagaaag gtgggaaagc acaccgaatg gctctcgaag   6600
agctgccaga tgcactggaa accattacac ttattgttgc tatcactgtg atgacaggag   6660 gattcttttct actcatgatg cagcgaaagg gtatagggaa gatgggtctt ggagctctag   6720
tgctcacgct agctaccttc ttcctgtggg cggcagaggt tcccggaaca aaaatagcag   6780
ggaccctgct gatcgccctg ctgcttatgg tggttctcat cccagaaccg gaaaagcaga   6840
ggtcacaaac agataatcaa ctggcggtgt ttctcatctg tgtcttgacc gtggttggag   6900
tggtggcagc aaacgagtac gggatgctag aaaaaaccaa agcagacctc aagagcatgt   6960
ttggcggaaa gacgcaggca tcaggactga ctggattacc aagcatggca ctggacctgc   7020
gtccagccac agcttgggca ctgtatgggg ggagcacagt cgtgctaacc cctcttctga   7080
agcacctgat cacgtcggaa tacgtcacca catcgctagc ctcaattaac tcacaagctg   7140
gctcattatt tgtcttgcca cgaggcgtgc cttttaccga cctagacttg accgttggcc   7200
tcgtcttcct tggctgttgg ggtcaaatca ccctcacaac gttttttgaca gccatggttc   7260 tggcgacact tcactatggg tacatgctcc ctggatggca agcagaagca ctcagggctg   7320
cccagagaag gacagcggct ggaataatga agaatgccgt tgttgacgga atggtcgcca   7380
ctgatgtgcc tgaactggaa aggaccactc tctgatgca aaagaaagtc ggacaggtgc   7440
tcctcatagg ggtaagcgtg gcagcgttcc tcgtcaaccc caaaatcacc actgtgagag   7500
aagcaggggt gttggtgaca gcggctacgc tctctttgtg ggacaacgga gccagtgccg   7560
tttggaattc caccactgcc acgggactct gccatgtaat gcgaggtagc tacctggctg   7620
gaggctccat tgcttggact ctcatcaaga acgctgacaa gccctcctta aaaaggggaa   7680
ggcctggggg caggacgcta ggggagcagt ggaaggaaaa actaaatgcc atgagcagag   7740
aagagttttt taaataccgg agagaggcca taatcgaggt ggaccgcact gaagcacgca   7800
gggctagacg tgaaaataac atagtgggag gacatccggt ttcgcgaggc tcagcaaaac   7860
tccgttggct cgtagagaaa ggatttgtct cgccaatagg aaaagtcatt gatctagggt   7920
gtgggcgtgg aggatggagc tactacgcag caaccctgaa gaaggtccag gaagtcagag   7980
gatacacgaa aggtggggcg ggacatgaag aaccgatgct catgcagagc tacggctgga   8040
acctggtctc catgaagagt ggagtggacg tgttttacaa accttcagag cccagtgaca   8100
ctctgttctg cgacataggg gaatcctccc cgagtccaga agtagaagaa caacgcacac   8160
tacgcgtcct agagatgaca tctgactggt tgcaccgagg acctagagag ttctgtataa   8220
aagttctttg cccctacatg cccaaggtta tagaaaaaat ggaagtcctg caacgccgct   8280
tcggaggtgg gctagtgcgt cttcccctgt cccgcaactc caatcacgag atgtactggg   8340
```

```
ttagtggagc cgctggcaat gtggtgcacg ctgtgaacat gaccagccag gtactactgg    8400
ggcgaatgga tcgcacagtg tggagagggc caaagtatga ggaagatgtc aacttaggga    8460
gcggaacaag agccgtggga aagggagaag tccatagcaa tcaggagaaa atcaagaaga    8520
gaatccagaa gcttaaagaa gaattcgcca caacgtggca caaagaccct gagcatccat    8580
accgcacttg gacataccac ggaagctatg aagtgaaggc tactggctca gctagttctc    8640
tcgtcaacgg agtggtgaag ctcatgagca aaccttggga cgccattgcc aacgtcacca    8700
ccatggccat gactgacacc accccttttg gacagcaaag agttttcaag gagaaagttg    8760
acacgaaggc tcctgagcca ccagctggag ctaaggaagt gctcaacgag accaccaact    8820
ggctgtgggc ctacttgtca cgggaaaaaa gaccccgctt gtgcaccaag gaagaattca    8880
taaagaaagt caatagcaac gcggctcttg gagcagtgtt cgctgaacag aatcaatgga    8940
gcacggcgcg tgaggctgtg gatgacccgc ggttttggga gatggttgat gaagagaggg    9000
aaaaccatct gcgaggagag tgtcacacat gtatctataa catgatggga aaaagagaga    9060
agaagcctgg agagtttgga aaagctaaag gaagcagggc catttggttc atgtggcttg    9120
gagcacggta tctagagttt gaagctttgg ggttcctgaa tgaagatcat tggctgagcc    9180
gagagaattc aggaggtgga gtggaaggct caggcgtcca aaagctggga tacatcctcc    9240
gtgatatagc aggaaagcaa ggaggaaaaa tgtacgctga tgataccgcc gggtgggaca    9300
ctagaattac cagaactgat ttagaaaatg aagccaaggt gctggagctt ctagacggtg    9360
aacaccgcat gctcgcccga gccataattg aattgactta caggcacaaa gtggtcaagg    9420
tcatgagacc tgcagcagaa ggaaagaccg tgatggacgt gatatcaagg gaggatcaaa    9480
gggggagtgg acaggtggtc acttatgctc ttaacacttt cacgaacatc gctgtccagc    9540
tcgtcaggct gatggaggct gagggggtca ttggaccaca acacttggaa cagctaccta    9600
gaaaaaacaa gatagctgtc aggacctggc tctttgagaa tggagaggag agagtgtcca    9660
ggatggctat cagcggagac gactgtgtcg tcaagccgct ggacgacaga ttcgccacgg    9720
ccctccactt cctcaacgca atgtcaaagg tcagaaaaga catccaggaa tggaagcctt    9780
cacatgctg gcacgattgg cagcaagttc ccttctgctc taaccatttt caggagattg    9840
tgatgaaaga tggaaggagt atagttgtcc cgtgcagagg acaggatgag ctgataggca    9900
gggctcgcat ctccccagga gctggatgga atgtgaagga cacagcttgt ctggccaaag    9960
catatgcaca gatgtggcta ctcctatact tccatcgtag ggacttgcgt ctcatggcaa   10020
atgcgatttg ctcagcagtg ccagtggatt gggtgcccac gggcaggaca tcctggtcga   10080
tacactcgaa aggagagtgg atgaccacag aagacatgct gcaggtctgg aacagagtct   10140
ggattgaaga aaatgaatgg atggtggaca agactccaat aacaagctgg acagacgttc   10200
cgtatgtggg aaagcgggag gacatctggt gtggcaacct catcggaacg cgatccagag   10260
caacctgggc tgagaacatc tacgcggcga taaaccaggt tagagctgtc attgggaaag   10320
aaaattatgt tgactacatg acctcactca ggagatacga agatgtcttg atccaggaag   10380
acagggtcat ctagtgtgat ttaaggtgga aaagcagatt atgtaaataa tgtaaatgag   10440
aaaatgcatg catatggagt caggccagca aaagctgcca ccggatactg ggtagacggt   10500
gctgtctgcg tcccagtccc aggaggactg ggttaacaaa tctgacaaca gaaagtgaga   10560
aaaccctcag aaccgtctcg gaagcaggtc cctgctcact ggaagttgaa ggaccaacgt   10620
caggccacaa atttgtgcca ctccgctgag gagtgcggcc tgcgcagccc caggaggact   10680
gggttaccaa agccgttgag cccccacggc ccaagcctcg tctaggatgc aatagacgag   10740
```

```
gtgtaaggac tagaggttag aggagacccc gtggaaacaa caacatgcgg cccaagcccc     10800
ctccaagctg tagaggaggt ggaaggacta gaggttagag gagacccgc atttgcatca      10860 aacagcatat tgacacctgg gaatagactg ggagatcttc tgctctatct caacatcagc     10920
tactaggcac agagcgccga agtatgtagc tggtggtgag aagaacaca ggatct          10976

<210> SEQ ID NO 3
<211> LENGTH: 10774
<212> TYPE: DNA
<213> ORGANISM: Tick-borne encephalitis virus

<400> SEQUENCE: 3
agattttctt gcacgtgtgt gcgtttgctc cggatagcaa cagcagcgag gtttgagaga       60
gataatttct cgtttgacca gtcgtgaacg tgttgagaaa aagacagctt aggagaacaa      120
gagctgggga tggccgggaa ggccattctg aaaggaaagg ggggcggtcc ccctcgacga      180
gtgtcgaaag agaccgcgag gaagacgcgt caatctaggg tccaaatgcc aaatggactc      240
gtgttgatgc gcatgttggg gatttttatgg catgccgtgg ccggcaccgc taggagtccc     300
gtgttgaagt ctttctggaa ttcagtccca ctgaaacagg ccatggcagc actccggaaa     360
attaaaaagg cagtgagcac cctgatggta ggtctgcaaa gacgtggcaa aagaaggtca     420
gcagcagact ggacaagttg gttgctggtt ctggttttgg tggggggtgac acttgcagcc     480 acagtgcgga aagaaaggga tggcactacc gtgatcagag ctgaaggaaa agatgcggca     540
acccaggtgc gtgtggaaaa tggcacctgt gtgatcctgg ccacggacat gggatcatgg     600
tgtgatgact cactaaccta tgagtgtgtg accatagacc agggggagga accagttgac     660
gtggattgct tctgcaggaa tgttgatgga gtttacctgg agtatggacg gtgtggaaaa     720
caagaaggat caagaacaag gcgctcagtg ctgatcccgt cccatgccca gggagacctc     780
acaggaaggg gacacaaatg gttagaaggg gattcactgc ggacgcatct cactagggtt     840
gaaggatggg tctggaagaa caaagtgctc accctggcgg tgatcgccat tgtgtggctg     900
accgtggaaa gcgtggtgac cagggtcgcc gtagtggtgg tgctcttgtg cctggctccg     960
gtttatgcct cacgatgcac acatttggaa aacagagatt ttgttactgg cactcaggga    1020
accactcgtg tgactctggt gctggaactg ggaggatgcg tcaccataac agccgagggg    1080
aagccctcga tggacgtgtg gcttgactcc atttatcagg agaatcctgc caaaacacgt    1140
gagtactgcc tgcacgcaaa gctgtcggac accaaggtcg cggccagatg ccccacaatg    1200
ggacctgcca ctttggctga agagcaccag agtggcacag tgtgcaagag agaccagagt    1260
gatcgaggct ggggtaatca ttgtggatta tttggaaaag gcagcattgt gacctgcgtc    1320
aaggcgtcct gtgggcaaa aaagaaggcc acaggacacg tgtatgatgc caacaaaatt    1380
gtgtacacgg ttaaagtaga gccgcatacg ggggattacg tcgccgctaa tgagacccat    1440
agtggaagaa aaacagcatc cttcacggtt tcctcggaaa aaaccatctt gaccatggga    1500
gactacggag atgtgtcctt gttgtgtcga gtagctagcg gtgttgacct tgctcagact    1560
gtcattctgg aacttgacaa gacttcagaa cacctaccga cggcctggca ggttcaccgg    1620
gactggttca atgatctggc cctgccgtgg aaacatgaag gggcacagaa ctggaacaat    1680
gctgaacggc tagttgagtt tggagcccca catgctgtga aaatggatgt gtataacctt    1740
ggagaccaga ctggagtgtt gcttaagtca cttgctggtg ttccagtggc gcacattgat    1800
ggaaccaagt accacctgaa aagtggccac gtgacatgcg aggtaggact agaaaaactc    1860
```

```
aagatgaaag gtctcacata cacaatgtgc gacaagacga aattcacgtg gaagagaatc    1920
ccaactgaca gtggacatga tacagtggtc atggaagttg cattctctgg aaccaaaccc    1980
tgtaggatcc cggtgagggc cgtggcacac ggctctccag atgtgaatgt ggctatgttg    2040
ataacaccca accccacaat cgaaaccaat ggtggtggtt tcatagaaat gcagttaccg    2100
ccaggagaca acatcatcta tgtcggggaa ctgagtcacc aatggttcca aaaagggagt    2160
agcattggaa gggtctttca aaaaaccagg aaaggtatag aacgactgac agtgatcgga    2220
gaacacgcct gggattttgg ctcaactggt ggattcctga cctcggttgg caaggcgcta    2280
cacacagttc ttggtggtgc cttcaacagc ctgtttggag gagtagggtt cttgcctaag    2340
atcctagtgg gagtggtcct ggcctggttg ggcctgaaca tgaggaatcc gaccatgtcc    2400
atgagcttcc tcctggccgg aggactggtt ctggccatga cactcggagt cggagctgat    2460
gttggctgtg ctgtggacac cgaacggatg gagctccgtt gtggtgaggg tctggttgta    2520
tggagggagg tttccgagtg gtatgacaat tatgcatact accctgagac accaggagct    2580
cttgcttcgg ccataaaaga gaccttcgag gagggaactt gtggtatagt gccccaaaac    2640
agacttgaaa tggccatgtg gagaagctcg gcgacagaac tgaatctggc cttggcggag    2700
ggagacgcaa atctcacagt ggtggtggac aaacttgatc ccacagacta tcgaggtggc    2760
attcctgggc tgctaaagaa ggggaaagac ataaaggttt cttggaagag ctggggccac    2820
tcaatgatct ggagtgtccc cgaggccccc cgtcggttta tggtgggaac agagggaagc    2880
agtgagtgtc cactagagag aaggaaaaca ggtgtcttca cggtggcaga gtttgggggtt    2940 ggcctgagaa caaagtatt cttggacttc agacaggaat caacacatga gtgtgacaca    3000
ggagtgatgg gagccgctgt caagaatggc atggcagtcc acacagacca gagcctctgg    3060
atgaaatccg tgagaaatga cacagggacc tacatagtgg aacttctggt tactgacctg    3120
agaaattgct catggccggc tagccacacc attgacaatg ctgaggtggt ggactcagaa    3180
ctcttccttc cagccagtct ggcagggcct agatcctggt ataacaggat acccgggtac    3240
tcagaacaag tgaaaggacc atggaagtac tcgcccatcc gagtgacaag agaagagtgc    3300
cctggcacga gggtcaccat aaatgccgac tgtgacaaaa ggggggcttc tgtgaggagt    3360
accacagaga gtggcaaggt gattccagag tggtgctgcc gaacgtgcac attacctcca    3420
gtgacgttcc gtacggggac agactgttgg tatgccatgg aaatacgacc agttcatgac    3480
cagggagggc ttgtttcctc aatggtggtg gcagacaatg gagagctgct tagtgagggg    3540
ggcattcccg ggatagtggc tttgtttgtg gtccttgagt acgtcatccg gaggggccca    3600
gccactggaa caacggccat gtggggaggc attgttgtcc ttgcattgct cgtcactggt    3660
ctggtgagaa tcgaaagcct ggtgcgttat gtcgtggcag ttgggatcac atttcatctt    3720
gagctagggc cagagattgt ggctctgaca ctgttacagg ctgtgtttga gttgagggtt    3780
ggcctgctca gcgcttttgc actacgcagc aacctcactg tcagagagat ggtaaccatc    3840
tacttccttc tgctggtttt ggagttggga ttgccaggtg agggtcttgg ggccctatgg    3900
aaatggggag atgcattggc catgggggca ttgattttca gagcctgcac ggcagaggaa    3960
aagactggtt ttggactcct gctcatggct ctcatgacac agcaagacct ggcgattgca    4020
cactatggac tcatgctctt cctgggcacg gcctcatgtt gttcaatctg gaaactgatt    4080
cgaggacaca gagaacagaa gggattgacc tgggttgtcc ccctggccgg gctactcgga    4140
ggagagggct ctgagtcag actgctggct ttttgggaac tggccatcca tggaaggaga    4200
cggtcattca gtgaaccact gactgttgtg ggagtcatgc taaccctggc cagcggcatg    4260
```

```
atgcggcaca cctctcagga ggcccttttgc gcgctcgccg tggcctcgtt ccttctgctc    4320
atgctggtgc tagggacaag gaagatgcag ctagtggctg aatggagtgg ctgtgtggag    4380
tggcacccag aactgatgaa tgaaggtgga gaggtgagcc tgcgggtccg gcaggactca    4440
atgggaaact ccacctgac agagcttgag aaagaggaga gagtgatggc tttctggctg     4500
ctggcaggac tggcggcttc ggccttccac tggtctggca ttcttggtgt gatgggattg    4560
tggacgctgt cggaaatgct gaggacggct cgaagatcag atttggtctt ctctggacag    4620
gggggacgtg agcgtggtga caggcccttt gaggtcaagg atggcgtcta tagaatcttc    4680
agcccaggac tgctctgggg gcagcgccag gtgggagttg gctatggctc caaaggtgtc    4740
ctacacacga tgtggcatgt gacgagaggg gcggcgctgt ccattgatga cgccgtcgca    4800
gggccctatt gggctgacgt caaagaggac gttgtatgct atggtggagc ctggagtctt    4860
gaggagaagt ggaaaggtga gacagtgcag gttcatgcct ccccaccggg gagagcccat    4920
gaggtgcatc aatgtcagcc cggggaactg ctcctggaca caggtaggag gatagggggca   4980
gtgccaattg atctggcaaa agggacatct ggcagcccca tcctcaactc caaggagtg    5040
gttgtgggac tgtatgggaa tggactgaag accaatgaaa cctacgtcag cagcattgct    5100
caaggtgagg ctgaaaaaag tcgacccaat ctcctgccgg ccgtcattgg cacaggctgg    5160
acagcaaaag ggcagatcac agtgctggac atgcacccag gctctgggaa gacccacaga    5220
gtcctcccgg agctcattcg ccaatgcatt gacagacgcc taaggacatt ggtgttggcc    5280
ccaacccgtg tggtgctcaa ggaaatggag cgtgccttga atgggaagag agtcatgttc    5340
cattctccgg cagttggaga tcagcaggtg ggaggggcca tcgtcgacgt gatgtgccat    5400
gcaacctatg tcaatagacg cctgctcccg caggggagac agaattggga agtggcaatc    5460
atggatgaag cccattggac ggatccacac agcatagccg ctcgggggtca cctgtacacc    5520
ttggctaagg aaaacaaatg tgccctggtt cttatgacag caacgccacc cgggaagagc    5580
gaacccttcc cagagtccaa cggggcaatc accagtgaag agaagcagat ccctgatggg    5640
gagtggcgtg atgggttcga ctggatcacc gagtatgagg ggcgtaccgc atggttcgtt    5700
ccctcgattg caaaaggtgg taccatagcc cgcaccctga cacaaaaagg aaaaagcgtg    5760
atctgtctga acagcaagac atttgaaaag gactactcca gagtgagaaa tgagaaaccc    5820
gacttcgtgg tcacaaccga catatctgaa atggggggcca acctcgatgt gagccgtgtc    5880
atagacgggc gaacaaacat caaaccggaa gaggttgatg ggagagttga gctcacaggg    5940
accagacgtg tgaccacggc ctctgcggcc caacgccgtg ggagagtcgg aagacaggag    6000
gaaagaacag atgaatacat atactctgga cagtgtgatg atgatgatag tggacttgtg    6060
cagtggaagg aagcgcagat acttcttgac aacataacaa cactgcgggg gcctgtggcc    6120
acctttatc gaccagagca ggacaagatg ccagaggtgg caggtcattt ccgcctcaca    6180
gaagagaaaa gaaagcactt tcgacatctt ctcacccatt gtgacttcac gccatggttg    6240
gcatggcacg tcgcagcaaa cgtgtctagt gtgacaagtc ggaactggac ttgggaaggc    6300
cctgaggaga acaccgtgga tgaggccaat ggagatctgg tcaccttcag gagcccgaat    6360
ggggctgaaa gaacactgag gccagtatgg aagggatgcgc gtatgttcag agaaggacgt    6420
gacatcagag agttcatcgc gtatgcctca gggagacgca gctttggaga tgtgttgagc    6480
ggaatgtccg tgttcctga gcttctgcgc catagatgtg ttagcgccat ggatgtcttc    6540
tacacactga tgcatgagga gcctggcagc agggcaatga agatggccga gagagatgct    6600
```

```
ccagaggctt ttttgacggt ggtagagatg atggtgctcg gcctggccac tcttggggtc   6660
gtctggtgct ttgttgttcg cacctcaatc agtcgcatga tgcttggcac gctggtactg   6720
ctggcctcac tggcgctcct gtgggccggt ggtgtaagct acgggattat ggcaggagtg   6780
gccctcattt tctacacgtt gttgacggtg ctgcagcctg aagcgggaa acagaggagc    6840
agtgatgaca acaagttggc ctacttcctg ttgacgctct gcagtctagc tggactggta   6900
gccgccaatg aaatgggatt tctggagaag actaaggcgg acctgtccac ggtgttgtgg   6960
agtgaacatg aagagttgcg gtcgtgggaa gagtggacca acatcgacat ccagcctgca   7020
cgttcctggg gaacttacgt gctggtggtc tctttgttca caccatacat aattcaccaa   7080
cttcagacca agatccaaca actcgtcaac agcgctgttg caactggggc tcaggccatg   7140
cgagacctcg gaggagggc tccattcttt ggggtagcag gcatgtaat ggctttggga     7200
gtggcatcgc tagttggtgc aacgccaaca tccttggtgg ttggtgttgg tctggcggcg   7260
ttccacctgg ccattgtggt gtccggacta gaggctgagt tgacacaaag agcccacaaa   7320
gtcttcttct cggcaatggt gcgcaatccc atggtggatg agacgtcat caatccattt    7380
ggagagggag aggcaaaacc tgctccgtat gagaggaaaa tgagcctggt cttggcgata   7440
gtgctttgct tgatgtcggt ggtcatgaac agaacggtgc cttctatcac tgaggcttct   7500
gctgtgggac tggcggcagc gggacaactg ctcagaccag aggcggatac cctgtggacg   7560
atgccagtgg cctgtggcct gagcggcgtg gtcaggggta gcctctgggg attcttgccc   7620
ctcgggcata gactctggct aagggcctct gggagtaggc gtggtggttc tgagggggac   7680
actctcggtg acttgtggaa acggaaactc aatggctgta ccaaagaaga gttcttcgcc   7740
tatagacgca ctggcatcct ggagacggaa agggacaagg cacgggaact cctcaggaga   7800
ggggagacca acatggggct ggctgtgtca cggggcacgg ctaaacttgc ctggcttgag   7860
gaacgaggtt acgcaactct caagggtgag gtcgtggacc ttggatgtgg aagaggcggc   7920
tggtcctact atgcggcctc tagaccggct gtcatgagtg tcaaagccta cacaattggt   7980
ggaaagggac acgagacccc aaagatggtg acaagcttgg gttggaacct gatcaagttc   8040
agagcgggaa tggatgtgtt cagcatgcag ccacaccgag ctgataccat tatgtgtgac   8100
atcggagaaa gcaacccaga tgccgtggtg gagggtgaga ggacacggaa agtgatacta   8160
ctcatggaac agtggaaaaa ccgcaatccc acggctacct gtgtgttcaa ggtgttggcc   8220
ccataccgcc cagaggtcat agaagcacta cacagattcc aactgcagtg gggcggagga   8280
ctggtgagga cccctttctc gaggaattca acccatgaaa tgtattactc gactgctgtc   8340
actggaaaca ttgtgaattc agttaacatc caatcaagaa aactcttggc ccggttcggg   8400
gaccagaggg gacccaccag ggtgcctgag ctggacctcg gagttgggac tcgatgcgtt   8460
gtcttggctg aggacaaggt gaaggaaaaa gatgtgcagg agaggatcag tgcgctgcga   8520
gagcagtatg gtgagacctg gcatatggac agagagcacc cgtacaggac ctggcagtac   8580
tggggcagct accgcaccgc gccaaccggg tcagcggcgt cactgatcaa tggagtcgtg   8640
aagcttctca gctggccatg gaacgcgcgg gaggatgtcg tgcgaatggc catgactgac   8700
accacagcct ttggacagca gcgagtgttc aaagagaagg ttgacaccaa ggctcaggaa   8760
cctcagcctg gcacaaaggt catcatgaga gcagtgaatg actggattct ggaacgattg   8820
gcacggaaaa gcaaaccacg aatgtgcagc agagaggagt tcatagcgaa agtgaaatcc   8880
aatgcggctc tggggcttg gtctgatgag cagaacaggg ggtcaagtgc aaaagaggct   8940
gtagaggatc ccgcattctg gcagctcgtg gatgaagaga gagagaca ccttgctggg   9000
```

```
agatgcgccc actgtgtgta caacatgatg ggcaaaagag aaaagaagct tggagagttt    9060
ggagtggcca aaggaagccg ggccatatgg tacatgtggc tggggagccg ctttctggag    9120
ttcgaagctc ttggcttttt gaatgaggac cactgggcct ctaggggtc cagtggatct     9180 ggagtggagg gaataagctt gaattacctg gctggtacc tcaaagggtt gtcaacactg     9240
gaaggaggcc ttttctacgc ggatgacaca gccggctggg acaccaaggt caccaacgca    9300
gacctagagg atgaagaaca gctcctacgc tacatggagg gtgaacacaa gcaactggcg    9360
gctacaataa tgcagaaggc ataccacgcc aaggtggtaa agtagcccg gccctcccga     9420 gatgggggct gtgtcatgga tgtcatcaca agaagagacc aaagacgcac agagcaggtt    9480
gtgacttatg ccctcaacac ccttaccaac ataaaggttc agctgatccg tatgatggag    9540
ggggagggag tcattgaggc ctcggacgca cataatccaa gattactccg agtgaacga     9600 tggctgagga accatggaga agaacgtctc ggaagaatgc tcgtgagcgg tgatgattgt    9660
gtggtgagac cggtggatga caggttcagt agggcactct attttctgaa tgacatggcc    9720
aaaaccagga aagacattgg ggagtgggag cattcggttg gcttctcgaa ctgggaggag    9780
gttcccttct gttcacacca cttccacgag ttggtgatga agatgggcg tgcccctcata    9840 gtgccatgcc gagaccaaga tgaactggtt ggaagagccc gcgtctcacc agggtgcggc    9900
tggagtgtcc gcgaaactgc ctgcctttca aaagcttatg gcagatgtg ctgctgagt     9960 tactttcacc ggcgcgactt gcggacgctt ggacttgcca tctgttcggc ggtgcccatt    10020
gactgggtcc ccactggccg cacgacctgg agcatccatg ctagcggagc ctggatgacc    10080
acagaggaca tgttggatgt ctggaacagg gtgtggattc tggacaaccc cttcatgcac    10140
agcaaagaaa agattgtgga atggaggat gtcccgtatc tccccaaatc ccatgacatg     10200
ctgtgttcct ctcttgttgg gaggaaagag agggcagagt gggctaagaa catctgggga    10260
gcagtagaga aagtcaggaa gatgatcgga caagagaagt tcaaggacta cctttcctgc    10320
atggaccggc atgacttgca ctgggagctc aaactggaga gctcaataat ctaaaactag    10380
attgtgactg agcacaacct ggagtgctcg ttaaacattg tccagaacca aaaaccacag    10440
caaacaattc acagaacacc cccagagtgc cccacggcaa cacgtcagtg agagtggcga    10500
cgggaaaatg gtcgatcccg acgtagggca ctctgtaaaa ctttgtgaga ccccccggcac   10560 catgataagc ccgaacatgg tgcaagaacg ggaggccccc ggaagcatgc ttccgggagg    10620
agggaagaga gaaattggca actctcttca ggattcttcc tcctcctata ccaaattccc    10680
cctcaacaga ggggggcgg ttcttgttct ccctgagcca ccatcaccca gacacagata    10740
gtctgacaag gaggtgacgt gtgactcgga aaaa                                10774

<210> SEQ ID NO 4
<211> LENGTH: 10471
<212> TYPE: DNA
<213> ORGANISM: Tick-borne encephalitis virus

<400> SEQUENCE: 4
agattctgtg gcacgtgcgt gcgtttgctt cggacagcat tagcagcggt tggtttgaaa      60
gagatattct tttgtttcta ccagtcgtga acgtgttgag gaaagacag cttaggagaa      120 caagagctgg ggatggtcaa gaaggccatc ctgaaaggta aggggggcgg tccccctcga      180
cgagtgtcga aagagaccgc aacgaagacg cgtcaaccca gagtccaaat gccaaatggg      240
cttgtgttga tgcgcatgat ggggatcttg tggcatgccg tagctggcac cgcgagaaac      300
```

```
cccgtattga aggcgttctg gaactcagtc cctctgaaac aggccacagc agcactgcgg      360
aggatcaaaa ggacagtgag tgccctaatg gttggcttgc aaaaacgtgg gaaaaggagg      420
tcagcgacgg actggatgag ctggttgctg gtcattactc tgttggggat gacgcttgct      480
gcaacggtgg ggaaagaaag ggacggctca actgtgatca gagctgaagg gaaggatgca      540
gcaactcagg tgcgtgtgga aaatggcacc tgtgtgatcc tggctactga catggggtca      600
tggtgtgatg attcactgtc ctatgagtgt gtgaccatag atcaaggaga gagcctgtt       660 gacgtggatt gttttttgccg gaacgttgat ggagtctatc tggagtatgg acgctgcggg     720
aaacaggaag gctcacggac aaggcgctca gtgctgatcc cgtcccatgc tcagggagag      780
ctgacgggga ggggacacaa atggctagaa ggagactcgc tgcgaacaca cctcactaga      840
gttgagggat gggtctggaa gaacaagcta cttgccttgg cgatggtcac cgttgtgtgg      900
ttgaccatgg agagtgtggt gaccagggtc gccgttctgg ttgtgctcct gtgtttagca      960
ccggtctacg cttcgcgttg cacacacttg gaaaacaggg actttgtgac tggtactcag     1020
gggactacga ggatcacttt ggtgctggag ctggtggat  gtgttaccat aacagctgag     1080
gggaagcctt caatgatgt gtggcttgac gccatttacc aggagaaccc tgctaagaca     1140
cgtgagtact gtcacacgc caagttgtcg gacactaagg ttgcagccag atgcccaacg     1200
atgggaccag ccactttggc tgaagaacac cagggtggca cagtgtgtaa gagagatcag     1260
agtgaccgag gctgggcaa ccactgtgga ctgtttggaa agggtagcat tgtggcctgt      1320
gtcaaggcgg cttgtgaggc aaaaaagaaa gccacaggac atgtgtacga cgccaacaaa     1380
atagtgtaca cggtcaaagt cgaaccacac acgggagact atgttgccgc aaacgagaca     1440
catagtggga ggaagacggc gtccttcaca gtttcttcag agaaaaccat tctgaccatg      1500
ggtgagtatg gagatgtgtc tttgttgtgc agggtcgcta gtggcgttga cttggcccag     1560
accgtcatcc ttgagcttga caaacagtg gaacaccttc caacggcttg gcaggtccac      1620
agggattggt tcaatgatct ggctctgcca tggaaacatg agggagcgca aaactggaat     1680
aacgcagaac gactggttga atttggagct cctcacgctg tcaagatgga cgtgtacaac      1740
ctcggagacc agactggagt gttactgaag gctctcgctg gggttcctgt ggcacacatt     1800
gagggaacca agtaccacct gaagagtggc catgtgacct gcgaagtcgg actggaaaaa     1860
ctgaagatga aagggcttac gtacacaatg tgtgacaaga caaagttcac atggaagaga     1920
gctccaacag atagtgggca tgacacagtg gtcatggaag tcacattctc tggaataaag     1980
ccctgtagga tcccagtcag ggcagtggca catggatctc cagatgtgaa cgtggccatg     2040
ctgataacgc caaacccaac aattgaaaac aatggaggtg gtttcataga gatgcagctg     2100 ccccagggg ataacatcat ctatgttggg gaactgagtc atcaatggtt ccaaaaaggg     2160
agcagcatcg gaagggttttt tcaaaagacc aagaaaggca tagaaagact gacagtgata     2220
ggagagcacg cctgggactt cggttctgct ggaggctttc taagttcaat gggaaggcg      2280 gtgcatacgg tccttggtgg tgcattcaac agcatcttcg ggggagtagg gtttctacca     2340
aagcttttat taggagtggc attggcttgg ttgggcctga acatgagaaa tcctacaatg     2400
tccatgagct ttctcttggc tggaggtctg gtcttggcca tgaccttgg agtggggcg      2460 gatgttggct gcgctgtgga cacggaacga atggagctcc gctgtggcga gggcctggtc     2520
gtgtggagag aggtctcaga atggtatgac aactatgcct actacccgga cacacgggg      2580 gcccttgcat cagccataaa ggagacattt gaggagggaa gctgtggcgt agtccccag      2640 aacaggctcg agatggccat gtggagaagc tcggtcacag agctgaatct ggctctggcg     2700
```

```
gaaggggagg caaatctcac agtggtggtg acaagtttg accccactga ctaccgaggt    2760
ggtgtccctg gtttactgaa aaaggaaag acataaaag tctcctggaa aagctggggc    2820
cattcaatga tctggagcat ccccgaggcc ccccgtcgtt tcatggtggg cacggaagga    2880
caaagtgagt gtcccctaga gagacggaag acaggtgttt tcacggtggc agaattcggg    2940
gttggcctga gaacaaaggt cttcttggat ttcagacaga aaccaacaca tgagtgtgac    3000
acaggagtga tgggagctgc cgtcaagaac ggcatggcaa tccacacaga tcaaagtctc    3060
tggatgagat caatgaaaaa tgacacaggc acctacatag ttgaacttct ggttactgac    3120
ctgaggaact gctcatggcc tgctagccac actatcgaca atgctgacat ggtggactcg    3180
gagctattcc ttccggcgag cctggcagga cccagatcct ggtacaacag atacccggt    3240 tattcagaac aggtgaaagg gccatggaag cacacgccta tccgagtcat cagagaggag    3300
tgtcccggca cgaccgttac catcaacgcc aagtgtgaca aagaggagc atctgtgagg    3360 agtaccacag agagtggcaa ggttatccca gaatggtgct gccgagcgtg cacaatgcca    3420
ccagtgacgt tccggactgg aactgattgc tggtatgcca tggaaatacg gccagtccat    3480 gaccagggg ggcttgttcg ctcaatggtg gttgcggaca acggtgaatt acttagtgag    3540 ggagggggtcc ccggaatagt ggcattgttt gtggtccttg aatacatcat ccgtaggaga    3600
ccctccacgg gaacaacggt tgtgtggggg gcatcgtcg tactcgctct gcttgtcacc    3660
gggatggtca ggatggagag cctggtgcgc tatgtggtgg cagtggggat cacattccac    3720
cttgagctag gaccagagat cgtggccttg atgctactcc aggctgtgtt tgagttgagg    3780
gtgggtttgc tcagcgcatt tgcactgcgc agaagcctca ccgtccgaga gatggtgacc    3840
acctacttcc ttttgttggt cctggaattg gggctgccgg gtgcgggact tgaggatctc    3900
tggaaatggg gtgatgcact ggccatgggg gcgctaatgt tcagggcttg cacggcagaa    3960
ggaaagactg gagcggggct cttgctcatg gctctcatga cacagcagga tgtggtgact    4020
gtgcatcatg gactggtgtg cttctgagt gtagcttcgg cttgctcggt ctggaggctg    4080
ctcaagggac acagagagca gaagggattg acctggattg tccccctggc tagattgctt    4140
gggggagagg gctctggaat caggctgctg gcgttttggg agctggcagc tcacagagga    4200
agacgatctt tcagtgaacc actaactgtg gtaggagtca tgctaacact ggccagcggc    4260
atgatgcgac acacctccca ggaggctctc tgtgcactcg cagtggcctc gtttctcttg    4320
ttgatgctgg tgctggggac aagaaagatg cagctggttg ccgaatggag tggctgcgtg    4380
gaatggcatc cggaactagt gaatgaggt ggagaggtta gcctgcgggt ccgtcaggac    4440
gcaatgggaa actttcactt gactgagctc gagaaagagg agagaatgat ggcttttttgg    4500 ctgctggccg gcttggcagc ttcagccatt cattggtcag gcattcttgg tgtgatggga    4560
ctgtggacgc tcacggaaat gctgaggtca tcccgaaggt ccgacctggt tttctctgga    4620 cagggggcc gagagcgtgg tgacagacct ttcgaggtta aggacggtgt ctacaggatt    4680
ttcagccccg gcttgttctg gggtcagaac caagtgggag ttggctacgg ttccaagggt    4740
gttttgcaca cgatgtggca cgtgacaaga ggagcggcgc tgtctattga tgatgctgtg    4800
gccggtccct actgggctga tgtgagggaa gatgtcgtgt gctacggagg agcctggagc    4860
ctggaggaaa aatggaaagg tgaaacagta caggtccatg ccttcccacc ggggaaggcc    4920
catgaggtgc atcagtgcca gcctgggag ttgattcttg acaccggaag gaagcttggg    4980
gcaataccaa ttgatttggt aaaaggaaca tcaggcagcc ccattcttaa cgcccaggga    5040
```

```
gtggttgtgg ggctatacgg aaatggccta aaaactaatg agacctacgt cagcagcatt    5100 gctcagggggg aagcggagaa gagtcgaccc aacctcccac aggctgttgt gggcacgggc    5160
tggacatcaa agggtcagat cacagtgctg acatgcacc caggctcagg gaagacccac     5220
agagtcctcc cggagctcat cgccaatgc attgacaggc gcctgagaac gttggtgttg     5280
gctccaactc gtgtggtgct caaagaaatg gagcgcgcct tgaatgggaa acgggtcagg    5340
ttccactcac cagcagtcag tgaccaacag gctggagggg caattgtcga cgtgatgtgt    5400
cacgcaacct acgtcaacag acggctactc ccacagggga gacaaaattg ggaggtggca    5460
atcatggacg aggcccactg gacgaccccc cacagcatag ctgccagagg tcatttgtac    5520
actctggcaa agaaaacaa gtgtgcattg gtcttgatga cagcgacacc tcctggtaag     5580
agtgaaccct ttccggagtc taacggagcc attactagtg aggaaagaca gattcctgat    5640
ggagagtggc gtgacgggtt tgactggatc actgagtatg aagggcgcac cgcctggttt    5700
gtcccttcga ttgcaaaagg tggtgccata gctcgcaccc tgagacagaa ggggaaaagt    5760
gtgatctgtt tgaacagcaa aacctttgaa aaggactact ccagagtgag ggatgagaag    5820
cctgactttg tggtgacgac tgatatctcg gagatgggag ccaaccttga cgtgagccgc    5880
gtcatagatg gaggacaaaa catcaagcct gaggaggttg atgggaaggt cgagctcatc    5940
gggaccaggc gcgtgaccac ggcttccgct gcccaacggc gcggaagagt tggtcggcag    6000
gacggacgaa cagacgaata catatactct ggacagtgtg atgatgatga cagtggatta    6060
gtgcaatgga agaggcgca aatacttctt gacaatataa caaccttgcg ggggcccgtg     6120
gccaccttct atggaccaga acaggacaag atgccggagg tggccggtca ctttcgactc    6180
actgaagaga aagaaagca cttccgacat cttctcaccc attgtgactt cacaccgtgg    6240
ctggcatgga cgtcgcagc gaatgtgtcc agcgtcacgg atcgaagctg acatgggaa     6300 gggccggagg caaatgccgt ggatgaggcc agtggtgatt tggtcacctt taggagcccg    6360 aatgggcgg agagaactct gaggccggtg tggaaggacg cacgcatgtt caaagaggga    6420
cgtgacatca aagagttcgt ggcgtacgcg tctgggcgtc gcagcttcgg agatgtcctg    6480
acaggaatgt cgggagttcc ggagcttttg cggcacagat gcgtcagtgc cctggatgtc    6540
ttctacacac tcatgcatga ggaacctggc agcagggcaa tgagaatggc ggagagagat    6600
gccccagagg cctttctgac tatggctgag atgatggtgc tgggtttggc aaccctgggt    6660
gtcatctggt gcttcgtcgt ccggacttca atcagccgca tgatgctggg cacgctggtc    6720
ctgctggcct cgttgctgct cttgtgggca ggtggtgtcg gctatgggaa catggccgga    6780
gtggctctca tcttctacac gttgctgacg gtgctgcagc ccgacgcggg aaaacagaca    6840
agcagtgacg acaacaaact ggcatatttc ttgctgacgc tctgcagcct tgctggactg    6900
gttgcagcca atgagatggg tttttctggag aagaccaagg cagacttgtc cacggtgttg    6960
tggagtgaac gggaggaacc ccggccatgg agtgaatgga cgaatgtgga cattcagcca    7020
gcgaggtcct gggggaccta tgtgctggtg gtgtctctgt ttacaccttta catcgtccat   7080 caactgcaga ccaaaatcca acaacttgtc aacagtgccg tggcatctgg agcacaggcc    7140
atgagagacc ttggaggagg tgcccccttc tttggtgtgg cggacatgt catgaccctt     7200 ggggtggtgt cactgattgg ggccactccc acctcactga tggtgggcgt tggcttagcg    7260
gcattccatc tggccattgt tgtgtctggt ctggaggctg aattaacaca gagagctcac    7320
aaggtctttt tctctgcaat ggtgcgcaac cccatggtgg atgggatgt catcaaccca    7380 ttcggggagg gggaggcaaa acctgctcta tatgaaagga aaatgagtct ggtgttggcc    7440
```

```
atagtgttgt gcctcatgtc ggtggtcatg aaccgaacgg tggcctccat aacagaagct    7500
tcagctgtgg gactggcagc agcgggacag ctgcttaggc cggaggctga cacactgtgg    7560
acgatgccgg ttgcttgtgg catgagtggt gtggtcaggg gtagcctgtg ggggtttctg    7620
cctcttgggc atagactctg gcttcgagct tctgggggca ggcgtggtgg ttctgaggga    7680
gacacgcttg gagatctctg gaaacggagg ctgaacaact gcaccaggga ggaattcttc    7740
gtgtacaggc gcactggcat cttggagacg gagcgtgaca aggctagaga gttgctcaga    7800
agaggagaga ccaatatggg attggctgtc tctcgggca cggcaaagct tgcctggctt    7860
gaggaacgcg gatatgccac cctcaaggga gaggtggtag atcttggatg tggaaggggc    7920
ggctggtcct attatgcggc atcccgaccg gcggtcatga gtgtcagggc atacaccatt    7980 ggtgaagag acacgaggc tccaaagatg gtaacaagcc tgggttggaa cttgattaaa    8040
ttcagatcag gaatggacgt gttcagcatg cagccacacc gggctgacac tgtcatgtgt    8100
gacatcggag agagcagccc agatgccgct gtggagggtg agaggacaag gaaagtgata    8160
ttgctcatgg agcaatggaa aaataggaac cccacggctg cctgtgtgtt caaggtgctg    8220
gccccatatc gcccagaagt gatagaagca ctgcacagat tccaactgca atgggggggg    8280
ggtctggtga ggacccccctt ttcaaggaac tccacccatg agatgtatta ctcaacagct    8340
gtcactggga acatagtgaa ctccgtcaac gtacagtcga ggaaactttt ggctcggttt    8400
ggagaccaga gagggccaac cagggtgcct gaacttgacc tgggagttgg aactcggtgt    8460
gtggtcttgg ctgaggacaa ggtaaaagaa caagacgtac aagagaggat cagagcgttg    8520
cgggagcagt acagcgaaac ctggcacatg gacgaggaac acccgtaccg gacatggcag    8580
tactggggta gttaccgcac ggcaccaacc ggctcggcgg cgtcactgat taatgggtt    8640 gtgaaacttc tcagctggcc atggaacgca cgggaagatg tggtgcgcat ggccatgact    8700
gacacaacgg ctttcggaca gcagagagtg ttcaaggata agttgacac aaaggcacaa    8760 gagcctcagc ccggtacaag agtcatcatg agagcagtaa atgattggat tttggaacga    8820
ctggcgcaga aaagcaaacc gcgcatgtgc agcaaagagg aattcatagc aaaagtgaaa    8880
tcaaatgcag ccttgggagc ttggtcagat gagcaaaaca gatgggcaag tgcaagggag    8940
gctgtagagg atcctgcatt ctggcacctc gtggatgaag agagagaaag gcacctcatg    9000
gggagatgcg cgcactgcgt gtacaacatg atgggcaaga gagagaagaa actgggagag    9060
tttggagtgg cgaaaggaag tcgggccatc tggtacatgt ggctggggag tcgcttcctg    9120
gagttcgagc tcttggatt cttgaatgaa gaccattggg cctctagaga gtccagtgga    9180
gctggagttg agggaataag cttgaactac ctgggctggc acctccagaa gttgtcaacc    9240
ctgaatggag gactcttcta tgcagatgac acagctggct gggacacgaa agtcaccaat    9300
gcagacctag aggatgaaga acagatccta cggtacatgg agggtgagca caacaattg    9360 gcaaccacaa taatgcaaaa agcataccat gccaaagtcg tgaaggtcgc gaggcccctcc    9420 cgtgatggag gctgcatcat ggatgtcatc acaagaagag atcaaagagg ctcgggccag    9480
gttgtgacct atgccctcaa caccctcacc aacataaagg tgcaactaat ccgaatgatg    9540
gaggggggag ggtcataga ggcagcggat gcacacaacc cgagactgct tcgagtggag    9600
cgctggctga agaacatggg agaagagcgt cttggaagaa tgctcgtcag tggtgacgat    9660
tgtgtggtga ggcccttgga tgacagattt gcaaagcac tttactttt gaatgacatg    9720 gccaagacca ggaaagacat tgggaatgg gagcactcgc ccggctttc aagctgggag    9780
```

```
gaggtcccct tttgttcaca ccatttccac gagctagtga tgaaggacgg acgcgccctg    9840
gtggtgccgt gccgagacca agatgaactc gttgggaggg cgcgcatctc accagggtgc    9900
ggctggagtg tccgcgagac ggcctgcctt tcaaaagcct acgggcagat gtggctgctg    9960
agctacttcc atcggcgaga cctgaggacg ctcgggcttg ccatcaactc agcagtgcct   10020
gtcgattggg ttcctaccgg ccgcacgaca tggagcatcc atgccagtgg ggcctggatg   10080
accacagaag acatgctgga tgtctggaac cgggtgtgga ttttggacaa ccctttcatg   10140
cagaacaagg aaaaggtcat ggagtggagg gatgttccgt acctccctaa agctcaggac   10200
atgttatgtt cctcccttgt cgggaggaaa gaaagagcag aatgggccaa gaacatctgg   10260
ggagcggtgg aaaaggttag gaagatgata ggtcctgaaa agttcaagga ctatctctcc   10320
tgtatggacc gccatgacct gcactgggag ctcagactgg agagctcaat aatctaaacc   10380
cagactgtga cagagcaaaa cccggagggc tcgtaaaaga ttgtccggaa ccaaaaggaa   10440
agcaagcaac ttatggaatg ctgcggcagc g                                  10471
```

```
<210> SEQ ID NO 5
<211> LENGTH: 11141
<212> TYPE: DNA
<213> ORGANISM: Tick-borne encephalitis virus

<400> SEQUENCE: 5
```

```
agatttctt  gcacgtgcat gcgtttgctt cggacagcat tagcagcggt tggtttgaaa      60
gagatattct tttgttttcta ccagtcgtga acgtgttgag aaaaagacag cttaggagaa     120
caagagctgg ggatggtcaa gaaggccatc ctgaaaggta aggggggcgg tcccccctcga    180 cgagtgtcga aagagaccgc aacgaagacg cgtcaaccca gagtccaaat gccaaatggg    240
cttgtgttga tgcgcatgat ggggatcttg tggcatgccg tagccggcac cgcgagaaac    300
cccgtattga aggcgttctg gaactcagtc cctctgaaac aggcaacagc agcactgcgg    360
aagatcaaaa ggacggtgag tgccctaatg gttggcttgc aaaaacgtgg gaaaaggagg    420
tcagcgacgg actggatgag ctggttgctg gtcatcactc tgttggggat gacgcttgct    480
gcaacggtga ggaaagaaag ggatggctca actgtgatca gagctgaagg aaaggatgca    540
gcaactcagg tgcgtgtgga gaatggcacc tgtgtgatcc tggctactga catggggtca    600
tggtgtgatg attcactgtc ctatgagtgt gtgaccatag atcaaggaga gagcctgtt    660 gacgtggatt gttttttgccg gaacgttgat ggagtctatc tggagtacgg acgctgtggg    720
aaacaggaag gctcacggac aaggcgctca gtgctgatcc catcccatgc tcagggagag    780
ctgacgggaa ggggacacaa atggctagaa ggagactcgc tgcgaacaca ccttactaga    840
gttgagggat gggtctggaa gaacaagcta cttgccttgg caatggttac cgttgtgtgg    900
ttgaccctgg agagtgtggt gaccagggtt gccgttcttg ttgtgctcct gtgtttggca    960
ccggtttacg cttcgcgttg cacacacttg gaaaacaggg actttgtgac tggtactcag   1020
gggactacga gggtcacctt ggtgctgaa ctgggtggat gtgttactat aacagctgag   1080
gggaagcctt caatggatgt gtggcttgac gccatttacc aggagaaccc tgctaagaca    1140
cgtgagtact gtttacacgc caagttgtcg gacactaagg ttgcagccag atgcccaaca    1200
atgggaccag ccactttggc tgaagaacac cagggtggca cagtgtgtaa gagagatcag    1260
agtgatcgag gctggggcaa ccactgtgga ctgtttggaa agggtagcat tgtggcctgt    1320
gtcaaggcgc cttgtgaggc aaaaaagaaa gccacggaca tgtgtacga cgccaacaaa    1380 atagtgtaca cggtcaaagt cgaaccacac acgggagact atgttgccgc aaacgagaca    1440
```

```
catagtggga ggaagacggc atccttcaca atttcttcag agaaaaccat tttgactatg   1500
ggtgagtatg gagatgtgtc tttgttgtgc agggtcgcta gtggcgttga cttggcccag   1560
accgtcatcc ttgagcttga caagacagtg gaacacctte caacggettg gcaggtccat   1620 agggactggt tcaatgatct ggctctgcca tggaaacatg agggagcgca aaactggaac   1680
aacgcagaaa gactggttga atttggggct cctcacgctg tcaagatgga cgtgtacaac   1740
ctcggagacc agactggagt gttactgaag gctctcgctg gggttcctgt ggcacacatt   1800
gagggaacca agtaccacct gaagagtggc cacgtgacct gcgaagtggg actggaaaaa   1860
ctgaagatga aggtcttacg gtacacaatg tgtgacaaaa caaagttcac atggaagaga   1920
gctccaacag acagtgggca tgatacagtg gtcatggaag tcacattctc tggaacaaag   1980
ccctgtagga tcccagtcag ggcagtggca catggatctc cagatgtgaa cgtggccatg   2040
ctgataacgc caaacccaac aattgaaaac aatggaggtg gcttcataga gatgcagctg   2100
cccccagggg ataacatcat ctatgttggg gaactgagtc atcaatggtt ccaaaagggg   2160
agcagcatcg gaagggtttt ccaaaagacc aagaaaggca tagaaagact gacagtgata   2220
ggagagcacg cctgggactt cggttctgct ggaggctttc tgagttcaat tgggaaggcg   2280
gtacatacgg tccttggtgg cgctttcaac agcatcttcg ggggagtggg gtttctacca   2340 aaactttat taggagtggc attggcttgg ttgggcctga acatgagaaa ccctacaatg   2400
tccatgagct ttctcttggc tggaggtctg gtcttggcca tgacccttgg agtggggcg   2460 gatgttggtt gcgctgtgga cacggaacga atggagctcc gctgtggcga gggcctggtc   2520
gtgtggagag aggtctcaga atggtatgac aattatgcct actacccgga gacaccgggg   2580
gcccttgcat cagccataaa ggagacattt gaggagggaa gctgtggtgt agtccccag   2640 aacaggctcg agatggccat gtggagaagc tcggtcacag agctgaattt ggctctggcg   2700 gaagggagg caaatctcac agtggtggtg gacaagtttg accccactga ctaccgaggt   2760
ggtgtccctg gtttactgaa aaaggaaag gacataaaag tctcctggaa aagctggggc   2820
cattcaatga tctggagcat tcctgaggcc ccccgtcgct tcatggtggg cacggaagga   2880
caaagtgagt gtcccctaga gagacggaag acaggtgttt tcacggtggc agaattcggg   2940
gttggcctga gaacaaaggt cttcttggat ttcagacagg aaccaacaca tgagtgtgac   3000
acaggagtga tgggagctgc agtcaagaac ggcatggcaa tccacacaga tcaaagtctc   3060
tggatgagat caatgaaaaa tgacacaggc acttacatag ttgaactttt ggtcactgac   3120
ctgaggaact gctcatggcc tgctagccac actatcgata tgctgacgt ggtggactca   3180 gagttattcc ttccggcgag cctggcagga cccagatcct ggtacaacag gatacctgc   3240 tattcagaac aggtgaaagg gccatggaag tacacgccta tccgagttat cagagaggag   3300
tgtcccggca cgaccgttac catcaacgcc aagtgtgaca aagaggagc atctgtgagg   3360 agtaccacag agagtggcaa ggttatccca gaatggtgct gccgagcgtg cacaatgcca   3420
ccagtgacgt tccggactgg aactgattgc tggtatgcca tggaaatacg gccagtccat   3480 gaccagggg ggcttgttcg ctcaatggtg gttgcggaca acgtgaatt acttagtgag   3540 ggaggagtcc ccggaatagt ggcattgttt gtggtccttg aatacatcat ccgtaggagg   3600
ccctccacgg gaacgacggt tgtgtggggg gtatcgtcg ttctcgctct gcttgtcacc   3660
gggatggtca ggatagagag cctggtcgcg tatgtggtgg cagtggggat cacattccac   3720
cttgagctgg ggccagagat cgtggccttg atgctactcc aggctgtgtt tgagctgagg   3780
```

```
gtgggtttgc tcagcgcatt tgcattgcgc agaagcctca ccgtccgaga gatggtgacc    3840
acctactttc ttttgctggt cctggaattg gggctgccgg gtgcgagcct tgaggagttc    3900
tggaaatggg gtgatgcact ggccatgggg gcgctgatat tcagggcttg cacggcagaa    3960
ggaaagactg gagcgggct tttgctcatg gctctcatga cacagcagga tgtggtgact     4020
gtgcaccatg gactggtgtg cttcctaagt gtagcttcgg catgctcggt ctggaggctg    4080
ctcaagggac acagagagca gaagggattg acctgggttg tccccctggc tgggttgctt    4140
gggggagagg gctctggaat cagactgctg gcgttttggg agttgtcagc gcacagagga    4200
agacgatctt tcagtgaacc actaactgtg gtaggagtca tgctaacact ggccagcggc    4260
atgatgcgac acacttccca ggaggctctc tgtgcactcg cagtggcctc gtttctcttg    4320
ctgatgctgg tgctggggac aagaaagatg cagctggttg ccgaatggag tggctgcgtt    4380
gaatggtatc cggaactagt gaatgagggt ggagaggtta gcctgcgggt ccggcaggac    4440
gcgatgggta actttcactt gactgagctc gagaaagaag agagaatgat ggcttttttgg   4500 ctgattgccg gcttggcagc ttcggccatt cactggtcag gcattcttgg tgtgatggga    4560
ctgtggacgc tcacggaaat gctgaggtca tcccgaaggt ctgacctggt tttctctgga    4620
caggggggtc gagagcgtgg tgacagacct ttcgaggtta aggacggtgt ctacaggatt    4680
tttagccccg gcttgttctg gggtcagaac caggtgggag ttggctacgg ttccaagggt    4740
gtcttgcaca cgatgtggca cgtgacgaga ggagcggcgc tgtctattga tgacgctgtg    4800
gccggtccct actgggctga tgtgagggaa gatgtcgtgt gttacggagg agcctggagc    4860
ctggaggaaa aatggaaagg tgaaacagta caggtccatg ccttcccacc ggggagggcg    4920
catgaggtgc atcagtgcca gcctggggag ttgatccttg acaccggaag aaagcttggg    4980
gcaataccaa ttgatttggt gaaaggaaca tcaggcagcc ccattctcaa cgcccaggga    5040
gtggttgtgg ggctatacgg aaatggccta aaaactaatg agacctacgt cagcagcatt    5100
gctcaagggg aagcggagaa gagtcgcccc aacctcccac aggctgttgt gggtacgggc    5160
tggacatcaa agggtcagat cacagtgctg gacatgcacc caggctcggg gaagacccac    5220
agagtcctcc cggagctcat tcgccaatgc attgacaggc gcctgagaac gttggtgttg    5280
gctccaactc gtgtggtact caaagaaatg gagcgtgctt tgaatgggaa acgggtcagg    5340
ttccactcac cagcagtcag tgaccaacag gctggagggg caattgtcga tgtgatgtgt    5400
cacgcaacct atgtcaacag aaggctactc ccacagggaa gacaaaattg ggaggtggca    5460
atcatggatg aggcccactg gacggacccc cacagcatag ctgccagagg tcatttgtat    5520
actctggcaa agaaaacaa gtgtgcactg gtcttgatga cagcgacacc tcctggtaag    5580
agtgaaccct ttccggagtc caatggagcc attactagtg aggaaagaca gattcctgat    5640
ggggagtggc gtgacgggtt tgactggatc actgagtatg aagggcgcac cgcctggttt    5700
gtcccttcga ttgcaaaagg tggtgctata gctcgcacct tgagacagaa ggggaaaagt    5760
gtgatttgtt tgaacagcaa aacctttgaa aaggactact ccagagtgag ggatgagaag    5820
cctgactttg tggtgacgac tgatatctcg gagatgggag ctaaccttga cgtgagccgc    5880
gtcatagatg gaggacaaaa catcaagccc gaggaggtta tgggaaagt cgagctcacc    5940 gggaccaggc gagtgaccac ggcttccgct gcccaacggc gcggaagagt tggtcggcaa    6000
gacggacgaa cagatgaata catatactct ggacagtgtg atgatgatga cagtggatta    6060
gtgcaatgga aagaggcgca aatacttctt gacaacataa caaccttgcg ggggcccgtg    6120
gccaccttct atggaccaga acaggacaag atgccggagg tggccggtca ctttcgactc    6180
```

```
actgaagaga aaagaaagca cttccgacat cttctcaccc attgtgactt cacaccgtgg   6240
ctggcatggc acgtcgcagc gaatgtatcc agcgtcacgg atcgaagctg acatgggaa    6300 gggccggagg caaatgccgt ggatgaggcc agtggtgact tggtcacctt taggagcccg   6360 aatgggcgg agagaactct caggccggtg tggaaggacg cacgtatgtt caagagggga    6420
cgtgacatca aagagttcgt ggcgtacgcg tctgggcgtc gcagcttcgg agatgttctg   6480
acaggaatgt cgggagttcc tgagctcctg cggcacagat gcgtcagtgc cctggatgtc   6540
ttctacacgc ttatgcatga ggaacctggc agcagggcaa tgagaatggc ggagagagat   6600
gccccagagg cctttctgac tatggttgag atgatggtgc tgggtttggc aaccctgggt   6660
gtcatctggt gcttcgtcgt ccggacttca atcagccgca tgatgctggg cacgctggtc   6720
ctgctggcct ccttgctact cttgtgggca ggtggcgtcg gctatgggaa catggctgga   6780
gtggctctca tcttttacac gttgctgacg gtgctgcagc ctgaggcggg aaaacagaga   6840
agcagtgacg acaacaaact ggcatatttc ttgctgacgc tctgcagcct tgctggactg   6900
gttgcagcca atgagatggg cttttctggag aagaccaagg cagacttgtc cacggcgctg   6960
tggagtgaac gggaggaacc ccggccatgg agtgaatgga cgaatgtgga catccagcca   7020
gcgaggtcct gggggaccta tgtgctggtg gtgtctctgt tcacaccttga catcatccac   7080 caactgcaga ccaaaatcca acaacttgtc aacagtgccg tggcatctgg tgcacaggcc   7140
atgagagacc ttgggggagg tgcccccttc tttggtgtgg cgggacatgt catgaccctc   7200 gggggtggtgt cactgattgg ggctactccc acctcactga tggtgggcgt tggcttggcg   7260
gcactccatc tggccattgt ggtgtctggt ctggaggctg aattaacaca gagagctcat   7320 aaggtcttttt tctctgcaat ggtgcgcaac cccatggtgg atggggatgt catcaaccca   7380
ttcggggagg gggaggcaaa acctgctcta tatgaaagga aaatgagtct ggtgttggcc   7440
acagtgttgt gcctcatgtc ggtggtcatg aaccgaacgg tggcctccat aacagaggct   7500
tcagcagtgg gactggcagc agcgggacag ctgcttagac cggaggctga cacgttgtgg   7560
acgatgccgg ttgcttgtgg catgagtggt gtggtcaggg gtagcctgtg ggggtttttg   7620
cctcttgggc atagactctg gcttcgagcc tctgggggta ggcgtggtgg ttctgaggga   7680
gacacgcttg gagatctctg gaagcggagg ctgaacaact gcacgaggga ggaattcttt   7740
gtgtacaggc gcaccggcat cctggagacg gaacgtgaca aggctagaga gttgctcaga   7800
agaggagaga ccaatgtggg attggctgtc tctcggggca cggcaaagct tgcctggctt   7860
gaggaacgcg gatatgccac cctcaaggga gaggtggtag atcttggatg tggaagggggc   7920 ggctggtcct attatgcggc atcccgaccg gcagtcatga gtgtcagggc atataccatt   7980
ggtgaaaaag gcacgagcc tccaaagatg gtaacaagcc tgggttggaa cttgattaaa   8040
ttcagatcag gaatggacgt gttcagcatg cagccacacc gggctgacac tgtcatgtgt   8100
gacatcggag agagcagccc agatgccgct gtggaggtg agaggacaag gaaagtgata   8160
ctgctcatgg agcaatggaa aaacaggaac cccacggctg cctgtgtgtt caaggtgctg   8220
gccccatatc gcccagaagt gatagaggca ctgcacagat tccaactgca atggggggggg   8280 ggtctggtga ggacccccttt ttcaaggaac tccacccatg agatgtatta ctcaacagcc   8340
gtcactggga acatagtgaa ctccgtcaat gtacagtcga ggaaacttt ggctcggttt   8400 ggagaccaga gagggccaac caaggtgcct gaactcgacc tggagttggg aacgaggtgt   8460
gtggtcttag ctgaggacaa ggtgaaagaa caagacgtac aagagaggat cagagcgttg   8520
```

```
cgggagcaat acagcgaaac ctggcatatg gacgaggaac acccgtaccg gacatggcag    8580
tactggggca gctaccgcac ggcaccaacc ggctcggcgg cgtcactgat caatggggtt    8640
gtgaaacttc tcagctggcc atggaacgca cgggaagatg tggtgcgcat ggctatgact    8700
gacacaacgg ctttcggaca gcagagagtg ttcaaagata aagttgacac aaaggcacag    8760
gagcctcagc ccggtacaag agtcatcatg agagctgtaa atgattggat tttggaacga    8820
ctggcgcaga aaagcaaacc gcgcatgtgc agcaggaag aattcatagc aaaagtgaaa    8880
tcaaatgcag ccttgggagc ttggtcagat gagcaaaaca gatgggcaag tgcaagagag    8940
gctgtagagg atcctgcatt ctggcgcctc gtggatgaag agagagaaag gcacctcatg    9000
gggagatgtg cgcactgcgt gtacaacatg atgggcaaga gagaaaagaa actgggagag    9060
ttcggagtgg cgaaaggaag tcgggccatt tggtacatgt ggctgggag tcgcttttg    9120
gagttcgagg ctcttggatt cttgaatgaa gaccattggg cctctagaga gtccagtgga    9180
gctggagttg agggaataag cttgaactac ctgggctggc acctcaagaa gttgtcaacc    9240
ctgaatggag gactcttcta tgcagatgac acagctggct gggacacgaa agttaccaat    9300
gcagacttag aggatgaaga acagatccta cggtacatgg agggtgagca caaacaattg    9360
gcaaccacaa taatgcaaaa agcataccat gccaaagtcg tgaaggtcgc gaggcctccc    9420
cgtgatggag gctgcatcat ggatgtcatc acaagaagag accaaagagg ttcgggtcag    9480
gttgtgacct atgcccttaa caccctcacc aacataaagg tgcaattaat ccgaatgatg    9540
gaaggggaag gggtcataga ggcagcggat gcacacaacc cgagactgct tcgagtggag    9600
cgctggctga agaacacgg agaagagcgt cttggaagaa tgctcgtcag tggtgacgat    9660
tgtgtggtga ggccctggga tgacagattt ggcaaagcac tttactttct gaatgacatg    9720
gccaagacca ggaaggacat tggggaatgg gagcactcag ccggcttttc aagctggag    9780
gaggtaccct tttgttcaca ccatttccac gagctagtga tgaaggatgg acgcacctg   9840
gtggtgccgt gccgagacca agatgaactc gttggggagg cgcgcatctc accgggtgc    9900
ggctggagtg tccgcgagac ggcctgcctt tcaaaagcct acgggcagat gtggctgctg    9960
agctacttcc accgacgaga cctgaggacg ctcgggcttg ccattaactc agcagtgcct   10020
gccgattggg ttcctaccgg ccgcacgacg tggagcattc atgccagtgg ggcctggatg   10080
accacagaag acatgctgga cgtttggaac cgggtgtgga ttctggacaa ccctttcatg   10140
cagaacaagg aaagggtcat ggagtggagg gatgttccgt acctccctaa agctcaggac   10200
atgttatgtt cctcccttgt tgggaggaga gaaagagcag aatgggcaa gaacatctgg   10260
ggagcggtgg aaaaggtgag gaagatgata ggtcctgaaa agttcaagga ctatctctcc   10320
tgtatggacc gccatgacct gcactgggag ctcagactgg agagctcaat aatctaaacc   10380
cagactgtga cagagcaaaa cccggaaggc tcgtaaaaga ttgtccggaa ccaaaagaaa   10440
agcaagcaac tcacagagat agagctcgga ctggagagct ctttaaacaa aaaaaaaaaa   10500
aaaaaaaaaa aaaaaaaaaa aaaaaaaaaa aaaaaagcc agaattgagc tgaacctgga   10560
gagctcatta aatacagtcc agacgaaaca aaacatgaca aagcaaagag gctgagctaa   10620
aagttcccac tacgggactg cttcatagcg gtttgtgggg ggaggctagg aggcgaagcc   10680
acagatcatg gaatgatgcg gcagcgcgcg agagcgacgg ggaagtggtc gcacccgacg   10740
caccatccat gaagcaatac ttcgtgagac ccccctgac cagcaaaggg ggcagaccgg   10800
tcaggggtga ggaatgcccc cagagtgcat tacggcagca cgccagtgag agtggcgacg   10860
ggaaaatggt cgatcccgac gtagggcact ctgaaaaatt ttgtgagacc ccctgcatca   10920
```

```
tgataaggcc gaacatggtg catgaaaggg gaggccccg gaagcacgct tccgggagga   10980
gggaagagag aaattggcag ctctcttcag gattttcct cctcctatac aaaattcccc   11040
ctcggtagag gggggcggt tcttgttctc cctgagccac catcacccag acacaggtag   11100
tctgacaagg aggtgatgtg tgactcggaa aaacacccgc t                      11141
```

<210> SEQ ID NO 6
<211> LENGTH: 10733
<212> TYPE: DNA
<213> ORGANISM: Dengue virus 1

<400> SEQUENCE: 6

```
agttgttagt ctgtctggac cgacaagaac agtttcgaat cggaagcttg cttaacgtag     60
ttctaacagt ttttattag agagcagatc tctgatgaac aaccaacgaa aaaagacggc    120
tcgaccgtct ttcaatatgc tgaaacgcgc gagaaaccgc gtgtcaactg tttcacagtt    180
ggcgaagaga ttctcaaaag gattgctctc aggccaagga cccatgaaat tggtgatggc    240
tttcatagca ttcctaagat ttctagccat accccccaaca gcaggaattt tggctagatg    300
gggttcattc aagaagagtg gagcgatcaa agtgctacgg ggtttcaaga agaaatctc    360
aaacatgttg aatataatga atagaaggaa aagatctgtg accatgctcc ttatgctgat    420
gcctacagcc ttggcgttcc atttgactac acgaggggga gagccgcaca tgatagtcag    480
caagcaggaa agaggaaaat cactcttgtt taagacctca gcaggtgtca acatgtgcac    540
ccttatagcg atggattttgg gagagttatg tgaggcacaca atgacttaca atgccctcg    600
aatcactgaa gctgaaccag atgacgttga ttgttggtgt aatgccacag acacatgggt    660
gacctatgga acatgttccc aaactggcga gcaccgacga gacaaacgtt ccgtcgcact    720
ggccccacac gtgggacttg gtttggaaac aagaaccgaa acgtggatgt cctctgaagg    780
cgcttggaaa cagatacaaa gagtggagac ttgggcctg agacacccag gattcacggt    840
gatagccctt tttctagcac atgccatagg aacatccatc actcagaaag ggattatttt    900
catttttgtta atgctggtaa caccatccat ggccatgcga tgcgtgggaa taggcagcag    960
ggacttcgtg gaaggactgt caggagcaac ctgggtagat gtggtactgg aacatggaag   1020
ttgcgtcacc accatggcaa agacaaaacc aacattggac attgaacttt tgaagacgga   1080
agtcacaaac cctgccatcc tgcgcaaact gtgcattgaa gctaaaatat caacaccac   1140
caccgactca agatgcccaa cacaaggaga agccacactg gtggaagaac aagacgcgaa   1200
cttgtgtgt cgacgaacgt tgtggacag aggctgggc aatggctgtg ggctcttcgg   1260
aaaaggaagc ctaataacgt gtgctaagtt caagtgtgtg acaaaactgg aaggaaagat   1320
agttcaatat gaaaacttga atattcagt aatagtcacc gttcacaccg agaccagca   1380
ccaggtggga aatgaaagca cagaacatgg acaactgca actataacac ctcaagctcc   1440
tacgacggaa atacagctga ctgactacg agctcttaca ttggattgtt cacctagaac   1500
aggactagac ttaatgaaa tggtgttgtt gacaatgaaa gaaaaatcat ggctagtcca   1560
caaacaatgg tttctagacc taccactgcc ttggaccctcg ggagcttcaa catcacaaga   1620
gacttggaac agacaagatt tgctggtgac atttaagaca gcccatgcaa agaagcagga   1680
agtagtcgta ctaggatcac aagaaggagc aatgcacact gcgttgaccg gagcaacaga   1740
aatccaaacg tctggaacga caacaatttt tgcaggacac ttgaaatgca gactaaagat   1800
ggacaaactg actctaaaag ggatgtcata tgtgatgtgc acaggctcat tcaagctaga   1860
```

```
gaaagaagtg gctgagaccc agcatggaac cgttctagtg cagattaaat atgaaggaac      1920
agatgcacca tgcaagatcc cttttcgac ccaagatgaa aaaggagtaa cccagaatgg       1980
gagattgata acagctaacc ctatagttac tgacaaagaa aaaccagtca acattgaggc      2040
agaaccgcct tttggtgaga gttacatcgt aataggagca ggtgaaaaag ctttgaaact      2100
aagctggttt aagaaaggaa gcagcatagg gaaaatgctt gaggcaactg ccagaggagc     2160
tcgaaggatg gccatactgg gagacaccgc atgggacttt ggttctatag gaggagtgtt     2220
cacgtctgtt ggaaaattag tacaccagat ttttggaact gcatatggag ttttgttcag     2280
cggtgtttcc tggaccatga aaataggaat aggggttctg ctgacatggc taggattaaa    2340
ctcaaggagc acgtcccttt cgatgacgtg cattgcagtt ggcctagtaa cactatacct     2400
aggagtcatg gttcaggcgg attcaggatg tgtaattaat tggaaaggta gagaactcaa    2460
atgtggaagt ggcatttttg tcaccaatga agttcacact tggacagagc aatacaaatt   2520
tcaagctgac tccccaaaga gactatcagc agccatcggg aaggcatggg aggagggtgt   2580
gtgtggaatt cgatcagcaa ctcgtctcga aacatcatg tggaagcaaa tatcaaatga     2640
actgaatcac atcttacttg aaaatgacat gaaattcaca gtggttgtag agatgttgc     2700 tgggatcttg gctcaaggaa agaaaatgat taggccacaa cccatggaat acaaatactc    2760
gtggaaaagc tggggaaagg ctaaaatcat aggggcagat gtacagaaca ccaccttttat  2820 catcgacggc ccaaacaccc cagaatgccc tgatgaccaa agagcatgga acatttggga    2880
agttgaggac tatggatttg aattttcac gacaaacata tggctgaaac tgcgtgattc    2940
ctatacccaa gtgtgtgacc accggctaat gtcagctgcc atcaaggaca gcaaggcagt   3000
tcacgctgac atggggtact ggatagaaag tgaaagaaac gagacctgga agctggcaag   3060
agcttctttc atagaagtta aaacatgtat ctggccaaaa tcccacactc tatgagtaa    3120 tggagttctg gaaagtgaaa tgataattcc aaagatctat ggaggaccaa tatctcagca   3180
caactacaga ccaggatatt tcacacaaac agcagggccg tggcacctgg gcaagttgga   3240
actggatttt gatttgtgtg agggcaccac agttgttgtg gatgaacatt gtggaaatcg   3300
aggaccatct cttaggacca caacagtcac aggaaagata attcatgaat ggtgttgcag   3360
atcttgcacg ctaccaccct tacgtttcag aggagaagat gggtgctggt acggtatgga   3420
aatcagacca gtcaaggaaa aggaagaaaa tctagtcaaa tcaatggtct ctgcagggtc    3480
aggggaagtg gacagctttt cactaggact gctatgcata tcaataatga tcgaagaggt   3540
gatgagatcc agatggagta gaaaaatgct gatgactgga acactggctg tgttcctcct   3600
tctcataata ggacaattga catggaatga tctgatcaga ttatgcatca tggttggagc   3660
caacgcttcc gacaggatgg ggatgggaac gacgtaccta gctctgatgg ccactttaa    3720 aatgagaccg atgtttgctg tagggctatt atttcgcaga ctaacatcca gagaagttct   3780
tcttctaaca attggattga gtctaatggc atctgtggag ttaccaaatt ccttggagga   3840
gctgggggat ggacttgcaa tggcattat gattttaaaa ttactgactg actttcaatc    3900
acatcagctg tgggctacct tgctgtcctt gacatttatc aaaacaacgt tttccttgca   3960
ctatgcatga agacaatgg ctatggtact gtcaattgta tctctcttcc ccttatgcct   4020
gtccacgacc tcccaaaaaa caacatggct tccggtgcta ttgggatccc ttggatgcaa   4080
accactaacc atgtttctta tagcagaaaa caaaatctgg ggaaggagaa gttggcccct   4140
caatgaagga atcatggctg ttggaatagt cagcatccta ctaagttcac ttctcaagaa   4200
tgatgtgccg ctagctgggc cactaatagc tggaggcatg ctaatagcat gttatgttat   4260
```

```
atctggaagc tcagccgacc tatcactaga gaaagcagct gaggtctcct gggaagaaga    4320
agcagaacac tctggtgcct cacacaacat attagtggag gtccaagatg atggaaccat    4380
gaagataaag gatgaagaga gagatgacac gctaaccatt ctccttaaag caactctgct    4440
agcagtttca ggggtgtatc cattatcaat accagcgacc cttttcgtgt ggtacttttg    4500
gcagaaaaag aaacagagat ctggagtgtt atgggacaca cccagccctc cagaagtgga    4560
aagagcagtt cttgatgatg gtatctatag aattatgcag agaggactgt tgggcaggtc    4620
ccaagtaggg gtaggagttt ccaagaaaa cgtgttccac acaatgtggc atgtcaccag    4680
gggagctgta ctcatgtatc aagggaagag actggaaccg agctgggcta gtgtcaaaaa    4740
agacctgatc tcatatggag gaggttggag gcttcaagga tcctggaaca caggagaaga    4800
agtgcaggta attgctgttg aaccagggaa aaaccccaaa aatgtacaaa cagcgccggg    4860
cacctttaag acccctgaag gtgaagttgg agccattgcc ctagatttta aacccggcac    4920
atctggatct cccatcgtga acagagaagg aaaaatagta ggtctttatg gaaatggagt    4980
agtgacaaca agtggaacct acgtcagtgc catagctcaa gccaaagcat cacaagaagg    5040
gcccctacca gagattgaag acgaggtgtt taggaaaaga aacttaacaa taatggacct    5100
acatccagga tcggggaaaa caagaagata ccttccagcc atagtccgtg aggccataaa    5160
aaggaagctg cgcacactaa ttttggctcc cacaagggtt gtcgcttccg aaatggcaga    5220
ggcgctcaag ggaatgccaa taggtaccaa acaacagca gtaaagagtg aacacacagg    5280
aaaagagata gttgatctca tgtgtcacgc cactttcacc atgcgcctcc tgtctcccgt    5340
gagagttccc aattacaaca tgattatcat ggatgaagca catttcaccg atccatccag    5400
tatagcggcc agagggtaca tctcaacccg agtgggcatg ggtgaagcag ctgcaatctt    5460
catgacagcc actcccccag gatcagtgga ggcctttcca cagagcaacg cagtaatcca    5520
agatgaggaa agagacattc ctgagagatc atggaactca ggctatgagt ggatcactga    5580
cttcccaggt aaaacagttt ggtttgttcc aagcattaaa tcaggaaatg acatagccaa    5640
ctgcttaaga aagaatggga aacgggtgat tcaattgagc aggaaaacct ttgatacaga    5700
gtaccaaaaa acaaaaaaca acgactggga ctacgtcgtc acaacagaca tctccgaaat    5760
gggagcaaat ttccgagcag acagggtgat agacccaaga cggtgtctga accggtaat    5820
actaaaagat ggtccagagc gtgtcatttt agcaggacca atgccagtga ctgtggccag    5880
tgccgcccag aggagaggaa gaattggaag gaaccacaat aaggaaggtg atcagtacat    5940
ctacatggga cagcctttaa acaacgatga agatcacgct cactggacag aagcaaaaat    6000
gctccttgac aatataaaca caccagaagg gattatccca gccctcttcg agccggagag    6060
agaaaagagt gcagcaatag acgggaata cagactgcgg ggtgaggcaa ggaaaacgtt    6120
tgtggagctc atgagaagag gagatctacc tgtctggcta tcttacaaag ttgcctcaga    6180
aggcttccag tactctgaca gaagatggtg ctttgacggg gaaaggaaca accaggtgtt    6240
ggaggagaac atggacgtgg agatctggac aaaagaggga gaaagaaaga aactacgacc    6300
ccgctggctg gatgccagaa catactcaga cccactagcc ctgcgcgagt ttaaagagtt    6360
tgcagcaggg agaagaagcg tctcaggtga tctaatattg gaaataggga aacttccaca    6420
acacttgacg caaagggccc agaatgcctt ggacaacctg gttatgttgc acaactccga    6480
acaaggagga gagcctaca gacatgcaat ggaagaactg ccagacacca tagaaacgtt    6540
gatgctccta gctttgatag ctgtgttaac tggtggagtg acactgttct tcctatcagg    6600
```

```
aaggggctta gggaaaacat ctattggcct actctgcgta atggcttcaa gcgtactgct    6660
atggatggcc agtgtagagc cccattggat agcggcctcc atcatactgg agttcttcct    6720
gatggtgctg cttattccag agccagacag acaacgcact ccgcaggaca atcagctggc    6780
atatgtggtg ataggtttgt tattcatgat actgacagta gcagccaatg agatgggact    6840
gctggaaacc acaaagaaag acttagggat tggccatgtg gctgttggaa atcaccacca    6900
tgccgcaatg ctggacgtag acttacatcc agcttcagcc tggaccctct atgcagtggc    6960
cacaacaatt atcactccca tgatgaggca cacaatcgaa aacacaacgg caaacatttc    7020
cctgacagcc attgcaaacc aggcagctat attgatggga cttgacaaag gatggccaat    7080
atcgaagatg gacataggag ttccacttct cgccttgggg tgctattccc aagtgaatcc    7140
actgacgctg acagcggcgg tattgatgct agtggctcat tacgccataa ttggacctgg    7200
actgcaagca aaagctacta gagaagctca aaaaaggaca gcggccggga taatgaaaaa    7260
tccaaccgtt gatgggattg ttgcaataga tttggaccct gtggtttatg atgcaaaatt    7320
tgagaaacaa ctaggccaaa taatgttgtt gatactatgc acatcacaga tcctcttgat    7380
gcggactaca tgggccttgt gcgaatccat cacactggcc actggacctc tgaccacgct    7440
ttgggaggga tctccaggaa aattttggaa caccacgata gcggtttcca tggcaaacat    7500
tttcagagga agttatctag caggagcagg tctggccttc tcattaatga aatctctagg    7560
aggaggtagg agaggcacgg gagcccaagg ggaaacactg ggagagaaat ggaaaagaca    7620
gctgaaccaa ctgagcaagt cagaatttaa cacctataaa aggagtggga ttatggaagt    7680
ggacagatcc gaagcaaaag agggattgaa agaggagaca caaccaaac atgcagtgtc    7740 gagaggaacc gctaaactga gatggtttgt ggagaggaac cttgtcaaac cagaagggaa    7800
agtcatagac ctcggctgtg gaagaggtgg ctggtcatac tattgcgctg ggctgaagaa    7860
agtcacagaa gtgaagggat atacaaaagg gggacctgga catgaggaac caatcccaat    7920
ggcgacctat ggatggaacc tagtaaagct gcactctggg aaagacgtat tctttatacc    7980
acctgagaaa tgtgacaccc ttttgtgtga tattggtgag tcctccccaa acccaactat    8040
agaggaagga agaacgctac gcgtcctaaa gatggtggaa ccatggctca gaggaaacca    8100
attttgcata aagattctga atccctacat gccaagtgtg gtggaaactc tggagcaaat    8160
gcaaagaaaa catggaggaa tgctagtgcg aaatccactt tcaagaaatt ctactcatga    8220
aatgtactgg gtttcatgtg aacaggaaa cattgtgtca gcagtaaaca tgacatctag    8280
aatgttgcta aatcgattca caatggctca caggaaacca acatatgaaa gagatgtgga    8340
cctaggcgcc ggaacaagac atgtggcagt ggaaccagag gtagctaacc tagatatcat    8400
tggccagagg atagagaaca taaaacatga acataagtca acatggtatt atgatgagga    8460
caatccatat aaaacatggg cctatcatgg atcatatgag gtcaagccat caggatcagc    8520
ctcatccatg gtcaatggcg tggtgaaact gctcaccaag cctagggatg tcatccccat    8580
ggttacacaa atagccatga ctgacactac acccttttgga caacagaggg tgtttaaaga    8640
gaaagttgac acacgcacac caaaagcaaa acgaggcaca gcacaaatca tggaggtgac    8700
agccaagtgg ttatggggtt ttcttttctag aaacaagaaa ccaagaattt gcacaagaga    8760
ggagttcaca agaaaagtta ggtcaaacgc agccattgga gcagtgttcg ttgatgaaaa    8820
tcaatggaac tcagcaaaag aagcagtgga agatgagcgg ttctgggacc ttgtgcataa    8880
agagagggag cttcacaaac agggaaaatg tgccacgtgt gtttacaaca tgatgggaaa    8940
gagagagaaa aagctaggag agttcggaaa ggcaaaagga agtcgtgcaa tatggtacat    9000
```

```
gtggttggga gcacgctttc tagagttcga agctcttggt ttcatgaacg aagatcactg    9060
gttcagcaga gagaattcat tcagcggagt ggaaggagaa ggactccaca aacttggata    9120
tatactcaga gacatatcaa agattccagg gggaaacatg tatgcagatg acacagccgg    9180
atgggataca aggataactg aggatgacct tcagaatgag gccagaatta ctgacatcat    9240
ggaacccgaa catgccctac tggctaagtc aatcttcaag ctgacctacc aaaataaggt    9300
ggtaagggta cagagaccag caaaaaatgg aaccgtgatg gatgtcgtat ccagacgtga    9360
ccagagagga agtggccagg tcggaactta tggcttaaac actttcacca acatggaagc    9420
ccagctgata agacaaatgg agtctgaggg aatcttttca cccagcgaat tagagacccc    9480
aaatttagcc gagagagttc tcgcctggct ggaaaaatat ggcgtcgaaa ggctgaaaag    9540
aatggcaatc agcggagatg attgcgtggt gaaaccaatt gatgataggt ttgcaacagc    9600
cttaacagct ctgaatgata tgggaaaagt aagaaaagat ataccacaat gggaaccttc    9660
aaaaggatgg aatgattggc aacaagtgcc ttttgttca caccacttcc accagctgat    9720
tatgaaggat gggagggaaa tagtggtgcc atgccgcaac caagatgaac ttgtgggtag    9780
ggctagagta tcacaaggtg ctggatggag cctgagagaa actgcatgcc taggcaagtc    9840
atatgcacag atgtggcagc tgatgtactt ccacaggaga gacctgagac tagccgctaa    9900
tgctatctgt tcagccgttc cagttaattg gatcccaacc agccgcacca cctggtcgat    9960
ccatgcccat caccaatgga tgacaacaga agacatgctg tcagtgtgga ataggtttg   10020 gatagaggaa aacccatgga tggaggacaa aacccatata tccagttggg gagatgttcc   10080
atatttaggg aaaagggaag atcaatggtg tggatccctg ataggcttaa cagcaagggc   10140
cacctgggcc accaacatac aagtggccat aaaccaagtg agaaaactaa ttgggaatga   10200
gaattaccta gattacatga catcaatgaa gagattcaag aacgagagtg atcccgaagg   10260
ggcactctgg tgagtcaaca catttacaaa ataaaggaaa ataagaaatc aaacaaggca   10320
agaagtcagg ccggattaag ccatagtacg gtaagagcta tgctgcctgt gagccccgtc   10380
taaggacgta aaatgaagtc aggccgaaag ccacggcttg agcaaaccgt gctgcctgta   10440
gctccatcgt ggggatgtaa aaacctggga ggctgcaacc catggaagct gtacgcatgg   10500
ggtagcagac tagtggttag aggagacccc tcccgaaaca taacgcagca gcggggccca   10560
acaccagggg aagctgtacc ctggtggtaa ggactagagg ttagaggaga ccccccgcac   10620
aacaataaac agcatattga cgctgggaga gaccagagat cctgctgtct ctacagcatc   10680
attccaggca cagaacgcca gaaaatggaa tggtgctgtt gaatcaacag gtt          10733

<210> SEQ ID NO 7
<211> LENGTH: 10176
<212> TYPE: DNA
<213> ORGANISM: Dengue virus 2

<400> SEQUENCE: 7
atgaataacc aacgaaaaaa ggcgagaagt acgcctttca atatgctgaa acgcgagaga     60
aaccgcgtgt caactgtgca acagctgaca aagagattct cacttggaat gctgcaagga    120
cgcggaccat taaaactgtt catggccctt gtggcgttcc ttcgtttcct aacaatccca    180
ccaacagcag ggatactaaa agatgggga cgatcaaga aatcaaaagc tatcaatgtt    240
ttgagagggt tcaggaaaga gattggaagg atgctgaaca tcttgaacag agacgtagg    300 acagcaggcg taattgttat gttgattcca acagcgatgg cgttccattt aaccacacgc    360
```

-continued

```
aatggagaac cacacatgat cgttggtagg caggagaaag ggaaaagtct tctgttcaaa    420
acagaggatg gtgttaacat gtgtaccctc atggccatgg accttggtga gttgtgtgaa    480
gatacaatca cgtacaagtg tcccctcctc agacaaaatg aaccagaaga catagattgt    540
tggtgcaact ctacgtccac atgggtaact tatgggacat gtaccaccac aggagaacac    600
agaagagaaa aaagatcagt ggcgctcgtt ccacatgtgg gtatgggact ggagacacga    660
actgaaacat ggatgtcatc ggaaggggcc tggaagcatg ttcagagaat tgaaacctgg    720
atcttgagac atccaggttt taccataatg gcagcgatcc tggcatacac cataggaacg    780
acacacttcc aaagggcctt gattttcatc ttactgacag ctgtcgctcc ttcaatgaca    840
atgcgctgca taggaatatc aaatagagac ttcgtagaag gggtttcagg aggaagctgg    900
gttgacatcg ttttagaaca tggaagttgt gtgacgacga tggcaaaaaa caaaccaaca    960
ttggattttg aactgataaa aacagaagcc aaacaacctg ccactctaag gaagtactgt   1020
atagaagcaa agctgaccaa cacaacaaca gaatcgcgtt gcccaacaca aggggaaccc   1080
agtctaaatg aagagcagga caaaaggttc atctgcaaac actccatggt agacagagga   1140
tggggaaatg gatgtggatt atttggaaag ggaggcattg tgacctgtgc tatgtttaca   1200
tgcaaaaaga acatggaagg aaaaatcgta cagccagaaa atttggaata ccatcgtg    1260
ataacacctc actcaggaga agagcacgct gtaggtaatg acacaggaaa gcatggcaag   1320
gaaatcaaaa taacaccaca gagttccacc acagaagcag aactgacagg ctatggcact   1380
gtcacgatgg agtgctctcc gagaacgggc ctcgacttca atgagatggt gctgctgcag   1440
atggaagaca agcttggct ggtgcacagg caatggttcc tagacctgcc gttgccatgg   1500
ctacccggag cggatacaca aggatcaaat tggatacaga agagacatt ggtcactttc   1560
aaaaatcccc acgccaagaa acaggatgtc gttgtcttag ggtctcaaga agggccatg   1620
cacacggcac tcacaggggc tacagaaatc cagatgtcat caggaaactt actgttcacg   1680
ggacatctca gtgcaggct gagaatggac aaactacagc tcaaaggaat gtcatactct   1740
atgtgtacag gaaagtttaa atcgtgaag gaaatagcag aaacacaaca tggaacaata   1800
gttatcagag tacaatatga agggacggt tctccatgta agatccctt tgagataaca   1860
gatttggaaa aagacacgt cttaggacgc ctgattacag ttaacccaat cgtaacagaa   1920
aaagatagcc cagtcaacat agaagcagaa ccccccattcg gagacagcta catcatcgta   1980
ggagtagagc cggacaact gaaactcaat tggtttaaga agggaagctc catcggccaa   2040
atgtttgaga caacaatgag aggagcaaag agaatggcca ttttaggtga cacagcctgg   2100
gattttggat ccctgggagg agtgtttaca tctataggaa aggctctcca tcaagttttc    2160
ggagcaatct atggggctgc ttttagtggg gtctcatgga ctatgaaaat cctcataggg   2220
gtcatcatca catggatagg aatgaattca cgtagcacct cactgtctgt gtcgctagta   2280
ttggtgggag tcgtgacact gtacctggga gctatggtgc aggctgatag tggttgcatt   2340
gtgagctgga aaaataaaga actgaaatgt ggcagcggga tcttcattac agataacgta   2400
cacacatgga cagagcaata taagttccaa ccagaatccc cttcaaaatt gcttcagct   2460
atccaaaaag ctcatgaaga aggcatttgt ggaatccgct cagtaacaag attggagaat   2520
ctgatgtgga aacaaataac accagaattg aatcatattc tatcagaaaa tgaggtaaag   2580
ttgaccatta tgacaggaga cattaaagga atcatgcagg caggaaaacg atccttgcgg   2640
cctcagccca ctgagctgaa gtactcatgg aaaacatggg gaaaggcgaa aatgctctct   2700
acagagtctc acaatcagac ctttctttatt gatggccctg aaacagcaga atgccccaac   2760
```

```
acaaacagag cttggaactc actggaagtt gaagactatg gttttggagt ttttaccacc    2820
aatatatggc taaaattgag agaaaaacag gatgtatttt gtgactcaaa actcatgtca    2880
gcggccatta aagacaacag agccgtccat gccgatatgg gttattggat agaaagtgca    2940
ctcaatgaca catggaagat ggagaaagcc tccttcattg aagttaaaag ctgccactgg    3000
ccaaagtcac acaccctctg gagcaatgga gtattagaaa gtgagatgat aattccaaaa    3060
aattttgccg ggccagtgtc acaacacaac tacagaccag gctaccatac acaaacagca    3120
ggaccttggc atctaggtaa gcttgagatg gactttgatt tctgcgaagg aactacagtg    3180
gtggtgactg aggactgtgg aaatagggga ccctctttaa gaacgaccac tgcctctgga    3240
aagctcataa cagaatggtg ctgccgatcc tgcacactac cacctctaag atacagaggt    3300
gaggatggat gctggtacgg gatggaaatc agacctttga agagaaaga agagaacttg     3360 gtcaactcct tggtcacagc cggacatggg cagattgaca acttttcact aggagtcttg    3420
ggaatggcac tgttcctgga agaaatgctt aggacccgag taggaacgaa acatgcaata    3480
ctgctagttg cactatcttt cgtgacattg attactggga acatgtcttt tagagacctg    3540
ggaagagtga tggtcatggt gggcgctacc atgacggatg acataggtat gggagtgact    3600
tatcttgccc tactagcagc tttcaaagtt agaccaactt ttgcagctgg actactcttg    3660
agaaaactga cctccaagga attgatgatg gccaccatag aatcgcact cctttcccaa     3720 agcaccttgc cagagaccat tctagaactg actgatgcgt tagccttggg catgatggcc    3780
ctcaaaatag tgagaaatat ggaaaaatac caattggcag tgactatcat ggctatttcg    3840
tgtgtcccaa atgcagtgat attgcaaaac gcatggaagg tgagttgcac aatattggca    3900
gcggtgtccg tttctccact gctcctaaca tcctcacagc agaaagcgga ttggatacca    3960
ctggcattga cgataaaagg tctcaaccca acagccattt ttctaacaac tctttcgaga    4020
accagcaaga aaaggagctg gccgctaaat gaagctatca tggcagtcgg gatggtgagc    4080
attttagcca gttctctcct aaagaatgat attcctatga caggtccatt agtggctgga    4140
gggctcctca ccgtatgtta cgtgctcact ggacgagcgg ccgatttgga actggagaga    4200
gctgccgatg taaaatggga agatcaggca gaaatatcag gaagcagccc aatcctgtca    4260
ataacaatat cagaagatgg cagcatgtcg ataaaaatg aagaggaaga acaaacactg     4320
accatactca ttagaacggg attgttggtg atctcaggag tctttccagt atcgataccc    4380
attacggcag cagcatggta cctgtgggaa gtgaagaaac aacgggctgg agtattgtgg    4440
gacgtccctt caccccacc agtgggaaaa gccgaactgg aagatggagc ctatagaatc     4500
aagcaaagag ggattcttgg atattctcag attggagccg agtttacaa agaaggaaca    4560 ttccatacaa tgtggcacgt cacacgtggt gctgttctga tgcatagagg gaagaggatt    4620
gaaccatcat gggcagatgt caagaaagat ctaatatcat atgggggagg ctggaagcta    4680
gaaggagaat ggaaggaagg agaggaagtc caagtcctgg cattggaacc tggaaaaaat    4740
cccagagctg tccaaacgaa acctggaatt ttcaaaacca caccggaac cataggcgct     4800 gtatctctgg acttttcccc tggaacgtca ggatctccaa ttgtcgacag aaaaggaaaa    4860
gttgtgggtc tttacggtaa tggtgttgtc acaaggagtg gagcatacgt aagtgccata    4920
gcccagaccg aaaaaagcat tgaagacaat ccagagatcg aagatgacat tttccgaaag    4980
aaaagattga ccatcatgga cctccatcca ggggcaggaa agacaaaaag ataccttcca    5040
gccatagtta gagaagccat aaaacgtggc ttgagaacat taatcctggc tcccactaga    5100
```

```
gtcgtggcag ctgaaatgga ggaagctctt agaggacttc aataagata ccaaacccca    5160
gccatcagag ccgagcacac cgggcgagag atcgtggacc taatgtgtca tgccacattt    5220
actatgaggc tgctatcacc agtcagagtg ccaaattaca acctgattat catggacgaa    5280
gcccacttca cagacccagc aagcatagca gctagaggat acatttcaac tcgagtagag    5340
atgggtgaag cagccgggat ttttatgaca gccactcctc cgggaagcag agacccattt    5400
cctcagagca atgcaccaat catggatgag gaaagagaaa tccctgagcg ttcatggaat    5460
tcaggacatg aatgggtcac ggattttaaa gggaagactg tttggtttgt tccaagtata    5520
aaagcaggaa atgacatagc agcttgtctt aggaaaaatg gaagaaagt gatacaactc    5580
agtaggaaga cttttgactc tgagtatgct aagactagag ccaatgattg gactttgtg    5640
gtcacaactg acatttcaga aatgggtgcc aacttcaagg ctgagagggt tatagaccct    5700
agacgctgca tgaaaccagt tatactaaca gatggcgaag agcgggtgat cttggcagga    5760
cctatgccag tgacccactc tagtgcagcg caaagaagag ggagaatagg aagaaatcca    5820
aaaaatgaaa atgaccagta catatacatg ggggaacctc tcgaaaatga tgaagactgt    5880
gcacactgga agaagctaa aatgctccta gataacatca acacacccga aggaatcatt    5940
cctagtatgt tcgaaccaga gcgtgaaaaa gtggatgcca ttgatggtga ataccgtttg    6000
agaggagaag caaggaaaac ctttgtggac taatgagaa gagggactt accagtctgg    6060
ttggcctaca aagtggcagc tgaaggcatc aactacgctg acagaaagtg gtgttttgat    6120
ggaattaaga caaccaaat actggaagaa aatgtggaag tggaaatctg acaaaagaa    6180
ggggaaagga aaaattaaa acccagatgg ttgatgctta ggatctattc tgacccactg    6240
gcactaaaag aattcaagga atttgcagct ggaagaaaat ctttgaccct gaacctaatc    6300
acagaaatgg gtaggcttcc aactttcatg actcagaagg caagaaacgc actgacaac    6360
ttggctgtgc tgcatacggc tgaggtaggt ggaaaggcgt acactcatgc tctcagtgaa    6420
ctgccggaga ctctggagac actgcttcta ctgacactcc tggcagcagt cacaggagga    6480
atcttcttat tcttaatgag cggaaaggt atagggaaga tgactctggg aatgtgttgc    6540
ataatcacag ctagcattct cctatggtat gcacagatac aaccacactg gatagcagct    6600
tcaataatac tggagttttt tctcatagtt ttgctcattc cagaaccaga aaacagaga    6660
acaccccaag acaaccaatt gacctacgtt gtcatagcca tcctcacagt ggtggctgca    6720
accatggcaa acgagatggg tttcctggaa aaaaccaaga aagacctcgg atttggaagc    6780
attacaaccc aggaatctga gagcaacatc ctggacatag atctacgtcc tgcatcagca    6840
tggacgctgt atgccgtggc tacaacattt gtcacaccaa tgttgcgaca tagcattgaa    6900
aattcctcag taaatgtctc cctaacagcc attgctaacc aagctacagt gctaatgggt    6960
cttgggaaag gatggccatt gtcaaagatg gacatcggag ttcccctcct tgccattgga    7020
tgctactcac aagtcaaccc tataaccctc acagcagctc ttcttttatt ggtagcacat    7080
tatgccatta tagggccagg acttcaagca aaagcaacca gagaagctca gaaaagagca    7140
gcagcaggca tcatgaaaaa cccaacagtc gatggaataa cagtgattga cctagaacca    7200
atacccctat atccaaaatt tgaaaagcag ttaggacaag taatgctcct aatcctctgc    7260
gtgactcaag tattaatgat gaggactaca tgggctttgt gtgaggctct aacccagcg    7320
accgggccca tctccacact gtgggaagga aatccaggga ggttttggaa caccaccatt    7380
gcagtgtcaa tggctaacat cttagggggg agctacttgg ccggagctgg acttctcttt    7440
tccatcatga agaacacaac aaacacaaga agaggaactg gcaacgtagg agagacactt    7500
```

```
ggagaaaaat ggaaaagccg attaaatgca ctgggaaaaa gtgaatttca gatctacaag    7560
aaaagtggaa tccaggaagt ggatagaacc ctagcaaaag aaggcatcaa agaggagaa     7620 acggaccacc atgctgtgtc acgaggatca gcaaaactga gatggttcgt cgagagaaac    7680
atggtcacac cggaagggaa ggtggtggat cttggttgcg gcagaggggg ctggtcatac    7740
tattgtgggg gactaaagaa tgtaagagaa gtcaaaggcc taacaaaagg aggaccagga    7800
cacgaagaac ccatccccat gtcaacatat gggtggaatc tagtgcgtct gcaaagtggg    7860
gtcgacgttt tcttcacccc gccagaaaag tgtgatacat tgttgtgtga catagggag     7920 tcgtcaccaa atcccacgat agaagcagga cgaacactca gagtcctcaa cttagtggaa    7980
aattggctga acaataacac ccaattttgc ataaaggtcc tcaatccata tatgccctca    8040
gtcatagaaa aaatgaaaac actacaaagg aaatatggag gagccttagt gaggaatcca    8100
ctctcacgaa actccacgca tgaaatgtac tgggtatcta atgctaccgg aacatagtg     8160 tcatcagtga acatgatttc aaggatgttg attaacagat tcacaatgaa acataagaaa    8220
gccacctacg agccagatgt tgacctagga agtggaaccc gcaacattgg aattgaaagt    8280
gagataccaa atctagacat aataggaaag agaatagaga aaataaaaca agagcatgaa    8340
acatcatggc attatgacca agaccaccca tacaaaacgt gggcttacca tggcagctat    8400
gaaacaaaac aaactggatc agcatcatct atggtgaacg gagtggtcag actgctgaca    8460
aaaccttggg acgtcgtccc tatggtgaca cagatggcaa tgacagacac gactccattt    8520
ggacaacagc gcgttttcaa agagaaagtg gacacgagaa ctcaagaacc gaaggaaggc    8580
acaaagaaac tgatgaaaat tacggcagag tggctttgga agaactagg aaaggaaaag    8640 acacctagaa tgtgtaccag agaagaattc acaagaaaag tgagaagcaa tgcagccttg    8700
ggggccgtat tcactgatga gaacaaatgg aaatcggcac gtgaggctgt tgaagatggt    8760
aggttttggg agctggttga cagggaaaga aatctccatc ttgaaggaaa gtgtgaaaca    8820
tgtgtgtaca acatgatggg aaaaagagag aagaaactag gggagttcgg caaggcaaaa    8880
ggtagcagag ccatatggta catgtggctt ggagcacgct tcttagagtt tgaagcccta    8940
ggatttctga atgaagatca ctggttctcc agagggaact ccctgagtgg agtggaagga    9000
gaagggctgc acaggctagg ctacatttta agagaggtgg gcaagaagga aggaggagca    9060
atgtacgccg atgatacagc aggatgggac acaagaatca cactagaaga cttaaaaaat    9120
gaagaaatgg taacaaacca catgaaagga gaacacaaga actagccga ggccatattc     9180 aaattaacgt accaaaataa ggtggtgcgt gtgcaaagac caacaccaag aggcacagta    9240
atggatatca tatcgagaaa agaccaaaga ggcagtgggc aagtcggtac ctatggcctt    9300
aatactttca ccaatatgga agcccaatta attagacaga tggaaggaga aggaatcttc    9360
aaaagcatcc agcacctgac cgccacagaa gaaatcgctg tacagaactg gttagcaaga    9420
gtggggcgtg aaaggctatc aagaatggcc atcagtggag atgactgtgt tgtaaaacct    9480
atagatgaca gatttgcaag tgctttaaca gctctaaatg acatgggaaa agttaggaaa    9540
gatatacaac aatgggaacc ttcaagagga tggaacgatt ggacacaggt gccttctgt    9600 tcacaccatt ttcatgagtt agtcatgaaa gatggtcgcg tgctcgtagt cccatgcaga    9660
aaccaagatg aactgattgg cagagcccga atttcccagg gagccgggtg gtctttgaag    9720
gagacggctt gtttgggaa gtcttacgcc caaatgtgga ccctgatgta cttccacaga    9780
cgtgacctca gattggcggc aaatgccatt tgctcggcag tcccgtcaca ttgggttcca    9840
```

```
acaagtcgaa caacctggtc catacacgcc aagcatgaat ggatgacgac ggaagacatg    9900
ctggcagtct ggaacagggt gtggatccaa gaaaacccat ggatggaaga caaaactcca    9960
gtggaatcat gggaagaagt cccatacctg gggaaagggaagaccaatg tgcggctca    10020 ttgattgggc taacaagcag ggctacctgg gcaaagaata tccagacagc aataaatcaa    10080
gtcagatccc ttataggcaa tgagggatac acagactaca tgccatccat gaagagattc    10140
agaagggaag aggaagaggc aggtgtccta tggtag                              10176
```

<210> SEQ ID NO 8
<211> LENGTH: 10696
<212> TYPE: DNA
<213> ORGANISM: Dengue virus 3

<400> SEQUENCE: 8

```
agttgttagt ctacgtggac cgacaagaac agtttcgact cggaagcttg cttaacgtag      60
tgctgacagt tttttattag agagcagatc tctgatgaac aaccaacgga aaaagacggg     120
aaaaccgtct atcaatatgc tgaaacgcgt gagaaaccgt gtgtcaactg gatcacagtt     180
ggcgaagaga ttctcaagag gattgctgaa cggccaagga ccaatgaaat tggttatggc     240
gtttatagct ttcctcagat ttctagccat tccaccgaca gcaggagtct tggctagatg     300
gggtaccttt aagaagtcgg gggctattaa ggtcttaaaa ggcttcaaga aggagatctc     360
aaacatgctg agcattatca acaaacggaa aaagacatcg ctctgtctca tgatgatgtt     420
accagcaaca cttgctttcc acttaacttc acgagatgga gagccgcgca tgattgtggg     480
gaagaatgaa agaggaaaat ccctactttt taagacagcc tctggaatca acatgtgcac     540
actcatagcc atggatttgg gagagatgtg tgatgacacg gtcacttaca atgcccccca     600
cattaccgaa gtggagcctg aagacattga ctgctggtgc aacctacat cgacatgggt     660 gacttatgga acatgcaatc aagctggaga gcatagacgc gataagagat cagtggcgtt     720
agctccccat gtcggcatgg gactggacta acgcactcaa acctggatgt cggctgaagg     780
agcttggaga caagtcgaga aggtagagac atgggccctt aggcacccag ggtttaccat     840
actagcccta tttcttgccc attacatagg cacttccttg acccagaaag tggttatttt     900
tatactatta atgctggtca ccccatccat gacaatgaga tgtgtgggag taggaaacag     960
agattttgtg gaaggcctat cgggagctac gtgggttgac gtggtgctcg agcacggtgg    1020
gtgtgtgact accatggcta agaacaagcc cacgctggac atagagcttc agaagaccga    1080
ggccacccaa ctggcgaccc taaggaagct atgcattgag ggaaaaatta ccaacataac    1140
aaccgactca agatgtccca cccaagggga agcgatttta cctgaggagc aggaccagaa    1200
ctacgtgtgt aagcatacat acgtggacag aggctgggga aacggttgtg gtttgtttgg    1260
caagggaagc ttggtgacat gcgcgaaatt tcaatgttta gaatcaatag agggaaaagt    1320
ggtgcaacat gagaacctca aatacaccgt catcatcaca gtgcacacag agaccaaca    1380 ccaggtggga aatgaaacgc agggagttac ggctgagata cacccaggg catcaaccgc    1440 tgaagccatt ttacctgaat atggaaccct cgggctagaa tgctcaccac ggacaggttt    1500
ggatttcaat gaaatgattt tattgacaat gaagaacaaa gcatggatgg tacatagaca    1560 atggttctt gacttacccc taccatggac atcaggagct acaacagaaa caccaacttg    1620
gaacaggaaa gagcttcttg tgacatttaa aaatgcacat gcaaaaaagc aagaagtagt    1680
tgtccttgga tcacaagagg gagcaatgca tacagcactg acaggagcta cagagatcca    1740
aaccttagga ggcacaagta tttttgcggg gcacttaaaa tgtagactca agatggacaa    1800
```

```
attggaactc aaggggatga gctatgcaat gtgcttgaat acctttgtgt tgaagaaaga    1860
agtctccgaa acgcagcatg ggacaatact cattaaggtt gagtacaaag ggaaagatgc    1920
accctgcaag attcctttct ccacggagga tggacaaggg aaagctcaca atggcagact    1980
gatcacagcc aatccagtgg tgaccaagga ggaggagcct gtcaacattg aggctgaacc    2040
tccttttggg gaaagtaata tagtaattgg aattggagac aaagccctga aaatcaactg    2100
gtacaggaag ggaagctcga ttgggaagat gttcgaggcc actgccagag gtgcaaggcg    2160
catggccatc ttgggagaca cagcctggga cttttggatca gtgggtggtg ttttgaattc    2220
attagggaaa atggtccacc aaatatttgg gagtgcttac acagccctat ttggtggagt    2280
ctcctggata atgaaaattg gaataggtgt cctcttaacc tggatagggt tgaattcaaa    2340
aaacacttct atgtcatttt catgcattgc gataggaatc attacactct atctgggagt    2400
cgtggtgcaa gctgacatgg ggtgtgtcat aaactggaaa ggcaaagaac tcaaatgtgg    2460
aagtggaatt ttcgtcacta atgaggtcca cacctggaca gagcaataca aatttcaagc    2520
agactccccc aaaagactgg caacagccat tgcaggcgct tgggagaatg gagtgtgcgg    2580
aattaggtca acaaccagaa tggagaacct cttgtggaag caaatagcca atgaactgaa    2640
ctacatatta tgggaaaaca acattaaatt aacggtagtt gtaggcgaca taactggggt    2700
cttagagcaa gggaaaagaa cactaacacc acaacccatg gagctaaaat attcttggaa    2760
aacatgggga aaggcaaaaa tagtgacagc tgaaacacaa aattcctctt tcataataga    2820
tgggccaagc acaccggagt gtccaagtgc ctcaagagca tggaatgtgt gggaggtgga    2880
agattacggg ttcggagttt tcacaaccaa catatggctg aaactccgag aggtgtacac    2940
ccaactatgt gaccataggc taatgtcggc agccgtcaag gatgagaggg ccgtacacgc    3000
cgacatgggc tattggatag aaagccaaaa gaatggaagt tggaagctag aaaaagcatc    3060
cctcatagag gtgaaaacct gcacatggcc aaaatcacac actctttgga gcaatggtgt    3120
gctagagagt gacatgatta tcccaaagag tctagctggt cccatttcgc aacacaacca    3180
caggcccggg taccacaccc aaacggcagg accctggcac ttaggaaaat tggagctgga    3240
cttcaactat tgtgaaggaa caacagttgt catctcagaa aactgtggga caagaggccc    3300
atcattgaga caacaacag tgtcaggaa gttgatacac gaatggtgtt gccgctcgtg    3360
cacacttcct cccctgcgat acatgggaga agacggctgc tggtatgca tggaaatcag    3420 acccattaat gagaaagaag agaacatggt aaagtctcta gcctcagcag ggagtggaaa    3480
ggtggacaac ttcacaatgg gtgtcttgtg tttggcaatc ctctttgaag aggtgatgag    3540
aggaaaattt gggaaaaaac acatgattgc aggggttctc ttcacgtttg tgctcctcct    3600
ctcagggcaa ataacatgga gagacatggc gcacacactc ataatgattg gtccaacgc    3660 ctctgacaga atggggatgg gcgtcactta cctagctcta attgcaacat ttaaaattca    3720
gccattcttg gctttgggat tcttcctgag gaaactgaca tctagagaaa atttattgct    3780
gggagttggg ttggccatgg cagcaacgtt acgactgcca gaggacattg aacaaatggc    3840
gaatggaatt gctttgggc tcatggctct taaactgata acacaatttg aaacatacca    3900
actatggacg gcattagttt ccctaacgtg ttcaaataca atttttcacgt tgactgttgc    3960 ctggagaaca gccactctga ttttagccgg aatttcgctt ttgccagtgt gccagtcttc    4020
gagcatgagg aaaacagatt ggctcccaat gactgtggca gctatgggag ttccaccct    4080 accactttt attttcagtc tgaaagatac actcaaaagg agaagctggc cactgaatga    4140
```

```
gggggtgatg gcagttggac ttgtgagcat tctagctagt tctctcctta ggaatgatgt    4200
gcccatggct ggaccattag tggctggggg cttgctgata gcgtgctacg tcataactgg    4260
cacgtcagca gacctcactg tagaaaaagc agcagatgta acatgggagg aagaggccga    4320
gcaaacagga gtgtcccaca atttaatgat cacagttgat gatgatggaa caatgagaat    4380
aaaagatgac gagactgaga acatcttaac agtgctttta aaacagcac tactaatagt     4440 atcaggcatc tttccatact ccatacccgc aacactgttg gtctggcata cttggcaaaa    4500
gcaaacccaa agatccggcg tcctatggga cgtacccagc cccccagaga cacagaaagc    4560
ggaactggaa aaggggtct ataggatcaa acagcaagga atttttggga aacccaagt      4620 gggggttgga gtacagaaag aaggagtttt ccacaccatg tggcacgtca agagggggc     4680 agtgttgaca cacaatggga aaagactgga accaaactgg gctagcgtga aaaagatct     4740 gatttcatac ggaggaggat ggagattgag tgcacaatgg caaaaggggg aggaggtgca    4800
ggttattgcc gtagagcctg ggaagaaccc aaagaacttt caaaccatgc caggcatttt    4860
tcagacaaca acagggaaa taggagcaat tgcactggat ttcaagcctg gaacttcagg    4920
atctcccatc ataaacagag agggaaaggt agtgggactg tatggcaatg gagtggttac    4980
aaagaatgga ggctatgtca gtggaatagc gcaaacaaat gcagaaccag atggaccgac    5040
accagagttg gaagaagaga tgttcaaaaa gcgaaatcta accataatgg atcttcatcc    5100
tgggtcagga aagacgcgga atatcttcc agctattgtt agagaggcaa tcaagagacg     5160
cttaaggact ctaattttgg caccaacaag ggtagttgca gctgagatgg aagaagcatt    5220
gaaagggctc ccaataaggt atcaaacaac tgcaacaaaa tctgaacaca caggaagaga    5280
gattgttgat ctaatgtgtc acgcaacgtt cacaatgcgc ttgctgtcac cagtcagggt    5340
tccaaactac aacttgataa taatggatga ggctcatttc acagaccag ccagtatagc     5400 ggctagaggg tacatatcaa ctcgtgtagg aatgggagag gcagccgcaa ttttcatgac    5460
agcaacaccc cctggaacag ctgatgcctt tcctcagagc aacgctccaa ttcaagatga    5520
agagagagac ataccggaac gctcatggaa ttcaggcaat gaatggatta ctgactttgt    5580
tgggaagaca gtgtggtttg tccctagcat caaagccgga aatgacatag caaactgctt    5640
gcggaaaaat ggaaaaaagg tcattcaact cagcaggaag accttgaca cagaatatca     5700 aaagaccaaa ctgaatgatt gggacttgt ggtgacaaca gacatttcag aaatgggagc      5760
caatttcaaa gcagatagag tgatcgaccc aagaagatgt ctcaagccgg tgattttgac    5820
aaatggaccc gagcgggtga tcctggctgg accaatgcca gtcaccgtag cgagcgctgc    5880
gcaaaggaga gggagagttg gcaggaaccc acaaaaagaa aatgaccagt acatattcat    5940
gggccagcct ctcaacaatg atgaagacca tgctcactgg acagaagcaa aaatgctgct    6000
ggacaacatc aacacaccag aagggattat accagctctc tttgaaccag aaagggagaa    6060
gtcagccgcc atagcggcg aataccgcct gaagggtgag tccaggaaga ctttcgtgga     6120
actcatgagg agggtgacc tcccagtttg gctagcccat aaagtagcat cagaagggat     6180
caaatataca gatagaaaat ggtgctttga tggagaacgt aataatcaaa ttttagagga    6240
gaatatggat gtgaaatct ggacaaagga aggagaaaag aaaaaactga gacctaggtg      6300
gcttgatgcc cgcacttatt cagatcctt agcactcaag gaattcaagg attttgcagc     6360
tggcagaaag tcaatcgccc ttgatcttgt gacagaaata ggaagagtgc cttcacactt    6420
agcccacaga acgagaaacg ccctggcaa tttggtgatg ctgcacacgt cagaacatgg     6480
cggtagggcc tacaggcatg cagtggagga actaccagaa acgatggaaa cactcttact    6540
```

```
cctgggactg atgatcttgt taacaggtgg agcaatgctc ttcttgatat caggtaaagg    6600
gattggaaag acttcaatag gactcatttg tgtaattgct tccagcggca tgttatggat    6660
ggctgatgtc ccactccaat ggatcgcgtc ggctatagtc ctggagtttt ttatgatggt    6720
gttgctcata ccagaaccag aaaagcagag aactccccaa gacaaccaac tcgcatatgt    6780
cgtgataggc atacttacat tggctgcaat agtagcggcc aatgaaatgg gactgttgga    6840
aactacaaag agagatttag gaatgtctaa agaaccaggt gttgtttctc caaccagcta    6900
tttggacgtg gacttgcacc cagcatcagc ctggacattg tacgccgtgg ccacaacagt    6960
aataacacca atgttgagac acaccataga gaattccaca gcaaatgtgt ccctggcagc    7020
catagctaac caggcagtgg tcctgatggg tttagacaaa ggatggccga tatcgaaaat    7080
ggacttgggc gtaccactat tggcactggg ttgctattca caagtgaacc cactaactct    7140
tgcagcggca gtacttttgc tagtcacaca ttatgcaatt ataggtccag gattgcaggc    7200
aaaagccact cgtgaagctc agaaaaggac agctgctgga ataatgaaga tccaacggt    7260
ggatggaata atgacaatag acctagatcc tgtaatatat gattcaaaat ttgaaaagca    7320
actaggacag gttatgctcc tggttctgtg tgcagttcaa cttttgttaa tgagaacatc    7380
atgggccttg tgtgaagctc tagccctagc cacaggacca ataacaacac tctgggaagg    7440
atcacctggg aagttctgga acaccacgat agctgtttcc atggcgaaca tctttagagg    7500
gagctattta gcaggagctg gcttgcttt ttctatcatg aaatcagttg gaacaggaaa    7560
gagaggaaca gggtcacaag gtgaaaacctt aggagaaaag tggaaaaaga attaaatca    7620
gttatcccgg aaagagtttg acctttacaa gaaatccgga atcaccgaag tggatagaac    7680
agaagccaaa gaagggttaa aaagaggaga ataacacac catgccgtgt ccagaggcag    7740
cgcaaaactt caatggttcg tggagagaaa catggtcatt cccgaaggaa gagtcataga    7800
cttaggttgt ggaagaggag gctggtcata ttactgtgca ggactgaaaa agttacaga    7860
agtgcgagga tacacaaaag gcggcccagg acacgaagaa ccagtaccta tgtctacata    7920
cggatggaac atagtcaagt taatgagtgg aaaggatgtt ttttatctgc cacctgaaaa    7980
gtgtgatacc ctattgtgtg acattggaga atcttcacca agcccaacag tggaagaaag    8040
cagaaccata agagtcttga agatggttga accatggcta aaaacaacc agttttgcat    8100
taagtattg aacccataca tgccaactgt gattgagcac ttagaagac tacaaaggaa    8160
acatggagga atgcttgtga gaaatccact ctcacgaaac tccacgcacg aaatgtattg    8220
gatatccaat ggtacaggca acatcgtctc ttcagtcaac atggtatcca gattgctact    8280
gaacagattc acaatgacac acaggagacc caccatagag aaagatgtgg atttaggagc    8340
aggaaccccga catgtcaatg cggaaccaga aacacccaac atggatgtca ttggggaaag    8400
aataaaaagg atcaaagagg agcatagttc aacatggcac tatgatgatg aaaatcctta    8460
caaaacgtgg gcttaccatg gatcctatga agtaaaagcc acaggctcag cctcctccat    8520
gataaatgga gtcgtgaaac tcctcacaaa accatgggat gtggtgccca tggtgacaca    8580
gatggcaatg acagatacaa ctccatttgg ccagcaaaga gttttaaag agaaagtgga    8640
caccaggaca cctaggccca tgccaggaac aagaaaggtt atggagatca cagcggagtg    8700
gctttggagg accctgggaa ggaacaaaag acccagatta tgcacaaggg aggagttcac    8760
aaagaaggtc agaaccaacg cagctatggg cgctgtcttc acagaagaga accaatggga    8820
cagtgcgaga gctgctgttg aggacgaaga attttggaaa cttgtggaca gagaacgtga    8880
```

```
actccacaaa ctgggcaagt gtggaagctg cgtttacaac atgatgggca agagagagaa    8940
aaaacttgga gagtttggta aagcaaaagg cagtagggct atatggtaca tgtggttggg    9000
agccaggtac cttgagttcg aggcgctcgg attcctcaat gaagaccact ggttctcgcg    9060
tgaaaactct tacagtggag tagaaggaga aggactgcac aagctgggat acatcttgag    9120
agatatttcc aagataccog gaggagccat gtatgctgat gacacagccg gttgggacac    9180
aagaataaca gaagatgacc tgcacaatga ggaaaaaatc acacagcaga tggaccctga    9240
acacaggcag ctagcgaacg ctatattcaa gctcacatac caaaacaaag tggtcaaagt    9300
ccaacgacca actccaaagg gcacggtaat ggacatcata tctaggaaag accaaagagg    9360
cagtggacag gtgggaactt atggtctgaa cacattcacc aacatggaag cccagctaat    9420
cagacaaatg gaaggagaag gcgtgttgtc aaaggcagac ctcgagaacc ccatccgct    9480
agagaagaaa attacacaat ggttggaaac taaaggagtg gagaggttaa aaagaatggc    9540
catcagcggg gatgattgcg tagtgaaacc aatcgacgac agattcgcca atgccctgct    9600
tgccctgaac gatatgggaa aggttaggaa ggacatacct caatggcagc catcaaaggg    9660
atggcatgat tggcaacagg tccctttctg ctcccaccac tttcatgaat tgatcatgaa    9720
agatggaaga agttggtag ttccctgcag acccccaggac gaactaatag gaagagcag    9780
aatctctcaa ggagcaggat ggagccttag agaaactgca tgtctaggga agcctacgc    9840
tcaaatgtgg actctcatgt attttcacag aagagatctt agactagcat ccaacgccat    9900
atgttcagca gtaccagtcc attgggtccc cacgagcaga acgacatggt ctattcatgc    9960
tcaccatcag tggatgacta cagaagacat gcttactgtc tggaacaggg tgtggataga    10020
ggacaatcca tggatggaag acaaaactcc agtcacaacg tgggaagatg ttccatatct    10080
agggaagaga gaagaccaat ggtgcggatc actcatagg ctcacttcca gagcaacctg    10140
ggcccagaac atactcacag caatccaaca ggtgagaagc ctcataggca tgaagagtt    10200
tctggactac atgccttcga tgaagagatt caggaaggag gaggagtcag agggagccat    10260
ttggtaaaag caggaggcaa actgtcaggc caccttaagc cacagtacgg aagaagctgt    10320
gcagcctgtg agccccgtcc aaggacgtta aaagaagaag tcaggcccaa aagccacggt    10380
ttgagcaaac cgtgctgcct gtagctccgt cgtggggacg taaagcctgg gaggctgcaa    10440
accgtggaag ctgtacgcac ggtgtagcag actagtggtt agaggagacc cctcccatga    10500
cacaacgcag cagcggggcc cgagcactga gggaagctgt acctccttgc aaaggactag    10560
aggttatagg agaccccccg caaacaaaaa cagcatattg acgctgggag agaccagaga    10620
tcctgctgtc tcctcagcat cattccaggc acagaacgcc agaaaatgga atggtgctgt    10680
tgaatcaaca ggttct                                                   10696
```

<210> SEQ ID NO 9
<211> LENGTH: 10649
<212> TYPE: DNA
<213> ORGANISM: Dengue virus 4

<400> SEQUENCE: 9

```
agttgttagt ctgtgtggac cgacaaggac agttccaaat cggaagcttg cttaacacag      60
ttctaacagt ttatttgaat agagagcaga tctctggaaa aatgaaccaa cgaaaaaagg     120
tggttagacc acctttcaat atgctgaaac gcgagagaaa ccgcgtatca acccctcaag     180
ggttggtgaa gagattctca accggacttt tttctgggaa ggaccctta cggatggtgc     240
tagcactcat cacgttttg cgagtccttt ccatcccacc aacagcaggg attctgaaga     300
```

-continued

```
gatggggaca gttgaagaaa aataaggcca ttaagatact gattggattc aggaaggaga      360
taggccgcat gctgaacatc ttgaacggga gaaaaaggtc aacgataaca ttgttgtgct      420
tgattcccac cgtaatggcg tttcacttgt caacaagaga tggcgaaccc ctcatgatag      480
tggcaaaaca tgaaggggg agacctctct tgtttaagac aacagagggg atcaacaaat       540
gcactctcat tgccatggac ttgggtgaaa tgtgtgagga cactgtcacg tacaaatgcc      600
ccctactggt caataccgaa cctgaagaca ttgattgctg gtgcaacctc acgtctacct      660
gggtcatgta tgggacatgc acccagagcg gagaacggag acgagagaag cgctcagtag      720
ctttaacacc acattcagga atgggattgg aaacaagagc tgagacatgg atgtcatcgg      780
aaggagcttg gaagcatgct cagagagtag agagctggat actcagaaac ccaggatttg      840
cactcttggc aggattttatg gcttatatga ttgggcaaac agggatccag cgaactgtct      900
tctttgtcct aatgatgctg gtcgccccat cctacggaat gcgatgcgta ggagtaggaa      960
acagagactt tgtggaagga gtctcaggtg gagcatgggc cgacctggtg ctagaacatg     1020
gaggatgcgt cacaaccatg gcccagggaa aaccaacctt ggattttgaa ctgaccaaga     1080
caacagccaa ggaagtggct ctgttaagaa cctattgcat tgaagcctta atatcaaaca     1140
taactacggc aacaagatgt ccaacgcaag gagagcctta tctgaaagag gaacaggacc     1200
aacagtacat tgccgtagaa gatgtggtag atagaggatg gggcaatggc tgtggcttgt     1260
ttggaaaagg aggagttgtg acatgtgcga gttctcatg ttcggggaag ataacaggca      1320
atctggtcca aattgagaac cttgaataca cagtggttgt gacagtccac aatgagacca     1380
cccatgcagt aggaaatgac acatccaacc atgggggttac agccacgata actcccaggt    1440
caccatcggt tgaagtcaaa ctgccggact atggagaact aacacttgat tgtgaaccca     1500
ggtctggaat tgacttcaat gagatgatcc taatgaaaat gaaaaagaaa acatggctcg     1560
tgcataagca atggttttg gatctgcctc ttccatggac gacaggagca gatacatcag      1620
aggttcactg gaattacaaa gagagaatgg tgacattta ggttcctcat gccaagagac     1680
aggatgtgac agtgctggga tctcaggaag gagccatgca ttctgccctc gctgagcca      1740 cagaagtgga ctccggtgat ggaaatcaca tgtttgcagg acatctcaag tgcaaagtcc     1800
gcatggagaa attgagaatc aagggaatgt catacacgat gtgttcagga agttttcaa      1860 ttgacaaaga gatggcagaa acacagcatg gacaacagt ggtgaaagtc aagtatgaag      1920
gtgctggagc tccgtgtaaa gtccccatag agataagaga tgtaaacaag gagaaagtgg     1980
ttgggcgcgt tatctcagcc accccttggg ctgagaacac caatagtgta accaacatag     2040
aattagaacc cccctttggg gacagctaca tagtgatagg tgttggaaac agcgcactaa     2100
cactccattg gttcaggaaa gggagttcca ttggcaagat gtttgagtcc acatacagag     2160
gtgcaaaacg catggccatc ctaggtgaaa cagcttggga ttttggttcc gttggtggac     2220
tgttcacatc attgggaaag gctgtgcacc aggttttgg aagtgtgtat caaccatgt      2280 ttggaggagt ctcatggatg attagaatcc taattgggtt cttagtgttg tggattggca     2340
cgaactcaag gaacacttca atggccatga cgtgcatagc tgttggggga atcactctgt     2400
ttttgggctt cacggttcaa gcggacatgg gttgtgtggt gtcatggagt gggagagaat     2460
tgaagtgtgg aagcggaatt tttgtggttg acaacgtgca cacttggaca gaacagtaca     2520
aattccaacc agagtcccca gcgagactag cgtctgcaat attaaatgcc cacaaagatg     2580
gggtctgtgg aattagatca accacgaggc tggaaaatgt tatgtggaag caaataacca     2640
```

```
atgagctaaa ctatgttctc tgggaaggag gacatgatct cactgtagtg gctggggacg    2700
tgaaaggggt gttgaccaag ggcaagagag cactcacacc cccagcgagc gatctgaaat    2760
attcatggaa gacatggggg aaagcaaaaa tcttcacccc tgaagcaaga aacagcacat    2820
ttttaataga cggaccagat acctctgaat gccccaatga acgaagagca tggaattctt    2880
ttgaggtgga agactatgga tttggcatgt tcacgaccaa catatggatg aaattccgag    2940
aaggaagttc agaagtgtgt gaccacaggc tgatgtcagc tgcaattaaa gaccagaaag    3000
ctgtgcatgc tgacatgggt tattggatag agagctcaaa aaaccagacc tggcagatag    3060
aaagagcatc tctcattgaa gtgaaaacat gtctgtggcc caagacccat acactgtgga    3120
gcaatggagt gctggagagc cagatgctta ttccaaaatc atatgcaggc ccttttttcac    3180 agcacaatta ccgccagggc tatgctacgc aaaccgtggg tccatggcac ttgggcaaac    3240
tagagataga cttttggagaa tgccccggaa caacagttac aattcaggag aattgtgacc    3300
atagaggccc atctttgagg accaccactg catctggaaa actagtcacg caatggtgtt    3360
gccgctcctg cacaatgccc cccttaaggt tcttaggaga agatgggtgc tggtatggga    3420
tggagattag gcccttgagt gaaaagaag agaacatggt taaatcacag gtgacggccg    3480
gacagggcac atcggaaact ttttctatgg gtctgttgtg cctgacctg tttgtggaag    3540 aatgcttgag aagaagagtc accagaaaac acatgatatt agctgtggta atcactcttt    3600
gtgctatcat cctgggggc ctcacatgga tggacttgct acgagccctc atcatattgg    3660
gggacactat gtctggcaga ataggaggac agacccacct agccatcatg cagtgttca    3720 agatgtcacc aggatacgtg ctgggtgtgt ttaaggaa actcacttca agagagacag    3780
cactaatggt aataggaatg gccatgacaa caacactttc aattccacat gacctcatgg    3840
aactcattga tggaatatca ctaggactaa ttttgctaaa aatagtaaca cagttttgaca    3900 acacccaagt ggggaacctta gctctttcct tgactttcat aagatcaaca atgtcattgg    3960
tcatggcctg gaggaccatt atggctgtgc tgttttgtgt cacactcatt cctttgtgta    4020
ggacaagctg tcttcaaaaa cagtctcatt gggtagaaat aacagcactc atcttaggag    4080
cccaagctct gccagtgtac ctaatgactc ttatgaaagg agcctcaaga agatcttggc    4140
ctcttaacga aggcataatg gctgtgggt tggttagtct cttaggaagc gctcttttaa    4200
agaatgatgt ccctttagct ggcccaatgg tggcaggagg cttacttctg gcggcttacg    4260
taatgagtgg cagctcagca gatctgtcac tagagaaggc cgctaatgtg cagtgggatg    4320
aaatggcaga cataacaggc tcaagtccaa tcatagaagt gaagcaagat gaggatggct    4380 cttttctccat acgggacgtc gaggaaacca atatgataac ccttttggtg aaactggcac    4440
tgataacggt gtcaggtctc taccccttgg caattccaat cacaatgacc ttatggtaca    4500
tgtggcaagt gaaaacacaa agatcaggag ccctgtggga cgttccttca cccgctgcca    4560
ctcaaaaagc cgcactgtcc gaaggagtgt acaggatcat gcaaagaggg ttattcggga    4620
aaacccaggt tggagtaggg atacacatgg aaggtgtatt tcacacaatg tggcatgtca    4680
caagaggatc ggtgatctgc cacgagactg ggagattgga ccatcttgg gctgacgtca    4740 ggaatgacat gatatcatac ggtggggat ggaggcttgg agataaatgg gacaaagaag    4800
aagacgttca ggtcctcgct atagaaccag ggaaaaatcc caaacatgtc caaacgaaac    4860
ctggcctttt caagacccta actggagaaa ttggagcagt aacattagat ttcaaacccg    4920
gaacgtctgg ttctcccatt atcaacagga aggaaaagt catcggactc tatgggaatg    4980
gagtggttac caaatcaggt gattacgtca gtgccataac gcaagccgaa agaattggag    5040
```

```
agccagatta tgaagtggat gaggacattt ttcggaagaa aagactaact ataatggact   5100
tacaccccgg agctggaaag acaaaaagaa ttcttccatc aatagtgaga gaagccttaa   5160
aaaggaggct gcgaactttg attctggctc ccacgagagt agtggcggcc gagatggaag   5220
aggccctacg tggactgcca atccgttacc aaacccagc tgtgaaatca gaacacacag    5280
gaagagagat tgtagacctc atgtgccatg caaccttcac aacaagactt ttgtcatcaa   5340
ccagagttcc aaactataac cttatagtaa tggatgaagc acatttcacc gatccttcca   5400
gtgtcgcggc tagaggatac atctcgacca gggtggaaat gggagaggca gcagccatct   5460
tcatgaccgc aaccccctccc ggagcgacgg atccatttcc ccagagcaac agcccaatag  5520
aagacatcga gagagagatt ccggaaaggt catggaacac agggttcgac tggataacag   5580
actaccaagg gaaaactgtg tggtttgttc ctagcataaa agctggaaat gacattgcaa   5640
attgtttgag gaagtcggga agaaagtta tccagttgag taggaaaacc tttgatacag     5700
aatatccaaa aacgaagctc acggactggg actttgtggt cactacagac atatctgaaa   5760
tgggggctaa ctttagagct gggagagtga tagaccctag aagatgcctc aagccagtta   5820
tcctaacaga tgggccagag agagtcatct tagcaggtcc cattccagtg actccagcaa   5880
gcgctgccca aagaagaggg cgaataggaa ggaacccagc acaagaagac gaccaatacg   5940
ttttctccgg agacccacta aaaaatgatg aagatcatgc ccactggaca gaagcaaaga   6000
tgctgcttga caatatctac accccagaag ggatcattcc aacattgttt ggtccggaaa   6060
gggaaaaaac ccaagctatt gatggagagt ttcgcctcag aggggaacaa aggaagactt   6120
ttgtggaatt aatgaggaga ggagaccttc cggtgtggct gagttataag gtagcttctg   6180
ctggcatttc ttacaaagat cgggaatggt gcttcactgg ggaaagaaat aaccaaattt   6240
tagaagaaaa catggaggtt gaaatttgga ctagagaggg agaaaagaaa aaactgaggc   6300
caaaatggtt agatgcacgt gtatacgctg accccatggc tttgaaggat ttcaaggagt   6360
ttgccagtgg aaggaagagt ataactctcg acatcctgac agagatcgcc agtttgccaa   6420
cctacctttc ctctagggcc aagctcgccc ttgacaacat agttatgctc cacacaacag   6480
aaagaggagg gagggcctat caacacgccc tgaacgaact tccggagtca ctggaaacac   6540
tcatgcttgt agccttactg ggtgctatga cagcaggtat cttcctgttt ttcatgcaag   6600
gtaaaggaat agggaaattg tcaatggggtt tgataaccat tgcggtggct agtggcttgc   6660
tctgggtagc agaaattcaa ccccagtgga tagcggcctc aatcatactg gagttttcc    6720 tcatggtact gttgatacca gaaccagaaa aacaaaggac cccacaagac aatcaattga   6780
tctacgtcat attgaccatt ctcaccatta ttggtctaat agcagccaac gagatggggc   6840
tgatagaaaa aacaaaaacg gattttgggt tttaccaggt aaaaacagaa accaccatcc   6900
tcgatgtgga cctgagacca gcttcagcat ggacgctcta tgcggtagcc accacaattc   6960
tgactcccat gctgagacac accatagaaa atacgtcggc caacctatct ttagcagcca   7020
ttgccaacca ggcagccgtc ctaatggggc ttggaaaagg atggccactc cacagaatgg   7080
acctcggtgt gccgctgtta gcaatgggat gctattctca agtgaaccca acaaccttga   7140
cagcatcctt agtcatgctt ctagtccatt atgcaataat aggcccagga ttgcaggcaa   7200 agccacaag agaggcccag aaaaggacag ctgctggaat catgaaaaat cccacagtgg    7260
acgggataac agtgatagat ctagaaccaa tatcctatga cccaaaattt gaaaagcaat   7320
tagggcaggt catgctactc gtcttgtgtg ctggacaact actcttgatg agaacaacat   7380
```

```
gggctttctg tgaagtcttg actttggcta caggaccaat cttgaccttg tgggagggca    7440
acccgggaag gttttggaac acgaccatag ccgtatctac cgccaacatt ttcaggggaa    7500
gttacttggc aggagctgga ctggcttttt cactcataaa gaatgcacaa accccagga    7560 ggggaactgg gaccgcagga gagacactgg gagagaagtg gaagagacag ctaaactcat    7620
tagacagaaa agagtttgaa gagtatataaaa gaagtggaat actagaagtg gacaggactg   7680
aagccaagtc cgccctgaaa gatgggtcca aaatcaagca tgcagtatct agagggtcca    7740
gtaagattag atggatcgta gagagaggga tggtaaagcc aaaagggaaa gttgtagatc    7800
ttggctgtgg gagaggagga tggtcttatt acatggcaac actcaagaac gtgactgaag    7860
tgaaagggta tacaaaagga ggtccaggac atgaagaacc gattcctatg gctacttatg    7920
gctggaattt ggtcaaactc cattcagggg ttgacgtgtt ctacaaaccc acagagcaag    7980
tggacaccct gctctgtgat attggggagt catcttctaa tccaacaata gaggaaggaa    8040
gaacattgag agttttgaag atggtggagc catggctctc ttcaaaacct gaattctgca    8100
tcaaggtcct taacccctac atgccaacag tcatagaaga gctggagaaa ctgcagaaga    8160
aacatggtgg gaaccttgtc agatgcccgc tgtccaggaa ctccacccat gagatgtatt    8220
gggtgtcagg agcgtcggga aacatcgtga gctctgtgaa cacaacatca aagatgttgt    8280
tgaacaggtt cacaacaagg cataggaaac ccactttatga aaggacgta atcttgggg     8340 caggaacgag aagtgtctcc actgaaacag aaaaaccaga catgacaatc attgggagaa    8400
ggcttcagcg attgcaagaa gagcacaaag aaacatggca ttatgatcaa gaaaacccat    8460
acagaacctg ggcgtatcat ggaagctatg aagctccttc gacaggctct cgtcctcca    8520 tggtgaacgg ggtggtgaaa ctgctaacaa acccctggga tgtaattccg atggtgactc    8580
agttagccat gacagacaca accccttttg ggcaacaaag agtgttcaaa gaaaaggtgg    8640
ataccagaac accgcaacca aaaccaggca cacgaatggt tatgaccacg acagccaatt    8700
ggctatgggc cctccttgga aagaagaaaa atcccagact gtgcacaagg gaagagttca    8760
tctcaaaagt tagatcaaac gcagccatag cgcagtctt ccaagaggaa cagggatgga    8820
catcagccag tgaagctgtg aatgacagcc ggttttggga actggttgac aaagaaaggg    8880
cccttcacca agaagggaaa tgtgaatcgt gtgtctacaa catgatggga aaacgtgaga    8940
aaaagttagg ggagttttggc agagccaagg gaagccgagc aatctggtat atgtggctag    9000
gagcgcggtt tctggaattt gaagccctgg gtttttttga tgaagatcat tggtttggca    9060
gagaaaactc atggagtgga gtggaagggg aaggtctgca cagattggga tacatcctgg    9120
aggagataga caagaaggat ggagacctaa tgtatgctga tgacacagca ggctgggaca    9180
caagaatcac tgaggatgac ctccaaaatg aggaactgat cacggaacag atggctcccc    9240
accacaagat cctagccaaa gccatttca aactaaccta ccaaaacaaa gtggtgaaag    9300
tcctcagacc cacaccgaga ggagcggtga tggatatcat atccaggaaa gaccagagag    9360
gtagtggaca agttggaaca tatggtttga acacattcac caacatggaa gttcaactca    9420
tccgccaaat ggaagcagaa ggagtcatca cacaagatga catgcagaac cctaaagggt    9480
tgaaagaaag agttgagaaa tggctgagag agtgtgtgt cgacaggtta aagaggatgg    9540
caattagtgg agacgattgc gtggtgaaac ccctagatga gaggtttggc acctccctcc    9600
tcttcttgaa cgacatggga aaggtgagga aagacattcc gcagtgggaa ccatctaagg    9660
gatgaaaaaa ctggcaagag gttccttttt gctcccacca ctttcacaag atctttatga    9720
aggatggccg ctcactagtt gttccatgta gaaaccagga tgaactgata gggagagcca    9780
```

```
gaatctcgca gggggctgga tggagcttaa gggaaacagc ttgcctaggc aaagcttacg    9840
cccagatgtg gtcgcttatg tacttccaca gaagggatct gcgtttagcc tccatggcca    9900
tatgctcagc agttccaacg gaatggtttc caacaagcag aacaacatgg tcaatccatg    9960
ctcatcacca atggatgacc actgaagaca tgctcaaggt gtggaacaga gtgtggatag   10020
aagacaaccc caatatgatt gacaagactc cagtccattc gtgggaagat atacccttacc  10080
tagggaaaag agaggatttg tggtgtggat ccctgattgg actttcttct agagccacct   10140
gggcgaagaa cattcacacg gccataactc aggtcaggaa tctgatcgga aaagaggaat   10200
acgtggatta tatgccagta atgaaaagat acagtgctcc ttcagagagt gaaggagttc   10260
tgtaatcacc aacaacaaac accaaaggct attgaagtca ggccacttgt gccacggctt   10320
gagcaaaccg tgctgcctgt agctccgcca ataatgggag cgtaataat ccctaggag      10380
gccatgcgcc acggaagctg tacgcgtggc atattggact agcggttaga ggagacccct   10440
cccatcactg acaaaacgca gcaaaagggg gcccgaagcc aggaggaagc tgtactcctg    10500
gtggaaggac tagaggttag aggagacccc cccaacataa aaacagcata ttgacgctgg    10560
gaaagaccag agatcctgct gtctctacaa catcaatcca ggcacagagc gccacaagat    10620
ggattggtgt tgttgatcca acaggttct                                      10649

<210> SEQ ID NO 10
<211> LENGTH: 11062
<212> TYPE: DNA
<213> ORGANISM: West Nile virus

<400> SEQUENCE: 10
agtagttcgc ccgtgtgagc tgacaaactt agtagtgttt gtgaggatta ataacgatta      60
acacagtgtg agctgtttct tagcacgaag atctcgatgt ctaagaaacc aggagggccc     120
ggcaaaagcc gggctgtcaa tatgctaaaa cgcggtatgc cccgcggatt gtccttgata     180
ggactgaaga gggctatgtt gagtctgatc gacgggaagg gccctatacg ctttgtgttg     240
gctcttttgg cgttcttcag attcactgca attgctccga ctcgtgcggt gctggaaagg     300
tggagaggcg tcaacaaaca aacagcaatg aagcatctct tgagttttaa gaagaactaa     360
ggaactttga ccagtgccat taaccgccgg agcacaaaac aaaagaaaag aggaggtcca     420
gcaggcttga ccatcctgtt tgggctgatg tcttgcgctg gagccgtgat cctatccaac     480
ttccagggca aagtgatgat gaccgtcaat gcaaccgatg tcaccgacgt gatcaccatt     540
ccaacagccg ccgggaaaaa cctgtgcatc gttagagcga tggatgtggg atacctctgt     600
gatgatacca tcacgtatga atgtccggtt ctagctgctg aaacgacccc tgaggacatt     660
gactgctggt gcacgaaatc atccgtctat gtgcgatatg aagatgtac gaagacccgg      720
cattcccgcc gcagcagaag gtctttgaca gtccagacac atggagaaag cacattggtt     780
aataagaagg gagcttggct ggacagcaca aaagccacga gatatctggt aaagacagaa     840
tcatggatac tgagaaaccc tggctacgcc ctcgtcgcag ctgttattgg atggatgcta     900
gggagcaaca caatgcagcg cgtcgtgttt gccatcctat tgcttttggt agcaccagca     960
tacagtttca actgcctggg aatgagcagc agggacttcc tggaggggt gtctggagcc   1020
acatgggttg acctgatact agagggcgac agttgtgtga ccataatgtc aaaagacaaa    1080
ccaacaattg atgtcaagat gatgaaaatg gaagcggcca atcttgcgga tgtgcgtcat    1140
tactgctatc tagcttcggt cagtgaactg tcaacaagag ccgcatgccc aaccatgggt    1200
```

```
gaagcccaca acgagaaaag agctgatccc gcctttgttt gcaagcaagg agttgtggac   1260
agaggatggg gaaatggatg tggattgttt ggaaagggta gcattgacac atgcgcaaag   1320
tttgcttgca caaccaaggc gactggctgg atcattcaga aggaaaacat caagtacgag   1380
gtcgccatct ttgtgcatgg ccccacgact gtcgaatctc atggcaatta ttcaacacaa   1440
gtgggagcca ctcaggctgg aagattcagt ataaccccgt cggcaccatc ttacacgctg   1500
aagttgggtg agtatggtga agtcacggtt gactgtgagc cacggtcagg gatagacatc   1560
agcctacatg tcatgtcagt tggtgctaag tcttttctgg ttcatcgaga atggttcatg   1620
gacctgaacc tgccatggag tagcgctgga ggcactacgt ggagaaaccg ggaagctctg   1680
atggaatttg aagaacctca tgccactaaa cagtctgttg tagccttggg atcgcaagaa   1740
ggtgctctgc accaagccct ggctggagcg attcccgttg agttctcaag taacactgtg   1800
aagttgacat cagggcattt gaagtgcagg gtgaagatgg agaagctgca actgaaggga   1860
acgacatatg gagtgtgttc aaaagcattc aaatttgttg ggactcccgc tgacactgga   1920
catgggacgg tggtgctgga actgcagtac actgggacag atgggccctg caaagtgccc   1980
atctcttccg tggcttctct aaatgacctc acgcccgtgg aagattggt gactgtgaat    2040 ccttttgtgt ctgtggccac ggccaactca agatcttga ttgaaattga accccattt     2100 ggtgactctt atattgtggt agggagaggg gagcagcaaa taaaccacca ttggcacaaa   2160
tctggaagca gcattggaaa agccttcacg actactctga gaggagcgca acgacttgca   2220
gcgcttggag acacagcttg ggacttcgga tcggttggag gggttttcac ctcggttggg   2280
aaagccatac accaagtctt tggaggagct tttagatcac tttttggagg gatgtcctgg   2340
attacacagg gacttctagg ggctcttcta ctgtggatgg ggatcaatgc tcgtgatagg   2400
tcaattgcta tgacgttcct tgcggttgga ggagttttgc tcttcctctc ggttaacgtc   2460
cacgctgaca cgggctgtgc catcgatctt ggtaggcaag agcttcggtg cgggagcgga   2520
gtgtttgttc acaatgatgt ggaagcttgg atggatcgct acaaattcta cccggagacg   2580
ccacaaggct tagcaaaaat tatccagaaa gcacgtgcag aaggagtttg tggtctgcgc   2640
tctgtctcca gactcgaaca ccagatgtgg gaggccatca aggatgagtt gaacaccctg   2700
ctgaaagaga acggagttga cttaagtgtc gtggttgaaa aacagaatgg gatgtacaaa   2760
gcagcgccaa aacgcctggc cgccaccacc gagaaactgg agatgggctg gaaagcttgg   2820
ggcaagagca tcatcttcgc tccagaacta gctaacaaca cctttgtcat tgatggtcct   2880
gagaccgaag aatgcccaac agctagccga gcatggaaca gcatggaggt ggaggatttt   2940
gggtttggac tgacgagcac ccggatgttc ctgaagatcc gggagacgaa cacgacggag   3000
tgcgactcga agatcattgg aaccgccatt aagaacaaca tggctgtgca cagtgacctg   3060
tcatactgga tagaaagtgg actcaatgac acctggaagc ttgagagagc ggttctagga   3120
gaggtcaaat catgcacctg gcctgagacc cacaccctat ggggcgatgg agttctagaa   3180
agtgatctca tcatacccat taccttagca gggcccagga gcaaccacaa cagaagacca   3240
gggtacaaaa ctcagaatca aggcccatgg gatgagggac gtgttgagat tgactttgac   3300
tattgcccag gaacaacagt aaccttaagt gacagttgtg acaccgtgg acccgcggca   3360 cgcacgacca ccgagagtgg gaagctcatt accgattggt gctgtaggag ttgcacccct   3420
cctccattac ggttcagaac cgaaaatggg tgttggtatg aatggaaat tcgccctctg   3480 cgacacgatg aaaagaccct cgtgcagtcg aaagtaaacg cgtacaacgc cgacatgatt   3540
gatccttttc agctgggcct tctggtcgta ttcttggcca cccaggaggt ccttcgcaag   3600
```

-continued

```
aggtggacgg ccaagatcag cattccggct attctgcttg cgctcgtggt cctcgtgctt    3660
gggggtatca cgtacactga tgttttgagg tatgtcattc ttgttggagc cgcgtttgct    3720
gaagcaaact caggcggaga tgttgtgcat ttggcgctta tggccacatt caaaattcag    3780
ccagttttct tggtggcctc tttcttaaaa gcaaggtgga ccaaccaaga gagcattttg    3840
cttatgcttg cggctgcctt tttccaaatg gcttattatg atgccaggaa cgtcttggca    3900
tgggatatgc ctgatgtttt gaattcccctt tccgtcgcct ggatgattct cagggccata    3960
agctttacca acacctcaaa tgtggtggtg ccgctactgg cccttttgac acctgggtta    4020
aaatgcttga atctggatgt gtaccggatt ttgctgctta tggttggagt tggaagcctc    4080 ataaagaaa agaggagctc tgcagcaaaa aagaaaggag cctgcctcat ctgcctagca    4140
ctggcgtcca cagaggtgtt caatccaatg atactagcag ctgggctgat ggcttgcgat    4200
cccaatcgca agcgaggctg gcctgccaca gaagtgatga ccgcggttgg acttatgttt    4260
gccattgttg ggggtctagc agaacttgac atagattcta tggctatccc catgaccatc    4320
gccggactta tgtttgtggc atttgtcatc tctgggaaat cgacggacat gtggatcgtg    4380
agggcggccg acatcacttg ggagagcgac gctgaaatca caggttctag cgagagagtg    4440
gatgttaggt tggatgatga tgggaacttc cagttgatga acgatcctgg ggcaccatgg    4500
aaaatctgga tgctcagaat ggcctgcttg gcaataagtg cctacacacc ctgggccata    4560 ctccccctcag tcattggatt ttggataacc cttcaataca caaagcgggg aggtgttctt    4620
tgggacacac catcgcccaa agagtacaag aagggtgaca ccactaccgg cgtctacagg    4680
atcatgaccc gaggtctgct cggaagttac caggctggag ccggtgtgat ggtagaagga    4740
gtgttccaca cactgtggca caccaccaaa ggagcagctc tcatgagcgg cgaagggagt    4800
ctagatccct attggggag cgtgaaagaa gaccgactgt gctatggagg gccttggaaa    4860
ctccaacaca gtggaatgg acatgatgag gttcaaatga ttgtcgtgaa accaggagaa    4920
aacgtgagga acgttcaaac aaaacccgga gtgtttaaga caccagaagg agagatcggg    4980
gcagtcacgc tagactaccc caccggaacg tcaggctctc ccattgtgga caaaaatggg    5040
gacgtgattg ggctgtatgg gaacggcgtc atcatgccga atggcgcgta catgagcgcc    5100
attgtgcaag agagagagaat ggaagaaccg cgccagctg gttttgagcc tgaaatgctg    5160
aggaagaaac aaatttctgt ccttgacctg caccccggat caggaaagac acgcaaaata    5220
cttccccaga tcattaagga ggctatcaac aagagactga ggacggccgt gctcgcacca    5280
accagggtcg ttgccgctga gatggctgag gccttgagag gactccccat tcgataccaa    5340
acctcagcgg tgcacagaga gcacagtgga aatgaaatcg ttgatgtgat gtgccgcccc    5400
ctcacgcaca ggttgatgtc tccacacaga gttcccaatt acaatctgtt tgtaatggat    5460
gaggcccatt tcacggaccc agctagtatt gcagctagag atacatagc aaccaaggtt    5520 gaactgggcg aagccgccgc gatcttcatg acggcgacgc cgcccgggac ctcagacccc    5580
ttcccagagt ccaatgcccc tatttcagat atgcaaacag agatcccaga tagagcttgg    5640
aacaccggat atgaatggat aaccgaatac atcggaaaga ccgtctggtt cgttccaagt    5700
gttaagatgg gaaatgaaat tgctctctgt ctgcaacggg cggggaagaa agtgatccag    5760
ctgaacagaa agtcctatga gacagagtat cccaagtgta aaaacgatga ttgggacttt    5820
gttgtcacca cggatatatc agaaatggga gctaacttca aggccaatag agtgattgat    5880
agtcgcaaga gcgtgaaacc cactatcatt gaggaaggcg atgggagagt cattctggga    5940
```

```
gaaccctcag ctattacagc tgctagtgca gcccagagga gaggacgcat aggaagaaat    6000
ccatcacaag ttggcgatga gtattgctat ggagggcaca caaatgaaga tgactccaac    6060
tttgctcatt ggacagaggc ccgcatcatg ctagacaata tcaacatgcc aaatggttta    6120
gtggcccagc tataccagcc tgagcgagag aaagtgtaca ccatgacgg ggagtacagg     6180 ctaagagggg aagaacggaa gaacttcctt gagttcctaa aacagctga tttgccggtc     6240 tggctcgcct acaaagtggc ggcggcagga atatcatatc acgatcgaaa gtggtgcttt    6300
gatggacccc gaaccaacac gattctggaa gataacaccg aagtggaagt tatcacaaag    6360
ctaggtgaga ggaagatctt aagacccagg tgggcagatg ccagagtgta ctcggaccac    6420
caagccctaa agtctttta ggattttgca tcagggaaac gatcgcagat cgggcttatt     6480
gaggtgcttg ggaggatgcc cgaacacttt atggggaaaa cttgggaggc cctggacact    6540
atgtatgtgg tggcaaccgc tgaaaaagga ggccgagctc acaggatggc tcttgaggag    6600
cttccggacg cccttcagac aatagctttg atcacgctct tgagtgtgat gtccctgggc    6660
gtgttttttc ttcttatgca aggaaaggc ataggcaaga ttggcttggg aggagtgatc      6720
ctaggagcgg ccacattctt ttgctggatg gctgacgtcc cgggaacgaa aatagcgggc    6780
atgctcttgc tctccctgct gctcatgatt gttttgattc cagagccaga aaagcagcgc    6840
tcacagactg acaatcagct tgctgtgttt ttgatctgtg tgctcacact ggtcagcgcc    6900
gtggccgcca atgaaatggg ttggctggac aaaacaaaga atgacattag cagcctgttg    6960
gggtacaagt cagaagccag agaaacaact ctgggagttg aaagcttctt gcttgatctg    7020
cggccagcca cggcatggtc actttacgcc gtgacaacag ccgttctcac ccctctgctg    7080
aagcatctaa tcacgtcaga ctacattaac acttcgttga cttcaataaa cgtccaagcc    7140
agcgcgttgt tcactctggc tagaggcttc cctttttgtgg atgttggtgt ctcagctctc    7200
ttgttggcgg ctgggtgttg gggtcaggta acactgacag tgacagtgac cgcagcttct    7260
ctgctttttt gccactatgc ttacatggtg ccaggctggc aagcagaagc tatgcgatcc    7320
gctcagcggc gtactgctgc cggtatcatg aagaatgcag tggtggatgg gatcgtggcc    7380
actgatgtgc ctgaacttga gcgaacgacc ccagtcatgc agaagaaagt tggacagatc    7440
atgctgatct tggtgtcagt ggccgcagtg gtcgtcaatc catcagtgag gaccgttaga    7500
gaggctggaa tcttgaccac agcagcagtg gtcacactat gggaaaatgg tgccagttca    7560
gtgtggaatg caacaacagc cattggcctt tgccatatta tgcgagggg aatactatcg     7620 tgtctttcca tcacgtggac tctcatcaaa aacatggaga agcccggcct caagagggga    7680
ggagccaagg ggcgcacact aggagaagtt tggaaggaga ggctcaacca catgacaaag    7740
gaagagttca ccagatacag gaaagaagcc atcactgagg ttgaccgctc cgccgcaaaa    7800
catgctagaa aagaaggaaa cattactgga ggccacccgg tttcgcgggg aaccgcgaag    7860
ttacggtggc tagtggaaag gagattcctc gagccagtgg ggaaggttgt ggaccttggg    7920
tgtggcagag gcggttggtg ctattacatg gccacccaga gagggtgca ggaagtaaaa     7980 gggtacacga aaggggggcc tggccatgaa gagccacaac tggtgcaaag ctatggttgg    8040
aatattgtca ccatgaaaag tggagttgat gtgttttaca gaccatcaga agtgagtgac    8100
acactgctct gtgacattgg agagtcatca tcaagtgccg aggtggaaga acatcgaacc    8160
gtccgggttt tggagatggt ggaagattgg ttgcacagag gaccgaagga gttttgcatc    8220
aaggtgctct gtccttacat gcctaaagtg attgagaaga tggaaacact tcaaaggcga    8280
tatggaggtg gtctcgtgag gaaccctctc tcacgtaact ccacccatga gatgtactgg    8340
```

```
gtgagccgtg cgtcaggcaa catcgtccac tccgtcaaca tgacgagtca ggtgctctta    8400
gggaggatgg aaaagaaaac atggaaaggg ccccagtatg aggaagatgt taatctggga    8460
agtggaacgc gagccgtagg gaagcctctc cttaattctg ataccagcaa aatcaagaat    8520
cgaatcgaga ggttgaaaaa agaatacagt tccacgtggc accaagacgt gaaccatcct    8580
tacaggacct ggaactacca tggaagttac gaagtgaaac caaccggctc agctagctcc    8640
cttgtgaatg gggtagtcag actgctatca aaaccgtggg acaccattac caacgtgacc    8700
acgatggcta tgactgatac cacccctttt ggtcagcaac gagtgttcaa ggagaaggtg    8760
gacacgaaag ctccagagcc tccggaagga gtcaaacatg tcctcaatga gaccacaaat    8820
tggctgtggg ccttttggc tcgtgagaag aagcccagga tgtgttcgcg agaggaattc    8880
attgccaaag tcaacagcaa cgccgctctt ggagcaatgt ttgaagaaca gaaccaatgg    8940
aagaacgcca gagaagccgt aaatgaccca agttctggg aaatggttga tgaggaacgt    9000
gaggcgcacc ttcgcgggga atgcaatacc tgcatataca acatgatggg caagagagag    9060
aagaaacctg gagagtttgg taaagccaaa ggcagcagag ccatttggtt catgtggcta    9120
ggggctcgct ttttagagtt tgaagctctt gggtttctca acgaggatca ctggctaggc    9180
agaaagaact caggaggcgg agttgaaggc ctggggctcc agaagcttgg ttacatcttg    9240
aaagcggtcg ggacaaaacc tggaggaaag atctacgctg atgacacggc cggctgggac    9300
acacgcatca ccaaagctga cctcgaaaat gaagcgaagg tccttgaatt gctggatggg    9360
gaacatcggc gcttagcacg gtccatcatt gagctaactt atcgacacaa agtcgtgaag    9420
gtgatgagac cagcggccga cggaaagact gtgatggacg ttatctctag agaggaccag    9480
agaggaagcg gccaagtggt tacctacgct ctgaacacct tcaccaattt agcagtccaa    9540
ctggtgagga tgatggaagg ggaaggagtc ataggacctg atgacgttga aaaactggga    9600
aagggaaaag ggcccaaggt cagaacctgg ctgtttgaga atggcgagga gcgcctcagc    9660
cgcatggccg tcagtggtga tgattgcgtg gtgaagcctt ggacgaccg gtttgccacg    9720
tcactgcact tccttaacgc tatgtcaaag gtccggaaag atatccagga atggaaaccc    9780
tcgacaggat ggtatgactg gcagcaggtt ccattttgct cgaaccattt cacgaactg    9840
atcatgaagg acggcaggac gctgatcgtc ccatgtcgtg gacaggacga gctgattgga    9900
cgtgccagga tctctccagg agctggatgg aacgtgcgcg cactgcctg cttggcgaaa    9960
tcatacgctc agatgtggct gctgctctac ttccaccgcc gtgacttgag actgatggcc   10020
aatgctattt gttccgcagt gcccgttaac tgggttccca cagggcgcac cacctggtcg   10080
atccatgcaa aggggaatg gatgacaaca gaggacatgc ttgcagtctg aatagggtg   10140
tggattgagg agaatgaatg gatggaagat aaaacgccag ttgagaagtg gagtgatgtt   10200
ccatactctg ggaagagaga agacatctgg tgtggcagcc tgattggcac gcgaatccgt   10260
gccacttggg ctgaaaacat ccatgtggca atcaatcagg tccgcgcggt gattgggaa   10320
gagaaatatg tggactacat gagctctttg aggagatatg aagacaccat tatagtggaa   10380
gatactgttt tgtagataat gaagttgaga tgaatagttt gtgattgtag tttagttaat   10440
tttataataa tagtcatttg gattatgatt agacatgtag gtgtaggata tgttatagt   10500
tagtgtagtg tatataaaat taattaagaa tggaagtcag gccagattaa tgctgccacc   10560
ggaagttgag tagacggtgc tgcctgcgac tcaaccccag gaggactggg tgaccaaagc   10620
tgcgaggtga tccacgtaag ccctcagaac cgtttcggaa ggaggacccc acgtgcttta   10680
```

```
gccccaaagc ccaatgtcag accacacttt ggtgtgccac tctgcggaga gtgcagtctg    10740
cgatagtgcc ccaggtggac tgggtcaaca aaggcaaaac atcgcccac gcggccataa      10800 ccctggctat ggtgttaacc agggagaagg gactagtggt tagaggagat ccccgcgtta    10860
aaaagtgcac ggcccaatct tggctgaagc tgtaagccaa gggaaggatc tagaggttag    10920
aggagaaccc cgtgccaaaa acaccaaaag caaacagcat attgacacct gggatagact    10980
aggggatctt ctgctctgca caaccagcca cacggcacag tgcgccgata taggtggctg    11040
gtggtgcgag aacacaggat ct                                             11062
```

```
<210> SEQ ID NO 11
<211> LENGTH: 10272
<212> TYPE: DNA
<213> ORGANISM: Zika virus
<220> FEATURE:
<221> NAME/KEY: modified_base
<222> LOCATION: (2711)..(2711)
<223> OTHER INFORMATION: a, c, t, g, unknown or other
<220> FEATURE:
<221> NAME/KEY: modified_base
<222> LOCATION: (8487)..(8487)
<223> OTHER INFORMATION: a, c, t, g, unknown or other

<400> SEQUENCE: 11
```

```
atgaaaaacc caaagaagaa atccggaaga ttccggattg tcaatatgct aaaacgcgga      60
gtagcccgtg taaacccctt gggaggtttg aagaggttgc cagccggact tctgctgggt    120
catggaccca tcagaatggt tttggcgata ctagcctttt tgagatttac agcaatcaag    180
ccatcactgg gccttatcaa cagatggggt tccgtgggga aaaagaggc tatgaaaata    240 ataaagaagt tcaagaaaga tcttgctgcc atgttgagaa taatcaatgc taggaaagag    300
aggaagagac gtgcgcagag caccagcatc ggaatcattg gcctcctgct gactacagcc    360
atggcagcag agatcactag acgcgggagt gcatactaca tgtacttgga taggagcgat    420
gccgggaagg ccatttcgtt tgctaccaca ttggagtga acaagtgcca cgtacgatc    480 atggacctcg ggcacatgtg tgacgccacc atgagttatg agtgccctat gctggatgag    540
ggagtggaac cagatgatgt cgattgctgg tgcaacacga catcaacttg ggttgtgtac    600
ggaacctgtc atcacaaaaa aggtgagaca cggcgatcta aagatctgt gtcgctccgt    660 tatcactata caaggaagtt gcaaacgcgg tcgcagacat ggttagaatc aagagaatac    720
aagaagcact tgatcatggt cgaaaactgg atattcagga ccccgggtt tgccatagtg    780 tccgttgcca ttacctggct gatgggaagc ttgacgagcc aaaaagtcat atacttggtc    840
atgatagtgt tgattgtccc ggcatacagt atcagctgca ttggagtcag caatagagac    900
ttagtggagg gcatgtcagg tgggacctgg gttgatgttg tcttggaaca tggagggtgc    960
gttaccgaga tggcacagga caagccaaca gttgacatag agttggtcac gatgacggtt    1020
agtaacatgg ccgaggtaag atcctattgc tacgaggcat cgttatccga catggcttcg    1080
gccagtcgtt gcccaacaca aggcgaaccc tccctcgaca gcaatcaga cactcaatct    1140 gtatgcaaaa gaacattagg agacagaggt tggggaaatg gttgtgggat ttttggcaaa    1200
gggagcttgg tgcatgtgtc caagttcacg tgttgtaaga gatgccccgg gaagagcatt    1260
caaccggaaa atctggagta tcggataatg ctcccagtgc atggctccca gcatagcggg    1320
atgattgtga tgacatagg acatgaaact gacgaaaaca gagcgaaagt cgaggtcaca    1380
cccaattcac caagagcaga agcaaccttg ggaggttttg gaagcttggg acttgactgt    1440
gaaccaagga caggccttga cttctcagat ctgtattatc tgaccatgaa caacaagcat    1500
```

```
tggttggtgc acaaggagtg gtttcatgac atcccattac cttggcatgc tggtgcagac   1560
actggaactc cacactggaa caacaaagag gcattggtgg agttcaagga cgcccacgcc   1620
aagaggcaaa ctgttgtggt tctggggagc caagagggag ctgttcacac ggccctcgct   1680
ggagctctgg aggctgagat ggatggtgca aagggaaggc tattctctgg ccatttgaaa   1740
tgccgcctaa aaatggacaa gcttaggttg aagggtgtgt catattccct gtgtactgca   1800
gcgttcacat ttaccaaggt cccagctgaa acattgcatg gaacagttac agtggaggtg   1860
cagtctgcag ggacagatgg accctgcaag gtcccagccc agatggcggt ggacatgcag   1920
accctgaccc cagttggaag gctgataacc gccaaccccg tgattactga aagcactgag   1980
aactcaaaga tgatgttgga gcttgaccca ccatttgggg attcttacat tgtcatagga   2040
gttggggaca agaaaatcac ccaccactgg cataggagtg gtagcaccat cggaaaggca   2100
tttgaagcca ctgtgagagg cgccaagaga atggcagtcc tgggggatac agcctgggac   2160
ttcggatcag tcgggggtgt gttcaactca ctgggtaagg gcattcacca gattttttgga  2220
gcagccttca aatcactgtt tggaggaatg tcctggttct cacagatcct cataggcacg   2280
ctgctagtgt ggttaggttt gaacacaaag aatggatcta tctccctcac atgcttggcc   2340
ctgggggggag tgatgatctt cctctccacg gctgtttctg ctgacgtggg gtgctcagtg   2400
gacttctcaa aaaaggaaac gagatgtggc acggggtat tcatctataa tgatgttgaa   2460
gcctggaggg accggtacaa gtaccatcct gactcccccc gcagattggc agcagcagtc   2520
aagcaggcct gggaagaggg gatctgtggg atctcatccg tttcaagaat ggaaaacatc   2580
atgtggaaat cagtagaagg ggagctcaat gctatcctag aggagaatgg agttcaactg   2640
acagttgttg tgggatctgt aaaaaacccc atgtggagag gtccacaaag attgccagtg   2700
cctgtgaatg ngctgcccca tggctggaaa gcctggggga aatcgtattt tgttagggcg   2760
gcaaagacca acaacagttt tgttgtcgac ggtgacacac tgaaggaatg tccgcttaag   2820
cacagagcat ggaatagttt tcttgtggag gatcacgggt ttggagtctt ccacaccagt   2880
gtttggctta aggtcagaga agattactca ttagaatgtg acccagccgt cataggaaca   2940
gctgttaagg gaagggaggc cgcgcacagt gatctgggct attggattga aagtgaaaag   3000
aatgacacat ggaggctgaa gagggcccac ctgattgaga tgaaaacatg tgaatggcca   3060
aagtctcaca cattgtggac agatggagta aagaagaagtg atcttatcat acccaagtct   3120
ttagctggtc cactcagcca ccacaacacc agagagggtt acagaaccca agtgaaaggg   3180
ccatggcaca gtgaagagct tgaaatccgg tttgaggaat gtccaggcac caaggttcac   3240
gtggaggaga catgcggaac tagaggacca tctctgagat caactactgc aagtggaagg   3300
gtcattgagg aatggtgctg tagggaatgc acaatgcccc cactatcgtt tcgagcaaaa   3360
gacggctgct ggtatggaat ggagataagg cccaggaaag aaccagagag caacttagtg   3420
aggtcaatgg tgacagcggg gtcaaccgat catatggacc acttctctct tggagtgctt   3480
gtgattctac tcatggtgca ggagggggttg aagaagagaa tgaccacaaa gatcatcatg   3540
agcacatcaa tggcagtgct ggtagtcatg atcttgggag gatttttcaat gagtgacctg   3600
gccaagcttg tgatcctgat gggtgctact ttcgcagaaa tgaacactgg aggagatgta   3660
gctcacttgg cattggtagc ggcatttaaa gtcagaccag ccttgctggt ctccttcatt   3720
ctcagagcca attggacacc ccgtgagagc atgctgctag ccctggcttc gtgtcttctg   3780
caaactgcga tctctgctct tgaaggtgac ttgatggtcc tcgttaatgg atttgctttg   3840
```

```
gcctggttgg caattcgagc aatggccgtg ccacgcactg acaacatcgc tctagcaatc    3900
ttggctgctc taacaccact agctcgaggc acactgctcg tggcatggag agcgggcctg    3960
gctacttgtg gagggttcat gctcctctcc ctgaaaggga aaggtagtgt gaagaagaac    4020
ctgccatttg tcatggccct gggattgaca gctgtgaggg tagtagaccc tattaatgtg    4080
gtaggactac tgttactcac aaggagtggg aagcggagct ggcccectag tgaagttctc    4140 acagccgttg gcctgatatg tgcactggcc ggagggtttg ccaaggcaga cattgagatg    4200
gctggaccca tggctgcagt aggcttgcta attgtcagct atgtggtctc gggaaagagt    4260
gtggacatgt acattgaaag agcaggtgac atcacatggg aaaaggacgc ggaagtcact    4320
ggaaacagtc ctcggcttga cgtggcactg gatgagagtg gtgatttctc cttggtagag    4380
gaagatggtc cacccatgag agagatcata ctcaaggtgg tcctgatggc catctgtggc    4440
atgaacccaa tagctatacc ttttgctgca ggagcgtggt atgtgtatgt gaagactggg    4500
aaaaggagtg gcgccctctg ggacgtgcct gctcccaaag aagtgaagaa aggagagacc    4560
acagatggag tgtacagagt gatgactcgc agactgctag gttcaacaca ggttggagtg    4620
ggagtcatgc aagagggagt cttccacacc atgtggcacg ttacaaaagg agccgcactg    4680
aggagccgtg agggaagact tgatccatac tgggggggatg tcaagcagga cttggtgtca    4740
tactgtgggc cttggaagtt ggatgcagct tgggatggac ttagcgaggt acagcttttg    4800
gccgtacctc ccgagagag ggccagaaac attcagaccc tgcctggaat attcaagaca    4860
aaggacgggg acatcggagc agttgctctg gactaccctg cagggacctc aggatctccg    4920
atcctagaca aatgtggaag agtgataggag ctctatggca atggggttgt gatcaagaat    4980
ggaagctatg ttagtgctat aacccaggga aagagggagg aggagactcc ggttgaatgt    5040
ttcgaaccct cgatgctgaa gaagaagcag ctaactgtcc tggatctgca tccaggagcc    5100
ggaaaaacca ggagagttct tcctgaaata gtccgtgaag ccataaaaaa gagactccgg    5160
acagtgatct tggcaccaac tccagttgag agatcatact caaggtggtc cttgtgccca    5220
tctgtggcac gtacccagac aacagcagtc aacgtcaccc attctgggac agaaatcgtt    5280
gatttgatgt gccatgccac tttcacttca cgcttactac aacccatcag agtccctaat    5340
tacaatctca acatcatgga tgaagcccac ttcacagacc cctcaagtat agctgcaaga    5400
ggatacatat caacaagggt tgaaatgggc gaggcggctg ccattttat gactgccaca    5460 ccaccaggaa cccgtgatgc gtttcctgac tctaactcac caatcatgga cacagaagtg    5520
gaagtcccag agagagcctg gagctcaggc tttgattggg tgacagacca ttctgggaaa    5580
acagtttggt tcgttccaag cgtgagatct ggagaagaaa gcgcagcctg tctgacaaag    5640
gctggaaagc gggtcataca gctcagcagg aagacttttg agacagaatt tcagaaaaca    5700
aaaaatcaag agtgggactt tgtcataaca actgacatct cagagatggg cgccaacttc    5760
aaggctgacc gggtcataga ctctaggaga tgcctaaagc cagtcatact tgatggtgag    5820
agagtcatct tggctgggcc catgcctgtc acgcatgcta gtgctgctca gaggagagga    5880
cgtataggca ggaaccctaa caaacctgga gatgagtaca tgtatggagg tgggtgtgca    5940
gagactgatg aagaccatgc acactggctt gaagcaagaa tgcttcttga caacatctac    6000
ctccaggatg gcctcatagc ctcgctctat cggcctgagg ccgataaggt agccgccatt    6060
gagggagagt ttaagctgag gacagagcaa aggaagacct tcgtggaact catgaagaga    6120
ggagaccttc ccgtctggct agcctatcag gttgcatctg ccggaataac ttacacagac    6180
agaagatggt gctttgatgg cacaaccaac aacaccataa tggaagacag cgtaccagca    6240
```

```
gaggtgtgga caaagtatgg agagaagaga gtgctcaaac cgagatggat ggatgctagg    6300
gtctgttcag accatgcggc cctgaagtcg ttcaaagaat tcgccgctgg aaaaagagga    6360
gcggctttgg gagtaatgga ggccctggga acactgccag gacacatgac agagaggttt    6420
caggaagcca ttgacaacct cgccgtgctc atgcgagcag agactggaag caggccttat    6480
aaggcagcgg cagcccaact gccggagacc ctagagacca ttatgctctt aggtttgctg    6540
ggaacagttt cactggggat cttcttcgtc ttgatgcgga ataagggcat cgggaagatg    6600
ggctttggaa tggtaaccct tggggccagt gcatggctca tgtggctttc ggaaattgaa    6660
ccagccagaa ttgcatgtgt cctcattgtt gtgtttttat tactggtggt gctcataccc    6720
gagccagaga agcaaagatc tccccaagat aaccagatgg caattatcat catggtggca    6780
gtgggccttc taggtttgat aactgcaaac gaacttggat ggctggaaag aacaaaaaat    6840
gacatagctc atctaatggg aaggagagaa gaaggagcaa ccatgggatt ctcaatggac    6900
attgatctgc ggccagcctc cgcctgggct atctatgccg cattgacaac tctcatcacc    6960
ccagctgtcc aacatgcggt aaccacttca tacaacaact actccttaat ggcgatggcc    7020
acacaagctg gagtgctgtt tggcatgggc aaagggatgc catttatgca tgggaccttt    7080
ggagtcccgc tgctaatgat gggttgctat tcacaattaa cacccctgac tctgatagta    7140
gctatcattc tgcttgtggc gcactacatg tacttgatcc caggcctaca agcggcagca    7200
gcgcgtgctg cccagaaaag gacagcagct ggcatcatga agaatcccgt tgtggatgga    7260
atagtggtaa ctgacattga cacaatgaca atagaccccc aggtggagaa gaagatggga    7320
caagtgttac tcatagcagt agccatctcc agtgctgtgc tgctgcggac cgcctgggga    7380
tgggggagg ctggagctct gatcacagca gcgacctcca ccttgtggga aggtctctcca    7440
aacaaatact ggaactcctc tacagccacc tcactgtgca acatcttcag aggaagctat    7500
ctggcaggag cttcccttat ctatacagtg acgagaaacg ctggcctggt taagagacgt    7560
ggaggtggga cgggagagac tctgggagag aagtggaaag ctcgtctgaa tcagatgtcg    7620
gccctggagt tctactctta taaaaagtca ggtatcactg aagtgtgtag agaggaggct    7680
cgccgtgccc tcaaggatgg agtggccaca ggaggacatg ccgtatcccg gggaagtgca    7740
aagctcagat ggttggtgga gagaggatat ctgcagcccc atgggaaggt tgttgacctc    7800
ggatgtggca gaggggctg gagctattat gccgccacca ccgcaaagt gcaggaggtg    7860
agaggataca caaagggagg tcccggtcat gaagaaccca tgctggtgca aagctatggg    7920
tggaacatag ttcgtctcaa gagtggagtg gacgtcttcc acatggcggc tgagccgtgt    7980
gacactctgc tgtgtgacat aggtgagtca tcatctagtc ctgaagtgga agagacacga    8040
acactcagag tgctctctat ggtgggggac tggcttgaaa aaagaccagg ggccttctgt    8100
ataaaggtgc tgtgcccata caccagcact atgatggaaa ccatggagcg actgcaacgt    8160
aggcatgggg gaggattagt cagagtgcca ttgtctcgca actccacaca tgagatgtac    8220
tgggtctctg ggcaaaaag caacatcata aaaagtgtgt ccaccacaag tcagctcctc    8280
ctggacgca tggatggccc caggaggcca gtgaaatatg aggaggatgt gaacctcggc    8340
tcgggtacac gagctgtggc aagctgtgct gaggctccta acatgaaaat catcggcagg    8400
cgcattgaga gaatccgcaa tgaacatgca gaaacatggt tcttgatga aaccacccca    8460
tacaggacat gggcctacca tggagntac gaagcccca cgcaaggatc agcgtcttcc    8520
ctcgtgaacg gggttgttag actcctgtca aagccttggg acgtggtgac tggagttaca    8580
```

| | |
|---|---:|
| ggaatagcca tgactgacac cacaccatac ggccaacaaa gagtcttcaa agaaaaagtg | 8640 |
| gacaccaggg tgccagatcc ccaagaaggc actcgccagg taatgaacat ggtctcttcc | 8700 |
| tggctgtgga aggagctggg gaaacgcaag cggccacgcg tctgcaccaa agaagagttt | 8760 |
| atcaacaagg tgcgcagcaa tgcagcactg ggagcaatat ttgaagagga aaagaatggg | 8820 |
| aagacggctg tggaagctgt gaatgatcca aggttttggg ccctagtgga tagggagaga | 8880 |
| gaacaccacc tgagaggaga gtgtcacagc tgtgtgtaca acatgatggg aaaaagagaa | 8940 |
| aagaagcaag gagagttcgg gaaagcaaaa gtagccgcg ccatctggta catgtggttg | 9000 |
| ggagccaggt ttctggagtt tgaatcactg gggtttctga tgaagatca ctggatggga | 9060 |
| agagagaact ctggaggcgg agttgaagga ctgggactgc agagactggg ctatgtcctt | 9120 |
| gaggagatga gccaggcacc aggagggaag atgtacgcag atgacactgc tggctgggac | 9180 |
| acccgcatta gtaagtttga tctggagaat gaagctttga ttaccaacca aatggaggaa | 9240 |
| gggcacagaa ctctggcgtt ggccgtgatt aaatacacat accaaaacaa agtggtgaag | 9300 |
| gtcctcagac cagctgaagg aggaaaaaca gttatggaca tcatttcaag acaagaccag | 9360 |
| agagggagtg gacaagttgt cacttatgct ctcaacacat tcaccaactt ggtggtgcag | 9420 |
| cttatccgga acatggaagc tgaggaagtg ttagagatgc aagacttatg ctgttgagg | 9480 |
| aagccagaga aagtgaccag atggttgcag agcaatggat gggatagact caaacgaatg | 9540 |
| gcggtcagtg gagatgactg cgttgtgaag ccaatcgatg ataggttttgc acatgccctc | 9600 |
| aggttcttga tgacatggg aaaagttagg aaagacacac aggagtggaa accctcgact | 9660 |
| ggatggagca attgggaaga gtcccgttc tgctcccacc acttcaacaa gctgtacctc | 9720 |
| aaggatggga gatccattgt ggtcccttgc cgccaccaag atgaactgat ggccgagct | 9780 |
| cgcgtttcac caggggcagg atggagcatc cgggagactg cctgtcttgc aaaatcatat | 9840 |
| gcgcagatgt ggcagctcct ttatttccac agaagagacc ttcgactgat ggctaatgcc | 9900 |
| atttgctcgg ctgtaccagt tgactgggta ccaactggga gaccacctg gtcaatccat | 9960 |
| ggaaagggag aatggatgac cactgaggac atgctcatgg tgtggaatag agtgtggatt | 10020 |
| gaggagaacg accatatgga ggacaagact cctgtaacaa aatggacaga cattccctat | 10080 |
| ctaggaaaaa gggaggactt atggtgtgga tcccttatag ggcacagacc ccgcaccact | 10140 |
| tgggctgaaa acatcaaaga cacagtcaac atggtgcgca ggatcatagg tgatgaagaa | 10200 |
| aagtacatgg actatctatc cacccaagtc cgctacttgg gtgaggaagg gtccacaccc | 10260 |
| ggagtgttgt aa | 10272 |

<210> SEQ ID NO 12
<211> LENGTH: 9981
<212> TYPE: DNA
<213> ORGANISM: Zika virus

<400> SEQUENCE: 12

| | |
|---|---:|
| atgaaaaacc caagaagaa atccggagga ttccggattg tcaatatgct aaaacgcgga | 60 |
| gtagcccgtg taaaccccctt gggaggtttg aagaggttgc agccggact tctgctgggt | 120 |
| catggaccca tcagaatggt tttggcgata ctagcctttt tgagatttac agcaatcaag | 180 |
| ccatcactgg gccttatcaa cagatggggt tccgtgggga aaaagaggc tatggaaata | 240 |
| ataaagaagt tcaagaaaga tcttgctgcc atgttgagaa taatcaatgc taggaaagag | 300 |
| aggaagagac gtggcgcaga caccagcatc ggaatcattg cctcctgct gactacagcc | 360 |
| atggcagcag agatcactag acgcgggagt gcatactaca tgtacttgga taggagcgat | 420 |

```
gccgggaagg ccatttcgtt tgctaccaca ttgggagtga acaagtgcca cgtacagatc    480
atggacctcg ggcacatgtg tgacgccacc atgagttatg agtgccctat gctggatgag    540
ggagtggaac cagatgatgt cgattgctgg tgcaacacga catcaacttg ggttgtgtac    600
ggaacctgtc atcacaaaaa aggtgaggca cggcgatcta aagagccgt gacgctccct    660
tctcactcta caaggaagtt gcaaacgcgg tcgcagacct ggttagaatc aagagaatac    720
acgaagcact tgatcaaggt tgaaaactgg atattcagga accccgggtt tgcgctagtg    780
gccgttgcca ttgcctggct tttgggaagc tcgacgagcc aaaaagtcat atacttggtc    840
atgatactgc tgattgcccc ggcatacagt atcaggtgca ttggagtcag caatagagac    900
ttcgtggagg gcatgtcagg tgggacctgg gttgatgttg tcttggaaca tggaggctgc    960
gttaccgtga tggcacagga caagccaaca gttgacatag agttggtcac gacgacggtt   1020
agtaacatgg ccgaggtaag atcctattgc tacgaggcat cgatatcgga catggcttcg   1080
gacagtcgtt gcccaacaca aggtgaagcc taccttgaca agcaatcaga cactcaatat   1140
gtctgcaaaa gaacattagt ggacagaggt tggggaaatg gttgtggact ttttggcaaa   1200
gggagcttgg tgacatgtgc caagttcacg tgttctaaga agatgaccgg gaagagcatt   1260
caaccggaaa atctggagta tcggataatg ctatcagtgc atggctccca gcatagcggg   1320
atgattgtca atgatatagg acatgaaact gacgaaaaca gagcgaaagt cgaggttacg   1380
cctaattcac caagagcgga agcaaccttg ggaggctttg gaagcttagg acttgactgt   1440
gaaccaagga caggccttga cttttcagat ctgtattacc tgaccatgaa caataagcat   1500
tggttggtgc acaaagagtg gtttcatgac atcccattgc cttggcatgc tggggcagac   1560
accggaactc cacactggaa caacaaagag gcattggtag aattcaagga tgcccacgcc   1620
aagaggcaaa ccgtcgtcgt tctggggagc caggaaggag ccgttcacac ggctctcgct   1680
ggagctctag aggctgagat ggatggtgca aagggaaggc tgttctctgg ccatttgaaa   1740
tgccgcctaa aaatggacaa gcttagattg aagggcgtgt catattcctt gtgcactgcg   1800
gcattcacat tcaccaaggt cccagctgaa acactgcatg gaacagtcac agtggaggtg   1860
cagtatgcag ggacagatgg accctgcaag gtcccagccc agatggcggt ggacatgcag   1920
accctgaccc cagttggaag gctgataacc gccaaccccg tgattactga aagcactgag   1980
aactcaaaga tgatgttgga gcttgaccca ccatttgggg attcttacat tgtcatagga   2040
gttggggaca gaaaatcac ccaccactgg cataggagtg gtagcaccat cggaaaggca   2100
tttgaagcca ctgtgagagg cgccaagaga atggcagtcc tggggatac agcctgggac   2160
ttcggatcag tcggggtgt gttcaactca ctgggtaagg gcattcacca gattttgga   2220
gcagccttca atcactgtt tggaggaatg tcctggttct cacagatcct cataggcacg   2280
ctgctagtgt ggttaggttt gaacacaaag aatggatcta tctccctcac atgcttggcc   2340
ctgggggag tgatgatctt cctctccacg gctgtttctg ctgacgtggg gtgctcagtg   2400
gacttctcaa aaagagaaac gagatgtggc acggggtat tcatctataa tgatgttgaa   2460
gcctggaggg accggtacaa gtaccatcct gactcccccc gcagattggc agcagcagtc   2520
aagcaggcct gggaagaggg gatctgtggg atctcatccg tttcaagaat ggaaaacatc   2580
atgtggaaat cagtagaagg ggagctcaat gctatcctag aggagaatgg agttcaactg   2640
acagttgttg tgggatctgt aaaaaacccc atgtgggaga gtccacaaag attgccagtg   2700
cctgtgaatg ggctgcccca tggctggaaa gcctggggga atcgtatttt tgttagggcg   2760
```

```
gcaaagacca acaacagttt tgttgtcgac ggtgacacac tgaaggaatg tccgcttaag    2820
cacagagcat ggaatagttt tcttgtggag gatcacgggt ttggagtctt ccacaccagt    2880
gtttggctta aggtcagaga agattactca ttagaatgtg acccagccgt cataggaaca    2940
gctgttaagg gaagggaggc cgcgcacagt gatctgggct attggattga aagtgaaaag    3000
aatgacacat ggaggctgaa gagggcccac ctgattgaga tgaaaacatg tgaatggcca    3060
aagtctcaca cattgtggac agatggagta aagaaaagtg atcttatcat acccaagtct    3120
ttagctggtc cactcagcca ccacaacacc agagagggtt acagaaccca agtgaaaggg    3180
ccatggcaca gtgaagagct tgaaatccgg tttgaggaat gtccaggcac caaggttcac    3240
gtggaggaga catgcggaac tagaggacca tctctgagat caactactgc aagtggaagg    3300
gtcattgagg aatggtgctg tagggaatgc acaatgcccc cactatcgtt tcgagcaaaa    3360
gacggctgct ggtatggaat ggagataagg cccaggaaag aaccagagag caacttagtg    3420
aggtcaatgg tgacagcggg gtcaaccgat catatggacc acttctctct tggagtgctt    3480
gtgattctac tcatggtgca ggaggggttg aagaagagaa tgaccacaaa gatcatcatg    3540
agcacatcaa tggcagtgct ggtagtcatg atcttgggag gattttcaat gagtgacctg    3600
gccaagcttg tgatcctgat gggtgctact ttcgcagaaa tgaacactgg aggagatgta    3660
gctcacttgg cattggtagc ggcatttaaa gtcagaccag ccttgctggt ctccttcatt    3720
ctcagagcca attggacacc ccgtgagagc atgctgctag ccctggcttc gtgtcttctg    3780
caaactgcga tctctgctct tgaaggtgac ttgatggtcc tcgttaatgg atttgctttg    3840
gcctggttgg caattcgagc aatggccgtg ccacgcactg acaacatcgc tctagcaatc    3900
ttggctgctc taacaccact agctcgaggc acactgctcg tggcatggag agcgggcctg    3960
gctacttgtg gagggttcat gctcctctcc ctgaaaggga aggtagtgt gaagaagaac    4020 ctgccatttg tcatggccct gggattgaca gctgtgaggg tagtagaccc tattaatgtg    4080
gtaggactac tgttactcac aaggagtggg aagcggagct ggcccctag tgaagttctc    4140 acagccgttg gcctgatatg tgcactggcc ggagggtttg ccaaggcaga cattgagatg    4200
gctggaccca tggctgcagt aggcttgcta attgtcagct atgtggtctc gggaaagagt    4260
gtggacatgt acattgaaag agcaggtgac atcacatggg aaaaggacgc ggaagtcact    4320
ggaaacagtc ctcggcttga cgtggcactg gatgagagtg gtgatttctc cttggtagag    4380
gaagatggtc cacccatgag agagatcata ctcaaggtgg tcctgatggc catctgtggc    4440
atgaacccaa tagctatacc tttttgctgca ggagcgtggt atgtgtatgt gaagactggg    4500
aaaaggagtg gcgccctctg ggacgtgcct gctcccaaag aagtgaagaa aggagagacc    4560
acagatggag tgtacagagt gatgactcgc agactgctag gttcaacaca ggttggagtg    4620
ggagtcatgc aagagggagt cttccacacc atgtggcacg ttacaaaagg agccgcactg    4680
aggagcggtg agggaagact tgatccatac tgggggatg tcaagcagga cttggtgtca    4740
tactgtgggc cttggaagtt ggatgcagct tgggatggac ttagcgaggt acagcttttg    4800
gccgtacctc ccggagagag ggccagaaac attcagaccc tgcctggaat attcaagaca    4860
aaggacgggg acatcggagc agttgctctg gactaccctg cagggacctc aggatctccg    4920
atcctagaca atgtggaag agtgatagga ctctatggca atgggttgt gatcaagaat    4980 ggaagctatg ttagtgctat aacccaggga aagagggagg aggagactcc ggttgaatgt    5040
ttcgaaccct cgatgctgaa gaagaagcag ctaactgtcc tggatctgca tccaggagcc    5100
ggaaaaacca ggagagttct tcctgaaata gtccgtgaag ccataaaaaa gagactccgg    5160
```

```
acagtgatct tggcaccaac tagggttgtc gctgctgaga tggaggaagc cttgagagga    5220
cttccggtgc gttacatgac aacagcagtc aacgtcaccc attctgggac agaaatcgtt    5280
gatttgatgt gccatgccac tttcacttca cgcttactac aacccatcag agtccctaat    5340
tacaatctca acatcatgga tgaagcccac ttcacagacc cctcaagtat agctgcaaga    5400
ggatacatat caacaagggt tgaaatgggc gaggcggctg ccattttat gactgccaca    5460 ccaccaggaa cccgtgatgc gtttcctgac tctaactcac caatcatgga cacagaagtg    5520
gaagtcccag agagagcctg gagctcaggc tttgattggg tgacagacca ttctgggaaa    5580
acagtttggt tcgttccaag cgtgagaaac ggaaatgaaa tcgcagcctg tctgacaaag    5640
gctggaaagc gggtcataca gctcagcagg aagacttttg agacagaatt cagaaaaca    5700 aaaaatcaag agtgggactt tgtcataaca actgacatct cagagatggg cgccaacttc    5760
aaggctgacc gggtcatgga ctctaggaga tgcctaaaac cagtcatact tgatggtgag    5820
agagtcatct tggctgggcc catgcctgtc acgcatgcta gtgctgctca gaggagagga    5880
cgtataggca ggaaccctaa caaacctgga gatgagtaca tgtatggagg tgggtgtgca    5940
gagactgatg aaggccatgc acactggctt gaagcaagaa tgcttcttga caacatctac    6000
ctccaggatg gcctcatagc ctcgctctat cggcctgagg ccgataaggt agccgccatt    6060
gagggagagt ttaagctgag gacagagcaa aggaagacct tcgtggaact catgaagaga    6120
ggagaccttc ccgtctggct agcctatcag gttgcatctg ccggaataac ttacacagac    6180
agaagatggt gctttgatgg cacaaccaac aacaccataa tggaagacag tgtaccagca    6240
gaggtttgga caaagtatgg agagaagaga gtgctcaaac cgagatggat ggatgctagg    6300
gtctgttcag accatgcggc cctgaagtcg ttcaaagaat cgccgctgg aaaaagagga    6360 gcggctttgg gagtaatgga ggccctggga acactgccag gacacatgac agagaggttt    6420
caggaagcca ttgacaacct cgccgtgctc atgcgagcag agactggaag caggccttat    6480
aaggcagcgg cagcccaact gccggagacc ctagagacca ttatgctctt aggtttgctg    6540
ggaacagttt cactggggat cttctttgtc ttgatgcgga ataagggcat cgggaagatg    6600
ggctttggaa tggtaaccct tggggccagt gcatggctca tgtggcttc ggaaattgaa    6660 ccagccagaa ttgcatgtgt cctcattgtt gtgtttttat tactggtggt gctcataccc    6720
gagccagaga agcaaagatc tccccaagat aaccagatgg caattatcat catggtggca    6780
gtgggccttc taggtttgat aactgcaaac gaacttggat ggctggaaag aacaaaaaat    6840
gacatagctc atcaatgggc aaggagagaa gaaggagcaa ccatgggatt ctcaatggac    6900
attgatctgc ggccagcctc cgcctgggct atctatgccg cattgacaac tctcatcacc    6960
ccagctgtcc aacatgcggt aaccacttca tacaacaact actccttaat ggcgatggcc    7020
acacaagctg gagtgctgtt tggcatgggc aaagggatgc cattttatgc atgggacttt    7080
ggagtcccgc tgctaatgat gggttgctat tcacaattaa cacccctgac tctgatagta    7140
gctatcattc tgcttgtggc gcactacatg tacttgatcc caggcctaca agcggcagca    7200
gcgcgtgctg cccagaaaag gacagcagct ggcatcatga agaatcccgt tgtggatgga    7260
atagtggtaa ctgacattga cacaatgaca atagacccc aggtgagaa gaagatggga    7320 caagtgttac tcatagcagt agccatctcc agtgctgtgc tgctgcggac cgcctgggga    7380 tgggggagg ctggagctct gatcacagca gcgacctcca ccttgtggga aggctctcca    7440
aacaaatact ggaactcctc tacagccacc tcactgtgca acatcttcag aggaagctat    7500
```

```
ctggcaggag cttcccttat ctatacagtg acgagaaacg ctggcctggt taagagacgt   7560
ggaggtggga cgggagagac tctgggagag aagtggaaag ctcgtctgaa tcagatgtcg   7620
gccctggagt tctactctta taaaaagtca ggtatcactg aagtgtgtag agaggaggct   7680
cgccgtgccc tcaaggatgg agtggccaca ggaggacatg ccgtatcccg gggaagtgca   7740
aagctcagat ggttggtgga gagaggatat ctgcagcccc atgggaaggt tgttgacctc   7800
ggatgtggca gaggggctg gagctattat gccgccacca tccgcaaagt gcaggaggtg   7860
agaggataca caaagggagg tcccggtcat gaagaaccca tgctggtgca aagctatggg   7920
tggaacatag ttcgtctcaa gagtggagtg acgtcttcc acatggcggc tgagccgtgt   7980
gacactctgc tgtgtgacat aggtgagtca tcatctagtc ctgaagtgga agagacacga   8040
acactcagag tgctctctat ggtggggac tggcttgaaa aaagaccagg ggccttctgt   8100
ataaaggtgc tgtgcccata caccagcact atgatggaaa ccatggagcg actgcaacgt   8160
aggcatgggg gaggattagt cagagtgcca ttgtctcgca actccacaca tgagatgtac   8220
tgggtctctg ggcaaaaag caacatcata aaaagtgtgt ccaccacaag tcagctcctc   8280
ctgggacgca tggatggccc caggaggcca gtgaaatatg aggaggatgt gaacctcggc   8340
tcgggtacac gagctgtggc aagctgtgct gaggctccta acatgaaaat catcggcagg   8400
cgcattgaga gaatccgcaa tgaacatgca gaaacatggt tcttgatga aaaccaccca   8460 tacaggacat gggcctacca tgggagctac gaagcccca cgcaaggatc agcgtcttcc   8520
ctcgtgaacg gggttgttag actcctgtca aagccttggg acgtggtgac tggagttaca   8580
ggaatagcca tgactgacac cacaccatac ggccaacaaa gagtcttcaa agaaaaagtg   8640
gacaccaggg tgccagatcc ccaagaaggc actcgccagg taatgaacat ggtctcttcc   8700
tggctgtgga aggagctggg gaaacgcaag cggccacgcg tctgcaccaa agaagagttt   8760
atcaacaagg tgcgcagcaa tgcagcactg ggagcaatat ttgaagagga aaaagaatgg   8820
aagacggctg tggaagctgt gaatgatcca aggttttggg ccctagtgga tagggagaga   8880
gaacaccacc tgagaggaga gtgtcacagc tgtgtgtaca acatgatggg aaaaagagaa   8940
aagaagcaag gagagttcgg gaaagcaaaa ggtagccgcg ccatctggta catgtggttg   9000
ggagccagat tcttggagtt tgaagccctt ggattcttga acgaggacca ttggatggga   9060
agagagaact ctgaggcgg agttgaagga ctgggactgc agagactggg ctatgtcctt   9120
gaggagatga gccaggcacc aggagggaag atgtacgcag atgacactgc tggctgggac   9180
acccgcatta gtaagtttga tctggagaat gaagctttga ttaccaacca aatggaggaa   9240
gggcacagaa ctctggcgtt ggccgtgatt aaatacacat accaaaacaa agtggtgaag   9300
gtcctcagac cagctgaagg aggaaaaaca gttatggaca tcatttcaag acaagaccag   9360
agagggagtg gacaagttgt cacttatgct ctcaacacat tcaccaactt ggtggtgcag   9420
cttatccgga acatggaagc tgaggaagtg ttagagatgc aagacttatg gctgttgagg   9480
aagccagaga aagtgaccag atggttgcag agcaatggat gggatggact caaacgaatg   9540
gcggtcagtg gagatgactg cgttgtgaag ccaatcgatg ataggtttgc acatgccctc   9600
aggttcttga atgacatggg aaaagttagg aaagacacac aggagtggaa accctcgact   9660
ggatggagca attgggaaga agtcccgttc tgctcccacc acttcaacaa gctgtacctc   9720
aaggatggga gatccattgt ggtcccttgc cgccaccaag atgaactgat tggccgagct   9780
cgcgtttcac caggggcagg atggagcatc cgggagactg cctgtcttgc aaaatcatat   9840
gcgcagatgt ggcagctcct ttatttccac agaagagacc ttcgactgat ggctaatgcc   9900
```

```
atttgctcgg ctgtaccagt tgactgggta ccaactggga gaaccacctg gtcaatccat    9960
ggaaagggag aatggatgac c                                              9981
```

<210> SEQ ID NO 13
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Phe Ala Cys Ser Lys Lys Met Thr Gly Lys Ser Ile Gln Pro Glu Asn
1               5                   10                  15

Leu Glu Tyr Arg Ile Met Leu Ser Val His Gly Ser Gln His Ser Gly
            20                  25                  30

Met Ile Val Asn Ile Thr Gly His Glu Thr Leu Glu Asn Arg Ala Lys
        35                  40                  45

Val Glu Ile Thr Pro Asn Ser Pro Arg Ala Glu Ala Thr Leu Gly Gly
    50                  55                  60

Phe Gly Ser Leu Gly Leu Asp Cys Glu Pro Arg Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Leu Ala His Ala Lys Arg Gln Thr Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Ser Ser Gly His Leu Lys Cys Arg Leu Lys
                165                 170                 175

Met Asp Lys Leu Arg Leu Lys Gly Val Ser Tyr Ser Leu Cys Thr Ala
            180                 185                 190

Ala Phe Thr Phe Thr Lys Ile Pro Ala Glu Thr Leu His Gly Thr Val
        195                 200                 205

Thr Val Glu Val Gln Tyr Ala Gly Thr Leu Gly Pro Cys Lys Val Pro
    210                 215                 220

Ala Gln Met Ala Val Asp Met Gln Thr Leu Thr Pro Val Gly Arg Leu
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Ile Ser Tyr Ile Val Ile Gly
            260                 265                 270

Val Gly Glu Lys Lys Ile Thr His His Trp
        275                 280
```

<210> SEQ ID NO 14
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Phe Thr Cys Cys Lys Lys Met Pro Gly Lys Ser Ile Gln Pro Glu Asn
1               5                   10                  15

Leu Glu Tyr Arg Asp Met Leu Pro Val His Gly Ser Gln His Ser Gly
            20                  25                  30

Met Ile Val Asn Asp Ile Gly His Glu Thr Asp Glu Asn Arg Ala Lys
        35                  40                  45

Val Glu Val Thr Pro Asn Ser Pro Arg Ala Glu Ala Thr Leu Gly Gly
    50                  55                  60

Phe Gly Ser Leu Gly Leu Asp Cys Glu Pro Arg Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Asp Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Phe Ser Gly His Leu Lys Cys Arg Asp Lys
                165                 170                 175

Met Asp Lys Leu Arg Leu Lys Gly Val Ser Tyr Ser Leu Cys Thr Ala
            180                 185                 190

Ala Phe Thr Phe Thr Lys Val Pro Ala Glu Thr Leu His Gly Thr Val
        195                 200                 205

Thr Val Glu Val Gln Ser Ala Gly Thr Asp Gly Pro Cys Lys Val Pro
    210                 215                 220

Ala Gln Met Ala Val Asp Met Gln Thr Leu Thr Pro Val Gly Arg Asp
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Asp Ser Tyr Ile Val Ile Gly
            260                 265                 270

Val Gly Asp Lys Lys Ile Thr His His Trp
        275                 280

<210> SEQ ID NO 15
<211> LENGTH: 282
<212> TYPE: PRT
<213> ORGANISM: Zika virus

<400> SEQUENCE: 15

Phe Thr Cys Ser Lys Lys Met Thr Gly Lys Ser Ile Gln Pro Glu Asn
1               5                   10                  15

Leu Glu Tyr Arg Ile Met Leu Ser Val His Gly Ser Gln His Ser Gly
            20                  25                  30

Met Ile Val Asn Asp Ile Gly His Glu Thr Asp Glu Asn Arg Ala Lys
        35                  40                  45

Val Glu Val Thr Pro Asn Ser Pro Arg Ala Glu Ala Thr Leu Gly Gly
    50                  55                  60

Phe Gly Ser Leu Gly Leu Asp Cys Glu Pro Arg Thr Gly Leu Asp Phe
65                  70                  75                  80

Ser Asp Leu Tyr Tyr Leu Thr Met Asn Asn Lys His Trp Leu Val His
              85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
            115                 120                 125

Asp Ala His Ala Lys Arg Gln Thr Val Val Val Leu Gly Ser Gln Glu
130                 135                 140

Gly Ala Val His Thr Ala Leu Ala Gly Ala Leu Glu Ala Glu Met Asp
145                 150                 155                 160

Gly Ala Lys Gly Arg Leu Phe Ser Gly His Leu Lys Cys Arg Leu Lys
                165                 170                 175

Met Asp Lys Leu Arg Leu Lys Gly Val Ser Tyr Ser Leu Cys Thr Ala
            180                 185                 190

Ala Phe Thr Phe Thr Lys Val Pro Ala Glu Thr Leu His Gly Thr Val
            195                 200                 205

Thr Val Glu Val Gln Tyr Ala Gly Thr Asp Gly Pro Cys Lys Val Pro
210                 215                 220

Ala Gln Met Ala Val Asp Met Gln Thr Leu Thr Pro Val Gly Arg Leu
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Asp Ser Tyr Ile Val Ile Gly
            260                 265                 270

Val Gly Asp Lys Lys Ile Thr His His Trp
            275                 280

<210> SEQ ID NO 16
<211> LENGTH: 282
<212> TYPE: PRT
<213> ORGANISM: Zika virus

<400> SEQUENCE: 16

Phe Thr Cys Cys Lys Lys Met Pro Gly Lys Ser Ile Gln Pro Glu Asn
1               5                   10                  15

Leu Glu Tyr Arg Ile Met Leu Pro Val His Gly Ser Gln His Ser Gly
            20                  25                  30

Met Ile Val Asn Asp Ile Gly His Glu Thr Asp Glu Asn Arg Ala Lys
        35                  40                  45

Val Glu Val Thr Pro Asn Ser Pro Arg Ala Glu Ala Thr Leu Gly Gly
50                  55                  60

Phe Gly Ser Leu Gly Leu Asp Cys Glu Pro Arg Thr Gly Leu Asp Phe
65                  70                  75                  80

Ser Asp Leu Tyr Tyr Leu Thr Met Asn Asn Lys His Trp Leu Val His
              85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
            115                 120                 125

Asp Ala His Ala Lys Arg Gln Thr Val Val Val Leu Gly Ser Gln Glu
130                 135                 140

Gly Ala Val His Thr Ala Leu Ala Gly Ala Leu Glu Ala Glu Met Asp
145                 150                 155                 160

Gly Ala Lys Gly Arg Leu Phe Ser Gly His Leu Lys Cys Arg Leu Lys
                165                 170                 175

```
Met Asp Lys Leu Arg Leu Lys Gly Val Ser Tyr Ser Leu Cys Thr Ala
            180                 185                 190

Ala Phe Thr Phe Thr Lys Val Pro Ala Glu Thr Leu His Gly Thr Val
        195                 200                 205

Thr Val Glu Val Gln Ser Ala Gly Thr Asp Gly Pro Cys Lys Val Pro
    210                 215                 220

Ala Gln Met Ala Val Asp Met Gln Thr Leu Thr Pro Val Gly Arg Leu
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Asp Ser Tyr Ile Val Ile Gly
            260                 265                 270

Val Gly Asp Lys Lys Ile Thr His His Trp
            275                 280

<210> SEQ ID NO 17
<211> LENGTH: 282
<212> TYPE: PRT
<213> ORGANISM: Zika virus

<400> SEQUENCE: 17

Phe Thr Cys Ser Lys Lys Met Thr Gly Lys Ser Ile Gln Pro Glu Asn
1               5                   10                  15

Leu Glu Tyr Arg Ile Met Leu Ser Val His Gly Ser Gln His Ser Gly
            20                  25                  30

Met Ile Val Asn Asp Ile Gly His Glu Thr Asp Glu Asn Arg Ala Lys
        35                  40                  45

Val Glu Val Thr Pro Asn Ser Pro Arg Ala Glu Ala Thr Leu Gly Gly
    50                  55                  60

Phe Gly Ser Leu Gly Leu Asp Cys Glu Pro Arg Thr Gly Leu Asp Phe
65                  70                  75                  80

Ser Asp Leu Tyr Tyr Leu Thr Met Asn Asn Lys His Arg Leu Val Arg
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Asp Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Phe Ser Gly His Leu Lys Cys Arg Leu Lys
                165                 170                 175

Met Asp Lys Leu Arg Leu Lys Gly Val Ser Tyr Ser Leu Cys Thr Ala
            180                 185                 190

Ala Phe Thr Phe Thr Lys Val Pro Ala Glu Thr Leu His Gly Thr Val
        195                 200                 205

Thr Val Glu Val Gln Tyr Ala Gly Thr Asp Gly Pro Cys Lys Val Pro
    210                 215                 220

Ala Gln Met Ala Val Asp Met Gln Thr Leu Thr Pro Val Gly Arg Leu
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Asp Ser Tyr Ile Val Ile Gly
```

Val Gly Asp Lys Lys Ile Thr His His Trp
        275                 280

<210> SEQ ID NO 18
<211> LENGTH: 282
<212> TYPE: PRT
<213> ORGANISM: Zika virus

<400> SEQUENCE: 18

Phe Thr Cys Ser Lys Lys Met Thr Gly Lys Ser Ile Gln Pro Glu Asn
1               5                   10                  15

Leu Glu Tyr Arg Ile Met Leu Ser Val His Gly Ser Gln His Ser Gly
            20                  25                  30

Met Ile Val Asn Asp Ile Gly His Glu Thr Asp Glu Asn Arg Ala Lys
        35                  40                  45

Val Glu Val Thr Pro Asn Ser Pro Arg Ala Glu Ala Thr Leu Gly Gly
    50                  55                  60

Phe Gly Ser Leu Gly Leu Asp Cys Glu Pro Arg Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Asp Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Phe Ser Gly His Leu Lys Cys Arg Leu Lys
                165                 170                 175

Met Asp Lys Leu Arg Leu Lys Gly Val Ser Tyr Ser Leu Cys Thr Ala
            180                 185                 190

Val Cys Thr Ala Ala Lys Val Pro Ala Glu Thr Leu His Gly Thr Val
        195                 200                 205

Thr Val Glu Val Gln Tyr Ala Gly Thr Asp Gly Pro Cys Lys Val Pro
    210                 215                 220

Ala Gln Met Ala Val Asp Met Gln Thr Leu Thr Pro Val Gly Arg Leu
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Asp Ser Tyr Ile Val Ile Gly
            260                 265                 270

Val Gly Asp Lys Lys Ile Thr His His Trp
        275                 280

<210> SEQ ID NO 19
<211> LENGTH: 282
<212> TYPE: PRT
<213> ORGANISM: Zika virus

<400> SEQUENCE: 19

Phe Ala Cys Ser Lys Lys Met Thr Gly Lys Ser Ile Gln Pro Glu Asn
1               5                   10                  15

Leu Glu Tyr Arg Ile Met Leu Ser Val His Gly Ser Gln His Ser Gly

```
                    20                  25                  30
Met Ile Val Asn Asp Thr Gly His Glu Thr Asp Glu Asn Arg Ala Lys
                35                  40                  45

Val Glu Ile Thr Pro Asn Ser Pro Arg Ala Glu Ala Thr Leu Gly Gly
         50                  55                  60

Phe Gly Ser Leu Gly Leu Asp Cys Glu Pro Arg Thr Gly Leu Asp Phe
 65                  70                  75                  80

Ser Asp Leu Tyr Tyr Leu Thr Met Asn Asn Lys His Trp Leu Val His
                 85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Asp Ala His Ala Lys Arg Gln Thr Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Ser Ser Gly His Leu Lys Cys Arg Leu Lys
                165                 170                 175

Met Asp Lys Leu Arg Leu Lys Gly Val Ser Tyr Ser Leu Cys Thr Ala
            180                 185                 190

Ala Phe Thr Phe Thr Lys Ile Pro Ala Glu Thr Leu His Gly Thr Val
        195                 200                 205

Thr Val Glu Val Gln Tyr Ala Gly Thr Asp Gly Pro Cys Lys Val Pro
    210                 215                 220

Ala Gln Met Ala Val Asp Met Gln Thr Leu Thr Pro Val Gly Arg Leu
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Asp Ser Tyr Ile Val Ile Gly
            260                 265                 270

Val Gly Glu Lys Lys Ile Thr His His Trp
        275                 280

<210> SEQ ID NO 20
<211> LENGTH: 1275
<212> TYPE: DNA
<213> ORGANISM: Zika virus

<400> SEQUENCE: 20
ctgttgctgc ttcagactgc gacagttcga gtttgaagcg aaagctagca acagtatcaa      60
caggttttat ttggatttgg aaacgagagt ttctggtcat gaaaacccca aaaagaaat     120 ccggaggatt ccggattgtc aatatgctaa acgcggagt agcccgtgtg agcccctttg     180
ggggcttgaa gaggctgcca gccggacttc tgctgggtca tgggcccatc aggatggtct     240
tggcgattct agcctttttg agattcacgg caatcaagcc atcactgggt ctcatcaata     300 gatgggttc agtggggaaa aagaggcta tggaaataat aaagaagttc aagaaagatc     360
tggctgccat gctgagaata atcaatgcta ggaaggagaa gagagacga ggcgcagaaa     420 ctagtgtcgg aattgttggc ctcctgctga ccacagctat ggcagcggag gtcactagac     480 gtggagtgc atactatatg tacttggaca gaaacgatgc tggggaggcc atatcttttc     540
caaccacatt ggggatgaat aagtgttata tacagatcat ggatcttgga cacatgtgtg     600
atgccaccat gagctatgaa tgccctatgc tggatgaggg ggtggaacca gatgacgtcg     660
```

```
attgttggtg caacacgacg tcaacttggg ttgtgtacgg aacctgccat cacaaaaaag    720
gtgaagcacg gagatctaga agagccgtga cgctcccctc ccattccact aggaagctgc    780
aaacgcggtc gcaaacctgg ttggaatcaa gagaatacac aaagcacttg attagagtcg    840
aaaattggat attcaggaac cctggtttcg ctttagcagc agctgccatc gcgtggcttt    900
tgggaagctc aacgagccaa aaagtcatat acttggtcat gatactgctg attgccccgg    960
catacagcat caggtgcata ggagtcagca atagggactt tgtggaaggt atgtcaggtg   1020
ggacttgggt tgatgttgtc ttggaacatg gaggttgtgt caccgtaatg gcacaggaca   1080
aaccgactgt cgacatagag ctggttacaa caacagtcag caacatggcg gaggtaagat   1140
cctactgcta tgaggcatca atatcagaca tggcttcgcc cagccgctgc ccaacacaag   1200
ccgctgccta ccttgacaag caatcagaca ctcaatatgt ctgcaaaaga acgttagtgg   1260
acagcgactg gggtt                                                    1275

<210> SEQ ID NO 21
<211> LENGTH: 10807
<212> TYPE: DNA
<213> ORGANISM: Zika virus

<400> SEQUENCE: 21
agttgttact gttgctgact cagactgcga cagttcgagt ttgaagcgaa agctagcaac     60
agtatcaaca ggttttattt ggatttggaa acgagagttt ctggtcatga aaacccaaa    120
aaagaaatcc ggaggattcc ggattgtcaa tatgctaaaa cgcggagtag cccgtgtgag    180
ccccctttggg ggcttgaaga ggctgccagc cggacttctg ctgggtcatg ggcccatcag    240
gatggtcttg gcaattctag cctttttgag attcacggca atcaagccat cactgggtct    300
catcaataga tggggttcag tggggaaaaa agaggctatg gaaataataa agaagttcaa    360
gaaagatctg gctgccatgc tgagaataat caatgctagg aaggagaaga gagacgaggt    420
cgcagatact agtgtcggaa ttgttggcct cctgctgacc acagctatgg cagcggaggt    480
cactagacgt gggagtgcat actatatgta cttggacaga aacgatgctg ggaggccat    540
atcttttcca accacattgg ggatgaataa gtgttatata cagatcatgg atcttggaca    600
catgtgtgat gccaccatga gctatgaatg ccctatgctg gatgaggggg tggaaccaga    660
tgacgtcgat tgttggtgca acacgacgtc aacttgggtt gtgtacgaa cctgccatca    720
caaaaaggt gaagcacgga gatctagaag agctgtgacg ctccccctccc attccactag    780
gaagctgcaa acgcggtcgc aaacctggtt ggaatcaaga gaatacacaa agcacttgat    840
tagagtcgaa aattggatat tcaggaaccc tggcttcgcg ttagcagcag ctgccatcgc    900
ttggcttttg ggaagctcaa cgagccaaaa agtcatatac ttggtcatga tactgctgat    960
tgccccggca tacagcatca ggtgcatagg agtcagcaat agggactttg tggaaggtat   1020
gtcaggtggg acttggttg atgttgtctt ggaacatgga ggttgtgtca ccgtaatggc   1080
acaggacaaa ccgactgtcg acatagagct ggttacaaca acagtcagca catggcgga   1140
ggtaagatcc tactgctatg aggcatcaat atcagacatg gcttcggaca gccgctgccc   1200
aacacaaggt gaagcctacc ttgacaagca atcagacact caatatgtct gcaaaagaac   1260
gttagtggac agaggctggg gaatggatg tggactttt ggcaaaggga gtctggtgac   1320
atgcgctaag tttgcatgct ccaagaaaat gaccgggaag agcatccagc cagagaatct   1380
ggagtaccgg ataatgctgt cagttcatgg ctcccagcac agtgggatga tcgttaatga   1440
```

-continued

```
cacaggacat gaaactgatg agaatagagc gaaggttgag ataacgccca attcaccaag    1500
agccgaagcc accctggggg gttttggaag cctaggactt gattgtgaac cgaggacagg    1560
ccttgacttt tcagatttgt attacttgac tatgaataac aagcactggt tggttcacaa    1620
ggagtggttc cacgcattc cattaccttg gcacgctggg gcagacaccg gaactccaca    1680
ctggaacaac aaagaagcac tggtagagtt caaggacgca catgccaaaa ggcaaactgt    1740
cgtggttcta gggagtcaag aaggagcagt tcacacggcc cttgctggag ctctggaggc    1800
tgagatggat ggtgcaaagg gaaggctgtc ctctggccac ttgaaatgtc gcctgaaaat    1860
ggataaactt agattgaagg gcgtgtcata ctccttgtgt accgcagcgt tcacattcac    1920
caagatcccg gctgaaacac tgcacgggac agtcacagtg gaggtacagt acgcagggac    1980
agatggacct tgcaaggttc cagctcagat ggcggtggac atgcaaactc tgacccagt    2040
tgggaggttg ataaccgcta accccgtaat cactgaaagc actgagaact ctaagatgat    2100
gctggaactt gatccaccat ttggggactc ttacattgtc ataggagtcg gggagaagaa    2160
gatcacccac cactggcaca ggagtggcag caccattgga aaagcatttg aagccactgt    2220
gagaggtgcc aagagaatgg cagtcttggg agacacagcc tgggactttg atcagttgg    2280
aggcgctctc aactcattgg gcaagggcat ccatcaaatt tttggagcag ctttcaaatc    2340
attgtttgga ggaatgtcct ggttctcaca aattctcatt ggaacgttgc tgatgtggtt    2400
gggtctgaac acaaagaatg gatctatttc ccttatgtgc ttggccttag ggggagtgtt    2460
gatcttctta tccacagccg tctctgctga tgtggggtgc tcggtggact tctcaaagaa    2520
ggagacgaga tgcggtacag gggtgttcgt ctataacgac gttgaagcct ggagggacag    2580
gtacaagtac catcctgact ccccccgtag attggcagca gcagtcaagc aagcctggga    2640
agatggtatc tgcgggatct cctctgtttc aagaatggaa aacatcatgt ggagatcagt    2700
agaaggggag ctcaacgcaa tcctggaaga gaatggagtt caactgacgg tcgttgtggg    2760
atctgtaaaa aaccccatgt ggagaggtcc acagagattg cccgtgcctg tgaacgagct    2820
gccccacggc tggaaggctt gggggaaatc gcacttcgtc agagcagcaa agacaaataa    2880
cagctttgtc gtggatggtg acacactgaa ggaatgccca ctcaaacata gagcatggaa    2940
cagctttctt gtggaggatc atgggttcgg ggtatttcac actagtgtct ggctcaaggt    3000
tagagaagat tattcattag agtgtgatcc agccgttatt ggaacagctg ttaagggaaa    3060
ggaggctgta cacagtgatc taggctactg gattgagagt gagaagaatg acacatggag    3120
gctgaagagg gcccatctga tcgagatgaa aacatgtgaa tggccaaagt cccacacatt    3180
gtggacagat ggaatagaag agagtgatct gatcataccc aagtctttag ctgggccact    3240
cagccatcac aataccagag agggctacag gacccaaatg aaaggccat ggcacagtga    3300
agagcttgaa attcggtttg aggaatgccc aggcactaag gtccacgtgg aggaaacatg    3360
tggaacaaga ggaccatctc tgagatcaac cactgcaagc ggaagggtga tcgaggaatg    3420
gtgctgcagg gagtgcacaa tgcccccact gtcgttccgg gctaaagatg gctgttggta    3480
tggaatggag ataaggcccc ggaaagaacc agaaagcaac ttagtaaggt caatggtgac    3540
tgcaggatca actgatcaca tggatcactt ctcccttgga gtgcttgtga ttctgctcat    3600
ggtgcaggaa gggctgaaga agagaatgac cacaaagatc atcataagca catcaatggc    3660
agtgctggta gctatgatcc tgggaggatt tcaatgagt gacctggcta agcttgcaat    3720
tttgatgggt gccaccttcg cggaaatgaa cactggagga gatgtgagctc atctggcgct    3780
gatagcggca ttcaaagtca gaccagcgtt gctggtatct ttcatcttca gagctaattg    3840
```

```
gacaccccgt gaaagcatgc tgctggcctt ggcctcgtgt cttttgcaaa ctgcgatctc    3900
cgccttggaa ggcgacctga tggttctcat caatggtttt gctttggcct ggttggcaat    3960
acgagcgatg gttgttccac gcactgataa catcaccttg caatcctggc tgctctgac     4020
accactggcc cggggcacac tgcttgtggc gtggagagca ggccttgcta cttgcggggg    4080
gtttatgctc ctctctctga agggaaaagg cagtgtgaag aagaacttac catttgtcat    4140
ggccctggga ctaaccgctg tgaggctggt cgacccatc aacgtggtgg gctgctgtt     4200
gctcacaagg agtgggaagc ggagctggcc cctagcgaa gtactcacag ctgttggcct    4260
gatatgcgca ttggctggag ggttcgccaa ggcagatata gagatggctg ggcccatggc    4320
cgcggtcggt ctgctaattg tcagttacgt ggtctcagga aagagtgtgg acatgtacat    4380
tgaaagagca ggtgacatca catgggaaaa agatgcggaa gtcactggaa acagtccccg    4440
gctcgatgtg cgctagatg agagtggtga tttctccctg gtggaggatg acggtccccc    4500
catgagagag atcatactca aggtggtcct gatgaccatc tgtggcatga acccaatagc    4560
catacccttt gcagctggag cgtggtacgt atacgtgaag actggaaaaa ggagtggtgc    4620
tctatgggat gtgcctgctc ccaaggaagt aaaaaagggg gagaccacag atggagtgta    4680
cagagtaatg actcgtagac tgctaggttc aacacaagtt ggagtgggag ttatgcaaga    4740
gggggtcttt cacactatgt ggcacgtcac aaaaggatcc cgctgagaa gcggtgaagg    4800
gagacttgat ccatactggg gagatgtcaa gcaggatctg tgtcatact gtggtccatg    4860
gaagctagat gccgcctggg acgggcacag cgaggtgcag ctcttggccg tgcccccgg    4920
agagagagcg aggaacatcc agactctgcc cggaatattt aagacaaagg atgggacat    4980
tggagcggtt gcgctggatt acccagcagg aacttcagga tctccaatcc tagacaagtg    5040
tgggagagtg ataggacttt atggcaatgg ggtcgtgatc aaaaatggga gttatgttag    5100
tgccatcacc caagggagga gggaggaaga gactcctgtt gagtgcttcg agccttcgat    5160
gctgaagaag aagcagctaa ctgtcttaga cttgcatcct ggagctggga aaaccaggag    5220
agttcttcct gaaatagtcc gtgaagccat aaaaacaaga ctccgtactg tgatcttagc    5280
tccaaccagg gttgtcgctg ctgaaatgga ggaagccctt agagggcttc cagtgcgtta    5340
tatgacaaca gcagtcaatg tcacccactc tggaacagaa atcgtcgact taatgtgcca    5400
tgccaccttc acttcacgtc tactacagcc aatcagagtc cccaactata atctgtatat    5460
tatggatgag gcccacttca cagatccctc aagtatagca gcaagaggat acatttcaac    5520
aagggttgag atgggcgagg cggctgccat cttcatgacc gccacgccac caggaacccg    5580
tgacgcattt ccggactcca actcaccaat tatggacacc gaagtggaag tcccagagag    5640
agcctggagc tcaggctttg attgggtgac ggattattct ggaaaaacag tttggtttgt    5700
tccaagcgtg aggaacggca atgagatcgc agcttgtctg acaaaggctg aaaacggt     5760
catacagctc agcagaaaga cttttgagac agagttccag aaaacaaaac atcaagagtg    5820
ggactttgtc gtgacaactg acatttcaga gatgggcgcc aactttaaag ctgaccgtgt    5880
catagattcc aggagatgcc taaagccggt catacttgat ggcgagagag tcattctggc    5940
tggacccatg cctgtcacac atgccagcgc tgcccgagg agggggcgca taggcaggaa    6000
tcccaacaaa cctggagatg agtatctgta tggaggtggg tgcgcagaga ctgacgaaga    6060
ccatgcacac tggcttgaag caagaatgct ccttgacaat atttacctcc aagatggcct    6120
catagcctcg ctctatcgac ctgaggccga caaagtagca gccattgagg gagagttcaa    6180
```

```
gcttaggacg gagcaaagga agacctttgt ggaactcatg aaaagaggag atcttcctgt    6240
ttggctggcc tatcaggttg catctgccgg aataacctac acagatagaa gatggtgctt    6300
tgatggcacg accaacaaca ccataatgga agacagtgtg ccggcagagg tgtggaccag    6360
acacggagag aaaagagtgc tcaaaccgag gtggatggac gccagagttt gttcagatca    6420
tgcggccctg aagtcattca aggagtttgc cgctgggaaa agaggagcgg cttttggagt    6480
gatggaagcc ctgggaacac tgccaggaca catgacagag agattccagg aagccattga    6540
caacctcgct gtgctcatgc gggcagagac tggaagcagg ccttacaaag ccgcggcggc    6600
ccaattgccg gagaccctag agaccattat gcttttgggg ttgctgggaa cagtctcgct    6660
gggaatcttt ttcgtcttga tgaggaacaa gggcataggg aagatgggct ttggaatggt    6720
gactcttggg gccagcgcat ggctcatgtg gctctcggaa attgagccag ccagaattgc    6780
atgtgtcctc attgttgtgt tcctattgct ggtggtgctc atacctgagc cagaaaagca    6840
aagatctccc caggacaacc aaatggcaat catcatcatg gtagcagtag gtcttctggg    6900
cttgattacc gccaatgaac tcggatggtt ggagagaaca aagagtgacc taagccatct    6960
aatgggaagg agagaggagg gggcaaccat gggattctca atggacattg acctgcggcc    7020
agcctcagct tgggccatct atgctgcctt gacaactttc attaccccag ccgtccaaca    7080
tgcagtgacc acttcataca acaactactc cttaatggcg atggccacgc aagctggagt    7140
gttgtttggt atgggcaaag gatgccatt ctacgcatgg gactttgag tcccgctgct    7200
```

```
ttaccatgga agctatgagg cccccacaca agggtcagcg tcctctctaa taaacggggt    8640
tgtcaggctc ctgtcaaaac cctgggatgt ggtgactgga gtcacaggaa tagccatgac    8700
cgacaccaca ccgtatggtc agcaaagagt tttcaaggaa aaagtggaca ctagggtgcc    8760 agaccccaa gaaggcactc gtcaggttat gagcatggtc tcttcctggt tgtggaaaga    8820
gctaggcaaa cacaaacggc cacgagtctg taccaaagaa gagttcatca acaaggttcg    8880
tagcaatgca gcattagggg caatatttga agaggaaaaa gagtggaaga ctgcagtgga    8940
agctgtgaac gatccaaggt tctgggctct agtggacaag gaaagagagc accacctgag    9000
aggagagtgc cagagttgtg tgtacaacat gatgggaaaa agagaaaaga aacaagggga    9060
atttggaaag gccaagggca gccgcgccat ctggtatatg tggctagggg ctagatttct    9120
agagttcgaa gcccttggat tcttgaacga ggatacactg gatgggagag agaactcagg    9180
aggtggtgtt gaagggctgg gattacaaag actcggatat gtcctagaag agatgagtcg    9240
cataccagga ggaaggatgt atgcagatga cactgctggc tgggacaccc gcatcagcag    9300
gtttgatctg gagaatgaag ctctaatcac caaccaaatg gagaaagggc acagggcctt    9360
ggcattggcc ataatcaagt acacatacca aaacaaagtg gtaaaggtcc ttagaccagc    9420
tgaaaaaggg aagacagtta tggacattat ttcgagacaa gaccaaaggg ggagcggaca    9480
agttgtcact tacgctctta acacatttac caacctagtg gtgcaactca ttcggaatat    9540
ggaggctgag gaagttctag agatgcaaga cttgtggctg ctgcggaggt cagagaaagt    9600
gaccaactgg ttgcagagca acggatggga taggctcaaa cgaatggcag tcagtggaga    9660
tgattgcgtt gtgaagccaa ttgatgatag gtttgcacat gccctcaggt tcttgaatga    9720
tatgggaaaa gttaggaagg acacacaaga gtggaaaccc tcaactggat gggacaactg    9780
ggaagaagtt ccgttttgct cccaccactt caacaagctc catctcaagg acgggaggtc    9840
cattgtggtt ccctgccgcc accaagatga actgattggc cgggcccgcg tctctccagg    9900
ggcgggatgg agcatccggg agactgcttg cctagcaaaa tcatatgcgc aaatgtggca    9960
gctcctttat ttccacagaa gggacctccg actgatggcc aatgccattt gttcatctgt    10020
gccagttgac tgggttccaa ctgggagaac tacctggtca atccatggaa agggagaatg    10080
gatgaccact gaagacatgc ttgtggtgtg gaacagagtg tggattgagg agaacgacca    10140
catgaaggac aagaccccag ttacgaaatg gacagacatt ccctatttgg gaaaagggag    10200
agacttgtgg tgtggatctc tcataggca cagaccgcgc accacctggg ctgagaacat    10260
taaaaacaca gtcaacatgg tgcgcaggat cataggtgat gaagaaaagt acatggacta    10320
cctatccacc caagttcgct acttgggtga agaagggtct acacctggag tgctgtaagc    10380
accaatctta atgttgtcag gcctgctagt cagccacagc ttggggaaag ctgtgcagcc    10440 tgtgacccc ccaggagaag ctgggaaacc aagcctatag tcaggccgag aacgccatgg    10500
cacggaagaa gccatgctgc ctgtgagccc ctcagaggac actgagtcaa aaaccccac    10560 gcgcttggag gcgcaggatg ggaaaagaag gtggcgacct tccccaccct tcaatctggg    10620
gcctgaactg gagatcagct gtggatctcc agaagaggga ctagtggtta gaggagaccc    10680 cccgaaaac gcaaacagc atattgacgc tgggaaagac cagagactcc atgagtttcc    10740
accacgctgg ccgccaggca cagatcgccg aatagcggcg gccggtgtgg ggaaatccat    10800
gggtctt                                                              10807
```

<210> SEQ ID NO 22

<211> LENGTH: 10862
<212> TYPE: DNA
<213> ORGANISM: Yellow fever virus

<400> SEQUENCE: 22

| | | | | | |
|---|---|---|---|---|---|
| agtaaatcct | gtgtgctaat | tgaggtgcat | tggtctgcaa | atcgagttgc | taggcaataa | 60 |
| acacatttgg | attaatttta | atcgttcgtt | gagcgattag | cagagaactg | accagaacat | 120 |
| gtctggtcgt | aaagctcagg | gaaaaaccct | gggcgtcaat | atggtacgac | gaggagttcg | 180 |
| ctccttgtca | aacaaaataa | aacaaaaaac | aaaacaaatt | ggaaacagac | ctggaccttc | 240 |
| aagaggtgtt | caaggattta | tcttttctt | tttgttcaac | attttgactg | gaaaaaagat | 300 |
| cacagcccac | ctaaagaggt | tgtggaaaat | gctggaccca | agacaaggct | tggctgttct | 360 |
| aaggaaagtc | aagagagtgg | tggccagttt | gatgagagga | ttgtcctcaa | ggaaacgccg | 420 |
| ttcccatgat | gttctgactg | tgcaattcct | aattttggga | atgctgttga | tgacgggtgg | 480 |
| agtgaccttg | gtgcggaaaa | acagatggtt | gctcctaaat | gtgacatctg | aggacctcgg | 540 |
| gaaaacattc | tctgtgggca | caggcaactg | cacaacaaac | attttggaag | ccaagtactg | 600 |
| gtgcccagac | tcaatggaat | acaactgtcc | caatctcagt | ccaagagagg | agccagatga | 660 |
| cattgattgc | tggtgctatg | gggtggaaaa | cgttagagtc | gcatatggta | agtgtgactc | 720 |
| agcaggcagg | tctaggaggt | caagaagggc | cattgacttg | cctacgcatg | aaaaccatgg | 780 |
| tttgaagacc | cggcaagaaa | aatggatgac | tggaagaatg | ggtgaaaggc | aactccaaaa | 840 |
| gattgagaga | tggttcgtga | ggaaccccett | ttttgcagtg | acggctctga | ccattgccta | 900 |
| ccttgtggga | agcaacatga | cgcaacgagt | cgtgattgcc | ctactggtct | ggctgttgg | 960 |
| tccggcctac | tcagctcact | gcattggaat | tactgacagg | gatttcattg | aggggtgca | 1020 |
| tggaggaact | tgggtttcag | ctaccctgga | gcaagacaag | tgtgtcactg | ttatggcccc | 1080 |
| tgacaagcct | tcattggaca | tctcactaga | gacagtagcc | attgatagac | tgctgaggt | 1140 |
| gaggaaagtg | tgttacaatg | cagttctcac | tcatgtgaag | attaatgaca | agtgccccag | 1200 |
| cactggagag | gcccacctag | ctgaagagaa | cgaaggggac | aatgcgtgca | agcgcactta | 1260 |
| ttctgataga | ggctggggca | atggctgtgg | cctatttggg | aaaggagca | ttgtggcatg | 1320 |
| cgccaaattc | acttgtgcca | atccatgag | tttgtttgag | gttgatcaga | ccaaaattca | 1380 |
| gtatgtcatc | agagcacaat | tgcatgtagg | ggccaagcag | gaaaattgga | ataccgacat | 1440 |
| taagactctc | aagtttgatg | ccctgtcagg | ctcccaggaa | gtcgagttca | ttgggtatgg | 1500 |
| aaaagctaca | ctggaatgcc | aggtgcaaac | tgccgtggac | tttggtaaca | gttacatcgc | 1560 |
| tgagatggaa | acagagagct | ggatagtgga | cagacagtgg | gcccaggact | tgaccctgcc | 1620 |
| atggcagagt | ggaagtggcg | gggtgtgag | agagatgcat | catcttgtcg | aatttgaacc | 1680 |
| tccgcatgcc | gccactatca | gagtactggc | cctgggaaac | caggaaggct | ccttgaaaac | 1740 |
| agctcttact | ggcgcaatga | gggttacaaa | ggacacaaat | gacaacaacc | tttacaaact | 1800 |
| acatggtgga | catgtttctt | gcagagtgaa | attgtcagct | ttgacactca | aggggacatc | 1860 |
| ctacaaaata | tgcactgaca | aaatgttttt | tgtcaagaac | ccaactgaca | ctggccatgg | 1920 |
| cactgttgtg | atgcaggtga | aagtgtcaaa | aggagccccc | tgcaggattc | cagtgatagt | 1980 |
| agctgatgat | cttacagcgg | caatcaataa | aggcattttg | gttacagtta | accccatcgc | 2040 |
| ctcaaccaat | gatgatgaag | tgctgattga | ggtgaaccca | ccttttggag | acagctacat | 2100 |
| tatcgttggg | agaggagatt | cacgtctcac | ttaccagtgg | cacaaagagg | gaagctcaat | 2160 |
| aggaaagttg | ttcactcaga | ccatgaaagg | cgtggaacgc | ctggccgtca | tgggagacac | 2220 |

```
cgcctgggat tcagctccg ctggagggtt cttcacttcg gttgggaaag gaattcatac    2280
ggtgtttggc tctgcctttc aggggctatt tggcggcttg aactggataa caaaggtcat    2340
catgggggcg gtacttatat gggttggcat caacacaaga aacatgacaa tgtccatgag    2400
catgatcttg gtaggagtga tcatgatgtt tttgtctcta ggagttgggg cggatcaagg    2460
atgcgccatc aactttggca agagagagct caagtgcgga gatggtatct tcatatttag    2520
agactctgat gactggctga acaagtactc atactatcca gaagatcctg tgaagcttgc    2580
atcaatagtg aaagcctctt ttgaagaagg gaagtgtggc ctaaattcag ttgactccct    2640
tgagcatgag atgtgtagaa gcagggcaga tgagatcaat gccatttttg aggaaaacga    2700
ggtggacatt tctgttgtcg tgcaggatcc aaagaatgtt taccagagag gaactcatcc    2760
attttccaga attcgggatg gtctgcagta tggttggaag acttggggta agaaccttgt    2820
gttctcccca gggaggaaga atggaagctt catcatagat ggaaagtcca ggaaagaatg    2880
cccgttttca aaccgggtct ggaattcttt ccagatagag gagtttggga cgggagtgtt    2940
caccacacgc gtgtacatgg acgcagtctt tgaatacacc atagactgcg atggatctat    3000
cttgggtgca gcggtgaacg gaaaaaagag tgcccatggc tctccaacat tttggatggg    3060
aagtcatgaa gtaaatggga catggatgat ccacaccttg gaggcattag attacaagga    3120
gtgtgagtgg ccactgacac atacgattgg aacatcagtt gaagagagtg aaatgttcat    3180
gccgagatca atcggaggcc cagttagctc tcacaatcat atccctggat acaaggttca    3240
gacgaacgga ccttggatgc aggtaccact agaagtgaag agagaagctt gcccagggac    3300
tagcgtgatc attgatggca actgtgatgg acggggaaaa tcaaccagat ccaccacgga    3360
tagcgggaaa gttattcctg aatggtgttg ccgctcctgc acaatgccgc ctgtgagctt    3420
ccatggtagt gatgggtgtt ggtatcccat ggaaattagg ccaaggaaaa cgcatgaaag    3480
ccatctggtg cgctcctggg ttacagctgg agaaatacat gctgtccctt ttggtttggt    3540
gagcatgatg atagcaatgg aagtggtcct aaggaaaaga cagggaccaa agcaaatgtt    3600
ggttggagga gtagtgctct gggagcaat gctggtcggg caagtaactc tccttgattt    3660
gctgaaactc acagtggctg tgggattgca tttccatgag atgaacaatg gaggagacgc    3720
catgtatatg gcgttgattg ctgccttttc aatcagacca gggctgctca tcggctttgg    3780
gctcaggacc ctatggagcc ctcgggaacg ccttgtgctg acctaggag cagccatggt    3840 ggagattgcc ttgggtggcg tgatgggcgg cctgtggaag tatctaaatg cagtttctct    3900
ctgcatcctg acaataaatg ctgttgcttc taggaaagca tcaaatacca tcttgccct    3960 catggctctg ttgacacctg tcactatggc tgaggtgaga cttgccgcaa tgttcttttg    4020
tgccgtggtt atcataggg tccttcacca gaatttcaag gacacctcca tgcagaagac    4080 tataccctg gtggccctca cactcacatc ttacctgggc ttgacacaac cttttttggg    4140
cctgtgtgca tttctggcaa cccgcatatt tgggcgaagg agtatcccag tgaatgaggc    4200
actcgcagca gctggtctag tgggagtgct ggcaggactg gcttttcagg agatggagaa    4260
cttccttggt ccgattgcag ttggaggact cctgatgatg ctggttagcg tggctgggag    4320
ggtggatggg ctagagctca agaagcttgg tgaagtttca tgggaagagg aggcggagat    4380
cagcgggagt tccgcccgct atgatgtggc actcagtgaa caagggagt tcaagctgct    4440 ttctgaagag aaagtgccat gggaccaggt tgtgatgacc tcgctggcct tggttggggc    4500
tgccctccat ccatttgctc ttctgctggt ccttgctggg tggctgtttc atgtcagggg    4560
```

```
agctaggaga agtggggatg tcttgtggga tattcccact cctaagatca tcgaggaatg    4620
tgaacatctg gaggatggga tttatggcat attccagtca accttcttgg gggcctccca    4680
gcgaggagtg ggagtggcac agggaggggt gttccacaca atgtggcatg tcacaagagg    4740
agctttcctt gtcaggaatg gcaagaagtt gattccatct tgggcttcag taaaggaaga    4800
ccttgtcgcc tatggtggct catggaagtt ggaaggcaga tgggatggag aggaagaggt    4860
ccagttgatc gcggctgttc caggaaagaa cgtggtcaac gtccagacaa aaccgagctt    4920
gttcaaagtg aggaatgggg gagaaatcgg ggctgtcgct cttgactatc cgagtggcac    4980
ttcaggatct cctattgtta acaggaacgg agaggtgatt gggctgtacg gcaatggcat    5040
ccttgtcggt gacaactcct tcgtgtccgc catatcccag actgaggtga aggaagaagg    5100
aaaggaggag ctccaagaga tcccgacaat gctaaagaaa ggaatgacaa ctgtccttga    5160
ttttcatcct ggagctggga agacaagacg tttcctccca cagatcttgg ccgagtgcgc    5220
acggagacgc ttgcgcactc ttgtgttggc ccccaccagg gttgttcttt ctgaaatgaa    5280
ggaggctttt cacggcctgg acgtgaaatt ccacacacag gcttttttccg ctcacggcag    5340 cgggagagaa gtcattgatg ccatgtgcca tgccacccta acttacagga tgttggaacc    5400
aactagggtt gttaactggg aagtgatcat tatggatgaa gcccattttt tggatccagc    5460
tagcatagcc gctagaggtt gggcagcgca cagagctagg gcaaatgaaa gtgcaacaat    5520
cttgatgaca gccacaccgc ctgggactag tgatgaattt ccacattcaa atggtgaaat    5580
agaagatgtt caaacggaca tacccagtga gccctggaac acagggcatg actggatcct    5640
agctgacaaa aggcccacgg catggttcct tccatccatc agagctgcaa atgtcatggc    5700
tgcctctttg cgtaaggctg aaagagtgt ggtggtcctg aacaggaaaa cctttgagag    5760
agaatacccc acgataaagc agaagaaacc tgactttata ttggccactg acatagctga    5820
aatgggagcc aacctttgcg tggagcgagt gctggattgc aggacggctt ttaagcctgt    5880
gcttgtggat gaagggagga aggtggcaat aaaaagggcca cttcgtatct ccgcatcctc    5940
tgctgctcaa aggaggggc gcattgggag aaatcccaac agagatggag actcatacta    6000
ctattctgag cctacaagtg aaaataatgc ccaccgtc tgctggttgg aggcctcaat    6060
gctcttggac aacatggagg tgaggggtgg aatggtcgcc ccactctatg gcgttgaagg    6120
aactaaaaca ccagtttccc ctggtgaaat gagactgagg gatgaccaga ggaaagtctt    6180
cagagaacta gtgaggaatt gtgacctgcc cgtttggctt tcgtggcaag tggccaaggc    6240
tggtttgaag acgaatgatc gtaagtggtg ttttgaaggc cctgaggaac atgagatctt    6300
gaatgacagc ggtgaaacag tgaagtgcag ggctcctgga ggagcaaaga agcctctgcg    6360
cccaaggtgg tgtgatgaaa gggtgtcatc tgaccagagt gcgctgtctg aatttattaa    6420
gtttgctgaa ggtaggaggg gagctgctga agtgctagtt gtgctgagtg aactccctga    6480
tttcctggct aaaaaaggtg gagaggcaat ggataccatc agtgtgttcc tccactctga    6540
ggaaggctct agggcttacc gcaatgcact atcaatgatg cctgaggcaa tgacaatagt    6600
catgctgttt atactggctg gactactgac atcgggaatg gtcatctttt tcatgtctcc    6660
caaaggcatc agtagaatgt ctatggcgat ggcacaatg gccggctgtg atatctcat     6720 gttccttgga ggcgtcaaac ccactcacat ctcctatgtc atgctcatat tctttgtcct    6780
gatggtggtt gtgatccccg agccagggca acaaaggtcc atccaagaca accaagtggc    6840 ataccctcatt attggcatcc tgacgctggt ttcagcggtg gcagccaacg agctaggcat    6900
gctggagaaa accaaagagg acctctttgg gaagaagaac ttaattccat ctagtgcttc    6960
```

```
accctggagt tggccggatc ttgacctgaa gccaggagct gcctggacag tgtacgttgg    7020
cattgttaca atgctctctc caatgttgca ccactggatc aaagtcgaat atggcaacct    7080
gtctctgtct ggaatagccc agtcagcctc agtcctttct ttcatggaca aggggatacc    7140
attcatgaag atgaatatct cggtcataat gctgctggtc agtggctgga attcaataac    7200
agtgatgcct ctgctctgtg gcataggGtg cgccatgctc cactggtctc tcattttacc    7260
tggaatcaaa gcgcagcagt caaagcttgc acagagaagg gtgttccatg gcgttgccga    7320
gaaccctgtg gttgatggga atccaacagt tgacattgag gaagctcctg aaatgcctgc    7380
cctttatgag aagaaactgg ctctatatct ccttcttgct ctcagcctag cttctgttgc    7440
catgtgcaga acgccctttt cattggctga aggcattgtc ctagcatcag ctgccttagg    7500
gccgctcata gagggaaaca ccagccttct ttggaatgga cccatggctg tctccatgac    7560
aggagtcatg agggggaatc actatgcttt tgtgggagtc atgtacaatc tatggaagat    7620
gaaaactgga cgccggggga gcgcgaatgg aaaaactttg ggtgaagtct ggaagaggga    7680
actgaatctg ttggacaagc gacagtttga gttgtataaa aggaccgaca ttgtggaggt    7740
ggatcgtgat acggcacgca ggcatttggc cgaagggaag gtggacaccg gggtggcggt    7800
ctccaggggg accgcaaagt taaggtggtt ccatgagcgt ggctatgtca agctggaagg    7860
tagggtgatt gacctggggt gtggccgcgg aggctggtgt tactacgctg ctgcgcaaaa    7920
ggaagtgagt ggggtcaaag gatttactct tggaagagac ggccatgaga acccatgaa    7980
tgtgcaaagt ctgggatgga acatcatcac cttcaaggac aaaactgata tccaccgcct    8040
agaaccagtg aaatgtgaca ccctttttgtg tgacattgga gagtcatcat cgtcatcggt    8100
cacagagggg gaaaggaccg tgagagttct tgatactgta gaaaaatggc tggcttgtgg    8160
ggttgacaac ttctgtgtga aggtgttagc tccatacatg ccagatgttc tcgagaaact    8220
ggaattgctc caaaggaggt ttggcggaac agtgatcagg aaccctctct ccaggaattc    8280
cactcatgaa atgtactacg tgtctggagc ccgcagcaat gtcacattta ctgtgaacca    8340
aacatcccgc ctcctgatga ggagaatgag gcgtccaact ggaaaagtga ccctggaggc    8400
tgacgtcatc ctcccaattg ggacacgcag tgttgagaca gacaagggac ccctggacaa    8460
agaggccata aagaaagggt ttgagaggat aaaatctgag tacatgacct cttggttta    8520
tgacaatgac aaccctaca ggacctggca ctactgtggc tcctatgtca caaaacctc    8580
aggaagtgcg gcgagcatgg taaatggtgt tattaaaatt ctgacatatc catgggacag    8640
gatagaggag gtcacaagaa tggcaatgac tgacacaacc cctttttggac agcaaagagt    8700
gtttaaagaa aaagttgaca ccagagcaaa ggatccacca gcgggaacta ggaagatcat    8760
gaaagttgtc aacaggtggc tgttccgcca cctggccaga aaaagaacc ccagactgtg    8820
cacaaaggaa gaatttattg caaaagtccg aagtcatgca gccattggag cttacctgga    8880
agaacaagaa cagtggaaga ctgccaatga ggctgtccaa gacccaaagt ctgggaact    8940
ggtggatgaa gaaaggaagc tgcaccaaca aggcaggtgt cggacttgtg tgtacaacat    9000
gatggggaaa agagaagaaa agctgtcaga gtttgggaaa gcaaagggaa gccgtgccat    9060
atggtatatg tggctgggag cgcggtatct tgagtttgag gccctgggat tcctgaatga    9120
ggaccattgg gcttccaggg aaaactcagg aggaggagtg gaaggcattg gcttacaata    9180
cctaggatat gtgatcagag acctggctgc aatggatggt ggtggtggat tctacgcgga tga    9240
caccgctgga tgggacacgc gcatcacaga ggcagacctt gatgatgaac aggagatctt    9300
```

```
gaactacatg agcccacatc acaaaaaact ggcacaagca gtgatggaaa tgacatacaa  9360
gaacaaagtg gtgaaagtgt tgagaccagc cccaggaggg aaagcctaca tggatgtcat  9420
aagtcgacga gaccagagag gatccgggca ggtagtgact tatgctctga acaccatcac  9480
caacttgaaa gtccaattga tcagaatggc agaagcagag atggtgatac atcaccaaca  9540
tgttcaagat tgtgatgaat cagttctgac caggctggag gcatggctca ctgagcacgg  9600
atgtgacaga ctgaagagga tggcggtgag tggagacgac tgtgtggtcc ggcccatcga  9660
tgacaggttc ggcctggccc tgtcccatct caacgccatg tccaaggtta gaaaggacat  9720
atctgaatgg cagccatcaa agggtggaaa tgattgggag aatgtgccct tctgttccca  9780
ccacttccat gaactacagc tgaaggatgg caggaggatt gtggtgcctt gccgagaaca  9840
ggacgagctc attgggagag aagggtgtc tccaggaaac ggctggatga tcaaggaaac  9900
agcttgcctc agcaaagcct atgccaacat gtggtcactg atgtattttc acaaaaggga  9960
catgaggcta ctgtcattgg ctgtttcctc agctgttccc acctcatggg ttccacaagg 10020
acgcacaaca tggtcgattc atgggaaagg ggagtggatg accacggaag acatgcttga 10080
ggtgtggaac agagtatgga taaccaacaa cccacacatg caggacaaga caatggtgaa 10140
aaaatggaga gatgtcccct tatctaaccaa gagacaagac aagctgtgcg atcactgat 10200
tggaatgacc aatagggcca cctgggcctc ccacatccat ttagtcatcc atcgtatccg 10260
aacgctgatt ggacaggaga atacactga ctacctaaca gtcatggaca ggtattctgt 10320
ggatgctgac ctgcaactgg gtgagcttat ctgaaacacc atctaacagg aataaccggg 10380
atacaaacca cgggtggaga accggactcc ccacaacctg aaaccgggat ataaaccacg 10440
gctggagaac cgggctccgc acttaaaatg aaacagaaac cgggataaaa actacggatg 10500
gagaaccgga ctccacacat tgagacagaa gaagttgtca gcccagaacc ccacacgagt 10560
tttgccactg ctaagctgtg aggcagtgca ggctgggaca gccgacctcc aggttgcgaa 10620
aaacctggtt tctgggacct cccacccccag agtaaaaaga acgagcctc cgctaccacc 10680
ctcccacgtg gtggtagaaa gacggggtct agaggttaga ggagaccctc cagggaacaa 10740
atagtgggac catattgacg ccagggaaag accggagtgg ttctctgctt ttcctccaga 10800
ggtctgtgag cacagtttgc tcaagaataa gcagaccttt ggatgacaaa cacaaaacca 10860
ct                                                                10862
```

<210> SEQ ID NO 23
<211> LENGTH: 3327
<212> TYPE: PRT
<213> ORGANISM: Zika virus

<400> SEQUENCE: 23

```
Met Lys Asn Pro Lys Lys Lys Ser Gly Gly Phe Arg Ile Val Asn Met
1               5                   10                  15

Leu Lys Arg Gly Val Ala Arg Val Asn Pro Leu Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95
```

```
Ala Arg Lys Glu Arg Lys Arg Gly Ala Asp Thr Ser Ile Gly Ile
            100                 105                 110

Ile Gly Leu Leu Leu Thr Thr Ala Met Ala Ala Glu Ile Thr Arg Arg
            115                 120                 125

Gly Ser Ala Tyr Tyr Met Tyr Leu Asp Arg Ser Asp Ala Gly Lys Ala
            130                 135                 140

Ile Ser Phe Ala Thr Thr Leu Gly Val Asn Lys Cys His Val Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
            195                 200                 205

Glu Ala Arg Arg Ser Arg Arg Ala Val Thr Leu Pro Ser His Ser Thr
        210                 215                 220

Arg Lys Leu Gln Thr Arg Ser Gln Thr Trp Leu Glu Ser Arg Glu Tyr
225                 230                 235                 240

Thr Lys His Leu Ile Lys Val Glu Asn Trp Ile Phe Arg Asn Pro Gly
                245                 250                 255

Phe Ala Leu Val Ala Val Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
        290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
            325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Thr Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Ile Gly His
    435                 440                 445

Glu Thr Asp Glu Asn Arg Ala Lys Val Glu Val Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510
```

-continued

Leu Pro Trp His Ala Gly Ala Asp Thr Gly Thr Pro His Trp Asn Asn
515                 520                 525

Lys Glu Ala Leu Val Glu Phe Lys Asp Ala His Ala Lys Arg Gln Thr
530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Phe Ser
                565                 570                 575

Gly His Leu Lys Cys Arg Leu Lys Met Asp Lys Leu Arg Leu Lys Gly
                580                 585                 590

Val Ser Tyr Ser Leu Cys Thr Ala Ala Phe Thr Phe Thr Lys Val Pro
                595                 600                 605

Ala Glu Thr Leu His Gly Thr Val Thr Val Glu Val Gln Tyr Ala Gly
610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
                660                 665                 670

Gly Asp Ser Tyr Ile Val Ile Gly Val Gly Asp Lys Lys Ile Thr His
                675                 680                 685

His Trp His Arg Ser Gly Ser Thr Ile Gly Lys Ala Phe Glu Ala Thr
                690                 695                 700

Val Arg Gly Ala Lys Arg Met Ala Val Leu Gly Asp Thr Ala Trp Asp
705                 710                 715                 720

Phe Gly Ser Val Gly Gly Val Phe Asn Ser Leu Gly Lys Gly Ile His
                725                 730                 735

Gln Ile Phe Gly Ala Ala Phe Lys Ser Leu Phe Gly Gly Met Ser Trp
                740                 745                 750

Phe Ser Gln Ile Leu Ile Gly Thr Leu Leu Val Trp Leu Gly Leu Asn
                755                 760                 765

Thr Lys Asn Gly Ser Ile Ser Leu Thr Cys Leu Ala Leu Gly Gly Val
770                 775                 780

Met Ile Phe Leu Ser Thr Ala Val Ser Ala Asp Val Gly Cys Ser Val
785                 790                 795                 800

Asp Phe Ser Lys Arg Glu Thr Arg Cys Gly Thr Gly Val Phe Ile Tyr
                805                 810                 815

Asn Asp Val Glu Ala Trp Arg Asp Arg Tyr Lys Tyr His Pro Asp Ser
                820                 825                 830

Pro Arg Arg Leu Ala Ala Ala Val Lys Gln Ala Trp Glu Glu Gly Ile
                835                 840                 845

Cys Gly Ile Ser Ser Val Ser Arg Met Glu Asn Ile Met Trp Lys Ser
850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Gly Leu Pro His Gly Trp Lys Ala Trp
                900                 905                 910

Gly Lys Ser Tyr Phe Val Arg Ala Ala Lys Thr Asn Asn Ser Phe Val
                915                 920                 925

Val Asp Gly Asp Thr Leu Lys Glu Cys Pro Leu Lys His Arg Ala Trp

```
                    930             935             940
Asn Ser Phe Leu Val Glu Asp His Gly Phe Gly Val Phe His Thr Ser
945                 950             955                 960

Val Trp Leu Lys Val Arg Glu Asp Tyr Ser Leu Glu Cys Asp Pro Ala
                965                 970             975

Val Ile Gly Thr Ala Val Lys Gly Arg Glu Ala Ala His Ser Asp Leu
            980                 985                 990

Gly Tyr Trp Ile Glu Ser Glu Lys Asn Asp Thr Trp Arg Leu Lys Arg
        995                 1000                1005

Ala His Leu Ile Glu Met Lys Thr Cys Glu Trp Pro Lys Ser His
    1010                1015                1020

Thr Leu Trp Thr Asp Gly Val Glu Glu Ser Asp Leu Ile Ile Pro
    1025                1030                1035

Lys Ser Leu Ala Gly Pro Leu Ser His His Asn Thr Arg Glu Gly
    1040                1045                1050

Tyr Arg Thr Gln Val Lys Gly Pro Trp His Ser Glu Glu Leu Glu
    1055                1060                1065

Ile Arg Phe Glu Glu Cys Pro Gly Thr Lys Val His Val Glu Glu
    1070                1075                1080

Thr Cys Gly Thr Arg Gly Pro Ser Leu Arg Ser Thr Thr Ala Ser
    1085                1090                1095

Gly Arg Val Ile Glu Glu Trp Cys Cys Arg Glu Cys Thr Met Pro
    1100                1105                1110

Pro Leu Ser Phe Arg Ala Lys Asp Gly Cys Trp Tyr Gly Met Glu
    1115                1120                1125

Ile Arg Pro Arg Lys Glu Pro Glu Ser Asn Leu Val Arg Ser Met
    1130                1135                1140

Val Thr Ala Gly Ser Thr Asp His Met Asp His Phe Ser Leu Gly
    1145                1150                1155

Val Leu Val Ile Leu Leu Met Val Gln Glu Gly Leu Lys Lys Arg
    1160                1165                1170

Met Thr Thr Lys Ile Ile Met Ser Thr Ser Met Ala Val Leu Val
    1175                1180                1185

Val Met Ile Leu Gly Gly Phe Ser Met Ser Asp Leu Ala Lys Leu
    1190                1195                1200

Val Ile Leu Met Gly Ala Thr Phe Ala Glu Met Asn Thr Gly Gly
    1205                1210                1215

Asp Val Ala His Leu Ala Leu Val Ala Ala Phe Lys Val Arg Pro
    1220                1225                1230

Ala Leu Leu Val Ser Phe Ile Leu Arg Ala Asn Trp Thr Pro Arg
    1235                1240                1245

Glu Ser Met Leu Leu Ala Leu Ala Ser Cys Leu Leu Gln Thr Ala
    1250                1255                1260

Ile Ser Ala Leu Glu Gly Asp Leu Met Val Leu Val Asn Gly Phe
    1265                1270                1275

Ala Leu Ala Trp Leu Ala Ile Arg Ala Met Ala Val Pro Arg Thr
    1280                1285                1290

Asp Asn Ile Ala Leu Ala Ile Leu Ala Ala Leu Thr Pro Leu Ala
    1295                1300                1305

Arg Gly Thr Leu Leu Val Ala Trp Arg Ala Gly Leu Ala Thr Cys
    1310                1315                1320

Gly Gly Phe Met Leu Leu Ser Leu Lys Gly Lys Gly Ser Val Lys
    1325                1330                1335
```

```
Lys Asn Leu Pro Phe Val Met Ala Leu Gly Leu Thr Ala Val Arg
1340                1345                1350

Val Val Asp Pro Ile Asn Val Val Gly Leu Leu Leu Thr Arg
1355                1360                1365

Ser Gly Lys Arg Ser Trp Pro Pro Ser Glu Val Leu Thr Ala Val
1370                1375                1380

Gly Leu Ile Cys Ala Leu Ala Gly Gly Phe Ala Lys Ala Asp Ile
1385                1390                1395

Glu Met Ala Gly Pro Met Ala Ala Val Gly Leu Leu Ile Val Ser
1400                1405                1410

Tyr Val Val Ser Gly Lys Ser Val Asp Met Tyr Ile Glu Arg Ala
1415                1420                1425

Gly Asp Ile Thr Trp Glu Lys Asp Ala Glu Val Thr Gly Asn Ser
1430                1435                1440

Pro Arg Leu Asp Val Ala Leu Asp Glu Ser Gly Asp Phe Ser Leu
1445                1450                1455

Val Glu Glu Asp Gly Pro Pro Met Arg Glu Ile Ile Leu Lys Val
1460                1465                1470

Val Leu Met Ala Ile Cys Gly Met Asn Pro Ile Ala Ile Pro Phe
1475                1480                1485

Ala Ala Gly Ala Trp Tyr Val Tyr Val Lys Thr Gly Lys Arg Ser
1490                1495                1500

Gly Ala Leu Trp Asp Val Pro Ala Pro Lys Glu Val Lys Lys Gly
1505                1510                1515

Glu Thr Thr Asp Gly Val Tyr Arg Val Met Thr Arg Arg Leu Leu
1520                1525                1530

Gly Ser Thr Gln Val Gly Val Gly Val Met Gln Glu Gly Val Phe
1535                1540                1545

His Thr Met Trp His Val Thr Lys Gly Ala Ala Leu Arg Ser Gly
1550                1555                1560

Glu Gly Arg Leu Asp Pro Tyr Trp Gly Asp Val Lys Gln Asp Leu
1565                1570                1575

Val Ser Tyr Cys Gly Pro Trp Lys Leu Asp Ala Ala Trp Asp Gly
1580                1585                1590

Leu Ser Glu Val Gln Leu Leu Ala Val Pro Pro Gly Glu Arg Ala
1595                1600                1605

Arg Asn Ile Gln Thr Leu Pro Gly Ile Phe Lys Thr Lys Asp Gly
1610                1615                1620

Asp Ile Gly Ala Val Ala Leu Asp Tyr Pro Ala Gly Thr Ser Gly
1625                1630                1635

Ser Pro Ile Leu Asp Lys Cys Gly Arg Val Ile Gly Leu Tyr Gly
1640                1645                1650

Asn Gly Val Val Ile Lys Asn Gly Ser Tyr Val Ser Ala Ile Thr
1655                1660                1665

Gln Gly Lys Arg Glu Glu Glu Thr Pro Val Glu Cys Phe Glu Pro
1670                1675                1680

Ser Met Leu Lys Lys Lys Gln Leu Thr Val Leu Asp Leu His Pro
1685                1690                1695

Gly Ala Gly Lys Thr Arg Arg Val Leu Pro Glu Ile Val Arg Glu
1700                1705                1710

Ala Ile Lys Lys Arg Leu Arg Thr Val Ile Leu Ala Pro Thr Arg
1715                1720                1725
```

-continued

Val Val Ala Ala Glu Met Glu Glu Ala Leu Arg Gly Leu Pro Val
1730                1735                1740

Arg Tyr Met Thr Thr Ala Val Asn Val Thr His Ser Gly Thr Glu
1745                1750                1755

Ile Val Asp Leu Met Cys His Ala Thr Phe Thr Ser Arg Leu Leu
1760                1765                1770

Gln Pro Ile Arg Val Pro Asn Tyr Asn Leu Asn Ile Met Asp Glu
1775                1780                1785

Ala His Phe Thr Asp Pro Ser Ile Ala Ala Arg Gly Tyr Ile
1790                1795                1800

Ser Thr Arg Val Glu Met Gly Glu Ala Ala Ile Phe Met Thr
1805                1810                1815

Ala Thr Pro Pro Gly Thr Arg Asp Ala Phe Pro Asp Ser Asn Ser
1820                1825                1830

Pro Ile Met Asp Thr Glu Val Glu Val Pro Glu Arg Ala Trp Ser
1835                1840                1845

Ser Gly Phe Asp Trp Val Thr Asp His Ser Gly Lys Thr Val Trp
1850                1855                1860

Phe Val Pro Ser Val Arg Asn Gly Asn Glu Ile Ala Ala Cys Leu
1865                1870                1875

Thr Lys Ala Gly Lys Arg Val Ile Gln Leu Ser Arg Lys Thr Phe
1880                1885                1890

Glu Thr Glu Phe Gln Lys Thr Lys Asn Gln Glu Trp Asp Phe Val
1895                1900                1905

Ile Thr Thr Asp Ile Ser Glu Met Gly Ala Asn Phe Lys Ala Asp
1910                1915                1920

Arg Val Ile Asp Ser Arg Arg Cys Leu Lys Pro Val Ile Leu Asp
1925                1930                1935

Gly Glu Arg Val Ile Leu Ala Gly Pro Met Pro Val Thr His Ala
1940                1945                1950

Ser Ala Ala Gln Arg Arg Gly Arg Ile Gly Arg Asn Pro Asn Lys
1955                1960                1965

Pro Gly Asp Glu Tyr Met Tyr Gly Gly Gly Cys Ala Glu Thr Asp
1970                1975                1980

Glu Gly His Ala His Trp Leu Glu Ala Arg Met Leu Leu Asp Asn
1985                1990                1995

Ile Tyr Leu Gln Asp Gly Leu Ile Ala Ser Leu Tyr Arg Pro Glu
2000                2005                2010

Ala Asp Lys Val Ala Ala Ile Glu Gly Glu Phe Lys Leu Arg Thr
2015                2020                2025

Glu Gln Arg Lys Thr Phe Val Glu Leu Met Lys Arg Gly Asp Leu
2030                2035                2040

Pro Val Trp Leu Ala Tyr Gln Val Ala Ser Ala Gly Ile Thr Tyr
2045                2050                2055

Thr Asp Arg Arg Trp Cys Phe Asp Gly Thr Thr Asn Asn Thr Ile
2060                2065                2070

Met Glu Asp Ser Val Pro Ala Glu Val Trp Thr Lys Tyr Gly Glu
2075                2080                2085

Lys Arg Val Leu Lys Pro Arg Trp Met Asp Ala Arg Val Cys Ser
2090                2095                2100

Asp His Ala Ala Leu Lys Ser Phe Lys Glu Phe Ala Ala Gly Lys
2105                2110                2115

Arg Gly Ala Ala Leu Gly Val Met Glu Ala Leu Gly Thr Leu Pro

```
                2120                2125                2130
Gly His Met Thr Glu Arg Phe Gln Glu Ala Ile Asp Asn Leu Ala
        2135                2140                2145
Val Leu Met Arg Ala Glu Thr Gly Ser Arg Pro Tyr Lys Ala Ala
        2150                2155                2160
Ala Ala Gln Leu Pro Glu Thr Leu Glu Thr Ile Met Leu Leu Gly
        2165                2170                2175
Leu Leu Gly Thr Val Ser Leu Gly Ile Phe Phe Val Leu Met Arg
        2180                2185                2190
Asn Lys Gly Ile Gly Lys Met Gly Phe Gly Met Val Thr Leu Gly
        2195                2200                2205
Ala Ser Ala Trp Leu Met Trp Leu Ser Glu Ile Glu Pro Ala Arg
        2210                2215                2220
Ile Ala Cys Val Leu Ile Val Val Phe Leu Leu Leu Val Val Leu
        2225                2230                2235
Ile Pro Glu Pro Glu Lys Gln Arg Ser Pro Gln Asp Asn Gln Met
        2240                2245                2250
Ala Ile Ile Ile Met Val Ala Val Gly Leu Leu Gly Leu Ile Thr
        2255                2260                2265
Ala Asn Glu Leu Gly Trp Leu Glu Arg Thr Lys Asn Asp Ile Ala
        2270                2275                2280
His Leu Met Gly Arg Arg Glu Glu Gly Ala Thr Met Gly Phe Ser
        2285                2290                2295
Met Asp Ile Asp Leu Arg Pro Ala Ser Ala Trp Ala Ile Tyr Ala
        2300                2305                2310
Ala Leu Thr Thr Leu Ile Thr Pro Ala Val Gln His Ala Val Thr
        2315                2320                2325
Thr Ser Tyr Asn Asn Tyr Ser Leu Met Ala Met Ala Thr Gln Ala
        2330                2335                2340
Gly Val Leu Phe Gly Met Gly Lys Gly Met Pro Phe Tyr Ala Trp
        2345                2350                2355
Asp Phe Gly Val Pro Leu Leu Met Met Gly Cys Tyr Ser Gln Leu
        2360                2365                2370
Thr Pro Leu Thr Leu Ile Val Ala Ile Ile Leu Leu Val Ala His
        2375                2380                2385
Tyr Met Tyr Leu Ile Pro Gly Leu Gln Ala Ala Ala Arg Ala
        2390                2395                2400
Ala Gln Lys Arg Thr Ala Ala Gly Ile Met Lys Asn Pro Val Val
        2405                2410                2415
Asp Gly Ile Val Val Thr Asp Ile Asp Thr Met Thr Ile Asp Pro
        2420                2425                2430
Gln Val Glu Lys Lys Met Gly Gln Val Leu Leu Ile Ala Val Ala
        2435                2440                2445
Ile Ser Ser Ala Val Leu Leu Arg Thr Ala Trp Gly Trp Gly Glu
        2450                2455                2460
Ala Gly Ala Leu Ile Thr Ala Ala Thr Ser Thr Leu Trp Glu Gly
        2465                2470                2475
Ser Pro Asn Lys Tyr Trp Asn Ser Ser Thr Ala Thr Ser Leu Cys
        2480                2485                2490
Asn Ile Phe Arg Gly Ser Tyr Leu Ala Gly Ala Ser Leu Ile Tyr
        2495                2500                2505
Thr Val Thr Arg Asn Ala Gly Leu Val Lys Arg Arg Gly Gly Gly
        2510                2515                2520
```

-continued

```
Thr Gly Glu Thr Leu Gly Glu Lys Trp Lys Ala Arg Leu Asn Gln
2525                2530                2535

Met Ser Ala Leu Glu Phe Tyr Ser Tyr Lys Lys Ser Gly Ile Thr
2540                2545                2550

Glu Val Cys Arg Glu Glu Ala Arg Arg Ala Leu Lys Asp Gly Val
2555                2560                2565

Ala Thr Gly Gly His Ala Val Ser Arg Gly Ser Ala Lys Leu Arg
2570                2575                2580

Trp Leu Val Glu Arg Gly Tyr Leu Gln Pro His Gly Lys Val Val
2585                2590                2595

Asp Leu Gly Cys Gly Arg Gly Gly Trp Ser Tyr Tyr Ala Ala Thr
2600                2605                2610

Ile Arg Lys Val Gln Glu Val Arg Gly Tyr Thr Lys Gly Gly Pro
2615                2620                2625

Gly His Glu Glu Pro Met Leu Val Gln Ser Tyr Gly Trp Asn Ile
2630                2635                2640

Val Arg Leu Lys Ser Gly Val Asp Val Phe His Met Ala Ala Glu
2645                2650                2655

Pro Cys Asp Thr Leu Leu Cys Asp Ile Gly Glu Ser Ser Ser Ser
2660                2665                2670

Pro Glu Val Glu Glu Thr Arg Thr Leu Arg Val Leu Ser Met Val
2675                2680                2685

Gly Asp Trp Leu Glu Lys Arg Pro Gly Ala Phe Cys Ile Lys Val
2690                2695                2700

Leu Cys Pro Tyr Thr Ser Thr Met Met Glu Thr Met Glu Arg Leu
2705                2710                2715

Gln Arg Arg His Gly Gly Gly Leu Val Arg Val Pro Leu Ser Arg
2720                2725                2730

Asn Ser Thr His Glu Met Tyr Trp Val Ser Gly Ala Lys Ser Asn
2735                2740                2745

Ile Ile Lys Ser Val Ser Thr Thr Ser Gln Leu Leu Leu Gly Arg
2750                2755                2760

Met Asp Gly Pro Arg Arg Pro Val Lys Tyr Glu Glu Asp Val Asn
2765                2770                2775

Leu Gly Ser Gly Thr Arg Ala Val Ala Ser Cys Ala Glu Ala Pro
2780                2785                2790

Asn Met Lys Ile Ile Gly Arg Arg Ile Glu Arg Ile Arg Asn Glu
2795                2800                2805

His Ala Glu Thr Trp Phe Leu Asp Glu Asn His Pro Tyr Arg Thr
2810                2815                2820

Trp Ala Tyr His Gly Ser Tyr Glu Ala Pro Thr Gln Gly Ser Ala
2825                2830                2835

Ser Ser Leu Val Asn Gly Val Val Arg Leu Leu Ser Lys Pro Trp
2840                2845                2850

Asp Val Val Thr Gly Val Thr Gly Ile Ala Met Thr Asp Thr Thr
2855                2860                2865

Pro Tyr Gly Gln Gln Arg Val Phe Lys Glu Lys Val Asp Thr Arg
2870                2875                2880

Val Pro Asp Pro Gln Glu Gly Thr Arg Gln Val Met Asn Met Val
2885                2890                2895

Ser Ser Trp Leu Trp Lys Glu Leu Gly Lys Arg Lys Arg Pro Arg
2900                2905                2910
```

```
Val Cys Thr Lys Glu Glu Phe Ile Asn Lys Val Arg Ser Asn Ala
2915                2920                2925

Ala Leu Gly Ala Ile Phe Glu Glu Lys Glu Trp Lys Thr Ala
2930                2935                2940

Val Glu Ala Val Asn Asp Pro Arg Phe Trp Ala Leu Val Asp Arg
2945                2950                2955

Glu Arg Glu His His Leu Arg Gly Glu Cys His Ser Cys Val Tyr
2960                2965                2970

Asn Met Met Gly Lys Arg Glu Lys Lys Gln Gly Glu Phe Gly Lys
2975                2980                2985

Ala Lys Gly Ser Arg Ala Ile Trp Tyr Met Trp Leu Gly Ala Arg
2990                2995                3000

Phe Leu Glu Phe Glu Ala Leu Gly Phe Leu Asn Glu Asp His Trp
3005                3010                3015

Met Gly Arg Glu Asn Ser Gly Gly Val Glu Gly Leu Gly Leu
3020                3025                3030

Gln Arg Leu Gly Tyr Val Leu Glu Glu Met Ser Gln Ala Pro Gly
3035                3040                3045

Gly Lys Met Tyr Ala Asp Asp Thr Ala Gly Trp Asp Thr Arg Ile
3050                3055                3060

Ser Lys Phe Asp Leu Glu Asn Glu Ala Leu Ile Thr Asn Gln Met
3065                3070                3075

Glu Glu Gly His Arg Thr Leu Ala Leu Ala Val Ile Lys Tyr Thr
3080                3085                3090

Tyr Gln Asn Lys Val Val Lys Val Leu Arg Pro Ala Glu Gly Gly
3095                3100                3105

Lys Thr Val Met Asp Ile Ile Ser Arg Gln Asp Gln Arg Gly Ser
3110                3115                3120

Gly Gln Val Val Thr Tyr Ala Leu Asn Thr Phe Thr Asn Leu Val
3125                3130                3135

Val Gln Leu Ile Arg Asn Met Glu Ala Glu Glu Val Leu Glu Met
3140                3145                3150

Gln Asp Leu Trp Leu Leu Arg Lys Pro Glu Lys Val Thr Arg Trp
3155                3160                3165

Leu Gln Ser Asn Gly Trp Asp Gly Leu Lys Arg Met Ala Val Ser
3170                3175                3180

Gly Asp Asp Cys Val Val Lys Pro Ile Asp Asp Arg Phe Ala His
3185                3190                3195

Ala Leu Arg Phe Leu Asn Asp Met Gly Lys Val Arg Lys Asp Thr
3200                3205                3210

Gln Glu Trp Lys Pro Ser Thr Gly Trp Ser Asn Trp Glu Glu Val
3215                3220                3225

Pro Phe Cys Ser His His Phe Asn Lys Leu Tyr Leu Lys Asp Gly
3230                3235                3240

Arg Ser Ile Val Val Pro Cys Arg His Gln Asp Glu Leu Ile Gly
3245                3250                3255

Arg Ala Arg Val Ser Pro Gly Ala Gly Trp Ser Ile Arg Glu Thr
3260                3265                3270

Ala Cys Leu Ala Lys Ser Tyr Ala Gln Met Trp Gln Leu Leu Tyr
3275                3280                3285

Phe His Arg Arg Asp Leu Arg Leu Met Ala Asn Ala Ile Cys Ser
3290                3295                3300

Ala Val Pro Val Asp Trp Val Pro Thr Gly Arg Thr Thr Trp Ser
```

-continued

```
3305 3310 3315

Ile His Gly Lys Gly Glu Trp Met Thr
3320 3325

<210> SEQ ID NO 24
<211> LENGTH: 852
<212> TYPE: DNA
<213> ORGANISM: Zika virus

<400> SEQUENCE: 24
atgttcacct gttgcaagaa gatgcccggc aagagcatcc agcccgagaa cctggaatac 60
cggatcatgc tgcctgtgca cggctcccag cacagcggca tgatcgtgaa cgacatcggc 120
cacgagacag acgagaaccg ggccaaggtg gaagtgaccc ccaacagccc tagagccgag 180
gccacactgg gcggctttgg atctctgggc ctggactgcg agcctagaac cggcctggat 240
ttcagcgacc tgtactacct gaccatgaac aacaagcact ggctggtgca caaagagtgg 300
ttccacgaca tccccctgcc ctggcatgcc ggcgctgata caggcacacc ccactggaac 360
aacaaagagg ccctggtgga gttcaaggac gcccacgcca agaggcagac cgtggtggtg 420
ctgggatctc aggaaggcgc cgtgcataca gctctggctg gcgccctgga agccgaaatg 480
gatggcgcta agggccggct gtttagcggc cacctgaagt gccggctgaa gatggacaag 540
ctgcggctga agggcgtgtc ctacagcctg tgtaccgccg ccttcacctt caccaaggtg 600
cccgccgaaa ccctgcacgg caccgtgaca gtggaagtgc agtctgccgg caccgacggc 660
ccttgtaaag tgcctgctca gatggccgtg gacatgcaga ccctgacccc tgtgggcaga 720
ctgatcaccg ccaaccccgt gatcaccgag agcaccgaga acagcaagat gatgctggaa 780
ctggaccccc ccttcggcga ctcctacatc gtgatcggcg tgggagacaa gaagatcacc 840
caccactggt ga 852

<210> SEQ ID NO 25
<211> LENGTH: 3423
<212> TYPE: PRT
<213> ORGANISM: Zika virus

<400> SEQUENCE: 25

Met Lys Asn Pro Lys Lys Lys Ser Gly Gly Phe Arg Ile Val Asn Met
1 5 10 15

Leu Lys Arg Gly Val Ala Arg Val Ser Pro Phe Gly Gly Leu Lys Arg
20 25 30

Leu Pro Ala Gly Leu Leu Leu Gly His Gly Pro Ile Arg Met Val Leu
35 40 45

Ala Ile Leu Ala Phe Leu Arg Phe Thr Ala Ile Lys Pro Ser Leu Gly
50 55 60

Leu Ile Asn Arg Trp Gly Ser Val Gly Lys Lys Glu Ala Met Glu Ile
65 70 75 80

Ile Lys Lys Phe Lys Lys Asp Leu Ala Ala Met Leu Arg Ile Ile Asn
85 90 95

Ala Arg Lys Glu Lys Lys Arg Arg Gly Ala Asp Thr Ser Val Gly Ile
100 105 110

Val Gly Leu Leu Leu Thr Thr Ala Met Ala Ala Glu Val Thr Arg Arg
115 120 125

Gly Ser Ala Tyr Tyr Met Tyr Leu Asp Arg Asn Asp Ala Gly Glu Ala
130 135 140

Ile Ser Phe Pro Thr Thr Leu Gly Met Asn Lys Cys Tyr Ile Gln Ile

-continued

```
            145                 150                 155                 160
        Met Asp Leu Gly His Met Cys Asp Ala Thr Met Ser Tyr Glu Cys Pro
                        165                 170                 175
        Met Leu Asp Glu Gly Val Glu Pro Asp Val Asp Cys Trp Cys Asn
                        180                 185                 190
        Thr Thr Ser Thr Trp Val Val Tyr Gly Thr Cys His His Lys Lys Gly
                        195                 200                 205
        Glu Ala Arg Arg Ser Arg Arg Ala Val Thr Leu Pro Ser His Ser Thr
        210                 215                 220
        Arg Lys Leu Gln Thr Arg Ser Gln Thr Trp Leu Glu Ser Arg Glu Tyr
        225                 230                 235                 240
        Thr Lys His Leu Ile Arg Val Glu Asn Trp Ile Phe Arg Asn Pro Gly
                        245                 250                 255
        Phe Ala Leu Ala Ala Ala Ala Ile Ala Trp Leu Leu Gly Ser Ser Thr
                        260                 265                 270
        Ser Gln Lys Val Ile Tyr Leu Val Met Ile Leu Leu Ile Ala Pro Ala
                        275                 280                 285
        Tyr Ser Ile Arg Cys Ile Gly Val Ser Asn Arg Asp Phe Val Glu Gly
                        290                 295                 300
        Met Ser Gly Gly Thr Trp Val Asp Val Val Leu Glu His Gly Gly Cys
        305                 310                 315                 320
        Val Thr Val Met Ala Gln Asp Lys Pro Thr Val Asp Ile Glu Leu Val
                        325                 330                 335
        Thr Thr Thr Val Ser Asn Met Ala Glu Val Arg Ser Tyr Cys Tyr Glu
                        340                 345                 350
        Ala Ser Ile Ser Asp Met Ala Ser Asp Ser Arg Cys Pro Thr Gln Gly
                        355                 360                 365
        Glu Ala Tyr Leu Asp Lys Gln Ser Asp Thr Gln Tyr Val Cys Lys Arg
                        370                 375                 380
        Thr Leu Val Asp Arg Gly Trp Gly Asn Gly Cys Gly Leu Phe Gly Lys
        385                 390                 395                 400
        Gly Ser Leu Val Thr Cys Ala Lys Phe Ala Cys Ser Lys Lys Met Thr
                        405                 410                 415
        Gly Lys Ser Ile Gln Pro Glu Asn Leu Glu Tyr Arg Ile Met Leu Ser
                        420                 425                 430
        Val His Gly Ser Gln His Ser Gly Met Ile Val Asn Asp Thr Gly His
                        435                 440                 445
        Glu Thr Asp Glu Asn Arg Ala Lys Val Glu Ile Thr Pro Asn Ser Pro
                        450                 455                 460
        Arg Ala Glu Ala Thr Leu Gly Gly Phe Gly Ser Leu Gly Leu Asp Cys
        465                 470                 475                 480
        Glu Pro Arg Thr Gly Leu Asp Phe Ser Asp Leu Tyr Tyr Leu Thr Met
                        485                 490                 495
        Asn Asn Lys His Trp Leu Val His Lys Glu Trp Phe His Asp Ile Pro
                        500                 505                 510
        Leu Pro Trp His Ala Gly Ala Asp Thr Gly Thr Pro His Trp Asn Asn
                        515                 520                 525
        Lys Glu Ala Leu Val Glu Phe Lys Asp Ala His Ala Lys Arg Gln Thr
                        530                 535                 540
        Val Val Val Leu Gly Ser Gln Glu Gly Ala Val His Thr Ala Leu Ala
        545                 550                 555                 560
        Gly Ala Leu Glu Ala Glu Met Asp Gly Ala Lys Gly Arg Leu Ser Ser
                        565                 570                 575
```

```
Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
            595                 600                 605

Ala Glu Thr Leu His Gly Thr Val Thr Val Glu Val Gln Tyr Ala Gly
610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
            675                 680                 685

His Trp His Arg Ser Gly Ser Thr Ile Gly Lys Ala Phe Glu Ala Thr
            690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
            755                 760                 765

Thr Lys Asn Gly Ser Ile Ser Leu Met Cys Leu Ala Leu Gly Gly Val
            770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
            835                 840                 845

Cys Gly Ile Ser Ser Val Ser Arg Met Glu Asn Ile Met Trp Arg Ser
850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
            915                 920                 925

Val Asp Gly Asp Thr Leu Lys Glu Cys Pro Leu Lys His Arg Ala Trp
            930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990
```

-continued

```
Gly Tyr Trp Ile Glu Ser Glu Lys Asn Asp Thr Trp Arg Leu Lys Arg
            995                 1000                1005

Ala His Leu Ile Glu Met Lys Thr Cys Glu Trp Pro Lys Ser His
    1010                1015                1020

Thr Leu Trp Thr Asp Gly Ile Glu Glu Ser Asp Leu Ile Ile Pro
    1025                1030                1035

Lys Ser Leu Ala Gly Pro Leu Ser His His Asn Thr Arg Glu Gly
    1040                1045                1050

Tyr Arg Thr Gln Met Lys Gly Pro Trp His Ser Glu Glu Leu Glu
    1055                1060                1065

Ile Arg Phe Glu Glu Cys Pro Gly Thr Lys Val His Val Glu Glu
    1070                1075                1080

Thr Cys Gly Thr Arg Gly Pro Ser Leu Arg Ser Thr Thr Ala Ser
    1085                1090                1095

Gly Arg Val Ile Glu Glu Trp Cys Cys Arg Glu Cys Thr Met Pro
    1100                1105                1110

Pro Leu Ser Phe Arg Ala Lys Asp Gly Cys Trp Tyr Gly Met Glu
    1115                1120                1125

Ile Arg Pro Arg Lys Glu Pro Glu Ser Asn Leu Val Arg Ser Met
    1130                1135                1140

Val Thr Ala Gly Ser Thr Asp His Met Asp His Phe Ser Leu Gly
    1145                1150                1155

Val Leu Val Ile Leu Leu Met Val Gln Glu Gly Leu Lys Lys Arg
    1160                1165                1170

Met Thr Thr Lys Ile Ile Ile Ser Thr Ser Met Ala Val Leu Val
    1175                1180                1185

Ala Met Ile Leu Gly Gly Phe Ser Met Ser Asp Leu Ala Lys Leu
    1190                1195                1200

Ala Ile Leu Met Gly Ala Thr Phe Ala Glu Met Asn Thr Gly Gly
    1205                1210                1215

Asp Val Ala His Leu Ala Leu Ile Ala Ala Phe Lys Val Arg Pro
    1220                1225                1230

Ala Leu Leu Val Ser Phe Ile Phe Arg Ala Asn Trp Thr Pro Arg
    1235                1240                1245

Glu Ser Met Leu Leu Ala Leu Ala Ser Cys Leu Leu Gln Thr Ala
    1250                1255                1260

Ile Ser Ala Leu Glu Gly Asp Leu Met Val Leu Ile Asn Gly Phe
    1265                1270                1275

Ala Leu Ala Trp Leu Ala Ile Arg Ala Met Val Val Pro Arg Thr
    1280                1285                1290

Asp Asn Ile Thr Leu Ala Ile Leu Ala Ala Leu Thr Pro Leu Ala
    1295                1300                1305

Arg Gly Thr Leu Leu Val Ala Trp Arg Ala Gly Leu Ala Thr Cys
    1310                1315                1320

Gly Gly Phe Met Leu Leu Ser Leu Lys Gly Lys Gly Ser Val Lys
    1325                1330                1335

Lys Asn Leu Pro Phe Val Met Ala Leu Gly Leu Thr Ala Val Arg
    1340                1345                1350

Leu Val Asp Pro Ile Asn Val Val Gly Leu Leu Leu Leu Thr Arg
    1355                1360                1365

Ser Gly Lys Arg Ser Trp Pro Pro Ser Glu Val Leu Thr Ala Val
    1370                1375                1380

Gly Leu Ile Cys Ala Leu Ala Gly Gly Phe Ala Lys Ala Asp Ile
```

-continued

```
            1385                1390                1395

Glu Met Ala Gly Pro Met Ala Ala Val Gly Leu Leu Ile Val Ser
            1400                1405                1410

Tyr Val Val Ser Gly Lys Ser Val Asp Met Tyr Ile Glu Arg Ala
            1415                1420                1425

Gly Asp Ile Thr Trp Glu Lys Asp Ala Glu Val Thr Gly Asn Ser
            1430                1435                1440

Pro Arg Leu Asp Val Ala Leu Asp Glu Ser Gly Asp Phe Ser Leu
            1445                1450                1455

Val Glu Asp Asp Gly Pro Pro Met Arg Glu Ile Ile Leu Lys Val
            1460                1465                1470

Val Leu Met Thr Ile Cys Gly Met Asn Pro Ile Ala Ile Pro Phe
            1475                1480                1485

Ala Ala Gly Ala Trp Tyr Val Tyr Val Lys Thr Gly Lys Arg Ser
            1490                1495                1500

Gly Ala Leu Trp Asp Val Pro Ala Pro Lys Glu Val Lys Lys Gly
            1505                1510                1515

Glu Thr Thr Asp Gly Val Tyr Arg Val Met Thr Arg Arg Leu Leu
            1520                1525                1530

Gly Ser Thr Gln Val Gly Val Gly Val Met Gln Glu Gly Val Phe
            1535                1540                1545

His Thr Met Trp His Val Thr Lys Gly Ser Ala Leu Arg Ser Gly
            1550                1555                1560

Glu Gly Arg Leu Asp Pro Tyr Trp Gly Asp Val Lys Gln Asp Leu
            1565                1570                1575

Val Ser Tyr Cys Gly Pro Trp Lys Leu Asp Ala Ala Trp Asp Gly
            1580                1585                1590

His Ser Glu Val Gln Leu Leu Ala Val Pro Pro Gly Glu Arg Ala
            1595                1600                1605

Arg Asn Ile Gln Thr Leu Pro Gly Ile Phe Lys Thr Lys Asp Gly
            1610                1615                1620

Asp Ile Gly Ala Val Ala Leu Asp Tyr Pro Ala Gly Thr Ser Gly
            1625                1630                1635

Ser Pro Ile Leu Asp Lys Cys Gly Arg Val Ile Gly Leu Tyr Gly
            1640                1645                1650

Asn Gly Val Val Ile Lys Asn Gly Ser Tyr Val Ser Ala Ile Thr
            1655                1660                1665

Gln Gly Arg Arg Glu Glu Thr Pro Val Glu Cys Phe Glu Pro
            1670                1675                1680

Ser Met Leu Lys Lys Lys Gln Leu Thr Val Leu Asp Leu His Pro
            1685                1690                1695

Gly Ala Gly Lys Thr Arg Arg Val Leu Pro Glu Ile Val Arg Glu
            1700                1705                1710

Ala Ile Lys Thr Arg Leu Arg Thr Val Ile Leu Ala Pro Thr Arg
            1715                1720                1725

Val Val Ala Ala Glu Met Glu Glu Ala Leu Arg Gly Leu Pro Val
            1730                1735                1740

Arg Tyr Met Thr Thr Ala Val Asn Val Thr His Ser Gly Thr Glu
            1745                1750                1755

Ile Val Asp Leu Met Cys His Ala Thr Phe Thr Ser Arg Leu Leu
            1760                1765                1770

Gln Pro Ile Arg Val Pro Asn Tyr Asn Leu Tyr Ile Met Asp Glu
            1775                1780                1785
```

-continued

```
Ala His Phe Thr Asp Pro Ser Ser Ile Ala Ala Arg Gly Tyr Ile
1790                1795                1800

Ser Thr Arg Val Glu Met Gly Glu Ala Ala Ile Phe Met Thr
1805                1810                1815

Ala Thr Pro Pro Gly Thr Arg Asp Ala Phe Pro Asp Ser Asn Ser
1820                1825                1830

Pro Ile Met Asp Thr Glu Val Glu Val Pro Glu Arg Ala Trp Ser
1835                1840                1845

Ser Gly Phe Asp Trp Val Thr Asp His Ser Gly Lys Thr Val Trp
1850                1855                1860

Phe Val Pro Ser Val Arg Asn Gly Asn Glu Ile Ala Ala Cys Leu
1865                1870                1875

Thr Lys Ala Gly Lys Arg Val Ile Gln Leu Ser Arg Lys Thr Phe
1880                1885                1890

Glu Thr Glu Phe Gln Lys Thr Lys His Gln Glu Trp Asp Phe Val
1895                1900                1905

Val Thr Thr Asp Ile Ser Glu Met Gly Ala Asn Phe Lys Ala Asp
1910                1915                1920

Arg Val Ile Asp Ser Arg Arg Cys Leu Lys Pro Val Ile Leu Asp
1925                1930                1935

Gly Glu Arg Val Ile Leu Ala Gly Pro Met Pro Val Thr His Ala
1940                1945                1950

Ser Ala Ala Gln Arg Arg Gly Arg Ile Gly Arg Asn Pro Asn Lys
1955                1960                1965

Pro Gly Asp Glu Tyr Leu Tyr Gly Gly Gly Cys Ala Glu Thr Asp
1970                1975                1980

Glu Asp His Ala His Trp Leu Glu Ala Arg Met Leu Leu Asp Asn
1985                1990                1995

Ile Tyr Leu Gln Asp Gly Leu Ile Ala Ser Leu Tyr Arg Pro Glu
2000                2005                2010

Ala Asp Lys Val Ala Ala Ile Glu Gly Glu Phe Lys Leu Arg Thr
2015                2020                2025

Glu Gln Arg Lys Thr Phe Val Glu Leu Met Lys Arg Gly Asp Leu
2030                2035                2040

Pro Val Trp Leu Ala Tyr Gln Val Ala Ser Ala Gly Ile Thr Tyr
2045                2050                2055

Thr Asp Arg Arg Trp Cys Phe Asp Gly Thr Thr Asn Asn Thr Ile
2060                2065                2070

Met Glu Asp Ser Val Pro Ala Glu Val Trp Thr Arg His Gly Glu
2075                2080                2085

Lys Arg Val Leu Lys Pro Arg Trp Met Asp Ala Arg Val Cys Ser
2090                2095                2100

Asp His Ala Ala Leu Lys Ser Phe Lys Glu Phe Ala Ala Gly Lys
2105                2110                2115

Arg Gly Ala Ala Phe Gly Val Met Glu Ala Leu Gly Thr Leu Pro
2120                2125                2130

Gly His Met Thr Glu Arg Phe Gln Glu Ala Ile Asp Asn Leu Ala
2135                2140                2145

Val Leu Met Arg Ala Glu Thr Gly Ser Arg Pro Tyr Lys Ala Ala
2150                2155                2160

Ala Ala Gln Leu Pro Glu Thr Leu Glu Thr Ile Met Leu Leu Gly
2165                2170                2175
```

-continued

Leu Leu Gly Thr Val Ser Leu Gly Ile Phe Phe Val Leu Met Arg
    2180            2185                2190

Asn Lys Gly Ile Gly Lys Met Gly Phe Gly Met Val Thr Leu Gly
    2195            2200                2205

Ala Ser Ala Trp Leu Met Trp Leu Ser Glu Ile Glu Pro Ala Arg
    2210            2215                2220

Ile Ala Cys Val Leu Ile Val Val Phe Leu Leu Leu Val Val Leu
    2225            2230                2235

Ile Pro Glu Pro Glu Lys Gln Arg Ser Pro Gln Asp Asn Gln Met
    2240            2245                2250

Ala Ile Ile Ile Met Val Ala Val Gly Leu Leu Gly Leu Ile Thr
    2255            2260                2265

Ala Asn Glu Leu Gly Trp Leu Glu Arg Thr Lys Ser Asp Leu Ser
    2270            2275                2280

His Leu Met Gly Arg Arg Glu Glu Gly Ala Thr Ile Gly Phe Ser
    2285            2290                2295

Met Asp Ile Asp Leu Arg Pro Ala Ser Ala Trp Ala Ile Tyr Ala
    2300            2305                2310

Ala Leu Thr Thr Phe Ile Thr Pro Ala Val Gln His Ala Val Thr
    2315            2320                2325

Thr Ser Tyr Asn Asn Tyr Ser Leu Met Ala Met Ala Thr Gln Ala
    2330            2335                2340

Gly Val Leu Phe Gly Met Gly Lys Gly Met Pro Phe Tyr Ala Trp
    2345            2350                2355

Asp Phe Gly Val Pro Leu Leu Met Ile Gly Cys Tyr Ser Gln Leu
    2360            2365                2370

Thr Pro Leu Thr Leu Ile Val Ala Ile Ile Leu Leu Val Ala His
    2375            2380                2385

Tyr Met Tyr Leu Ile Pro Gly Leu Gln Ala Ala Ala Arg Ala
    2390            2395                2400

Ala Gln Lys Arg Thr Ala Ala Gly Ile Met Lys Asn Pro Val Val
    2405            2410                2415

Asp Gly Ile Val Val Thr Asp Ile Asp Thr Met Thr Ile Asp Pro
    2420            2425                2430

Gln Val Glu Lys Lys Met Gly Gln Val Leu Leu Ile Ala Val Ala
    2435            2440                2445

Val Ser Ser Ala Ile Leu Ser Arg Thr Ala Trp Gly Trp Gly Glu
    2450            2455                2460

Ala Gly Ala Leu Ile Thr Ala Ala Thr Ser Thr Leu Trp Glu Gly
    2465            2470                2475

Ser Pro Asn Lys Tyr Trp Asn Ser Ser Thr Ala Thr Ser Leu Cys
    2480            2485                2490

Asn Ile Phe Arg Gly Ser Tyr Leu Ala Gly Ala Ser Leu Ile Tyr
    2495            2500                2505

Thr Val Thr Arg Asn Ala Gly Leu Val Lys Arg Arg Gly Gly Gly
    2510            2515                2520

Thr Gly Glu Thr Leu Gly Glu Lys Trp Lys Ala Arg Leu Asn Gln
    2525            2530                2535

Met Ser Ala Leu Glu Phe Tyr Ser Tyr Lys Lys Ser Gly Ile Thr
    2540            2545                2550

Glu Val Cys Arg Glu Glu Ala Arg Arg Ala Leu Lys Asp Gly Val
    2555            2560                2565

Ala Thr Gly Gly His Ala Val Ser Arg Gly Ser Ala Lys Leu Arg

```
                     2570                2575                2580

Trp Leu Val Glu Arg Gly Tyr Leu Gln Pro Tyr Gly Lys Val Ile
    2585                2590                2595

Asp Leu Gly Cys Gly Arg Gly Gly Trp Ser Tyr Tyr Ala Ala Thr
    2600                2605                2610

Ile Arg Lys Val Gln Glu Val Lys Gly Tyr Thr Lys Gly Gly Pro
    2615                2620                2625

Gly His Glu Glu Pro Val Leu Val Gln Ser Tyr Gly Trp Asn Ile
    2630                2635                2640

Val Arg Leu Lys Ser Gly Val Asp Val Phe His Met Ala Ala Glu
    2645                2650                2655

Pro Cys Asp Thr Leu Leu Cys Asp Ile Gly Glu Ser Ser Ser Ser
    2660                2665                2670

Pro Glu Val Glu Glu Ala Arg Thr Leu Arg Val Leu Ser Met Val
    2675                2680                2685

Gly Asp Trp Leu Glu Lys Arg Pro Gly Ala Phe Cys Ile Lys Val
    2690                2695                2700

Leu Cys Pro Tyr Thr Ser Thr Met Met Glu Thr Leu Glu Arg Leu
    2705                2710                2715

Gln Arg Arg Tyr Gly Gly Gly Leu Val Arg Val Pro Leu Ser Arg
    2720                2725                2730

Asn Ser Thr His Glu Met Tyr Trp Val Ser Gly Ala Lys Ser Asn
    2735                2740                2745

Thr Ile Lys Ser Val Ser Thr Thr Ser Gln Leu Leu Leu Gly Arg
    2750                2755                2760

Met Asp Gly Pro Arg Arg Pro Val Lys Tyr Glu Glu Asp Val Asp
    2765                2770                2775

Leu Gly Ser Gly Thr Arg Ala Val Val Ser Cys Ala Glu Ala Pro
    2780                2785                2790

Asn Met Lys Ile Ile Gly Asn Arg Ile Glu Arg Ile Arg Ser Glu
    2795                2800                2805

His Ala Glu Thr Trp Phe Phe Asp Glu Asn His Pro Tyr Arg Thr
    2810                2815                2820

Trp Ala Tyr His Gly Ser Tyr Glu Ala Pro Thr Gln Gly Ser Ala
    2825                2830                2835

Ser Ser Leu Ile Asn Gly Val Val Arg Leu Leu Ser Lys Pro Trp
    2840                2845                2850

Asp Val Val Thr Gly Val Thr Gly Ile Ala Met Thr Asp Thr Thr
    2855                2860                2865

Pro Tyr Gly Gln Gln Arg Val Phe Lys Glu Lys Val Asp Thr Arg
    2870                2875                2880

Val Pro Asp Pro Gln Glu Gly Thr Arg Gln Val Met Ser Met Val
    2885                2890                2895

Ser Ser Trp Leu Trp Lys Glu Leu Gly Lys His Lys Arg Pro Arg
    2900                2905                2910

Val Cys Thr Lys Glu Glu Phe Ile Asn Lys Val Arg Ser Asn Ala
    2915                2920                2925

Ala Leu Gly Ala Ile Phe Glu Glu Glu Lys Glu Trp Lys Thr Ala
    2930                2935                2940

Val Glu Ala Val Asn Asp Pro Arg Phe Trp Ala Leu Val Asp Lys
    2945                2950                2955

Glu Arg Glu His His Leu Arg Gly Glu Cys Gln Ser Cys Val Tyr
    2960                2965                2970
```

```
Asn Met Met Gly Lys Arg Glu Lys Lys Gln Gly Glu Phe Gly Lys
2975                 2980                2985

Ala Lys Gly Ser Arg Ala Ile Trp Tyr Met Trp Leu Gly Ala Arg
2990                 2995                3000

Phe Leu Glu Phe Glu Ala Leu Gly Phe Leu Asn Glu Asp His Trp
3005                 3010                3015

Met Gly Arg Glu Asn Ser Gly Gly Val Gly Leu Gly Leu
3020                 3025                3030

Gln Arg Leu Gly Tyr Val Leu Glu Glu Met Ser Arg Ile Pro Gly
3035                 3040                3045

Gly Arg Met Tyr Ala Asp Asp Thr Ala Gly Trp Asp Thr Arg Ile
3050                 3055                3060

Ser Arg Phe Asp Leu Glu Asn Glu Ala Leu Ile Thr Asn Gln Met
3065                 3070                3075

Glu Lys Gly His Arg Ala Leu Ala Leu Ala Ile Ile Lys Tyr Thr
3080                 3085                3090

Tyr Gln Asn Lys Val Val Lys Val Leu Arg Pro Ala Glu Lys Gly
3095                 3100                3105

Lys Thr Val Met Asp Ile Ile Ser Arg Gln Asp Gln Arg Gly Ser
3110                 3115                3120

Gly Gln Val Val Thr Tyr Ala Leu Asn Thr Phe Thr Asn Leu Val
3125                 3130                3135

Val Gln Leu Ile Arg Asn Met Glu Ala Glu Glu Val Leu Glu Met
3140                 3145                3150

Gln Asp Leu Trp Leu Leu Arg Arg Ser Glu Lys Val Thr Asn Trp
3155                 3160                3165

Leu Gln Ser Asn Gly Trp Asp Arg Leu Lys Arg Met Ala Val Ser
3170                 3175                3180

Gly Asp Asp Cys Val Val Lys Pro Ile Asp Asp Arg Phe Ala His
3185                 3190                3195

Ala Leu Arg Phe Leu Asn Asp Met Gly Lys Val Arg Lys Asp Thr
3200                 3205                3210

Gln Glu Trp Lys Pro Ser Thr Gly Trp Asp Asn Trp Glu Glu Val
3215                 3220                3225

Pro Phe Cys Ser His His Phe Asn Lys Leu His Leu Lys Asp Gly
3230                 3235                3240

Arg Ser Ile Val Val Pro Cys Arg His Gln Asp Glu Leu Ile Gly
3245                 3250                3255

Arg Ala Arg Val Ser Pro Gly Ala Gly Trp Ser Ile Arg Glu Thr
3260                 3265                3270

Ala Cys Leu Ala Lys Ser Tyr Ala Gln Met Trp Gln Leu Leu Tyr
3275                 3280                3285

Phe His Arg Arg Asp Leu Arg Leu Met Ala Asn Ala Ile Cys Ser
3290                 3295                3300

Ser Val Pro Val Asp Trp Val Pro Thr Gly Arg Thr Thr Trp Ser
3305                 3310                3315

Ile His Gly Lys Gly Glu Trp Met Thr Thr Glu Asp Met Leu Val
3320                 3325                3330

Val Trp Asn Arg Val Trp Ile Glu Glu Asn Asp His Met Glu Asp
3335                 3340                3345

Lys Thr Pro Val Thr Lys Trp Thr Asp Ile Pro Tyr Leu Gly Lys
3350                 3355                3360
```

```
Arg Glu Asp Leu Trp Cys Gly Ser Leu Ile Gly His Arg Pro Arg
    3365                3370                3375

Thr Thr Trp Ala Glu Asn Ile Lys Asn Thr Val Asn Met Val Arg
    3380                3385                3390

Arg Ile Ile Gly Asp Glu Glu Lys Tyr Met Asp Tyr Leu Ser Thr
    3395                3400                3405

Gln Val Arg Tyr Leu Gly Glu Glu Gly Ser Thr Pro Gly Val Leu
    3410                3415                3420

<210> SEQ ID NO 26
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gccgccacca tgttcacctg ttgcaagaag atgcccggca agagcatcca gcccgagaac      60
ctggaatacc ggatcatgct gcctgtgcac ggctcccagc acagcggcat gatcgtgaac     120
gacatcggcc acgagacaga cgagaaccgg gccaaggtgg aagtgacccc caacagccct     180
agagccgagg ccacactggg cggctttgga tctctgggcc tggactgcga gcctagaacc     240
ggcctggatt tcagcgacct gtactacctg accatgaaca acaagcactg gctggtgcac     300
aaagagtggt tccacgacat cccctgccc tggcatgccg gcgctgatac aggcacaccc     360
cactggaaca acaagaggc cctggtggag ttcaaggacg cccacgccaa gaggcagacc     420
gtggtggtgc tgggatctca ggaaggcgcc gtgcatacag ctctggctgg cgccctggaa     480
gccgaaatgg atggcgctaa gggccggctg tttagcggcc acctgaagtg ccggctgaag     540
atggacaagc tgcggctgaa gggcgtgtcc tacagcctgt gtaccgccgc cttcaccttc     600
accaaggtgc ccgccgaaac cctgcacggc accgtgacag tggaagtgca gtctgccggc     660
accgacggcc cttgtaaagt gcctgctcag atggccgtgg acatgcagac cctgaccct      720 gtgggcagac tgatcaccgc caacccccgtg atcaccgaga gcaccgagaa cagcaagatg     780
atgctggaac tggaccccccc cttcggcgac tcctacatcg tgatcggcgt gggagacaag     840
aagatcaccc ccaccactggtg a                                              861

<210> SEQ ID NO 27
<211> LENGTH: 283
<212> TYPE: PRT
<213> ORGANISM: Zika virus

<400> SEQUENCE: 27

Met Phe Thr Cys Cys Lys Lys Met Pro Gly Lys Ser Ile Gln Pro Glu
1               5                   10                  15

Asn Leu Glu Tyr Arg Ile Met Leu Pro Val His Gly Ser Gln His Ser
                20                  25                  30

Gly Met Ile Val Asn Asp Ile Gly His Glu Thr Asp Glu Asn Arg Ala
            35                  40                  45

Lys Val Glu Val Thr Pro Asn Ser Pro Arg Ala Glu Ala Thr Leu Gly
        50                  55                  60

Gly Phe Gly Ser Leu Gly Leu Asp Cys Glu Pro Arg Thr Gly Leu Asp
65                  70                  75                  80

Phe Ser Asp Leu Tyr Tyr Leu Thr Met Asn Asn Lys His Trp Leu Val
                85                  90                  95
```

```
His Lys Glu Trp Phe His Asp Ile Pro Leu Pro Trp His Ala Gly Ala
                100                 105                 110
Asp Thr Gly Thr Pro His Trp Asn Asn Lys Glu Ala Leu Val Glu Phe
            115                 120                 125
Lys Asp Ala His Ala Lys Arg Gln Thr Val Val Leu Gly Ser Gln
130                 135                 140
Glu Gly Ala Val His Thr Ala Leu Ala Gly Ala Leu Glu Ala Glu Met
145                 150                 155                 160
Asp Gly Ala Lys Gly Arg Leu Phe Ser Gly His Leu Lys Cys Arg Leu
                165                 170                 175
Lys Met Asp Lys Leu Arg Leu Lys Gly Val Ser Tyr Ser Leu Cys Thr
            180                 185                 190
Ala Ala Phe Thr Phe Thr Lys Val Pro Ala Glu Thr Leu His Gly Thr
        195                 200                 205
Val Thr Val Glu Val Gln Ser Ala Gly Thr Asp Gly Pro Cys Lys Val
    210                 215                 220
Pro Ala Gln Met Ala Val Asp Met Gln Thr Leu Thr Pro Val Gly Arg
225                 230                 235                 240
Leu Ile Thr Ala Asn Pro Val Ile Thr Glu Ser Thr Glu Asn Ser Lys
                245                 250                 255
Met Met Leu Glu Leu Asp Pro Pro Phe Gly Asp Ser Tyr Ile Val Ile
            260                 265                 270
Gly Val Gly Asp Lys Lys Ile Thr His His Trp
        275                 280

<210> SEQ ID NO 28
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gccgccacca tgttcacctg ttgcaagaag atgcccggca agagcatcca gcccgagaac      60
ctggaatacc gggacatgct gcctgtgcac ggctctcagc acagcggcat gatcgtgaac     120
gacatcggcc acgagacaga cgagaaccgg gccaaggtgg aagtgacccc caacagccct     180
agagccgagg ccacactggg cggctttgga tctctgggcc tggactgcga gcctagaacc     240
ggcctggatt tcagcgacct gtactacctg accatgaaca acaagcactg gctggtgcac     300
aaagagtggt tccacgacat cccccctgccc tggcatgccg gcgctgatac aggcacaccc     360
cactggaaca acaaagaggc cctggtggag ttcaaggacg cccacgccaa gaggcagacc     420
gtggtggtgc tgggatctca ggaaggcgcc gtgcatacag ctctggctgg cgccctggaa     480
gccgaaatgg atggcgctaa gggccggctg tttagcggcc acctgaagtg ccggacaag      540
atggacaagc tgcggctgaa gggcgtgtcc tacagcctgt gtaccgccgc cttcaccttc     600
accaaggtgc ccgccgaaac cctgcacggc accgtgacag tggaagtgca gtctgccggc     660
accgacggcc cttgtaaagt gcctgctcag atggccgtgg acatgcagac cctgaccct      720
gtgggcagag acatcaccgc caaccccgtg atcaccgaga gcaccgagaa cagcaagatg     780
atgctggaac tggacccccc cttcggcgac tcctacatcg tgatcggcgt gggagacaag     840
aagatcaccc accactggtg a                                              861

<210> SEQ ID NO 29
```

<211> LENGTH: 283
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Met Phe Thr Cys Cys Lys Lys Met Pro Gly Lys Ser Ile Gln Pro Glu
1               5                   10                  15
Asn Leu Glu Tyr Arg Asp Met Leu Pro Val His Gly Ser Gln His Ser
            20                  25                  30
Gly Met Ile Val Asn Asp Ile Gly His Glu Thr Asp Glu Asn Arg Ala
        35                  40                  45
Lys Val Glu Val Thr Pro Asn Ser Pro Arg Ala Glu Ala Thr Leu Gly
    50                  55                  60
Gly Phe Gly Ser Leu Gly Leu Asp Cys Glu Pro Arg Thr Gly Leu Asp
65                  70                  75                  80
Phe Ser Asp Leu Tyr Tyr Leu Thr Met Asn Asn Lys His Trp Leu Val
                85                  90                  95
His Lys Glu Trp Phe His Asp Ile Pro Leu Pro Trp His Ala Gly Ala
            100                 105                 110
Asp Thr Gly Thr Pro His Trp Asn Asn Lys Glu Ala Leu Val Glu Phe
        115                 120                 125
Lys Asp Ala His Ala Lys Arg Gln Thr Val Val Leu Gly Ser Gln
    130                 135                 140
Glu Gly Ala Val His Thr Ala Leu Ala Gly Ala Leu Glu Ala Glu Met
145                 150                 155                 160
Asp Gly Ala Lys Gly Arg Leu Phe Ser Gly His Leu Lys Cys Arg Asp
                165                 170                 175
Lys Met Asp Lys Leu Arg Leu Lys Gly Val Ser Tyr Ser Leu Cys Thr
            180                 185                 190
Ala Ala Phe Thr Phe Thr Lys Val Pro Ala Glu Thr Leu His Gly Thr
        195                 200                 205
Val Thr Val Glu Val Gln Ser Ala Gly Thr Asp Gly Pro Cys Lys Val
    210                 215                 220
Pro Ala Gln Met Ala Val Asp Met Gln Thr Leu Thr Pro Val Gly Arg
225                 230                 235                 240
Asp Ile Thr Ala Asn Pro Val Ile Thr Glu Ser Thr Glu Asn Ser Lys
                245                 250                 255
Met Met Leu Glu Leu Asp Pro Pro Phe Gly Asp Ser Tyr Ile Val Ile
            260                 265                 270
Gly Val Gly Asp Lys Lys Ile Thr His His Trp
        275                 280

<210> SEQ ID NO 30
<211> LENGTH: 1620
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30
gccgccacca tgctgaccag ccagaaagtg atctacctcg tgatgatcgt gctgattgtg      60
cccgcctaca gcatcagctg catcggcgtg tccaaccggg acctggtgga aggcatgtct     120
ggcggcacat gggtggacgt ggtgctggaa catggcggct gcgtgacaga gatggcccag    180

```
gacaagccca ccgtggacat cgagctcgtg accatgaccg tgtccaatat ggccgaagtg      240
cggagctact gctacgaggc cagcctgagc gatatggcca cgccagcag atgtcctacc       300 cagggcgagc ccagcctgga caagcagagc gatacacaga gcgtgtgcaa gcggaccctg      360
ggcgatagag gctggggcaa tggctgcggc atcttcggca agggcagcct cgtgacctgc      420
agcaagttca cctgttgcaa gaagatgccc ggcaagagca tccagcccga gaacctggaa      480
taccggatca tgctgcctgt gcacggctcc cagcacagcg catgatcgt gaacgacatc       540 ggccacgaga cagacgagaa ccgggccaag gtggaagtga cccccaacag ccctagagcc      600
gaggccacac tgggcggctt tggatctctg gcctggact gcgagcctag aaccggcctg       660
gatttcagcg acctgtacta cctgaccatg aacaacaagc actggctggt gcacaaagag      720
tggttccacg acatccccct gccctggcat gccggcgctg atacaggcac ccccactgg       780 aacaacaaag aggctctggt ggaattcaag gacgccacg ccaagcggca gaccgtggtg       840
gtgctgggat ctcaggaagg cgccgtgcat acagctctgg ctggcgccct ggaagccgaa      900
atggatggcc caagggcag gctgtttagc ggccacctga agtgccggct gaagatggac       960
aagctgcggc tgaagggcgt gtcctacagc ctgtgtaccg ccgccttcac cttcaccaag      1020
gtgcccgccg aaaccctgca cggcaccgtg acagtggaag tgcagagcgc cggaaccgac      1080
ggcccttgta agtgcctgc ccagatggcc gtggatatgc agaccctgac ccccgtgggc       1140
agactgatca ccgccaaccc tgtgatcacc gagagcaccg agaacagcaa gatgatgctg      1200
gaactggacc cccccttcgg cgactcctac atcgtgatcg gcgtgggaga caagaagatc      1260
acccaccact ggcacagaag cggcagcacc atcggcaagg cctttgaggc tacagtgcgg      1320
ggagccaaga gaatggccgt gctgggggat accgcctggg attttggctc tgtgggcggc      1380
gtgttcaact ccctgggcaa gggaatccac cagatcttcg gcgctgcctt caagagcctg      1440
ttcggcggca tgagctggtt cagccagatc ctgatcggca ccctgctcgt gtggctgggc      1500
ctgaacacca gaacggcag catctccctg acctgcctgg ctctgggcgg agtgatgatc       1560
ttcctgagca ccgccgtgtc cgccgatgtg ggctgtagcg tggacttcag caagaagtga     1620
```

<210> SEQ ID NO 31
<211> LENGTH: 536
<212> TYPE: PRT
<213> ORGANISM: Zika virus

<400> SEQUENCE: 31

```
Met Leu Thr Ser Gln Lys Val Ile Tyr Leu Val Met Ile Val Leu Ile
1               5                   10                  15

Val Pro Ala Tyr Ser Ile Ser Cys Ile Gly Val Ser Asn Arg Asp Leu
            20                  25                  30

Val Glu Gly Met Ser Gly Gly Thr Trp Val Asp Val Val Leu Glu His
        35                  40                  45

Gly Gly Cys Val Thr Glu Met Ala Gln Asp Lys Pro Thr Val Asp Ile
    50                  55                  60

Glu Leu Val Thr Met Thr Val Ser Asn Met Ala Glu Val Arg Ser Tyr
65                  70                  75                  80

Cys Tyr Glu Ala Ser Leu Ser Asp Met Ala Ser Ala Ser Arg Cys Pro
                85                  90                  95

Thr Gln Gly Glu Pro Ser Leu Asp Lys Gln Ser Asp Thr Gln Ser Val
            100                 105                 110

Cys Lys Arg Thr Leu Gly Asp Arg Gly Trp Gly Asn Gly Cys Gly Ile
```

```
            115                 120                 125
Phe Gly Lys Gly Ser Leu Val Thr Cys Ser Lys Phe Thr Cys Cys Lys
        130                 135                 140
Lys Met Pro Gly Lys Ser Ile Gln Pro Glu Asn Leu Glu Tyr Arg Ile
145                 150                 155                 160
Met Leu Pro Val His Gly Ser Gln His Ser Gly Met Ile Val Asn Asp
                165                 170                 175
Ile Gly His Glu Thr Asp Glu Asn Arg Ala Lys Val Glu Val Thr Pro
            180                 185                 190
Asn Ser Pro Arg Ala Glu Ala Thr Leu Gly Gly Phe Gly Ser Leu Gly
        195                 200                 205
Leu Asp Cys Glu Pro Arg Thr Gly Leu Asp Phe Ser Asp Leu Tyr Tyr
    210                 215                 220
Leu Thr Met Asn Asn Lys His Trp Leu Val His Lys Glu Trp Phe His
225                 230                 235                 240
Asp Ile Pro Leu Pro Trp His Ala Gly Ala Asp Thr Gly Thr Pro His
                245                 250                 255
Trp Asn Lys Glu Ala Leu Val Glu Phe Lys Asp Ala His Ala Lys
            260                 265                 270
Arg Gln Thr Val Val Leu Gly Ser Gln Glu Gly Ala Val His Thr
        275                 280                 285
Ala Leu Ala Gly Ala Leu Glu Ala Glu Met Asp Gly Ala Lys Gly Arg
    290                 295                 300
Leu Phe Ser Gly His Leu Lys Cys Arg Leu Lys Met Asp Lys Leu Arg
305                 310                 315                 320
Leu Lys Gly Val Ser Tyr Ser Leu Cys Thr Ala Ala Phe Thr Phe Thr
                325                 330                 335
Lys Val Pro Ala Glu Thr Leu His Gly Thr Val Thr Val Glu Val Gln
            340                 345                 350
Ser Ala Gly Thr Asp Gly Pro Cys Lys Val Pro Ala Gln Met Ala Val
        355                 360                 365
Asp Met Gln Thr Leu Thr Pro Val Gly Arg Leu Ile Thr Ala Asn Pro
    370                 375                 380
Val Ile Thr Glu Ser Thr Glu Asn Ser Lys Met Met Leu Glu Leu Asp
385                 390                 395                 400
Pro Pro Phe Gly Asp Ser Tyr Ile Val Ile Gly Val Gly Asp Lys Lys
                405                 410                 415
Ile Thr His His Trp His Arg Ser Gly Ser Thr Ile Gly Lys Ala Phe
            420                 425                 430
Glu Ala Thr Val Arg Gly Ala Lys Arg Met Ala Val Leu Gly Asp Thr
        435                 440                 445
Ala Trp Asp Phe Gly Ser Val Gly Gly Val Phe Asn Ser Leu Gly Lys
    450                 455                 460
Gly Ile His Gln Ile Phe Gly Ala Ala Phe Lys Ser Leu Phe Gly Gly
465                 470                 475                 480
Met Ser Trp Phe Ser Gln Ile Leu Ile Gly Thr Leu Leu Val Trp Leu
                485                 490                 495
Gly Leu Asn Thr Lys Asn Gly Ser Ile Ser Leu Thr Cys Leu Ala Leu
            500                 505                 510
Gly Gly Val Met Ile Phe Leu Ser Thr Ala Val Ser Ala Asp Val Gly
        515                 520                 525
Cys Ser Val Asp Phe Ser Lys Lys
    530                 535
```

```
<210> SEQ ID NO 32
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gccgccacca tgttcgcctg cagcaagaag atgaccggca agagcatcca gcccgagaac      60
ctggaatacc ggatcatgct gagcgtgcac ggcagccagc acagcggcat gatcgtgaac     120
gacaccggcc acgagacaga cgagaaccgg gccaaggtgg aaatcacccc caacagccct     180
agagccgagg ccacactggg cggctttgga tctctgggcc tggactgcga gcctagaacc     240
ggcctggatt tcagcgacct gtactacctg accatgaaca acaagcactg gctggtgcac     300
aaagagtggt tccacgacat cccccctgcc tggcatgccg gcgctgatac aggcacaccc     360
cactggaaca acaaagaggc cctggtggag ttcaaggacg cccacgccaa gaggcagacc     420
gtggtggtgc tgggatctca ggaaggcgcc gtgcatacag ctctggctgg cgccctggaa     480
gccgaaatgg atggcgctaa gggcagactg agcagcggcc acctgaagtg ccggctgaag     540
atggacaagc tgcggctgaa gggcgtgtcc tacagcctgt gtaccgccgc cttcaccttc     600
accaagatcc ccgccgagac actgcacggc accgtgacag tggaagtgca gtacgccggc     660
accgacggcc cttgtaaagt gcctgctcag atggccgtgg acatgcagac cctgaccoct     720 gtgggcaggc tgatcaccgc caaccctgtg atcaccgaga gcaccgagaa cagcaagatg     780
atgctggaac tggaccccc cttcggcgac tcctacatcg tgatcggcgt gggagagaag     840
aagatcaccc accactggtg a                                                861

<210> SEQ ID NO 33
<211> LENGTH: 283
<212> TYPE: PRT
<213> ORGANISM: Zika virus

<400> SEQUENCE: 33

Met Phe Ala Cys Ser Lys Lys Met Thr Gly Lys Ser Ile Gln Pro Glu
1               5                   10                  15

Asn Leu Glu Tyr Arg Ile Met Leu Ser Val His Gly Ser Gln His Ser
            20                  25                  30

Gly Met Ile Val Asn Asp Thr Gly His Glu Thr Asp Glu Asn Arg Ala
        35                  40                  45

Lys Val Glu Ile Thr Pro Asn Ser Pro Arg Ala Glu Ala Thr Leu Gly
    50                  55                  60

Gly Phe Gly Ser Leu Gly Leu Asp Cys Glu Pro Arg Thr Gly Leu Asp
65                  70                  75                  80

Phe Ser Asp Leu Tyr Tyr Leu Thr Met Asn Asn Lys His Trp Leu Val
                85                  90                  95

His Lys Glu Trp Phe His Asp Ile Pro Leu Pro Trp His Ala Gly Ala
            100                 105                 110

Asp Thr Gly Thr Pro His Trp Asn Asn Lys Glu Ala Leu Val Glu Phe
        115                 120                 125

Lys Asp Ala His Ala Lys Arg Gln Thr Val Val Val Leu Gly Ser Gln
    130                 135                 140

Glu Gly Ala Val His Thr Ala Leu Ala Gly Ala Leu Glu Ala Glu Met
145                 150                 155                 160
```

```
Asp Gly Ala Lys Gly Arg Leu Ser Ser Gly His Leu Lys Cys Arg Leu
            165                 170                 175

Lys Met Asp Lys Leu Arg Leu Lys Gly Val Ser Tyr Ser Leu Cys Thr
        180                 185                 190

Ala Ala Phe Thr Phe Thr Lys Ile Pro Ala Glu Thr Leu His Gly Thr
        195                 200                 205

Val Thr Val Glu Val Gln Tyr Ala Gly Thr Asp Gly Pro Cys Lys Val
    210                 215                 220

Pro Ala Gln Met Ala Val Asp Met Gln Thr Leu Thr Pro Val Gly Arg
225                 230                 235                 240

Leu Ile Thr Ala Asn Pro Val Ile Thr Glu Ser Thr Glu Asn Ser Lys
            245                 250                 255

Met Met Leu Glu Leu Asp Pro Pro Phe Gly Asp Ser Tyr Ile Val Ile
            260                 265                 270

Gly Val Gly Glu Lys Lys Ile Thr His His Trp
        275                 280
```

<210> SEQ ID NO 34
<211> LENGTH: 861
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
gccgccacca tgttcgcctg cagcaagaag atgaccggca agagcatcca gcccgagaac    60
ctggaatacc ggatcatgct gagcgtgcac ggcagccagc acagcggcat gatcgtgaac   120
atcaccggcc acgagacact ggaaaaccgg gccaaggtgg aaatcacccc caacagccct   180
agagccgagg ccacactggg cggctttgga tctctgggcc tggactgcga gcctagaacc   240
ggcctggatt tcagcgacct gtactacctg accatgaaca acaagcactg gctggtgcac   300
aaagagtggt tccacgacat ccccctgccc tggcatgccg gcgctgatac aggcacaccc   360
cactggaaca caaagaggc cctggtggag ttcaagctgg cccacgccaa gagacagacc   420
gtggtggtgc tgggctctca ggaaggcgcc gtgcatacag ctctggctgg cgccctggaa   480
gccgaaatgg atgcgccaa gggcagactg tctagcggcc acctgaagtg ccggctgaag   540
atggacaagc tgcggctgaa gggcgtgtcc tacagcctgt gtaccgccgc cttcaccttc   600
accaagatcc ccgccgaaac cctgcacggc accgtgacag tggaagtgca gtacgccggc   660
accctgggcc cttgtaaagt gcctgctcag atggccgtgg acatgcagac cctgacccct   720
gtgggcaggc tgatcaccgc caaccctgtg atcaccgaga gcaccgagaa cagcaagatg   780
atgctggaac tggacccccc cttcggcatc tcctacatcg tgatcggcgt gggcgagaag   840
aagatcaccc accactggtg a                                             861
```

<210> SEQ ID NO 35
<211> LENGTH: 283
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Met Phe Ala Cys Ser Lys Lys Met Thr Gly Lys Ser Ile Gln Pro Glu
1               5                   10                  15
```

Asn Leu Glu Tyr Arg Ile Met Leu Ser Val His Gly Ser Gln His Ser
              20                  25                  30

Gly Met Ile Val Asn Ile Thr Gly His Glu Thr Leu Glu Asn Arg Ala
              35                  40                  45

Lys Val Glu Ile Thr Pro Asn Ser Pro Arg Ala Glu Ala Thr Leu Gly
 50                  55                  60

Gly Phe Gly Ser Leu Gly Leu Asp Cys Glu Pro Arg Thr Gly Leu Asp
65                  70                  75                  80

Phe Ser Asp Leu Tyr Tyr Leu Thr Met Asn Asn Lys His Trp Leu Val
                 85                  90                  95

His Lys Glu Trp Phe His Asp Ile Pro Leu Pro Trp His Ala Gly Ala
             100                 105                 110

Asp Thr Gly Thr Pro His Trp Asn Asn Lys Glu Ala Leu Val Glu Phe
             115                 120                 125

Lys Leu Ala His Ala Lys Arg Gln Thr Val Val Leu Gly Ser Gln
130                 135                 140

Glu Gly Ala Val His Thr Ala Leu Ala Gly Ala Leu Glu Ala Glu Met
145                 150                 155                 160

Asp Gly Ala Lys Gly Arg Leu Ser Ser Gly His Leu Lys Cys Arg Leu
                165                 170                 175

Lys Met Asp Lys Leu Arg Leu Lys Gly Val Ser Tyr Ser Leu Cys Thr
            180                 185                 190

Ala Ala Phe Thr Phe Thr Lys Ile Pro Ala Glu Thr Leu His Gly Thr
            195                 200                 205

Val Thr Val Glu Val Gln Tyr Ala Gly Thr Leu Gly Pro Cys Lys Val
        210                 215                 220

Pro Ala Gln Met Ala Val Asp Met Gln Thr Leu Thr Pro Val Gly Arg
225                 230                 235                 240

Leu Ile Thr Ala Asn Pro Val Ile Thr Glu Ser Thr Glu Asn Ser Lys
                245                 250                 255

Met Met Leu Glu Leu Asp Pro Pro Phe Gly Ile Ser Tyr Ile Val Ile
            260                 265                 270

Gly Val Gly Glu Lys Lys Ile Thr His His Trp
        275                 280

<210> SEQ ID NO 36
<211> LENGTH: 1620
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gccgccacca tgagcaccag ccagaaagtg atctacctcg tgatgatcct gctgatcgcc      60
cctgcctaca gcatccggtg tatcggcgtg tccaaccggg acttcgtgga aggcatgagc     120
ggcggcacat gggtggacgt ggtgctggaa catggcggct gcgtgacagt gatggcccag     180
gacaagccca ccgtggacat cgagctcgtg accaccaccg tgtccaatat ggccgaagtg     240
cggagctact gctacgaggc cagcatcagc gacatggcca cgacagcag atgcccctaca     300 cagggcgagg cctacctgga caagcagagc gacacccagt acgtgtgcaa gcggaccctg     360
gtggatagag ctggggcaa tggctgcggc ctgtttggca agggcagcct cgtgacctgc     420
gccaagttcg cctgcagcaa gaagatgacc ggcaagagca tccagcccga gaacctggaa     480

-continued

| | |
|---|---|
| taccggatca tgctgagcgt gcacggcagc cagcactccg gcatgatcgt gaacgacacc | 540 |
| ggccacgaga cagacgagaa ccgggccaag gtggaaatca cccccaacag ccctagagcc | 600 |
| gaggccacac tgggcggctt tggatctctg gcctggact gcgagcctag aaccggcctg | 660 |
| gatttcagcg acctgtacta cctgaccatg aacaacaaac actggctggt gcacaaagag | 720 |
| tggttccacg acatcccect gccctggcat gccggcgctg atacaggcac accccactgg | 780 |
| aacaacaaag aggccctggt ggaattcaag gacgcccacg ccaagcggca gaccgtggtg | 840 |
| gtgctgggat ctcaggaagg cgccgtgcat acagctctgg ctggcgccct ggaagccgaa | 900 |
| atggatggcg ccaaaggcag actgagcagc ggccacctga gtgccggct gaagatggac | 960 |
| aagctgcggc tgaagggcgt gtcctacagc ctgtgtaccg ccgccttcac cttcaccaag | 1020 |
| atccccgccg agacactgca cggcaccgtg actgtggaag tgcagtacgc cggcaccgac | 1080 |
| ggcccttgta aagtgcctgc tcagatggcc gtggatatgc agaccctgac ccccgtgggc | 1140 |
| aggctgatca cagccaaccc tgtgatcacc gagagcaccg agaacagcaa gatgatgctg | 1200 |
| gaactggacc ccccttcgg cgactcctac atcgtgatcg gcgtgggaga agaagaagatc | 1260 |
| acccaccact ggcacagaag cggcagcacc atcggcaagg cctttgaggc tacagtgcgg | 1320 |
| ggagccaaga gaatggccgt gctggagat accgcctggg actttggctc tgtgggcgga | 1380 |
| gccctgaact ctctgggcaa gggaatccac cagatcttcg gcgctgcctt caagagcctg | 1440 |
| ttcggcggca tgagctggtt cagccagatc ctgatcggca ccctgctgat gtggctgggc | 1500 |
| ctgaacacca gaacggcag catctccctg atgtgcctgg ctctgggagg cgtgctgatc | 1560 |
| ttcctgagca cagccgtgtc tgccgacgtg ggctgcagcg tggacttctc caagaagtga | 1620 |

<210> SEQ ID NO 37
<211> LENGTH: 536
<212> TYPE: PRT
<213> ORGANISM: Zika virus

<400> SEQUENCE: 37

Met Ser Thr Ser Gln Lys Val Ile Tyr Leu Val Met Ile Leu Leu Ile
1               5                   10                  15

Ala Pro Ala Tyr Ser Ile Arg Cys Ile Gly Val Ser Asn Arg Asp Phe
            20                  25                  30

Val Glu Gly Met Ser Gly Gly Thr Trp Val Asp Val Val Leu Glu His
        35                  40                  45

Gly Gly Cys Val Thr Val Met Ala Gln Asp Lys Pro Thr Val Asp Ile
    50                  55                  60

Glu Leu Val Thr Thr Thr Val Ser Asn Met Ala Glu Val Arg Ser Tyr
65                  70                  75                  80

Cys Tyr Glu Ala Ser Ile Ser Asp Met Ala Ser Asp Ser Arg Cys Pro
                85                  90                  95

Thr Gln Gly Glu Ala Tyr Leu Asp Lys Gln Ser Asp Thr Gln Tyr Val
            100                 105                 110

Cys Lys Arg Thr Leu Val Asp Arg Gly Trp Gly Asn Gly Cys Gly Leu
        115                 120                 125

Phe Gly Lys Gly Ser Leu Val Thr Cys Ala Lys Phe Ala Cys Ser Lys
    130                 135                 140

Lys Met Thr Gly Lys Ser Ile Gln Pro Glu Asn Leu Glu Tyr Arg Ile
145                 150                 155                 160

Met Leu Ser Val His Gly Ser Gln His Ser Gly Met Ile Val Asn Asp
                165                 170                 175

```
Thr Gly His Glu Thr Asp Glu Asn Arg Ala Lys Val Glu Ile Thr Pro
            180                 185                 190

Asn Ser Pro Arg Ala Glu Ala Thr Leu Gly Gly Phe Gly Ser Leu Gly
        195                 200                 205

Leu Asp Cys Glu Pro Arg Thr Gly Leu Asp Phe Ser Asp Leu Tyr Tyr
    210                 215                 220

Leu Thr Met Asn Asn Lys His Trp Leu Val His Lys Glu Trp Phe His
225                 230                 235                 240

Asp Ile Pro Leu Pro Trp His Ala Gly Ala Asp Thr Gly Thr Pro His
                245                 250                 255

Trp Asn Asn Lys Glu Ala Leu Val Glu Phe Lys Asp Ala His Ala Lys
            260                 265                 270

Arg Gln Thr Val Val Val Leu Gly Ser Gln Glu Gly Ala Val His Thr
        275                 280                 285

Ala Leu Ala Gly Ala Leu Glu Ala Glu Met Asp Gly Ala Lys Gly Arg
    290                 295                 300

Leu Ser Ser Gly His Leu Lys Cys Arg Leu Lys Met Asp Lys Leu Arg
305                 310                 315                 320

Leu Lys Gly Val Ser Tyr Ser Leu Cys Thr Ala Ala Phe Thr Phe Thr
                325                 330                 335

Lys Ile Pro Ala Glu Thr Leu His Gly Thr Val Thr Val Glu Val Gln
            340                 345                 350

Tyr Ala Gly Thr Asp Gly Pro Cys Lys Val Pro Ala Gln Met Ala Val
        355                 360                 365

Asp Met Gln Thr Leu Thr Pro Val Gly Arg Leu Ile Thr Ala Asn Pro
    370                 375                 380

Val Ile Thr Glu Ser Thr Glu Asn Ser Lys Met Met Leu Glu Leu Asp
385                 390                 395                 400

Pro Pro Phe Gly Asp Ser Tyr Ile Val Ile Gly Val Gly Glu Lys Lys
                405                 410                 415

Ile Thr His His Trp His Arg Ser Gly Ser Thr Ile Gly Lys Ala Phe
            420                 425                 430

Glu Ala Thr Val Arg Gly Ala Lys Arg Met Ala Val Leu Gly Asp Thr
        435                 440                 445

Ala Trp Asp Phe Gly Ser Val Gly Gly Ala Leu Asn Ser Leu Gly Lys
    450                 455                 460

Gly Ile His Gln Ile Phe Gly Ala Ala Phe Lys Ser Leu Phe Gly Gly
465                 470                 475                 480

Met Ser Trp Phe Ser Gln Ile Leu Ile Gly Thr Leu Leu Met Trp Leu
                485                 490                 495

Gly Leu Asn Thr Lys Asn Gly Ser Ile Ser Leu Met Cys Leu Ala Leu
            500                 505                 510

Gly Gly Val Leu Ile Phe Leu Ser Thr Ala Val Ser Ala Asp Val Gly
        515                 520                 525

Cys Ser Val Asp Phe Ser Lys Lys
    530                 535

<210> SEQ ID NO 38
<211> LENGTH: 132
<212> TYPE: PRT
<213> ORGANISM: Mycobacterium tuberculosis

<400> SEQUENCE: 38

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile Arg Ser
        20                  25                  30

Gly Gly Gly Ser Pro Thr Val His Ile Gly Pro Thr Ala Phe Leu Gly
            35                  40                  45

Leu Gly Val Val Asp Asn Asn Gly Asn Gly Ala Arg Val Gln Arg Val
 50                  55                  60

Val Gly Ser Ala Pro Ala Ala Ser Leu Gly Ile Ser Thr Gly Asp Val
 65                  70                  75                  80

Ile Thr Ala Val Asp Gly Ala Pro Ile Asn Ser Ala Thr Ala Met Ala
                85                  90                  95

Asp Ala Leu Asn Gly His His Pro Gly Asp Val Ile Ser Val Thr Trp
            100                 105                 110

Gln Thr Lys Ser Gly Gly Thr Arg Thr Gly Asn Val Thr Leu Ala Glu
            115                 120                 125

Gly Pro Pro Ala
        130

<210> SEQ ID NO 39
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met His His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
            20                  25                  30

Ile Ala Gly Gln Ile Arg Ser Gly Gly Gly Ser Pro Thr Val His Ile
        35                  40                  45

Gly Pro Thr Ala Phe Leu Gly Leu Gly Val Val Asp Asn Asn Gly Asn
 50                  55                  60

Gly Ala Arg Val Gln Arg Val Val Gly Ser Ala Pro Ala Ala Ser Leu
 65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
            115                 120                 125

Gly Asn Val Thr Leu Ala Glu Gly Pro Pro Ala Glu Phe Asp Asp Asp
        130                 135                 140

Asp Lys Asp Pro Pro Asp Pro His Gln Pro Asp Met Thr Lys Gly Tyr
145                 150                 155                 160

Cys Pro Gly Gly Arg Trp Gly Phe Gly Asp Leu Ala Val Cys Asp Gly
                165                 170                 175

Glu Lys Tyr Pro Asp Gly Ser Phe Trp His Gln Trp Met Gln Thr Trp
            180                 185                 190

Phe Thr Gly Pro Gln Phe Tyr Phe Asp Cys Val Ser Gly Gly Glu Pro
        195                 200                 205

Leu Pro Gly Pro Pro Pro Gly Gly Cys Gly Gly Ala Ile Pro Ser
    210                 215                 220

Glu Gln Pro Asn Ala Pro 225                 230

<210> SEQ ID NO 40
<211> LENGTH: 578
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
            20                  25                  30

Ile Ala Gly Gln Ile Arg Ser Gly Gly Ser Pro Thr Val His Ile
            35                  40                  45

Gly Pro Thr Ala Phe Leu Gly Leu Val Val Asp Asn Asn Gly Asn
50                  55                  60

Gly Ala Arg Val Gln Arg Val Val Gly Ser Ala Pro Ala Ser Leu
65                  70                  75                  80

Gly Ile Ser Thr Gly Asp Val Ile Thr Ala Val Asp Gly Ala Pro Ile
            85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
            115                 120                 125

Gly Asn Val Thr Leu Ala Glu Gly Pro Pro Ala Glu Phe Pro Leu Val
130                 135                 140

Pro Arg Gly Ser Pro Met Gly Ser Asp Val Arg Asp Leu Asn Ala Leu
145                 150                 155                 160

Leu Pro Ala Val Pro Ser Leu Gly Gly Gly Gly Cys Ala Leu Pro
            165                 170                 175

Val Ser Gly Ala Ala Gln Trp Ala Pro Val Leu Asp Phe Ala Pro Pro
            180                 185                 190

Gly Ala Ser Ala Tyr Gly Ser Leu Gly Gly Pro Ala Pro Pro Ala
            195                 200                 205

Pro Pro Pro Pro Pro Pro Pro Pro His Ser Phe Ile Lys Gln Glu
            210                 215                 220

Pro Ser Trp Gly Gly Ala Glu Pro His Glu Glu Gln Cys Leu Ser Ala
225                 230                 235                 240

Phe Thr Val His Phe Ser Gly Gln Phe Thr Gly Thr Ala Gly Ala Cys
            245                 250                 255

Arg Tyr Gly Pro Phe Gly Pro Pro Pro Ser Gln Ala Ser Ser Gly
            260                 265                 270

Gln Ala Arg Met Phe Pro Asn Ala Pro Tyr Leu Pro Ser Cys Leu Glu
            275                 280                 285

Ser Gln Pro Ala Ile Arg Asn Gln Gly Tyr Ser Thr Val Thr Phe Asp
            290                 295                 300

Gly Thr Pro Ser Tyr Gly His Thr Pro Ser His His Ala Ala Gln Phe
305                 310                 315                 320

Pro Asn His Ser Phe Lys His Glu Asp Pro Met Gly Gln Gln Gly Ser
            325                 330                 335

Leu Gly Glu Gln Gln Tyr Ser Val Pro Pro Pro Val Tyr Gly Cys His
            340                 345                 350

```
Thr Pro Thr Asp Ser Cys Thr Gly Ser Gln Ala Leu Leu Leu Arg Thr
            355                 360                 365

Pro Tyr Ser Ser Asp Asn Leu Tyr Gln Met Thr Ser Gln Leu Glu Cys
370                 375                 380

Met Thr Trp Asn Gln Met Asn Leu Gly Ala Thr Leu Lys Gly His Ser
385                 390                 395                 400

Thr Gly Tyr Glu Ser Asp Asn His Thr Thr Pro Ile Leu Cys Gly Ala
                405                 410                 415

Gln Tyr Arg Ile His Thr His Gly Val Phe Arg Gly Ile Gln Asp Val
            420                 425                 430

Arg Arg Val Pro Gly Val Ala Pro Thr Leu Val Arg Ser Ala Ser Glu
        435                 440                 445

Thr Ser Glu Lys Arg Pro Phe Met Cys Ala Tyr Ser Gly Cys Asn Lys
    450                 455                 460

Arg Tyr Phe Lys Leu Ser His Leu Gln Met His Ser Arg Lys His Thr
465                 470                 475                 480

Gly Glu Lys Pro Tyr Gln Cys Asp Phe Lys Asp Cys Glu Arg Arg Phe
                485                 490                 495

Phe Arg Ser Asp Gln Leu Lys Arg His Gln Arg Arg His Thr Gly Val
            500                 505                 510

Lys Pro Phe Gln Cys Lys Thr Cys Gln Arg Lys Phe Ser Arg Ser Asp
        515                 520                 525

His Leu Lys Thr His Thr Arg Thr His Thr Gly Glu Lys Pro Phe Ser
    530                 535                 540

Cys Arg Trp Pro Ser Cys Gln Lys Lys Phe Ala Arg Ser Asp Glu Leu
545                 550                 555                 560

Val Arg His His Asn Met His Gln Arg Asn Met Thr Lys Leu Gln Leu
                565                 570                 575

Ala Leu

<210> SEQ ID NO 41
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
                20                  25                  30

Ile Ala Gly Gln Ile Arg Ser Gly Gly Ser Pro Thr Val His Ile
            35                  40                  45

Gly Pro Thr Ala Phe Leu Gly Leu Gly Val Val Asp Asn Asn Gly Asn
    50                  55                  60

Gly Ala Arg Val Gln Arg Val Val Gly Ser Ala Pro Ala Ser Leu
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125
```

```
Gly Asn Val Thr Leu Ala Glu Gly Pro Pro Ala Glu Phe Ile Glu Gly
    130                 135                 140

Arg Gly Ser Gly Cys Pro Leu Leu Glu Asn Val Ile Ser Lys Thr Ile
145                 150                 155                 160

Asn Pro Gln Val Ser Lys Thr Glu Tyr Lys Glu Leu Leu Gln Glu Phe
                165                 170                 175

Ile Asp Asp Asn Ala Thr Thr Asn Ala Ile Asp Glu Leu Lys Glu Cys
            180                 185                 190

Phe Leu Asn Gln Thr Asp Glu Thr Leu Ser Asn Val Glu Val Phe Met
        195                 200                 205

Gln Leu Ile Tyr Asp Ser Ser Leu Cys Asp Leu Phe
210                 215                 220

<210> SEQ ID NO 42
<211> LENGTH: 729
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
                20                  25                  30

Ile Ala Gly Gln Ile Arg Ser Gly Gly Ser Pro Thr Val His Ile
            35                  40                  45

Gly Pro Thr Ala Phe Leu Gly Leu Gly Val Val Asp Asn Asn Gly Asn
50                  55                  60

Gly Ala Arg Val Gln Arg Val Val Gly Ser Ala Pro Ala Ala Ser Leu
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
                100                 105                 110

Asp Val Ile Ser Val Thr Trp Gln Thr Lys Ser Gly Gly Thr Arg Thr
            115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
210                 215                 220

Ala Glu Leu Thr Ala Ala Gln Val Arg Val Ala Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270
```

```
Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
    290                 295                 300

Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
                325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
        355                 360                 365

Trp Lys Thr Val Ser Pro His Arg Ser Pro Ile Ser Asn Met Val Ser
    370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Ala
                405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Val Ala Ala
        435                 440                 445

Asn Leu Gly Arg Ala Ala Ser Val Gly Ser Leu Ser Val Pro Gln Ala
        450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
                485                 490                 495

Gly Gly Leu Pro Val Gly Gln Met Gly Ala Arg Ala Gly Gly Gly Leu
                500                 505                 510

Ser Gly Val Leu Arg Val Pro Pro Arg Pro Tyr Val Met Pro His Ser
            515                 520                 525

Pro Ala Ala Gly Asp Ile Ala Pro Pro Ala Leu Ser Gln Asp Arg Phe
        530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
        595                 600                 605

Ser Val Gly Ser Gly Gln Thr Tyr Gly Val Asp Val Val Gly Tyr Asp
    610                 615                 620

Arg Thr Gln Asp Val Ala Val Leu Gln Leu Arg Gly Ala Gly Gly Leu
625                 630                 635                 640

Pro Ser Ala Ala Ile Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685
```

```
Thr Gly Ala Glu Glu Thr Leu Asn Gly Leu Ile Gln Phe Asp Ala Ala
        690                 695                 700

Ile Gln Pro Gly Asp Ser Gly Pro Val Val Asn Gly Leu Gly Gln
705                 710                 715                 720

Val Val Gly Met Asn Thr Ala Ala Ser
                725

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile
            20                  25                  30

<210> SEQ ID NO 44
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile Lys Leu
            20                  25                  30

Pro Thr Val His Ile Gly Pro Thr Ala Phe Leu Gly Leu Gly Val Val
        35                  40                  45

Asp Asn Asn Gly Asn Gly Ala Arg Val Gln Arg Val Val Gly Ser Ala
    50                  55                  60

Pro Ala Ala Ser Leu Gly Ile Ser Thr Gly Asp Val Ile Thr Ala Val
65                  70                  75                  80

Asp Gly Ala Pro Ile Asn Ser Ala Thr Ala Met Ala Asp Ala Leu Asn
                85                  90                  95

Gly His His Pro Gly Asp Val Ile Ser Val Thr Trp Gln Thr Lys Ser
            100                 105                 110

Gly Gly Thr Arg Thr Gly Asn Val Thr Leu Ala Glu Gly Pro Pro Ala
        115                 120                 125

<210> SEQ ID NO 45
<211> LENGTH: 128
<212> TYPE: PRT
<213> ORGANISM: Mycobacterium tuberculosis

<400> SEQUENCE: 45

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile Arg Ser
            20                  25                  30

Gly Gly Gly Ser Pro Thr Val His Ile Gly Pro Thr Ala Phe Leu Gly
        35                  40                  45

Leu Gly Val Val Asp Asn Asn Gly Asn Gly Ala Arg Val Gln Arg Val
```

```
                50                  55                  60
Val Gly Ser Ala Pro Ala Ser Leu Gly Ile Ser Thr Gly Asp Val
 65                  70                  75                  80

Ile Thr Ala Val Asp Gly Ala Pro Ile Asn Ser Ala Thr Ala Met Ala
                     85                  90                  95

Asp Ala Leu Asn Gly His His Pro Gly Asp Val Ile Ser Val Thr Trp
                100                 105                 110

Gln Thr Lys Ser Gly Gly Thr Arg Thr Gly Asn Val Thr Leu Ala Glu
                115                 120                 125

<210> SEQ ID NO 46
<211> LENGTH: 355
<212> TYPE: PRT
<213> ORGANISM: Mycobacterium tuberculosis

<400> SEQUENCE: 46

Met Ser Asn Ser Arg Arg Arg Ser Leu Arg Trp Ser Trp Leu Leu Ser
  1               5                  10                  15

Val Leu Ala Ala Val Gly Leu Gly Leu Ala Thr Ala Pro Ala Gln Ala
                 20                  25                  30

Ala Pro Pro Ala Leu Ser Gln Asp Arg Phe Ala Asp Phe Pro Ala Leu
                 35                  40                  45

Pro Leu Asp Pro Ser Ala Met Val Ala Gln Val Gly Pro Gln Val Val
 50                  55                  60

Asn Ile Asn Thr Lys Leu Gly Tyr Asn Asn Ala Val Gly Ala Gly Thr
 65                  70                  75                  80

Gly Ile Val Ile Asp Pro Asn Gly Val Val Leu Thr Asn Asn His Val
                 85                  90                  95

Ile Ala Gly Ala Thr Asp Ile Asn Ala Phe Ser Val Gly Ser Gly Gln
                100                 105                 110

Thr Tyr Gly Val Asp Val Val Gly Tyr Asp Arg Thr Gln Asp Val Ala
                115                 120                 125

Val Leu Gln Leu Arg Gly Ala Gly Gly Leu Pro Ser Ala Ala Ile Gly
130                 135                 140

Gly Gly Val Ala Val Gly Glu Pro Val Val Ala Met Gly Asn Ser Gly
145                 150                 155                 160

Gly Gln Gly Gly Thr Pro Arg Ala Val Pro Gly Arg Val Val Ala Leu
                165                 170                 175

Gly Gln Thr Val Gln Ala Ser Asp Ser Leu Thr Gly Ala Glu Glu Thr
                180                 185                 190

Leu Asn Gly Leu Ile Gln Phe Asp Ala Ala Ile Gln Pro Gly Asp Ser
                195                 200                 205

Gly Gly Pro Val Val Asn Gly Leu Gly Gln Val Val Gly Met Asn Thr
                210                 215                 220

Ala Ala Ser Asp Asn Phe Gln Leu Ser Gln Gly Gly Gln Gly Phe Ala
225                 230                 235                 240

Ile Pro Ile Gly Gln Ala Met Ala Ile Ala Gly Gln Ile Arg Ser Gly
                245                 250                 255

Gly Gly Ser Pro Thr Val His Ile Gly Pro Thr Ala Phe Leu Gly Leu
                260                 265                 270

Gly Val Val Asp Asn Asn Gly Asn Gly Ala Arg Val Gln Arg Val Val
                275                 280                 285

Gly Ser Ala Pro Ala Ala Ser Leu Gly Ile Ser Thr Gly Asp Val Ile
                290                 295                 300
```

```
Thr Ala Val Asp Gly Ala Pro Ile Asn Ser Ala Thr Ala Met Ala Asp
305                 310                 315                 320

Ala Leu Asn Gly His His Pro Gly Asp Val Ile Ser Val Thr Trp Gln
            325                 330                 335

Thr Lys Ser Gly Gly Thr Arg Thr Gly Asn Val Thr Leu Ala Glu Gly
            340                 345                 350

Pro Pro Ala
        355

<210> SEQ ID NO 47
<211> LENGTH: 364
<212> TYPE: PRT
<213> ORGANISM: Haemophilus influenzae

<400> SEQUENCE: 47

Met Lys Leu Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
            20                  25                  30

Ser Asp Lys Ile Ile Ile Ala His Arg Gly Ala Ser Gly Tyr Leu Pro
        35                  40                  45

Glu His Thr Leu Glu Ser Lys Ala Leu Ala Phe Ala Gln Gln Ala Asp
    50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                85                  90                  95

Pro His Arg His Arg Lys Asp Gly Arg Tyr Tyr Val Ile Asp Phe Thr
            100                 105                 110

Leu Lys Glu Ile Gln Ser Leu Glu Met Thr Glu Asn Phe Glu Thr Lys
        115                 120                 125

Asp Gly Lys Gln Ala Gln Val Tyr Pro Asn Arg Phe Pro Leu Trp Lys
    130                 135                 140

Ser His Phe Arg Ile His Thr Phe Glu Asp Glu Ile Glu Phe Ile Gln
145                 150                 155                 160

Gly Leu Glu Lys Ser Thr Gly Lys Lys Val Gly Ile Tyr Pro Glu Ile
                165                 170                 175

Lys Ala Pro Trp Phe His His Gln Asn Gly Lys Asp Ile Ala Ala Glu
            180                 185                 190

Thr Leu Lys Val Leu Lys Lys Tyr Gly Tyr Asp Lys Lys Thr Asp Met
        195                 200                 205

Val Tyr Leu Gln Thr Phe Asp Phe Asn Glu Leu Lys Arg Ile Lys Thr
    210                 215                 220

Glu Leu Leu Pro Gln Met Gly Met Asp Leu Lys Leu Val Gln Leu Ile
225                 230                 235                 240

Ala Tyr Thr Asp Trp Lys Glu Thr Gln Glu Lys Asp Pro Lys Gly Tyr
                245                 250                 255

Trp Val Asn Tyr Asn Tyr Asp Trp Met Phe Lys Pro Gly Ala Met Ala
            260                 265                 270

Glu Val Val Lys Tyr Ala Asp Gly Val Gly Pro Gly Trp Tyr Met Leu
        275                 280                 285

Val Asn Lys Glu Glu Ser Lys Pro Asp Asn Ile Val Tyr Thr Pro Leu
    290                 295                 300

Val Lys Glu Leu Ala Gln Tyr Asn Val Glu Val His Pro Tyr Thr Val
305                 310                 315                 320
```

Arg Lys Asp Ala Leu Pro Ala Phe Phe Thr Asp Val Asn Gln Met Tyr
            325                 330                 335

Asp Val Leu Leu Asn Lys Ser Gly Ala Thr Gly Val Phe Thr Asp Phe
        340                 345                 350

Pro Asp Thr Gly Val Glu Phe Leu Lys Gly Ile Lys
    355                 360

<210> SEQ ID NO 48
<211> LENGTH: 313
<212> TYPE: PRT
<213> ORGANISM: Streptococcus pneumonae

<400> SEQUENCE: 48

Met Glu Ile Asn Val Ser Lys Leu Arg Thr Asp Leu Pro Gln Val Gly
1               5                   10                  15

Val Gln Pro Tyr Arg Gln Val His Ala His Ser Thr Gly Asn Pro His
            20                  25                  30

Ser Thr Val Gln Asn Glu Ala Asp Tyr His Trp Arg Lys Asp Pro Glu
        35                  40                  45

Leu Gly Phe Phe Ser His Ile Val Gly Asn Gly Cys Ile Met Gln Val
    50                  55                  60

Gly Pro Val Asp Asn Gly Ala Trp Asp Val Gly Gly Trp Asn Ala
65              70                  75                  80

Glu Thr Tyr Ala Ala Val Glu Leu Ile Glu Ser His Ser Thr Lys Glu
                85                  90                  95

Glu Phe Met Thr Asp Tyr Arg Leu Tyr Ile Glu Leu Leu Arg Asn Leu
            100                 105                 110

Ala Asp Glu Ala Gly Leu Pro Lys Thr Leu Asp Thr Gly Ser Leu Ala
        115                 120                 125

Gly Ile Lys Thr His Glu Tyr Cys Thr Asn Asn Gln Pro Asn Asn His
130             135                 140

Ser Asp His Val Asp Pro Tyr Pro Tyr Leu Ala Lys Trp Gly Ile Ser
145                 150                 155                 160

Arg Glu Gln Phe Lys His Asp Ile Glu Asn Gly Leu Thr Ile Glu Thr
                165                 170                 175

Gly Trp Gln Lys Asn Asp Thr Gly Tyr Trp Tyr Val His Ser Asp Gly
            180                 185                 190

Ser Tyr Pro Lys Asp Lys Phe Glu Lys Ile Asn Gly Thr Trp Tyr Tyr
        195                 200                 205

Phe Asp Ser Ser Gly Tyr Met Leu Ala Asp Arg Trp Arg Lys His Thr
    210                 215                 220

Asp Gly Asn Trp Tyr Trp Phe Asp Asn Ser Gly Glu Met Ala Thr Gly
225                 230                 235                 240

Trp Lys Lys Ile Ala Asp Lys Trp Tyr Tyr Phe Asn Glu Glu Gly Ala
                245                 250                 255

Met Lys Thr Gly Trp Val Lys Tyr Lys Asp Thr Trp Tyr Tyr Leu Asp
            260                 265                 270

Ala Lys Glu Gly Ala Met Val Ser Asn Ala Phe Ile Gln Ser Ala Asp
        275                 280                 285

Gly Thr Gly Trp Tyr Tyr Leu Lys Pro Asp Gly Thr Leu Ala Asp Arg
    290                 295                 300

Pro Glu Phe Arg Met Ser Gln Met Ala
305                 310

-continued

```
<210> SEQ ID NO 49
<211> LENGTH: 166
<212> TYPE: PRT
<213> ORGANISM: Homo sapiens

<400> SEQUENCE: 49

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 50
<211> LENGTH: 233
<212> TYPE: PRT
<213> ORGANISM: Homo sapiens

<400> SEQUENCE: 50

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
```

```
                    165                 170                 175
Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 51
<211> LENGTH: 153
<212> TYPE: PRT
<213> ORGANISM: Homo sapiens

<400> SEQUENCE: 51

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr
145                 150

<210> SEQ ID NO 52
<211> LENGTH: 99
<212> TYPE: PRT
<213> ORGANISM: Homo sapiens

<400> SEQUENCE: 52

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
                20                  25                  30

Arg Cys Gln Cys Ile Lys Thr Tyr Ser Lys Pro Phe His Pro Lys Phe
            35                  40                  45

Ile Lys Glu Leu Arg Val Ile Glu Ser Gly Pro His Cys Ala Asn Thr
        50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser
```

<210> SEQ ID NO 53
<211> LENGTH: 662
<212> TYPE: PRT
<213> ORGANISM: Homo sapiens

<400> SEQUENCE: 53

```
Met Glu Pro Leu Val Thr Trp Val Val Pro Leu Leu Phe Leu Phe Leu
1               5                   10                  15

Leu Ser Arg Gln Gly Ala Ala Cys Arg Thr Ser Glu Cys Cys Phe Gln
            20                  25                  30

Asp Pro Pro Tyr Pro Asp Ala Asp Ser Gly Ser Ala Ser Gly Pro Arg
        35                  40                  45

Asp Leu Arg Cys Tyr Arg Ile Ser Ser Asp Arg Tyr Glu Cys Ser Trp
50                  55                  60

Gln Tyr Glu Gly Pro Thr Ala Gly Val Ser His Phe Leu Arg Cys Cys
65                  70                  75                  80

Leu Ser Ser Gly Arg Cys Cys Tyr Phe Ala Ala Gly Ser Ala Thr Arg
                85                  90                  95

Leu Gln Phe Ser Asp Gln Ala Gly Val Ser Val Leu Tyr Thr Val Thr
            100                 105                 110

Leu Trp Val Glu Ser Trp Ala Arg Asn Gln Thr Glu Lys Ser Pro Glu
        115                 120                 125

Val Thr Leu Gln Leu Tyr Asn Ser Val Lys Tyr Glu Pro Pro Leu Gly
    130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp Asp
            180                 185                 190

Thr Glu Ser Cys Leu Cys Pro Leu Glu Met Asn Val Ala Gln Glu Phe
        195                 200                 205

Gln Leu Arg Arg Arg Gln Leu Gly Ser Gln Gly Ser Ser Trp Ser Lys
    210                 215                 220

Trp Ser Ser Pro Val Cys Val Pro Glu Asn Pro Gln Pro Gln
225                 230                 235                 240

Val Arg Phe Ser Val Glu Gln Leu Gly Gln Asp Gly Arg Arg Arg Leu
                245                 250                 255

Thr Leu Lys Glu Gln Pro Thr Gln Leu Glu Leu Pro Glu Gly Cys Gln
            260                 265                 270

Gly Leu Ala Pro Gly Thr Glu Val Thr Tyr Arg Leu Gln Leu His Met
        275                 280                 285

Leu Ser Cys Pro Cys Lys Ala Lys Ala Thr Arg Thr Leu His Leu Gly
    290                 295                 300

Lys Met Pro Tyr Leu Ser Gly Ala Ala Tyr Asn Val Ala Val Ile Ser
305                 310                 315                 320

Ser Asn Gln Phe Gly Pro Gly Leu Asn Gln Thr Trp His Ile Pro Ala
                325                 330                 335

Asp Thr His Thr Glu Pro Val Ala Leu Asn Ile Ser Val Gly Thr Asn
            340                 345                 350

Gly Thr Thr Met Tyr Trp Pro Ala Arg Ala Gln Ser Met Thr Tyr Cys
        355                 360                 365

Ile Glu Trp Gln Pro Val Gly Gln Asp Gly Gly Leu Ala Thr Cys Ser
```

```
                 370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr Tyr Ile
                    405                 410                 415

Thr Ile Phe Ala Ser Ala His Pro Glu Lys Leu Thr Leu Trp Ser Thr
                420                 425                 430

Val Leu Ser Thr Tyr His Phe Gly Gly Asn Ala Ser Ala Ala Gly Thr
            435                 440                 445

Pro His His Val Ser Val Lys Asn His Ser Leu Asp Ser Val Ser Val
        450                 455                 460

Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu His
                    485                 490                 495

Pro Val Gln Pro Thr Glu Thr Gln Val Thr Leu Ser Gly Leu Arg Ala
                500                 505                 510

Gly Val Ala Tyr Thr Val Gln Val Arg Ala Asp Thr Ala Trp Leu Arg
            515                 520                 525

Gly Val Trp Ser Gln Pro Gln Arg Phe Ser Ile Glu Val Gln Val Ser
        530                 535                 540

Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
                    565                 570                 575

Leu Cys Pro Pro Leu Pro Thr Pro Cys Ala Ser Ser Ala Ile Glu Phe
                580                 585                 590

Pro Gly Gly Lys Glu Thr Trp Gln Trp Ile Asn Pro Val Asp Phe Gln
            595                 600                 605

Glu Glu Ala Ser Leu Gln Glu Ala Leu Val Val Glu Met Ser Trp Asp
        610                 615                 620

Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
                    645                 650                 655

Arg Cys Lys Ala Lys Met
                660

<210> SEQ ID NO 54
<211> LENGTH: 193
<212> TYPE: PRT
<213> ORGANISM: Homo sapiens

<400> SEQUENCE: 54

Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
                20                  25                  30

Leu Glu Ser Asp Tyr Phe Gly Lys Leu Glu Ser Lys Leu Ser Val Ile
            35                  40                  45

Arg Asn Leu Asn Asp Gln Val Leu Phe Ile Asp Gln Gly Asn Arg Pro
        50                  55                  60

Leu Phe Glu Asp Met Thr Asp Ser Asp Cys Arg Asp Asn Ala Pro Arg
65                  70                  75                  80
```

```
Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp

<210> SEQ ID NO 55
<211> LENGTH: 177
<212> TYPE: PRT
<213> ORGANISM: Homo sapiens

<400> SEQUENCE: 55

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 56
<211> LENGTH: 152
<212> TYPE: PRT
<213> ORGANISM: Homo sapiens

<400> SEQUENCE: 56

Met Ser Arg Leu Pro Val Leu Leu Leu Gln Leu Leu Val Arg Pro
1               5                   10                  15

Gly Leu Gln Ala Pro Met Thr Gln Thr Thr Ser Leu Lys Thr Ser Trp
            20                  25                  30
```

-continued

Val Asn Cys Ser Asn Met Ile Asp Glu Ile Ile Thr His Leu Lys Gln
          35                  40                  45

Pro Pro Leu Pro Leu Leu Asp Phe Asn Asn Leu Asn Gly Glu Asp Gln
 50                  55                  60

Asp Ile Leu Met Glu Asn Asn Leu Arg Arg Pro Asn Leu Glu Ala Phe
 65                  70                  75                  80

Asn Arg Ala Val Lys Ser Leu Gln Asn Ala Ser Ala Ile Glu Ser Ile
              85                  90                  95

Leu Lys Asn Leu Leu Pro Cys Leu Pro Leu Ala Thr Ala Ala Pro Thr
             100                 105                 110

Arg His Pro Ile His Ile Lys Asp Gly Asp Trp Asn Glu Phe Arg Arg
             115                 120                 125

Lys Leu Thr Phe Tyr Leu Lys Thr Leu Glu Asn Ala Gln Ala Gln Gln
             130                 135                 140

Thr Thr Leu Ser Leu Ala Ile Phe
145                 150

<210> SEQ ID NO 57
<211> LENGTH: 153
<212> TYPE: PRT
<213> ORGANISM: Homo sapiens

<400> SEQUENCE: 57

Met Gly Leu Thr Ser Gln Leu Leu Pro Pro Leu Phe Phe Leu Leu Ala
 1               5                  10                  15

Cys Ala Gly Asn Phe Val His Gly His Lys Cys Asp Ile Thr Leu Gln
             20                  25                  30

Glu Ile Ile Lys Thr Leu Asn Ser Leu Thr Glu Gln Lys Thr Leu Cys
             35                  40                  45

Thr Glu Leu Thr Val Thr Asp Ile Phe Ala Ala Ser Lys Asn Thr Thr
 50                  55                  60

Glu Lys Glu Thr Phe Cys Arg Ala Ala Thr Val Leu Arg Gln Phe Tyr
 65                  70                  75                  80

Ser His His Glu Lys Asp Thr Arg Cys Leu Gly Ala Thr Ala Gln Gln
             85                  90                  95

Phe His Arg His Lys Gln Leu Ile Arg Phe Leu Lys Arg Leu Asp Arg
             100                 105                 110

Asn Leu Trp Gly Leu Ala Gly Leu Asn Ser Cys Pro Val Lys Glu Ala
             115                 120                 125

Asn Gln Ser Thr Leu Glu Asn Phe Leu Glu Arg Leu Lys Thr Ile Met
             130                 135                 140

Arg Glu Lys Tyr Ser Lys Cys Ser Ser
145                 150

<210> SEQ ID NO 58
<211> LENGTH: 134
<212> TYPE: PRT
<213> ORGANISM: Homo sapiens

<400> SEQUENCE: 58

Met Arg Met Leu Leu His Leu Ser Leu Leu Ala Leu Gly Ala Ala Tyr
 1               5                  10                  15

Val Tyr Ala Ile Pro Thr Glu Ile Pro Thr Ser Ala Leu Val Lys Glu
             20                  25                  30

Thr Leu Ala Leu Leu Ser Thr His Arg Thr Leu Leu Ile Ala Asn Glu
             35                  40                  45

```
Thr Leu Arg Ile Pro Val Pro Val His Lys Asn His Gln Leu Cys Thr
     50                  55                  60

Glu Glu Ile Phe Gln Gly Ile Gly Thr Leu Glu Ser Gln Thr Val Gln
 65                  70                  75                  80

Gly Gly Thr Val Glu Arg Leu Phe Lys Asn Leu Ser Leu Ile Lys Lys
                 85                  90                  95

Tyr Ile Asp Gly Gln Lys Lys Lys Cys Gly Glu Glu Arg Arg Arg Val
                100                 105                 110

Asn Gln Phe Leu Asp Tyr Leu Gln Glu Phe Leu Gly Val Met Asn Thr
            115                 120                 125

Glu Trp Ile Ile Glu Ser
            130
```

```
<210> SEQ ID NO 59
<211> LENGTH: 212
<212> TYPE: PRT
<213> ORGANISM: Homo sapiens

<400> SEQUENCE: 59

Met Asn Ser Phe Ser Thr Ser Ala Phe Gly Pro Val Ala Phe Ser Leu
 1               5                  10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
             35                  40                  45

Ser Ser Glu Arg Ile Asp Lys Gln Ile Arg Tyr Ile Leu Asp Gly Ile
     50                  55                  60

Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                 85                  90                  95

Glu Lys Asp Gly Cys Phe Gln Ser Gly Phe Asn Glu Glu Thr Cys Leu
                100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
            195                 200                 205

Leu Arg Gln Met
        210
```

```
<210> SEQ ID NO 60
<211> LENGTH: 140
<212> TYPE: PRT
<213> ORGANISM: Homo sapiens

<400> SEQUENCE: 60

Met Val Leu Thr Ser Ala Leu Leu Leu Cys Ser Val Ala Gly Gln Gly
 1               5                  10                  15
```

Cys Pro Thr Leu Ala Gly Ile Leu Asp Ile Asn Phe Leu Ile Asn Lys
             20                  25                  30

Met Gln Glu Asp Pro Ala Ser Lys Cys His Cys Ser Ala Asn Val Thr
         35                  40                  45

Ser Cys Leu Cys Leu Gly Ile Pro Ser Asp Asn Cys Thr Arg Pro Cys
 50                  55                  60

Phe Ser Glu Arg Leu Ser Gln Met Thr Asn Thr Thr Met Gln Thr Arg
65                  70                  75                  80

Tyr Pro Leu Ile Phe Ser Arg Val Lys Lys Ser Val Glu Val Leu Lys
                 85                  90                  95

Asn Asn Lys Cys Pro Tyr Phe Ser Cys Glu Gln Pro Cys Asn Gln Thr
             100                 105                 110

Thr Ala Gly Asn Ala Leu Thr Phe Leu Lys Ser Leu Leu Glu Ile Phe
         115                 120                 125

Gln Lys Glu Lys Met Arg Gly Met Arg Gly Lys Ile
    130                 135                 140

<210> SEQ ID NO 61
<211> LENGTH: 178
<212> TYPE: PRT
<213> ORGANISM: Homo sapiens

<400> SEQUENCE: 61

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
             20                  25                  30

Phe Pro Gly Asn Leu Pro Asn Met Leu Arg Asp Leu Arg Asp Ala Phe
         35                  40                  45

Ser Arg Val Lys Thr Phe Phe Gln Met Lys Asp Gln Leu Asp Asn Leu
 50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                 85                  90                  95

Gln Ala Glu Asn Gln Asp Pro Asp Ile Lys Ala His Val Asn Ser Leu
             100                 105                 110

Gly Glu Asn Leu Lys Thr Leu Arg Leu Arg Leu Arg Arg Cys His Arg
         115                 120                 125

Phe Leu Pro Cys Glu Asn Lys Ser Lys Ala Val Glu Gln Val Lys Asn
 130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                 165                 170                 175

Arg Asn

<210> SEQ ID NO 62
<211> LENGTH: 145
<212> TYPE: PRT
<213> ORGANISM: Homo sapiens

<400> SEQUENCE: 62

Met Ala Leu Leu Leu Thr Thr Val Ile Ala Leu Thr Cys Leu Gly Gly
1               5                   10                  15

```
Phe Ala Ser Pro Gly Pro Val Pro Ser Thr Ala Leu Arg Glu Leu
            20                  25                  30

Ile Glu Glu Leu Val Asn Ile Thr Gln Asn Gln Lys Ala Pro Leu Cys
         35                  40                  45

Asn Gly Ser Met Val Trp Ser Ile Asn Leu Thr Ala Gly Met Tyr Cys
 50                  55                  60

Ala Ala Leu Glu Ser Leu Ile Asn Val Ser Gly Cys Ser Ala Ile Glu
 65                  70                  75                  80

Lys Thr Gln Arg Met Leu Ser Gly Phe Cys Pro His Lys Val Ser Ala
                 85                  90                  95

Gly Gln Phe Ser Ser Leu His Val Arg Asp Thr Lys Ile Glu Val Ala
                100                 105                 110

Gln Phe Val Lys Asp Leu Leu Leu His Leu Lys Lys Leu Phe Arg Glu
            115                 120                 125

Gly Gln Phe Asn Arg Asn Phe Glu Ser Ile Ile Ile Cys Arg Asp Arg
        130                 135                 140

Thr
145

<210> SEQ ID NO 63
<211> LENGTH: 136
<212> TYPE: PRT
<213> ORGANISM: Homo sapiens

<400> SEQUENCE: 63

Met Asp Phe Gln Val Gln Ile Phe Ser Phe Leu Leu Ile Ser Ala Ser
  1               5                  10                  15

Val Ile Met Ser Arg Ala Asn Trp Val Asn Val Ile Ser Asp Leu Lys
             20                  25                  30

Lys Ile Glu Asp Leu Ile Gln Ser Met His Ile Asp Ala Thr Leu Tyr
         35                  40                  45

Thr Glu Ser Asp Val His Pro Ser Cys Lys Val Thr Ala Met Lys Cys
 50                  55                  60

Phe Leu Leu Glu Leu Gln Val Ile Ser Leu Glu Ser Gly Asp Ala Ser
 65                  70                  75                  80

Ile His Asp Thr Val Glu Asn Leu Ile Ile Leu Ala Asn Asn Ser Leu
                 85                  90                  95

Ser Ser Asn Gly Asn Val Thr Glu Ser Gly Cys Lys Glu Cys Glu Glu
                100                 105                 110

Leu Glu Glu Lys Asn Ile Lys Glu Phe Leu Gln Ser Phe Val His Ile
            115                 120                 125

Val Gln Met Phe Ile Asn Thr Ser
        130                 135

<210> SEQ ID NO 64
<211> LENGTH: 656
<212> TYPE: PRT
<213> ORGANISM: Homo sapiens

<400> SEQUENCE: 64

Met Glu Gly Asp Gly Ser Asp Pro Glu Pro Pro Asp Ala Gly Glu Asp
  1               5                  10                  15

Ser Lys Ser Glu Asn Gly Glu Asn Ala Pro Ile Tyr Cys Ile Cys Arg
             20                  25                  30

Lys Pro Asp Ile Asn Cys Phe Met Ile Gly Cys Asp Asn Cys Asn Glu
         35                  40                  45
```

```
Trp Phe His Gly Asp Cys Ile Arg Ile Thr Glu Lys Met Ala Lys Ala
 50                  55                  60
Ile Arg Glu Trp Tyr Cys Arg Glu Cys Arg Glu Lys Asp Pro Lys Leu
 65                  70                  75                  80
Glu Ile Arg Tyr Arg His Lys Lys Ser Arg Glu Arg Asp Gly Asn Glu
                     85                  90                  95
Arg Asp Ser Ser Glu Pro Arg Asp Glu Gly Gly Arg Lys Arg Pro
                100                 105                 110
Val Pro Asp Pro Asn Leu Gln Arg Ala Gly Ser Gly Thr Gly Val
                115                 120                 125
Gly Ala Met Leu Ala Arg Gly Ser Ala Ser Pro His Lys Ser Ser Pro
                130                 135                 140
Gln Pro Leu Val Ala Thr Pro Ser Gln His His Gln Gln Gln Gln Gln
145                 150                 155                 160
Gln Ile Lys Arg Ser Ala Arg Met Cys Gly Glu Cys Glu Ala Cys Arg
                165                 170                 175
Arg Thr Glu Asp Cys Gly His Cys Asp Phe Cys Arg Asp Met Lys Lys
                180                 185                 190
Phe Gly Gly Pro Asn Lys Ile Arg Gln Lys Cys Arg Leu Arg Gln Cys
                195                 200                 205
Gln Leu Arg Ala Arg Glu Ser Tyr Lys Tyr Phe Pro Ser Ser Leu Ser
210                 215                 220
Pro Val Thr Pro Ser Glu Ser Leu Pro Arg Pro Arg Arg Pro Leu Pro
225                 230                 235                 240
Thr Gln Gln Gln Pro Gln Pro Ser Gln Lys Leu Gly Arg Ile Arg Glu
                245                 250                 255
Asp Glu Gly Ala Val Ala Ser Ser Thr Val Lys Glu Pro Pro Glu Ala
                260                 265                 270
Thr Ala Thr Pro Glu Pro Leu Ser Asp Glu Asp Leu Pro Leu Asp Pro
                275                 280                 285
Asp Leu Tyr Gln Asp Phe Cys Ala Gly Ala Phe Asp Asp Asn Gly Leu
                290                 295                 300
Pro Trp Met Ser Asp Thr Glu Glu Ser Pro Phe Leu Asp Pro Ala Leu
305                 310                 315                 320
Arg Lys Arg Ala Val Lys Val Lys His Val Lys Arg Arg Glu Lys Lys
                325                 330                 335
Ser Glu Lys Lys Lys Glu Glu Arg Tyr Lys Arg His Arg Gln Lys Gln
                340                 345                 350
Lys His Lys Asp Lys Trp Lys His Pro Glu Arg Ala Asp Ala Lys Asp
                355                 360                 365
Pro Ala Ser Leu Pro Gln Cys Leu Gly Pro Gly Cys Val Arg Pro Ala
                370                 375                 380
Gln Pro Ser Ser Lys Tyr Cys Ser Asp Asp Cys Gly Met Lys Leu Ala
385                 390                 395                 400
Ala Asn Arg Ile Tyr Glu Ile Leu Pro Gln Arg Ile Gln Gln Trp Gln
                405                 410                 415
Gln Ser Pro Cys Ile Ala Glu Glu His Gly Lys Lys Leu Leu Glu Arg
                420                 425                 430
Ile Arg Arg Glu Gln Gln Ser Ala Arg Thr Arg Leu Gln Glu Met Glu
                435                 440                 445
Arg Arg Phe His Glu Leu Glu Ala Ile Ile Leu Arg Ala Lys Gln Gln
450                 455                 460
Ala Val Arg Glu Asp Glu Glu Ser Asn Glu Gly Asp Ser Asp Asp Thr
```

```
        465                 470                 475                 480
Asp Leu Gln Ile Phe Cys Val Ser Cys Gly His Pro Ile Asn Pro Arg
                485                 490                 495

Val Ala Leu Arg His Met Glu Arg Cys Tyr Ala Lys Tyr Glu Ser Gln
                500                 505                 510

Thr Ser Phe Gly Ser Met Tyr Pro Thr Arg Ile Glu Gly Ala Thr Arg
                515                 520                 525

Leu Phe Cys Asp Val Tyr Asn Pro Gln Ser Lys Thr Tyr Cys Lys Arg
530                 535                 540

Leu Gln Val Leu Cys Pro Glu His Ser Arg Asp Pro Lys Val Pro Ala
545                 550                 555                 560

Asp Glu Val Cys Gly Cys Pro Leu Val Arg Asp Val Phe Glu Leu Thr
                565                 570                 575

Gly Asp Phe Cys Arg Leu Pro Lys Arg Gln Cys Asn Arg His Tyr Cys
                580                 585                 590

Trp Glu Lys Leu Arg Arg Ala Glu Val Asp Leu Glu Arg Val Arg Val
                595                 600                 605

Trp Tyr Lys Leu Asp Glu Leu Phe Glu Gln Glu Arg Asn Val Arg Thr
                610                 615                 620

Ala Met Thr Asn Arg Ala Gly Leu Leu Ala Leu Met Leu His Gln Thr
625                 630                 635                 640

Ile Gln His Asp Pro Leu Thr Thr Asp Leu Arg Ser Ser Ala Asp Arg
                645                 650                 655

<210> SEQ ID NO 65
<211> LENGTH: 124
<212> TYPE: PRT
<213> ORGANISM: Vibrio cholerae

<400> SEQUENCE: 65

Met Ile Lys Leu Lys Phe Gly Val Phe Phe Thr Val Leu Leu Ser Ser
1               5                   10                  15

Ala Tyr Ala His Gly Thr Pro Gln Asn Ile Thr Asp Leu Cys Ala Glu
                20                  25                  30

Tyr His Asn Thr Gln Ile Tyr Thr Leu Asn Asp Lys Ile Phe Ser Tyr
                35                  40                  45

Thr Glu Ser Leu Ala Gly Lys Arg Glu Met Ala Ile Ile Thr Phe Lys
50                  55                  60

Asn Gly Ala Ile Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
                100                 105                 110

Thr Pro His Ala Ile Ala Ala Ile Ser Met Ala Asn
                115                 120

<210> SEQ ID NO 66
<211> LENGTH: 258
<212> TYPE: PRT
<213> ORGANISM: Vibrio cholerae

<400> SEQUENCE: 66

Met Val Lys Ile Ile Phe Val Phe Phe Ile Phe Leu Ser Ser Phe Ser
1               5                   10                  15

Tyr Ala Asn Asp Asp Lys Leu Tyr Arg Ala Asp Ser Arg Pro Pro Asp
```

```
                20                  25                  30
Glu Ile Lys Gln Ser Gly Gly Leu Met Pro Arg Gly Gln Asn Glu Tyr
             35                  40                  45
Phe Asp Arg Gly Thr Gln Met Asn Ile Asn Leu Tyr Asp His Ala Arg
         50                  55                  60
Gly Thr Gln Thr Gly Phe Val Arg His Asp Asp Gly Tyr Val Ser Thr
 65                  70                  75                  80
Ser Ile Ser Leu Arg Ser Ala His Leu Val Gly Gln Thr Ile Leu Ser
                 85                  90                  95
Gly His Ser Thr Tyr Tyr Ile Tyr Val Ile Ala Thr Ala Pro Asn Met
            100                 105                 110
Phe Asn Val Asn Asp Val Leu Gly Ala Tyr Ser Pro His Pro Asp Glu
        115                 120                 125
Gln Glu Val Ser Ala Leu Gly Gly Ile Pro Tyr Ser Gln Ile Tyr Gly
    130                 135                 140
Trp Tyr Arg Val His Phe Gly Val Leu Asp Glu Gln Leu His Arg Asn
145                 150                 155                 160
Arg Gly Tyr Arg Asp Arg Tyr Tyr Ser Asn Leu Asp Ile Ala Pro Ala
                165                 170                 175
Ala Asp Gly Tyr Gly Leu Ala Gly Phe Pro Pro Glu His Arg Ala Trp
            180                 185                 190
Arg Glu Glu Pro Trp Ile His His Ala Pro Pro Gly Cys Gly Asn Ala
        195                 200                 205
Pro Arg Ser Ser Met Ser Asn Thr Cys Asp Glu Lys Thr Gln Ser Leu
    210                 215                 220
Gly Val Lys Phe Leu Asp Glu Tyr Gln Ser Lys Val Lys Arg Gln Ile
225                 230                 235                 240
Phe Ser Gly Tyr Gln Ser Asp Ile Asp Thr His Asn Arg Ile Lys Asp
                245                 250                 255
Glu Leu

<210> SEQ ID NO 67
<211> LENGTH: 124
<212> TYPE: PRT
<213> ORGANISM: Vibrio cholerae

<400> SEQUENCE: 67

Met Ile Lys Leu Lys Phe Gly Val Phe Phe Thr Val Leu Leu Ser Ser
 1               5                  10                  15
Ala Tyr Ala His Gly Thr Pro Gln Asn Ile Thr Asp Leu Cys Ala Glu
            20                  25                  30
Tyr His Asn Thr Gln Ile His Thr Leu Asn Asp Lys Ile Leu Ser Tyr
         35                  40                  45
Thr Glu Ser Leu Ala Gly Asn Arg Glu Met Ala Ile Ile Thr Phe Lys
     50                  55                  60
Asn Gly Ala Thr Phe Gln Val Glu Val Pro Gly Ser Gln His Ile Asp
 65                  70                  75                  80
Ser Gln Lys Lys Ala Ile Glu Arg Met Lys Asp Thr Leu Arg Ile Ala
                 85                  90                  95
Tyr Leu Thr Glu Ala Lys Val Glu Lys Leu Cys Val Trp Asn Asn Lys
            100                 105                 110
Thr Pro His Ala Ile Ala Ala Ile Ser Met Ala Asn
        115                 120
```

```
<210> SEQ ID NO 68
<211> LENGTH: 18
<212> TYPE: PRT
<213> ORGANISM: Homo sapiens

<400> SEQUENCE: 68

Asp Pro Asn Ala Pro Lys Arg Pro Pro Ser Ala Phe Phe Leu Phe Cys
1               5                   10                  15

Ser Glu

<210> SEQ ID NO 69
<211> LENGTH: 96
<212> TYPE: PRT
<213> ORGANISM: Homo sapiens

<400> SEQUENCE: 69

Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
            20                  25                  30

Cys Leu Gly Tyr Thr Asp Arg Ile Leu His Pro Lys Phe Ile Val Gly
        35                  40                  45

Phe Thr Arg Gln Leu Ala Asn Glu Gly Cys Asp Ile Asn Ala Ile Ile
    50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95

<210> SEQ ID NO 70
<211> LENGTH: 92
<212> TYPE: PRT
<213> ORGANISM: Homo sapiens

<400> SEQUENCE: 70

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
            20                  25                  30

Cys Cys Phe Ser Tyr Thr Ser Arg Gln Ile Pro Gln Asn Phe Ile Ala
        35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90

<210> SEQ ID NO 71
<211> LENGTH: 144
<212> TYPE: PRT
<213> ORGANISM: Homo sapiens

<400> SEQUENCE: 71

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
```

```
              35                  40                  45
Thr Ala Ala Glu Met Asn Glu Thr Val Glu Val Ile Ser Glu Met Phe
 50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
130                 135                 140

<210> SEQ ID NO 72
<211> LENGTH: 204
<212> TYPE: PRT
<213> ORGANISM: Homo sapiens

<400> SEQUENCE: 72

Met Ala Gly Pro Ala Thr Gln Ser Pro Met Lys Leu Met Ala Leu Gln
 1               5                  10                  15

Leu Leu Leu Trp His Ser Ala Leu Trp Thr Val Gln Glu Ala Thr Pro
                20                  25                  30

Leu Gly Pro Ala Ser Ser Leu Pro Gln Ser Phe Leu Leu Lys Cys Leu
             35                  40                  45

Glu Gln Val Arg Lys Ile Gln Gly Asp Gly Ala Ala Leu Gln Glu Lys
 50                  55                  60

Leu Cys Ala Thr Tyr Lys Leu Cys His Pro Glu Glu Leu Val Leu Leu
 65                  70                  75                  80

Gly His Ser Leu Gly Ile Pro Trp Ala Pro Leu Ser Ser Cys Pro Ser
                 85                  90                  95

Gln Ala Leu Gln Leu Ala Gly Cys Leu Ser Gln Leu His Ser Gly Leu
                100                 105                 110

Phe Leu Tyr Gln Gly Leu Leu Gln Ala Leu Glu Gly Ile Ser Pro Glu
            115                 120                 125

Leu Gly Pro Thr Leu Asp Thr Leu Gln Leu Asp Val Ala Asp Phe Ala
130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
195                 200

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Glu Ile Asn Ser Ser Tyr
```

```
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser His Pro Arg Leu Ser Ala
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Met Pro Asn Pro Met Val
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Leu Gln Gln Val Leu Leu
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

His Glu Leu Ser Val Leu Leu
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Ala Pro Gln Arg Leu Pro
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 79

Thr Pro Arg Thr Leu Pro Thr
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Pro Val His Ser Ser Ile
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Pro Pro His Ala Leu Ser
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Phe Ser Asn Arg Phe Ile
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Val Val Pro Thr Pro Pro Tyr
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Leu Ala Pro Asp Ser Pro
1               5

<210> SEQ ID NO 85

```
<211> LENGTH: 69
<212> TYPE: PRT
<213> ORGANISM: Shigella dysenteria 1

<400> SEQUENCE: 85

Thr Pro Asp Cys Val Thr Gly Lys Val Glu Tyr Thr Lys Tyr Asn Asp
1               5                   10                  15

Asp Asp Thr Phe Thr Val Lys Val Gly Asp Lys Glu Leu Phe Thr Asn
            20                  25                  30

Arg Trp Asn Leu Gln Ser Leu Leu Ser Ala Gln Ile Thr Gly Met
        35                  40                  45

Thr Val Thr Ile Lys Gln Asn Ala Cys His Asn Gly Gly Phe Ser
    50                  55                  60

Glu Val Ile Phe Arg
65

<210> SEQ ID NO 86
<211> LENGTH: 560
<212> TYPE: PRT
<213> ORGANISM: Corynephage omega

<400> SEQUENCE: 86

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
            260                 265                 270
```

Glu Glu Phe His Gln Thr Ala Leu Glu His Pro Glu Leu Ser Glu Leu
            275                 280                 285

Lys Thr Val Thr Gly Thr Asn Pro Val Phe Ala Gly Ala Asn Tyr Ala
    290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
            355                 360                 365

Ile Pro Leu Val Gly Glu Leu Val Asp Ile Gly Phe Ala Ala Tyr Asn
        370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Leu His
                405                 410                 415

Asp Gly Tyr Ala Val Ser Trp Asn Thr Val Glu Asp Ser Ile Ile Arg
            420                 425                 430

Thr Gly Phe Gln Gly Glu Ser Gly His Asp Ile Lys Ile Thr Ala Glu
        435                 440                 445

Asn Thr Pro Leu Pro Ile Ala Gly Val Leu Leu Pro Thr Ile Pro Gly
            450                 455                 460

Lys Leu Asp Val Asn Lys Ser Lys Thr His Ile Ser Val Asn Gly Arg
465                 470                 475                 480

Lys Ile Arg Met Arg Cys Arg Ala Ile Asp Gly Asp Val Thr Phe Cys
                485                 490                 495

Arg Pro Lys Ser Pro Val Tyr Val Gly Asn Gly Val His Ala Asn Leu
            500                 505                 510

His Val Ala Phe His Arg Ser Ser Glu Lys Ile His Ser Asn Glu
        515                 520                 525

Ile Ser Ser Asp Ser Ile Gly Val Leu Gly Tyr Gln Lys Thr Val Asp
            530                 535                 540

His Thr Lys Val Asn Ser Lys Leu Ser Leu Phe Phe Glu Ile Lys Ser
545                 550                 555                 560

<210> SEQ ID NO 87
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asp Ser Leu Ser Ser Asn Gly Asn Val

```
              65                  70                  75                  80
Thr Glu Ser Gly Cys Lys Glu Cys Glu Leu Glu Glu Lys Asn Ile
                85                  90                  95
Lys Glu Phe Leu Gln Ser Phe Val His Ile Val Gln Met Phe Ile Asn
               100                 105                 110
Thr Ser

<210> SEQ ID NO 88
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Ile Thr Cys Pro Pro Pro Met Ser Val Glu His Ala Asp Ile Trp Val
1               5                  10                  15
Lys Ser Tyr Ser Leu Tyr Ser Arg Glu Arg Tyr Ile Cys Asn Ser Gly
                20                  25                  30
Phe Lys Arg Lys Ala Gly Thr Ser Ser Leu Thr Glu Cys Val Leu Asn
                35                  40                  45
Lys Ala Thr Asn Val Ala His Trp Thr Thr Pro Ser Leu Lys Cys Ile
 50                  55                  60
Arg Glu Pro Lys Ser Cys Asp Lys Thr His Thr Cys Pro Pro Cys Pro
 65                  70                  75                  80
Ala Pro Glu Leu Leu Gly Gly Pro Ser Val Phe Leu Phe Pro Pro Lys
                85                  90                  95
Pro Lys Asp Thr Leu Met Ile Ser Arg Thr Pro Glu Val Thr Cys Val
               100                 105                 110
Val Val Asp Val Ser His Glu Asp Pro Glu Val Lys Phe Asn Trp Tyr
               115                 120                 125
Val Asp Gly Val Glu Val His Asn Ala Lys Thr Lys Pro Arg Glu Glu
           130                 135                 140
Gln Tyr Asn Ser Thr Tyr Arg Val Val Ser Val Leu Thr Val Leu His
145                 150                 155                 160
Gln Asp Trp Leu Asn Gly Lys Glu Tyr Lys Cys Lys Val Ser Asn Lys
               165                 170                 175
Ala Leu Pro Ala Pro Ile Glu Lys Thr Ile Ser Lys Ala Lys Gly Gln
               180                 185                 190
Pro Arg Glu Pro Gln Val Tyr Thr Leu Pro Pro Ser Arg Asp Glu Leu
               195                 200                 205
Thr Lys Asn Gln Val Ser Leu Thr Cys Leu Val Lys Gly Phe Tyr Pro
           210                 215                 220
Ser Asp Ile Ala Val Glu Trp Glu Ser Asn Gly Gln Pro Glu Asn Asn
225                 230                 235                 240
Tyr Lys Thr Thr Pro Pro Val Leu Asp Ser Asp Gly Ser Phe Phe Leu
               245                 250                 255
Tyr Ser Lys Leu Thr Val Asp Lys Ser Arg Trp Gln Gln Gly Asn Val
               260                 265                 270
Phe Ser Cys Ser Val Met His Glu Ala Leu His Asn His Tyr Thr Gln
               275                 280                 285
Lys Ser Leu Ser Leu Ser Pro Gly Lys
           290                 295
```

<210> SEQ ID NO 89
<211> LENGTH: 535
<212> TYPE: PRT
<213> ORGANISM: Corynebacterium diphtheriae

<400> SEQUENCE: 89

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380
```

```
Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
        450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser
                485                 490                 495

Glu Lys Ile His Ser Asn Glu Ile Ser Ser Asp Ser Ile Gly Val Leu
                500                 505                 510

Gly Tyr Gln Lys Thr Val Asp His Thr Lys Val Asn Ser Lys Leu Ser
            515                 520                 525

Leu Phe Phe Glu Ile Lys Ser
            530                 535

<210> SEQ ID NO 90
<211> LENGTH: 1331
<212> TYPE: PRT
<213> ORGANISM: Homo sapiens

<400> SEQUENCE: 90

Met Glu Ser His Ser Arg Ala Gly Lys Ser Arg Lys Ser Ala Lys Phe
1               5                   10                  15

Arg Ser Ile Ser Arg Ser Leu Met Leu Cys Asn Ala Lys Thr Ser Asp
                20                  25                  30

Asp Gly Ser Ser Pro Asp Glu Lys Tyr Pro Asp Pro Phe Glu Ile Ser
            35                  40                  45

Leu Ala Gln Gly Lys Glu Gly Ile Phe His Ser Ser Val Gln Leu Ala
        50                  55                  60

Asp Thr Ser Glu Ala Gly Pro Ser Ser Val Pro Asp Leu Ala Leu Ala
65                  70                  75                  80

Ser Glu Ala Ala Gln Leu Gln Ala Ala Gly Asn Asp Arg Gly Lys Thr
                85                  90                  95

Cys Arg Arg Ile Phe Phe Met Lys Glu Ser Thr Ala Ser Ser Arg
                100                 105                 110

Glu Lys Pro Gly Lys Leu Glu Ala Gln Ser Ser Asn Phe Leu Phe Pro
            115                 120                 125

Lys Ala Cys His Gln Arg Ala Arg Ser Asn Ser Thr Ser Val Asn Pro
        130                 135                 140

Tyr Cys Thr Arg Glu Ile Asp Phe Pro Met Thr Lys Lys Ser Ala Ala
145                 150                 155                 160

Pro Thr Asp Arg Gln Pro Tyr Ser Leu Cys Ser Asn Arg Lys Ser Leu
                165                 170                 175

Ser Gln Gln Leu Asp Cys Pro Ala Gly Lys Ala Ala Gly Thr Ser Arg
            180                 185                 190

Pro Thr Arg Ser Leu Ser Thr Ala Gln Leu Val Gln Pro Ser Gly Gly
        195                 200                 205

Leu Gln Ala Ser Val Ile Ser Asn Ile Val Leu Met Lys Gly Gln Ala
        210                 215                 220
```

-continued

```
Lys Gly Leu Gly Phe Ser Ile Val Gly Gly Lys Asp Ser Ile Tyr Gly
225                 230                 235                 240

Pro Ile Gly Ile Tyr Val Lys Thr Ile Phe Ala Gly Gly Ala Ala Ala
            245                 250                 255

Ala Asp Gly Arg Leu Gln Glu Gly Asp Glu Ile Leu Glu Leu Asn Gly
        260                 265                 270

Glu Ser Met Ala Gly Leu Thr His Gln Asp Ala Leu Gln Lys Phe Lys
    275                 280                 285

Gln Ala Lys Lys Gly Leu Leu Thr Leu Thr Val Arg Thr Arg Leu Thr
290                 295                 300

Ala Pro Pro Ser Leu Cys Ser His Leu Ser Pro Pro Leu Cys Arg Ser
305                 310                 315                 320

Leu Ser Ser Ser Thr Cys Ile Thr Lys Asp Ser Ser Ser Phe Ala Leu
                325                 330                 335

Glu Ser Pro Ser Ala Pro Ile Ser Thr Ala Lys Pro Asn Tyr Arg Ile
            340                 345                 350

Met Val Glu Val Ser Leu Gln Lys Glu Ala Gly Val Gly Leu Gly Ile
        355                 360                 365

Gly Leu Cys Ser Val Pro Tyr Phe Gln Cys Ile Ser Gly Ile Phe Val
370                 375                 380

His Thr Leu Ser Pro Gly Ser Val Ala His Leu Asp Gly Arg Leu Arg
385                 390                 395                 400

Cys Gly Asp Glu Ile Val Glu Ile Ser Asp Ser Pro Val His Cys Leu
                405                 410                 415

Thr Leu Asn Glu Val Tyr Thr Ile Leu Ser Arg Cys Asp Pro Gly Pro
            420                 425                 430

Val Pro Ile Ile Val Ser Arg His Pro Asp Pro Gln Val Ser Glu Gln
        435                 440                 445

Gln Leu Lys Glu Ala Val Ala Gln Ala Val Glu Asn Thr Lys Phe Gly
    450                 455                 460

Lys Glu Arg His Gln Trp Ser Leu Glu Gly Val Lys Arg Leu Glu Ser
465                 470                 475                 480

Ser Trp His Gly Arg Pro Thr Leu Glu Lys Glu Arg Glu Lys Asn Ser
                485                 490                 495

Ala Pro Pro His Arg Arg Ala Gln Lys Val Met Ile Arg Ser Ser Ser
            500                 505                 510

Asp Ser Ser Tyr Met Ser Gly Ser Pro Gly Gly Ser Pro Gly Ser Gly
        515                 520                 525

Ser Ala Glu Lys Pro Ser Ser Asp Val Asp Ile Ser Thr His Ser Pro
530                 535                 540

Ser Leu Pro Leu Ala Arg Glu Pro Val Val Leu Ser Ile Ala Ser Ser
545                 550                 555                 560

Arg Leu Pro Gln Glu Ser Pro Leu Pro Glu Ser Arg Asp Ser His
                565                 570                 575

Pro Pro Leu Arg Leu Lys Lys Ser Phe Glu Ile Leu Val Arg Lys Pro
            580                 585                 590

Met Ser Ser Lys Pro Lys Pro Pro Arg Lys Tyr Phe Lys Ser Asp
        595                 600                 605

Ser Asp Pro Gln Lys Ser Leu Glu Glu Arg Glu Asn Ser Ser Cys Ser
    610                 615                 620

Ser Gly His Thr Pro Pro Thr Cys Gly Gln Glu Ala Arg Glu Leu Leu
625                 630                 635                 640
```

```
Pro Leu Leu Leu Pro Gln Glu Asp Thr Ala Gly Arg Ser Pro Ser Ala
            645                 650                 655

Ser Ala Gly Cys Pro Gly Pro Gly Ile Gly Pro Gln Thr Lys Ser Ser
            660                 665                 670

Thr Glu Gly Glu Pro Gly Trp Arg Arg Ala Ser Pro Val Thr Gln Thr
            675                 680                 685

Ser Pro Ile Lys His Pro Leu Leu Lys Arg Gln Ala Arg Met Asp Tyr
        690                 695                 700

Ser Phe Asp Thr Thr Ala Glu Asp Pro Trp Val Arg Ile Ser Asp Cys
705                 710                 715                 720

Ile Lys Asn Leu Phe Ser Pro Ile Met Ser Glu Asn His Gly His Met
            725                 730                 735

Pro Leu Gln Pro Asn Ala Ser Leu Asn Glu Glu Glu Gly Thr Gln Gly
            740                 745                 750

His Pro Asp Gly Thr Pro Pro Lys Leu Asp Thr Ala Asn Gly Thr Pro
            755                 760                 765

Lys Val Tyr Lys Ser Ala Asp Ser Ser Thr Val Lys Lys Gly Pro Pro
    770                 775                 780

Val Ala Pro Lys Pro Ala Trp Phe Arg Gln Ser Leu Lys Gly Leu Arg
785                 790                 795                 800

Asn Arg Ala Ser Asp Pro Arg Gly Leu Pro Asp Pro Ala Leu Ser Thr
            805                 810                 815

Gln Pro Ala Pro Ala Ser Arg Glu His Leu Gly Ser His Ile Arg Ala
            820                 825                 830

Ser Ser Ser Ser Ser Ser Ile Arg Gln Arg Ile Ser Ser Phe Glu Thr
            835                 840                 845

Phe Gly Ser Ser Gln Leu Pro Asp Lys Gly Ala Gln Arg Leu Ser Leu
    850                 855                 860

Gln Pro Ser Ser Gly Glu Ala Ala Lys Pro Leu Gly Lys His Glu Glu
865                 870                 875                 880

Gly Arg Phe Ser Gly Leu Leu Gly Arg Gly Ala Ala Pro Thr Leu Val
            885                 890                 895

Pro Gln Gln Pro Glu Gln Val Leu Ser Ser Gly Ser Pro Ala Ala Ser
            900                 905                 910

Glu Ala Arg Asp Pro Gly Val Ser Glu Ser Pro Pro Pro Gly Arg Gln
            915                 920                 925

Pro Asn Gln Lys Thr Leu Pro Pro Gly Pro Asp Pro Leu Leu Arg Leu
        930                 935                 940

Leu Ser Thr Gln Ala Glu Glu Ser Gln Gly Pro Val Leu Lys Met Pro
945                 950                 955                 960

Ser Gln Arg Ala Arg Ser Phe Pro Leu Thr Arg Ser Gln Ser Cys Glu
            965                 970                 975

Thr Lys Leu Leu Asp Glu Lys Thr Ser Lys Leu Tyr Ser Ile Ser Ser
            980                 985                 990

Gln Val Ser Ser Ala Val Met Lys Ser Leu Leu Cys Leu Pro Ser Ser
        995                 1000                1005

Ile Ser Cys Ala Gln Thr Pro Cys Ile Pro Lys Glu Gly Ala Ser
        1010                1015                1020

Pro Thr Ser Ser Ser Asn Glu Asp Ser Ala Ala Asn Gly Ser Ala
        1025                1030                1035

Glu Thr Ser Ala Leu Asp Thr Gly Phe Ser Leu Asn Leu Ser Glu
        1040                1045                1050

Leu Arg Glu Tyr Thr Glu Gly Leu Thr Glu Ala Lys Glu Asp Asp
```

```
              1055                1060                1065

Asp Gly Asp His Ser Ser Leu Gln Ser Gly Gln Ser Val Ile Ser
        1070                1075                1080

Leu Leu Ser Ser Glu Glu Leu Lys Lys Leu Ile Glu Glu Val Lys
        1085                1090                1095

Val Leu Asp Glu Ala Thr Leu Lys Gln Leu Asp Gly Ile His Val
        1100                1105                1110

Thr Ile Leu His Lys Glu Glu Gly Ala Gly Leu Gly Phe Ser Leu
        1115                1120                1125

Ala Gly Gly Ala Asp Leu Glu Asn Lys Val Ile Thr Val His Arg
        1130                1135                1140

Val Phe Pro Asn Gly Leu Ala Ser Gln Glu Gly Thr Ile Gln Lys
        1145                1150                1155

Gly Asn Glu Val Leu Ser Ile Asn Gly Lys Ser Leu Lys Gly Thr
        1160                1165                1170

Thr His His Asp Ala Leu Ala Ile Leu Arg Gln Ala Arg Glu Pro
        1175                1180                1185

Arg Gln Ala Val Ile Val Thr Arg Lys Leu Thr Pro Glu Ala Met
        1190                1195                1200

Pro Asp Leu Asn Ser Ser Thr Asp Ser Ala Ala Ser Ala Ser Ala
        1205                1210                1215

Ala Ser Asp Val Ser Val Glu Ser Thr Glu Ala Thr Val Cys Thr
        1220                1225                1230

Val Thr Leu Glu Lys Met Ser Ala Gly Leu Gly Phe Ser Leu Glu
        1235                1240                1245

Gly Gly Lys Gly Ser Leu His Gly Asp Lys Pro Leu Thr Ile Asn
        1250                1255                1260

Arg Ile Phe Lys Gly Ala Ala Ser Glu Gln Ser Glu Thr Val Gln
        1265                1270                1275

Pro Gly Asp Glu Ile Leu Gln Leu Gly Gly Thr Ala Met Gln Gly
        1280                1285                1290

Leu Thr Arg Phe Glu Ala Trp Asn Ile Ile Lys Ala Leu Pro Asp
        1295                1300                1305

Gly Pro Val Thr Ile Val Ile Arg Arg Lys Ser Leu Gln Ser Lys
        1310                1315                1320

Glu Thr Thr Ala Ala Gly Asp Ser
        1325                1330

<210> SEQ ID NO 91
<211> LENGTH: 155
<212> TYPE: PRT
<213> ORGANISM: Homo sapiens

<400> SEQUENCE: 91

Met Thr Pro Gly Lys Thr Ser Leu Val Ser Leu Leu Leu Leu Ser
1               5                   10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
            35                  40                  45

Leu Asn Ile His Asn Arg Asn Thr Asn Thr Pro Lys Arg Ser Ser
        50                  55                  60

Asp Tyr Tyr Asn Arg Ser Thr Ser Pro Trp Asn Leu His Arg Asn Glu
65                  70                  75                  80
```

```
Asp Pro Glu Arg Tyr Pro Ser Val Ile Trp Glu Ala Lys Cys Arg His
            85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
            115                 120                 125

Cys Pro Asn Ser Phe Arg Leu Glu Lys Ile Leu Val Ser Val Gly Cys
            130                 135                 140

Thr Cys Val Thr Pro Ile Val His His Val Ala
145                 150                 155

<210> SEQ ID NO 92
<211> LENGTH: 476
<212> TYPE: PRT
<213> ORGANISM: Homo sapiens

<400> SEQUENCE: 92

Arg Ala Val Pro Gly Gly Ser Ser Pro Ala Trp Thr Gln Cys Gln Gln
1               5                   10                  15

Leu Ser Gln Lys Leu Cys Thr Leu Ala Trp Ser Ala His Pro Leu Val
            20                  25                  30

Gly His Met Asp Leu Arg Glu Glu Gly Asp Glu Glu Thr Thr Asn Asp
            35                  40                  45

Val Pro His Ile Gln Cys Gly Asp Gly Cys Asp Pro Gln Gly Leu Arg
        50                  55                  60

Asp Asn Ser Gln Phe Cys Leu Gln Arg Ile His Gln Gly Leu Ile Phe
65              70                  75                  80

Tyr Glu Lys Leu Leu Gly Ser Asp Ile Phe Thr Gly Glu Pro Ser Leu
            85                  90                  95

Leu Pro Asp Ser Pro Val Gly Gln Leu His Ala Ser Leu Leu Gly Leu
            100                 105                 110

Ser Gln Leu Leu Gln Pro Glu Gly His His Trp Glu Thr Gln Gln Ile
            115                 120                 125

Pro Ser Leu Ser Pro Ser Gln Pro Trp Gln Arg Leu Leu Leu Arg Phe
        130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro Ile Trp Glu Leu Lys Lys
            165                 170                 175

Asp Val Tyr Val Val Glu Leu Asp Trp Tyr Pro Asp Ala Pro Gly Glu
            180                 185                 190

Met Val Val Leu Thr Cys Asp Thr Pro Glu Glu Asp Gly Ile Thr Trp
            195                 200                 205

Thr Leu Asp Gln Ser Ser Glu Val Leu Gly Ser Gly Lys Thr Leu Thr
        210                 215                 220

Ile Gln Val Lys Glu Phe Gly Asp Ala Gly Gln Tyr Thr Cys His Lys
225                 230                 235                 240

Gly Gly Glu Val Leu Ser His Ser Leu Leu Leu Leu His Lys Lys Glu
            245                 250                 255

Asp Gly Ile Trp Ser Thr Asp Ile Leu Lys Asp Gln Lys Glu Pro Lys
            260                 265                 270

Asn Lys Thr Phe Leu Arg Cys Glu Ala Lys Asn Tyr Ser Gly Arg Phe
        275                 280                 285

Thr Cys Trp Trp Leu Thr Thr Ile Ser Thr Asp Leu Thr Phe Ser Val
            290                 295                 300
```

```
Lys Ser Ser Arg Gly Ser Ser Asp Pro Gln Gly Val Thr Cys Gly Ala
305                 310                 315                 320

Ala Thr Leu Ser Ala Glu Arg Val Arg Gly Asp Asn Lys Glu Tyr Glu
            325                 330                 335

Tyr Ser Val Glu Cys Gln Glu Asp Ser Ala Cys Pro Ala Ala Glu Glu
        340                 345                 350

Ser Leu Pro Ile Glu Val Met Val Asp Ala Val His Lys Leu Lys Tyr
    355                 360                 365

Glu Asn Tyr Thr Ser Ser Phe Phe Ile Arg Asp Ile Ile Lys Pro Asp
370                 375                 380

Pro Pro Lys Asn Leu Gln Leu Lys Pro Leu Lys Asn Ser Arg Gln Val
385                 390                 395                 400

Glu Val Ser Trp Glu Tyr Pro Asp Thr Trp Ser Thr Pro His Ser Tyr
                405                 410                 415

Phe Ser Leu Thr Phe Cys Val Gln Val Gln Gly Lys Ser Lys Arg Glu
            420                 425                 430

Lys Lys Asp Arg Val Phe Thr Asp Lys Thr Ser Ala Thr Val Ile Cys
        435                 440                 445

Arg Lys Asn Ala Ser Ile Ser Val Arg Ala Gln Asp Arg Tyr Tyr Ser
    450                 455                 460

Ser Ser Trp Ser Glu Trp Ala Ser Val Pro Cys Ser
465                 470                 475

<210> SEQ ID NO 93
<211> LENGTH: 234
<212> TYPE: PRT
<213> ORGANISM: Homo sapiens

<400> SEQUENCE: 93

Met Cys Phe Pro Lys Val Leu Ser Asp Asp Met Lys Lys Leu Lys Ala
1               5                   10                  15

Arg Met Val Met Leu Leu Pro Thr Ser Ala Gln Gly Leu Gly Ala Trp
            20                  25                  30

Val Ser Ala Cys Asp Thr Glu Asp Thr Val Gly His Leu Gly Pro Trp
        35                  40                  45

Arg Asp Lys Asp Pro Ala Leu Trp Cys Gln Leu Cys Leu Ser Ser Gln
    50                  55                  60

His Gln Ala Ile Glu Arg Phe Tyr Asp Lys Met Gln Asn Ala Glu Ser
65                  70                  75                  80

Gly Arg Gly Gln Val Met Ser Ser Leu Ala Glu Leu Glu Asp Asp Phe
                85                  90                  95

Lys Glu Gly Tyr Leu Glu Thr Val Ala Ala Tyr Tyr Glu Glu Gln His
            100                 105                 110

Pro Glu Leu Thr Pro Leu Leu Glu Lys Glu Arg Asp Gly Leu Arg Cys
        115                 120                 125

Arg Gly Asn Arg Ser Pro Val Pro Asp Val Glu Asp Pro Ala Thr Glu
    130                 135                 140

Glu Pro Gly Glu Ser Phe Cys Asp Lys Val Met Arg Trp Phe Gln Ala
145                 150                 155                 160

Met Leu Gln Arg Leu Gln Thr Trp Trp His Gly Val Leu Ala Trp Val
                165                 170                 175

Lys Glu Lys Val Val Ala Leu Val His Ala Val Gln Ala Leu Trp Lys
            180                 185                 190

Gln Phe Gln Ser Phe Cys Cys Ser Leu Ser Glu Leu Phe Met Ser Ser
```

```
            195                 200                 205
Phe Gln Ser Tyr Gly Ala Pro Arg Gly Asp Lys Glu Glu Leu Thr Pro
        210                 215                 220
Gln Lys Cys Ser Glu Pro Gln Ser Ser Lys
225                 230

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Met Ala Val Pro Met Gln Leu Ser Cys Ser Arg
1               5                   10

<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Ser Thr Gly
1

<210> SEQ ID NO 96
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Arg
1

<210> SEQ ID NO 97
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Ser Gln
1

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Ser Ala Gly Glu
1               5
```

```
<210> SEQ ID NO 99
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Ser
1

<210> SEQ ID NO 100
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Gly
1

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Ser Gly Gly Ser Gly Gly Ser Gly
1               5

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Gly Ser Gly Gly Ser Gly Gly Ser Gly Gly
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Gly Ser Gly Gly Ser Gly Gly Ser Gly Gly Ser Gly Gly
1               5                   10

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104
```

Gly Gly Ser Gly Gly Ser Gly Gly Ser Gly Gly Ser Gly Gly Ser Gly
1               5                   10                  15

Gly

<210> SEQ ID NO 105
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Gly Ser Gly Gly Ser Gly Gly Ser Gly Gly Ser Gly Gly Ser Gly
1               5                   10                  15

Gly Ser Gly Gly
            20

<210> SEQ ID NO 106
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Gly Ser Gly Gly Ser Gly Gly Ser Gly Gly Ser Gly Gly Ser Gly
1               5                   10                  15

Gly Ser Gly Gly Ser Gly Gly
            20

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Gly Ser Gly Gly Ser Gly Gly Ser Gly Gly Ser Gly Gly Ser Gly
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Ser Gly Gly Ser Gly Gly Ser Gly Gly Ser Gly Gly Ser Gly Gly
1               5                   10                  15

<210> SEQ ID NO 109
<211> LENGTH: 1872
<212> TYPE: DNA
<213> ORGANISM: Mycobacterium tuberculosis

<400> SEQUENCE: 109
gactacgttg gtgtagaaaa atcctgccgc ccggacccct aaggctggga caatttctga      60
tagctacccc gacacaggag gttacgggat gagcaattcg cgccgccgct cactcaggtg     120

```
gtcatggttg ctgagcgtgc tggctgccgt cgggctgggc ctggccacgg cgccggccca      180
ggcggccccg ccggccttgt cgcaggaccg gttcgccgac ttccccgcgc tgcccctcga      240
cccgtccgcg atggtcgccc aagtggggcc acaggtggtc aacatcaaca ccaaactggg      300
ctacaacaac gccgtgggcg ccgggaccgg catcgtcatc gatcccaacg gtgtcgtgct      360
gaccaacaac cacgtgatcg cgggcgccac cgacatcaat gcgttcagcg tcggctccgg      420
ccaaacctac ggcgtcgatg tggtcgggta tgaccgcacc caggatgtcg cggtgctgca      480
gctgcgcggt gccggtggcc tgccgtcggc ggcgatcggt ggcggcgtcg cggttggtga      540
gcccgtcgtc gcgatgggca acagcggtgg gcagggcgga acgccccgtg cggtgcctgg      600
cagggtggtc gcgctcggcc aaaccgtgca ggcgtcggat tcgctgaccg gtgccgaaga      660
gacattgaac gggttgatcc agttcgatgc cgcgatccag cccggtgatt cgggcgggcc      720
cgtcgtcaac ggcctaggac aggtggtcgg tatgaacacg gccgcgtccg ataacttcca      780
gctgtcccag ggtgggcagg gattcgccat tccgatcggg caggcgatgg cgatcgcggg      840
ccagatccga tcgggtgggg ggtcacccac cgttcatatc gggcctaccg ccttcctcgg      900
cttgggtgtt gtcgacaaca acggcaacgg cgcacgagtc caacgcgtgg tcgggagcgc      960
tccggcggca agtctcggca tctccaccgg cgacgtgatc accgcggtcg acggcgctcc     1020
gatcaactcg gccaccgcga tggcggacgc gcttaacggg catcatcccg tgacgtcat      1080
ctcggtgacc tggcaaacca gtcgggcgg cacgcgtaca gggaacgtga cattggccga      1140
gggaccccccg gcctgatttc gtcgcggata ccacccgccg gccggccaat tggattggcg     1200
ccagccgtga ttgccgcgtg agccccgag ttccgtctcc cgtgcgcgtg gcatcgtgga     1260
agcaatgaac gaggcagaac acagcgtcga gcaccctccc gtgcagggca gtcacgtcga     1320
aggcggtgtg gtcgagcatc cggatgccaa ggacttcggc agcgccgccg ccctgcccgc     1380
cgatccgacc tggtttaagc acgccgtctt ctacgaggtg ctggtccggg cgttcttcga     1440
cgccagcgcg gacggttccg gcgatctgcg tggactcatc gatcgcctcg actacctgca     1500
gtggcttggc atcgactgca tctggttgcc gccgttctac gactcgccgc tgcgcgacgg     1560
cggttacgac attcgcgact tctacaaggt gctgcccgaa ttcggcaccg tcgacgattt     1620
cgtcgccctg gtcgacgccg ctcaccggcg aggtatccgc atcatcaccg acctggtgat     1680
gaatcacacc tcggagtcgc acccctggtt tcaggagtcc cgccgcgacc cagacggacc     1740
gtacggtgac tattacgtgt ggagcgacac cagcgagcgc tacaccgacg cccggatcat     1800
cttcgtcgac accgaagagt cgaactggtc attcgatcct gtccgccgac agttctactg     1860
gcaccgattc tt                                                        1872
```

<210> SEQ ID NO 110
<211> LENGTH: 396
<212> TYPE: DNA
<213> ORGANISM: Mycobacterium tuberculosis

<400> SEQUENCE: 110

```
acggccgcgt ccgataactt ccagctgtcc cagggtgggc aggattcgc cattccgatc       60
gggcaggcga tggcgatcgc gggccagatc cgatcgggtg gggggtcacc caccgttcat      120
atcgggccta ccgccttcct cggcttgggt gttgtcgaca caacggcaa cggcgcacga      180
gtccaacgcg tggtcgggag cgctccggcg gcaagtctcg gcatctccac cggcgacgtg     240
atcaccgcgg tcgacggcgc tccgatcaac tcggccaccg cgatggcgga cgcgcttaac     300
```

| gggcatcatc ccggtgacgt catctcggtg acctggcaaa ccaagtcggg cggcacgcgt | 360 |
| acagggaacg tgacattggc cgagggaccc ccggcc | 396 |

<210> SEQ ID NO 111
<211> LENGTH: 702
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111

| catatgcatc accatcacca tcacacggcc gcgtccgata acttccagct gtcccagggt | 60 |
| gggcagggat tcgccattcc gatcgggcag gcgatggcga tcgcgggcca gatccgatcg | 120 |
| ggtgggggt cacccaccgt tcatatcggg cctaccgcct tcctcggctt gggtgttgtc | 180 |
| gacaacaacg gcaacggcgc acgagtccaa cgcgtggtcg ggagcgctcc ggcggcaagt | 240 |
| ctcggcatct ccaccggcga cgtgatcacc gcggtcgacg gcgctccgat caactcggcc | 300 |
| accgcgatgg cggacgcgct taacgggcat catcccggtg acgtcatctc ggtgacctgg | 360 |
| caaaccaagt cgggcggcac gcgtacaggg aacgtgacat tggccgaggg accccccggcc | 420 |
| gaattcgacg acgacgacaa ggatccacct gacccgcatc agccggacat gacgaaaggc | 480 |
| tattgcccgg gtggccgatg gggttttggc gacttggccg tgtgcgacgg cgagaagtac | 540 |
| cccgacggct cgttttggca ccagtggatg caaacgtggt ttaccggccc acagttttac | 600 |
| ttcgattgtg tcagcggcgg tgagcccctc cccggcccgc cgccaccggg tggttgcggt | 660 |
| ggggcaattc cgtccgagca gcccaacgct ccctgagaat tc | 702 |

<210> SEQ ID NO 112
<211> LENGTH: 1746
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112

| catatgcatc accatcacca tcacacggcc gcgtccgata acttccagct gtcccagggt | 60 |
| gggcagggat tcgccattcc gatcgggcag gcgatggcga tcgcgggcca gatccgatcg | 120 |
| ggtgggggt cacccaccgt tcatatcggg cctaccgcct tcctcggctt gggtgttgtc | 180 |
| gacaacaacg gcaacggcgc acgagtccaa cgcgtggtcg ggagcgctcc ggcggcaagt | 240 |
| ctcggcatct ccaccggcga cgtgatcacc gcggtcgacg gcgctccgat caactcggcc | 300 |
| accgcgatgg cggacgcgct taacgggcat catcccggtg acgtcatctc ggtgacctgg | 360 |
| caaaccaagt cgggcggcac gcgtacaggg aacgtgacat tggccgaggg accccccggcc | 420 |
| gaattcccgc tggtgccgcg cggcagcccg atgggctccg acgttcggga cctgaacgca | 480 |
| ctgctgccgg cagttccgtc cctgggtggt ggtggtggtt gcgcactgcc ggttagcggt | 540 |
| gcagcacagt gggctccggt tctggacttc gcaccgccgg tgcatccgc atacggttcc | 600 |
| ctgggtggtc cggcaccgcc gccggcaccg ccgccgccgc cgccgccgcc gccgcactcc | 660 |
| ttcatcaaac aggaaccgag ctgggtggt gcagaaccgc acgaagaaca gtgcctgagc | 720 |
| gcattcaccg ttcacttctc cggccagttc actggcacag ccggagcctg tcgctacggg | 780 |
| cccttcggtc ctcctccgcc cagccaggcg tcatccggcc aggccaggat gtttcctaac | 840 |
| gcgccctacc tgcccagctg cctcgagagc cagcccgcta ttcgcaatca gggttacagc | 900 |

```
acggtcacct tcgacgggac gcccagctac ggtcacacgc cctcgcacca tgcggcgcag        960
ttccccaacc actcattcaa gcatgaggat cccatgggcc agcagggctc gctgggtgag       1020
cagcagtact cggtgccgcc cccggtctat ggctgccaca cccccaccga cagctgcacc       1080
ggcagccagg ctttgctgct gaggacgccc tacagcagtg acaatttata ccaaatgaca       1140
tcccagcttg aatgcatgac ctggaatcag atgaacttag gagccacctt aaagggccac       1200
agcacagggt acgagagcga taaccacaca acgcccatcc tctgcggagc caatacaga        1260 atacacacgc acggtgtctt cagaggcatt caggatgtgc gacgtgtgcc tggagtagcc       1320
ccgactcttg tacggtcggc atctgagacc agtgagaaac gccccttcat gtgtgcttac       1380
tcaggctgca ataagagata ttttaagctg tcccacttac agatgcacag caggaagcac       1440
actggtgaga aaccatacca gtgtgacttc aaggactgtg aacgaaggtt ttttcgttca       1500
gaccagctca aaagacacca aaggagacat acaggtgtga accattcca gtgtaaaact       1560 tgtcagcgaa agttctcccg gtccgaccac ctgaagaccc acaccaggac tcatacaggt       1620
gaaaagccct tcagctgtcg gtggccaagt tgtcagaaaa agtttgcccg gtcagatgaa       1680
ttagtccgcc atcacaacat gcatcagaga acatgacca aactccagct ggcgctttga       1740
gaattc                                                                  1746

<210> SEQ ID NO 113
<211> LENGTH: 672
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
catatgcatc accatcacca tcacacggcc gcgtccgata acttccagct gtcccagggt         60
gggcagggat tcgccattcc gatcgggcag gcgatggcga tcgcgggcca gatccgatcg        120 ggtgggggt cacccaccgt tcatatcggg cctaccgcct tcctcggctt gggtgttgtc        180
gacaacaacg gcaacggcgc acgagtccaa cgcgtggtcg ggagcgctcc ggcggcaagt        240
ctcggcatct ccaccggcga cgtgatcacc gcggtcgacg gcgctccgat caactcggcc        300
accgcgatgg cggacgcgct taacgggcat catcccggtg acgtcatctc ggtgacctgg        360
caaaccaagt cgggcggcac gcgtacaggg aacgtgacat tggccgaggg accccggcc        420 gaattcatcg agggaagggg ctctggctgc cccttattgg agaatgtgat ttccaagaca        480
atcaatccac aagtgtctaa gactgaatac aaagaacttc ttcaagagtt catagacgac        540
aatgccacta caaatgccat agatgaattg aaggaatgtt ttcttaacca acggatgaa        600 actctgagca atgttgaggt gtttatgcaa ttaatatatg acagcagtct ttgtgattta        660
ttttaagaat tc                                                           672

<210> SEQ ID NO 114
<211> LENGTH: 2191
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
atgcatcacc atcaccatca cacggccgcg tccgataact tccagctgtc ccagggtggg         60
```

```
cagggattcg ccattccgat cgggcaggcg atggcgatcg cgggccagat ccgatcgggt      120 gggggggtcac ccaccgttca tatcgggcct accgccttcc tcggcttggg tgttgtcgac    180
aacaacggca acggcgcacg agtccaacgc gtggtcggga gcgctccggc ggcaagtctc     240
ggcatctcca ccgcgacgt gatcaccgcg gtcgacggcg ctccgatcaa ctcggccacc      300
gcgatggcgg acgcgcttaa cgggcatcat cccggtgacg tcatctcggt gacctggcaa     360
accaagtcgg gcggcacgcg tacagggaac gtgacattgg ccgagggacc cccgccgaa      420 ttcatggtgg atttcggggc gttaccaccg gagatcaact ccgcgaggat gtacgccggc     480
ccgggttcgg cctcgctggt ggccgcggct cagatgtggg acagcgtggc gagtgacctg     540
ttttcggccg cgtcggcgtt tcagtcggtg gtctggggtc tgacggtggg gtcgtggata     600
ggttcgtcgg cgggtctgat ggtggcggcg gcctcgccgt atgtggcgtg gatgagcgtc     660
accgcggggc aggccgagct gaccgccgcc caggtccggg ttgctgcggc ggcctacgag     720
acggcgtatg ggctgacggt gccccgccg gtgatcgccg agaaccgtgc tgaactgatg      780
attctgatag cgaccaacct cttggggcaa aacaccccgg cgatcgcggt caacgaggcc     840
gaatacggcg agatgtgggc ccaagacgcc gccgcgatgt ttggctacgc cgcggcgacg     900
gcgacggcga cggcgacgtt gctgccgttc gaggaggcgc cggagatgac cagcgcgggt     960
gggctcctcg agcaggccgc cgcggtcgag gaggcctccg acaccgccgc ggcgaaccag    1020
ttgatgaaca atgtgcccca ggcgctgcaa cagctggccc agcccacgca gggcaccacg    1080
ccttcttcca agctgggtgg cctgtggaag acggtctcgc cgcatcggtc gccgatcagc    1140
aacatggtgt cgatggccaa caaccacatg tcgatgacca actcgggtgt gtcgatgacc    1200
aacaccttga gctcgatgtt gaagggcttt gctccggcgg cggccgccca ggccgtgcaa    1260
accgcggcgc aaaacggggt ccgggcgatg agctcgctgg gcagctcgct gggttcttcg    1320
ggtctgggcg gtggggtggc cgccaacttg ggtcgggcgg cctcggtcgg ttcgttgtcg    1380
gtgccgcagg cctgggccgc ggccaaccag gcagtcaccc cggcggcgcg ggcgctgccg    1440
ctgaccagcc tgaccagcgc cgcggaaaga gggcccgggc agatgctggg cgggctgccg    1500
gtggggcaga tgggcgccag ggccggtggt gggctcagtg gtgtgctgcg tgttccgccg    1560
cgaccctatg tgatgccgca ttctccggca gccggcgata tcgccccgcc ggccttgtcg    1620
caggaccggt tcgccgactt ccccgcgctg ccctcgacc cgtccgcgat ggtcgcccaa     1680
gtggggccac aggtggtcaa catcaacacc aaactgggct acaacaacgc cgtgggcgcc    1740
gggaccggca tcgtcatcga tcccaacggt gtcgtgctga ccaacaacca cgtgatcgcg    1800
ggcgccaccg acatcaatgc gttcagcgtc ggctccggcc aaacctacgg cgtcgatgtg    1860
gtcgggtatg accgcaccca ggatgtgcgc gtgctgcagc tgcgcggtgc cggtggcctg    1920
ccgtcggcgg cgatcggtgg cggcgtcgcg gttggtgagc ccgtcgtcgc gatgggcaac    1980
agcggtgggc agggcggaac gccccgtgcg gtgcctggca gggtggtcgc gctcggccaa    2040
accgtgcagg cgtcggattc gctgaccggt gccgaagaga cattgaacgg gttgatccag    2100
ttcgatgccg cgatccagcc cggtgattcg ggcgggcccg tcgtcaacgg cctaggacag    2160
gtggtcggta tgaacacggc cgcgtcctag g                                   2191
```

<210> SEQ ID NO 115
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 115
caattacata tgcatcacca tcaccatcac acggccgcgt ccgataactt c            51

<210> SEQ ID NO 116
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ctaatcgaat tcggccgggg gtccctcggc caa            33

<210> SEQ ID NO 117
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
caattagaat tcgacgacga cgacaaggat ccacctgacc cgcatcag            48

<210> SEQ ID NO 118
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
caattagaat tctcagggag cgttgggctg ctc            33

<210> SEQ ID NO 119
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gcgaagctta tgaagttgct gatggtcctc atgc            34

<210> SEQ ID NO 120
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
cggctcgagt taaataaat cacaaagact gctgtc            36

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Met His His His His His
1               5

<210> SEQ ID NO 122
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Asp Asp Asp Lys
1

<210> SEQ ID NO 123
<211> LENGTH: 95
<212> TYPE: PRT
<213> ORGANISM: Homo sapiens

<400> SEQUENCE: 123

Met Cys Cys Thr Lys Ser Leu Leu Leu Ala Ala Leu Met Ser Val Leu
1               5                   10                  15

Leu Leu His Leu Cys Gly Glu Ser Glu Ala Ser Asn Phe Asp Cys Cys
            20                  25                  30

Leu Gly Tyr Thr Asp Arg Ile Leu His Pro Lys Phe Ile Val Gly Phe
        35                  40                  45

Thr Arg Gln Leu Ala Asn Glu Gly Cys Asp Ile Asn Ala Ile Ile Phe
    50                  55                  60

His Thr Lys Lys Lys Leu Ser Val Cys Ala Asn Pro Lys Gln Thr Trp
65                  70                  75                  80

Val Lys Tyr Ile Val Arg Leu Leu Ser Lys Lys Val Lys Asn Met
                85                  90                  95

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ggggtcaacg ttgagggggg                                            20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gggggacgat cgtcgggggg                                            20

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 126 gggacgacg tcgtgggggg g                                          21

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tccatgacgt tcctgatgct                                           20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tccatgacgt tcctgacgtt                                           20

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tcgtcgtttt gtcgttttgt cgtt                                      24

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
tcgtcgttgt cgttttgtcg tt                                        22

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tcgacgttcg tcgttcgtcg ttc                                       23

<210> SEQ ID NO 132
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 132
tcgcgacgtt cgcccgacgt tcggta                                      26

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tcgtcgtttt cggcgcgcgc cg                                          22

<210> SEQ ID NO 134
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tcgtcgtcgt tcgaacgacg ttgat                                       25

<210> SEQ ID NO 135
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tcgcgaacgt tcgccgcgtt cgaacgcgg                                   29
```